United States Patent
Robertsen et al.

(10) Patent No.: US 11,466,302 B2
(45) Date of Patent: Oct. 11, 2022

(54) PRODUCTION OF STEVIOL GLYCOSIDES IN RECOMBINANT HOSTS

(71) Applicant: EVOLVA SA, Reinach (CH)

(72) Inventors: Helene Lunde Robertsen, Horsholm (DK); Iben Nordmark Andersen, Vedbaek (DK); Adam Matthew Takos, Valby (DK); Swee Chuang Lim Hallwyl, Vallensbaek Strand (DK); Francesca Ambri, Hillerod (DK); Manuel Quiros Asensio, Soborg (DK); Michael Dalgaard Mikkelsen, Vaerlose (DK); Jens Houghton-Larsen, Birkerod (DK); Veronique Douchin, Frederiksberg (DK); Jane Dannow Dyekjaer, Copenhagen (DK); Simon Carlsen, Copenhagen (DK); Nina Nicoline Rasmussen, Hvidovre (DK); Esben Halkjaer Hansen, Frederiksberg (DK)

(73) Assignee: EVOLVA SA, Reinach (CH)

( * ) Notice: Subject to any disclaimer, the term of this patent is extended or adjusted under 35 U.S.C. 154(b) by 0 days.

(21) Appl. No.: 16/801,200

(22) Filed: Feb. 26, 2020

(65) Prior Publication Data
US 2020/0392552 A1 Dec. 17, 2020

Related U.S. Application Data

(62) Division of application No. 15/506,196, filed as application No. PCT/EP2015/070620 on Sep. 9, 2015, now Pat. No. 10,612,064.

(60) Provisional application No. 62/048,178, filed on Sep. 9, 2014, provisional application No. 62/103,547, filed on Jan. 14, 2015, provisional application No. 62/117,396, filed on Feb. 17, 2015, provisional application No. 62/148,585, filed on Apr. 16, 2015.

(51) Int. Cl.
| C12P 19/56 | (2006.01) |
| A23L 27/30 | (2016.01) |
| C12N 9/02 | (2006.01) |
| C12N 15/52 | (2006.01) |
| C07H 15/256 | (2006.01) |
| C12N 9/10 | (2006.01) |
| C12N 9/88 | (2006.01) |
| C12N 9/90 | (2006.01) |

(52) U.S. Cl.
CPC .............. *C12P 19/56* (2013.01); *A23L 27/36* (2016.08); *C07H 15/256* (2013.01); *C12N 9/0042* (2013.01); *C12N 9/0073* (2013.01); *C12N 9/1085* (2013.01); *C12N 9/88* (2013.01); *C12N 9/90* (2013.01); *C12N 15/52* (2013.01); *C12Y 106/02004* (2013.01); *C12Y 114/13078* (2013.01); *C12Y 114/13079* (2013.01); *C12Y 205/01029* (2013.01); *C12Y 402/03019* (2013.01); *C12Y 505/01013* (2013.01); *A23V 2002/00* (2013.01); *C07K 2319/00* (2013.01)

(58) Field of Classification Search
None
See application file for complete search history.

(56) References Cited

U.S. PATENT DOCUMENTS

| 4,590,160 | A | 5/1986 | Nishihashi et al. |
| 5,198,360 | A | 3/1993 | Ballou |
| 5,204,253 | A | 4/1993 | Sanford et al. |
| 5,306,862 | A | 4/1994 | Chappell et al. |
| 5,460,949 | A | 10/1995 | Saunders et al. |
| 5,538,880 | A | 7/1996 | Lundquist et al. |
| 6,013,863 | A | 1/2000 | Lundquist et al. |
| 6,215,051 | B1 | 4/2001 | Yu et al. |
| 6,255,557 | B1 | 7/2001 | Brandle |
| 6,284,493 | B1 | 9/2001 | Roth |
| 6,284,506 | B1 | 9/2001 | Hoshino et al. |
| 6,329,571 | B1 | 12/2001 | Hiei |
| 6,586,202 | B2 | 7/2003 | Hoshino et al. |
| 6,660,507 | B2 | 12/2003 | Cheng et al. |
| 6,806,076 | B1 | 10/2004 | Miyake et al. |
| 6,969,595 | B2 | 11/2005 | Brzostowicz et al. |
| 7,034,140 | B2 | 4/2006 | Bramucci et al. |
| 7,056,717 | B2 | 6/2006 | Cheng et al. |
| 7,098,000 | B2 | 8/2006 | Cheng et al. |
| 7,129,392 | B2 | 10/2006 | Hahn et al. |
| 7,132,268 | B2 | 11/2006 | Miyake et al. |
| 7,172,886 | B2 | 2/2007 | Keasling et al. |
| 7,183,089 | B2 | 2/2007 | Keasling et al. |
| 7,186,891 | B1 | 3/2007 | Chappell et al. |
| 7,208,298 | B2 | 4/2007 | Miyake et al. |
| 7,335,815 | B2 | 2/2008 | Boronat et al. |
| 7,364,885 | B2 | 4/2008 | Miyake et al. |
| 7,422,884 | B2 | 9/2008 | Bai et al. |
| 7,514,597 | B2 | 4/2009 | Nakamura et al. |
| 7,569,389 | B2 | 9/2009 | Feldmann et al. |

(Continued)

FOREIGN PATENT DOCUMENTS

| CN | 101314776 | 12/2008 |
| CN | 101720910 | 6/2010 |
| CN | 102216313 | 10/2011 |
| CN | 102559528 | 7/2012 |
| CN | 103397064 | 11/2013 |
| CN | 104845990 | 8/2015 |

(Continued)

OTHER PUBLICATIONS

Jones et al., "UGT73C6 and UGT78D1, Glycosyltransferases Involved in Flavonol Glycoside Biosynthesis in *Arabidopsis thaliana*," J. Biol. Chem., vol. 278, No. 45, pp. 43910-43918 (2003).

(Continued)

*Primary Examiner* — Hope A Robinson
(74) *Attorney, Agent, or Firm* — McDonnell Boehnen Hulbert & Berghoff LLP

(57) ABSTRACT

The invention relates to recombinant microorganisms and methods for producing steviol glycosides and steviol glycoside precursors.

16 Claims, 20 Drawing Sheets

Specification includes a Sequence Listing.

(56) References Cited

U.S. PATENT DOCUMENTS

| | | |
|---|---|---|
| 7,692,065 B2 | 4/2010 | Harper et al. |
| 7,838,287 B2 | 11/2010 | Goldsmith et al. |
| 7,923,541 B2 | 4/2011 | Yang et al. |
| 7,927,851 B2 | 4/2011 | Brandle et al. |
| 9,441,233 B2 | 9/2016 | Apuya et al. |
| 9,562,251 B2 | 2/2017 | Kishore et al. |
| 9,957,539 B2 | 5/2018 | Ono et al. |
| 9,957,540 B2 | 5/2018 | Mikkelsen et al. |
| 10,364,450 B2 | 7/2019 | Olsson et al. |
| 10,815,514 B2 | 10/2020 | Olsson et al. |
| 10,947,515 B2 | 3/2021 | Boer et al. |
| 2002/0142408 A1 | 10/2002 | DiCosimo et al. |
| 2003/0033626 A1 | 2/2003 | Hahn et al. |
| 2003/0148416 A1 | 8/2003 | Berry et al. |
| 2003/0148479 A1 | 8/2003 | Keasling et al. |
| 2003/0190734 A1 | 10/2003 | Hoshino et al. |
| 2003/0219798 A1 | 11/2003 | Gokarn et al. |
| 2004/0010815 A1 | 1/2004 | Lange et al. |
| 2004/0072311 A1 | 4/2004 | DiCosimo et al. |
| 2004/0078846 A1 | 4/2004 | Desouza et al. |
| 2004/0176570 A1 | 9/2004 | Bacher et al. |
| 2004/0194162 A1 | 9/2004 | Hahn et al. |
| 2005/0003474 A1 | 1/2005 | Desouza et al. |
| 2005/0032169 A1 | 2/2005 | Miyake et al. |
| 2006/0014264 A1 | 1/2006 | Sauer et al. |
| 2006/0079476 A1 | 4/2006 | Keasling et al. |
| 2006/0083838 A1 | 4/2006 | Jackson et al. |
| 2007/0004000 A1 | 1/2007 | Miyake et al. |
| 2007/0077616 A1 | 4/2007 | Keasling et al. |
| 2007/0099261 A1 | 5/2007 | Keasling et al. |
| 2007/0118916 A1 | 5/2007 | Puzio et al. |
| 2007/0128311 A1 | 6/2007 | Prakash et al. |
| 2007/0166782 A1 | 7/2007 | Keasling et al. |
| 2007/0202579 A1 | 8/2007 | Berry et al. |
| 2007/0238157 A1 | 10/2007 | Millis et al. |
| 2007/0238159 A1 | 10/2007 | Millis et al. |
| 2007/0238160 A1 | 10/2007 | Millis et al. |
| 2007/0254354 A1 | 11/2007 | Millis et al. |
| 2007/0269857 A1 | 11/2007 | Miyake et al. |
| 2007/0286850 A1 | 12/2007 | Bai et al. |
| 2008/0064063 A1 | 3/2008 | Brandle et al. |
| 2008/0081358 A1 | 4/2008 | Vittanen et al. |
| 2008/0131926 A1 | 6/2008 | Miyake et al. |
| 2008/0216397 A1 | 9/2008 | Busby et al. |
| 2008/0261280 A1 | 10/2008 | Hahn et al. |
| 2008/0271205 A1 | 10/2008 | Yamaguchi et al. |
| 2008/0286870 A1 | 11/2008 | Vittanen et al. |
| 2008/0292775 A1 | 11/2008 | Prakash et al. |
| 2008/0318227 A1 | 12/2008 | Bacher et al. |
| 2009/0004724 A1 | 1/2009 | Keasling et al. |
| 2009/0047718 A1 | 2/2009 | Blaschek et al. |
| 2009/0055974 A1 | 2/2009 | Tanksley et al. |
| 2009/0074935 A1 | 3/2009 | Lee |
| 2009/0143308 A1 | 6/2009 | Monk et al. |
| 2009/0286262 A1 | 11/2009 | Slack |
| 2009/0298706 A1 | 12/2009 | Lee et al. |
| 2010/0112156 A1 | 5/2010 | Abelyan et al. |
| 2010/0120096 A1 | 5/2010 | Kitaoka et al. |
| 2010/0221801 A1 | 9/2010 | Van Dyk |
| 2010/0297722 A1 | 11/2010 | Anterola et al. |
| 2010/0316782 A1 | 12/2010 | Shi et al. |
| 2011/0087011 A1 | 4/2011 | Chiang et al. |
| 2011/0092684 A1 | 4/2011 | Abelyan et al. |
| 2011/0126318 A1 | 5/2011 | Allen et al. |
| 2011/0160311 A1 | 6/2011 | Prakash et al. |
| 2012/0021111 A1 | 1/2012 | Pfister et al. |
| 2012/0083593 A1 | 4/2012 | Liu et al. |
| 2012/0164678 A1 | 6/2012 | Stephanopoulos et al. |
| 2012/0178169 A1 | 7/2012 | Voytas et al. |
| 2013/0137138 A1 | 5/2013 | Hansen |
| 2013/0171328 A1 | 7/2013 | Kishore et al. |
| 2014/0329281 A1 | 11/2014 | Houghton-Larsen et al. |
| 2015/0159188 A1 | 6/2015 | Ono et al. |
| 2015/0342234 A1 | 12/2015 | Hicks et al. |
| 2020/0392552 A1* | 12/2020 | Robertsen ...... C12Y 106/02004 |
| 2021/0147815 A1 | 5/2021 | Boer et al. |

FOREIGN PATENT DOCUMENTS

| | | |
|---|---|---|
| EP | 0955363 | 11/1999 |
| EP | 1072683 | 1/2001 |
| EP | 1171610 | 4/2007 |
| EP | 1198575 | 9/2007 |
| EP | 1383864 | 1/2008 |
| EP | 1897951 | 3/2008 |
| EP | 1947189 | 7/2008 |
| EP | 1392824 | 8/2008 |
| EP | 2575432 | 4/2013 |
| EP | 2902410 | 8/2015 |
| JP | 5910-001408 | 6/1984 |
| JP | 3-277275 | 12/1991 |
| JP | 05-115298 | 5/1993 |
| JP | 2005185101 | 7/2005 |
| JP | 2009034080 | 2/2009 |
| KR | 1020120088035 | 8/2012 |
| KR | 2015 0000258 | 1/2015 |
| WO | WO 1999/018224 | 4/1999 |
| WO | WO 2000/036081 | 6/2000 |
| WO | WO 2000/037663 | 6/2000 |
| WO | WO 2000/063400 | 10/2000 |
| WO | WO 2001/012828 | 2/2001 |
| WO | WO 2001/083769 | 11/2001 |
| WO | WO 2001/094561 | 12/2001 |
| WO | 2002/024865 | 3/2002 |
| WO | WO 2002/020728 | 3/2002 |
| WO | WO 2002/020815 | 3/2002 |
| WO | WO 2002/055709 | 7/2002 |
| WO | WO 2003/008540 | 1/2003 |
| WO | WO 2004/029255 | 4/2004 |
| WO | WO 2005/079183 | 9/2005 |
| WO | WO 2006/016395 | 2/2006 |
| WO | WO 2006/093289 | 9/2006 |
| WO | WO 2006/096392 | 9/2006 |
| WO | WO 2007/136847 | 11/2007 |
| WO | WO 2008/008256 | 1/2008 |
| WO | WO 2008/034648 | 3/2008 |
| WO | WO 2008/039499 | 4/2008 |
| WO | WO 2008/051349 | 5/2008 |
| WO | WO 2008/091547 | 7/2008 |
| WO | WO 2009/005704 | 1/2009 |
| WO | WO 2009/071277 | 6/2009 |
| WO | WO 2009/086049 | 7/2009 |
| WO | WO 2009/105612 | 8/2009 |
| WO | WO 2009/108680 | 9/2009 |
| WO | 2009/140394 | 11/2009 |
| WO | WO 2009/140394 | 11/2009 |
| WO | WO 2010/021001 | 2/2010 |
| WO | WO 2010/038911 | 4/2010 |
| WO | 2010/142305 | 12/2010 |
| WO | WO 2010/146463 | 12/2010 |
| WO | WO 2011/028671 | 3/2011 |
| WO | WO 2011/037959 | 3/2011 |
| WO | WO 2011/046423 | 4/2011 |
| WO | WO 2011/056834 | 5/2011 |
| WO | WO 2011/153378 | 8/2011 |
| WO | 2011/140329 | 11/2011 |
| WO | 2011/151326 | 12/2011 |
| WO | 2011/153378 | 12/2011 |
| WO | WO 2011/151326 | 12/2011 |
| WO | WO 2011/153144 | 12/2011 |
| WO | WO 2012/075030 | 6/2012 |
| WO | 2013/022989 | 2/2013 |
| WO | WO 2013/019050 | 2/2013 |
| WO | WO 2013/022989 | 2/2013 |
| WO | WO 2013/076577 | 5/2013 |
| WO | WO 2013/096420 | 6/2013 |
| WO | WO 2013/102793 | 7/2013 |
| WO | WO 2013/110673 | 8/2013 |
| WO | WO 2013/176738 | 11/2013 |
| WO | WO 2014/086890 | 6/2014 |
| WO | WO 2014/122227 | 8/2014 |
| WO | WO 2014/122328 | 8/2014 |

(56) References Cited

FOREIGN PATENT DOCUMENTS

| WO | 2014/191580 | 12/2014 |
|---|---|---|
| WO | 2014/191581 | 12/2014 |
| WO | 2015/011209 | 1/2015 |
| WO | WO 2015007748 | 1/2015 |
| WO | 2015/014959 | 2/2015 |
| WO | 2015/016393 | 2/2015 |
| WO | WO 2015/014969 | 2/2015 |
| WO | WO 2015/028324 | 3/2015 |
| WO | WO 2015051454 | 4/2015 |
| WO | WO 2015/132411 | 9/2015 |
| WO | WO 2016/023844 | 2/2016 |
| WO | WO 2016/038095 | 3/2016 |
| WO | WO 2016/120486 | 8/2016 |
| WO | WO 2017/025362 | 2/2017 |
| WO | WO 2018/083338 | 5/2018 |

OTHER PUBLICATIONS

Popenberger et al., Heterologous Expression of *Arabidopsis* UDP-Glucosyltransferases in *Saccharomyces cerevisiae* for Production ofZearalenone-4-0-Glucoside, Appl. Environ. Microbial., vol. 72, pp. 4404-4410 (2006).
Wang et al., "Glycosylation and Glycosyltransferase of Small Molecular Compounds of Plant," China Academic Journal, vol. 44-5, 997-1003 (2008).
International Search Report issued by the International Searching Authority for International Application No. PCT/US2011/038967, dated Sep. 1, 2011 (10 pages).
Written Opinion of the International Searching Authority for International Application No. PCT/US2011/038967, dated Sep. 1, 2011 (12 pages).
International Preliminary Report on Patentability issued by the International Bureau for International Application No. PCT/US2011/038967, dated Dec. 4, 2012 (13 pages).
Extended European Search Report and Opinion issued by the European Patent Office for European Application No. 11790428.4, dated Dec. 20, 2013.
International Search Report issued by the International Searching Authority for International Application No. PCT/US2012/050021, dated Apr. 12, 2013.
Written Opinion of the International Searching Authority for International Application No. PCT/US2012/050021, dated Apr. 12, 2013.
Shao et al., "Crystal structures of a multifunctional triterpene/flavonoid glycosyltransferase from Medicago truncatula," Plant Cell 17(11):3141-54 (2005).
Shibata et al., "Glucosylation of Steviol and Steviol-Glucosides in Extracts from Stevia rebaudiana Bertoni" Plant Physiol. 95(1):152-56 (1991).
Singh et al., "Compendium of Transgenic Crop Plants: Transgenic Sugar, Tuber and Fiber," Ed. Kole & Hall, Blackwell Publishing Ltd. pp. 97-115 (2008).
U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).
U.S Food and Drug Administration GRAS Notice Notice 329, "Notice to the U.S. Food and Drug Administration that the use of RebpureTM (Rebaudioside A) derived from Stevia rebaudiana, as a Food Ingredient is Generally Recognized as Safe (GRAS)," pp. 1-275 (Mar. 2010).
Van Ooyen et al., "Heterologous protein production in the yeast *Kluyveromyces lactis*," FEMS Yeast Res. 6(3):381-92 (May 2006).
Vazquez De Aldana et al., "Nucleotide sequence of the exo-1,3-beta-glucanase-encoding gene, EXG1, of the yeast *Saccharomyces cerevisiae*," Gene 97(2):173-82 (1991).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73(13):4342-50 (2007).

Wallin, "Steviol Glycosides," Chem. Tech Assessment—63rd JECFA, pp. 1-5 (2004).
Wallin, "Steviol Glycosides," Chem. Tech Assessment—69th JECFA, pp. 1-7 (2007).
Wallner & Elofsson, "Can correct protein models be identified?," Protein Sci. 12(5):1073-86 (May 2003).
Wang, "Structure, mechanism and engineering of plant natural product glycosyltransferases," FEBS Letters 583(20):3303-9 (2009).
Yadav et al., "A review on the improvement of stevia [*Stevia rebaudiana* (Bertoni)]," Can J Plant Sci. 91:1-27 (2011).
Yao et al., "A genetic linkage map for Stevia rebaudiana," Genome 42:657-61 (1999).
Yang et al., Base substitution mutations in uridinediphosphate-dependent glycosyltransferase 76G1 gene of Stevia rebaudiana causes the low levels of rebaudioside A: mutations in UGT76G1, a key gene of steviol glycosides synthesis, Plant Physiol Biochem. 80:220-5 (2014).
Yazaki, "ABC transporters involved in the transport of plant secondary metabolites," FEBS Lett. 580(4):1183-91 (Feb. 2006).
Yu et al., "Bioconversion of ethyl 4-chloro-3-oxobutanoate by permeabilized fresh brewer's yeast cells in the presence of allyl bromide," J Ind Microbiol Biotechnol. 34(2)151-6 (2007).
Yuan et al., "Kinetics and activation parameters for oxidations of styrene by Compounds I from the cytochrome P450 (BM-3) (CYP102A1) heme domain and from CYP119," Biochemistry 48(38):9140-6 (Sep. 2009).
Zheng et al. "An efficient one-step site-directed and site-saturation mutagenesis protocol," Nucleic Acids Res. 32(14):e115 (Aug. 2004).
Zhu et al., "A multi-omic map of the lipid-producing yeast *Rhodosporidium toruloides*," Nature Commun. 3:1112 (Oct. 2012).
GenBank Accession No. AAF61439.1, dated Sep. 25, 2000 (2 pages).
GenBank Accession No. AAM53963.1, dated Jun. 17, 2002 (2 pages).
GenBank Accession No. AAR06918.1, dated Dec. 28, 2004 (2 pages).
GenBank Accession No. AAT93110.1, dated Apr. 24, 2007 (2 pages).
GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).
GenBank Accession No. AY345982.1, dated Dec. 28, 2004 (2 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. DQ269454.4, dated May 28, 2008 (2 pages).
GenBank Accession No. EU722415.1, dated Jun. 10, 2008 (2 pages).
GenBank Accession No. EU751291.1, dated Jun. 24, 2008 (2 pages).
EBI Accession No. AAY05902, "Jerusalem artichoke in-chain hydroxylase CYP81B1" (1 page), Jun. 15, 2009.
EBI Accession No. ABM86477, "Rice abiotic stress responsive polypeptide SEQ ID No. 4723" (1 page), dated Jun. 2, 2005.
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
Jewett et al. "An integrated cell-free metabolic platform for protein production and synthetic biology," Mol Syst Biol. 4:220 (2008).

(56) References Cited

OTHER PUBLICATIONS

Johnstone et al., "Cloning an Aspergillus nidulans developmental gene by transformation," EMBO J. 4(5):1307-11 (1985).
Khoury et al., "Computational design of Candida boidinii xylose reductase for altered cofactor specificity," Protein Sci. 18(10):2125-38 (Oct. 2009).
Kim et al., "Hydroxylation of ent-Kaurenoic Acid to Steviol in Stevia rebaudiana Bertoni-Purification and Partial Characterization of the Enzyme," Arch Biochem Biophys. 332(2):223-30 (1996).
Kim & Shibata, "Characterization of ent-kaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10),806-11 (2000).
Kumar et al., "A comprehensive analysis of fifteen genes of steviol glycosides biosynthesis pathwayin Stevia rebaudiana (Bertoni)" Gene 492:276-84 (Epub Oct. 20, 2011).
Kusama et al., "Transglucosylation into stevioside by the enzyme system from *Streptomyces* sp.," Agric. Biol. Chem. 50(10):2445-51 (Oct. 1986).
Li et al., "Crystal structure of Medicago truncatula UGT85H2--insights into the structural basis of a multifunctional (iso) flavonoid glycosyltransferase," J Mol Biol. 370(5):951-63 (2007).
Li et al., "Systematic Mutational Analysis of Peptide Inhibition of the p53-MDM2/MDMX," J Mol Biol. 398(2):200-13 (2010).
Li et al., "High-density cultivation of oleaginous yeast *Rhodosporidium toruloides* Y4 in fed-batch culture," Enzyme and Microbial Technology 41(3):312-7 (Aug. 2007).
Liu et al., "Preparation of high-activity whole cell biocatalysts by permeabilization of recombinant yeasts with alcohol," J Biosci Bioeng. 89(6):554-8 (2000).
Ma et al., "Molecular cloning and characterization of Stevia Rebaudiana UDP-glucosyltransferase," Acta Biologiae Expertmentalis Sinica 36(2):123-9 (2003).
Ma "Part 1. Molecular Cloning and Functional Analysis of UDPG Glucosyltransferase Gene. Part 2. Molecular Cloning, Sequence Analysis and Evolution of Actin and EF1a Genes in Stevia Rebaudiana." Chinese Doctor and Master Dissertations Full-Text Database, Agricultural Technology Part, vol. 2; pp. 1-74 (2004).
Madan et al., "Stevia rebaudiana (Bert.) Bertoni—A Review," Indian Journal of Natural Products and Resources 1(3):267-86 (2010).
Madhav et al., "Functional and structural variation of uridine diphosphate glycosyltransferase (UGT) gene of Stevia rebaudiana-UGTSr involved in the synthesis of rebaudioside A," Plant Physiol. Biochem. 63:245-53 (Feb. 2013).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed bed column with zeolites," Braz J Chem Eng. 21(3):449-58 (2004).
Mattanovich et al., "Recombinant protein production in yeasts," Methods Mol Biol. 824:329-58 (2012).
Megeji et al., "Introducing Stevia rebaudiana, a natural zero-calorie sweetener," Current Science 88(5):801-4 (2005).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Mumberg et al., "Yeast vectors for the controlled expression of heterologous proteins in different genetic backgrounds," Gene 156(1):119-22 (1995).

Naesby et al., "Yeast artificial chromosomes employed for random assembly of biosynthetic pathways and production of diverse compounds in *Saccharomyces cerevisiae*," Microb Cell Fact. 8:45 (2009).
Naglak & Wang, "Rapid protein release from *Escherichia coli* by chemical permeabilization under fermentation conditions," Biotechnol Bioeng. 39(7):732-40 (1991).
Nakagiri et al., "cDNA cloning, functional expression and characterization of ent-copalyl diphosphate synthase from Scoparia dulcis L.," Plant Sci. 169:760-7 (2005).
Nelson et al., "P450 superfamily: update on new sequences, gene mapping, accession numbers and nomenclature," Pharmacogenetics 6:1-42 (1996).
Newman et al., "High-level production of amorpha-4,11-diene in a two-phase partitioning bioreactor of metabolically engineered *Escherichia coli*," Biotechnol Bioeng 95(4):684-91 (2006).
Nicaud, "Yarrowia lipolytica," Yeast29(10):409-18 (Oct. 2012).
Nielsen et al., "Efficient PCR-based gene targeting with a recyclable marker for Aspergillus nidulans," Fungal Genet Biol. 43(1):54-64 (2006).
Nour-Eldin et al., "USER cloning and USER fusion: the ideal cloning techniques for small and big laboratories," Methods Mol Biol. 643:185-200 (2010).
Ohta et al., "Characterization of Novel Steviol Glycosides from Leaves of Stevia rebaudiana Morita," J. Applied Glycosides 57(3):199-209 (Mar. 2010).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka & Jigami, "Reconstruction of de novo pathway for synthesis of UDP-glucuronic acid and UDP-xylose from intrinsic UDP-glucose in *Saccharomyces cerevisiae*," FEBS J. 273(12):2645-57 (2006).
Orihara et al., "Biotransformation of steviol by cultured cells of eucalyptus perriniana and Coffea Arabica," Phytochemistry 30(12):3989-92 (1991).
Paradise et al., "Redirection of flux through the FPP branch-point in *Saccharomyces cerevisiae* by down-regulating squalene synthase," Biotechnol Bioeng 100(2):371-8 (2008).
Pearson & Lipman, "Improved tools for biological sequence comparison," Proc Natl Acad Sci. 85(8):2444-8 (1998).
Pompon et al., "Yeast Expression of Animal and Plant P450s in Optimized RedoxEnvironments," Methods Enzymol 272:51-64 (1996).
Prelich, "Gene overexpression: uses, mechanisms, and interpretation," Genetics 190(3):841-54 (Mar. 2012).
Presecki & Vasic-Racki, "Production of L-malic acid by permeabilized cells of commercial *Saccharomyces* sp. strains," Biotechnol Lett. 27(23-24):1835-9 (2005).
Ro et al., "Production of the antimalarial drug precursor artemisinic acid in engineered yeast," Nature 440(7086):940-3 (2006).
Saenge et al., "Potential use of oleaginous red yeast *Rhodotorula glutinis* for the bioconversion of crude glycerol from biodiesel plant to lipids and carotenoids," Process Biochemistry 46(1):210-8 (Jan. 2011).
Schwab et al., Poster, "Watchmaker®—Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol.143(3):212-23 (2007).
English Translation of First Office Action issued by the State Intellectual Property Office of People's Republic of China for CN Application No. 201180038475.4, dated Nov. 21, 2013.
First Examination Report issued by the Intellectual Property Office of New Zealand for New Zealand Application No. 604915, dated Sep. 2, 2013.
Abraham & Bhat, "Permeabilization of baker's yeast with N-lauroyl sarcosine," J Ind Microbial Biotechnol. 35(8):799-804 (2008).
Ageitos et al., "Oily yeasts as oleaginous cell factories," Appl Microbiol Biotechnol. 90(4):1219-27 (May 2011).
Agrawal, "NMR spectroscopy in the structural elucidation of oligosaccharides and glycosides," Phytochemistry 31(10):3307-30 (1992).

(56) References Cited

OTHER PUBLICATIONS

Ajikumar et al., "Terpenoids: opportunities for biosynthsis of natural product drugs using engineered microorganisms," Molecular Pharmaceuticals 5(2):167-90 (2008).
Alakomi et al., "Lactic acid permeabilizes gram-negative bacteria by disrupting the outer membrane," Appl Environ Microbiol. 66(5):2001-5 (2000).
Ali et al., "Biochemical investigation during different stages of in vitro propagation of Stevia rebaudiana," Pak J Bot. 42(4):2827-37 (2010).
Bankar et al., "Environmental and industrial applications of Yarrowia lipolytica," Appl Microbiol Biotechnol. 84(5):847-65 (Oct. 2009).
Baykov et al., "A malachite green procedure for orthophosphate determination and its use in alkaline phosphatase-based enzyme immunoassay," Anal Biochem. 171(2):266-70 (Jun. 1988).
Beopoulos et al., "Yarrowia lipolytica: A model and a tool to understand the mechanisms implicated in lipid accumulation," Biochimie 91(6):692-6 (Jun. 2009).
Brandle et al., "Leaf ESTs from Stevia rebaudiana: A Resource for Gene Discovery in Diterpene Synthesis," Plant Mol Biol. 50(4-5):613-22 (2002).
Brandle & Telmer, "Steviol glycoside biosynthesis," Phytochemistry 68(14):1855-63 (2007).
Brochado et al. "Improved vanillin production in baker's yeast through in silico design," Microb Cell Fact. 9:84-98 (2010).
Carretero-Paulet et al., "Expression and Molecular Analysis of the *Arabidopsis* DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).
Ceunen & Geuns, "Steviol glycosides: chemical diversity, metabolism, and function," J. Nat. Prod. 76(6):1201-28 (Jun. 2013).
Chemler et al., "Biosynthesis of isoprenoids, polyunsaturated fatty acids and flavonoids in *Saccharomyces cerevisiae*," Microb Cell Fact. 5:20 (2006).
Chen et al., "MolProbity: all-atom structure validation for macromolecular crystallography," Acta Crystallogr D Biol Crystallogr (Pt 1):12-21 (Jan. 2010).
Chica et al., "Semi-rational approaches to engineering enzyme activity: combining the benefits of directed evolution and rational design," Curr Opin Biotechnol.16(4):378-84 (2005).
Chow & Palecek, "Enzyme encapsulation in permeabilized *Saccharomyces cerevisiae* cells," Biotechnol Prog. 20(2):449-56 (2004).
Correa et al., "Genetic mapping of 1,3-beta-glucanase-encoding genes in *Saccharomyces cerevisiae*," Current Genet. 22(4):283-8 (1992).
Darise et al., "Enzymic Transglucosylation of Rubusoside and the Structure-Sweetness Relationship of Steviol-Bisglycosides," Agric. Biol. Chem. 48(10):2483-8 (Jan. 1984).
Davis et al., "MolProbity: all-atom contacts and structure validation for proteins and nucleic acids," Nucleic Acids Res. 35:W375-83 (Apr. 2007).
Del Sorbo et al., "Fungal transporters involved in efflux of natural toxic compounds and fungicides," Fungal. Genet. Biol. 30(1):1-15 (Jun. 2000).
Diener et al., "*Arabidopsis* ALF5, a multidrug efflux transporter gene family member, confers resistance to toxins," Plant Cell 13(7):1625-38 (Jul. 2001).
Dodhia et al., "Engineering human cytochrome P450 enzymes into catalytically self-sufficient chimeras using molecular Lego," J Biol Inorg Chem. 11(7):903-16 (Oct. 2006).
Dubey, et al., An overview of the non-mevalonate pathway for terpenoid biosynthesis in plants, J. Biosci. 28(5):637-46 (2003).
Dubois & Stephenson, "Diterpenoid sweeteners. Synthesis and sensory evaluation of stevioside analogues with improved organoleptic properties," J. Med. Chem. 28(1):93-8 (Jan. 1985).

EFSA Panel on Food Additives and Nutrient Sources added to Food (ANS), "Scientific Opinion on the safety of steviol glycosides for the proposed uses as a food additive," EFSA Journal 8(4):1537 (2010).
Eisenreich et al., "Biosynthesis of isoprenoids via the non-mevalonate pathway," Cell Mol Life Sci. 61(12):1401-6 (2004).
Emboss Needle results for Pairwise Sequence Alignment of UGT91D1 and UGT91D2; dated Apr. 4, 2016, 2 pages.
Estrada De Martin et al., "Ice2p is important for the distribution and structure of the cortical ER network in *Saccharomyces cerevisiae*," J Cell Sci. 118(Pt 1):65-77 (Oct. 2006).
Fernandez et al., "Activation of chitin synthetase in permeabilized cells of a *Saccharomyces cerevisiae* mutant lacking proteinase B," J Bacteriol. 152(3):1255-64 (1982).
Flores et al., "Permeabilization of yeast cells (*Kluyveromyces lactis*) with organic solvents," Enzyme Microb Technol. 16(4):340-6 (1994).
Fowler & Zabin, "Effects of Dimethylsulfoxide on the Lactose Operon in *Escherichia coli*," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Geuns, "Stevioside," Phytochemistry 64(5):913-21 (2003).
Gietz & Schiestl, "High-efficiency yeast transformation using the LiAc/SS carrier DNA/PEG method," Nat Protoc. 2(1):31-4 (2007).
Girvan et al., "Flavocytochrome P450 BM3 mutant W1046A is a NADH-dependent fatty acid hydroxylase: implications for the mechanism of electron transfer in the P450 BM3 dimer," Arch Biochem Biophys. 507(1):75-85 (Mar. 2011).
Goralczyk, "Compounds from Stevia for Improving and Maintaining Mental Performance," Stevia World Forum, Feb. 24-25, 2010, 17 pages.
Guleria & Yadav, "Insights into Steviol Glycoside Biosynthesis Pathway Enzymes Through Structural Homology Modeling," Am. J. Biochem. Molec. Biol. 3(1):1-19 (2013).
Gunel et al., "Metabolic Engineering for Production of Geranylgeranyl Pyrophosphate Synthase in Non-Carotenogenic Yeast *Schizosaccharomyces pombe*," Biotechnol. & Biotechnol. Eq. 20(3):76-82 (2006).
Hansen et al., "De novo biosynthesis of vanillin in fission yeast (*Schizosaccharomyces pombe*) and baker's yeast (*Saccharomyces cerevisiae*)," Appl Environ Microbiol 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).
Hellfritsch et al., "Human psychometric and taste receptor responses to steviol glycosides," J. Agric. Food Chem. 60(27):6782-93 (Jul. 2012).
Humphrey et al., "Spatial organisation of four enzymes from Stevia rebaudiana that are involved in steviol glycoside synthesis," Plant Mol Bio. 61(1-2):47-62 (2006).
Iandolino et al., "High-Quality RNA, cDNA, and Derived EST Libraries From Grapevine (*Vitis vinifera* L.)," Plant Mol Biol Reporter 22:269-78 (2004).
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosynthesis: baxane 13 alpha-hydroxylase is a cytochrome P450-dependent monooxygenase," Proc Natl Acad Sci U S A 98(24):13595-600 (2001).
Mahe et al., "The ATP Binding Cassette Transporters Pdr5 and Snq2 of *Saccharomyces cerevisiae* Can Mediate Transport of Steriods via in Vivo", JBC, 271 (41):25167-25172. (Oct. 1996).
Starratt et al., "Rebaudioside F, a diterpene glycoside from Stevia redaudiana", Phytochemistry, 59(4):367-370. (Feb. 2002). Abstract.
Uniprot Accession No. Q75183, dated Jul. 5, 2004 (pp. 1-2).
Uniprot Accession No. Q75183, dated Jul. 22, 2008 (pp. 1-4).
Broun et al., "Catalytic plasticity of fatty acid modification enzymes underlying chemical diversity of plant lipids," Science, vol. 282: 1315-1317 (1998).

(56) References Cited

OTHER PUBLICATIONS

Cheng, "Food Biotechnology," Inner Mongolia Science and Technology Press (2008). (Book).
Devos et al., "Practical limits of function prediction," Proteins: Structure, Function, and Genetics, vol. 41: 98-107 (2000).
Seffernick et al., "Melamine deaminase and Atrazine chlorohydrolase: 98 percent identical but functionally different," J. Bacterial., vol. 183 (8): 2405-2410 (2001).
Whisstock et al., "Prediction of protein function from protein sequence," Q. Rev. Biophysics., vol. 36 (3): 307-340 (2003).
Witkowski et al., "Conversion of b-ketoacyl synthase to a Malonyl Decarboxylase by replacement of the active cysteine with glutamine," Biochemistry, vol. 38: 11643-11650 (1999).
Pearson, et al., "Improved tools for biological sequence comparison," Proc Natl Acad Sci. 85(8):2444-8 (1988).
First Examination Report issued by the Intellectual Property Office of New Zealand for New Zealand Application No. 700097, dated Oct. 6, 2014 (pp. 1-2).
Notice of Acceptance issued by the Intellectual Property Office of New Zealand for New Zealand Application No. 700097, dated Oct. 7, 2015 (1 page).
First Examination Report issued by the Intellectual Property Office of New Zealand for New Zealand Application No. 708078, dated May 28, 2015 (pp. 1-3).
Search Report issued by the Intellectual Property Office of Singapore for Singaporean Application No. 201208854-8, dated Nov. 3, 2014.
Written Opinion issued by the Intellectual Property Office of Singapore for Singaporean Application No. 201208854-8, dated Nov. 3, 2014.
Non-Final Office Action for U.S. Appl. No. 14/237,540, dated Dec. 30, 2015 (pp. 1-19).
Final Office Action issued in U.S. Appl. No. 14/237,540; dated Jul. 8, 2016, pp. 1-19.
International Preliminary Report on Patentability issued by the International Bureau for International Application No. PCT/US2012/050021, dated Feb. 11, 2014.
English Translation of First Office Action and Search Report issued by the State Intellectual Property Office of People's Republic of China for Chinese Application No. 201280038853.3, dated Feb. 16, 2015.
English Translation of Second Office Action and Search Report issued by the State Intellectual Property Office of People's Republic of China for Chinese Application No. 201280038853.3, dated Jan. 11, 2016.
Communication pursuant to Rules 161(1) and 162 (EPC) issued by the European Patent Office for European Application No. 12750513.9, dated Mar. 14, 2014.
Response to Communication pursuant to Rules 161(1) and 162 (EPC) issued by the European Patent Office for European Application No. 12750513.9, dated Aug. 4, 2014.
Examination Report issued by the European Patent Office for European Application No. 12750513.9, dated Nov. 26, 2014.
Response to Examination Report issued by the European Patent Office for European Application No. 12750513.9, dated Mar. 25, 2015.
Extended European Search Report issued in EP 15193074.0; dated Feb. 12, 2016, pp. 1-9.
Statement of Facts and Arguments In Support Of Opposition for EP Application No. 12750513.9; mailed Feb. 28, 2017 pp. 1-24.
Communication of Notice of Opposition against EP Application No. 12750513.9; mailed Mar. 6, 2017 pp. 1-8.
Sequence alignment between the sequence of Uniprot database entry Q75183 version 31, updated Jul. 22, 2008 and SEQ ID No. 152 (from European Patent No. 2742142) as cited in Notice of Opposition against EP Application No. 12750513.9; mailed Mar. 6, 2017; pp. 1-2.
International Search Report from the International Searching Authority for International Application No. PCT/EP2014/052363, dated Sep. 22, 2014 (12 pages).
Written Opinion of the International Searching Authority for International Application No. PCT/EP2014/052363, dated Sep. 22, 2014 (10 pages).
International Preliminary Report on Patentability issued by the International Bureau for International Application No. PCT/EP2014/052363, dated Aug. 11, 2015. (11 pages).
Non-Final Office Action for U.S. Appl. No. 14/761,629, dated Mar. 21, 2017 (pp. 1-19).
International Search Report by the International Searching Authority for International Application No. PCT/EP2014/052675, dated Apr. 23, 2014 (5 pages).
Written Opinion of the International Searching Authority for International Application No. PCT/EP2014/052675, dated Apr. 23, 2014 (7 pages).
International Preliminary Report on Patentability issued by the International Bureau for International Application No. PCT/EP2014/052675, dated Aug. 11, 2015 (8 pages).
Communication pursuant to Rules 161(1) and 162 EPC for European Application No. 14704558.7, dated Sep. 18, 2015 (2 pages).
International Search Report of the International Searching Authority for International Application No. PCT/EP2013/075587, dated Feb. 20, 2014 (pp. 1-5).
Written Opinion of the International Searching Authority for International Application No. PCT/EP2013/075587, dated Feb. 20, 2014 (pp. 1-9).
International Preliminary Report on Patentability from the International Bureau for International Application No. PCT/EP2013/075587, dated Jun. 9, 2015 (pp. 1-10).
Final Office Action for U.S. Appl. No. 14/648,747, dated Sep. 6, 2017 (pp. 1-19).
Third Party Observation in EP Application No. 13801569.8; mailed Oct. 23, 2017, pp. 1-6.
Third Party Submission in U.S. Appl. No. 14/648,747; dated Mar. 28, 2016, pp. 1-231.
Non-Final Office Action for U.S. Appl. No. 14/648,747, dated Mar. 23, 2017, pp. 1-20.
Third Party Observation in EP Application No. 13801569.8; mailed Apr. 26, 2017. pp. 1-5.
Invitation to Pay Additional Fees and, Where Applicable, Protest Fee by the International Searching Authority for International Application No. PCT/EP2015/070620, dated Nov. 27, 2015 (pp. 1-14).
International Search Report by the International Searching Authority for International Application No. PCT/EP2015/070620; dated Mar. 29, 2016, pp. 1-10.
Written Opinion of the International Searching Authority for International Application No. PCT/EP2015/070620; dated Mar. 29, 2016, pp. 1-24.
International Search Report and Written Opinion of the International Searching Authority for International Application No. PCT/EP2015/068314, dated Jan. 20, 2016 (pp. 1-7).
Written Opinion of the International Searching Authority for International Application No. PCT/EP2015/068314, dated Jan. 20, 2016 (pp. 1-9).
International Preliminary Report on Patentability from the International Bureau for International Application PCTEP2015/068314; dated Feb. 14, 2017 (pp. 1-10).
International Search Report and Written Opinion of the International Searching Authority for International Application No. PCT/EP2015/052007; dated Jul. 4, 2016, pp. 1-24.
International Search Report and Written Opinion of the International Searching Authority for International Application No. PCT/EP2016/068259; dated Jan. 24, 2017, pp. 1-18.
International Search Report and Written Opinion of International Search Authority for International Application No. PCTEP2016/080516; dated Mar. 15, 2017, pp. 1-22.
International Search Report and Written Opinion of International Search Authority for International Application No. PCTEP2017/059028; dated Jun. 27, 2017, pp. 1-15.
Saier, "Families of transmembrane sugar transport proteins," Mol Microbiol., 35(4):699-710 (2000).
Final Office Action for U.S. Appl. No. 14/761,629, dated Aug. 11, 2017 (pp. 1-16).

(56) References Cited

OTHER PUBLICATIONS

English Translation of First Office Action issued by the State Intellectual Property Office of People's Republic of China for CN Application No. 201180038475.4, dated Nov. 21, 2013 (2 pages).
Liu et al., "Functional and Biochemical Characteritzation of *Escherichia coli* Sugar Efflux Transporters," JBC, 274 (33):22977-22984 (Aug. 1999).
Sun et al., "Regulation and Function of *Escherichia coli* Sugar Efflux Transporter A (Set A) during Glucose-Phosphate Stress," J of Bacteriology, 193(1):143-153 (Jan. 2011).
GenBank Accession No. AAS07253.1, dated Jan. 31, 2004 (3 pages).
Guo et al., "Protein tolerance to random amino acid change", Proceedings of the National Academy of Sciences USA, vol. 101, No. 25, pp. 9205-9210 (2004).
Ni et al., "Outer membrane mutation effects on UDP-glucose permeability and whole-cell catalysis rate," Appl Microbiol Biotechnol. 73(2):384-93 (2006).
Prisic et al., "Synergistic substrate inhibition of ent-copalyl diphosphate synthase: a potential feed-forward inhibition mechanism limiting gibberellin metabolism," Plant Physiol. 144(1):445-54 (2007).
Unligil et al., "Glycosyltransferase structure and mechanism," Curr Opin Struct Biol. 10(5):510-7 (2000).
Wanchao et al., "Advances on the Stevoil Glycoside Biosynthesis and Its Key Enzymes," Biotechnology Bulletin, Feb. 2008 (English Abstract translation).
Bateman et al., "Pfam 3.1: 1313 multiple alignments and profile HMMs match the majority of proteins," Nucleic Acids Res. 27(1):260-2 (Jan. 1999).
Bay & Turner, "Diversity and evolution of the small multidrug resistance protein family," BMC Evol. Biol. 9:140 (Jun. 2009).
Brachmann et al., "Designer deletion strains derived from *Saccharomyces cerevisiae* S288C: a useful set of strains and plasmids for PCR-mediated gene disruption and other applications," Yeast 14:115-32 (1998).
Chen et al., "Transferring a biosynthetic cycle into a productive *Escherichia coli* strain: large-scale synthesis of galactosides," J. Am. Chem. Soc. 123(36):8866-7 (Sep. 2001).
Chenna et al., "Multiple sequence alignment with the Clustal series of programs," Nucleic Acids Res. 31(13):3497-500 (Jul. 2003).
GenBank Accession No. AAB62280, dated Jul. 2, 1997 (2 pages).
GenBank Accession No. AAB87091, dated Mar. 22, 2000 (2 pages).
GenBank Accession No. AAC28895.1, dated Aug. 6, 1998 (2 pages).
GenBank Accession No. AAC39505, dated Jul. 26, 1998 (1 page).
GenBank Accession No. AAD34294, dated Mar. 22, 2000 (2 pages).
GenBank Accession No. AAD34295, dated Mar. 22, 2000 (2 pages).
GenBank Accession No. AAD47596, dated Aug. 9, 1999 (2 pages).
GenBank Accession No. AAH69913, dated Jul. 15, 2006 (2 pages).
GenBank Accession No. NP_197872.1, dated Jan. 22, 2014 (2 pages).
GenBank Accession No. AAR06912, dated Dec. 28, 2004 (2 pages).
GenBank Accession No. AAR06916.1, dated Dec. 28, 2004 (2 pages).
GenBank Accession No. AAR06920.1, dated Dec. 28, 2004 (2 pages).
GenBank Accession No. ABA42921, dated Jun. 21, 2006 (1 page).
GenBank Accession No. ABB88839, dated May 28, 2008 (2 pages).
GenBank Accession No. ABC59076, dated Jun. 6, 2007 (1 page).
GenBank Accession No. ABC98596, dated Jan. 31, 2014 (2 pages).
GenBank Accession No. ABD60225, dated May 28, 2008 (2 pages).
GenBank Accession No. ABD92926, dated Oct. 10, 2007 (2 pages).
GenBank Accession No. AC133334, dated Jan. 31, 2004 (44 pages).
GenBank Accession No. ACD93722, dated Jun. 10, 2008 (1 page).
GenBank Accession No. AF034774, dated Apr. 17, 1998 (2 pages).
GenBank Accession No. AY562490, dated May 23, 2006 (3 pages).
GenBank Accession No. BAA43200, dated Mar. 13, 1999 (2 pages).
GenBank Accession No. BAB59027, dated Jan. 30, 2002 (1 page).
GenBank Accession No. BAF61135, dated May 9, 2007 (2 pages).
GenBank Accession No. BAG30962, dated Nov. 12, 2012 (2 pages).
GenBank Accession No. BC153262, dated Oct. 4, 2007 (3 pages).
GenBank Accession No. CAA75568, dated Nov. 14, 2006 (2 pages).
GenBank Accession No. CAA76703, dated Nov. 14, 2006 (1 page).
GenBank Accession No. CAE09055, dated Nov. 14, 2006 (2 pages).
GenBank Accession No. DQ398871.3, dated May 28, 2008 (2 pages).
GenBank Accession No. EDY51667, dated Sep. 2, 2008 (2 pages).
GenBank Accession No. EU263989, dated Jun. 11, 2008 (2 pages).
GenBank Accession No. NM_116512, dated Jan. 22, 2014 (3 pages).
GenBank Accession No. NP_194183, dated Jan. 22, 2014 (4 pages).
GenBank Accession No. NP_195399, dated Jan. 22, 2014 (3 pages).
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
Gossen & Bujard, "Studying gene function in eukaryotes by conditional gene inactivation," Annu. Rev. Genet. 36:153-73 (Jun. 2002).
Gritz & Davies, "Plasmid-encoded hygromycin B resistance: the sequence of hygromycin B phosphotransferase gene and its expression in *Escherichia coli* and *Saccharomyces cerevisiae*," Gene 25(2-3):179-88 (Nov. 1983).
Hallstrom & Moye-Rowley, "Divergent transcriptional control of multidrug resistance genes in *Saccharomyces cerevisiae*," J. Biol. Chem. 273(4):2098-104 (Jan. 1998).
Katzmann et al., "Expression of an ATP-binding cassette transporter-encoding gene (YOR1) is required for bligomycin resistance in *Saccharomyces cerevisiae*," Mol. Cell Biol. 15(12):6875-83 (Dec. 1995).
Li et al., "Phylogenetic analysis of the UDP-glycosyltransferase multigene family of *Arabidopsis thaliana*," J. Biol. Chem. 276(6):4338-43 (Oct. 2000).
Masada et al., "An efficient chemoenzymatic production of small molecule glucosides with in situ UDP-glucose recycling," FEBS Lett. 581(13):2562-6 (May 2007).
Morita et al., "Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2"-O-glucosyltransferase, due to 4-bp insertions in the gene," Plant J. 42(3):353-63 (May 2005).
Nagy et al., "Role of the yeast ABC transporter Yor1p in cadmium detoxification," Biochimie 88(11):1665-71 (Jun. 2006).
Nikaido & Takatsuk, "Mechanisms of RND multidrug efflux pumps," Biochim. Biophys. Acta. 1794(5):769-81 (May 2009).
Osmani et al., "Catalytic key amino acids and UDP-sugar donor specificity of a plant glucuronosyltransferase, UGT94B1: molecular modeling substantiated by site-specific mutagenesis and biochemical analyses," Plant Physiol. 148(3):1295-308 (Nov. 2008).
Osmani et al., "Substrate specificity of plant UDP-dependent glycosyltransferases predicted from crystal structures and homology modeling," Phytochemistry 70(3):325-47 (Feb. 2009).
Richman et al., "Functional genomics uncovers three glucosyltransferases involved in the synthesis of the major sweet glucosides of Stevia rebaudiana," Plant J. 41(1):56-67 (Jan. 2005).
Riesmeier et al., "Isolation and characterization of a sucrose carrier cDNA from spinach by functional expression in yeast," EMBO J. 11(13):4705-13 (Dec. 1992).
Rodríguez-Concepción & Boronat, "Elucidation of the methylerythritol phosphate pathway for isoprenoid biosynthesis in bacteria and plastids. A metabolic milestone achieved through genomics," Plant Physiol 130(3):1079-89 (Nov. 2002).
Saier Jr et al., "The major facilitator superfamily," J. MoL Microbiol. Biotechnol. 1(2):257-79 (Nov. 1999).
Saier Jr et al., "The Transporter Classification Database: recent advances," Nucleic Acids Res. 37:D274-8 (Jan. 2009).

(56) References Cited

OTHER PUBLICATIONS

Sauer et al., "The soluble and membrane-bound transhydrogenases UdhA and PntAB have divergent functions in NADPH metabolism of *Escherichia coli*," J. Biol. Chem. 279(8):6613-9 (Dec. 2003).
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis," J. Biol. Chem. 280(2):899-906 (Jan. 2005).
Shao et al., "Enhanced production of alpha-galactosyl epitopes by metabolically engineered Pichia pastoris," Appl. Environ. Microbiol. 69(9):5238-42 (Sep. 2003).
Son et al., "Production of flavonoid O-glucoside using sucrose synthase and flavonoid O-glucosyltransferase fusion protein," J. Microbiol. Biotechnol. 19(7):709-12 (Jul. 2009).
Sonnhammer et al., "Pfam: a comprehensive database of protein domain families based on seed alignments," Proteins 28(3):405-20 (Jul. 1997).
Sonnhammer et al., "Pfam: multiple sequence alignments and HMM-profiles of protein domains," Nucleic Acids Res. 26(1):320-2 (Jan. 1998).
Yadav et al., "Steviol Glycosides from Stevia: Biosynthesis Pathway Review and their Application in Foods and Medicine", Critical Reviews in Food Science and Nutrition, vol. 52, No. 11, pp. 988-998; (2012).
Boer, "Strain and process development for fermentative production of Rebaudiosides" Abstract of Offered Oral from 33rd International Specialised Symposium on Yeasts; Jun. 26-29, 2017 University of College Cork, Ireland; pp. 1-2.
Chen, "Summary on Study of Stevioside," China Pharmacist, vol. 10, No. 6, p. 598-599 (2007).
Chen et al., "Progress in the Application of Affinity Tags for the Expression and Purification of Recombinant Proteins," China Biotechnology, vol. 32, No. 12, pp. 93-103, Dec. 15, 2012 (English Abstract).
Emmerstorfer et al., "Over-expression of ICE2 stabilizes cytochrome P450 reductase in *Saccharomyces cerevisiae* and Pichia pastoris," Biotechnol J. 10(4):623-35 (Apr. 2015).
Giaever & Nislow, "The yeast deletion collection: a decade of functional genomics," Genetics 197(2):451-65 (Jun. 2014).
Piirainen et al., "Glycoengineering of yeasts from the perspective of glycosylation efficiency," N Biotechnol. 31(6):532-7 (Dec. 2014).
Senthilraja et al., "RNA secondary structure prediction: Analysis of *Saccharomyces cerevisiae* RNAs," Int. J Pharm. Rev. Res. 25(2):287-91 (Mar.-Apr. 2014).
Xu et al., "Generation of hepatitis B virus PreS2-S antigen in Hansenula polymorpha," Virol Sin. 29(6):403-9 (Dec. 2014).
Yang Quanhua et.al., "Analysis of the Chemical constituents of Stevia rebaudiana and its sweetness," Journal of Beijing University of Chemical Technology, vol. 39, No. 2., p. 28-32 (2012) (English Abstract).
Wilhelm et al., "Defining transcribed regions using RNA-seq," Nature Protocols 5:255-66 (2010).
GenBank Accession No. AEE36246, dated Oct. 6, 2014 (3 pages).
GenBank Accession No. CAG41604, dated Feb. 6, 2015 (2 pages).
GenBank Accession No. NP_001105097, dated Aug. 4, 2015 (2 pages).
GenBank Accession No. NP_013636.1 (YML075C), dated Jul. 16, 2015 (3 pages).
GenBank Accession No. Q9UVY5.1, dated Apr. 1, 2015 (3 pages).
International Preliminary Report on Patentability from the International Bureau for International Application PCT/EP2016/068259; dated Feb. 13, 2018 (pp. 1-11).
International Search Report and Written Opinion of the International Searching Authority for International Application No. PCT/EP2017/061775; dated Sep. 6, 2017, pp. 1-17.
International Search Report of the International Searching Authority for International Application No. PCT/EP2017/061774; dated Aug. 30, 2017, pp. 1-20.

Written Opinion of the International Searching Authority for International Application No. PCT/EP2017/061774; dated Aug. 30, 2017, pp. 1-13.
Third-Party Submission under 37 CFR 1.290 for U.S. Appl. No. 13/701,406, dated Mar. 7, 2014 (238 pages).
Patent Examination Report No. 1 issued by IP Australia for Australian Application No. 2011261394, dated Jan. 15, 2015.
Response to Patent Examination Report No. 1 issued by IP Australia for Australian Application No. 2011261394, dated Feb. 5, 2015.
Patent Examination Report No. 2 issued by IP Australia for Australian Application No. 2011261394, dated Feb. 23, 2015.
Notice of Acceptance issued by IP Australia for Australian Application No. 2011261394, dated Aug. 13, 2015 (pp. 1-3).
Office Action for Canadian Patent Application No. 2,802,627, dated Dec. 15, 2015 (pp. 1-5).
English Translation on Response to First Office Action issued by the State Intellectual Property Office of People's Republic of China for CN Application No. 201180038475.4, dated Apr. 8, 2014.
English Translation of Second Office Action issued by the State Intellectual Property Office of People's Republic of China for Chinese Application No. 201180038475.4, dated Aug. 13, 2014.
English Translation of Response to Second Office Action issued by the State Intellectual Property Office of People's Republic of China for CN Application No. 201180038475.4, dated Oct. 28, 2014.
English Translation of Third Office Action issued by the State Intellectual Property Office of People's Republic of China for Chinese Application No. 201180038475.4, dated Mar. 3, 2015.
Notification of Grant of Patent Application issued by the State Intellectual Property Office of People's Republic of China for Chinese Application No. 201180038475.4, dated Dec. 1, 2015 (pp. 1-5). English translation included.
Response to Extended Search Report and Opinion issued by the European Patent Office for European Application No. 11790428.4, dated Jul. 16, 2014.
Communication pursuant to Rule 114(2) EPC for European Application No. 11790428.4, dated Nov. 28, 2014.
Examination Report issued by the European Patent Office for European Application No. 11790428.4, dated Dec. 1, 2014.
Response to Examination Report issued by the European Patent Office for European Application No. 11790428.4, dated Jun. 1, 2015 (16 pages).
English Translation of Notification of Reasons for Refusal of Japanese Application No. 2013-513355, dated Aug. 4, 2015 (pp. 1-10).
Examination Report issued by the Intellectual Property Corporation of Malaysia for Malaysian Application No. PI 2012005201, dated Jul. 31, 2014.
Response to Examination Report issued by the Intellectual Property Corporation of Malaysian for MY Application No. PI 2012005201, dated Sep. 18, 2014.
Response to First Examination Report issued by the Intellectual Property Office of New Zealand for New Zealand Application No. 604915, dated Jan. 17, 2014.
Further Examination Report issued by the Intellectual Property Office of New Zealand for New Zealand Application No. 504915, dated Feb. 3, 2014.
Response to Further Examination Report issued by the Intellectual Property Office of New Zealand for New Zealand Application No. 604915, dated May 27, 2014.
Further Examination Report issued by the Intellectual Property Office of New Zealand for New Zealand Application No. 604915, dated Jun. 18, 2014.
Response to Further Examination Report issued by the Intellectual Property Office of New Zealand for New Zealand Application No. 604915, dated Sep. 15, 2014.
Notice of Acceptance issued by the Intellectual Property Office of New Zealand for New Zealand Application No. 604915, dated Oct. 7, 2014 (1 page).
Bruyn et al., "Metabolic engineering of *Escherichia coli* into a versatile glycosylation platform: production of bio-active quercetin glycosides," Microb Cell Fact., 14:138 (2015).

(56) References Cited

OTHER PUBLICATIONS

Bruyn et al., "Development of an in vivo glucosylation platform by coupling production to growth: production of phenolic glucosides by a glycosyltransferase of Vitis vinifera," Biotechnol Bioeng., 112(8):1594-603 (2015).
Chen et al., "Sugar transporters for intercellular exchange and nutrition of pathogens," Nature 468(7323):527-32 (2010).
Chen et al., "Fusion protein linkers: Property, design, and functionality", Advanced Drug Delivery reviews, 65(0):1257-69 (2013).
Daran et al., "Genetic and biochemical characterization of the UGP1 gene encoding the UDP-glucose pyrophosphorylase from *Saccharomyces cerevisiae*," Eur J Biochem. 233(2):520-30 (1995).
Duetz, "Microtiter plates as mini-bioreactors: miniaturization offermentation methods," Trends Microbiol 15(10):469-75 (2007).
François et al., "Reserve carbohydrates metabolism in the yeast *Saccharomyces cerevisiae*," FEMS Microbiol Rev., 25(1):125-45 (2001).
Garber et al., "Computational methods for transcriptome annotation and quantification using RNA-seq," Nat Methods 8(6):469-77 (2011).
Gloster, "Advances in understanding glycosyltransferases from a structural perspective," Curr Opin Struct Biol. 28:131-41 (2014).
Husar et al., Overexpression of the UGT73C6 alters brassinosteriod glucoside formation in *Arabidopsis thaliana*, BMC Plant Biology, 11:1-14 (2011).
Kawai et al., "Transformation of *Saccharomyces cerevisiae* and other fungi: methods and possible underlying mechanism," Bioeng Bugs. 1(6):395-403 (2010).
Khan et al., "Physical and chemical mutagenesis in Stevia rebaudiana: variant generation with higher UGT expression and glycosidic profile but with low photosynthetic capabilities," Acta Physiologiae Plantarum 38(1) (2016).
Lin et al., "Arrestin-related ubiquitin-ligase adaptors regulate endocytosis and protein turnover at the cell surface," Cell 135(4):714-25 (2008).
Liu et al., "Biosynthesis of Rebaudioside A by Whole Cell of Recombinant *Saccharomyces cerevisiae*," Food and Fermentation Industries, 38(7) : 6-10 (2012) (Abstract translation).
Mao et al., "Produce steviol glycosides in engineered yeast", 2015 Synthetic Biology: Engineering, Evolution & Design (SEED), Poster Abstract (Jun. 2015).
Nagalakshmi et al., "The transcriptional landscape of the yeast genome defined by RNA sequencing," Science 320(5881 ): 1344-9 (2008).
Nagatoshi et al., "UGT75L6 and UGT94E5 mediate sequential glucosylation of crocetin to crocin in Gardenia iasminoides", FEBS Letters, 586:1055-1061 (2012).
Nikko et al. "Arrestin-like proteins mediate ubiquitination and endocytosis of the yeast metal transporter Smf1," EMBO Rep. 9(12):1216-21 (2008).
Nikko & Pelham, "Arrestin-mediated endocytosis of yeast plasma membrane transporters," Traffic 10(12):1856-67 (2009).
Ohta et al., MassBank Accession No. FU000299 (May 2016).
Ohta et al., MassBank Accession No. FU000332 (May 2016).
Olsson et al., "Microbial production of next-generation stevia sweeteners," Microbial Cell Factories, 15:1-14 (2016).
Partow et al., "Characterization of different promoters for designing a new expression vector in *Saccharomyces cerevisiae*," Yeast 27:955-64 (2010).
Robinson & Oshlack et al., "A scaling normalization method for differential expression analysis of RNA-seq data," Genome Bioi. 11(3):R25 (2010).
Saier Jr. et al., "The transporter classification database," Nucl. Acids Res., 42(1):D251-258 (2014).
Song et al., "The Aspergillus fumigatus 1-29 damage resistance protein family coordinately regulates ergosterol biosynthesis and azole susceptibility," MBIO, 7:1-13 (2016).
Tiwari et al., "Plant secondary metabolism linked glycosyltransferases: An update on expaning knowledge and scopes", Biotechnology Advances, 34:714-739 (May 2016).
Wang et al., "Pathway mining-based integration of critical enzyme parts for de novo biosynthesis of steviolglycoside sweetener in *Escherichia coli*", Cell Research, 26:258-261 (Sep. 2015).
Wang et al., "Efficient enzymatic production of rebaudioside A from stevioside", Bioscience, Biotechnology, and Biochemistry, 80:67-73 (Aug. 2015).
Wang et al., "RNA-Seq: a revolutionary tool for transcriptomics," Nat Rev Genet. 10(1):57-63 (2009).
Wang et al., "Design and construction of artificial biological systems for complex natural products biosynthesis," Chinese Journal of Biotechnology, 29(8):1146-60 (2013).
Warth et al., "Hydrophilic interaction liquid chromatography coupled with tandem mass spectrometry for the quantification of uridine diphosphate-glucose, uridine diphosphate-glucuronic acid, deoxynivalenol and its glucoside in-house validation and application to wheat," Journal of Chromatography A, 1423, pp. 183-189 (2015).
International Search Report and Written Opinion of the International Searching Authority for International Application No. PCT/EP2017/078473; dated Jan. 25, 2018, pp. 1-16.
Non-Final Office Action for U.S. Appl. No. 14/764,898, dated Mar. 30, 2017 (pp. 1-17).
International Preliminary Report on Patentability from the International Bureau for International Application PCT/EP2015/070620; dated Mar. 14, 2017 (pp. 1-25).
Third Party Submission in U.S. Appl. No. 15/506,196; dated Mar. 9, 2018 pp. 1-68.
Non-Final Office Action for U.S. Appl. No. 15/506,196, dated Sep. 17, 2018 (pp. 1-8).
Final Office Action for U.S. Appl. No. 15/506,196, dated Feb. 21, 2019 (pp. 1-10).
Non-Final Office Action for U.S. Appl. No. 15/506,196, dated Jun. 19, 2019 (pp. 1-10).
International Preliminary Report on Patentability from the International Bureau for International Application PCT/EP2015/052007; dated Aug. 1, 2017 (pp. 1-16).
International Search Report and Written Opinion of International Search Authority for International Application No. PCT/EP2017/055589; dated May 12, 2017, pp. 1-18.
Third party submission in European Patent Application No. 15762581.5 dated Aug. 29, 2019 (300 pages).

\* cited by examiner

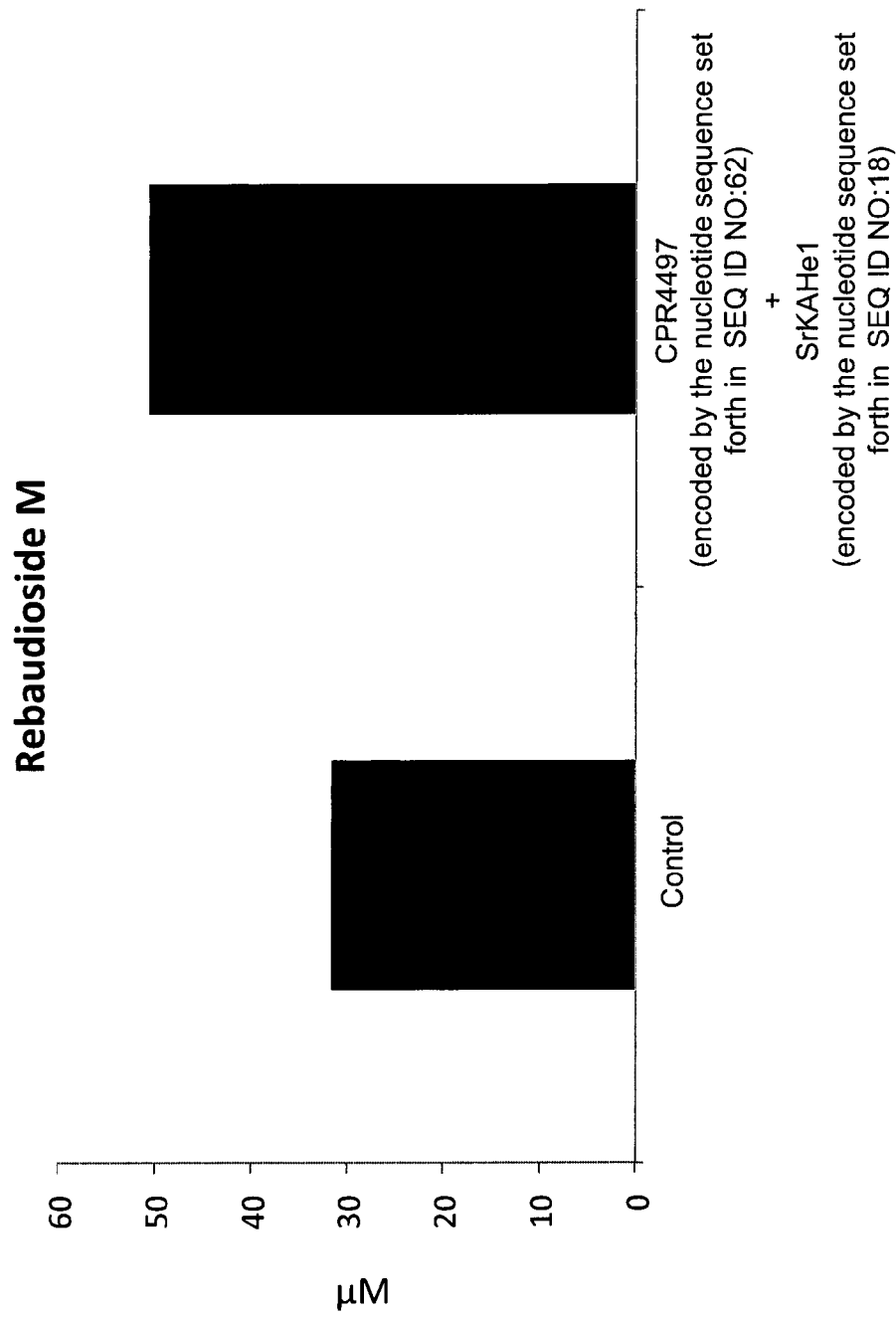

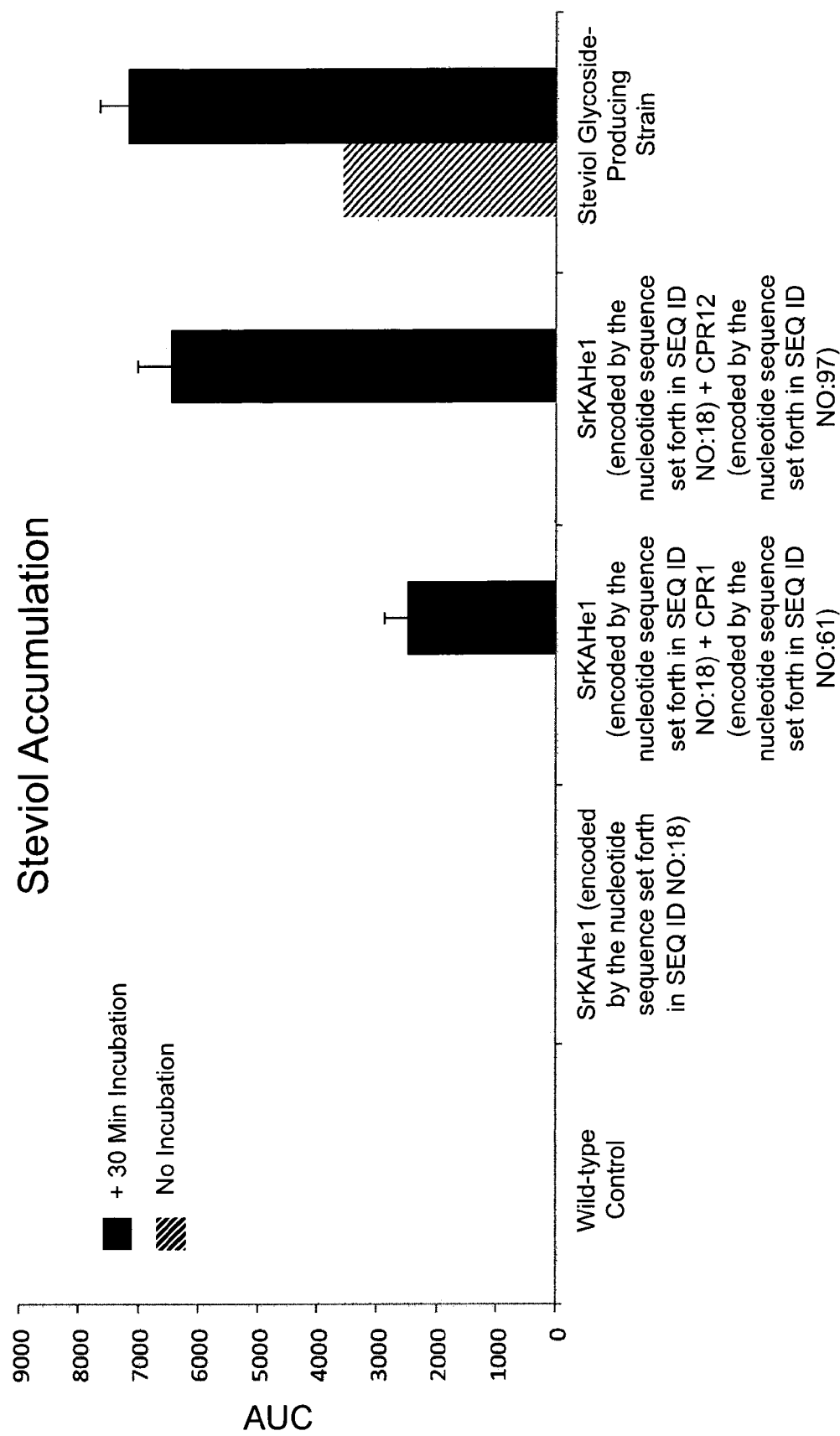

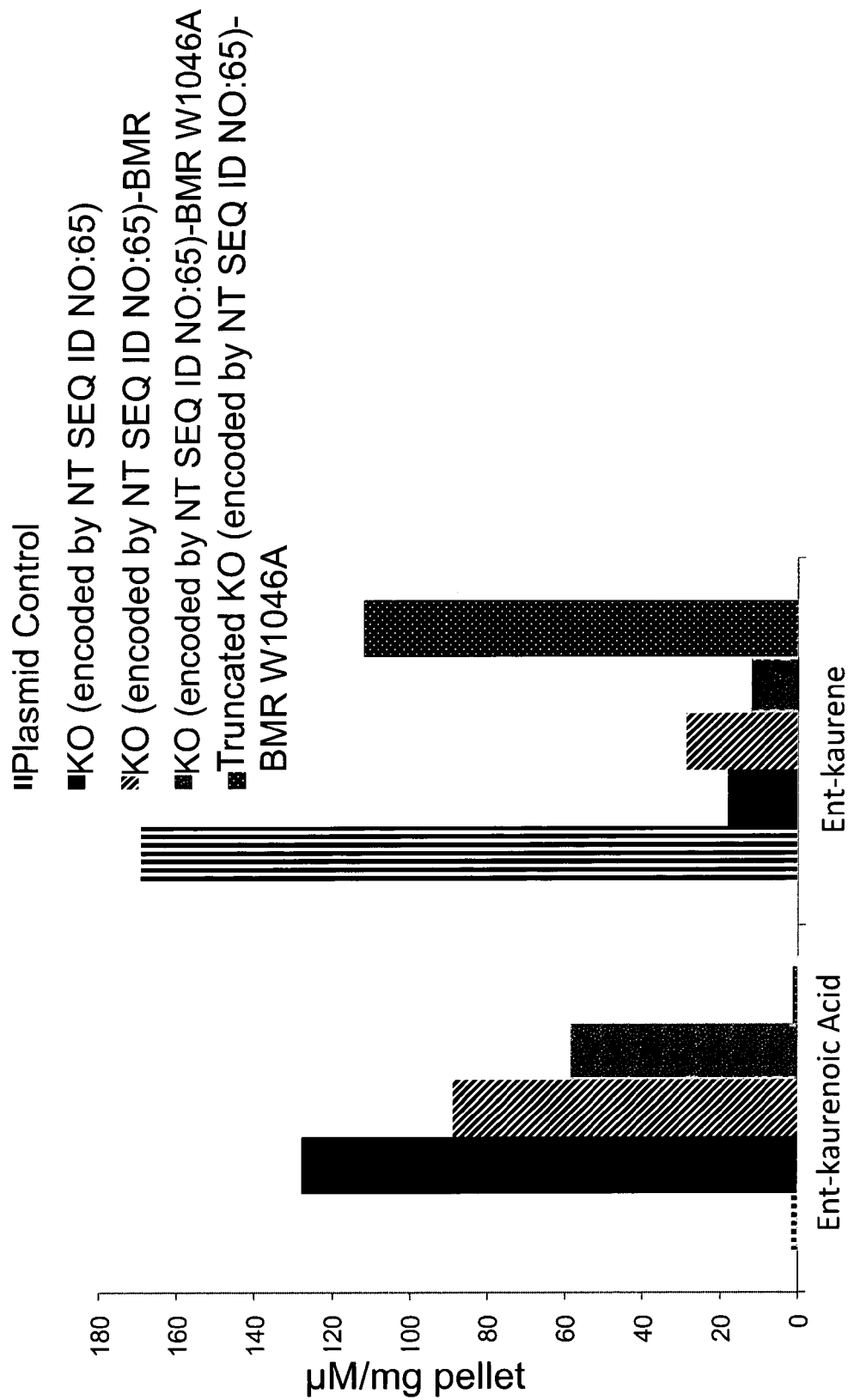

PRODUCTION OF STEVIOL GLYCOSIDES IN RECOMBINANT HOSTS

This application is a divisional of Ser. No. 15/506,196, filed on Feb. 23, 2017, now U.S. Pat. No. 10,612,064, which is a U.S. national phase of International Application No. PCT/EP2015/070620 filed Sep. 9, 2015, which claims the benefit of U.S. Provisional Application No. 62/048,178 filed on Sep. 9, 2014, U.S. Provisional Application No. 62/103,547, filed on Jan. 14, 2015, U.S. Provisional Application No. 62/117,396, filed on Dec. 17, 2015, and U.S. Provisional Application No. 62/148,585, filed on Apr. 16, 2015. The entire disclosure contents of these applications are herewith incorporated by reference in their entirety into the present application.

BACKGROUND OF THE INVENTION

Field of the Invention

This disclosure relates to recombinant production of steviol glycosides and steviol glycoside precursors in recombinant hosts. In particular, this disclosure relates to production of steviol glycosides comprising steviol-13-O-glucoside (13-SMG), steviol-1,2-bioside, steviol-1,3-bioside, steviol-19-O-glucoside (19-SMG), stevioside, 1,3-stevioside, rubusoside, Rebaudioside A (RebA), Rebaudioside B (RebB), Rebaudioside C (RebC), Rebaudioside D (RebD), Rebaudioside E (RebE), Rebaudioside F (RebF), Rebaudioside M (RebM), Rebaudioside Q (RebQ), Rebaudioside I (RebI), dulcoside A, or isomers thereof in recombinant hosts.

Description of Related Art

Sweeteners are well known as ingredients used most commonly in the food, beverage, or confectionery industries. The sweetener can either be incorporated into a final food product during production or for stand-alone use, when appropriately diluted, as a tabletop sweetener or an at-home replacement for sugars in baking. Sweeteners include natural sweeteners such as sucrose, high fructose corn syrup, molasses, maple syrup, and honey and artificial sweeteners such as aspartame, saccharine, and sucralose. *Stevia* extract is a natural sweetener that can be isolated and extracted from a perennial shrub, *Stevia rebaudiana*. *Stevia* is commonly grown in South America and Asia for commercial production of *stevia* extract. *Stevia* extract, purified to various degrees, is used commercially as a high intensity sweetener in foods and in blends or alone as a tabletop sweetener.

Chemical structures for several steviol glycosides are shown in FIG. 1, including the diterpene steviol and various steviol glycosides. Extracts of the *Stevia* plant generally comprise steviol glycosides that contribute to the sweet flavor, although the amount of each steviol glycoside often varies, inter alia, among different production batches.

As recovery and purification of steviol glycosides from the *Stevia* plant have proven to be labor intensive and inefficient, there remains a need for a recombinant production system that can accumulate high yields of desired steviol glycosides, such as RebD and RebM. There also remains a need for improved production of steviol glycosides in recombinant hosts for commercial uses.

SUMMARY OF THE INVENTION

It is against the above background that the present invention provides certain advantages and advancements over the prior art.

Although this invention disclosed herein is not limited to specific advantages or functionalities, the invention provides a recombinant host comprising one or more of:
(a) a gene encoding an ent-kaurene oxidase (KO) polypeptide;
(b) a gene encoding a cytochrome P450 reductase (CPR) polypeptide; and/or
(c) a gene encoding an ent-kaurenoic acid hydroxylase (KAH) polypeptide;
wherein at least one of the genes is a recombinant gene; and
wherein the recombinant host is capable of producing a steviol glycoside precursor.

The invention also provides a recombinant host comprising:
(a) a gene encoding a geranylgeranyl diphosphate synthase (GGPPS) polypeptide;
(b) a gene encoding an ent-copalyl diphosphate synthase (CDPS) polypeptide;
(c) a gene encoding an ent-kaurene synthase (KS) polypeptide
(d) a gene encoding an ent-kaurene oxidase (KO) polypeptide;
(e) a gene encoding a cytochrome P450 reductase (CPR) polypeptide; and
(f) a gene encoding an ent-kaurenoic acid hydroxylase (KAH) polypeptide;
wherein at least one of the genes is a recombinant gene; and
wherein the recombinant host is capable of producing steviol.

In one aspect of the recombinant hosts disclosed herein,
(a) the KO polypeptide comprises a KO polypeptide having at least 60% identity to an amino acid sequence set forth in SEQ ID NO:72 or SEQ ID NO:75; 65% identity to an amino acid sequence set forth in SEQ ID NO:54; at least 70% identity to an amino acid sequence set forth in SED ID NO: 70, SEQ ID NO:71, or SEQ ID NO:79; at least 40% identity to an amino acid sequence set forth in SEQ ID NO:77; or at least 50% identity to an amino acid sequence set forth in SEQ ID NO:78;
(b) the CPR polypeptide comprises a CPR polypeptide having at least 70% identity to an amino acid sequences set forth in SEQ ID NO:69, SEQ ID NO:74, SEQ ID NO:76, or SEQ ID NO:87; at least 80% identity to an amino acid sequence set forth in SEQ ID NO:73; at least 85% identity to an amino acid sequence set forth in SEQ ID NO:22; at least 65% identity to an amino acid sequence set forth in SEQ ID NO:28; or at least 50% identity to an amino acid sequence set forth in SEQ ID NO:98; and/or
(c) the KAH polypeptide comprises a KAH polypeptide having at least 40% identity to an amino acid sequence set forth in SEQ ID NO:82; at least 50% identity to an amino acid sequence set forth in SEQ ID NO:91; or at least 60% identity to an amino acid sequence set forth in SEQ ID NO:68.

The invention further provides a recombinant host comprising one or more of:
(a) a gene encoding a KO polypeptide having at least 60% identity to an amino acid sequence set forth in SEQ ID NO:75;
(b) a gene encoding a KAH polypeptide having at least 40% identity to an amino acid sequence set forth in SEQ ID NO:82; and/or (c) a gene encoding a CPR polypeptide having at least 50% identity to an amino acid sequence set forth in SEQ ID NO:98;
wherein at least one of the genes is a recombinant gene; and
wherein the recombinant host is capable of producing a steviol glycoside precursor.

The invention further provides a recombinant host comprising one or more of:
(a) a gene encoding a KO polypeptide having at least 70% identity to an amino acid sequence set forth in SEQ ID NO:70;
(b) a gene encoding a KAH polypeptide having at least 40% identity to an amino acid sequence set forth in SEQ ID NO:82; and/or
(c) a gene encoding a CPR polypeptide having at least 50% identity to an amino acid sequence set forth in SEQ ID NO:98;
wherein at least one of the genes is a recombinant gene; and
wherein the recombinant host is capable of producing a steviol glycoside precursor.

In one aspect of the recombinant hosts disclosed herein, the host further comprises a gene encoding a KO polypeptide having at least 65% identity to an amino acid sequence set forth in SEQ ID NO:54.

In another aspect of the recombinant hosts disclosed herein, the recombinant host further comprises a gene encoding a KAH polypeptide having at least 60% identity to an amino acid sequence set forth in SEQ ID NO:68.

In another aspect of the recombinant hosts disclosed herein, the recombinant host further comprises a gene encoding a KO polypeptide having at least 70% identity to an amino acid sequence set forth in SEQ ID NO:79.

In one aspect of the recombinant hosts disclosed herein, the host further comprises one or more of:
(a) a gene encoding a geranylgeranyl diphosphate synthase (GGPPS) polypeptide;
(b) a gene encoding an ent-copalyl diphosphate synthase (CDPS) polypeptide; and/or
(c) a gene encoding an ent-kaurene synthase (KS) polypeptide;
wherein at least one of the genes is a recombinant gene; and
wherein the recombinant host is capable of producing a steviol glycoside precursor.

In some aspects of the recombinant hosts disclosed herein,
(a) the GGPPS polypeptide comprises a polypeptide having at least 70% identity to an amino acid sequence set forth in SEQ ID NO:49;
(b) the CDPS polypeptide comprises a polypeptide having at least 70% identity to an amino acid sequence set forth in SEQ ID NO:37; and/or
(c) the KS polypeptide comprises a polypeptide having at least 40% identity to an amino acid sequence set forth in SEQ ID NO:6.

In one aspect of the recombinant hosts disclosed herein, the recombinant host further comprises a gene encoding an endoplasmic reticulum membrane polypeptide.

In another aspect of the recombinant hosts disclosed herein, the endoplasmic reticulum membrane polypeptide comprises an Inheritance of cortical ER protein 2 (ICE2) polypeptide having at least 50% identity to the amino acid sequence set forth in SEQ ID NO:114.

In one aspect of the recombinant host disclosed herein, the KO polypeptide is a fusion construct.

In another aspect, the fusion construct comprises a polypeptide having at least 60% identity to an amino acid sequence set forth in SEQ ID NO:118 or SEQ ID NO:120.

In another aspect, the fusion construct has at least 50% identity to an amino acid sequence set forth in SEQ ID NO:100, SEQ ID NO:102, SEQ ID NO:104, SEQ ID NO:106, SEQ ID NO:108, SEQ ID NO:110, or SEQ ID NO:112.

In one aspect of the recombinant hosts disclosed herein, the host further comprises one or more of:
(a) a gene encoding a UGT85C polypeptide;
(b) a gene encoding a UGT76G polypeptide;
(c) a gene encoding a UGT74G1 polypeptide;
(d) a gene encoding a UGT91D2 functional homolog polypeptide; and/or
(e) a gene encoding an EUGT11 polypeptide;
wherein at least one of the genes is a recombinant gene; and
wherein the host is capable of producing a steviol glycoside.

In some aspects of the recombinant hosts disclosed herein,
(a) the UGT85C2 polypeptide comprises a polypeptide having at least 55% identity to an amino acid sequence set forth in SEQ ID NO:30;
(b) the UGT76G1 polypeptide comprises a polypeptide having at least 50% identity to an amino acid sequence set forth in SEQ ID NO:83;
(c) the UGT74G1 polypeptide comprises a polypeptide having at least 55% identity to an amino acid sequence set forth in SEQ ID NO:29;
(d) the UGT91D2 functional homolog polypeptide comprises a UGT91D2 polypeptide having 90% or greater identity to the amino acid sequence set forth in SEQ ID NO:84 or a UGT91D2e-b polypeptide having 90% or greater identity to the amino acid sequence set forth in SEQ ID NO:88; and/or
(e) the EUGT11 polypeptide comprises a polypeptide having at least 65% identity to an amino acid sequence set forth in SEQ ID NO:86.

In some aspects, the recombinant hosts disclosed herein comprise a plant cell, a mammalian cell, an insect cell, a fungal cell, or a bacterial cell.

In one aspect, the bacterial cell comprises *Escherichia* bacteria cells, for example, *Escherichia coli* cells; *Lactobacillus* bacteria cells; *Lactococcus* bacteria cells; *Cornebacterium* bacteria cells; *Acetobacter* bacteria cells; *Acinetobacter* bacteria cells; or *Pseudomonas* bacterial cells.

In one aspect, the fungal cell comprises a yeast cell.

In one aspect, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous,* or *Candida albicans* species.

In one aspect, the yeast cell is a *Saccharomycete*.

In one aspect, the yeast cell is a cell from the *Saccharomyces cerevisiae* species.

The invention further provides a method of producing a steviol glycoside or a steviol glycoside precursor, comprising:
(a) growing a recombinant host disclosed herein in a culture medium, under conditions in which any of the genes disclosed herein are expressed;
wherein the steviol glycoside or the steviol glycoside precursor is synthesized by said host; and/or (b) optionally quantifying the steviol glycoside or the steviol glycoside precursor; and/or (c) optionally isolating the steviol glycoside or the steviol glycoside precursor.

In some aspects, the steviol glycoside comprises steviol-13-O-glucoside (13-SMG), steviol-1,2-bioside, steviol-1,3-bioside, steviol-19-O-glucoside (19-SMG), stevioside, 1,3-stevioside, rubusoside, Rebaudioside A (RebA), Rebaudioside B (RebB), Rebaudioside C (RebC), Rebaudioside D (RebD), Rebaudioside E (RebE), Rebaudioside F (RebF), Rebaudioside M (RebM), Rebaudioside Q (RebQ), Rebaudioside I (RebI), dulcoside A, di-glycosylated steviol, tri-glycosylated steviol, tetra-glycosylated steviol, penta-glycosylated steviol, hexa-glycosylated steviol, hepta-glycosylated steviol, or isomers thereof.

In some aspects, the steviol glycoside or steviol glycoside precursor produced by the recombinant hosts or methods disclosed herein accumulates to a detectable concentration when cultured under said conditions.

In some aspects, the steviol glycoside or steviol glycoside precursor produced by the recombinant hosts or methods disclosed herein has an undetectable concentration of *stevia* plant-derived contaminants.

In some aspects, the steviol glycoside or steviol glycoside precursor produced by the recombinant hosts or methods disclosed herein has a steviol glycoside composition enriched for RebD or RebM relative to the steviol glycoside composition of a wild-type *Stevia* plant.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which:

FIG. 10 shows Rebaudioside M (RebM) production in a steviol glycoside-producing *S. cerevisiae* strain overexpressing SrKAHe1 (encoded by the codon-optimized nucleotide sequence set forth in SEQ ID NO:18) and further expressing CPR4497 encoded by the nucleotide sequence set forth in SEQ ID NO:62. Values plotted on the y-axis indicate μM concentration of RebM. See Example 5.

FIG. 15A shows steviol accumulation upon 30 min incubation of ent-kaurenoic acid with microsomal protein prepared from *S. cerevisiae* strains expressing SrKAHe1 (encoded by the nucleotide sequence set forth in SEQ ID NO:18) alone or in combination with CPR1 (encoded by the nucleotide sequence set forth in SEQ ID NO:61) or CPR12 (encoded by the nucleotide sequence set forth in SEQ ID NO:97). Results are shown in AUC as an average of three biological replicates. Control reactions comprised the microsomal protein described above, but these were not incubated for 30 min prior to measurement of steviol accumulation.

FIG. 16D shows levels of ent-kaurenoic acid or ent-kaurene accumulated by a steviol glycoside-producing *S. cerevisiae* strain expressing the KO encoded by the nucleotide sequence set forth in SEQ ID NO:65, a fusion construct of the KO encoded by the nucleotide sequence set forth in SEQ ID NO:65 and BMR (SEQ ID NO:107, SEQ ID NO:108), a fusion construct of the KO encoded by the nucleotide sequence set forth in SEQ ID NO:65 and BMR W1046A (SEQ ID NO:109, SEQ ID NO:110), a fusion construct of a truncated KO encoded by the nucleotide sequence set forth in SEQ ID NO:65 and BMR W1046A (SEQ ID NO:111, SEQ ID NO:112), or a plasmid control. See Example 10.

DETAILED DESCRIPTION OF THE INVENTION

Figure 1:
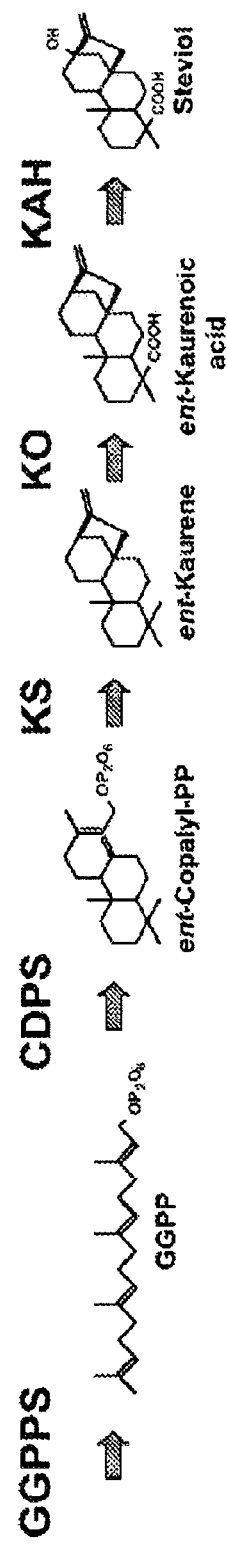
FIG. 1 shows a schematic of the engineered biosynthetic pathway for producing steviol in yeast from geranylgeranyl diphosphate using geranylgeranyl diphosphate synthase (GGPPS), ent-copalyl diphosphate synthase (CDPS), ent-kaurene synthase (KS), ent-kaurene oxidase (KO), and ent-kaurenoic acid hydroxylase (KAH) polypeptides.

Before describing the present invention in detail, a number of terms will be defined. As used herein, the singular forms "a," "an," and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Green & Sambrook, 2012, MOLECULAR CLONING: A LABORATORY MANUAL, Fourth Edition, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

As used herein, the terms "polynucleotide", "nucleotide", "oligonucleotide", and "nucleic acid" can be used interchangeably to refer to nucleic acid comprising DNA, RNA, derivatives thereof, or combinations thereof.

As used herein, the terms "microorganism," "microorganism host," "microorganism host cell," "recombinant host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ("expressed"), and other genes or DNA sequences which one desires to introduce into a host. It will be appreciated that typically the genome of a recombinant host described herein is augmented through stable introduction of one or more recombinant genes. Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene can be a DNA sequence from another species or can be a DNA sequence that originated from or is present in the same species but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. In some aspects, said recombinant genes are encoded by cDNA. In other embodiments, recombinant genes are synthetic and/or codon-optimized for expression in *S. cerevisiae*.

As used herein, the term "engineered biosynthetic pathway" refers to a biosynthetic pathway that occurs in a recombinant host, as described herein. In some aspects, one or more steps of the biosynthetic pathway do not naturally occur in an unmodified host. In some embodiments, a heterologous version of a gene is introduced into a host that comprises an endogenous version of the gene.

As used herein, the term "endogenous" gene refers to a gene that originates from and is produced or synthesized within a particular organism, tissue, or cell. In some embodiments, the endogenous gene is a yeast gene. In some embodiments, the gene is endogenous to *S. cerevisiae*, including, but not limited to *S. cerevisiae* strain S288C. In some embodiments, an endogenous yeast gene is overexpressed. As used herein, the term "overexpress" is used to refer to the expression of a gene in an organism at levels higher than the level of gene expression in a wild type organism. See, e.g., Prelich, 2012, Genetics 190:841-54. In some embodiments, an endogenous yeast gene is deleted. See, e.g., Giaever & Nislow, 2014, Genetics 197(2):451-65. As used herein, the terms "deletion," "deleted," "knockout," and "knocked out" can be used interchangabley to refer to an endogenous gene that has been manipulated to no longer be expressed in an organism, including, but not limited to, *S. cerevisiae*.

As used herein, the terms "heterologous sequence" and "heterologous coding sequence" are used to describe a sequence derived from a species other than the recombinant host. In some embodiments, the recombinant host is an *S. cerevisiae* cell, and a heterologous sequence is derived from an organism other than *S. cerevisiae*. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

A "selectable marker" can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, PCR or Southern blot analysis. Subsequent to its use in selection, a selectable marker can be removed from the genome of the host cell by, e.g., Cre-LoxP systems (see, e.g., Gossen et al., 2002, Ann. Rev. Genetics 36:153-173 and U.S. 2006/0014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

As used herein, the terms "variant" and "mutant" are used to describe a protein sequence that has been modified at one or more amino acids, compared to the wild-type sequence of a particular protein.

As used herein, the term "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of a gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene with inactivation thereof.

As used herein, the term "steviol glycoside" refers to Rebaudioside A (RebA) (CAS #58543-16-1), Rebaudioside B (RebB) (CAS #58543-17-2), Rebaudioside C (RebC)

Figure 2:
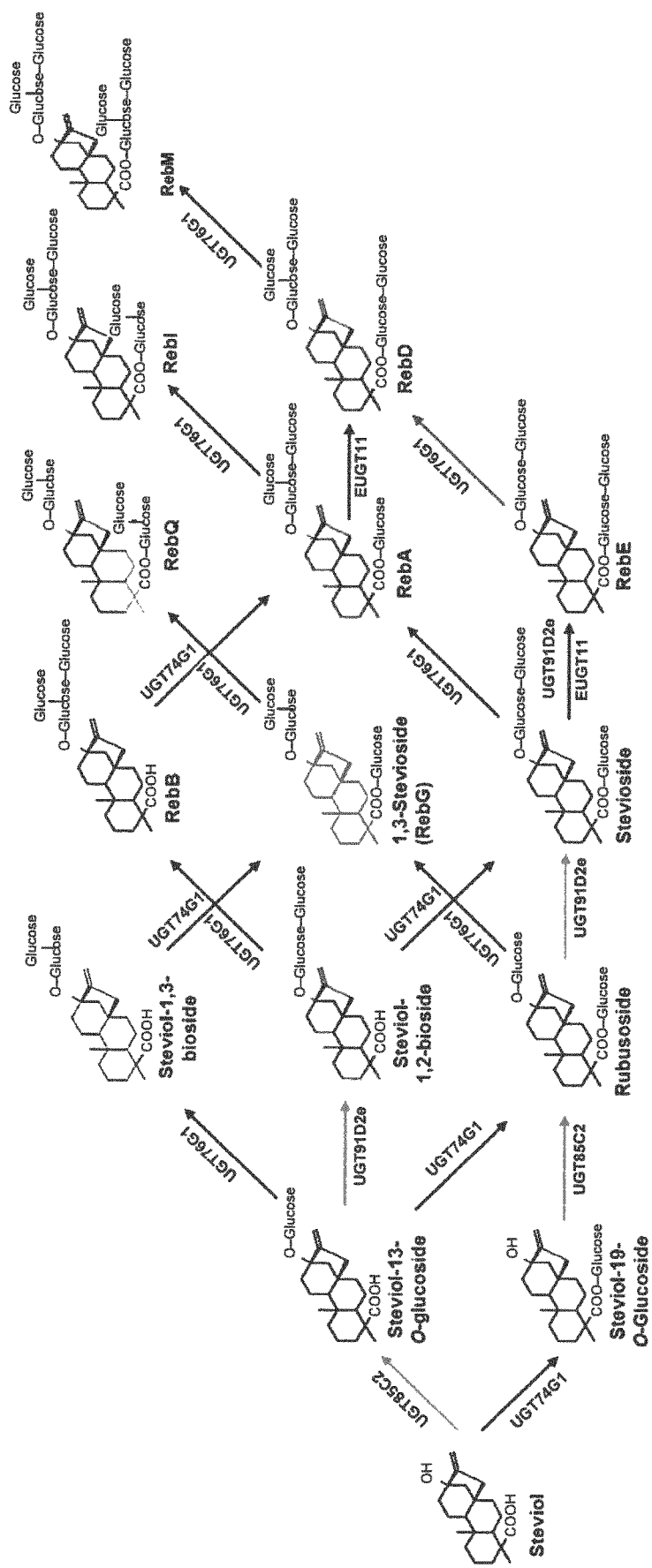
FIG. 2 shows representative steviol glycoside glycosylation reactions catalyzed by suitable uridine 5'-diphospho (UDP) glycosyl transferases (UGT) enzymes and chemical structures for several steviol glycoside compounds.

(CAS #63550-99-2), Rebaudioside D (RebD) (CAS #63279-13-0), Rebaudioside E (RebE) (CAS #63279-14-1), Rebaudioside F (RebF) (CAS #438045-89-7), Rebaudioside M (RebM) (CAS #1220616-44-3), Rubusoside (CAS #63849-39-4), Dulcoside A (CAS #64432-06-0), Rebaudioside I (RebI) (MassBank Record: FU000332), Rebaudioside Q (RebQ), 1,2-Stevioside (CAS #57817-89-7), 1,3-Stevioside (RebG), 1,2-bioside (MassBank Record: FU000299), 1,3-bioside, Steviol-13-O-glucoside (13-SMG), Steviol-19-O-glucoside (19-SMG), a tri-glucosylated steviol glycoside, a tetra-glycosylated steviol glycoside, a penta-glucosylated steviol glycoside, a hexa-glucosylated steviol glycoside, a hepta-glucosylated steviol glycoside, and isomers thereof. See FIG. 2; see also, Steviol Glycosides Chemical and Technical Assessment 69th JECFA, 2007, prepared by Harriet Wallin, Food Agric. Org.

As used herein, the terms "steviol glycoside precursor" and "steviol glycoside precursor compound" are used to refer to intermediate compounds in the steviol glycoside biosynthetic pathway. Steviol glycoside precursors include, but are not limited to, geranylgeranyl diphosphate (GGPP), ent-copalyl-diphosphate, ent-kaurene, ent-kaurenol, ent-kaurenal, ent-kaurenoic acid, and steviol. See FIG. 1. In some embodiments, steviol glycoside precursors are themselves steviol glycoside compounds. For example, 19-SMG, rubusoside, stevioside, and RebE are steviol glycoside precursors of RebM. See FIG. 2. Steviol glycosides and/or steviol glycoside precursors can be produced in vivo (i.e., in a recombinant host), in vitro (i.e., enzymatically), or by whole cell bioconversion. As used herein, the terms "produce" and "accumulate" can be used interchangeably to describe synthesis of steviol glycosides and steviol glycoside precursors in vivo, in vitro, or by whole cell bioconversion.

As used herein, the term "di-glycosylated steviol" can be used to refer to a steviol molecule comprising two sugar moieties, such as glucose or N-acetylglucosamine (GlcNAc). Non-limiting examples of di-glycosylated steviol molecules include steviol-1,3-bioside, steviol-1,2-bioside, rubusoside, a steviol molecule comprising two glucose moieties, a steviol molecule comprising one glucose moiety and one GlcNAc moiety, and isomers thereof.

As used herein, the term "tri-glycosylated steviol" can be used to refer to a steviol molecule comprising three sugar moieties, such as glucose or GlcNAc. Non-limiting examples of tri-glycosylated steviol molecules include RebB, RebG, stevioside, a steviol molecule comprising two glucose moieties and one GlcNAc moiety, and isomers thereof.

As used herein, the term "tetra-glycosylated steviol" can be used to refer to a steviol molecule comprising four sugar moieties, such as glucose or GlcNAc. Non-limiting examples of tetra-glycosylated steviol molecules include RebA, RebE, RebQ, a steviol molecule comprising four glucose moieties, a steviol molecule comprising three glucose moieties and one GlcNAc moiety, and isomers thereof.

As used herein, the term "penta-glycosylated steviol" can be used to refer to a steviol molecule comprising five sugar moieties, such as glucose or GlcNAc. Non-limiting examples of penta-glycosylated steviol molecules include RebD, a steviol molecule comprising five glucose moieties, a steviol molecule comprising four glucose moieties and one GlcNAc moiety, and isomers thereof.

As used herein, the term "hexa-glycosylated steviol" can be used to refer to a steviol molecule comprising six sugar moieties, such as glucose or GlcNAc. Non-limiting examples of hexa-glycosylated steviol molecules include RebM, a steviol molecule comprising six glucose moieties, a steviol molecule comprising five glucose moieties and one GlcNAc moiety, and isomers thereof.

As used herein, the term "hepta-glycosylated steviol" can be used to refer to a steviol molecule comprising seven sugar moieties, such as glucose or GlcNAc. Non-limiting examples of hepta-glycosylated steviol molecules include a steviol molecule comprising seven glucose moieties and isomers thereof.

As used herein, the term "glycosylated ent-kaurenoic acid" can be used to refer to an ent-kaurenoic acid molecule comprising sugar moieties, such as glucose or GlcNAc. Non-limiting examples of glycosylated ent-kaurenoic acid molecules include ent-kaurenoic acid molecule comprising two glucose moieties and one GlcNAc moiety, an ent-kaurenoic acid molecule comprising three glucose moieties, an ent-kaurenoic acid molecule comprising one glucose moiety and one GlcNAc moiety, an ent-kaurenoic acid molecule comprising two glucose moieties, and isomers thereof.

As used herein, the term "glycosylated ent-kaurenol" can be used to refer to an ent-kaurenol molecule comprising sugar moieties, such as glucose or GlcNAc. Non-limiting examples of glycosylated ent-kaurenol molecules include an ent-kaurenol molecule comprising three glucose moieties, an ent-kaurenol molecule comprising one glucose moiety and one GlcNAc moiety, an ent-kaurenol molecule comprising two glucose moieties, and isomers thereof.

Recombinant steviol glycoside-producing *Saccharomyces cerevisiae* (*S. cerevisiae*) strains are described in WO 2011/153378, WO 2013/022989, WO 2014/122227, and WO 2014/122328. Methods of producing steviol glycosides in recombinant hosts, by whole cell bioconversion, and in vitro are also described in WO 2011/153378, WO 2013/022989, WO 2014/122227, and WO 2014/122328.

In some embodiments, steviol glycosides and/or steviol glycoside precursors are produced in vivo through expression of one or more enzymes involved in the steviol glycoside biosynthetic pathway in a recombinant host. For example, a steviol-producing recombinant host expressing one or more of a gene encoding a GGPPS polypeptide, a gene encoding a CDPS polypeptide, a gene encoding a KS polypeptide, a gene encoding a KO polypeptide, a gene encoding a KAH polypeptide, a gene encoding a CPR polypeptide, and a gene encoding a UGT polypeptide can produce a steviol glycoside and/or steviol glycoside precursors in vivo. See, e.g., FIGS. 1 and 2. The skilled worker will appreciate that one or more of these genes can be endogenous to the host provided that at least one (and in some embodiments, all) of these genes is a recombinant gene introduced into the recombinant host.

In another example, a recombinant host expressing a gene encoding a GGPPS polypeptide, a gene encoding a CDPS polypeptide, a gene encoding a KS polypeptide, a gene encoding a KO polypeptide, a gene encoding a KAH polypeptide, and a gene encoding a CPR polypeptide can produce steviol in vivo. See, e.g., FIG. 1. The skilled worker will appreciate that one or more of these genes can be endogenous to the host provided that at least one (and in some embodiments, all) of these genes is a recombinant gene introduced into the recombinant host.

In another example, a steviol-producing recombinant host expressing a gene encoding a GGPPS polypeptide, a gene encoding a CDPS polypeptide, a gene encoding a KS polypeptide, a gene encoding a KO polypeptide, a gene encoding a KAH polypeptide, a gene encoding a CPR polypeptide, and one or more of a gene encoding a UGT polypeptide can produce a steviol glycoside in vivo. See, e.g., FIGS. 1 and 2. The skilled worker will appreciate that one or more of these genes can be endogenous to the host provided that at least one (and in some embodiments, all) of these genes is a recombinant gene introduced into the recombinant host.

Non-limiting examples of KS polypeptides are set forth in SEQ ID NOs:1-4 and SEQ ID NO:6. Non-limiting examples of KO polypeptides are set forth in SEQ ID NOs:7-10, 54, 70-72, 75, and 77-79. Non-limiting examples of KAH polypeptides are set forth in SEQ ID NOs:13-17, 68, 82, and 91. Non-limiting examples of CPR polypeptides are set forth in SEQ ID NOs:20-22, 28, 69, 73, 74, 76, 87, and 98. Non-limiting examples of CDPS polypeptides are set forth in SEQ ID NOs:33-39. Non-limiting examples of CDPS-KS polypeptides are set forth in SEQ ID NOs:40-42. Non-limiting examples of GGPPS polypeptides are set forth in SEQ ID NOs:43-50.

In some embodiments, a recombinant host comprises a nucleic acid encoding a UGT85C2 polypeptide (SEQ ID NO:32), a nucleic acid encoding a UGT76G1 polypeptide (SEQ ID NO:83), a nucleic acid encoding a UGT74G1 polypeptide (SEQ ID NO:29), a nucleic acid encoding a UGT91D2 polypeptide, and/or a nucleic acid encoding a EUGT11 polypeptide (SEQ ID NO:86). In some aspects, the UGT91D2 polypeptide can be a UGT91D2e polypeptide (SEQ ID NO:84) or a UGT91D2e-b polypeptide (SEQ ID NO:88). The skilled worker will appreciate that expression of these genes may be necessary to produce a particular steviol glycoside but that one or more of these genes can be endogenous to the host provided that at least one (and in some embodiments, all) of these genes is a recombinant gene introduced into the recombinant host. In a particular embodiment, a steviol-producing recombinant microorganism comprises exogenous nucleic acids encoding UGT85C2, UGT76G1, or UGT91D2 polypeptides. In another particular embodiment, a steviol-producing recombinant microorganism comprises exogenous nucleic acids encoding UGT85C2, UGT76G1, UGT74G1, and UGT91D2 polypeptides. In yet another particular embodiment, a steviol-producing recombinant microorganism comprises exogenous nucleic acids encoding UGT85C2, UGT76G1, UGT74G1, and EUGT11 polypeptides. In yet another particular embodiment, a steviol-producing recombinant microorganism comprises the exogenous nucleic acids encoding UGT85C2, UGT76G1, UGT74G1, UGT91D2 (including inter alia 91D2e, 91D2m, 91D2e-b, and functional homologs thereof), and EUGT11 polypeptides.

In certain embodiments, the steviol glycoside is RebA, RebB, RebD, and/or RebM. RebA can be synthesized in a steviol-producing recombinant microorganism expressing UGT85C2, UGT76G1, UGT74G1, and UGT91D2. RebB can be synthesized in a steviol-producing recombinant microorganism expressing UGT85C2, UGT76G1, and UGT91D2. RebD can be synthesized in a steviol-producing recombinant microorganism expressing UGT85C2, UGT76G1 UGT74G1, and UGT91D2 and/or EUGT11. RebM can be synthesized in a steviol-producing recombinant microorganism expressing UGT85C2, UGT76G1, UGT74G1, and UGT91D2 and/or EUGT11 (see FIG. 2).

In some embodiments, steviol glycosides and/or steviol glycoside precursors are produced through contact of a steviol glycoside precursor with one or more enzymes involved in the steviol glycoside pathway in vitro. For example, contacting steviol with a UGT polypeptide can result in production of a steviol glycoside in vitro. In some embodiments, a steviol glycoside precursor is produced through contact of an upstream steviol glycoside precursor with one or more enzymes involved in the steviol glycoside pathway in vitro. For example, contacting ent-kaurenoic acid with a KAH enzyme can result in production of steviol in vitro.

In some embodiments, a steviol glycoside or steviol glycoside precursor is produced by whole cell bioconversion. For whole cell bioconversion to occur, a host cell expressing one or more enzymes involved in the steviol glycoside pathway takes up and modifies a steviol glycoside precursor in the cell; following modification in vivo, a steviol glycoside remains in the cell and/or is excreted into the culture medium. For example, a host cell expressing a gene encoding a UGT polypeptide can take up steviol and glycosylate steviol in the cell; following glycosylation in vivo, a steviol glycoside can be excreted into the culture medium. In some embodiments, the cell is permeabilized to take up a substrate to be modified or to excrete a modified product.

In some embodiments, steviol, one or more steviol glycoside precursors, and/or one or more steviol glycosides are produced by co-culturing of two or more hosts. In some embodiments, one or more hosts, each expressing one or more enzymes involved in the steviol glycoside pathway, produce steviol, one or more steviol glycoside precursors, and/or one or more steviol glycosides. For example, a host comprising a GGPPS, a CDPS, a KO, a KS, a KAH, and/or a CPR and a host comprising one or more UGTs produce one or more steviol glycosides.

In some embodiments, a steviol glycoside or steviol glycoside precursor composition produced in vivo, in vitro, or by whole cell bioconversion comprises less contaminants than a *stevia* extract from, inter alia, a *stevia* plant. Contaminants include plant-derived compounds that contribute to off-flavors. Potential contaminants include pigments, lipids, proteins, phenolics, saccharides, spathulenol and other sesquiterpenes, labdane diterpenes, monoterpenes, decanoic acid, 8,11,14-eicosatrienoic acid, 2-methyloctadecane, pentacosane, octacosane, tetracosane, octadecanol, stigmasterol, β-sitosterol, α-amyrin, β-amyrin, lupeol, β-amyrin acetate, pentacyclic triterpenes, centauredin, quercitin, epi-alpha-cadinol, carophyllenes and derivatives, beta-pinene, beta-sitosterol, and gibberellin.

As used herein, the terms "detectable amount," "detectable concentration," "measurable amount," and "measurable concentration" refer to a level of steviol glycosides measured in AUC, $\mu M/OD_{600}$, mg/L, $\mu M$, or mM. Steviol glycoside production (i.e., total, supernatant, and/or intracellular steviol glycoside levels) can be detected and/or analyzed by techniques generally available to one skilled in the art, for example, but not limited to, liquid chromatography-mass spectrometry (LC-MS), thin layer chromatography (TLC), high-performance liquid chromatography (HPLC), ultraviolet-visible spectroscopy/spectrophotometry (UV-Vis), mass spectrometry (MS), and nuclear magnetic resonance spectroscopy (NMR).

As used herein, the term "undetectable concentration" refers to a level of a compound that is too low to be measured and/or analyzed by techniques such as TLC, HPLC, UV-Vis, MS, or NMR. In some embodiments, a compound of an "undetectable concentration" is not present in a steviol glycoside or steviol glycoside precursor composition.

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z,"

"x or (y and z)," or "x or y or z." In some embodiments, "and/or" is used to refer to the exogenous nucleic acids that a recombinant cell comprises, wherein a recombinant cell comprises one or more exogenous nucleic acids selected from a group. In some embodiments, "and/or" is used to refer to production of steviol glycosides and/or steviol glycoside precursors. In some embodiments, "and/or" is used to refer to production of steviol glycosides, wherein one or more steviol glycosides are produced. In some embodiments, "and/or" is used to refer to production of steviol glycosides, wherein one or more steviol glycosides are produced through one or more of the following steps: culturing a recombinant microorganism, synthesizing one or more steviol glycosides in a recombinant microorganism, and/or isolating one or more steviol glycosides.

In some embodiments, the nucleotide sequence of a nucleic acid encoding a KO polypeptide is set forth in SEQ ID NO: 55, SEQ ID NO:56, SEQ ID NO:57, SEQ ID NO:58, SEQ ID NO:59, or SEQ ID NO:60, SEQ ID NO:63, SEQ ID NO:64, or SEQ ID NO:65. In some aspects, the nucleic acid encoding the KO polypeptide has at least 70% identity to the nucleotide sequence set forth in SEQ ID NO:55, SEQ ID NO:57, SEQ ID NO:59 or SEQ ID NO:60, at least 80% identity to the nucleotide sequence set forth in SEQ ID NO:56 or SEQ ID NO:58, at least 95% identity to the nucleotide sequence set forth in SEQ ID NO:63, or at least 75% identity to the nucleotide sequence set forth in SEQ ID NO:64 or SEQ ID NO:65. In some embodiments, the amino acid sequence of a KO enzyme is set forth in SEQ ID NO:54, SEQ ID NO:70, SEQ ID NO:71, SEQ ID NO:72, SEQ ID NO:75, SEQ ID NO:77, SEQ ID NO:78, OR SEQ ID NO:79. In some embodiments, a host cell comprises one or more copies of one or more nucleic acids encoding a KO polypeptide.

In some embodiments, expression of a KO gene set forth in SEQ ID NO:55 or SEQ ID NO:56 in a RebB-producing S. cerevisiae strain results in higher production of RebB compared to expression of SrKO1 (SEQ ID NO:59, SEQ ID NO:79) in a RebB-producing S. cerevisiae strain. See Example 3.

In some embodiments, expression of a KO gene set forth in SEQ ID NO:55, SEQ ID NO:56, or SEQ ID NO:57 in an S. cerevisiae strain capable of producing RebB with a functional KO results in production of ent-kaurenoic acid. See Example 3.

As used herein, the terms "ent-kaurenoic acid hydroxylase" and "steviol synthase" can be used interchangeably and be abbreviated "KAH." In some embodiments, the nucleotide sequence of a nucleic acid encoding a KAH enzyme is set forth in SEQ ID NO:18, SEQ ID NO:80, SEQ ID NO:81, SEQ ID NO:90, or SEQ ID NO:96. In some aspects, the nucleic acid encoding the KAH polypeptide has at least 75% identity to a nucleotide sequence set forth in SEQ ID NO:80; or at least 70% identity to a nucleotide sequence set forth in SEQ ID NO:18, SEQ ID NO:81, SEQ ID NO:90, or SEQ ID NO:96. In some embodiments, the amino acid sequence of a KAH enzyme is set forth in SEQ ID NO:68, SEQ ID NO:82, or SEQ ID NO:91. In some embodiments, a host cell comprises one or more copies of one or more nucleic acids encoding a KAH enzyme.

In some embodiments, one or more copies of SrKAHe1 (SEQ ID NO:18, SEQ ID NO:68) are expressed in an S. cerevisiae strain. For example, in some embodiments, two copies of SrKAHe1 (SEQ ID NO:18, SEQ ID NO:68) are expressed in an S. cerevisiae strain.

In some embodiments, the nucleotide sequence of a nucleic acid encoding a KAH enzyme is set forth in SEQ ID NO:80. The nucleic acid of SEQ ID NO:80 encodes a KAH with an amino acid sequence set forth in SEQ ID NO:82. A version of SEQ ID NO:80 codon-optimized for expression in S. cerevisiae is set forth in SEQ ID NO:81. In some embodiments, a host cell comprises one or more copies of one or more nucleic acids encoding a KAH enzyme. See Example 7.

In some embodiments, SrKAHe1 (SEQ ID NO:18, SEQ ID NO:68) and either the KAH encoded by the nucleotide sequence set forth in SEQ ID NO:80 or the KAH encoded by the codon-optimized nucleotide sequence set forth in SEQ ID NO:81 are co-expressed in a steviol glycoside-producing S. cerevisiae strain. In some embodiments, co-expression of SrKAHe1 (SEQ ID NO:18, SEQ ID NO:68) and either the KAH encoded by the nucleotide sequence set forth in SEQ ID NO:80 or the KAH encoded by the codon-optimized nucleotide sequence set forth in SEQ ID NO:81 in a steviol glycoside-producing strain results in higher production of steviol glycosides compared to a control steviol glycoside-producing strain or a steviol glycoside producing strain overexpressing SrKAHe1. See Example 7 and Table 6. In some aspects, overexpressing SrKAHe1 results in production of 85.5 µM 13-SMG, expression of SrKAHe1 and the KAH encoded by the nucleotide set forth in SEQ ID NO:80 results in production of 153.8 µM 13-SMG, and expression of SrKAHe1 and the KAH encoded by the nucleotide set forth in SEQ ID NO:81 results in production of 130.5 µM 13-SMG.

In some embodiments, a KO gene is expressed in a steviol glycoside-producing S. cerevisiae strain that further overexpresses SrKAHe1 (SEQ ID NO:18, SEQ ID NO:68). In some embodiments, expression of a KO gene of SEQ ID NO:55, SEQ ID NO:56, SEQ ID NO:57, SEQ ID NO:58, SEQ ID NO:59, or SEQ ID NO:60, SEQ ID NO:65 in a steviol glycoside-producing S. cerevisiae strain overexpressing SrKAHe1 results in higher expression of steviol glycosides compared to a control steviol-glycoside producing strain or a steviol glycoside-producing strain overexpressing SrKAHe1 (SEQ ID NO:18, SEQ ID NO:68). See Example 4.

In some embodiments, expression of a KO gene of SEQ ID NO:55, SEQ ID NO:56, SEQ ID NO:57, or SEQ ID NO:60 in a steviol glycoside-producing S. cerevisiae strain overexpressing SrKAHe1 (SEQ ID NO:18, SEQ ID NO:68) results in higher levels of glycosylated ent-kaurenoic acid compared to a control S. cerevisiae strain. See Example 4.

In some embodiments, expression of a KO gene of SEQ ID NO:55, SEQ ID NO:56, SEQ ID NO:57, SEQ ID NO:59, or SEQ ID NO:60 in a steviol glycoside-producing S. cerevisiae strain overexpressing SrKAHe1 (SEQ ID NO:18, SEQ ID NO:68) results in improved metabolic conversion of a glycosylated ent-kaurenol intermediate compound relative to a control S. cerevisiae strain or a steviol glycoside-producing S. cerevisiae strain overexpressing SrKAHe1 (SEQ ID NO:18, SEQ ID NO:68). See Example 4.

In some embodiments, a KAH is a *Prunus* KAH, such as a *Prunus avium*, *Prunus mume*, or *Prunus persica* KAH. In some embodiments, a KAH is a KAH of the CYP72A219 or CYP71A219-like family. In some embodiments, the nucleotide sequence of a nucleic acid encoding a KAH enzyme is set forth in SEQ ID NO:90 or SEQ ID NO:96. The nucleic acids of SEQ ID NO:90 and SEQ ID NO:96 encode a KAH from *Prunus avium* with an amino acid sequence set forth in SEQ ID NO:91. In some embodiments, a KAH polypeptide is a polypeptide with an amino acid sequence set forth in SEQ ID NO:92, SEQ ID NO:93, SEQ ID NO:94, or SEQ ID NO:95. In some embodiments, a KAH polypeptide is a KAH polypeptide with at least 50% sequence identity to an amino acid sequence set forth in SEQ ID NO:91, SEQ ID NO:92, SEQ ID NO:93, SEQ ID NO:94, or SEQ ID NO:95. In some embodiments, expression of a gene encoding a polypeptide having at least 50% sequence identity to an amino acid sequence set forth in SEQ ID NO:91, SEQ ID NO:92, SEQ ID NO:93, SEQ ID NO:94, or SEQ ID NO:95 in a recombinant host results in production of a steviol glycoside or steviol glycoside precursor, such as 13-SMG and/or rubusoside. See Example 8.

In some embodiments, the nucleotide sequence of the nucleic acid encoding a CPR enzyme is set forth in SEQ ID NO:23, SEQ ID NO:51, SEQ ID NO:61, SEQ ID NO:62, SEQ ID NO:66, SEQ ID NO:67, or SEQ ID NO:97. In some aspects, the nucleic acid encoding the CPR polypeptide has at least 75% identity to the nucleotide sequence set forth in SEQ ID NO:23, SEQ ID NO:61, or SEQ ID NO:62, or at least 70% identity to the nucleotide sequence set forth in SEQ ID NO:24, SEQ ID NO:66, SEQ ID NO:67, SEQ ID NO:51, or SEQ ID NO:97. In some embodiments, the amino acid sequence of the CPR enzyme is set forth in SEQ ID NO:22, SEQ ID NO:28, SEQ ID NO:69, SEQ ID NO:73, SEQ ID NO:74, or SEQ ID NO:76, SEQ ID NO:87, or SEQ ID NO:98. In some embodiments, a host cell comprises one or more copies of one or more nucleic acids encoding a CPR enzyme.

In a non-limiting example, SrKAHe1 is activated by the S. cerevisiae CPR encoded by gene NCP1 (YHR042VV). Enhanced activation of the KAH encoded by SrKAHe1 is observed when the Arabidopsis thaliana CPR encoded by the gene ATR2 (SEQ ID NO:51) or the S. rebaudiana CPR encoded by the genes CPR7 (SEQ ID NO:23) or CPR8 (SEQ ID NO:24, SEQ ID NO:28) are co-expressed in a recombinant cell. Amino acid sequences of the A. thaliana polypeptides ATR1 and ATR2 are set forth in SEQ ID NO:25 and SEQ ID NO:26, respectively. The S. rebaudiana polypeptides CPR7 and CPR8 are set forth in SEQ ID NO:27 and SEQ ID NO:28, respectively.

In some embodiments, expression of CPR1 (SEQ ID NO:61, SEQ ID NO:76) or of CPR7 in the steviol glycoside-producing S. cerevisiae strain co-expressing S. rebaudiana CPR8 (SEQ ID NO:24, SEQ ID NO:28) and A. thaliana ATR2 (SEQ ID NO:51) results in higher levels of RebM compared to a control steviol glycoside-producing S. cerevisiae strain expressing S. rebaudiana CPR8 (SEQ ID NO:24, SEQ ID NO:28) and A. thaliana ATR2 (SEQ ID NO:51). In some embodiments, expression of the CPR set forth in SEQ ID NO:62 in a steviol glycoside-producing S. cerevisiae strain overexpressing SrKAHe1 (SEQ ID NO:18, SEQ ID NO:68) results in higher levels of RebM compared to a steviol glycoside-producing S. cerevisiae strain that does not express the nucleic acid set forth in SEQ ID NO:62 or overexpress SrKAHe1. See Example 5.

In some embodiments, co-expression of SrKO1 (SEQ ID NO:59, SEQ ID NO:79) and a CPR gene of SEQ ID NO:66 or SEQ ID NO:77 in a RebB-producing strain results in higher production of 13-SMG and RebB than co-expression of a KO gene of SEQ ID NO:63 or SEQ ID NO:64 and a CPR gene of SEQ ID NO:66 or SEQ ID NO:77. See Example 6.

In some embodiments, CPR1 (SEQ ID NO:61, SEQ ID NO:76) or CPR12 (SEQ ID NO:97, SEQ ID NO:98) activates cytochrome c. In some embodiments, CPR1 (SEQ ID NO:61, SEQ ID NO:76) or CPR12 (SEQ ID NO:97, SEQ ID NO:98) in the presence of SrKAHe1 (SEQ ID NO:18, SEQ ID NO:68) activate cytochrome c. In some embodiments, CPR1 (SEQ ID NO:61, SEQ ID NO:76) or CPR12 (SEQ ID NO:97, SEQ ID NO:98) regulate conversion of ent-kaurenoic acid to steviol. In some embodiments, CPR1 (SEQ ID NO:61, SEQ ID NO:76) or CPR12 (SEQ ID NO:97, SEQ ID NO:98) in combination with SrKAHe1 (SEQ ID NO:18, SEQ ID NO:68) convert ent-kaurenoic acid to steviol. In some embodiments, steviol production is detected upon incubation of ent-kaurenoic acid with microsomal protein prepared from S. cerevisiae strains expressing CPR1 (SEQ ID NO:61, SEQ ID NO:76) or CPR12 (SEQ ID NO:97, SEQ ID NO:98) in combination with SrKAHe1 (SEQ ID NO:18, SEQ ID NO:68). In some embodiments, expression of CPR1 (SEQ ID NO:61, SEQ ID NO:76) or CPR12 (SEQ ID NO:97, SEQ ID NO:98) in a recombinant host results in production of a steviol glycoside or steviol glycoside precursor. See Example 9.

In some embodiments, a steviol glycoside-producing strain expresses a fusion construct comprising a KO and the NADPH-dependent P450 oxidoreductase domain of CYP102A1, referred to herein as "BMR." The codon-optimized nucleotide sequence encoding the BMR polypeptide is set forth in SEQ ID NO:117; the BMR amino acid sequence is set forth in SEQ ID NO:118. In some embodiments, BMR is a mutant BMR, including, but not limited to a BMR W1046A mutant (SEQ ID NO:119, SEQ ID NO:120). The BMR mutant can be specific for NADH. In some embodiments, the KO-BMR fusion construct comprises a linker (SEQ ID NO:121, SEQ ID NO:122). In some embodiments, the KO of the fusion construct is SrKO1 (SEQ ID NO:59, SEQ ID NO:79) or the KO encoded by the nucleotide sequence set forth in SEQ ID NO:65 (corresponding to the amino acid sequence set forth in SEQ ID NO:75). In some embodiments, the KO of the fusion construct is a truncated KO. Exemplary KO-BMR fusion constructs are set forth in SEQ ID NOs:99-112. See Example 10.

In some embodiments, expression of SrKO1-BMR fusion constructs (SEQ ID NOs:99-106) in a steviol glycoside-producing strain results in an increase in ent-kaurenoic acid, 13-SMG, and RebB levels, compared to expression of SrKO1 (SEQ ID NO:59, SEQ ID NO:79) in a steviol glycoside-producing strain. In some embodiments, expression of a fusion construct (SEQ ID NO:107, SEQ ID NO:108) in a steviol glycoside-producing strain results in greater conversion of ent-kaurene to ent-kaurenoic acid and greater conversion of ent-kaurenoic acid to 13-SMG, compared to expression of the KO encoded by the nucleotide sequence set forth in SEQ ID NO:65 in a steviol glycoside-producing strain. In some embodiments, expression of a fusion construct comprising the KO encoded by the nucleotide sequence set forth in SEQ ID NO:65 and the W1046A mutant BMR (SEQ ID NO:109, SEQ ID NO:110) results in increased ent-kaurenoic acid levels. See FIG. 16 (B and D) and Example 10.

In some embodiments, a steviol glycoside-producing strain comprises inheritance of cortical ER protein 2 (ICE2; SEQ ID NO:113, SEQ ID NO:114). ICE2 is also referred to as YIL090W. In some aspects, ICE2 is overexpressed. ICE2 can be expressed in a strain comprising CPR1 (SEQ ID NO:61, SEQ ID NO:76) and/or CPR12 (SEQ ID NO:97, SEQ ID NO:98). In some embodiments, a steviol glycoside-producing strain comprises two copies of ICE2. In some embodiments, expression of ICE2 increases ent-kaurene metabolism (resulting in decreased accumulation of ent-kaurene, ent-kaurenol, ent-kaurenal, and ent-kaurenol glycosides), resulting in increased accumulation of steviol glycosides, compared to a control strain. See Table 10 and Example 11.

In some embodiments, expression of the KO encoded by nucleotide sequence set forth in SEQ ID NO:56 in a steviol glycoside-producing strain cultivated by fermentation results in a lower accumulation of ent-kaurene compounds, compared to a control steviol glycoside-producing strain. In some aspects, higher levels of ent-kaurenoic acid and steviol glycosides result, as compared to a control strain. In some embodiments, expression of the KAH encoded by nucleotide sequence set forth in SEQ ID NO:80, the KO encoded by nucleotide sequence set forth in SEQ ID NO:56, and the KO encoded by nucleotide sequence set forth in SEQ ID NO:65 in a steviol glycoside-producing strain cultivated by fermentation results in decreased accumulation of ent-kaurene, ent-kaurenol, ent-kaurenal, ent-kaurenol glycosides, ent-kaurenoic acid, and ent-kaurenoic acid glycosides and increased production of steviol glycosides, as compared to a control strain. In some embodiments, expression of CPR12 (SEQ ID NO:97, SEQ ID NO:98), the KAH encoded by nucleotide sequence set forth in SEQ ID NO:80, and the KO encoded by nucleotide sequence set forth in SEQ ID NO:56 cultivated by fermentation results in decreased ent-kaurene, ent-kaurenol, ent-kaurenal, ent-kaurenol glycosides, ent-kaurenoic acid, and ent-kaurenoic acid glycosides accumulation and higher levels of steviol glycosides, as compared to a control strain. See Table 12 and Example 12.

Functional Homologs

Functional homologs of the polypeptides described above are also suitable for use in producing steviol glycosides in a recombinant host. A functional homolog is a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of steviol glycoside biosynthesis polypeptides. Sequence analysis can involve BLAST, Reciprocal BLAST, or PSI-BLAST analysis of non-redundant databases using a KO, KAH, or CPR amino acid sequence as the reference sequence. Amino acid sequence is, in some instances, deduced from the nucleotide sequence. Those polypeptides in the database that have greater than 40% sequence identity are candidates for further evaluation for suitability as a steviol glycoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in steviol glycoside biosynthesis polypeptides, e.g., conserved functional domains. In some embodiments, nucleic acids and polypeptides are identified from transcriptome data based on expression levels rather than by using BLAST analysis.

Conserved regions can be identified by locating a region within the primary amino acid sequence of a steviol glycoside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., *Nucl. Acids Res.*, 26:320-322 (1998); Sonnhammer et al., Proteins, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing steviol in a recombinant host include functional homologs of KO, KAH, and CPR.

Methods to modify the substrate specificity of, for example, KO, KAH, or CPR, are known to those skilled in the art, and include without limitation site-directed/rational mutagenesis approaches, random directed evolution approaches and combinations in which random mutagenesis/saturation techniques are performed near the active site of the enzyme. For example see Osmani et al., 2009, *Phytochemistry* 70: 325-347.

A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200% of the length of the reference sequence. A functional homolog polypeptide typically has a length that is from 95% to 105% of the length of the reference sequence, e.g., 90, 93, 95, 97, 99, 100, 105, 110, 115, or 120% of the length of the reference sequence, or any range between. A % identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program ClustalW (version 1.83, default parameters), which allows alignments of nucleic acid or polypeptide sequences to be carried out across their entire length (global alignment). Chenna et al., 2003, *Nucleic Acids Res.* 31(13):3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: % age; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method:% age; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine % identity of a candidate nucleic acid or amino acid sequence to a reference sequence, the sequences are aligned using ClustalW, the number of identical matches in the alignment is divided by the length of the reference sequence, and the result is multiplied by 100. It is noted that the % identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional KO, KAH, or CPR proteins can include additional amino acids that are not involved in the enzymatic activities carried out by the enzymes. In some embodiments, KO, KAH, or CPR proteins are fusion proteins. The terms "chimera," "fusion polypeptide," "fusion protein," "fusion enzyme," "fusion construct," "chimeric protein," "chimeric polypeptide," "chimeric construct," and "chimeric enzyme" can be used interchangeably herein to refer to proteins engineered through the joining of two or more genes that code for different proteins. In some embodiments, a nucleic acid sequence encoding a KO, KAH, or CPR polypeptide can include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the polypeptide such that the encoded tag is located at either the carboxyl or amino terminus of the polypeptide. Non-limiting examples of encoded tags include green fluorescent protein (GFP), human influenza hemagglutinin (HA), glutathione S transferase (GST), polyhistidine-tag (HIS tag), and Flag™ tag (Kodak, New Haven, Conn.). Other examples of tags include a chloroplast transit peptide, a mitochondrial transit peptide, an amyloplast peptide, signal peptide, or a secretion tag.

In some embodiments, a fusion protein is a protein altered by domain swapping. As used herein, the term "domain swapping" is used to describe the process of replacing a domain of a first protein with a domain of a second protein. In some embodiments, the domain of the first protein and the domain of the second protein are functionally identical or functionally similar. In some embodiments, the structure and/or sequence of the domain of the second protein differs from the structure and/or sequence of the domain of the first protein. In some embodiments, a KO polypeptide is altered by domain swapping. See Example 10.

Steviol and Steviol Glycoside Biosynthesis Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes can be combined in a recombinant nucleic acid construct in "modules" useful for a discrete aspect of steviol and/or steviol glycoside production. Combining a plurality of genes in a module, particularly a polycistronic module, facilitates the use of the module in a variety of species. For example, a steviol biosynthesis gene cluster, or a UGT gene cluster, can be combined in a polycistronic module such that, after insertion of a suitable regulatory region, the module can be introduced into a wide variety of species. As another example, a UGT gene cluster can be combined such that each UGT coding sequence is operably linked to a separate regulatory region, to form a UGT module. Such a module can be used in those species for which monocistronic expression is necessary or desirable. In addition to genes useful for steviol or steviol glycoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards steviol or steviol glycoside biosynthesis. For example, it may be desirable to downregulate synthesis of sterols in a yeast strain in order to further increase steviol or steviol glycoside production, e.g., by downregulating squalene epoxidase. As another example, it may be desirable to inhibit degradative functions of certain endogenous gene products, e.g., glycohydrolases that remove glucose moieties from secondary metabolites or phosphatases as discussed herein. In such cases, a nucleic acid that overexpresses the polypeptide or gene product may be included in a recombinant construct that is transformed into the strain. Alternatively, mutagenesis can be used to generate mutants in genes for which it is desired to increase or enhance function.

Host Microorganisms

Recombinant hosts can be used to express polypeptides for the producing steviol glycosides, including mammalian, insect, plant, and algal cells. A number of prokaryotes and eukaryotes are also suitable for use in constructing the recombinant microorganisms described herein, e.g., gram-negative bacteria, yeast, and fungi. A species and strain selected for use as a steviol glycoside production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function(s).

Typically, the recombinant microorganism is grown in a fermenter at a defined temperature(s) for a desired period of time. The constructed and genetically engineered microorganisms provided by the invention can be cultivated using conventional fermentation processes, including, inter alia, chemostat, batch, fed-batch cultivations, semi-continuous fermentations such as draw and fill, continuous perfusion fermentation, and continuous perfusion cell culture. Depending on the particular microorganism used in the method, other recombinant genes such as isopentenyl biosynthesis genes and terpene synthase and cyclase genes may also be present and expressed. Levels of substrates and intermediates, e.g., isopentenyl diphosphate, dimethylallyl diphosphate, GGPP, ent-kaurene and ent-kaurenoic acid, can be determined by extracting samples from culture media for analysis according to published methods.

Carbon sources of use in the instant method include any molecule that can be metabolized by the recombinant host cell to facilitate growth and/or production of the steviol glycosides. Examples of suitable carbon sources include, but are not limited to, sucrose (e.g., as found in molasses), fructose, xylose, ethanol, glycerol, glucose, cellulose, starch, cellobiose or other glucose-comprising polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

After the recombinant microorganism has been grown in culture for the desired period of time, steviol and/or one or more steviol glycosides can then be recovered from the culture using various techniques known in the art. In some embodiments, a permeabilizing agent can be added to aid the feedstock entering into the host and product getting out. For example, a crude lysate of the cultured microorganism can be centrifuged to obtain a supernatant. The resulting supernatant can then be applied to a chromatography column, e.g., a C-18 column, and washed with water to remove hydrophilic compounds, followed by elution of the compound(s) of interest with a solvent such as methanol. The compound(s) can then be further purified by preparative HPLC. See also, WO 2009/140394.

It will be appreciated that the various genes and modules discussed herein can be present in two or more recombinant hosts rather than a single host. When a plurality of recombinant hosts is used, they can be grown in a mixed culture to accumulate steviol and/or steviol glycosides.

Alternatively, the two or more hosts each can be grown in a separate culture medium and the product of the first culture medium, e.g., steviol, can be introduced into second culture medium to be converted into a subsequent intermediate, or into an end product such as, for example, RebA. The product produced by the second, or final host is then recovered. It will also be appreciated that in some embodiments, a recombinant host is grown using nutrient sources other than a culture medium and utilizing a system other than a fermenter.

Exemplary prokaryotic and eukaryotic species are described in more detail below. However, it will be appreciated that other species can be suitable. For example, suitable species can be in a genus such as *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia, Phy-* scomitrella, *Rhodoturula*, *Saccharomyces*, *Schizosaccharomyces*, *Sphaceloma*, *Xanthophyllomyces* or *Yarrowia*. Exemplary species from such genera include *Lentinus tigrinus*, *Laetiporus sulphureus*, *Phanerochaete chrysosporium*, *Pichia pastoris*, *Cyberlindnera jadinii*, *Physcomitrella patens*, *Rhodoturula glutinis*, *Rhodoturula mucilaginosa*, *Phaffia rhodozyma*, *Xanthophyllomyces dendrorhous*, *Fusarium fujikuroi/Gibberella fujikuroi*, *Candida utilis*, *Candida glabrata*, *Candida albicans*, and *Yarrowia lipolytica*.

In some embodiments, a microorganism can be a prokaryote such as *Escherichia* bacteria cells, for example, *Escherichia coli* cells; *Lactobacillus* bacteria cells; *Lactococcus* bacteria cells; *Cornebacterium* bacteria cells; *Acetobacter* bacteria cells; *Acinetobacter* bacteria cells; or *Pseudomonas* bacterial cells.

In some embodiments, a microorganism can be an Ascomycete such as *Gibberella fujikuroi*, *Kluyveromyces lactis*, *Schizosaccharomyces pombe*, *Aspergillus niger*, *Yarrowia lipolytica*, *Ashbya gossypii*, or *S. cerevisiae*.

In some embodiments, a microorganism can be an algal cell such as *Blakeslea trispora*, *Dunaliella salina*, *Haematococcus pluvialis*, *Chlorella* sp., *Undaria pinnatifida*, *Sargassum*, *Laminaria japonica*, *Scenedesmus almeriensis* species.

In some embodiments, a microorganism can be a cyanobacterial cell such as *Blakeslea trispora*, *Dunaliella salina*, *Haematococcus pluvialis*, *Chlorella* sp., *Undaria pinnatifida*, *Sargassum*, *Laminaria japonica*, *Scenedesmus almeriensis*.

*Saccharomyces* spp.

*Saccharomyces* is a widely used chassis organism in synthetic biology, and can be used as the recombinant microorganism platform. For example, there are libraries of mutants, plasmids, detailed computer models of metabolism and other information available for *S. cerevisiae*, allowing for rational design of various modules to enhance product yield. Methods are known for making recombinant microorganisms.

*Aspergillus* spp.

*Aspergillus* species such as *A. oryzae*, *A. niger* and *A. sojae* are widely used microorganisms in food production and can also be used as the recombinant microorganism platform. Nucleotide sequences are available for genomes of *A. nidulans*, *A. fumigatus*, *A. oryzae*, *A. clavatus*, *A. flavus*, *A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for producing steviol glycosides.

*E. coli*

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus*, *Gibberella*, and *Phanerochaete* spp.

*Agaricus*, *Gibberella*, and *Phanerochaete* spp. can be useful because they are known to produce large amounts of isoprenoids in culture. Thus, the terpene precursors for producing large amounts of steviol glycosides are already produced by endogenous genes. Thus, modules comprising recombinant genes for steviol glycoside biosynthesis polypeptides can be introduced into species from such genera without the necessity of introducing mevalonate or MEP pathway genes.

*Arxula adeninivorans* (*Blastobotrys adeninivorans*)

*Arxula adeninivorans* is dimorphic yeast (it grows as budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica*

*Yarrowia lipolytica* is dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g. alkanes, fatty acids, oils) and can grow on sugars. It has a high potential for industrial applications and is an oleaginous microorgamism. *Yarrowia lipolytica* can accumulate lipid content to approximately 40% of its dry cell weight and is a model organism for lipid accumulation and remobilization. See e.g., Nicaud, 2012, *Yeast* 29(10):409-18; Beopoulos et al., 2009, *Biochimie* 91(6):692-6; Bankar et al., 2009, *Appl Microbiol Biotechnol.* 84(5):847-65.

*Rhodotorula* sp.

*Rhodotorula* is unicellular, pigmented yeast. The oleaginous red yeast, *Rhodotorula glutinis*, has been shown to produce lipids and carotenoids from crude glycerol (Saenge et al., 2011, *Process Biochemistry* 46(1):210-8). *Rhodotorula toruloides* strains have been shown to be an efficient fed-batch fermentation system for improved biomass and lipid productivity (Li et al., 2007, *Enzyme and Microbial Technology* 41:312-7).

*Rhodosporidium toruloides*

*Rhodosporidium toruloides* is oleaginous yeast and useful for engineering lipid-production pathways (See e.g. Zhu et al., 2013, *Nature Commun.* 3:1112; Ageitos et al., 2011, *Applied Microbiology and Biotechnology* 90 (4): 1219-27).

*Candida boidinii*

*Candida boidinii* is methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, *Methods Mol Biol.* 824:329-58; Khoury et al., 2009, *Protein Sci.* 18(10):2125-38.

*Hansenula polymorpha* (*Pichia angusta*)

*Hansenula polymorpha* is methylotrophic yeast (see *Candida boidinii*). It can furthermore grow on a wide range of other substrates; it is thermo-tolerant and can assimilate nitrate (see also *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, *Virol Sin.* 29(6):403-9.

*Kluyveromyces lactis*

*Kluyveromyces lactis* is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, *FEMS Yeast Res.* 6(3):381-92.

Pichia pastoris

*Pichia pastoris* is methylotrophic yeast (see *Candida boidinii* and *Hansenula polymorpha*). It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al., 2014, *N Biotechnol.* 31(6):532-7.

Physcomitrella spp.

*Physcomitrella* mosses, when grown in suspension culture, have characteristics similar to yeast or other fungal cultures. This genera can be used for producing plant secondary metabolites, which can be difficult to produce in other types of cells.

Steviol Glycoside Compositions

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides (e.g., RebD or RebM) and have a consistent taste profile. As used herein, the term "enriched" is used to describe a steviol glycoside composition with an increased proportion of a particular steviol glycoside, compared to a steviol glycoside composition (extract) from a *stevia* plant. Thus, the recombinant hosts described herein can facilitate the production of compositions that are tailored to meet the sweetening profile desired for a given food product and that have a proportion of each steviol glycoside that is consistent from batch to batch. In some embodiments, hosts described herein do not produce or produce a reduced amount of undesired plant by-products found in *Stevia* extracts. Thus, steviol glycoside compositions produced by the recombinant hosts described herein are distinguishable from compositions derived from *Stevia* plants.

The amount of an individual steviol glycoside (e.g., RebA, RebB, RebD, or RebM) accumulated can be from about 1 to about 7,000 mg/L, e.g., about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L, at least about 1,000 mg/L, at least about 1,200 mg/L, at least about at least 1,400 mg/L, at least about 1,600 mg/L, at least about 1,800 mg/L, at least about 2,800 mg/L, or at least about 7,000 mg/L. In some aspects, the amount of an individual steviol glycoside can exceed 7,000 mg/L. The amount of a combination of steviol glycosides (e.g., RebA, RebB, RebD, or RebM) accumulated can be from about 1 mg/L to about 7,000 mg/L, e.g., about 200 to about 1,500, at least about 2,000 mg/L, at least about 3,000 mg/L, at least about 4,000 mg/L, at least about 5,000 mg/L, at least about 6,000 mg/L, or at least about 7,000 mg/L. In some aspects, the amount of a combination of steviol glycosides can exceed 7,000 mg/L. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce steviol and/or steviol glycosides. For example, a first microorganism can comprise one or more biosynthesis genes for producing a steviol glycoside precursor, while a second microorganism comprises steviol glycoside biosynthesis genes. The product produced by the second, or final microorganism is then recovered. It will also be appreciated that in some embodiments, a recombinant microorganism is grown using nutrient sources other than a culture medium and utilizing a system other than a fermenter.

Alternatively, the two or more microorganisms each can be grown in a separate culture medium and the product of the first culture medium, e.g., steviol, can be introduced into second culture medium to be converted into a subsequent intermediate, or into an end product such as RebA. The product produced by the second, or final microorganism is then recovered. It will also be appreciated that in some embodiments, a recombinant microorganism is grown using nutrient sources other than a culture medium and utilizing a system other than a fermenter.

Steviol glycosides and compositions obtained by the methods disclosed herein can be used to make food products, dietary supplements and sweetener compositions. See, e.g., WO 2011/153378, WO 2013/022989, WO 2014/122227, and WO 2014/122328.

For example, substantially pure steviol or steviol glycoside such as RebM or RebD can be included in food products such as ice cream, carbonated beverages, fruit juices, yogurts, baked goods, chewing gums, hard and soft candies, and sauces. Substantially pure steviol or steviol glycoside can also be included in non-food products such as pharmaceutical products, medicinal products, dietary supplements and nutritional supplements. Substantially pure steviol or steviol glycosides may also be included in animal feed products for both the agriculture industry and the companion animal industry. Alternatively, a mixture of steviol and/or steviol glycosides can be made by culturing recombinant microorganisms separately, each producing a specific steviol or steviol glycoside, recovering the steviol or steviol glycoside in substantially pure form from each microorganism and then combining the compounds to obtain a mixture comprising each compound in the desired proportion. The recombinant microorganisms described herein permit more precise and consistent mixtures to be obtained compared to current *Stevia* products.

In another alternative, a substantially pure steviol or steviol glycoside can be incorporated into a food product along with other sweeteners, e.g. saccharin, dextrose, sucrose, fructose, erythritol, aspartame, sucralose, monatin, or acesulfame potassium. The weight ratio of steviol or steviol glycoside relative to other sweeteners can be varied as desired to achieve a satisfactory taste in the final food product. See, e.g., U.S. 2007/0128311. In some embodiments, the steviol or steviol glycoside may be provided with a flavor (e.g., citrus) as a flavor modulator.

Compositions produced by a recombinant microorganism described herein can be incorporated into food products. For example, a steviol glycoside composition produced by a recombinant microorganism can be incorporated into a food product in an amount ranging from about 20 mg steviol glycoside/kg food product to about 1800 mg steviol glycoside/kg food product on a dry weight basis, depending on the type of steviol glycoside and food product. For example, a steviol glycoside composition produced by a recombinant microorganism can be incorporated into a dessert, cold confectionary (e.g., ice cream), dairy product (e.g., yogurt), or beverage (e.g., a carbonated beverage) such that the food product has a maximum of 500 mg steviol glycoside/kg food on a dry weight basis. A steviol glycoside composition produced by a recombinant microorganism can be incorporated into a baked good (e.g., a biscuit) such that the food product has a maximum of 300 mg steviol glycoside/kg food on a dry weight basis. A steviol glycoside composition produced by a recombinant microorganism can be incorporated into a sauce (e.g., chocolate syrup) or vegetable product (e.g., pickles) such that the food product has a maximum of 1000 mg steviol glycoside/kg food on a dry weight basis. A steviol glycoside composition produced by a recombinant microorganism can be incorporated into a bread such that the food product has a maximum of 160 mg steviol glycoside/kg food on a dry weight basis. A steviol glycoside composition produced by a recombinant microorganism, plant, or plant cell can be incorporated into a hard or soft candy such that the food product has a maximum of 1600 mg steviol glycoside/kg food on a dry weight basis. A steviol glycoside composition produced by a recombinant microorganism, plant, or plant cell can be incorporated into a processed fruit product (e.g., fruit juices, fruit filling, jams, and jellies) such that the food product has a maximum of 1000 mg steviol glycoside/kg food on a dry weight basis. In some embodiments, a steviol glycoside composition produced herein is a component of a pharmaceutical composition. See, e.g., Steviol Glycosides Chemical and Technical Assessment 69th JECFA, 2007, prepared by Harriet Wallin, Food Agric. Org.; EFSA Panel on Food Additives and Nutrient Sources added to Food (ANS), "Scientific Opinion on the safety of steviol glycosides for the proposed uses as a food additive," 2010, *EFSA Journal* 8(4):1537; U.S. Food and Drug Administration GRAS Notice 323; U.S Food and Drug Administration GRAS Notice Notice 329; WO 2011/037959; WO 2010/146463; WO 2011/046423; and WO 2011/056834.

For example, such a steviol glycoside composition can have from 90-99 weight % RebA and an undetectable amount of *stevia* plant-derived contaminants, and be incorporated into a food product at from 25-1600 mg/kg, e.g., 100-500 mg/kg, 25-100 mg/kg, 250-1000 mg/kg, 50-500 mg/kg or 500-1000 mg/kg on a dry weight basis.

Such a steviol glycoside composition can be a RebB-enriched composition having greater than 3 weight % RebB and be incorporated into the food product such that the amount of RebB in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebB-enriched composition has an undetectable amount of *stevia* plant-derived contaminants.

Such a steviol glycoside composition can be a RebD-enriched composition having greater than 3 weight % RebD and be incorporated into the food product such that the amount of RebD in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebD-enriched composition has an undetectable amount of *stevia* plant-derived contaminants.

Such a steviol glycoside composition can be a RebE-enriched composition having greater than 3 weight % RebE and be incorporated into the food product such that the amount of RebE in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebE-enriched composition has an undetectable amount of *stevia* plant-derived contaminants.

Such a steviol glycoside composition can be a RebM-enriched composition having greater than 3 weight % RebM and be incorporated into the food product such that the amount of RebM in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebM-enriched composition has an undetectable amount of *stevia* plant-derived contaminants.

In some embodiments, a substantially pure steviol or steviol glycoside is incorporated into a tabletop sweetener or "cup-for-cup" product. Such products typically are diluted to the appropriate sweetness level with one or more bulking agents, e.g., maltodextrins, known to those skilled in the art. Steviol glycoside compositions enriched for RebA, RebB, RebD, RebE, or RebM, can be package in a sachet, for example, at from 10,000 to 30,000 mg steviol glycoside/kg product on a dry weight basis, for tabletop use. In some embodiments, a steviol glycoside produced in vitro, in vivo, or by whole cell bioconversion The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Example 1. LC-MS Analytical Procedures

Three LC-MS procedures were used herein. In the first method used for Examples 2-6, LC-MS analyses were performed using an Ultimate 3000 UPLC system (Dionex) fitted with a Waters Acquity UPLC®BEH shield RP18 column (2.1×50 mm, 1.7 µm particles, 130 Å pore size) connected to a TSQ Quantum Access (ThermoFisher Scientific) triple quadropole mass spectrometer with a heated electrospray ion (HESI) source. Elution was carried out using a mobile phase of eluent B (MeCN with 0.1% formic acid) and eluent A (water with 0.1% formic acid) by increasing the gradient from 25% to 47% B from min 0.0 to 4.0, increasing 47% to 100% B from min 4.0 to 5.0, and holding 100% B from min 5.0 to 6.5. The flow rate was 0.4 mL/min and the column temperature 35° C. Steviol glycosides were detected using SIM (Single Ion Monitoring) with the following m/z-traces.

TABLE 1A

LC-MS analytical information for Steviol Glycosides.

| Description | Exact Mass | m/z trace (Da) | compound (typical $t_R$ in min) |
|---|---|---|---|
| Steviol + 1 Glucose | [M + H]$^+$ 481.2796 [M + Na]$^+$ 503.2615 | 481.2 ± 0.5 503.1 ± 0.5 | 19-SMG (2.29), 13-SMG (3.5) |
| Steviol + 2 Glucose | [M + Na]$^+$ 665.3149 | 665 ± 0.5 | Rubusoside (2.52) Steviol-1,2-bioside (2.92) Steviol-1,3-bioside (2.28) |
| Steviol + 3 Glucose | [M + Na]$^+$ 827.3677 | 827.4 ± 0.5 | 1,2-Stevioside (2.01) 1,3-Stevioside (2.39) Rebaudioside B (2.88) |
| Steviol + 4 Glucose | [M + Na]$^+$ 989.4200 | 989.4 ± 0.5 | Rebaudioside A (2.0) |
| Steviol + 5 Glucose | [M + Na]$^+$ 1151.4728 | 1151.4 ± 0.5 | Rebaudioside D (1.1) |

TABLE 1A-continued

LC-MS analytical information for Steviol Glycosides.

| Description | Exact Mass | m/z trace (Da) | compound (typical $t_R$ in min) |
|---|---|---|---|
| Steviol + 6 Glucose | [M + Na]⁺ 1313.5257 | 1313.5 ± 0.5 | Rebaudioside M (1.3) |

In the second method used for Examples 7, 8, and 10, LC-MS analyses were performed on Waters ACQUITY UPLC (Waters Corporation, Milford, Mass.) with coupled to a Waters ACQUITY ESI (electrospray ionization)-TQD triple quadropole mass spectrometer. Compound separation was achieved on Waters ACQUITY UPLC® BEH C18 column (2.1×50 mm, 1.7 μm particles, 130 Å pore size) equipped with ACQUITY UPLC BEH C18 VanGuard pre-column (130 Å, 1.7 μm, 2.1 mm×5 mm) by using a gradient of the two mobile phases: A (Water with 0.1% formic acid) and B (Acetonitrile with 0.1% formic acid) increasing B from 20% to 50% between 0.3 to 2.0 min up to 100% at 2.01 min, holding to 100% for 0.6 min, and re-equilibrating for 0.6 min. The flow rate was 0.6 mL/min, and the column temperature was 55° C. The MS acquisition was in negative ion-mode using SIM mode (Single Ion Monitoring). Steviol glycoside quantification was done by comparison with authentic standards.

TABLE 1B

MS analytical information for Steviol Glycosides.

| Compound | m/z trace (Da) | Retention time (min) |
|---|---|---|
| RebE | 965.42 | 1.06 |
| RebD | 1127.48 | 1.09 |
| RebM | 1289.53 | 1.15 |
| RebA | 965.42 | 1.43 |
| 1,3-Stevioside | 803.37 | 1.60 |
| Rubusoside | 641.32 | 1.67 |
| RebB | 803.37 | 1.76 |
| 1,2-bioside | 641.32 | 1.77 |
| 13-SMG | 479.26 | 2.04 |

In the third method used for Example 9, LC-MS analyses were performed on Waters ACQUITY UPLC (Waters Corporation, Milford, Mass.) using a Waters Acquity UPLC® BEH C18 column (2.1×50 mm, 1.7 μm particles, 130 Å) coupled to a Waters single quadrupole mass spectrometer (SQD), equipped with an ESI and operated in negative mode. Compound separation was achieved by a gradient of the two mobile phases: A (water with 0.1% formic acid) and B (acetonitrile with 0.1% formic acid) by increasing from 60% to 100% B between 0.3 to 2.5 min, holding 100% B for 0.1 min, and re-equilibrating for 0.2 min. The flow rate was 0.6 mL/min, and the column temperature was set at 55° C. Steviol or ent-kaurenoic acid was monitored using SIM (Single Ion Monitoring) and quantified by comparing with authentic standards.

TABLE 1C

MS analytical information for steviol and ent-kaurenoic acid.

| Compound | m/z trace (Da) | Retention time (min) |
|---|---|---|
| Steviol | 317.21 | 0.61 |
| Ent-kaurenoic acid | 301.001 | 1.46 |

Example 2. Construction of Steviol Glycoside-Producing and RebB-Producing Yeast Strains Steviol glycoside-producing *S. cerevisiae* strains were constructed as described in WO 2011/153378, WO 2013/022989, WO 2014/122227, and WO 2014/122328. For example, a yeast strain comprising a recombinant gene encoding a *Synechococcus* sp. GGPPS (SEQ ID NO:49) polypeptide, a recombinant gene encoding a truncated *Zea mays* CDPS (SEQ ID NO:37) polypeptide, a recombinant gene encoding an *A. thaliana* KS (SEQ ID NO:6) polypeptide, a recombinant gene encoding an *S. rebaudiana* KO (SEQ ID NO:59, SEQ ID NO:79) polypeptide, a recombinant gene encoding an *A. thaliana* ATR2 (SEQ ID NO:51, SEQ ID NO:87) polypeptide, a recombinant gene encoding an *O. sativa* EUGT11 (SEQ ID NO:86) polypeptide, a recombinant gene encoding an SrKAHe1 (SEQ ID NO:18, SEQ ID NO:68) polypeptide, a recombinant gene encoding an *S. rebaudiana* CPR8 (SEQ ID NO:24, SEQ ID NO:28) polypeptide, a recombinant gene encoding an *S. rebaudiana* UGT85C2 (SEQ ID NO:30) polypeptide, a recombinant gene encoding an *S. rebaudiana* UGT74G1 (SEQ ID NO:29) polypeptide, a recombinant gene encoding an *S. rebaudiana* UGT76G1 (SEQ ID NO:2) polypeptide, and a recombinant gene encoding an *S. rebaudiana* UGT91D2 variant, UGT91D2e-b (SEQ ID NO:88), polypeptide accumulated steviol glycosides.

The UGT91D2e-b variant of UGT91D2 (SEQ ID NO:5 from PCT/US2012/050021) includes a substitution of a methionine for leucine at position 211 and a substitution of an alanine for valine at position 286. Additional variants can include variants (except T144S, M152L, L213F, S364P, and G384C variants) described in Table 14 and Example 11 of the PCT/US2012/050021. GeneArt codon-optimized sequence encoding a *S. rebaudiana* UGT91D2e-b with the amino acid modifications L211M and V286A (SEQ ID NO:88 for amino acid sequence; codon optimized nucleotide sequence is set forth in SEQ ID NO:89) and expressed from the native yeast TDH3 promoter and followed by the native yeast CYC1 terminator.

Cells were grown in Synthetic Complete (SC) medium at 30° C. for 5 days with shaking (400 rpm for deep wells and 200 rpm for 15 mL Falcon growth tubes) prior to harvest. Culture samples (without cell removal) were heated in the presence of DMSO for detection of total glycoside levels with LC-MS. The strain accumulated total amounts of RebD of over 2500 mg/L, total amounts of RebM of over 2500 mg/L, and total amounts of RebA of over 700 mg/L. See WO 2014/122227.

A separate *S. cerevisiae* strain was constructed to accumulate RebB. This strain comprised a recombinant gene encoding a *Synechococcus* sp. GGPPS (SEQ ID NO:49) polypeptide, a recombinant gene encoding a truncated *Z. mays* CDPS (SEQ ID NO:37) polypeptide, a recombinant gene encoding an *A. thaliana* KS (SEQ ID NO:6) polypeptide, a recombinant gene encoding an *S. rebaudiana* KO (SEQ ID NO:59, SEQ ID NO:79) polypeptide, a recombinant gene encoding an *A. thaliana* ATR2 (SEQ ID NO:51, SEQ ID NO:87) polypeptide, a recombinant gene encoding an *O. sativa* EUGT11 (SEQ ID NO:86) polypeptide, a recombinant gene encoding an SrKAHe1 (SEQ ID NO:18, SEQ ID NO:68) polypeptide, a recombinant gene encoding an *S. rebaudiana* CPR8 (SEQ ID NO:24, SEQ ID NO:28) polypeptide, a recombinant gene encoding an *S. rebaudiana* UGT85C2 (SEQ ID NO:30) polypeptide, a recombinant gene encoding an *S. rebaudiana* UGT76G1 (SEQ ID NO:2)

polypeptide, and a recombinant gene encoding an *S. rebaudiana* UGT91D2 variant, UGT91D2e-b (SEQ ID NO:88), polypeptide accumulated steviol glycosides.

Example 3. Steviol Glycoside Production in Yeast Strains Expressing KO Genes

To determine whether increased levels of ent-kaurenoic acid improve steviol glycoside production, the activity of KO genes from various species were analyzed. Putative KO genes were identified using the NCBI Basic Local Alignment Sequence Search Tool (BLAST). Genes encoding KO polypeptides were cloned and expressed the RebB-producing *S. cerevisiae* strain described in Example 2, which was modified to lack KO genes. Thus, RebB was only accumulated upon expression of a functional KO.

Figure 3:
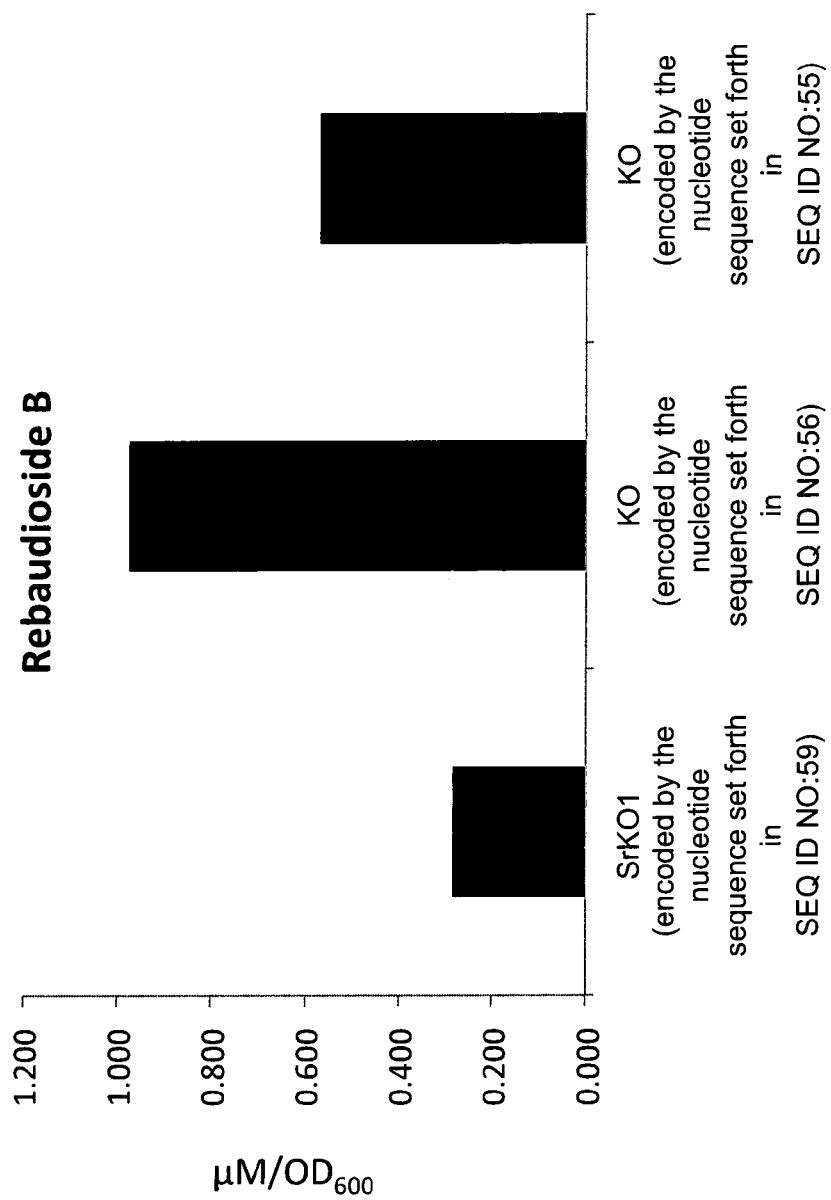
FIG. 3 shows Rebaudioside B (RebB) production in a steviol glycoside-producing *S. cerevisiae* strain individually expressing *S. rebaudiana* KO1 (SrKO1) encoded by the nucleotide sequence set forth in SEQ ID NO:59, the KO encoded by the codon-optimized nucleotide sequence set forth in SEQ ID NO:55, or the KO encoded by the nucleotide sequence set forth in SEQ ID NO:56. RebB production was measured by liquid chromatography-mass spectrometry (LC-MS) analysis as $\mu M/OD_{600}$ of individual cultures. See Example 3.

Two KO polypeptides identified by the amino acid sequences set forth in SEQ ID NO:54 (nucleotide sequence set forth in SEQ ID NO:55) and SEQ ID NO:75 (nucleotide sequences set forth in SEQ ID NO:56) were found to accumulate higher levels of RebB than SrKO1 (nucleotide sequence set forth in SEQ ID NO:59, amino acid sequences set forth in SEQ ID NO:79) in the RebB-producing strain. RebB levels ($\mu M/OD_{600}$) are shown in FIG. 3.

Figure 4:
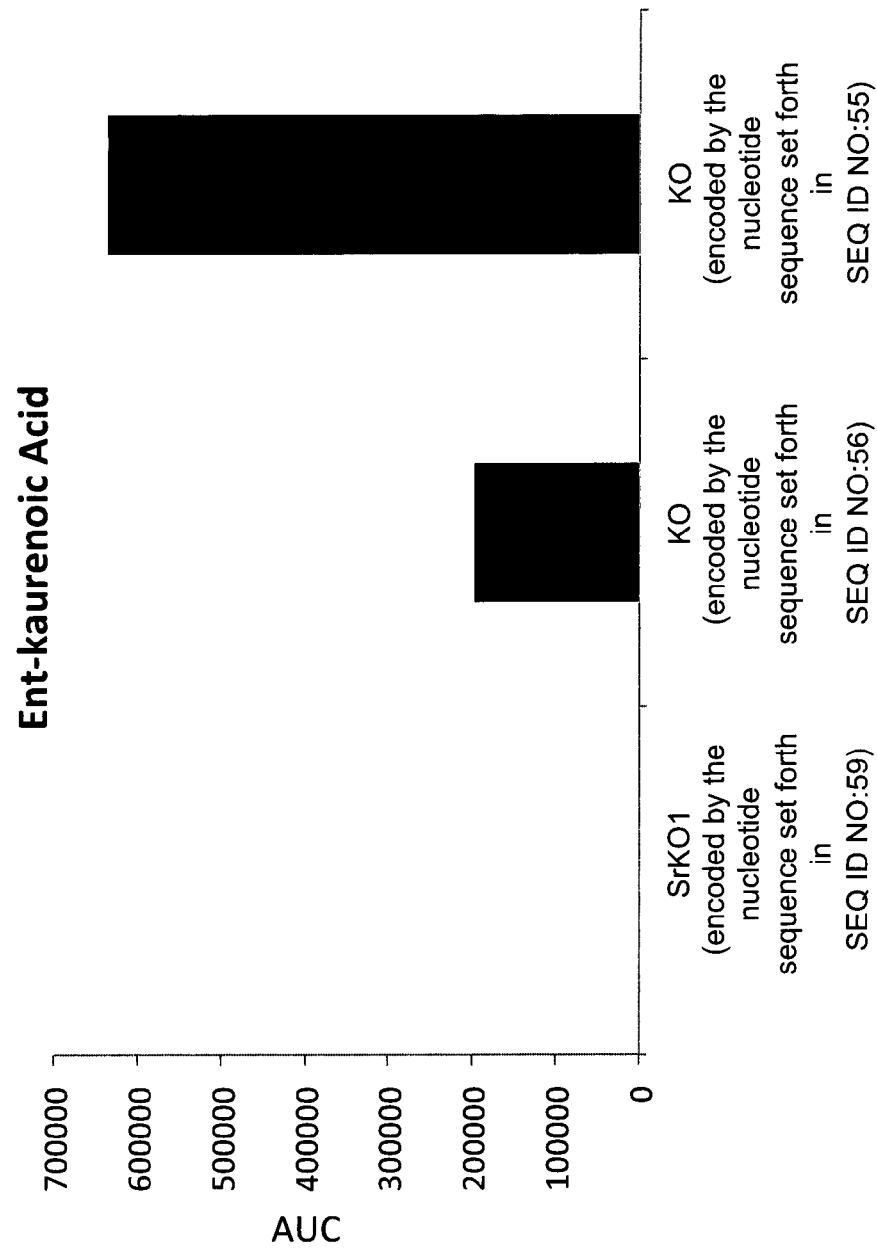
FIG. 4 shows production of ent-kaurenoic acid in steviol glycoside-producing *S. cerevisiae* strains individually expressing SrKO1 encoded by the nucleotide sequence set forth in SEQ ID NO:59, the KO encoded by the codon-optimized nucleotide sequence set forth in SEQ ID NO:55, or the KO encoded by the nucleotide sequence set forth in SEQ ID NO:56, as measured by LC-MS analysis of culture samples. Ent-kaurenoic acid levels were calculated as the Area under Curve (AUC) of LC-MS peaks corresponding to ent-kaurenoic acid. See Example 3.

Expression of genes (SEQ ID NO:55 or SEQ ID NO:56) encoding KO polypeptides in an *S. cerevisiae* steviol glycoside-producing strain also resulted in accumulation of ent-kaurenoic acid (FIG. 4). Expression of a gene encoding a codon-optimized KO polypeptide (SEQ ID NO:57) and a gene encoding the KO polypeptide set forth in SEQ ID NO:70 also resulted in accumulation of ent-kaurenoic acid. However, expression of SrKO1 (SEQ ID NO:59, SEQ ID NO:79) did not result in measurable levels of ent-kaurenoic acid. Thus, the KO polypeptides encoded by nucleotide sequences set forth in SEQ ID NOs: 55-57 more efficiently converted ent-kaurene, ent-kaurenol, and/or ent-kaurenal to ent-kaurenoic acid in *S. cerevisiae*, as compared to the SrKO1 polypeptide encoded by nucleotide sequence set forth in SEQ ID NO:59.

Example 4. Steviol Glycoside Production in Yeast Strains Expressing KO Genes and Further Overexpressing SrKAHe1

Cloned KO genes were individually expressed in a steviol glycoside-producing *S. cerevisiae* strain. The *S. cerevisiae* strain described in Example 2, which expresses SrKO1 (SEQ ID NO:59, SEQ ID NO:79), was modified to comprise overexpress SrKAHe1 (SEQ ID NO:18, SEQ ID NO:68). The coding sequences of the KO genes tested, as well as their corresponding amino acid sequences, are set forth in Table 2. The sequences set forth in SEQ ID NOs: 55, 57, 58, 59, and 60 were codon-optimized for expression in *S. cerevisiae*.

TABLE 2

KO Genes Expressed in Steviol Glycoside-Producing
S. cerevisiae strain that Further Overexpresses SrKAHe1.

| KO Nucleotide Sequence | Corresponding KO Amino Acid Sequence |
|---|---|
| SEQ ID NO: 55 | SEQ ID NO: 54 |
| SEQ ID NO: 56 | SEQ ID NO: 75 |
| SEQ ID NO: 57 | SEQ ID NO: 70 |
| SEQ ID NO: 58 | SEQ ID NO: 71 |
| SEQ ID NO: 59 | SEQ ID NO: 79 |
| SEQ ID NO: 60 | SEQ ID NO: 72 |

Figure 5:
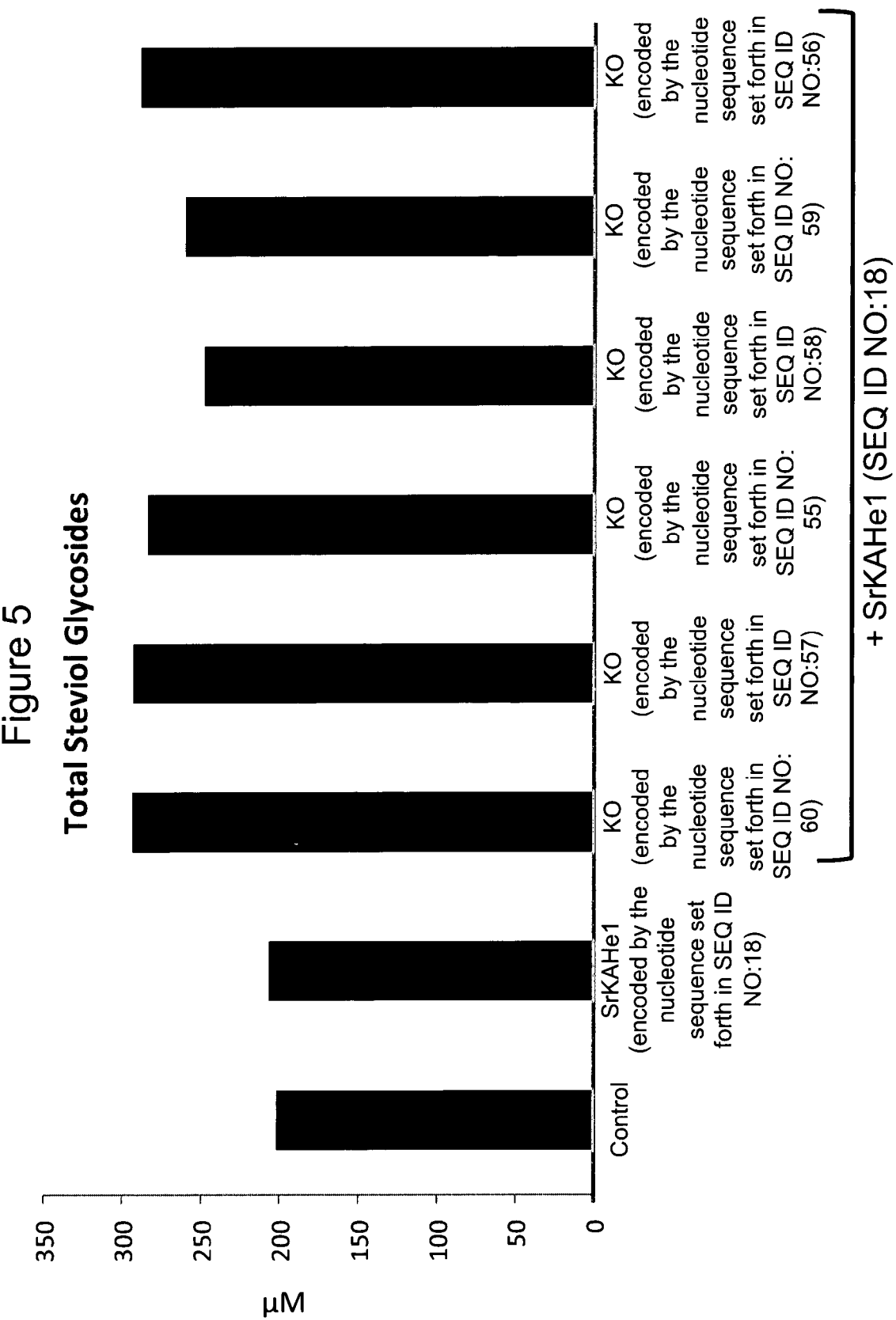
FIG. 5 shows production of total (extracellular plus intracellular) steviol glycosides in a steviol glycoside-producing *S. cerevisiae* strain overexpressing *S. rebaudiana* KAHe1 (SrKAHe1; encoded by the nucleotide sequence set forth in SEQ ID NO:18) or in a steviol glycoside-producing *S. cerevisiae* stain co-expressing SrKAHe1 (encoded by the nucleotide sequence set forth in SEQ ID NO:18) and a KO encoded by the nucleotide sequences set forth in any one of SEQ ID NOs: 55-60, compared to a control strain that does not overexpress SrKAHe1 or express a KO encoded by the nucleotide sequence set forth in any one of SEQ ID NOs: 55-60. Production of total steviol glycosides was quantified by comparision to a standard curve. Values plotted on the y-axis in μM are an average of three biological replicates. See Example 4.
Figure 6:
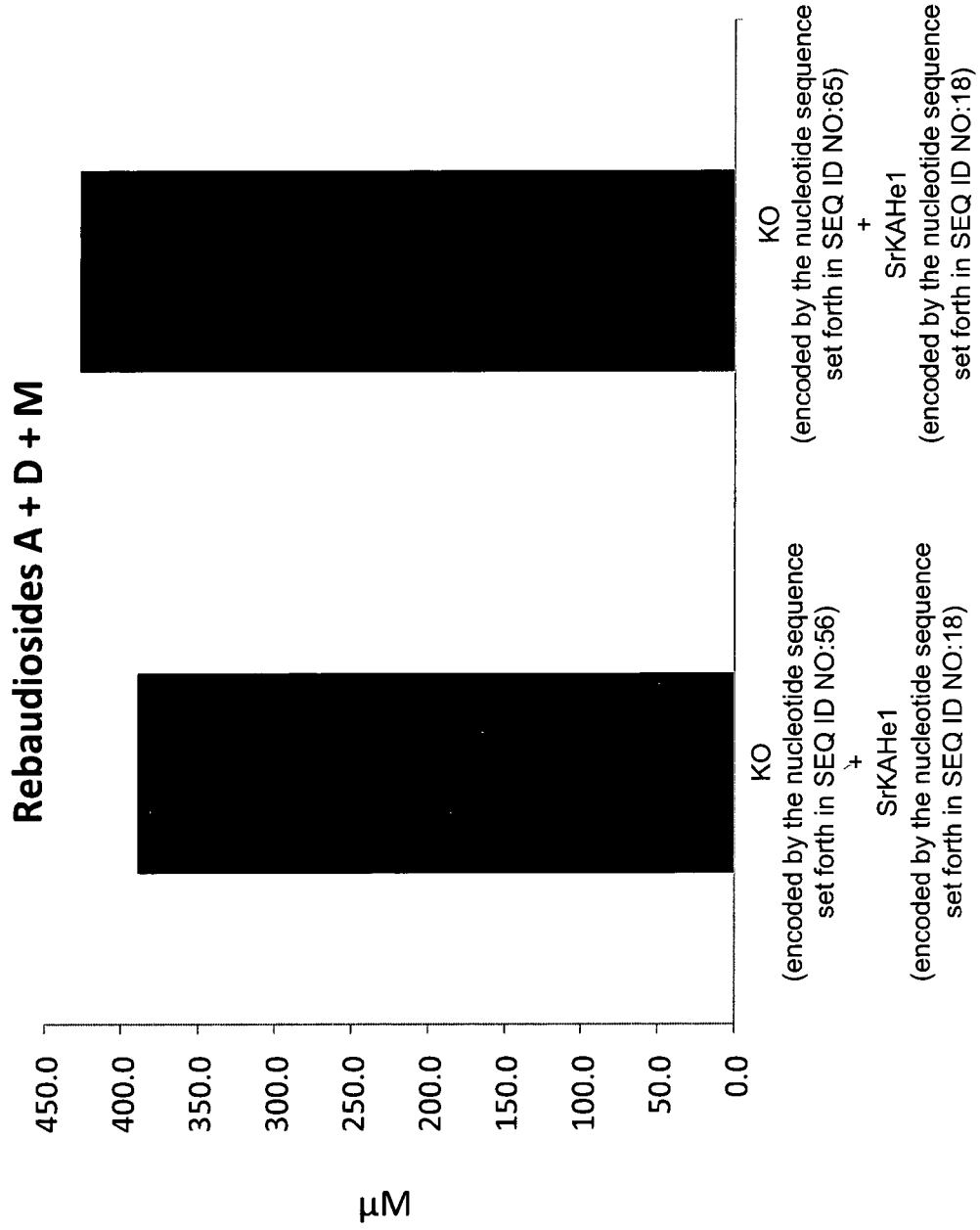
FIG. 6 shows production of Rebaudioside A (RebA), Rebaudioside D (RebD), and Rebaudioside M (RebM) in a steviol glycoside-producing *S. cerevisiae* strain overexpressing SrKAHe1 (encoded by the nucleotide sequence set forth in SEQ ID NO:18) and further expressing either the KO encoded by the nucleotide sequence set forth in SEQ ID NO:56 or the KO encoded by the nucleotide sequence set forth in SEQ ID NO:65. Production of RebA+RebD+RebM was measured in μM. See Example 4.

*S. cerevisiae* strains co-expressing any of the heterologous nucleic acids encoding a KO enzyme of Table 2 and further overexpressing SrKAHe1 (SEQ ID NO:18, SEQ ID NO:68) accumulated higher levels of steviol glycosides than the control *S. cerevisiae* strain (not expressing a KO of Table 2) or a steviol glycoside-producing *S. cerevisiae* strain only overexpressing SrKAHe1, as shown in FIG. 5. A steviol glycoside-producing *S. cerevisiae* strain expressing a codon-optimized version of SEQ ID NO:56, identified herein as SEQ ID NO:65, and overexpressing SrKAHe1 accumulated higher levels of steviol glycosides (RebA, RebD, and RebM) than the steviol glycoside-producing *S. cerevisiae* strain co-expressing the nucleic acid set forth in SEQ ID NO:56 and SrKAHe1 (FIG. 6).

Figure 7:
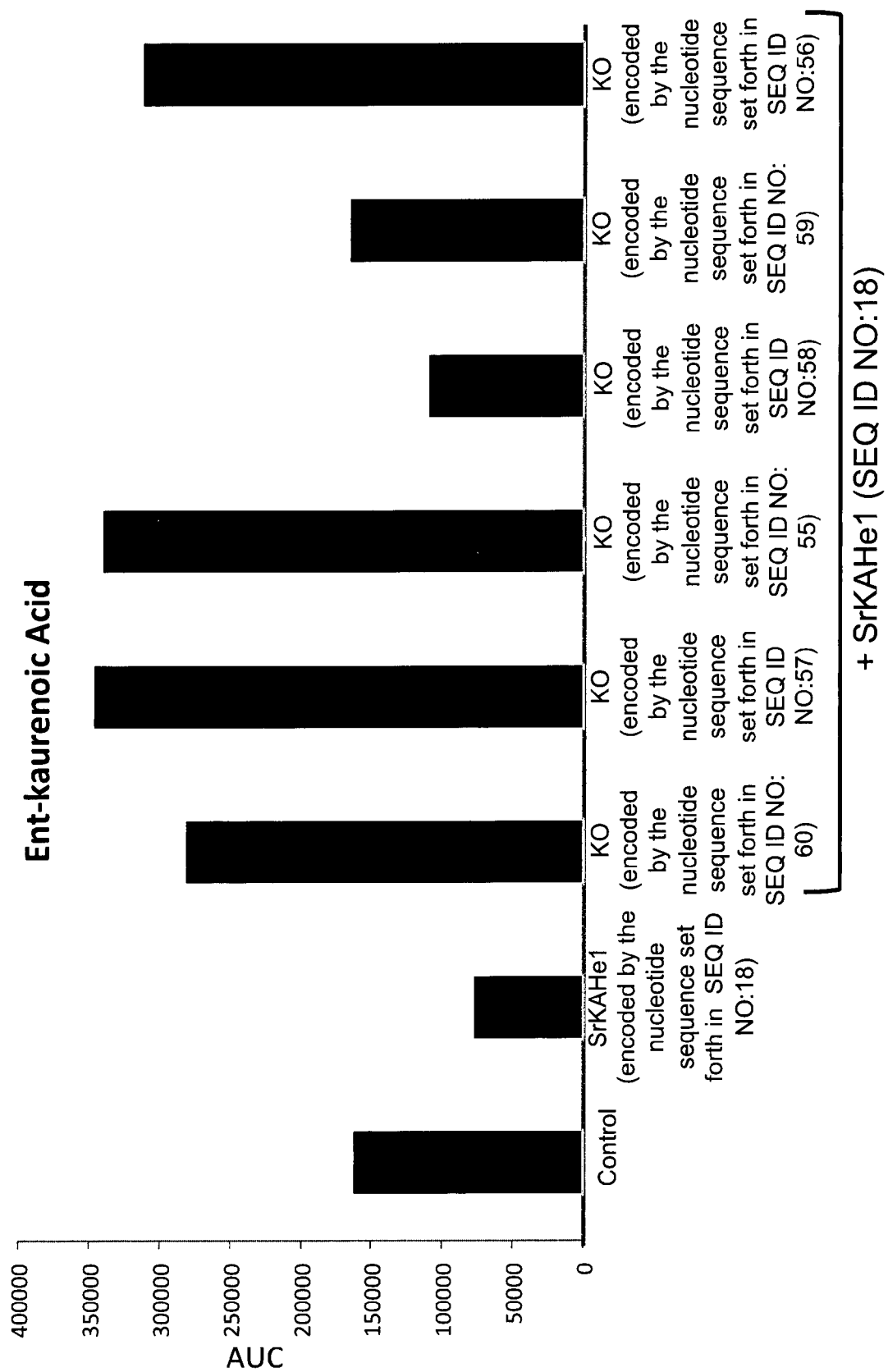
FIG. 7 shows production of glycosylated ent-kaurenoic acid in a steviol glycoside-producing *S. cerevisiae* strain overexpressing SrKAHe1 (encoded by the nucleotide sequence set forth in SEQ ID NO:18) or in a steviol glycoside-producing strain coexpressing SrKAHe1 (encoded by the nucleotide sequence set forth in SEQ ID NO:18) and a KO encoded by the nucleotide sequences set forth in any one of SEQ ID NOs: 55-60). Values were calculated as the AUC of LC-MS peaks corresponding to glycosylated ent-kaurenoic acid and as an average of three biological replicates. See Example 4.

Additionally, *S. cerevisiae* strains co-expressing a nucleic acid set forth in SEQ ID NO:55, SEQ ID NO:56, SEQ ID NO:57, or SEQ ID NO:60 and further overexpressing SrKAHe1 accumulated higher levels of glycosylated ent-kaurenoic acid than the control *S. cerevisiae* strain not expressing a KO of Table 2 (FIG. 7).

Figure 8:
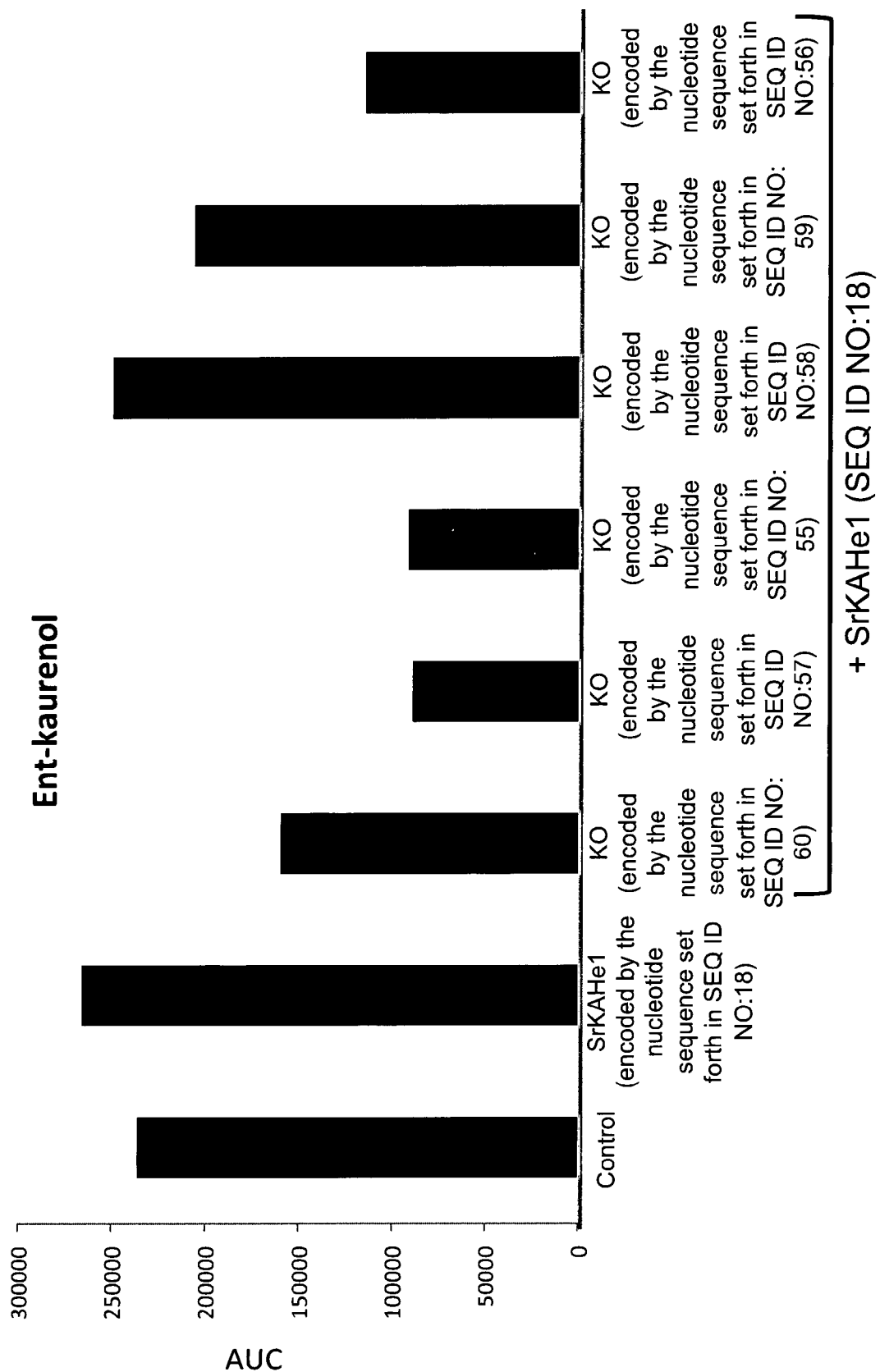
FIG. 8 shows production of glycosylated ent-kaurenol in a steviol glycoside-producing *S. cerevisiae* strain overexpressing SrKAHe1 (encoded by the nucleotide sequence set forth in SEQ ID NO:18) or in a steviol glycoside-producing *S. cerevisiae* strain co-expressing SrKAHe1 (encoded by the nucleotide sequence set forth in SEQ ID NO:18) and a KO encoded by the nucleotide sequence set forth in SEQ ID NOs: 55-60). Values plotted on the y-axis were calculated as the AUC of LC-MS peaks corresponding to glycosylated ent-kaurenol. See Example 4.

As well, *S. cerevisiae* strains co-expressing a nucleic acid set forth in SEQ ID NO:55, SEQ ID NO:56, SEQ ID NO:57, SEQ ID NO:59, or SEQ ID NO:60 and further overexpressing SrKAHe1 demonstrated improved metabolic conversion of intermediate compound, ent-kaurenol, which, in turn, resulted in reduced accumulation of glycosylated ent-kaurenol, relative to the control *S. cerevisiae* strain not expressing a KO of Table 2 or the steviol glycoside-producing *S. cerevisiae* strain only overexpressing SrKAHe1, as shown in FIG. 8. The control *S. cerevisiae* strain and the steviol glycoside-producing *S. cerevisiae* strain only overexpressing SrKAHe1 each accumulated higher levels of glycosylated ent-kaurenol than did *S. cerevisiae* strains expressing a nucleic acid set forth in SEQ ID NO:55, SEQ ID NO:56, SEQ ID NO:57, SEQ ID NO:59, or SEQ ID NO:60 and further overexpressing SrKAHe1.

Example 5. Steviol Glycoside Production in Yeast Strains Expressing CPR Genes

Cloned CPR genes were individually expressed in a steviol glycoside-producing *S. cerevisiae* strain. The steviol glycoside-producing *S. cerevisiae* strain described in Example 2, which expresses *S. rebaudiana* CPR8 (SEQ ID NO:24, SEQ ID NO:28) and *A. thaliana* ATR2 (SEQ ID NO:51), was modified to co-express a nucleic acid encoding a CPR of Table 3. The coding sequences of the CPR genes tested, as well as their corresponding amino acid sequences, are set forth in Table 3.

TABLE 3

CPR Genes Tested in Combination with CPR8 and ATR2.

| Gene | Nucleotide Sequence | Amino Acid Sequence |
|---|---|---|
| S. rebaudiana CPR1 | SEQ ID NO: 61 | SEQ ID NO: 76 |
| S. rebaudiana CPR7 | SEQ ID NO: 23 | SEQ ID NO: 69 |
| CPR4497 | SEQ ID NO: 62 | SEQ ID NO: 74 |

Figure 9:
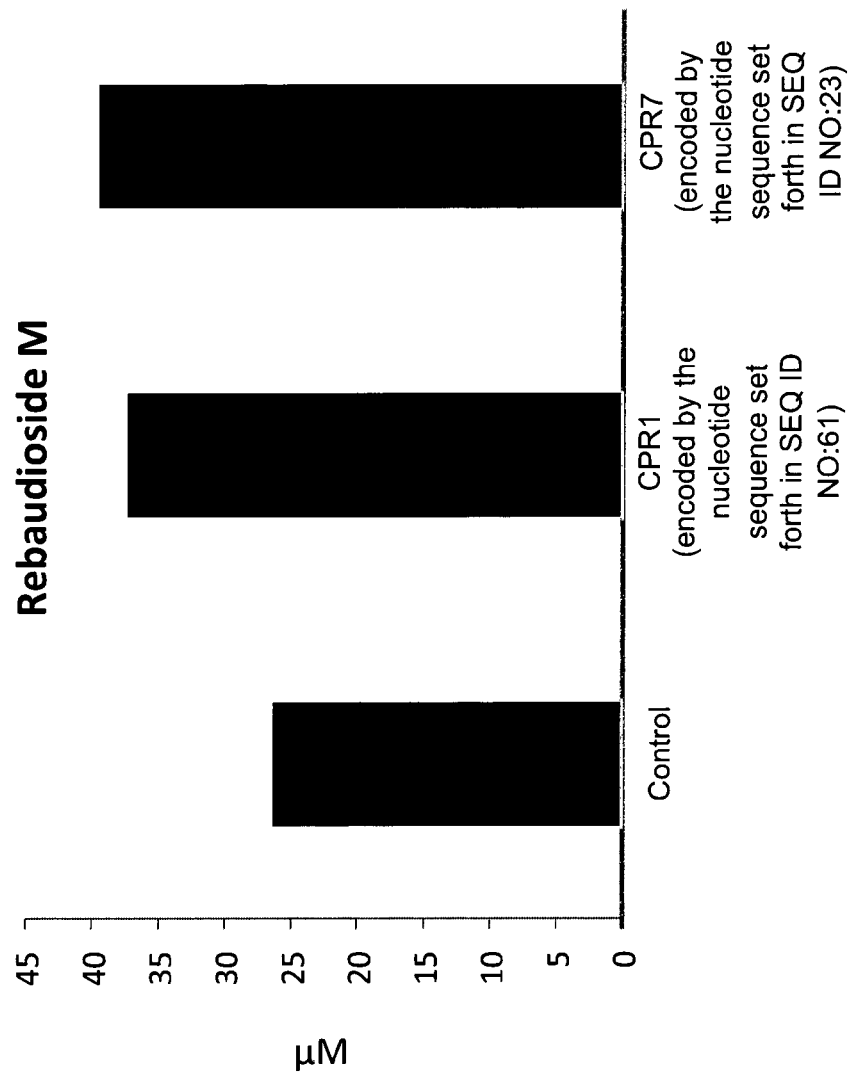
FIG. 9 shows Rebaudioside M (RebM) production in a steviol glycoside-producing *S. cerevisiae* strain expressing CPR1 (encoded by the codon-optimized nucleotide sequence set forth in SEQ ID NO:61) or CPR7 (encoded by the nucleotide sequence set forth in SEQ ID NO:23). Values plotted on the y-axis were measured in μM. See Example 5.

As shown in FIG. 9, expression of CPR1 (SEQ ID NO:61, SEQ ID NO:76) or of CPR7 (SEQ ID NO:23, SEQ ID NO:69) in the steviol glycoside-producing *S. cerevisiae* strain already expressing *S. rebaudiana* CPR8 (SEQ ID NO:24, SEQ ID NO:28) and *A. thaliana* ATR2 (SEQ ID NO:51) resulted in higher levels of RebM than those accumulated by the control steviol glycoside-producing *S. cere-* visiae strain not expressing CPR1 or CPR7. As well, a steviol glycoside-producing *S. cerevisiae* strain expressing the nucleic acid set forth in SEQ ID NO:62 and overexpressing SrKAHe1 (SEQ ID NO:18, SEQ ID NO:68) accumulated higher levels of RebM than those accumulated by the control steviol glycoside-producing *S. cerevisiae* strain that only overexpressed SrKAHe1 (FIG. 10).

Example 6. Steviol Glycoside Production in Yeast Strains Co-Expressing KO and CPR Genes Steviol glycoside production was tested in the RebB-producing *S. cerevisiae* strain described in Example 2, which was modified to co-express a KO gene of Table 4 and a CPR of Table 5.

TABLE 4

KO Genes Tested in Combination with CPR Genes.

| Gene | Nucleotide Sequence | Amino Acid Sequence |
| --- | --- | --- |
| SrKO1 | SEQ ID NO: 59 | SEQ ID NO: 79 |
| Codon-optimized KO | SEQ ID NO: 63 | SEQ ID NO: 77 |
| Codon-optimized KO | SEQ ID NO: 64 | SEQ ID NO: 78 |

TABLE 5

CPR Genes Tested in Combination with KO Genes.

| Nucleotide Sequence | Amino Acid Sequence |
| --- | --- |
| SEQ ID NO: 66 | SEQ ID NO: 73 |
| SEQ ID NO: 67 | SEQ ID NO: 22 |

Figure 12:
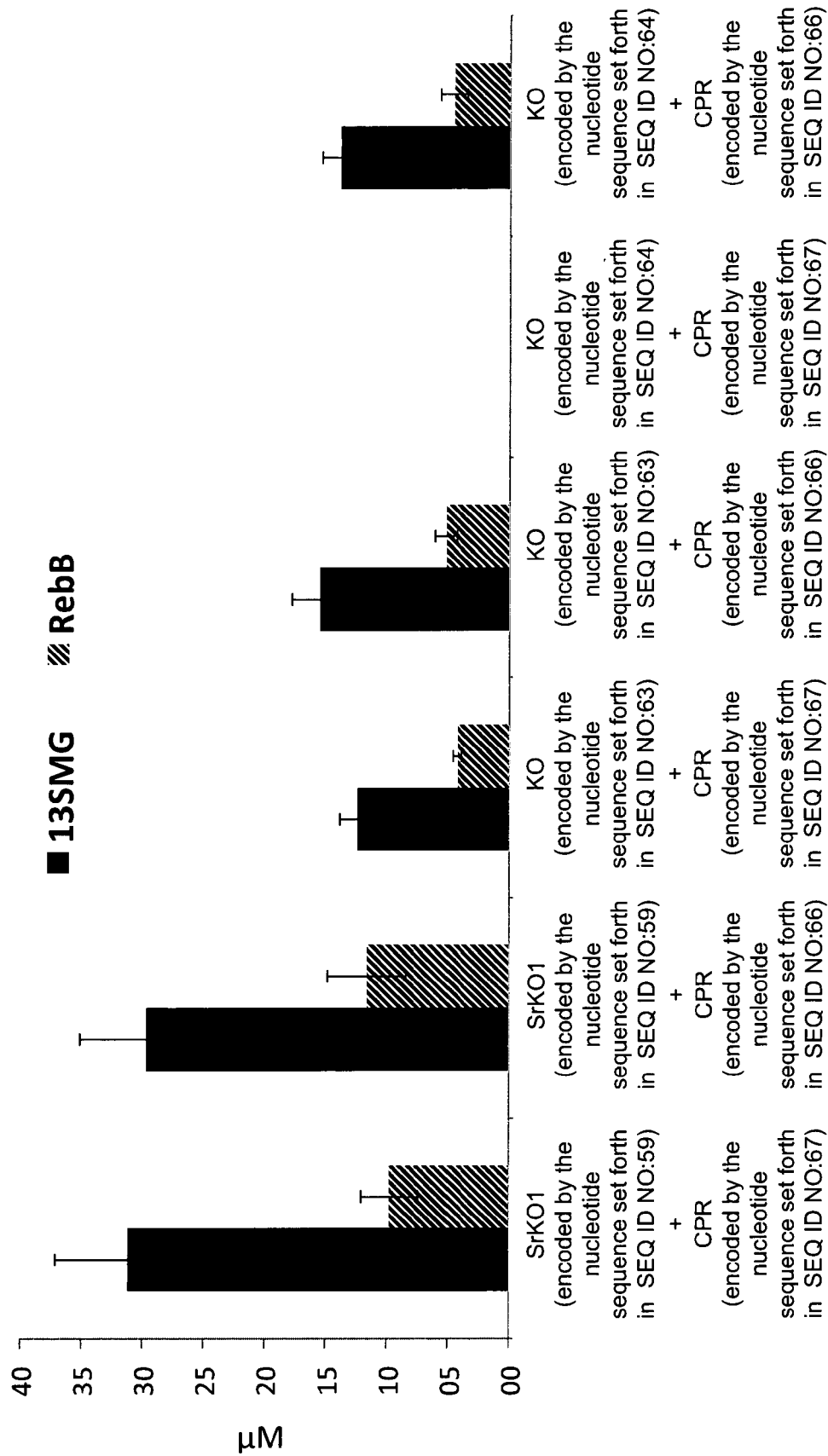
FIG. 12 shows steviol-13-O-glucoside (13-SMG) and Rebaudioside B (RebB) production in a steviol glycoside-producing *S. cerevisiae* strain co-expressing a KO and a CPR. The KO was selected from SrKO1 (encoded by the codon-optimized nucleotide sequence set forth in SEQ ID NO:59), the KO encoded by the codon-optimized nucleotide sequence set forth in SEQ ID NO:63, or the KO encoded by the codon-optimized nucleotide sequence set forth in SEQ ID NO:64. The cytochrome P450 reductase (CPR) polypeptide was selected from the CPR encoded by the codon-optimized nucleotide sequence set forth in SEQ ID NO:66 or the CPR encoded by the codon-optimized nucleotide sequence set forth in SEQ ID NO:67. Values displayed on the y-axis are µM concentrations of the indicated steviol glycosides. See Example 6.

As shown in FIG. 12, co-expression of SrKO1 (SEQ ID NO:59, SEQ ID NO:79) and either of the CPR genes of Table 5 in the RebB-producing strain resulted in higher production of 13-SMG and RebB than co-expression of a nucleic acid set forth in SEQ ID NO:63 or SEQ ID NO:64 and either of the cytochrome P450 genes of Table 5.

Example 7. Steviol Glycoside Production in Yeast Strains Expressing KAH Genes

Figure 11A:
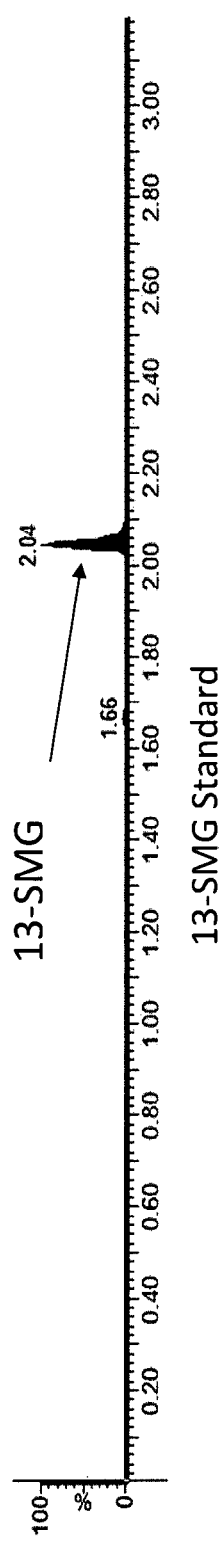
FIG. 11A shows an LC-MS chromatogram of a steviol-13-O-glucose (13-SMG) standard.
Figure 11B:
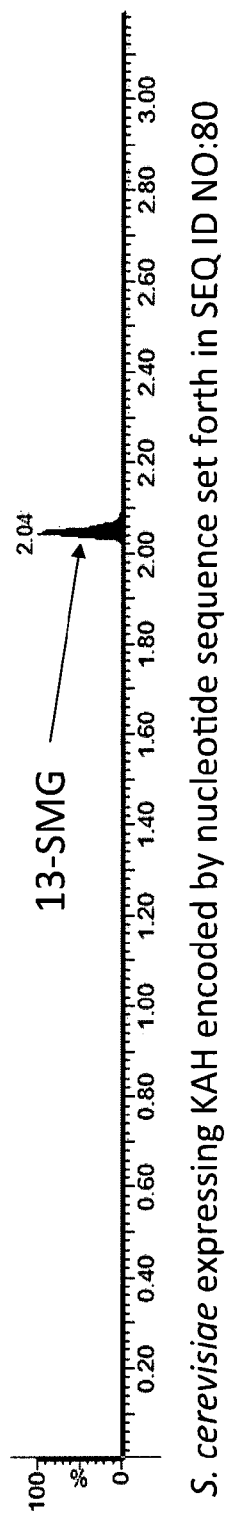
FIG. 11B shows production of 13-SMG by a steviol glycoside-producing *S. cerevisiae* strain expressing the KAH encoded by the nucleotide sequence set forth in SEQ ID NO:80 (amino acid sequence set forth in SEQ ID NO:82). See Example 7.

Candidate KAH enzymes were cloned and expressed in an *S. cerevisiae* strain engineered to accumulate 13-SMG. The 13-SMG-producing *S. cerevisiae* strain comprised a recombinant gene encoding a *Synechococcus* sp. GGPPS7 polypeptide (SEQ ID NO:49), a recombinant gene encoding a truncated *Z. mays* CDPS polypeptide (SEQ ID NO:37), a recombinant gene encoding an *A. thaliana* KS polypeptide (SEQ ID NO:6), SrKO1 (SEQ ID NO:59, SEQ ID NO:79), CPR8 (SEQ ID NO:24, SEQ ID NO:28), the KO encoded by the nucleotide sequence set forth in SEQ ID NO:56 (amino acid sequence set forth in SEQ ID NO:75), and UGT85C2 (SEQ ID NO:30) chromosomally integrated in separate expression cassettes (FIG. 11B). The strain lacked SrKAHe1 (SEQ ID NO:18, SEQ ID NO:68); thus, 13-SMG was only accumulated upon transformation of the *S. cerevisiae* strain with a functional KAH (FIG. 11B).

Transformants were grown in SC-URA medium for 4 days and extracted with 1:1 with DMSO at 80° C. for 10 min. The extracts were analyzed by LC-MS (method 2 of Example 1). *S. cerevisiae* transformed with the nucleic acid set forth in SEQ ID NO:80 accumulated 13-SMG (FIG. 11B). Thus, the protein encoded by SEQ ID NO:80, set forth in SEQ ID NO:82, is a KAH.

Figure 13:
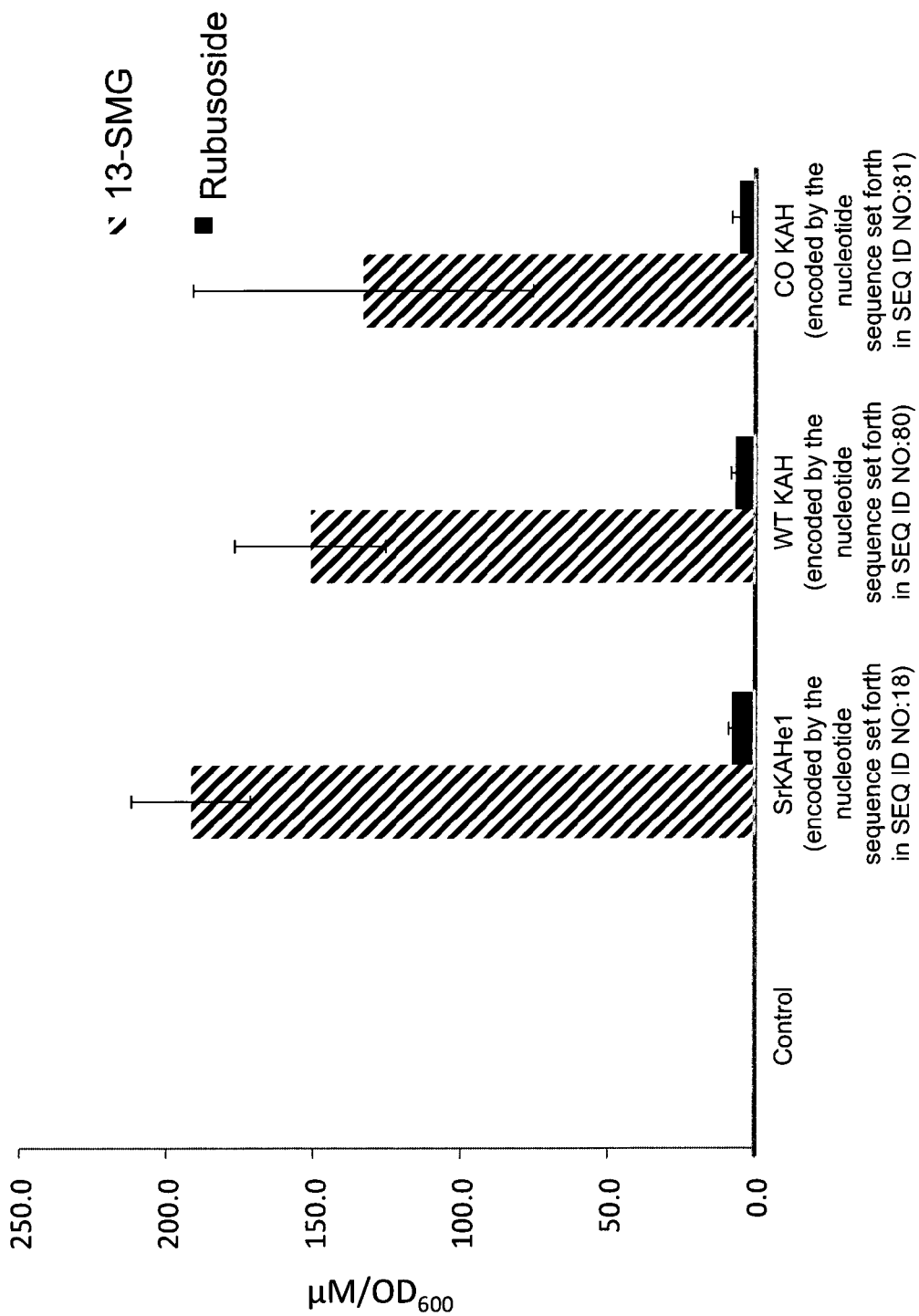
FIG. 13 shows production of steviol-13-O-glucoside (13-SMG) and rubusoside in a steviol glycoside-producing *S. cerevisiae* strain expressing SrKAHe1 (encoded by the nucleotide sequence set forth in SEQ ID NO:18), the KAH encoded by the nucleotide sequence set forth in SEQ ID NO:80, or the KAH encoded by the codon-optimized nucleotide sequence set forth in SEQ ID NO:81. Values displayed in the y-axis are µM concentrations of 13-SMG and rubusoside, averaged over eight biological replicates and normalized to $OD_{600}$ measured using a plate reader. Error bars are ±the respective standard deviation. See Example 7.

The KAH encoded by the nucleotide sequence set forth in SEQ ID NO:80 was codon-optimized for expression in yeast (SEQ ID NO:81) and expressed in the above-described 13-SMG-producing *S. cerevisiae* strain. Similar to expression of SrKAHe1 (SEQ ID NO:18) or the KAH encoded by the nucleotide sequence set forth in SEQ ID NO:80, expression of the codon-optimized nucleotide sequence set forth in SEQ ID NO:81 resulted in production of 13-SMG plus rubusoside (FIG. 13).

The KAHs encoded by the nucleotide sequence set forth in SEQ ID NO:80 and the codon-optimized nucleotide sequence set forth in SEQ ID NO:81 were also individually expressed in a steviol glycoside-producing strain, as described in Example 2, which expresses SrKAHe1. Production of 13-SMG was increased upon overexpression of SrKAHe1 (SEQ ID NO:18), of the KAH encoded by the nucleotide sequence set forth in SEQ ID NO:80, or of the KAH encoded by the codon-optimized nucleotide sequence set forth in SEQ ID NO:81, as compared to a control strain not expressing the KAH encoded by the nucleotide sequence set forth in SEQ ID NO:80, the KAH encoded by the codon-optimized nucleotide sequence set forth in SEQ ID NO:81, or overexpressing SrKAHe1. See Table 6. Expression of either the KAH encoded by the nucleotide sequence set forth in SEQ ID NO:80 or the KAH encoded by the codon-optimized nucleotide sequence set forth in SEQ ID NO:81 resulted in higher steviol glycoside production (13-SMG+1,2-bioside+rubusoside+RebB+RebA+RebD+RebM) than either the control strain or the *S. cerevisiae* strain overexpressing SrKAHe1 (SEQ ID NO:18). See Table 6.

TABLE 6

Quantification of Steviol Glycosides Accumulated by Yeast Expressing KAH Genes.

| | Control (μM) | Overexpression of SrKAHe1 (encoded by the nucleotide set forth in SEQ ID NO: 18) (μM) | SrKAHe1 + KAH (encoded by the nucleotide set forth in SEQ ID NO: 80) (μM) | SrKAHe1 + KAH (encoded by the nucleotide sequence set forth in SEQ ID NO: 81) (μM) |
| --- | --- | --- | --- | --- |
| 13-SMG | 67.6 | 85.5 | 153.8 | 130.5 |
| Steviol-1,2-bioside | 0.4 | 0.3 | 0.4 | 0.4 |
| Rubusoside | 1.2 | 1.0 | 1.4 | 1.1 |
| RebB | 8.6 | 7.6 | 9.6 | 9.6 |
| RebA | 30.7 | 26.0 | 26.8 | 28.7 |
| RebD | 36.2 | 27.6 | 32.9 | 36.5 |
| RebM | 138.3 | 118.9 | 100.0 | 90.3 |
| Sum | 282.7 | 266.2 | 324.0 | 296.7 |

Example 8. Steviol Glycoside Production in Yeast Strain Expressing KAH Gene of the CYP72A219 Family A nucleic acid of SEQ ID NO:90, which was codon-optimized for expression in *S. cerevisiae* and encodes the polypeptide of SEQ ID NO:91, was cloned and expressed in an *S. cerevisiae* strain described in Example 7, which was engineered to accumulate 13-SMG. The 13-SMG-producing *S. cerevisiae* strain comprised a recombinant gene encoding a *Synechococcus* sp. GGPPS7 polypeptide (SEQ ID NO:49), a recombinant gene encoding a truncated *Z. mays* CDPS polypeptide (SEQ ID NO:37), a recombinant gene encoding an *A. thaliana* KS polypeptide (SEQ ID NO:6), SrKO1 (SEQ ID NO:59, SEQ ID NO:79), CPR8 (SEQ ID NO:24, SEQ ID NO:28), the KO encoded by the nucleotide sequence set forth in SEQ ID NO:56 (amino acid sequence set forth in SEQ ID NO:75), and UGT85C2 (SEQ ID NO:30) chromosomally integrated in separate expression cassettes.

Transformants were grown in SC-URA medium for 4 days and extracted 1:1 with DMSO at 80° C. for 10 min. The extracts were analyzed by LC-MS (method 2 of Example 1). *S. cerevisiae* transformed with the nucleic acid set forth in SEQ ID NO:90 accumulated 13-SMG as well as rubusoside (Table 7). Thus, the protein encoded by the nucleic acid sequence of SEQ ID NO:90, set forth in SEQ ID NO:91, is a KAH.

TABLE 7

Quantification of Steviol Glycosides Accumulated by Yeast Expressing the KAH encoded by the Nucleotide Sequence Set Forth in SEQ ID NO: 90 (Amino Acid Sequence Set Forth in SEQ ID NO: 91).

| | 13-SMG (µM) | Rubusoside (µM) |
|---|---|---|
| KAH (encoded by the nucleotide sequence set forth in SEQ ID NO: 90) | 4.3 ± 0.1 | 0.2 ± 0.0 |

Example 9. Determination of CPR1 and CPR12 Activity

Activity of CPR1 and CPR12 were measured using an in vitro microsomal assay. Microsomes were prepared by a modified version of the method taught by Pompon et al., "Yeast expression of animal and plant P450s in optimized redox environments," *Methods Enzymol.* 272:51-64 (1996). *S. cerevisiae* cells were sedimented for 10 min at 4° C. The pellets were washed with 10 mL TEK buffer (50 mM Tris-HCl (pH 7.5), 1 mM EDTA, 100 mM KCl.) The cells were sedimented again for 10 min at 4° C., and the pellets were resuspended in 1-3 mL of TES2 buffer (50 mM Tri-HCl (pH 7.5) 1 mM EDTA, 600 mM sorbitol). Glass beads (425-600 microns) were added to the samples, and the cells were broken vigorously by shaking and vortexing for 5 min at 4° C. The supernatant was collected, and the beads were washed several times with TES2 buffer. The washes were combined with the supernatant, and the samples were centrifuged for 15 min at 4° C. to remove unbroken cells and glass beads. Samples were then ultracentrifuged for 1 h at 4° C. The pellets were washed twice with TES buffer (50 mM Tris-HCl (pH 7.5), 1 mM EDTA, 600 mM sorbitol, 1% (w/V) BSA, 5 mM DTT), and once with TEG buffer (50 mM Tris-HCl (pH 7.5), 1 mM EDTA, 30% (V/V) glycerol). The samples were resuspended in 1-3 mL TEG, and the pellets were homogenized.

Wild-type control microsomal protein was prepared as described above from wild-type *S. cerevisiae* cells that did not comprise a heterologous KAH or CPR. Microsomal protein was also prepared from *S. cerevisiae* cells expressing i) SrKAHe1 (SEQ ID NO:18, SEQ ID NO:68), ii) SrKAHe1 (SEQ ID NO:18, SEQ ID NO:68) and CPR1 (SEQ ID NO:61, SEQ ID NO:76), or iii) SrKAHe1 (SEQ ID NO:18, SEQ ID NO:68) and CPR12 (SEQ ID NO:97, SEQ ID NO:98) from a genetic construct integrated at the chromosome level. Microsomal protein from a steviol glycoside-producing strain was prepared from *S. cerevisiae* cells expressing the genes described in Example 2 and additionally comprising codon-optimized CPR1 from *S. rebaudiana* (SEQ ID NO:61 corresponding to amino acid sequence SEQ ID NO:76) as well as the KO encoded by SEQ ID NO:75).

CPR1 and CPR12 activities were first determined using a cytochrome C reductase assay kit (Sigma-Aldrich; CY0100-1KT) to measure the ability of CPR1 or CPR12 to reduce cytochrome C in the presence of NADPH in vitro. Reduction of cytochrome C resulted in an increase in absorbance at 550 nm, which could quantified spectrophotometrically. Working solution was prepared by adding 9 mg cytochrome C to 20 mL assay buffer, and solution was stored at 25° C. until use. NADPH was diluted in $H_2O$ to a concentration of 0.85 mg/mL. Final reaction volumes were 1.1 mL (950 µL working solution (0.43 mg cytochrome C), 28 µL enzyme dilution buffer, 100 µL NADPH solution (0.085 mg NADPH), 20 µL cytochrome C oxidase inhibitor, 2 µL microsomal protein.) Blank samples did not comprise microsomal protein and were prepared with 950 µL working solution (0.43 mg cytochrome C), 30 µL enzyme dilution buffer, 100 µL NADPH solution (0.085 mg NADPH), and 20 µL cytochrome C oxidase inhibitor. The spectrophotometer was blanked with all components added to the reactions except for NADPH. The enzymatic reactions were initiated by addition of NADPH, the samples were thoroughly mixed by pipetting, and absorbance was measured at 550 nm for 70 s with 10 s intervals between reads. Two independent rate measurements were taken for each microsomal preparation, and rates were averaged for calculation of specific activity. After the reactions were completed, results were normalized to protein concentration, which was measured using a standard BCA assay (Thermo Scientific).

Units/mL was calculated using the following equation, where $\Delta A_{550}$/min represents the change in absorbance at 550 nm during the absorbance reading period, 1.1 represents the reaction volume in mL, and 21.1 represents the extinction coefficient for reduced cytochrome c:

$$\text{Units/mL} = (\Delta A_{550}/\text{min} \times \text{dilution factor} \times 1.1)/(21.1 \times \text{enzyme volume})$$

Figure 14:
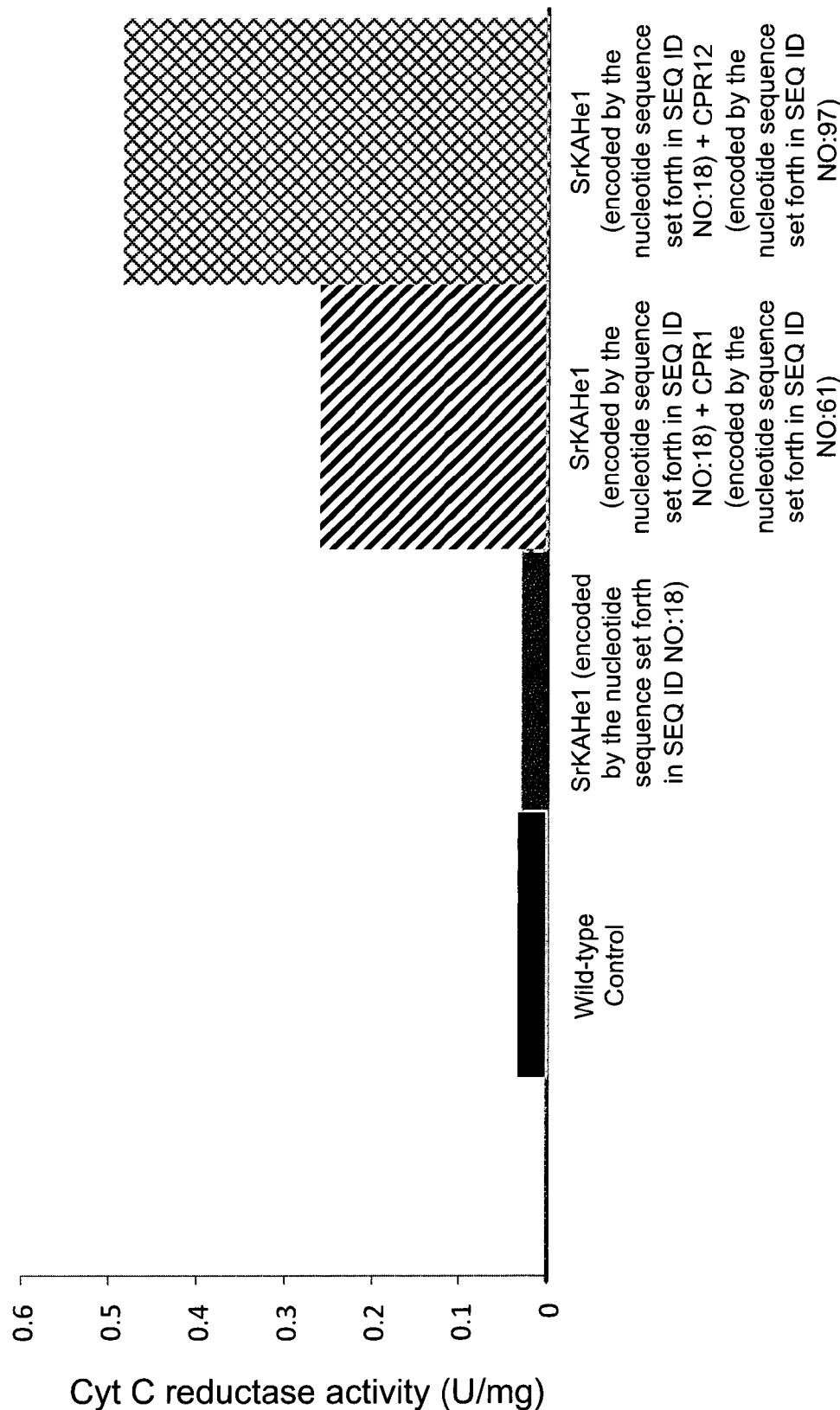
FIG. 14 shows cytochrome P450 reductase (CPR) polypeptide activity on cytochrome c upon incubation with microsomal protein prepared from *S. cerevisiae* strains expressing SrKAHe1 (encoded by the nucleotide sequence set forth in SEQ ID NO:18) alone or in combination with CPR1 (encoded by the nucleotide sequence set forth in SEQ ID NO:61) or CPR12 (encoded by the nucleotide sequence set forth in SEQ ID NO:97). Results are shown in U/mg as an average of two biological replicates. See Example 9.

The units/mL value of each sample was divided by its respective microsomal protein concentrations to calculate CPR activity in units/mg. FIG. 14 shows the activity measurements of the i) SrKAHe1 (SEQ ID NO:18, SEQ ID NO:68), ii) SrKAHe1 (SEQ ID NO:18 SEQ ID NO:68) and CPR1 (SEQ ID NO:61, SEQ ID NO:76), and iii) SrKAHe1 (SEQ ID NO:18, SEQ ID NO:68) and CPR12 (SEQ ID NO:97, SEQ ID NO:98) microsomal samples.

The microsomal preparation from the wild-type control showed only minimal CPR activity, reflecting the low activity of native NCP1 (YHR042VV). Likewise, the microsomal preparation from a yeast strain overexpressing KAHe1 did not demonstrate an increase in CPR activity. In contrast, microsomal preparation from strains expressing SrKAHe1 (SEQ ID NO:18, SEQ ID NO:68) and CPR1 (SEQ ID NO:61, SEQ ID NO:76) or SrKAHe1 (SEQ ID NO:18, SEQ ID NO:68) and CPR12 (SEQ ID NO:97, SEQ ID NO:98) demonstrated high CPR activity, with 7- and 14-fold higher activity, respectively, compared to the negative control (FIG. 14).

In a separate experiment, formation of steviol and consumption of ent-kaurenoic acid in microsomes, as prepared above, were measured. 33 µM ent-kaurenoic acid, 10 mM NADPH, and 10 µL of microsomal protein in 50 mM phosphate buffer (pH 7.5) were incubated for 30 min at 30° C. in a total reaction volume of 100 µL. Control reactions were extracted immediately after addition of all the reaction components, which were mixed on ice and aliquoted prior to incubation. Steviol and ent-kaurenoic acid levels were quantified using the second LC-MS procedure described in Example 1. For steviol quantification, the microsomal reactions were extracted with DMSO (1:1) at 80° C. for 10 min and submitted for LC-MS analysis after centrifugation. For ent-kaurenoic acid quantification the microsomes reactions were extracted with acetonitrile 1:4 (20% microsomal reaction and 80% acetonitrile) at 80° C. for 10 min and after centrifugation submitted for LC-MS analysis. The AUC values obtained for the ent-kaurenoic acid measurements were converted to concentrations using a standard curve.

Figure 15B:
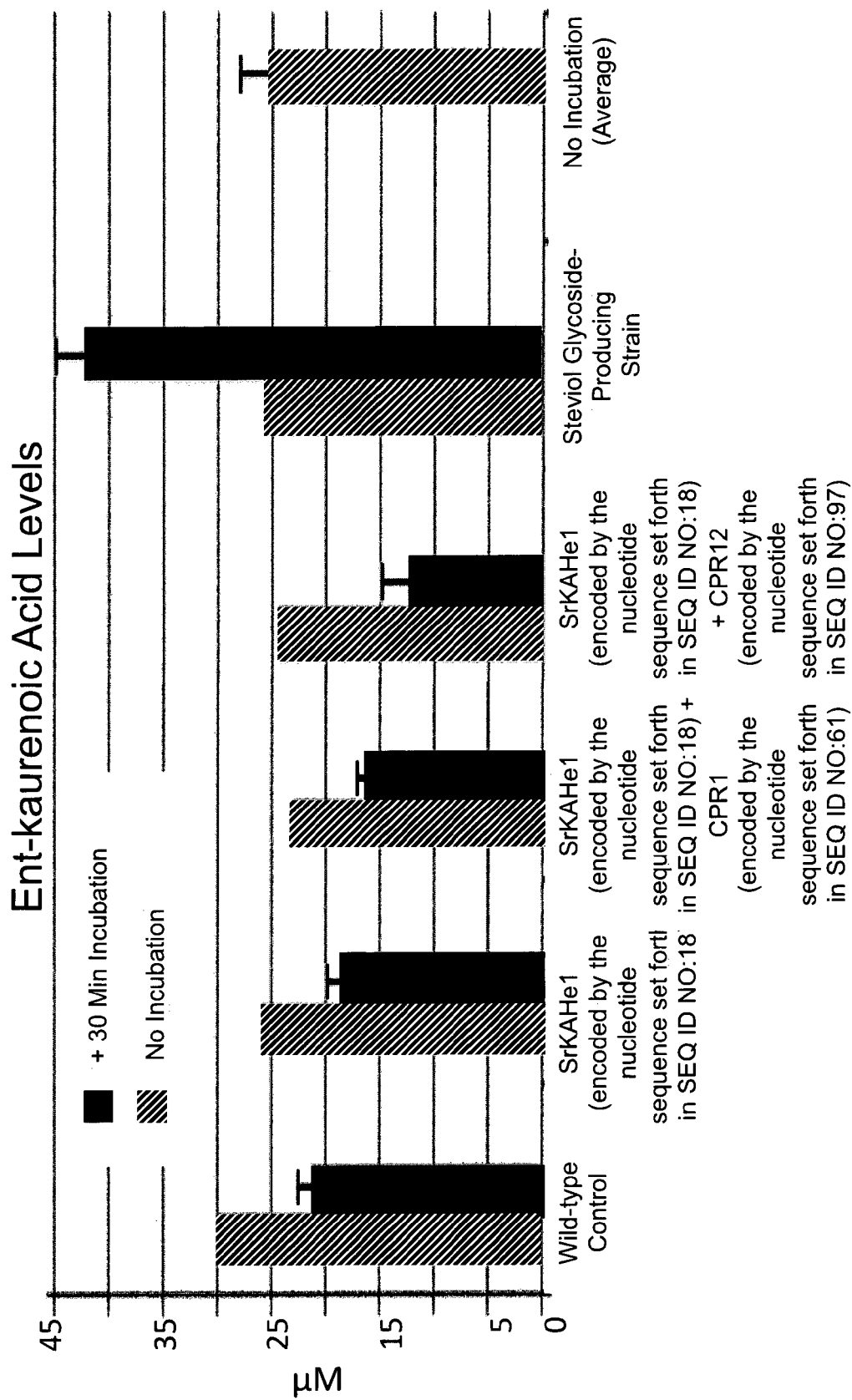
FIG. 15B shows levels of ent-kaurenoic acid following 30 min incubation of ent-kaurenoic acid with microsomal protein prepared from *S. cerevisiae* strains expressing SrKAHe1 (encoded by the nucleotide sequence set forth in SEQ ID NO:18) alone or in combination with CPR1 (encoded by the nucleotide sequence set forth in SEQ ID NO:61) or CPR12 (encoded by the nucleotide sequence set forth in SEQ ID NO:97). Results are shown in µM as an average of three biological replicates. Control reactions comprised the microsomal protein described above but were not incubated for 30 min prior to measurement of ent-kaurenoic acid levels. See Example 9.

As shown in FIG. 15A, microsomal protein prepared from an *S. cerevisiae* strain expressing SrKAHe1 (SEQ ID NO:18, SEQ ID NO:68) and either CPR1 (SEQ ID NO:61, SEQ ID NO:76) or CPR12 (SEQ ID NO:97, SEQ ID NO:98) converted ent-kaurenoic acid to steviol during the 30 minute incubation period. The steviol level shown in FIG. 15A for the steviol-glycoside-producing strain control (extracted immediately with no 30 min incubation period) corresponds to steviol that was accumulated by the strain prior to microsomal preparation and that had co-purified with the microsomes. As shown in FIG. 15B, ent-kaurenoic acid levels decreased upon incubation with microsomal protein prepared from *S. cerevisiae* strains expressing SrKAHe1 (SEQ ID NO:18, SEQ ID NO:68) alone or in combination with CPR1 (SEQ ID NO:61, SEQ ID NO:76) or CPR12 (SEQ ID NO:97, SEQ ID NO:98). The increased ent-kaurenoic acid levels shown in FIG. 15B for the steviol glycoside-producing strain microsomal sample incubated for 30 min corresponds to ent-kaurenoic acid that was accumulated by the strain prior to microsomal preparation and to ent-kaurenoic acid accumulated from ent-kaurene that had co-purified with the microsomes. The levels of ent-kaurenoic acid shown in FIG. 15B were corrected for the dilution factor used.

Example 10. Steviol Glycoside Production in *S. cerevisiae* Strains Comprising Fusion Constructs Between a KO and a P450 Reductase Domain CYP102A1 (also referred to as P450$_{BM3}$; SEQ ID NO:115, SEQ ID NO:116) is a catalytically self-sufficient soluble enzyme from *Bacillus megatarium*. See, e.g., Whitehouse et al., 2012, Chem Soc Rev. 41(3):1218-60. Two domains are present in the CYP102A1 polypeptide chain: a P450 heme domain (BMP) and an NADPH-dependent P450 oxidoreductase domain (BMR). CYP102A1 utilizes nearly 100% of the reducing power of NADPH to produce a monooxygenated product. See, e.g., Yuan et al., 2009, *Biochemistry* 48(38):9140-6.

The BMR domain of CYP102A1 ("BMR"; codon-optimized nucleotide sequence set forth in SEQ ID NO:117, SEQ ID NO:118) was fused to SrKO1 (SEQ ID NO:59, SEQ ID NO:79) or a KO encoded by the nucleotide sequence set forth in SEQ ID NO:65 (amino acid sequence set forth in SEQ ID NO:75) with a linker (SEQ ID NO:121, SEQ ID NO:122), as described in Dodhia et al., 2006, J Biol Inorg Chem. 11(7):903-16. A wild-type version of the BMR domain of CYP102A1, as well as a W1046A mutant of the BMR domain (SEQ ID NO:119, SEQ ID NO:120), which has been found to switch the cofactor specificity of CYP102A1 from NADPH to NADH, were used. See, Girvan et al., 2011, Arch Biochem Biophys. 507(1):75-85. SrKO1 (SEQ ID NO:59, SEQ ID NO:79) and the KO encoded by the nucleotide sequence set forth in SEQ ID NO:65 were also truncated prior to fusion with the BMR domain of CYP102A1; these truncations were predicted by bioinformatics to result in loss of membrane anchors of the KO genes and in cytosolic versions of the KO-BMR fusion constructs. The KO-BMR fusion constructs analyzed are shown in Table 8.

TABLE 8

KO-BMR fusion constructs and sequences.

| Fusion Construct | Codon-Optimized Nucleotide Sequence | Amino Acid Sequence |
| --- | --- | --- |
| SrKO1-BMR | SEQ ID NO: 99 | SEQ ID NO: 100 |
| SrKO1-BMR W1046A mutant | SEQ ID NO: 101 | SEQ ID NO: 102 |
| Truncated SrKO1-BMR | SEQ ID NO: 103 | SEQ ID NO: 104 |
| Truncated SrKO1-BMR W1046A mutant | SEQ ID NO: 105 | SEQ ID NO: 106 |
| KO (encoded by nucleotide sequence set forth in SEQ ID NO: 65)-BMR | SEQ ID NO: 107 | SEQ ID NO: 108 |
| KO (encoded by nucleotide sequence set forth in SEQ ID NO: 65)-BMR W1046A mutant | SEQ ID NO: 109 | SEQ ID NO: 110 |
| Truncated KO (encoded by nucleotide sequence set forth in SEQ ID NO: 65)-BMR W1046A mutant | SEQ ID NO: 111 | SEQ ID NO: 112 |

The KO-BMR fusion constructs were cloned and transformed in the RebB-producing strain described in Example 2, which was modified to not comprise any additional KO genes. Thus, steviol glycosides, including 13-SMG, 1,2-bioside, and RebB, were only accumulated upon expression of a functional KO. Three scrapes (1 μL loop of cells) from each transformation plate were resuspended in 200 μl nanopure H$_2$O. 70 μL were then transferred to 1 mL SC-URA in a 96 deep well plate and incubated at 30° C. for 5 days at 400 rpm. Biological triplicates were analyzed by LC-MS (method 2 of Example 1) to measure 13-SMG, 1,2-bioside, and RebB levels, and single samples were analyzed by LC-UV to measure ent-kaurene and ent-kaurenoic acid levels.

For LC-MS, 50 μL samples were mixed with 50 μL 100% DMSO and heated to 80° C. for 10 min. Subsequently, the samples were spun down at 4000 RCF for 10 min, and 85 μL of the resulting supernatant was transferred to an LC-MS plate. The LC-MS results were normalized by OD$_{600}$ of individual cultures, which was measured by a Wallac, 2104 EnVision (Perkin Elmer) plate reader.

LC-UV was conducted with an Agilent 1290 instrument comprising a variable wavelength detector (VWD), a thermostatted column compartment (TCC), an autosampler, an autosampler cooling unit, and a binary pump and using SB-C18 rapid resolution high definition (RRHD) 2.1 mm×300 mm, 1.8 μm analytical columns (two 150 mm columns in series; column temperature of 65° C.). Steviol glycosides and steviol glycoside precursors were separated by a reversed phase C18 column followed by detection by UV absorbance at 210 mm. Quantification of steviol glycosides was done by comparing the peak area of each analyte to standards of RebA and applying a correction factor for species with differing molar absorptivities. Quantification of steviol glycoside precursors (such as kaurenoic acid, kaurenal, kaurenol, ent-kaurene, and geranylgeraniol) was done by comparing the peak area of each analyte to standards of kaurenoic acid and applying a correction factor for species with differing molar absorptivities. For LC-UV, 0.5 mL cultures were spun down, the supernatant was removed, and the wet weight of the pellets was calculated. The LC-UV results were normalized by pellet wet weight.

Figure 16A:
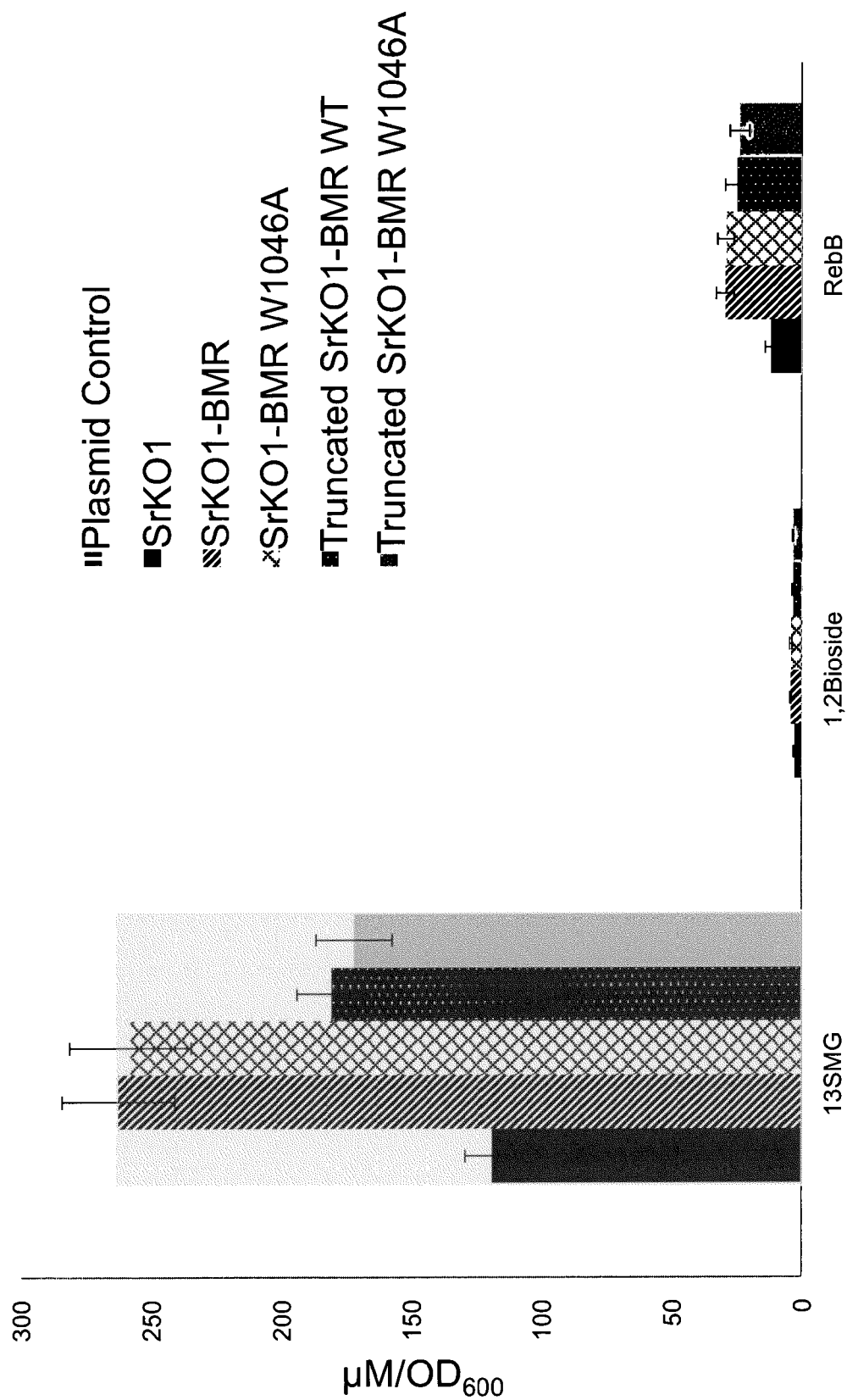
FIG. 16A shows levels of 13-SMG, 1,2-bioside, and RebB measured by LC-MS for a steviol glycoside-producing *S. cerevisiae* strain expressing SrKO1 (SEQ ID NO:59, SEQ ID NO:79), a fusion construct of SrKO1 and BMR (SEQ ID NO:99, SEQ ID NO:100), a fusion construct of SrKO1 and BMR W1046A (SEQ ID NO:101, SEQ ID NO:102), a fusion construct of truncated SrKO1 and BMR (SEQ ID NO:103, SEQ ID NO:104), a fusion construct of truncated SrKO1 and BMR W1046A (SEQ ID NO:105, SEQ ID NO:106), or a control plasmid.
Figure 16B:
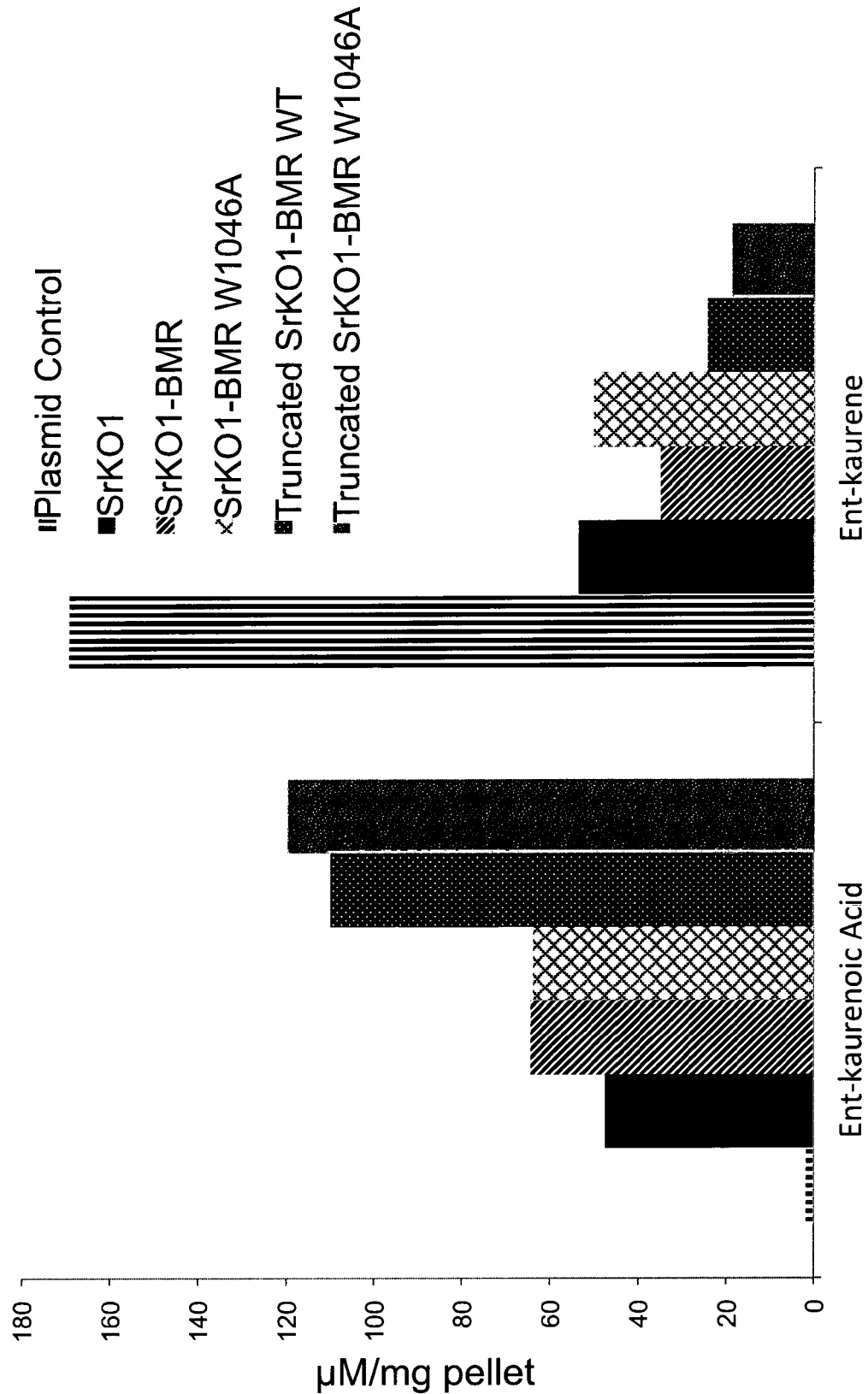
FIG. 16B shows levels of ent-kaurenoic acid and ent-kaurene measured by LC-UV for a steviol glycoside-producing *S. cerevisiae* strain expressing SrKO1 (SEQ ID NO:59, SEQ ID NO:79), a fusion construct of SrKO1 and BMR (SEQ ID NO:99, SEQ ID NO:100), a fusion construct of SrKO1 and BMR W1046A (SEQ ID NO:101, SEQ ID NO:102), a fusion construct of truncated SrKO1 and BMR (SEQ ID NO:103, SEQ ID NO:104), a fusion construct of truncated SrKO1 and BMR W1046A (SEQ ID NO:105, SEQ ID NO:106), or a control plasmid.

As shown in FIGS. 16B and 16D, the *S. cerevisiae* strain transformed with empty plasmid accumulated ent-kaurene. Transformation with a plasmid comprising SrKO1 (SEQ ID NO:59, SEQ ID NO:79) or with a plasmid comprising the KO gene having the nucleotide sequence set forth in SEQ ID NO:65 resulted in accumulation of 13-SMG, 1,2-bioside, and RebB (FIGS. 16A and 16C).

Expression of full-length SrKO1-BMR fusion constructs (wild type or W1046A mutant BMR; SEQ ID NOs:99-102), resulted in an increase in ent-kaurenoic acid, 13-SMG, and RebB, compared to expression of SrKO1 (SEQ ID NO:59, SEQ ID NO:79). See FIGS. 16A and 16B. Expression of truncated SrKO1-BMR fusion constructs (wild type or W1046A mutant BMR; SEQ ID NOs:103-106) resulted in an increase in ent-kaurenoic acid, compared to expression of SrKO1 (SEQ ID NO:59, SEQ ID NO:79) (FIG. 16B). Although the truncated SrKO1-BMR fusion constructs also increased steviol glycoside production, glycosylation activity was higher for the full-length SrKO1-BMR fusion constructs than for the truncated SrKO1-BMR fusion constructs (FIG. 16A).

Figure 16C:
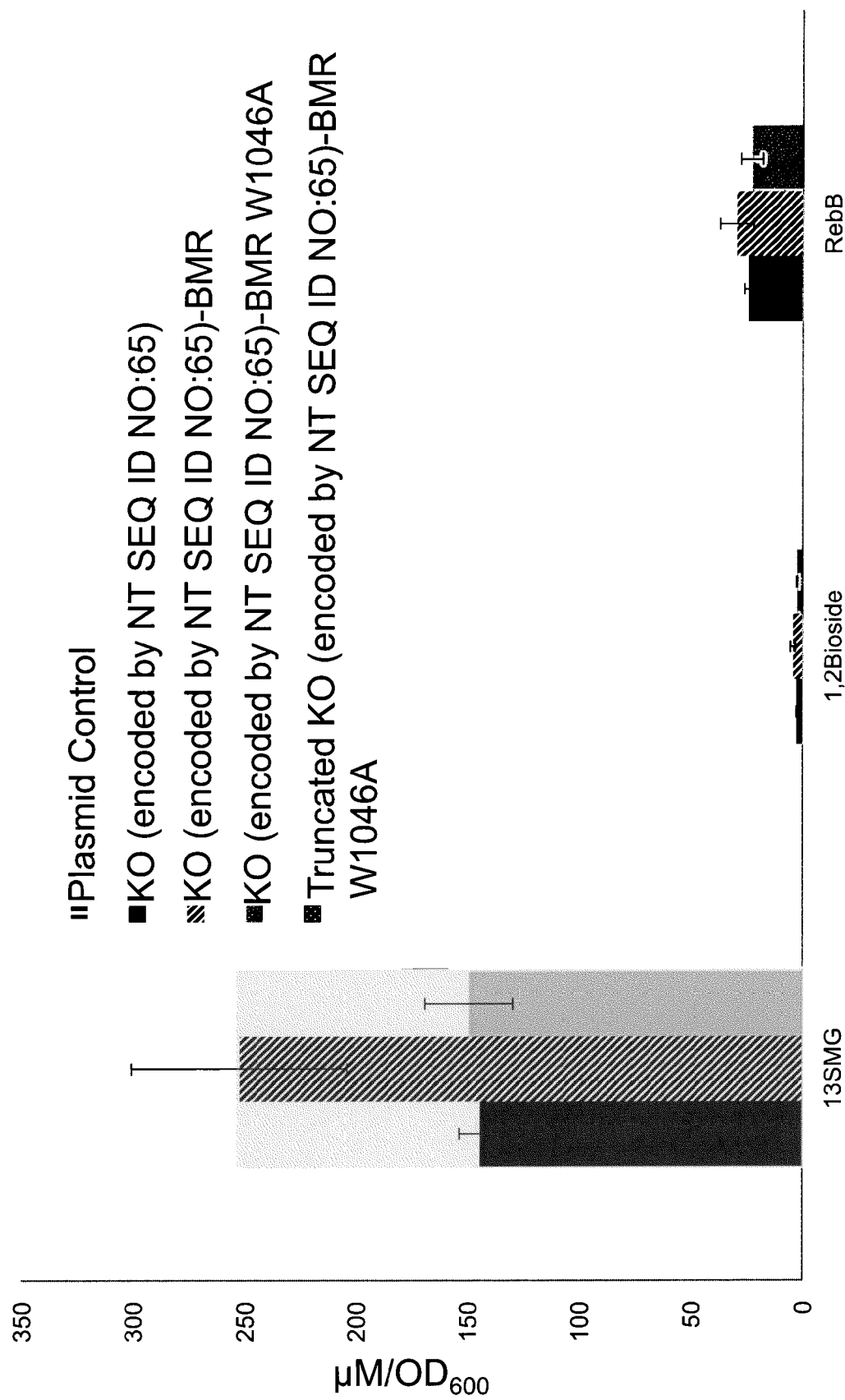
FIG. 16C shows levels of 13-SMG, 1,2-bioside, and RebB measured by LC-MS for a steviol glycoside-producing *S. cerevisiae* strain expressing the KO encoded by the nucleotide sequence set forth in SEQ ID NO:65, a fusion construct of the KO encoded by the nucleotide sequence set forth in SEQ ID NO:65 and BMR (SEQ ID NO:107, SEQ ID NO:108), a fusion construct of the KO encoded by the nucleotide sequence set forth in SEQ ID NO:65 and BMR W1046A (SEQ ID NO:109, SEQ ID NO:110), a fusion construct of a truncated KO encoded by the nucleotide sequence set forth in SEQ ID NO:65 and BMR W1046A (SEQ ID NO:111, SEQ ID NO:112), or a plasmid control.

Expression of a fusion construct comprising the KO encoded by the nucleotide sequence set forth in SEQ ID NO:65 and the wild type BMR (SEQ ID NO:107, SEQ ID NO:108) resulted in greater conversion of ent-kaurenoic acid to 13-SMG, compared to the KO encoded by the nucleotide sequence set forth in SEQ ID NO:65 (FIG. 16C). Expression of a fusion construct comprising the KO encoded by the nucleotide sequence set forth in SEQ ID NO:65 and the W1046A mutant BMR (SEQ ID NO:109, SEQ ID NO:110) resulted in decreases in ent-kaurenoic acid levels but glycosylation activity similar to that of the KO encoded by the nucleotide sequence set forth in SEQ ID NO:65 (FIG. 16C).

Example 11. Evaluation of Steviol Glycoside Pathway in *S. cerevisiae* Strain Comprising ICE2

ICE2 is an endoplasmic reticulum (ER) membrane protein involved in mechanisms such as ER zinc homeostasis and cytochrome P450 stability and/or activity. See, e.g., Estrada de Martin et al., 2005, J Cell Sci. 118(Pt 1):65-77 and Emmerstorfer et al., 2015, Biotechnol J. 10(4):623-35. ICE2 (SEQ ID NO:113, SEQ ID NO:114) was cloned and overexpressed in a steviol glycoside-producing *S. cerevisiae* strain comprising a recombinant gene encoding a *Synechococcus* sp. GGPPS polypeptide (SEQ ID NO:49), a recombinant gene encoding a truncated *Z. mays* CDPS polypeptide (SEQ ID NO:37), a recombinant gene encoding an *A. thaliana* KS polypeptide (SEQ ID NO:6), a recombinant gene encoding a recombinant *S. rebaudiana* KO polypeptide (SEQ ID NO:59, SEQ ID NO:79), a recombinant gene encoding an *A. thaliana* ATR2 polypeptide (SEQ ID NO:51, SEQ ID NO:87), a recombinant gene encoding an SrKAHe1 (SEQ ID NO:18, SEQ ID NO:68) polypeptide, a recombinant gene encoding an *S. rebaudiana* CPR8 polypeptide (SEQ ID NO:24, SEQ ID NO:28), a recombinant KAH gene encoded by the nucleotide sequence set forth in SEQ ID NO:81 (corresponding to the amino acid sequence set forth in SEQ ID NO:82), a recombinant KO gene encoded by the nucleotide sequence set forth in SEQ ID NO:56 (corresponding to the amino acid sequence set forth in SEQ ID NO:75), a recombinant KO gene encoded by the nucleotide sequence set forth in SEQ ID NO:65 (corresponding to the amino acid sequence set forth in SEQ ID NO:75), a recombinant gene encoding a UGT76G1 (SEQ ID NO:83) polypeptide, a recombinant gene encoding an *S. rebaudiana* UGT85C2 polypeptide (SEQ ID NO:30), a recombinant gene encoding an *S. rebaudiana* UGT74G1 polypeptide (SEQ ID NO:29), a recombinant gene encoding an EUGT11 (SEQ ID NO:86) polypeptide, a recombinant gene encoding a UGT91D2e (SEQ ID NO:84) polypeptide, and a recombinant gene encoding a CPR1 (SEQ ID NO:61, SEQ ID NO:76) polypeptide. Overexpression was performed by integration using the USER cloning system; see, e.g., Nour-Eldin et al., 2010, Methods Mol Biol. 643:185-200. Table 9 shows additional recombinant genes (ICE2 and/or CPR12) expressed in the above-described strain. The control strain did not comprise recombinant genes encoding ICE2 (SEQ ID NO:113, SEQ ID NO:114) or CPR12 (SEQ ID NO:97, SEQ ID NO:98) polypeptides.

TABLE 9

ICE2 steviol glycoside-producing strains.

| Strain | Sequences |
|---|---|
| ICE2 "strain A" | ICE2 (SEQ ID NO: 113, SEQ ID NO: 114) Overexpressed CPR1 (SEQ ID NO: 61, SEQ ID NO: 76) |
| ICE2 "strain B" | ICE2 (SEQ ID NO: 113, SEQ ID NO: 114) (2 copies) |
| ICE2 "strain C" | ICE2 (SEQ ID NO: 113, SEQ ID NO: 114) CPR12 (SEQ ID NO: 97, SEQ ID NO: 98) |

Fed-batch fermentation was carried out aerobically in 2 L fermenters at 30° C. with an approximate 16 h growth phase in minimal medium comprising glucose, ammonium sulfate, trace metals, vitamins, salts, and buffer followed by an approximate 110 h feeding phase with a glucose-comprising defined feed medium. A pH near 6.0 and glucose-limiting conditions were maintained. Whole culture samples (without cell removal) were analysed by the LC-UV method of Example 10 to determine levels of steviol glycosides and steviol pathway intermediates.

The following values were calculated based upon the measured levels of steviol glycosides and steviol glycoside precursors. "Total Flux" was calculated as a sum (in g/L RebD equivalents) of measured RebA, RebB, RebD, RebE, RebM, 13-SMG, rubusoside, steviol-1,2-bioside, di-glycosylated steviol, tri-glycosylated steviol, tetra-glycosylated steviol, penta-glycosylated steviol, hexa-glycosylated steviol, hepta-glycosylated steviol, copalol, ent-kaurenoic acid, glycosylated ent-kaurenoic acid, glycosylated ent-kaurenol, ent-kaurenal, geranylgeraniol, ent-kaurenal, and ent-kaurene levels. "Pre-steviol glycoside/flux" was calculated as (("total flux" (geranylgeraniol+copalol+ent-kaurene+glycosylated ent-kaurenol+ent-kaurenol+ent-kaurenal+ent-kaurenoic acid+glycosylated ent-kaurenoic acid)/"total flux"). "KAH step/flux" was calculated as ((ent-kaurenoic acid+glycosylated ent-kaurenoic acid)/"total flux"). "KO step/flux" was calculated as ((ent-kaurene+glycosylated ent-kaurenol+ent-kaurenol+ent-kaurenal)/"total flux").

The pre-steviol glycoside/flux, KO step/flux, and KAH step/flux values are shown in Table 10 below. Decreased amounts of ent-kaurene, ent-kaurenol, ent-kaurenal, glycosylated ent-kaurenol and increased amounts of ent-kaurenoic acid and glycosylated ent-kaurenoic acid were observed in the strains comprising ICE2, as compared to the control steviol glycoside-producing strain. These effects were stronger in the presence of CPR1 and/or CPR12 (Table 10). Overexpression of two copies of ICE2 (ICE2 strain B) resulted decreased ent-kaurene, ent-kaurenol, ent-kaurenal, and ent-kaurenol glycoside levels and increased steviol glycoside levels, compared to the control strain, ICE2 strain A, or ICE2 strain C (Table 10). Steviol glycoside levels increased most in the steviol glycoside-producing strain comprising two copies of ICE2. Thus, ICE2 was found to improve cytochrome P450 function.

TABLE 10

Pre-steviol glycoside/flux, KO step/flux, and KAH step/flux values for steviol glycoside-producing strains comprising ICE2.

| Strain | Pre-Steviol Glycoside/Flux | KO step/Flux | KAH step/Flux |
| --- | --- | --- | --- |
| ICE2 "strain A" | 0.38 | 0.36 | 0.22 |
| ICE2 "strain B" | 0.43 | 0.42 | 0.10 |
| ICE2 "strain C" | 0.39 | 0.38 | 0.19 |
| Control | 0.41 | 0.48 | 0.08 |

Example 12. Steviol Glycoside Production by Fermentation of S. cerevisiae Strain Comprising CPR1 and CPR12

Steviol glycoside-producing S. cerevisiae strains comprising a recombinant gene encoding a Synechococcus sp. GGPPS polypeptide (SEQ ID NO:49), a recombinant gene encoding a truncated Z. mays CDPS polypeptide (SEQ ID NO:37), a recombinant gene encoding an A. thaliana KS polypeptide (SEQ ID NO:6), a recombinant gene encoding a recombinant S. rebaudiana KO polypeptide (SEQ ID NO:59, SEQ ID NO:79), a recombinant gene encoding an A. thaliana ATR2 polypeptide (SEQ ID NO:51, SEQ ID NO:87), a recombinant gene encoding an SrKAHe1 (SEQ ID NO:18, SEQ ID NO:68) polypeptide, a recombinant gene encoding an S. rebaudiana CPR8 polypeptide (SEQ ID NO:24, SEQ ID NO:28), a recombinant gene encoding a CPR1 (SEQ ID NO:61, SEQ ID NO:76) polypeptide, a recombinant gene encoding an SrKAHe1 (SEQ ID NO:18, SEQ ID NO:68) polypeptide, a recombinant KO gene encoded by the nucleotide sequence set forth in SEQ ID NO:56 (corresponding to the amino acid sequence set forth in SEQ ID NO:75), a recombinant gene encoding a UGT76G1 (SEQ ID NO:83) polypeptide, a recombinant gene encoding an S. rebaudiana UGT85C2 (SEQ ID NO:30) polypeptide, a recombinant gene encoding an S. rebaudiana UGT74G1 (SEQ ID NO:29) polypeptide, a recombinant gene encoding a UGT91D2e-b polypeptide (SEQ ID NO:88), and a recombinant gene encoding an EUGT11 (SEQ ID NO:86) polypeptide, as well as the recombinant genes shown in Table 11, which were genomically integrated into the strains, were cultivated by fermentation. Levels of steviol glycosides and steviol glycoside precursors were measured by LC-UV as described in Example 11. The pre-KO/flux, pre-KAH/flux, pre-steviol glycoside/flux values were calculated as described in Example 11.

The pre-steviol glycoside/flux, KO step/flux, and KAH step/flux values are shown in Table 12 below. In the strain comprising the KO encoded by nucleotide sequence set forth in SEQ ID NO:56 (strain A), lower accumulation of ent-kaurene, ent-kaurenol, ent-kaurnal, and ent-kaurenol glycosides resulted. Higher levels of ent-kaurenoic acid and steviol glycosides were also measured, as compared to the control strain. In the strain comprising the KAH encoded by nucleotide sequence set forth in SEQ ID NO:80, the KO encoded by nucleotide sequence set forth in SEQ ID NO:56 (corresponding to amino acid sequence set forth in SEQ ID NO:75), and the KO encoded by nucleotide sequence set forth in SEQ ID NO:65 (strain B), ent-kaurene, ent-kaurenol, ent-kaurenal, ent-kaurenol glycosides, and ent-kaurenoic acid accumulation decreased and accumulation of steviol glycosides increased, as compared to the control strain. In the strain comprising CPR12 (SEQ ID NO:97, SEQ ID NO:98), the KAH encoded by nucleotide sequence set forth in SEQ ID NO:80, and the KO encoded by nucleotide sequence set forth in SEQ ID NO:56 (strain C), ent-kaurenol, ent-kaurenal, ent-kaurenol glycosides, and ent-kaurenoic acid accumulation decreased and accumulation of steviol glycosides increased, as compared to the control. See Table 12. Thus, CPR12 was found to be a reductase protein that improves KAH and/or KO activity.

TABLE 12

Pre-steviol glycoside/flux, KO step/flux, and KAH step/flux values for steviol glycoside-producing strains of Example 12.

| Strain | Pre-Steviol Glycoside/Flux | KO step/Flux | KAH step/Flux |
| --- | --- | --- | --- |
| Example 12, Strain A | 0.48 | 0.28 | 0.22 |
| Example 12, Strain B | 0.64 | 0.18 | 0.12 |
| Example 12, Strain C | 0.55 | 0.24 | 0.12 |
| Control | 0.40 | 0.43 | 0.17 |

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

TABLE 11

Recombinant genes also expressed in steviol glycoside-producing S. cerevisiae strain in Example 12.

| Strain | Genes |
| --- | --- |
| Example 12, Strain A | KO encoded by nucleotide sequence set forth in SEQ ID NO: 56 (corresponding to amino acid sequence set forth in SEQ ID NO: 75) |
| Example 12, Strain B | KAH encoded by nucleotide sequence set forth in SEQ ID NO: 80 (corresponding to amino acid sequence set forth in SEQ ID NO: 82) KO encoded by nucleotide sequence set forth in SEQ ID NO: 56 (corresponding to amino acid sequence set forth in SEQ ID NO: 75) KO encoded by nucleotide sequence set forth in SEQ ID NO: 65 (corresponding to amino acid sequence set forth in SEQ ID NO: 75) |
| Example 12, Strain C | CPR12 (SEQ ID NO: 97, SEQ ID NO: 98) KAH encoded by nucleotide sequence set forth in SEQ ID NO: 80 (corresponding to amino acid sequence set forth in SEQ ID NO: 82) KO encoded by nucleotide sequence set forth in SEQ ID NO: 56 (corresponding to amino acid sequence set forth in SEQ ID NO: 75) |

TABLE 13

Sequences disclosed herein.

SEQ ID NO: 1
| | | | | | |
|---|---|---|---|---|---|
| MNLSLCIASP | LLTKSNRPAA | LSAIHTASTS | HGGQTNPTNL | IIDTTKERIQ | KQFKNVEISV | 60
| SSYDTAWVAM | VPSPNSPKSP | CFPECLNWLI | NNQLNDGSWG | LVNHTHNHNH | PLLKDSLSST | 120
| LACIVALKRW | NVGEDQINKG | LSFIESNLAS | ATEKSQPSPI | GFDIIFPGLL | EYAKNLDINL | 180
| LSKQTDFSLM | LHKRELEQKR | CHSNEMDGYL | AYISEGLGNL | YDWNMVKKYQ | MKNGSVFNSP | 240
| SATAAAFINH | QNPGCLNYLN | SLLDKFGNAV | PTVYPHDLFI | RLSMVDTIER | LGISHHFRVE | 300
| IKNVLDETYR | CWVERDEQIF | MDVVTCALAF | RLLRINGYEV | SPDPLAEITN | ELALKDEYAA | 360
| LETYHASHIL | YQEDLSSGKQ | ILKSADFLKE | IISTDSNRLS | KLIHKEVENA | LKFPINTGLE | 420
| RINTRRNIQL | YNVDNTRILK | TTYHSSNISN | TDYLRLAVED | FYTCQSIYRE | ELKGLERWVV | 480
| ENKLDQLKFA | RQKTAYCYFS | VAATLSSPEL | SDARISWAKN | GILTTVVDDF | FDIGGTIDEL | 540
| TNLIQCVEKW | NVDVDKDCCS | EHVRILFLAL | KDAICWIGDE | AFKWQARDVT | SHVIQTWLEL | 600
| MNSMLREAIW | TRDAYVPTLN | EYMENAYVSF | ALGPIVKPAI | YFVGPKLSEE | IVESSEYHNL | 660
| FKLMSTQGRL | LNDIHSFKRE | FKEGKLNAVA | LHLSNGESGK | VEEEVVEEMM | MMIKNKRKEL | 720
| MKLIFEENGS | IVPRACKDAF | WNMCHVLNFF | YANDDGFTGN | TILDTVKDII | YNPLVLVNEN | 780
| EEQR | | | | | | 784

SEQ ID NO: 2
| | | | | | |
|---|---|---|---|---|---|
| MNLSLCIASP | LLTKSSRPTA | LSAIHTASTS | HGGQTNPTNL | IIDTTKERIQ | KLFKNVEISV | 60
| SSYDTAWVAM | VPSPNSPKSP | CFPECLNWLI | NNQLNDGSWG | LVNHTHNHNH | PLLKDSLSST | 120
| LACIVALKRW | NVGEDQINKG | LSFIESNLAS | ATDKSQPSPI | GFDIIFPGLL | EYAKNLDINL | 180
| LSKQTDFSLM | LHKRELEQKR | CHSNEIDGYL | AYISEGLGNL | YDWNMVKKYQ | MKNGSVFNSP | 240
| SATAAAFINH | QNPGCLNYLN | SLLDKFGNAV | PTVYPLDLYI | RLSMVDTIER | LGISHHFRVE | 300
| IKNVLDETYR | CWVERDEQIF | MDVVTCALAF | RLLRIHGYKV | SPDQLAEITN | ELAFKDEYAA | 360
| LETYHASQIL | YQEDLSSGKQ | ILKSADFLKG | ILSTDSNRLS | KLIHKEVENA | LKFPINTGLE | 420
| RINTRRNIQL | YNVDNTRILK | TTYHSSNISN | TYYLRLAVED | FYTCQSIYRE | ELKGLERWVV | 480
| QNKLDQLKFA | RQKTAYCYFS | VAATLSSPEL | SDARISWAKN | GILTTVVDDF | FDIGGTIDEL | 540
| TNLIQCVEKW | NVDVDKDCCS | EHVRILFLAL | KDAICWIGDE | AFKWQARDVT | SHVIQTWLEL | 600
| MNSMLREAIW | TRDAYVPTLN | EYMENAYVSF | ALGPIVKPAI | YFVGPKLSEE | IVESSEYHNL | 660
| FKLMSTQGRL | LNDIHSFKRE | FKEGKLNAVA | LHLSNGESGK | VEEEVVEEMM | MMIKNKRKEL | 720
| MKLIFEENGS | IVPRACKDAF | WNMCHVLNFF | YANDDGFTGN | TILDTVKDII | YNPLVLVNEN | 780
| EEQR | | | | | | 784

SEQ ID NO: 3
| | | | | | |
|---|---|---|---|---|---|
| MAMPVKLTPA | SLSLKAVCCR | FSSGGHALRF | GSSLPCWRRT | PTQRSTSSST | TRPAAEVSSG | 60
| KSKQHDQEAS | EATIRQQLQL | VDVLENMGIS | RHFAAEIKCI | LDRTYRSWLQ | RHEEIMLDTM | 120
| TCAMAFRILR | LNGYNVSSDE | LYHVVEASGL | HNSLGGYLND | TRTLLELHKA | STVSISEDES | 180
| ILDSIGSRSR | TLLREQLESG | GALRKPSLFK | EVEHALDGPF | YTTLDRLHHR | WNIENFNIIE | 240
| QHMLETPYLS | NQHTSRDILA | LSIRDFSSSQ | FTYQQELQHL | ESWVKECRLD | QLQFARQKLA | 300
| YFYLSAAGTM | FSPELSDART | LWAKNGVLTT | IVDDFFDVAG | SKEELENLVM | LVEMWDEHHK | 360
| VEFYSEQVEI | IFSSIYDSVN | QLGEKASLVQ | DRSITKHLVE | IWLDLLKSMM | TEVEWRLSKY | 420
| VPTEKEYMIN | ASLIFGLGPI | VLPALYFVGP | KISESIVKDP | EYDELFKLMS | TCGRLLNDVQ | 480
| TFEREYNEGK | LNSVSLLVLH | GGPMSISDAK | RKLQKPIDTC | RRDLLSLVLR | EESVVPRPCK | 540
| ELFWKMCKVC | YFFYSTTDGF | SSQVERAKEV | DAVINEPLKL | QGSHTLVSDV | | 590

TABLE 13-continued

Sequences disclosed herein.

SEQ ID NO: 4

| | | | | | |
|---|---|---|---|---|---|
| MSCIRPWFCP | SSISATLTDP | ASKLVTGEFK | TTSLNFHGTK | ERIKKMFDKI | ELSVSSYDTA | 60 |
| WVAMVPSPDC | PETPCFPECT | KWILENQLGD | GSWSLPHGNP | LLVKDALSST | LACILALKRW | 120 |
| GIGEEQINKG | LRFIELNSAS | VTDNEQHKPI | GFDIIFPGMI | EYAKDLDLNL | PLKPTDINSM | 180 |
| LHRRALELTS | GGGKNLEGRR | AYLAYVSEGI | GKLQDWEMAM | KYQRKNGSLF | NSPSTTAAAF | 240 |
| IHIQDAECLH | YIRSLLQKFG | NAVPTIYPLD | IYARLSMVDA | LERLGIDRHF | RKERKFVLDE | 300 |
| TYRFWLQGEE | EIFSDNATCA | LAFRILRLNG | YDVSLEDHFS | NSLGGYLKDS | GAALELYRAL | 360 |
| QLSYPDESLL | EKQNSRTSYF | LKQGLSNVSL | CGDRLRKNII | GEVHDALNFP | DHANLQRLAI | 420 |
| RRRIKHYATD | DTRILKTSYR | CSTIGNQDFL | KLAVEDFNIC | QSIQREEFKH | IERWVVERRL | 480 |
| DKLKFARQKE | AYCYFSAAAT | LFAPELSDAR | MSWAKNGVLT | TVVDDFFDVG | GSEEELVNLI | 540 |
| ELIERWDVNG | SADFCSEEVE | IIYSAIHSTI | SEIGDKSFGW | QGRDVKSHVI | KIWLDLLKSM | 600 |
| LTEAQWSSNK | SVPTLDEYMT | TAHVSFALGP | IVLPALYFVG | PKLSEEVAGH | PELLNLYKVM | 660 |
| STCGRLLNDW | RSFKRESEEG | KLNAISLYMI | HSGGASTEEE | TIEHFKGLID | SQRRQLLQLV | 720 |
| LQEKDSIIPR | PCKDLFWNMI | KLLHTFYMKD | DGFTSNEMRN | VVKAIINEPI | SLDEL | 775 |

SEQ ID NO: 5

| | | | | | |
|---|---|---|---|---|---|
| cgtcagtcat | caaggctaat | tcgtcgcgag | ttgctacgac | gccgtttcgg | ttgcttctgg | 60 |
| tttctttatg | tctatcaacc | ttcgctcctc | cggttgttcg | tctccgatct | cagctacttt | 120 |
| ggaacgagga | ttggactcag | aagtacagac | aagagctaac | aatgtgagct | ttgagcaaac | 180 |
| aaaggagaag | attaggaaga | tgttggagaa | agtggagctt | tctgtttcgg | cctacgatac | 240 |
| tagttgggta | gcaatggttc | catcaccgag | ctcccaaaat | gctccacttt | tcccacagtg | 300 |
| tgtgaaatgg | ttattggata | tcaacatgaa | agatggatct | tggggacttg | ataaccatga | 360 |
| ccatcaatct | cttaagaagg | atgtgttatc | atctacactg | gctagtatcc | tcgcgttaaa | 420 |
| gaagtgggga | attggtgaaa | gacaaataaa | caagggtctc | agtttattg | agctgaattc | 480 |
| tgcattagtc | actgatgaaa | ccatacagaa | accaacaggg | tttgatatta | tatttcctgg | 540 |
| gatgattaaa | tatgctagag | atttgaatct | gacgattcca | ttgggctcag | aagtggtgga | 600 |
| tgacatgata | cgaaaaagag | atctggatct | taaatgtgat | agtgaaaagt | tttcaaaggg | 660 |
| aagagaagca | tatctggcct | atgttttaga | ggggacaaga | aacctaaaag | attgggattt | 720 |
| gatagtcaaa | tatcaaagga | aaaatgggtc | actgtttgat | tctccagcca | aacagcagc | 780 |
| tgcttttact | cagtttggga | atgatggttg | tctccgttat | ctctgttctc | tccttcagaa | 840 |
| attcgaggct | gcagttcctt | cagtttatcc | atttgatcaa | tatgcacgcc | ttagtataat | 900 |
| tgtcactctt | gaaagcttag | gaattgatag | agatttcaaa | accgaaatca | aaagcatatt | 960 |
| ggatgaaacc | tatagatatt | ggcttcgtgg | ggatgaagaa | atatgtttgg | acttggccac | 1020 |
| ttgtgctttg | gctttccgat | tattgcttgc | tcatggctat | gatgtgtctt | acgatccgct | 1080 |
| aaaaccattt | gcagaagaat | ctggtttctc | tgatactttg | gaaggatatg | ttaagaatac | 1140 |
| gttttctgtg | ttagaattat | ttaaggctgc | tcaaagttat | ccacatgaat | cagctttgaa | 1200 |
| gaagcagtgt | tgttggacta | aacaatatct | ggagatggaa | ttgtccagct | gggttaagac | 1260 |
| ctctgttcga | gataaatacc | tcaagaaaga | ggtcgaggat | gctcttgctt | ttccctccta | 1320 |
| tgcaagccta | gaaagatcag | atcacaggag | aaaaatactc | aatggttctg | ctgtggaaaa | 1380 |
| caccagagtt | acaaaaacct | catatcgttt | gcacaatatt | tgcacctctg | atatcctgaa | 1440 |
| gttagctgtg | gatgacttca | atttctgcca | gtccatacac | cgtgaagaaa | tggaacgtct | 1500 |

TABLE 13-continued

Sequences disclosed herein.

| | | | | | |
|---|---|---|---|---|---|
| tgataggtgg | attgtggaga | atagattgca | ggaactgaaa | tttgccagac | agaagctggc | 1560 |
| ttactgttat | ttctctgggg | ctgcaactttt | attttctcca | gaactatctg | atgctcgtat | 1620 |
| atcgtgggcc | aaaggtggag | tacttacaac | ggttgtagac | gacttctttg | atgttggagg | 1680 |
| gtccaaagaa | gaactggaaa | acctcataca | cttggtcgaa | aagtgggatt | gaacggtgt | 1740 |
| tcctgagtac | agctcagaac | atgttgagat | catattctca | gttctaaggg | acaccattct | 1800 |
| cgaaacagga | gacaaagcat | tcacctatca | aggacgcaat | gtgacacacc | acattgtgaa | 1860 |
| aatttggttg | gatctgctca | agtctatgtt | gagagaagcc | gagtggtcca | gtgacaagtc | 1920 |
| aacaccaagc | ttggaggatt | acatggaaaa | tgcgtacata | tcatttgcat | taggaccaat | 1980 |
| tgtcctccca | gctacctatc | tgatcggacc | tccacttcca | gagaagacag | tcgatagcca | 2040 |
| ccaatataat | cagctctaca | agctcgtgag | cactatgggt | cgtcttctaa | atgacataca | 2100 |
| aggttttaag | agagaaagcg | cggaagggaa | gctgaatgcg | gtttcattgc | acatgaaaca | 2160 |
| cgagagagac | aatcgcagca | agaagtgat | catagaatcg | atgaaaggtt | tagcagagag | 2220 |
| aaagagggaa | gaattgcata | agctagtttt | ggaggagaaa | ggaagtgtgg | ttccaaggga | 2280 |
| atgcaaagaa | gcgttcttga | aaatgagcaa | agtgttgaac | ttattttaca | ggaaggacga | 2340 |
| tggattcaca | tcaaatgatc | tgatgagtct | tgttaaatca | gtgatctacg | agcctgttag | 2400 |
| cttacagaaa | gaatctttaa | cttgatccaa | gttgatctgg | caggtaaact | cagtaaatga | 2460 |
| aaataagact | ttggtcttct | tctttgttgc | ttcagaacaa | gaagag | | 2506 |

SEQ ID NO: 6

| | | | | | |
|---|---|---|---|---|---|
| MSINLRSSGC | SSPISATLER | GLDSEVQTRA | NNVSFEQTKE | KIRKMLEKVE | LSVSAYDTSW | 60 |
| VAMVPSPSSQ | NAPLFPQCVK | WLLDNQHEDG | SWGLDNHDHQ | SLKKDVLSST | LASILALKKW | 120 |
| GIGERQINKG | LQFIELNSAL | VTDETIQKPT | GFDIIFPGMI | KYARDLNLTI | PLGSEVVDDM | 180 |
| IRKRDLDLKC | DSEKFSKGRE | AYLAYVLEGT | RNLKDWDLIV | KYQRKNGSLF | DSPATTAAAF | 240 |
| TQFGNDGCLR | YLCSLLQKFE | AAVPSVYPFD | QYARLSIIVT | LESLGIDRDF | KTEIKSILDE | 300 |
| TYRYWLRGDE | EICLDLATCA | LAFRLLLAHG | YDVSYDPLKP | FAEESGFSDT | LEGYVKNTFS | 360 |
| VLELFKAAQS | YPHESALKKQ | CCWTKQYLEM | ELSSWVKTSV | RDKYLKKEVE | DALAFPSYAS | 420 |
| LERSDHRRKI | LNGSAVENTR | VTKTSYRLHN | ICTSDILKLA | VDDFNFCQSI | HREEMERLDR | 480 |
| WIVENRLQEL | KFARQKLAYC | YFSGAATLFS | PELSDARISW | AKGGVLTTVV | DDFFDVGGSK | 540 |
| EELENLIHLV | EKWDLNGVPE | YSSEHVEIIF | SVLRDTILET | GDKAFTYQGR | NVTHHIVKIW | 600 |
| LDLLKSMLRE | AEWSSDKSTP | SLEDYMENAY | ISFALGPIVL | PATYLIGPPL | PEKTVDSHQY | 660 |
| NQLYKLVSTM | GRLLNDIQGF | KRESAEGKLN | AVSLHMKHER | DNRSKEVIIE | SMKGLAERKR | 720 |
| EELHKLVLEE | KGSVVPRECK | EAFLKMSKVL | NLFYRKDDGF | TSNDLMSLVK | SVIYEPVSLQ | 780 |
| KESLT | | | | | | 785 |

SEQ ID NO: 7

| | | | | | |
|---|---|---|---|---|---|
| MDAVTGLLTV | PATAITIGGT | AVALAVALIF | WYLKSYTSAR | RSQSNHLPRV | PEVPGVPLLG | 60 |
| NLLQLKEKKP | YMTFTRWAAT | YGPIYSIKTG | ATSMVVVSSN | EIAKEALVTR | FQSISTRNLS | 120 |
| KALKVLTADK | TMVAMSDYDD | YHKTVKRHIL | TAVLGPNAQK | KHRIHRDIMM | DNISTQLHEF | 180 |
| VKNNPEQEEV | DLRKIFQSEL | FGLAMRQALG | KDVESLYVED | LKITMNRDEI | FQVLVVDPMM | 240 |
| GAIDVDWRDF | FPYLKWVPNK | KFENTIQQMY | IRREAVMKSL | IKEHKKRIAS | GEKLNSYIDY | 300 |
| LLSEAQTLTD | QQLLMSLWEP | IIESSDTTMV | TTEWAMYELA | KNPKLQDRLY | RDIKSVCGSE | 360 |
| KITEEHLSQL | PYITAIFHET | LRRHSPVPII | PLRHVHEDTV | LGGYHVPAGT | ELAVNIYGCN | 420 |

TABLE 13-continued

Sequences disclosed herein.

```
MDKNVWENPE EWNPERFMKE NETIDFQKTM AFGGGKRVCA GSLQALLTAS IGIGRMVQEF    480

EWKLKDMTQE EVNTIGLTTQ MLRPLRAIIK PRI                                 513

SEQ ID NO: 8
MAFFSMISIL LGFVISSFIF IFFFKKLLSF SRKNMSEVST LPSVPVVPGF PVIGNLLQLK     60

EKKPHKTFTR WSEIYGPIYS IKMGSSSLIV LNSTETAKEA MVTRFSSIST RKLSNALTVL    120

TCDKSMVATS DYDDFHKLVK RCLLNGLLGA NAQKRKRHYR DALIENVSSK LHAHARDHPQ    180

EPVNFRAIFE HELFGVALKQ AFGKDVESIY VKELGVTLSK DEIFKVLVHD MMEGAIDVDW    240

RDFFPYLKWI PNKSFEARIQ QKHKRRLAVM NALIQDRLKQ NGSESDDDCY LNFLMSEAKT    300

LTKEQIAILV WETIIETADT TLVTTEWAIY ELAKHPSVQD RLCKEIQNVC GGEKFKEEQL    360

SQVPYLNGVF HETLRKYSPA PLVPIRYAHE DTQIGGYHVP AGSEIAINIY GCNMDKKRWE    420

RPEDWWPERF LDDGKYETSD LHKTMAFGAG KRVCAGALQA SLMAGIAIGR LVQEFEWKLR    480

DGEEENVDTY GLTSQKLYPL MAIINPRRS                                     509

SEQ ID NO: 9
MSKSNSMNST SHETLFQQLV LGLDRMPLMD VHWLIYVAFG AWLCSYVIHV LSSSSTVKVP     60

VVGYRSVFEP TWLLRLRFVW EGGSIIGQGY NKFKDSIFQV RKLGTDIVII PPNYIDEVRK    120

LSQDKTRSVE PFINDFAGQY TRGMVFLQSD LQNRVIQQRL TPKLVSLTKV MKEELDYALT    180

KEMPDMKNDE WVEVDISSIM VRLISRISAR VFLGPEHCRN QEWLTTTAEY SESLFITGFI    240

LRVVPHILRP FIAPLLPSYR TLLRNVSSGR RVIGDIIRSQ QGDGNEDILS WMRDAATGEE    300

KQIDNIAQRM LILSLASIHT TAMTMTHAMY DLCACPEYIE PLRDEVKSVV GASGWDKTAL    360

NRFHKLDSFL KESQRFNPVF LLTFNRIYHQ SMTLSDGTNI PSGTRIAVPS HAMLQDSAHV    420

PGPTPPTEFD GFRYSKIRSD SNYAQKYLFS MTDSSNMAFG YGKYACPGRF YASNEMKLTL    480

AILLLQFEFK LPDGKGRPRN ITIDSDMIPD PRARLCVRKR SLRDE                   525

SEQ ID NO: 10
MEDPTVLYAC LAIAVATFVV RWYRDPLRSI PTVGGSDLPI LSYIGALRWT RRGREILQEG     60

YDGYRGSTFK IAMLDRWIVI ANGPKLADEV RRRPDEELNF MDGLGAFVQT KYTLGEAIHN    120

DPYHVDIIRE KLTRGLPAVL PDVIEELTLA VRQYIPTEGD EWVSVNCSKA ARDIVARASN    180

RVFVGLPACR NQGYLDLAID FTLSVVKDRA IINMFPELLK PIVGRVVGNA TRNVRRAVPF    240

VAPLVEERRR LMEEYGEDWS EKPNDMLQWI MDEAASRDSS VKAIAERLLM VNFAAIHTSS    300

NTITHALYHL AEMPETLQPL REEIEPLVKE EGWTKAAMGK MWWLDSFLRE SQRYNGINIV    360

SLTRMADKDI TLSDGTFLPK GTLVAVPAYS THRDDAVYAD ALVFDPFRFS RMRAREGEGT    420

KHQFVNTSVE YVPFGHGKHA CPGRFFAANE LKAMLAYIVL NYDVKLPGDG KRPLNMYWGP    480

TVLPAPAGQV LFRKRQVSL                                                499

SEQ ID NO: 11
aaacaaagaa tgattcaagt tctaacaccg atccttctct tcctcatttt cttcgttttc     60
tggaaggttt acaagcacca gaaaaccaaa atcaatcttc caccgggaag cttcggatgg    120
ccatttctgg gcgaaactct ggcactccta cgtgcaggtt gggactcaga gccgagaga    180 tttgttcgtg aacggatcaa gaaacacgga agtcctctag tgtttaagac gtcgttgttt    240
ggcgaccgtt ttgcggtgtt gtgtggacct gccggaaaca agttcctgtt ctgcaacgag    300
aacaagctgg tggcgtcgtg gtggccggtt ccggtgagga agcttttcgg caagtctctg    360
ctcacgattc gtggtgatga agctaagtgg atgaggaaga tgttgttatc gtatctcggt    420
```

TABLE 13-continued

Sequences disclosed herein.

```
cctgatgctt tcgcaactca ttatgccgtc accatggacg tcgtcacccg tcggcatatc      480
gacgttcatt ggcgagggaa ggaagaggtg aacgtattcc aaaccgttaa gttatatgcc      540
tttgagcttg catgtcgttt attcatgaac ctagacgacc caaaccacat tgcaaaactc      600
ggttccttgt tcaacatttt cttgaaaggc atcattgagc ttccaatcga cgtcccaggg      660
acacgatttt atagctccaa aaaagcagca gcagctatca ggattgaact aaaaaaattg      720
attaaagcaa gaaaactgga actgaaagaa gggaaggcat catcttcaca agacctctta      780
tcacatttgc ttacatctcc agatgaaaat ggtatgtttc taaccgaaga agagattgta      840
gacaacatct tgttactact ctttgcgggt catgatacct cggctctttc aatcactttg      900
ctcatgaaga ctcttggcga acattctgat gtttatgaca aggtgttaaa agagcaacta      960
gagatatcga agacgaaaga agcatgggag tccctgaaat gggaggacat acaaaagatg     1020
aaatactcct ggagtgttat atgtgaagtc atgagactaa atccacctgt tataggaacc     1080
tatagagagg cccttgtgga tattgattat gcgggttata ccatccccaa aggatggaag     1140
ctgcactgga gtgctgtatc gacacaaagg gacgaggcta actttgaaga cgtaacacgt     1200
tttgacccat cacggtttga aggcgcagga ccgactccat tcacctttgt tccgtttgga     1260 gggggggccta gaatgtgttt agggaaagaa tttgctcgat ggaagtactg tgcgtttctt     1320
cacaatattg tcaccaattt caaatgggac ctgttgatac ctgatgagaa aatagaatat     1380
gatcccatgg ctaccccagc aaaggggctt ccaattcgtc ttcatcccca tcaagtttga     1440
ttacttcaag catgaatcag tgatgtgaag gtaaaccata atggatctta ttggtagtta     1500
cagattatgt gtttttatgg catgaagaag ttatgataaa taaaattgtg ttattctaca     1560
acttatgtaa tttgtgcctg taagtaactg aatctattaa tgttttatgt gacatgaaac     1620
ataaatgtat aattagtaaa ttttctgctc aaaaaaaaaa aaaaaaaaaa aaaaaaa       1678
```

SEQ ID NO: 12
```
MIQVLTPILL FLIFFVFWKV YKHQKTKINL PPGSFGWPFL GETLALLRAG WDSEPERFVR      60

ERIKKHGSPL VFKTSLFGDR FAVLCGPAGN KFLFCNENKL VASWWPVPVR KLFGKSLLTI     120

RGDEAKWMRK MLLSYLGPDA FATHYAVTMD VVTRRHIDVH WRGKEEVNVF QTVKLYAFEL     180

ACRLFMNLDD PNHIAKLGSL FNIFLKGIIE LPIDVPGTRF YSSKKAAAAI RIELKKLIKA     240

RKLELKEGKA SSSQDLLSHL LTSPDENGMF LTEEEIVDNI LLLLFAGHDT SALSITLLMK     300

TLGEHSDVYD KVLKEQLEIS KTKEAWESLK WEDIQKMKYS WSVICEVMRL NPPVIGTYRE     360

ALVDIDYAGY TIPKGWKLHW SAVSTQRDEA NFEDVTRFDP SRFEGAGPTP FTFVPFGGGP     420

RMCLGKEFAR LEVLAFLHNI VTNFKWDLLI PDEKIEYDPM ATPAKGLPIR LHPHQV         476
```

SEQ ID NO: 13
```
MGLFPLEDSY ALVFEGLAIT LALYYLLSFI YKTSKKTCTP PKASGEHPIT GHLNLLSGSS      60

GLPHLALASL ADRCGPIFTI RLGIRRVLVV SNWEIAKEIF TTHDLIVSNR PKYLAAKILG     120

FNYVSFSFAP YGPYWVGIRK IIATKLMSSS RLQKLQFVRV FELENSMKSI RESWKEKKDE     180

EGKVLVEMKK WFWELNMNIV LRTVAGKQYT GTVDDADAKR ISELFREWFH YTGRFVVGDA     240

FPFLGWLDLG GYKKTMELVA SRLDSMVSKW LDEHRKKQAN DDKKEDMDFM DIMISMTEAN     300

SPLEGYGTDT IIKTTCMTLI VSGVDTTSIV LTWALSLLLN NRDTLKKAQE ELDMCVGKGR     360

QVNESDLVNL IYLEAVLKEA LRLYPAAFLG GPRAFLEDCT VAGYRIPKGT CLLINMWKLH     420

RDPNIWSDPC EFKPERFLTP NQKDVDVIGM DFELIPFGAG RRYCPGTRLA LQMLHIVLAT     480

LLQNFEMSTP NDAPVDMTAS VGMTNAKASP LEVLLSPRVK WS                       522
```

TABLE 13-continued

Sequences disclosed herein.

SEQ ID NO: 14
```
MIQVLTPILL FLIFFVFWKV YKHQKTKINL PPGSFGWPFL GETLALLRAG WDSEPERFVR        60
ERIKKHGSPL VFKTSLFGDR FAVLCGPAGN KFLFCNENKL VASWWPVPVR KLFGKSLLTI       120
RGDEAKWMRK MLLSYLGPDA FATHYAVTMD VVTRRHIDVH WRGKEEVNVF QTVKLYAFEL       180
ACRLFMNLDD PNHIAKLGSL FNIFLKGIIE LPIDVPGTRF YSSKKAAAAI RIELKKLIKA       240
RKLELKEGKA SSSQDLLSHL LTSPDENGMF LTEEEIVDNI LLLLFAGHDT SALSITLLMK       300
TLGEHSDVYD KVLKEQLEIS KTKEAWESLK WEDIQKMKYS WSVICEVMRL NPPVIGTYRE       360
ALVDIDYAGY TIPKGWKLHW SAVSTQRDEA NFEDVTRFDP SRFEGAGPTP FTFVPFGGGP       420
RMCLGKEFAR LEVLAFLHNI VTNFKWDLLI PDEKIEYDPM ATPAKGLPIR LHPHQV          476
```

SEQ ID NO: 15
```
MESLVVHTVN AIWCIVIVGI FSVGYHVYGR AVVEQWRMRR SLKLQGVKGP PPSIFNGNVS        60
EMQRIQSEAK HCSGDNIISH DYSSSLFPHF DHWRKQYGRI YTYSTGLKQH LYINHPEMVK       120
ELSQTNTLNL GRITHITKRL NPILGNGIIT SNGPHWAHQR RIIAYEFTHD KIKGMVGLMV       180
ESAMPMLNKW EEMVKRGGEM GCDIRVDEDL KDVSADVIAK ACFGSSFSKG KAIFSMIRDL       240
LTAITKRSVL FRFNGFTDMV FGSKKHGDVD IDALEMELES SIWETVKERE IECKDTHKKD       300
LMQLILEGAM RSCDGNLWDK SAYRRFVVDN CKSIYFAGHD STAVSVSWCL MLLALNPSWQ       360
VKIRDEILSS CKNGIPDAES IPNLKTVTMV IQETMRLYPP APIVGREASK DIRLGDLVVP       420
KGVCIWTLIP ALHRDPEIWG PDANDFKPER FSEGISKACK YPQSYIPFGL GPRTCVGKNF       480
GMMEVKVLVS LIVSKFSFTL SPTYQHSPSH KLLVEPQHGV VIRVV                      525
```

SEQ ID NO: 16
```
MYFLLQYLNI TTVGVFATLF LSYCLLLWRS RAGNKKIAPE AAAAWPIIGH LHLLAGGSHQ        60
LPHITLGNMA DKYGPVFTIR IGLHRAVVVS SWEMAKECST ANDQVSSSRP ELLASKLLGY       120
NYAMFGFSPY GSYWREMRKI ISLELLSNSR LELLKDVRAS EVVTSIKELY KLWAEKKNES       180
GLVSVEMKQW FGDLTLNVIL RMVAGKRYFS ASDASENKQA QRCRRVFREF FHLSGLFVVA       240
DAIPFLGWLD WGRHEKTLKK TAIEMDSIAQ EWLEEHRRRK DSGDDNSTQD FMDVMQSVLD       300
GKNLGGYDAD TINKATCLTL ISGGSDTTVV SLTWALSLVL NNRDTLKKAQ EELDIQVGKE       360
RLVNEQDISK LVYLQAIVKE TLRLYPPGPL GGLRQFTEDC TLGGYHVSKG TRLIMNLSKI       420
QKDPRIWSDP TEFQPERFLT THKDVDPRGK HFEFIPFGAG RRACPGITFG LQVLHLTLAS       480
FLHAFEFSTP SNEQVNMRES LGLTNMKSTP LEVLISPRLS SCSLYN                     526
```

SEQ ID NO: 17
```
MEPNFYLSLL LLFVTFISLS LFFIFYKQKS PLNLPPGKMG YPIIGESLEF LSTGWKGHPE        60
KFIFDRMRKY SSELFKTSIV GESTVVCCGA ASNKFLFSNE NKLVTAWWPD SVNKIFPTTS       120
LDSNLKEESI KMRKLLPQFF KPEALQRYVG VMDVIAQRHF VTHWDNKNEI TVYPLAKRYT       180
FLLACRLFMS VEDENHVAKF SDPFQLIAAG IISLPIDLPG TPFNKAIKAS NFIRKELIKI       240
IKQRRVDLAE GTASPTQDIL SHMLLTSDEN GKSMNELNIA DKILGLLIGG HDTASVACTF       300
LVKYLGELPH IYDKVYQEQM EIAKSKPAGE LLNWDDLKKM KYSWNVACEV MRLSPPLQGG       360
FREAITDFMF NGFSIPKGWK LYWSANSTHK NAECFPMPEK FDPTRFEGNG PAPYTFVPFG       420
GGPRMCPGKE YARLEILVFM HNLVKRFKWE KVIPDEKIIV DPFPIPAKDL PIRLYPHKA       479
```

SEQ ID NO: 18
```
atggaagcct cttacctata catttctatt ttgcttttac tggcatcata cctgttcacc        60
actcaactta gaaggaagag cgctaatcta ccaccaaccg tgtttccatc aataccaatc       120
attggacact tatacttact caaaaagcct ctttatagaa ctttagcaaa aattgccgct       180
```

TABLE 13-continued

Sequences disclosed herein.

```
aagtacggac caatactgca attacaactc ggctacagac gtgttctggt gatttcctca    240
ccatcagcag cagaagagtg ctttaccaat aacgatgtaa tcttcgcaaa tagacctaag    300
acattgtttg gcaaaatagt gggtggaaca tcccttggca gtttatccta cggcgatcaa    360
tggcgtaatc taaggagagt agcttctatc gaaatcctat cagttcatag gttgaacgaa    420
tttcatgata tcagagtgga tgagaacaga ttgttaatta gaaaacttag aagttcatct    480
tctcctgtta ctcttataac agtcttttat gctctaacat tgaacgtcat tatgagaatg    540
atctctggca aaagatattt cgacagtggg gatagagaat ggaggagga aggtaagaga    600 tttcgagaaa tcttagacga aacgttgctt ctagccggtg cttctaatgt tggcgactac    660
ttaccaatat tgaactggtt gggagttaag tctcttgaaa agaaattgat cgctttgcag    720
aaaaagagag atgactttt ccagggtttg attgaacagg ttagaaaatc tcgtggtgct    780
aaagtaggca aaggtagaaa aacgatgatc gaactcttat tatctttgca agagtcagaa    840
cctgagtact atacagatgc tatgataaga tcttttgtcc taggtctgct ggctgcaggt    900
agtgatactt cagcgggcac tatggaatgg gccatgagct tactggtcaa tcacccacat    960
gtattgaaga aagctcaagc tgaaatcgat agagttatcg gtaataacag attgattgac   1020
gagtcagaca ttggaaatat cccttacatc gggtgtatta tcaatgaaac tctaagactc   1080
tatccagcag ggccattgtt gttcccacat gaaagttctg ccgactgcgt tatttccggt   1140
tacaatatac ctagaggtac aatgttaatc gtaaaccaat gggcgattca tcacgatcct   1200
aaagtctggg atgatcctga aacctttaaa cctgaaagat ttcaaggatt agaaggaact   1260
agagatggtt tcaaacttat gccattcggt tctgggagaa gaggatgtcc aggtgaaggt   1320
ttggcaataa ggctgttagg gatgacacta ggctcagtga tccaatgttt tgattgggag   1380
agagtaggag atgagatggt tgacatgaca gaaggtttgg gtgtcacact tcctaaggcc   1440
gttccattag ttgccaaatg taagccacgt tccgaaatga ctaatctcct atccgaactt   1500
taa                                                                  1503
```

SEQ ID NO: 19
```
MEASYLYISI LLLLASYLFT TQLRRKSANL PPTVFPSIPI IGHLYLLKKP LYRTLAKIAA     60

KYGPILQLQL GYRRVLVISS PSAAEECFTN NDVIFANRPK TLFGKIVGGT SLGSLSYGDQ    120

WRNLRRVASI EILSVHRLNE FHDIRVDENR LLIRKLRSSS SPVTLITVFY ALTLNVIMRM    180

ISGKRYFDSG DRELEEEGKR FREILDETLL LAGASNVGDY LPILNWLGVK SLEKKLIALQ    240

KKRDDFFQGL IEQVRKSRGA KVGKGRKTMI ELLLSLQESE PEYYTDAMIR SFVLGLLAAG    300

SDTSAGTMEW AMSLLVNHPH VLKKAQAEID RVIGNNRLID ESDIGNIPYI GCIINETLRL    360

YPAGPLLFPH ESSADCVISG YNIPRGTMLI VNQWAIHHDP KVWDDPETFK PERFQGLEGT    420

RDGFKLMPFG SGRRGCPGEG LAIRLLGMTL GSVIQCFDWE RVGDEMVDMT EGLGVTLPKA    480

VPLVAKCKPR SEMTNLLSEL                                                500
```

SEQ ID NO: 20
```
MQSDSVKVSP FDLVSAAMNG KAMEKLNASE SEDPTTLPAL KMLVENRELL TLFTTSFAVL     60

IGCLVFLMWR RSSSKKLVQD PVPQVIVVKK KEKESEVDDG KKKVSIFYGT QTGTAEGFAK    120

ALVEEAKVRY EKTSFKVIDL DDYAADDDEY EEKLKKESLA FFFLATYGDG EPTDNAANFY    180

KWFTEGDDKG EWLKKLQYGV FGLGNRQYEH FNKIAIVVDD KLTEMGAKRL VPVGLGDDDQ    240

CIEDDFTAWK ELVWPELDQL LRDEDDTSVT TPYTAAVLEY RVVYHDKPAD SYAEDQTHTN    300

GHVVHDAQHP SRSNVAFKKE LHTSQSDRSC THLEFDISHT GLSYETGDHV GVYSENLSEV    360
```

TABLE 13-continued

Sequences disclosed herein.

```
VDEALKLLGL SPDTYFSVHA DKEDGTPIGG ASLPPPFPPC TLRDALTRYA DVLSSPKKVA      420

LLALAAHASD PSEADRLKFL ASPAGKDEYA QWIVANQRSL LEVMQSFPSA KPPLGVFFAA      480

VAPRLQPRYY SISSSPKMSP NRIHVTCALV YETTPAGRIH RGLCSTWMKN AVPLTESPDC      540

SQASIFVRTS NFRLPVDPKV PVIMIGPGTG LAPFRGFLQE RLALKESGTE LGSSIFFFGC      600

RNRKVDFIYE DELNNFVETG ALSELIVAFS REGTAKEYVQ HKMSQKASDI WKLLSEGAYL      660

YVCGDAKGMA KDVHRTLHTI VQEQGSLDSS KAELYVKNLQ MSGRYLRDVW                 710

SEQ ID NO: 21
MTSALYASDL FKQLKSIMGT DSLSDDVVLV IATTSLALVA GFVVLLWKKT TADRSGELKP       60

LMIPKSLMAK DEDDDLDLGS GKTRVSIFFG TQTGTAEGFA KALSEEIKAR YEKAAVKVID      120

LDDYAADDDQ YEEKLKKETL AFFCVATYGD GEPTDNAARF YKWFTEENER DIKLQQLAYG      180

VFALGNRQYE HFNKIGIVLD EELCKKGAKR LIEVGLGDDD QSIEDDFNAW KESLWSELDK      240

LLKDEDDKSV ATPYTAVIPE YRVVTHDPRF TTQKSMESNV ANGNTTIDIH HPCRVDVAVQ      300

KELHTHESDR SCIHLEFDIS RTGITYETGD HVGVYAENHV EIVEEAGKLL GHSLDLVFSI      360

HADKEDGSPL ESAVPPPFPG PCTLGTGLAR YADLLNPPRK SALVALAAYA TEPSEAEKLK      420

HLTSPDGKDE YSQWIVASQR SLLEVMAAFP SAKPPLGVFF AAIAPRLQPR YYSISSSPRL      480

APSRVHVTSA LVYGPTPTGR IHKGVCSTWM KNAVPAEKSH ECSGAPIFIR ASNFKLPSNP      540

STPIVMVGPG TGLAPFRGFL QERMALKEDG EELGSSLLFF GCRNRQMDFI YEDELNNFVD      600

QGVISELIMA FSREGAQKEY VQHKMMEKAA QVWDLIKEEG YLYVCGDAKG MARDVHRTLH      660

TIVQEQEGVS SSEAEAIVKK LQTEGRYLRD VW                                    692

SEQ ID NO: 22
MAELDTLDIV VLGVIFLGTV AYFTKGKLWG VTKDPYANGF AAGGASKPGR TRNIVEAMEE       60

SGKNCVVFYG SQTGTAEDYA SRLAKEGKSR FGLNTMIADL EDYDFDNLDT VPSDNIVMFV      120

LATYGEGEPT DNAVDFYEFI TGEDASFNEG NDPPLGNLNY VAFGLGNNTY EHYNSMVRNV      180

NKALEKLGAH RIGEAGEGDD GAGTMEEDFL AWKDPMWEAL AKKMGLEERE AVYEPIFAIN      240

ERDDLTPEAN EVYLGEPNKL HLEGTAKGPF NSHNPYIAPI AESYELFSAK DRNCLHMEID      300

ISGSNLKYET GDHIAIWPTN PGEEVNKFLD ILDLSGKQHS VVTVKALEPT AKVPFPNPTT      360

YDAILRYHLE ICAPVSRQFV STLAAFAPND DIKAEMNRLG SDKDYFHEKT GPHYYNIARF      420

LASVSKGEKW TKIPFSAFIE GLTKLQPRYY SISSSSLVQP KKISITAVVE SQQIPGRDDP      480

FRGVATNYLF ALKQKQNGDP NPAPFGQSYE LTGPRNKYDG IHVPVHVRHS NFKLPSDPGK      540

PIIMIGPGTG VAPFRGFVQE RAKQARDGVE VGKTLLFFGC RKSTEDFMYQ KEWQEYKEAL      600

GDKFEMITAF SREGSKKVYV QHRLKERSKE VSDLLSQKAY FYVCGDAAHM AREVNTVLAQ      660

IIAEGRGVSE AKGEEIVKNM RSANQYQVCS DFVTLHCKET TYANSELQED VWS             713

SEQ ID NO: 23
atgcaatcgg aatccgttga agcatcgacg attgatttga tgactgctgt tttgaaggac       60
acagtgatcg atacagcgaa cgcatctgat aacggagact caaagatgcc gccggcgttg      120
gcgatgatgt tcgaaattcg tgatctgttg ctgattttga ctacgtcagt tgctgttttg      180
gtcggatgtt tcgttgtttt ggtgtggaag agatcgtccg ggaagaagtc cggcaaggaa      240
ttggagccgc cgaagatcgt tgtgccgaag aggcggctgg agcaggaggt tgatgatggt      300
aagaagaagg ttacgatttt cttcggaaca caaactggaa cggctgaagg tttcgctaag      360
gcacttttcg aagaagcgaa agcgcgatat gaaaaggcag cgtttaaagt gattgatttg      420
gatgattatg ctgctgattt ggatgagtat gcagagaagc tgaagaagga aacatatgct      480
```

TABLE 13-continued

Sequences disclosed herein.

| | |
|---|---|
| ttcttcttct tggctacata tggagatggt gagccaactg ataatgctgc caaattttat | 540 |
| aaatggttta ctgagggaga cgagaaaggc gtttggcttc aaaaacttca atatggagta | 600 |
| tttggtcttg gcaacagaca atatgaacat tcaacaaga ttggaatagt ggttgatgat | 660 |
| ggtctcaccg agcagggtgc aaaacgcatt gttcccgttg gtcttggaga cgacgatcaa | 720 |
| tcaattgaag acgattttc ggcatggaaa gagttagtgt ggcccgaatt ggatctattg | 780 |
| cttcgcgatg aagatgacaa agctgctgca actccttaca cagctgcaat ccctgaatac | 840 |
| cgcgtcgtat ttcatgacaa acccgatgcg ttttctgatg atcatactca aaccaatggt | 900 |
| catgctgttc atgatgctca acatccatgc agatccaatg tggctgttaa aaaagagctt | 960 |
| catactcctg aatccgatcg ttcatgcaca catcttgaat ttgacatttc tcacactgga | 1020 |
| ttatcttatg aaactgggga tcatgttggt gtatactgtg aaaacctaat tgaagtagtg | 1080 |
| gaagaagctg ggaaattgtt aggattatca acagatactt atttctcgtt acatattgat | 1140 |
| aacgaagatg gttcaccact tggtggacct tcattacaac ctccttttcc tccttgtact | 1200 |
| ttaagaaaag cattgactaa ttatgcagat ctgttaagct ctcccaaaaa gtcaactttg | 1260 |
| cttgctctag ctgctcatgc ttccgatccc actgaagctg atcgtttaag atttcttgca | 1320 |
| tctcgcgagg gcaaggatga atatgctgaa tgggttgttg caaaccaaag aagtcttctt | 1380 |
| gaagtcatgg aagctttccc gtcagctaga ccgccacttg gtgttttctt tgcagcggtt | 1440 |
| gcaccgcgtt tacagcctcg ttactactct atttcttcct ccccaaagat ggaaccaaac | 1500 |
| aggattcatg ttacttgcgc gttggtttat gaaaaaactc ccgcaggtcg tatccacaaa | 1560 |
| ggaatctgct caacctggat gaagaacgct gtacctttga ccgaaagtca agattgcagt | 1620 |
| tgggcaccga ttttgttag aacatcaaac ttcagacttc caattgaccc gaaagtcccg | 1680 |
| gttatcatga ttggtcctgg aaccggggttg gctccattta gggttttct tcaagaaaga | 1740 |
| ttggctctta aagaatccgg aaccgaactc gggtcatcta tttttattctt cggttgtaga | 1800 |
| aaccgcaaag tggattacat atatgagaat gaactcaaca actttgttga aaatggtgcg | 1860 |
| cttttctgagc ttgatgttgc tttctcccgc gatggcccga cgaaagaata cgtgcaacat | 1920 |
| aaaatgaccc aaaaggcttc tgaaatatgg aatatgcttt ctgagggagc atatttatat | 1980 |
| gtatgtggtg atgctaaagg catggctaaa gatgtacacc gtacacttca caccattgtg | 2040 |
| caagaacagg gaagtttgga ctcgtctaaa gcggagttgt atgtgaagaa tctacaaatg | 2100 |
| tcaggaagat acctccgtga tgtttggtaa | 2130 |
| SEQ ID NO: 24 | |
| atgcaatcta actccgtgaa gatttcgccg cttgatctgg taactgcgct gtttagcggc | 60 |
| aaggttttgg acacatcgaa cgcatcggaa tcggagaat ctgctatgct gccgactata | 120 |
| gcgatgatta tggagaatcg tgagctgttg atgatactca aacgtcggt tgctgtattg | 180 |
| atcggatgcg ttgtcgtttt ggtgtggcgg agatcgtcta cgaagaagtc ggcgttggag | 240 |
| ccaccggtga ttgtggttcc gaagagagtg caagaggagg aagttgatga tggtaagaag | 300 |
| aaagttacgg ttttcttcgg cacccaaact ggaacagctg aaggcttcgc taaggcactt | 360 |
| gttgaggaag ctaaagctcg atatgaaaag gctgtcttta agtaattga tttggatgat | 420 |
| tatgctgctg atgacgatga gtatgaggag aaactaaaga aagaatcttt ggcctttttc | 480 |
| tttttggcta cgtatggaga tggtgagcca acagataatg ctgccagatt ttataaatgg | 540 |
| tttactgagg gagatgcgaa aggagaatgg cttaataagc ttcaatatgg agtatttggt | 600 |
| ttgggtaaca gacaatatga acattttaac aagatcgcaa aagtggttga tgatggtctt | 660 |

TABLE 13-continued

Sequences disclosed herein.

```
gtagaacagg gtgcaaagcg tcttgttcct gttggacttg agatgatga tcaatgtatt    720 gaagatgact tcaccgcatg gaaagagtta gtatggccgg agttggatca attacttcgt    780
gatgaggatg acacaactgt tgctactcca tacacagctg ctgttgcaga atatcgcgtt    840
gtttttcatg aaaaaccaga cgcgcttttct gaagattata gttatacaaa tggccatgct    900
gttcatgatg ctcaacatcc atgcagatcc aacgtggctg tcaaaaagga acttcatagt    960
cctgaatctg accggtcttg cactcatctt gaatttgaca tctcgaacac cggactatca   1020
tatgaaactg gggaccatgt tggagtttac tgtgaaaact tgagtgaagt tgtgaatgat   1080
gctgaaagat tagtaggatt accaccagac acttactcct ccatccacac tgatagtgaa   1140
gacgggtcgc cacttggcgg agcctcattg ccgcctcctt tcccgccatg cactttaagg   1200
aaagcattga cgtgttatgc tgatgttttg agttctccca agaagtcggc tttgcttgca   1260
ctagctgctc atgccaccga tcccagtgaa gctgatagat tgaaatttct tgcatccccc   1320
gccggaaagg atgaatattc tcaatggata gttgcaagcc aaagaagtct ccttgaagtc   1380
atggaagcat tcccgtcagc taagccttca cttggtgttt tctttgcatc tgttgccccg   1440
cgcttacaac caagatacta ctctatttct tcctcaccca agatggcacc ggataggatt   1500
catgttacat gtgcattagt ctatgagaaa acacctgcag ccgcatcca caaggagtt    1560 tgttcaactt ggatgaagaa cgcagtgcct atgaccgaga gtcaagattg cagttgggcc   1620
ccaatatacg tccgaacatc caatttcaga ctaccatctg accctaaggt cccggttatc   1680
atgattggac ctggcactgg tttggctcct tttagaggtt tccttcaaga gcggttagct   1740
ttaaaggaag ccggaactga cctcggttta tccattttat tcttcggatg taggaatcgc   1800
aaagtggatt tcatatatga aaacgagctt aacaactttg tggagactgg tgctcttttct   1860 gagcttattg ttgctttctc ccgtgaaggc ccgactaagg aatatgtgca acacaagatg   1920
agtgagaagg cttcggatat ctggaacttg cttctgaag gagcatattt atacgtatgt    1980
ggtgatgcca aaggcatggc caaagatgta catcgaaccc tccacacaat tgtgcaagaa   2040
cagggatctc ttgactcgtc aaaggcagaa ctctacgtga gaatctaca aatgtcagga   2100 agatacctcc gtgacgtttg gtaa                                         2124
```

SEQ ID NO: 25

```
MTSALYASDL FKQLKSIMGT DSLSDDVVLV IATTSLALVA GFVVLLWKKT TADRSGELKP     60

LMIPKSLMAK DEDDDLDLGS GKTRVSIFFG TQTGTAEGFA KALSEEIKAR YEKAAVKVID    120

LDDYAADDDQ YEEKLKKETL AFFCVATYGD GEPTDNAARF YKWFTEENER DIKLQQLAYG    180

VFALGNRQYE HFNKIGIVLD EELCKKGAKR LIEVGLGDDD QSIEDDFNAW KESLWSELDK    240

LLKDEDDKSV ATPYTAVIPE YRVVTHDPRF TTQKSMESNV ANGNTTIDIH HPCRVDVAVQ    300

KELHTHESDR SCIHLEFDIS RTGITYETGD HVGVYAENHV EIVEEAGKLL GHSLDLVFSI    360

HADKEDGSPL ESAVPPPFPG PCTLGTGLAR YADLLNPPRK SALVALAAYA TEPSEAEKLK    420

HLTSPDGKDE YSQWIVASQR SLLEVMAAFP SAKPPLGVFF AAIAPRLQPR YYSISSSPRL    480

APSRVHVTSA LVYGPTPTGR IHKGVCSTWM KNAVPAEKSH ECSGAPIFIR ASNFKLPSNP    540

STPIVMVGPG TGLAPFRGFL QERMALKEDG EELGSSLLFF GCRNRQMDFI YEDLNNFVD    600

QGVISELIMA FSREGAQKEY VQHKMMEKAA QVWDLIKEEG YLYVCGDAKG MARDVHRTLH    660

TIVQEQEGVS SSEAEAIVKK LQTEGRYLRD VW                                  692
```

TABLE 13-continued

Sequences disclosed herein.

```
SEQ ID NO: 26
MSSSSSSSTS MIDLMAAIIK GEPVIVSDPA NASAYESVAA ELSSMLIENR QFAMIVTTSI         60

AVLIGCIVML VWRRSGSGNS KRVEPLKPLV IKPREEEIDD GRKKVTIFFG TQTGTAEGFA        120

KALGEEAKAR YEKTRFKIVD LDDYAADDDE YEEKLKKEDV AFFFLATYGD GEPTDNAARF        180

YKWFTEGNDR GEWLKNLKYG VFGLGNRQYE HFNKVAKVVD DILVEQGAQR LVQVGLGDDD        240

QCIEDDFTAW REALWPELDT ILREEGDTAV ATPYTAAVLE YRVSIHDSED AKFNDITLAN        300

GNGYTVFDAQ HPYKANVAVK RELHTPESDR SCIHLEFDIA GSGLTMKLGD HVGVLCDNLS        360

ETVDEALRLL DMSPDTYFSL HAEKEDGTPI SSSLPPPFPP CNLRTALTRY ACLLSSPKKS        420

ALVALAAEAS DPTEAERLKH LASPAGKDEY SKWVVESQRS LLEVMAEFPS AKPPLGVFFA        480

GVAPRLQPRF YSISSSPKIA ETRIHVTCAL VYEKMPTGRI HKGVCSTWMK NAVPYEKSEK        540

LFLGRPIFVR QSNFKLPSDS KVPIIMIGPG TGLAPFRGFL QERLALVESG VELGPSVLFF        600

GCRNRRMDFI YEEELQRFVE SGALAELSVA FSREGPTKEY VQHKMMDKAS DIWNMISQGA        660

YLYVCGDAKG MARDVHRSLH TIAQEQGSMD STKAEGFVKN LQTSGRYLRD VW                712

SEQ ID NO: 27
MQSESVEAST IDLMTAVLKD TVIDTANASD NGDSKMPPAL AMMFEIRDLL LILTTSVAVL         60

VGCFVVLVWK RSSGKKSGKE LEPPKIVVPK RRLEQEVDDG KKKVTIFFGT QTGTAEGFAK        120

ALFEEEAKARY EKAAFKVIDL DDYAADLDEY AEKLKKETYA FFFLATYGDG EPTDNAAKFY       180

KWFTEGDEKG VWLQKLQYGV FGLGNRQYEH FNKIGIVVDD GLTEQGAKRI VPVGLGDDDQ        240

SIEDDFSAWK ELVWPELDLL LRDEDDKAAA TPYTAAIPEY RVVFHDKPDA FSDDHTQTNG        300

HAVHDAQHPC RSNVAVKKEL HTPESDRSCT HLEFDISHTG LSYETGDHVG VYCENLIEVV        360

EEAGKLLGLS TDTYFSLHID NEDGSPLGGP SLQPPFPPCT LRKALTNYAD LLSSPKKSTL        420

LALAAHASDP TEADRLRFLA SREGKDEYAE WVVANQRSLL EVMEAFPSAR PPLGVFFAAV        480

APRLQPRYYS ISSSPKMEPN RIHVTCALVY EKTPAGRIHK GICSTWMKNA VPLTESQDCS        540

WAPIFVRTSN FRLPIDPKVP VIMIGPGTGL APFRGFLQER LALKESGTEL GSSILFFGCR        600

NRKVDYIYEN ELNNFVENGA LSELDVAFSR DGPTKEYVQH KMTQKASEIW NMLSEGAYLY        660

VCGDAKGMAK DVHRTLHTIV QEQGSLDSSK AELYVKNLQM SGRYLRDVW                    709

SEQ ID NO: 28
MQSNSVKISP LDLVTALFSG KVLDTSNASE SGESAMLPTI AMIMENRELL MILTTSVAVL         60

IGCVVVLVWR SSTKKSALE PPVIVVPKRV QEEEVDDGKK KVTVFFGTQT GTAEGFAKAL        120

VEEAKARYEK AVFKVIDLDD YAADDDEYEE KLKKESLAFF FLATYGDGEP TDNAARFYKW        180

FTEGDAKGEW LNKLQYGVFG LGNRQYEHFN KIAKVVDDGL VEQGAKRLVP VGLGDDDQCI        240

EDDFTAWKEL VWPELDQLLR DEDDTTVATP YTAAVAEYRV VFHEKPDALS EDYSYTNGHA        300

VHDAQHPCRS NVAVKKELHS PESDRSCTHL EFDISNTGLS YETGDHVGVY CENLSEVVND        360

AERLVGLPPD TYSSIHTDSE DGSPLGGASL PPPFPPCTLR KALTCYADVL SSPKKSALLA        420

LAAHATDPSE ADRLKFLASP AGKDEYSQWI VASQRSLLEV MEAFPSAKPS LGVFFASVAP        480

RLQPRYYSIS SSPKMAPDRI HVTCALVYEK TPAGRIHKGV CSTWMKNAVP MTESQDCSWA        540

PIYVRTSNFR LPSDPKVPVI MIGPGTGLAP FRGFLQERLA LKEAGTDLGL SILFFGCRNR        600

KVDFIYENEL NNFVETGALS ELIVAFSREG PTKEYVQHKM SEKASDIWNL LSEGAYLYVC        660

GDAKGMAKDV HRTLHTIVQE QGSLDSSKAE LYVKNLQMSG RYLRDVW                      707
```

TABLE 13-continued

Sequences disclosed herein.

SEQ ID NO: 29
```
MAEQQKIKKS PHVLLIPFPL QGHINPFIQF GKRLISKGVK TTLVTTIHTL NSTLNHSNTT    60

TTSIEIQAIS DGCDEGGFMS AGESYLETFK QVGSKSLADL IKKLQSEGTT IDAIIYDSMT   120

EWVLDVAIEF GIDGGSFFTQ ACVVNSLYYH VHKGLISLPL GETVSVPGFP VLQRWETPLI   180

LQNHEQIQSP WSQMLFGQFA NIDQARWVFT NSFYKLEEEV IEWTRKIWNL KVIGPTLPSM   240

YLDKRLDDDK DNGFNLYKAN HHECMNWLDD KPKESVVYVA FGSLVKHGPE QVEEITRALI   300

DSDVNFLWVI KHKEEGKLPE NLSEVIKTGK GLIVAWCKQL DVLAHESVGC FVTHCGFNST   360

LEAISLGVPV VAMPQFSDQT TNAKLLDEIL GVGVRVKADE NGIVRRGNLA SCIKMIMEEE   420

RGVIIRKNAV KWKDLAKVAV HEGGSSDNDI VEFVSELIKA                        460
```

SEQ ID NO: 30
```
MDAMATTEKK PHVIFIPFPA QSHIKAMLKL AQLLHHKGLQ ITFVNTDFIH NQFLESSGPH    60

CLDGAPGFRF ETIPDGVSHS PEASIPIRES LLRSIETNFL DRFIDLVTKL PDPPTCIISD   120

GFLSVFTIDA AKKLGIPVMM YWTLAACGFM GFYHIHSLIE KGFAPLKDAS YLTNGYLDTV   180

IDWVPGMEGI RLKDFPLDWS TDLNDKVLMF TTEAPQRSHK VSHHIFHTFD ELEPSIIKTL   240

SLRYNHIYTI GPLQLLLDQI PEEKKQTGIT SLHGYSLVKE EPECFQWLQS KEPNSVVYVN   300

FGSTTVMSLE DMTEFGWGLA NSNHYFLWII RSNLVIGENA VLPPELEEHI KKRGFIASWC   360

SQEKVLKHPS VGGFLTHCGW GSTIESLSAG VPMICWPYSW DQLTNCRYIC KEWEVGLEMG   420

TKVKRDEVKR LVQELMGEGG HKMRNKAKDW KEKARIAIAP NGSSSLNIDK MVKEITVLAR   480

N                                                                 481
```

SEQ ID NO: 31
```
atggatgcaa tggctacaac tgagaagaaa ccacacgtca tcttcatacc atttccagca    60
caaagccaca ttaaagccat gctcaaacta gcacaacttc tccaccacaa aggactccag   120
ataaccttcg tcaacaccga cttcatccac aaccagtttc ttgaatcatc gggcccacat   180
tgtctagacg gtgcaccggg tttccggttc gaaaccattc cggatggtgt ttctcacagt   240
ccggaagcga gcatcccaat cagagaatca ctcttgagat ccattgaaac caacttcttg   300
gatcgtttca ttgatcttgt aaccaaactt ccggatcctc cgacttgtat tatctcagat   360
gggttcttgt cggttttcac aattgacgct gcaaaaaagc ttggaattcc ggtcatgatg   420
tattggacac ttgctgcctg tgggttcatg gttttttacc atattcattc tctcattgag   480
aaaggatttg caccacttaa agatgcaagt tacttgacaa atgggtattt ggacaccgtc   540
attgattggg ttccgggaat ggaaggcatc cgtctcaagg atttcccgct ggactggagc   600
actgacctca tgacaaagt tttgatgttc actacggaag ctcctcaaag gtcacacaag   660
gtttcacatc atatttccca cacgttcgat gagttggagc ctagtattat aaaaactttg   720
tcattgaggt ataatcacat ttacaccatc ggcccactgc aattacttct tgatcaaata   780
cccgaagaga aaaagcaaac tggaattacg agtctccatg gatacagttt agtaaaagaa   840
gaaccagagt gtttccagtg gcttcagtct aaagaaccaa attccgtcgt ttatgtaaat   900 tttgaagta ctacagtaat gtcttttagaa gacatgacgg aatttggttg gggacttgct   960
aatagcaacc attatttcct ttggatcatc cgatcaaact tggtgatagg ggaaaatgca  1020
gttttgcccc ctgaacttga ggaacatata agaaaagag ctttattgc tagctggtgt  1080 tcacaagaaa aggtcttgaa gcacccttcg gttggagggt tcttgactca ttgtgggtgg  1140
ggatcgacca tcgagagctt gtctgctggg gtgccaatga tatgctggcc ttattcgtgg  1200
gaccagctga ccaactgtag gtatatatgc aaagaatggg aggttgggct cgagatggga  1260
```

TABLE 13-continued

Sequences disclosed herein.

| | |
|---|---|
| accaaagtga aacgagatga agtcaagagg cttgtacaag agttgatggg agaaggaggt | 1320 |
| cacaaaatga ggaacaaggc taaagattgg aaagaaaagg ctcgcattgc aatagctcct | 1380 |
| aacggttcat cttctttgaa catagacaaa atggtcaagg aaatcaccgt gctagcaaga | 1440 |
| aactagttac aaagttgttt cacattgtgc tttctattta agatgtaact ttgttctaat | 1500 |
| ttaatattgt ctagatgtat tgaaccataa gtttagttgg tctcaggaat tgatttttaa | 1560 |
| tgaaataatg gtcattaggg gtgagt | 1586 |

SEQ ID NO: 32

| | |
|---|---|
| atggatgcaa tggcaactac tgagaaaaag cctcatgtga tcttcattcc atttcctgca | 60 |
| caatctcaca taaaggcaat gctaaagtta gcacaactat tacaccataa gggattacag | 120 |
| ataactttcg tgaataccga cttcatccat aatcaatttc tggaatctag tggccctcat | 180 |
| tgtttggacg gagccccagg gtttagattc gaaacaattc ctgacggtgt ttcacattcc | 240 |
| ccagaggcct ccatcccaat aagagagagt ttactgaggt caatagaaac caacttttg | 300 |
| gatcgtttca ttgacttggt cacaaaactt ccagacccac caacttgcat aatctctgat | 360 |
| ggctttctgt cagtgtttac tatcgacgct gccaaaaagt gggtatccc agttatgatg | 420 |
| tactggactc ttgctgcatg cggtttcatg ggtttctatc acatccattc tcttatcgaa | 480 |
| aagggttttg ctccactgaa agatgcatca tacttaacca acggctacct ggatactgtt | 540 |
| attgactggg taccaggtat ggaaggtata agacttaaag attttccttt ggattggtct | 600 |
| acagaccttta atgataaagt attgatgttt actacagaag ctcccacaaag atctcataag | 660 |
| gtttcacatc atatctttca cacctttgat gaattggaac catcaatcat caaaaccttg | 720 |
| tctctaagat acaatcatat ctacactatt ggtccattac aattacttct agatcaaatt | 780 |
| cctgaagaga aaaagcaaac tggtattaca tccttacacg gctactcttt agtgaaagag | 840 |
| gaaccagaat gttttcaatg gctacaaagt aaagagccta attctgtggt ctacgtcaac | 900 |
| tcggaagta caacagtcat gtccttggaa gatatgactg aatttggttg gggccttgct | 960 |
| aattcaaatc attactttct atggattatc aggtccaatt tggtaatagg gaaaacgcc | 1020 |
| gtattacctc cagaattgga ggaacacatc aaaaagagag gtttcattgc ttcctggtgt | 1080 |
| tctcaggaaa aggtattgaa acatccttct gttggtggtt tccttactca ttgcggttgg | 1140 |
| ggctctacaa tcgaatcact aagtgcagga gttccaatga tttgttggcc atattcatgg | 1200 |
| gaccaactta caaattgtag gtatatctgt aaagagtggg aagttggatt agaaatggga | 1260 |
| acaaaggtta aacgtgatga agtgaaaaga ttggttcagg agttgatggg ggaaggtggc | 1320 |
| cacaagatga gaaacaaggc caaagattgg aaggaaaaag ccagaattgc tattgctcct | 1380 |
| aacgggtcat cctctctaaa cattgataag atggtcaaag agattacagt cttagccaga | 1440 |
| aactaa | 1446 |

SEQ ID NO: 33

| | |
|---|---|
| MKTGFISPAT VFHHRISPAT TFRHHLSPAT TNSTGIVALR DINFRCKAVS KEYSDLLQKD | 60 |
| EASFTKWDDD KVKDHLDTNK NLYPNDEIKE FVESVKAMFG SMNDGEINVS AYDTAWVALV | 120 |
| QDVDGSGSPQ FPSSLEWIAN NQLSDGSWGD HLLFSAHDRI INTLACVIAL TSWNVHPSKC | 180 |
| EKGLNFLREN ICKLEDENAE HMPIGFEVTF PSLIDIAKKL NIEVPEDTPA LKEIYARRDI | 240 |
| KLTKIPMEVL HKVPTTLLHS LEGMPDLEWE KLLKLQCKDG SFLFSPSSTA FALMQTKDEK | 300 |
| CLQYLTNIVT KFNGGVPNVY PVDLFEHIWV VDRLQRLGIA RYFKSEIKDC VEYINKYWTK | 360 |
| NGICWARNTH VQDIDDTAMG FRVLRAHGYD VTPDVFRQFE KDGKFVCFAG QSTQAVTGMF | 420 |

TABLE 13-continued

Sequences disclosed herein.

```
NVYRASQMLF PGERILEDAK KFSYNYLKEK QSTNELLDKW IIAKDLPGEV GYALDIPWYA    480

SLPRLETRYY LEQYGGEDDV WIGKTLYRMG YVSNNTYLEM AKLDYNNYVA VLQLEWYTIQ    540

QWYVDIGIEK FESDNIKSVL VSYYLAAASI FEPERSKERI AWAKTTILVD KITSIFDSSQ    600

SSKEDITAFI DKFRNKSSSK KHSINGEPWH EVMVALKKTL HGFALDALMT HSQDIHPQLH    660

QAWEMWLTKL QDGVDVTAEL MVQMINMTAG RWVSKELLTH PQYQRLSTVT NSVCHDITKL    720

HNFKENSTTV DSKVQELVQL VFSDTPDDLD QDMKQTFLTV MKTFYYKAWC DPNTINDHIS    780

KVFEIVI                                                              787

SEQ ID NO: 34
MPDAHDAPPP QIRQRTLVDE ATQLLTESAE DAWGEVSVSE YETARLVAHA TWLGGHATRV     60

APLLERQHED GSWGPPGGYR LVPTLSAVHA LLTCLASPAQ DHGVPHDRLL RAVDAGLTAL    120

RRLGTSDSPP DTIAVELVIP SLLEGIQHLL DPAHPSRPA FSQHRGSLVC PGGLDGRTLG     180

ALRSHAAAGT PVPGKVWHAS ETLGLSTEAA SHLQPAQGII GGSAAATATW LTRVAPSQQS    240

DSARRYLEEL QHRYSGPVPS ITPITYFERA WLLNNFAAAG VPCEAPAALL DSLEAALTPQ    300

GAPAGAGLPP DADDTAAVLL ALATHGRGRR PEVLMDYRTD GYFQCFIGER TPSISTNAHV    360

LETLGHHVAQ HPQDRARYGS AMDTASAWLL AAQKQDGSWL DKWHASPYYA TVCCTQALAA    420

HASPATAPAR QRAVRWVLAT QRSDGGWGLW HSTVEETAYA LQILAPPSGG GNIPVQQALT    480

RGRARLCGAL PLTPLWHDKD LYTPVRVVRA ARAAALYTTR DLLLPPL                  527

SEQ ID NO: 35
MNALSEHILS ELRRLLSEMS DGGSVGPSVY DTAQALRFHG NVTGRQDAYA WLIAQQQADG     60

GWGSADFPLF RHAPTWAALL ALQRADPLPG AADAVQTATR FLQRQPDPYA HAVPEDAPIG    120

AELILPQFCG EAAWLLGGVA FPRHPALLPL RQACLVKLGA VAMLPSGHPL LHSWEAWGTS    180

PTTACPDDDG SIGISPAATA AWRAQAVTRG STPQVGRADA YLQMASRATR SGIEGVFPNV    240

WPINVFEPCW SLYTLHLAGL FAHPALAEAV RVIVAQLEAR LGVHGLGPAL HFAADADDTA    300

VALCVLHLAG RDPAVDALRH FEIGELFVTF PGERNASVST NIHALHALRL LGKPAAGASA    360

YVEANRNPHG LWDNEKWHVS WLYPTAHAVA ALAQGKPQWR DERALAALLQ AQRDDGGWGA    420

GRGSTFEETA YALFALHVMD GSEEATGRRR IAQVVARALE WMLARHAAHG LPQTPLWIGK    480

ELYCPTRVVR VAELAGLWLA LRWGRRVLAE GAGAAP                              516

SEQ ID NO: 36
gacctgacca ccaccccccg gccggcccct tcattctttc cttactttct tcctcctgct     60
gctcttgccg tttcagtgat tattagctgc tgtacgtgcg tgcgtacatt gttctctctg    120
ctgacaccca tacacgctgt agcttctaca cataccagtt cgatcgcaag ctatagcatg    180
gggcttcaat catcgcccat gctgctgcca gcgccgacgg caacggcggc cggcagcggg    240
tcacagtggc gcacggctgt ggcgggtaat ggtaactcgt ttatcttctt ctacacgtaa    300
tctctattat atacctagat tttctccaca ggcagatcag attctttaca cagctgtatt    360
ctcaaaaaaa actcatagaa aaaaagaaa aaactaaacc aaggagcga cctcaacctg     420 taccagtgcc cctgctagca gtagcttcgt tctgtccctt ttttttcatt tggatcctct    480
acataaatgc tgggtggtgg tgtccttca cgcacacatc cgcagatagc gcccagcag     540 catttatgtg gggacgacgg ctctgaaatg aattactagt cagtttcatg cgtttcagtg    600 cgagttattat agtagtagat ctcttctccg atatatccgg ccaaaggaag aagagaagag    660
aaaccacaca tctcattctc aactagtagt agaaaagtaa aaacgtacta caagcgcaag    720
cgcaaagatg gttctttcat cgtcttgcac aacagttcct caccttttctt cccttgcggt    780
```

TABLE 13-continued

Sequences disclosed herein.

```
cgttcaacta ggcccatgga gttcccgcat caagaagaag acggatacag tcgccgtccc     840
cgcggccgcc ggccggtgga ggagggcact ggcgcgggcc cagcacacca gcgaatccgc     900
cgccgtcgcc aaaggtacgg gtgatcgcta gctttgatag ctccaaatct gagcagcaaa     960
ttaaatagct aggtttgtaa cgcacgcacg catgcaggtt cgtccctaac gcccatcgtg    1020
agaaccgatg ccgaaagccg ccgcacgaga tggcctacgg acgacgacga cgctgagccg    1080
ctggtcgacg agatcagggc aatgctgacg tcgatgagcg acggggacat cagcgtgtcg    1140
gcgtacgaca ccgcctgggt gggtcttgtg cccaggctgg acggcggcga gggcccgcag    1200
ttcccggccg ccgtgcggtg gatccggaac aaccagctcc ccgacggctc gtggggcgac    1260
gcggccctgt tctccgcgta cgaccgcctg atcaacacgc tggcgtgcgt cgtcacgctc    1320
accaggtggt cgctggagcc cgagatgcgc ggcagaggta cgtaattact gtgtgctggc    1380
cgatcgagag aacacacgac ggcagtgtac ctcgacagaa acgggcgtt gctgaagact    1440
caagtgtgtg tgtgtgtgtg ttcacagggc tctctttcct cggccggaac atgtggaagc    1500
tagcgacgga ggacgaggag tccatgccga tagggttcga gctcgcgttc ccttctctca    1560
tcgaactagc caagagtctg ggcgtccacg acttcccgta cgaccaccag gctctgcagg    1620
gaatatactc gagcagggag atcaagatga agaggattcc taaggaagtg atgcacacgg    1680
ttcccacatc cattctccac agcctggaag ggatgcccgg gctagactgg gcgaagctgc    1740
tgaaactgca gtcgacgac gggtccttcc tcttctctcc cgcggccacc gcgtacgctc    1800
tcatgaacac cggcgacgac aggtgcttca gctacatcga caggacagtc aagaaattca    1860
acggaggagg tacgcaagca gtagcgtaga tacatgggca tagcatgcat gcatgcaatg    1920
cagcgttgcc cactgcatgc gccttccttc cttccttctc gtctcttcaa cggttcgtct    1980
tctctcgccg tttctcgcag tgcccaacgt ctaccccgtg gaccttttcg agcacatatg    2040
ggctgtcgat cgcctggagc gtctcgggat ctcccgctac ttccagaaag agattgagca    2100
gtgcatggac tacgtgaaca ggcactggac tgaggacggg atctgctggg cgaggaactc    2160
cgacgtgaag gaggtggacg acacggccat ggctttccgc ctgctacggc tgcacggata    2220
cagcgtctcg ccaggtacgt aacaaacaca aaaaaaaaaa acgcgcagac aacagagatc    2280
gtcacgtcat acacacgcgt gtcctgaaca tttttcattt ggtctcccac ccatcgtacg    2340
taataataat aaaaaaaaac gtgcttctgc cctgcctgtg tacgtgtaga tgtgttcaag    2400
aacttcgaga aggacgggga gttcttcgcc ttcgtgggc agtcgaacca ggcggtgacg    2460
gggatgtaca acctcaacag ggcctcccag ataagcttcc cggggagga cgtcctgcac    2520
cgtgcagggg ctttctcgta cgagtttctc aggcggaaag aggccgaggg agcgctccgt    2580
gacaaatgga tcatatctaa ggacctgcct ggggaggtag tgtacaccct ggacttccct    2640
tggtatggga acctgccgcg cgtggaggcg agagactatc tggaacagta cggcggcggc    2700
gacgatgtct ggatcgggaa gacgctctac aggtagatag atcttttag ctattaattg    2760
gtttcagatc gaccagataa aatttgcatt attggttctt ttgatgcatg taattgaaag    2820
ccaataaata acctcagtat gcgtgatggc tgacttttgc attggcagga tgcctcttgt    2880
gaataacgat gtgtatcttg agctggctag gatggacttc aaccattgcc aagccctaca    2940
tcagcttgag tggcaaggcc tgaaaaggta tgtatgttac tatatatata cagcccggtt    3000
gttgagtttt ttttttattt tatttttttc gcgattacca tttcttctcg atgcaaaata    3060
aatctgcaca gatcatcata tatatccttg atgatatata agggcttctc gtatatatat    3120
```

TABLE 13-continued

Sequences disclosed herein.

```
cttatcacct atatatacat aggtggtaca ctgagaaccg gctcatggat ttcggagtgg    3180
cgcaagagga tgctctgcga gcgtatttcc tggccgccgc ttccgtctac gagccgtgcc    3240
gagccgcgga gcggcttgcg tgggccagag cggcgatact tgccaacgcc gtctctaccc    3300
atctccgtaa cagcccctca ttcagagaac gcttggaaca ctccttgcgt tgccgcccca    3360
gtgaagaaac ggatggatca tggtaataag ctgatcgatg ggaaattaaa aatttaagtt    3420
ttttttttct tttttgttgc cattatctga gaccaatgca atgtggtgca tatatatcca    3480
ggttcaactc atcaagtgga agtgacgctg ttcttgtgaa ggcagttctg cggcttaccg    3540
actcgttagc gcgagaagcg cagccgattc atggcggtga tccggaggac atcatccaca    3600
agctactgag atcagctgta agttaaacgt aacgttcaga agaagatttt ttttttttt    3660 tgcagttaac aagtactacg acatctatcg ttttttgttca gcatgcacag tcatcctagc    3720
tactaatacc attattcttc tgtgaacttg tgtagtgggc tgaatgggtc agggagaagg    3780
cagatgcagc agacagcgtg tgtaatggat ccagtgctgt ggaacaagaa gggtcgcgca    3840
tggttcatga caagcaaacg tgtctgcttt tagctcgaat gatcgagatc agcgctgggc    3900
gagctgcagg tgaggctgcg agcgaagatg gtgaccgtcg gattatccag ctcactgggt    3960
ctatatgtga cagtctcaag cagaagatgc tagtatctca ggtatagcac atatatacta    4020
cagaaagttt gtgcgtagtt attatttccc ttttttcatg tgacgaacat gatgacctga    4080
tgatgcatgt atatggcttc ataggaccc ccgagaagaa cgaagagatg atgagccatg    4140
tcgatgacga attgaagctg cgtatacgag agttcgttca gtatcttctg agactcggtg    4200
agaagaaaac cggcagcagc gagacaaggc agacctttct gagcatcgtg aaaagctgtt    4260
actacgctgc tcactgcccg ccgcatgtgg tagacaggca tatttccaga gttatttttg    4320
aacctgtttc cgccgcaaaa taatggtaat ggtagatgtg aatgtgatat ggagataaga    4380
gagagagaaa atgttgatag tggaaattgg cgttgatgtc gcctccacat tctttacgca    4440
aaagtagcgt ctgttttgga taaaaaaat ccagtttctg taaattatag aataaatcaa    4500
tcgctgtgtc ccaaactcta aaatgttatt ctgtgaagta tggaataaat cggtcactat    4560
acctatcttg tggatgc                                                  4577
```

SEQ ID NO: 37
```
MVLSSSCTTV PHLSSLAVVQ LGPWSSRIKK KTDTVAVPAA AGRWRRALAR AQHTSESAAV     60

AKGSSLTPIV RTDAESRRTR WPTDDDDAEP LVDEIRAMLT SMSDGDISVS AYDTAWVGLV    120

PRLDGGEGPQ FPAAVRWIRN NQLPDGSWGD AALFSAYDRL INTLACVVTL TRWSLEPEMR    180

GRGLSFLGRN MWKLATEDEE SMPIGFELAF PSLIELAKSL GVHDFPYDHQ ALQGIYSSRE    240

IKMKRIPKEV MHTVPTSILH SLEGMPGLDW AKLLKLQSSD GSFLFSPAAT AYALMNTGDD    300

RCFSYIDRTV KKFNGGVPNV YPVDLFEHIW AVDRLERLGI SRYFQKEIEQ CMDYVNRHWT    360

EDGICWARNS DVKEVDDTAM AFRLLRLHGY SVSPDVFKNF EKDGEFFAFV GQSNQAVTGM    420

YNLNRASQIS FPGEDVLHRA GAFSYEFLRR KEAEGALRDK WIISKDLPGE VVYTLDFPWY    480

GNLPRVEARD YLEQYGGGDD VWIGKTLYRM PLVNNDVYLE LARMDFNHCQ ALHQLEWQGL    540

KRWYTENRLM DFGVAQEDAL RAYFLAAASV YEPCRAAERL AWARAAILAN AVSTHLRNSP    600

SFRERLEHSL RCRPSEETDG SWFNSSSGSD AVLVKAVLRL TDSLAREAQP IHGGDPEDII    660

HKLLRSAWAE WVREKADAAD SVCNGSSAVE QEGSRMVHDK QTCLLLARMI EISAGRAAGE    720

AASEDGDRRI IQLTGSICDS LKQKMLVSQD PEKNEEMMSH VDDELKLRIR EFVQYLLRLG    780

EKKTGSSETR QTFLSIVKSC YYAAHCPPHV VDRHISRVIF EPVSAAK                 827
```

TABLE 13-continued

Sequences disclosed herein.

SEQ ID NO: 38

| | | | | | |
|---|---|---|---|---|---|
| cttcttcact | aaatacttag | acagagaaaa | cagagctttt | taaagccatg | tctcttcagt | 60 |
| atcatgttct | aaactccatt | ccaagtacaa | cctttctcag | ttctactaaa | acaacaatat | 120 |
| cttcttcttt | ccttaccatc | tcaggatctc | ctctcaatgt | cgctagagac | aaatccagaa | 180 |
| gcggttccat | acattgttca | aagcttcgaa | ctcaagaata | cattaattct | caagaggttc | 240 |
| aacatgattt | gcctctaata | catgagtggc | aacagcttca | aggagaagat | gctcctcaga | 300 |
| ttagtgttgg | aagtaatagt | aatgcattca | agaagcagt | gaagagtgtg | aaaacgatct | 360 |
| tgagaaacct | aacggacggg | gaaattacga | tatcggctta | cgatacagct | tgggttgcat | 420 |
| tgatcgatgc | cggagataaa | actccggcgt | ttccctccgc | cgtgaaatgg | atcgccgaga | 480 |
| accaactttc | cgatggttct | tggggagatg | cgtatctctt | ctcttatcat | gatcgtctca | 540 |
| tcaataccct | tgcatgcgtc | gttgctctaa | gatcatggaa | tctctttcct | catcaatgca | 600 |
| acaaaggaat | cacgttttc | cgggaaaata | ttgggaagct | agaagacgaa | aatgatgagc | 660 |
| atatgccaat | cggattcgaa | gtagcattcc | catcgttgct | tgagatagct | cgaggaataa | 720 |
| acattgatgt | accgtacgat | tctccggtct | taaaagatat | atacgccaag | aaagagctaa | 780 |
| agcttacaag | gataccaaaa | gagataatgc | acaagatacc | aacaacattg | ttgcatagtt | 840 |
| tggaggggat | gcgtgattta | gattgggaaa | agctcttgaa | acttcaatct | caagacggat | 900 |
| ctttcctctt | ctctccttcc | tctaccgctt | ttgcattcat | gcagacccga | gacagtaact | 960 |
| gcctcgagta | tttgcgaaat | gccgtcaaac | gtttcaatgg | aggagttccc | aatgtctttc | 1020 |
| ccgtggatct | tttcgagcac | atatggatag | tggatcggtt | acaacgttta | gggatatcga | 1080 |
| gatactttga | agaagagatt | aaagagtgtc | ttgactatgt | ccacagatat | tggaccgaca | 1140 |
| atggcatatg | ttgggctaga | tgttcccatg | tccaagacat | cgatgataca | gccatggcat | 1200 |
| ttaggctctt | aagacaacat | ggataccaag | tgtccgcaga | tgtattcaag | aactttgaga | 1260 |
| aagagggaga | gtttttctgc | tttgtggggc | aatcaaacca | agcagtaacc | ggtatgttca | 1320 |
| acctataccg | ggcatcacaa | ttggcgtttc | caagggaaga | gatattgaaa | aacgccaaag | 1380 |
| agttttctta | taattatctg | ctagaaaaac | gggagagaga | ggagttgatt | gataagtgga | 1440 |
| ttataatgaa | agacttacct | ggcgagattg | ggtttgcgtt | agagattcca | tggtacgcaa | 1500 |
| gcttgcctcg | agtagagacg | agattctata | ttgatcaata | tggtggagaa | aacgacgttt | 1560 |
| ggattggcaa | gactctttat | aggatgccat | acgtgaacaa | taatggatat | ctggaattag | 1620 |
| caaaacaaga | ttacaacaat | tgccaagctc | agcatcagct | cgaatgggac | atattccaaa | 1680 |
| agtggtatga | agaaaatagg | ttaagtgagt | ggggtgtgcg | cagaagtgag | cttctcgagt | 1740 |
| gttactactt | agcggctgca | actatatttg | aatcagaaag | gtcacatgag | agaatggttt | 1800 |
| gggctaagtc | aagtgtattg | gttaaagcca | tttcttcttc | ttttgggaa | tcctctgact | 1860 |
| ccagaagaag | cttctccgat | cagtttcatg | aatacattgc | caatgctcga | cgaagtgatc | 1920 |
| atcactttaa | tgacaggaac | atgagattgg | accgaccagg | atcggttcag | gccagtcggc | 1980 |
| ttgccggagt | gttaatcggg | actttgaatc | aaatgtcttt | tgacctttc | atgtctcatg | 2040 |
| gccgtgacgt | taacaatctc | ctctatctat | cgtggggaga | ttggatggaa | aaatggaaac | 2100 |
| tatatggaga | tgaaggagaa | ggagagctca | tggtgaagat | gataattcta | atgaagaaca | 2160 |
| atgacctaac | taacttcttc | acccacactc | acttcgttcg | tctcgcggaa | atcatcaatc | 2220 |
| gaatctgtct | tcctcgccaa | tacttaaagg | caaggagaaa | cgatgagaag | gagaagacaa | 2280 |
| taaagagtat | ggagaaggag | atggggaaaa | tggttgagtt | agcattgtcg | gagagtgaca | 2340 |

| TABLE 13-continued | | | | |
|---|---|---|---|---|
| Sequences disclosed herein. | | | | |
| catttcgtga | cgtcagcatc | acgtttcttg | atgtagcaaa | agcattttac tactttgctt | 2400 |
| tatgtggcga | tcatctccaa | actcacatct | ccaaagtctt | gtttcaaaaa gtctagtaac | 2460 |
| ctcatcatca | tcatcgatcc | attaacaatc | agtggatcga | tgtatccata gatgcgtgaa | 2520 |
| taatatttca | tgtagagaag | gagaacaaat | tagatcatgt | agggttatca | 2570 |

SEQ ID NO: 39
```
MSLQYHVLNS IPSTTFLSST KTTISSSFLT ISGSPLNVAR DKSRSGSIHC SKLRTQEYIN    60
SQEVQHDLPL IHEWQQLQGE DAPQISVGSN SNAFKEAVKS VKTILRNLTD GEITISAYDT   120
AWVALIDAGD KTPAFPSAVK WIAENQLSDG SWGDAYLFSY HDRLINTLAC VVALRSWNLF   180
PHQCNKGITF FRENIGKLED ENDEHMPIGF EVAFPSLLEI ARGINIDVPY DSPVLKDIYA   240
KKELKLTRIP KEIMHKIPTT LLHSLEGMRD LDWEKLLKLQ SQDGSFLFSP SSTAFAFMQT   300
RDSNCLEYLR NAVKRFNGGV PNVFPVDLFE HIWIVDRLQR LGISRYFEEE IKECLDYVHR   360
YWTDNGICWA RCSHVQDIDD TAMAFRLLRQ HGYQVSADVF KNFEKEGEFF CFVGQSNQAV   420
TGMFNLYRAS QLAFPREEIL KNAKEFSYNY LLEKREREEL IDKWIIMKDL PGEIGFALEI   480
PWYASLPRVE TRFYIDQYGG ENDVWIGKTL YRMPYVNNNG YLELAKQDYN NCQAQHQLEW   540
DIFQKWYEEN RLSEWGVRRS ELLECYYLAA ATIFESERSH ERMVWAKSSV LVKAISSSFG   600
ESSDSRRSFS DQFHEYIANA RRSDHHFNDR NMRLDRPGSV QASRLAGVLI GTLNQMSFDL   660
FMSHGRDVNN LLYLSWGDWM EKWKLYGDEG EGELMVKMII LMKNNDLTNF FTHTHFVRLA   720
EIINRICLPR QYLKARRNDE KEKTIKSMEK EMGKMVELAL SESDTFRDVS ITFLDVAKAF   780
YYFALCGDHL QTHISKVLFQ KV                                          802
```

SEQ ID NO: 40
```
MEFDEPLVDE ARSLVQRTLQ DYDDRYGFGT MSCAAYDTAW VSLVTKTVDG RKQWLFPECF    60
EFLLETQSDA GGWEIGNSAP IDGILNTAAS LLALKRHVQT EQIIQPQHDH KDLAGRAERA   120
AASLRAQLAA LDVSTTEHVG FEIIVPAMLD PLEAEDPSLV FDFPARKPLM KIHDAKMSRF   180
RPEYLYGKQP MTALHSLEAF IGKIDFDKVR HHRTHGSMMG SPSSTAAYLM HASQWDGDSE   240
AYLRHVIKHA AGQGTGAVPS AFPSTHFESS WILTTLFRAG FSASHLACDE LNKLVEILEG   300
SFEKEGGAIG YAPGFQADVD DTAKTISTLA VLGRDATPRQ MIKVFEANTH FRTYPGERDP   360
SLTANCNALS ALLHQPDAAM YGSQIQKITK FVCDYWWKSD GKIKDKWNTC YLYPSVLLVE   420
VLVDLVSLLE QGKLPDVLDQ ELQYRVAITL FQACLRPLLD QDAEGSWNKS IEATAYGILI   480
LTEARRVCFF DRLSEPLNEA IRRGIAFADS MSGTEAQLNY IWIEKVSYAP ALLTKSYLLA   540
ARWAAKSPLG ASVGSSLWTP PREGLDKHVR LFHQAELFRS LPEWELRASM IEAALFTPLL   600
RAHRLDVFPR QDVGEDKYLD VVPFFWTAAN NRDRTYASTL FLYDMCFIAM LNFQLDEFME   660
ATAGILFRDH MDDLRQLIHD LLAEKTSPKS SGRSSQGTKD ADSGIEEDVS MSDSASDSQD   720
RSPEYDLVFS ALSTFTKHVL QHPSIQSASV WDRKLLAREM KAYLLAHIQQ AEDSTPLSEL   780
KDVPQKTDVT RVSTSTTTFF NWVRTTSADH ISCPYSFHFV ACHLGAALSP KGSNGDCYPS   840
AGEKFLAAAV CRHLATMCRM YNDLGSAERD SDEGNLNSLD FPEFADSAGN GGIEIQKAAL   900
LRLAEFERDS YLEAFRRLQD ESNRVHGPAG GDEARLSRRR MAILEFFAQQ VDLYGQVYVI   960
RDISARIPKN EVEKKRKLDD AFN                                          983
```

SEQ ID NO: 41
```
MASSTLIQNR SCGVTSSMSS FQIFRGQPLR FPGTRTPAAV QCLKKRRCLR PTESVLESSP    60
GSGSYRIVTG PSGINPSSNG HLQEGSLTHR LPIPMEKSID NFQSTLYVSD IWSETLQRTE   120
CLLQVTENVQ MNEWIEEIRM YFRNMTLGEI SMSPYDTAWV ARVPALDGSH GPQFHRSLQW   180
```

TABLE 13-continued

Sequences disclosed herein.

```
IIDNQLPDGD WGEPSLFLGY DRVCNTLACV IALKTWGVGA QNVERGIQFL QSNIYKMEED      240

DANHMPIGFE IVFPAMMEDA KALGLDLPYD ATILQQISAE REKKMKKIPM AMVYKYPTTL      300

LHSLEGLHRE VDWNKLLQLQ SENGSFLYSP ASTACALMYT KDVKCFDYLN QLLIKFDHAC      360

PNVYPVDLFE RLWMVDRLQR LGISRYFERE IRDCLQYVYR YWKDCGIGWA SNSSVQDVDD      420

TAMAFRLLRT HGFDVKEDCF RQFFKDGEFF CFAGQSSQAV TGMFNLSRAS QTLFPGESLL      480

KKARTFSRNF LRTKHENNEC FDKWIITKDL AGEVEYNLTF PWYASLPRLE HRTYLDQYGI      540

DDIWIGKSLY KMPAVTNEVF LKLAKADFNM CQALHKKELE QVIKWNASCQ FRDLEFARQK      600

SVECYFAGAA TMFEPEMVQA RLVWARCCVL TTVLDDYFDH GTPVEELRVF VQAVRTWNPE      660

LINGLPEQAK ILFMGLYKTV NTIAEEAFMA QKRDVHHHLK HYWDKLITSA LKEAEWAESG      720

YVPTFDEYME VAEISVALEP IVCSTLFFAG HRLDEDVLDS YDYHLVMHLV NRVGRILNDI      780

QGMKREASQG KISSVQIYME EHPSVPSEAM AIAHLQELVD NSMQQLTYEV LRFTAVPKSC      840

KRIHLNMAKI MHAFYKDTDG FSSLTAMTGF VKKVLFEPVP E                         881

SEQ ID NO: 42
MPGKIENGTP KDLKTGNDFV SAAKSLLDRA FKSHHSYYGL CSTSCQVYDT AWVAMIPKTR       60

DNVKQWLFPE CFHYLLKTQA ADGSWGSLPT TQTAGILDTA SAVLALLCHA QEPLQILDVS      120

PDEMGLRIEH GVTSLKRQLA VWNDVEDTNH IGVEFIIPAL LSMLEKELDV PSFEFPCRSI      180

LERMHGEKLG HFDLEQVYGK PSSLLHSLEA FLGKLDFDRL SHHLYHGSMM ASPSSTAAYL      240

IGATKWDDEA EDYLRHVMRN GAGHGNGGIS GTFPTTHFEC SWIIATLLKV GFTLKQIDGD      300

GLRGLSTILL EALRDENGVI GFAPRTADVD DTAKALLALS LVNQPVSPDI MIKVFEGKDH      360

FTTFGSERDP SLTSNLHVLL SLLKQSNLSQ YHPQILKTTL FTCRWWWGSD HCVKDKWNLS      420

HLYPTMLLVE AFTEVLHLID GGELSSLFDE SFKCKIGLSI FQAVLRIILT QDNDGSWRGY      480

REQTCYAILA LVQARHVCFF THMVDRLQSC VDRGFSWLKS CSFHSQDLTW TSKTAYEVGF      540

VAEAYKLAAL QSASLEVPAA TIGHSVTSAV PSSDLEKYMR LVRKTALFSP LDEWGLMASI      600

IESSFFVPLL QAQRVEIYPR DNIKVDEDKY LSIIPFTWVG CNNRSRTFAS NRWLYDMMYL      660

SLLGYQTDEY MEAVAGPVFG DVSLLHQTID KVIDNTMGNL ARANGTVHSG NGHQHESPNI      720

GQVEDTLTRF TNSVLNHKDV LNSSSSDQDT LRREFRTFMH AHITQIEDNS RFSKQASSDA      780

FSSPEQSYFQ WVNSTGGSHV ACAYSFAFSN CLMSANLLQG KDAFPSGTQK YLISSVMRHA      840

TNMCRMYNDF GSIARDNAER NVNSIHFPEF TLCNGTSQNL DERKERLLKI ATYEQGYLDR      900

ALEALERQSR DDAGDRAGSK DMRKLKIVKL FCDVTDLYDQ LYVIKDLSSS MK             952

SEQ ID NO: 43
MALVNPTALF YGTSIRTRPT NLLNPTQKLR PVSSSSLPSF SSVSAILTEK HQSNPSENNN       60

LQTHLETPFN FDSYMLEKVN MVNEALDASV PLKDPIKIHE SMRYSLLAGG KRIRPMMCIA      120

ACEIVGGNIL NAMPAACAVE MIHTMSLVHD DLPCMDNDDF RRGKPISHKV YGEEMAVLTG      180

DALLSLSFEH IATATKGVSK DRIVRAIGEL ARSVGSEGLV AGQVVDILSE GADVGLDHLE      240

YIHIHKTAML LESSVVIGAI MGGGSDQQIE KLRKFARSIG LLFQVVDDIL DVTKSTEELG      300

KTAGKDLLTD KTTYPKLLGI EKSREFAEKL NKEAQEQLSG FDRRKLAPLI ALANYNAYRQ      360

N                                                                     361

SEQ ID NO: 44
MAEQQISNLL SMFDASHASQ KLEITVQMMD TYHYRETPPD SSSSEGGSLS RYDERRVSLP       60

LSHNAASPDI VSQLCFSTAM SSELNHRWKS QRLKVADSPY NYILTLPSKG IRGAFIDSLN      120

VWLEVPEDET SVIKEVIGML HNSSLIIDDF QDNSPLRRGK PSTHTVFGPA QAINTATYVI      180
```

TABLE 13-continued

Sequences disclosed herein.

| | | | | | |
|---|---|---|---|---|---|
| VKAIEKIQDI | VGHDALADVT | GTITTIFQGQ | AMDLWWTANA | IVPSIQEYLL | MVNDKTGALF | 240 |
| RLSLELLALN | SEASISDSAL | ESLSSAVSLL | GQYFQIRDDY | MNLIDNKYTD | QKGFCEDLDE | 300 |
| GKYSLTLIHA | LQTDSSDLLT | NILSMRRVQG | KLTAQKRCWF | WK | | 342 |

SEQ ID NO: 45
| | | | | | |
|---|---|---|---|---|---|
| MEKTKEKAER | ILLEPYRYLL | QLPGKQVRSK | LSQAFNHWLK | VPEDKLQIII | EVTEMLHNAS | 60 |
| LLIDDIEDSS | KLRRGFPVAH | SIYGVPSVIN | SANYVYFLGL | EKVLTLDHPD | AVKLFTRQLL | 120 |
| ELHQGQGLDI | YWRDTYTCPT | EEEYKAMVLQ | KTGGLFGLAV | GLMQLFSDYK | EDLKPLLDTL | 180 |
| GLFFQIRDDY | ANLHSKEYSE | NKSFCEDLTE | GKFSFPTIHA | IWSRPESTQV | QNILRQRTEN | 240 |
| IDIKKYCVQY | LEDVGSFAYT | RHTLRELEAK | AYKQIEACGG | NPSLVALVKH | LSKMFTEENK | 300 |

SEQ ID NO: 46
| | | | | | |
|---|---|---|---|---|---|
| MARFYFLNAL | LMVISLQSTT | AFTPAKLAYP | TTTTALNVAS | AETSFSLDEY | LASKIGPIES | 60 |
| ALEASVKSRI | PQTDKICESM | AYSLMAGGKR | IRPVLCIAAC | EMFGGSQDVA | MPTAVALEMI | 120 |
| HTMSLIHDDL | PSMDNDDLRR | GKPTNHVVFG | EDVAILAGDS | LLSTSFEHVA | RETKGVSAEK | 180 |
| IVDVIARLGK | SVGAEGLAGG | QVMDLECEAK | PGTTLDDLKW | IHIHKTATLL | QVAVASGAVL | 240 |
| GGATPEEVAA | CELFAMNIGL | AFQVADDILD | VTASSEDLGK | TAGKDEATDK | TTYPKLLGLE | 300 |
| ESKAYARQLI | DEAKESLAPF | GDRAAPLLAI | ADFIIDRKN | | | 339 |

SEQ ID NO: 47
| | | | | | |
|---|---|---|---|---|---|
| MHLAPRRVPR | GRRSPPDRVP | ERQGALGRRR | GAGSTGCARA | AAGVHRRRGG | GEADPSAAVH | 60 |
| RGWQAGGGTG | LPDEVVSTAA | ALEMFHAFAL | IHDDIMDDSA | TRRGSPTVHR | ALADRLGAAL | 120 |
| DPDQAGQLGV | STAILVGDLA | LTWSDELLYA | PLTPHRLAAV | LPLVTAMRAE | TVHGQYLDIT | 180 |
| SARRPGTDTS | LALRIARYKT | AAYTMERPLH | IGAALAGARP | ELLAGLSAYA | LPAGEAFQLA | 240 |
| DDLLGVFGDP | RRTGKPDLDD | LRGGKHTVLV | ALAREHATPE | QRHTLDTLLG | TPGLDRQGAS | 300 |
| RLRCVLVATG | ARAEAERLIT | ERRDQALTAL | NALTLPPPLA | EALARLTLGS | TAHPA | 355 |

SEQ ID NO: 48
| | | | | | |
|---|---|---|---|---|---|
| MSYFDNYFNE | IVNSVNDIIK | SYISGDVPKL | YEASYHLFTS | GGKRLRPLIL | TISSDLFGGQ | 60 |
| RERAYYAGAA | IEVLHTFTLV | HDDIMDQDNI | RRGLPTVHVK | YGLPLAILAG | DLLHAKAFQL | 120 |
| LTQALRGLPS | ETIIKAFDIF | TRSIIIISEG | QAVDMEFEDR | IDIKEQEYLD | MISRKTAALF | 180 |
| SASSSIGALI | AGANDNDVRL | MSDFGTNLGI | AFQIVDDILG | LTADEKELGK | PVFSDIREGK | 240 |
| KTILVIKTLE | LCKEDEKKIV | LKALGNKSAS | KEELMSSADI | IKKYSLDYAY | NLAEKYYKNA | 300 |
| IDSLNQVSSK | SDIPGKALKY | LAEFTIRRRK | | | | 330 |

SEQ ID NO: 49
| | | | | | |
|---|---|---|---|---|---|
| MVAQTFNLDT | YLSQRQQQVE | EALSAALVPA | YPERIYEAMR | YSLLAGGKRL | RPILCLAACE | 60 |
| LAGGSVEQAM | PTACALEMIH | TMSLIHDDLP | AMDNDDFRRG | KPTNHKVFGE | DIAILAGDAL | 120 |
| LAYAFEHIAS | QTRGVPPQLV | LQVIARIGHA | VAATGLVGGQ | VVDLESEGKA | ISLETLEYIH | 180 |
| SHKTGALLEA | SVVSGGILAG | ADEELLARLS | HYARDIGLAF | QIVDDILDVT | ATSEQLGKTA | 240 |
| GKDQAAAKAT | YPSLLGLEAS | RQKAEELIQS | AKEALRPYGS | QAEPLLALAD | FITRRQH | 297 |

SEQ ID NO: 50
| | | | | | |
|---|---|---|---|---|---|
| MASVTLGSWI | VVHHHNHHHP | SSILTKSRSR | SCPITLTKPI | SFRSKRTVSS | SSSIVSSSVV | 60 |
| TKEDNLRQSE | PSSFDFMSYI | ITKAELVNKA | LDSAVPLREP | LKIHEAMRYS | LLAGGKRVRP | 120 |
| VLCIAACELV | GGEESTAMPA | ACAVEMIHTM | SLIHDDLPCM | DNDDLRRGKP | TNHKVFGEDV | 180 |
| AVLAGDALLS | FAFEHLASAT | SSDVVSPVRV | VRAVGELAKA | IGTEGLVAGQ | VVDISSEGLD | 240 |
| LNDVGLEHLE | FIHLHKTAAL | LEASAVLGAI | VGGGSDDEIE | RLRKFARCIG | LLFQVVDDIL | 300 |

TABLE 13-continued

Sequences disclosed herein.

| | |
|---|---|
| DVTKSSKELG KTAGKDLIAD KLTYPKIMGL EKSREFAEKL NREARDQLLG FDSDKVAPLL | 360 |
| ALANYIAYRQ N | 371 |

SEQ ID NO: 51

| | |
|---|---|
| atgtcttcct cttcctcttc cagtacctct atgattgatt tgatggctgc tattattaaa | 60 |
| ggtgaaccag ttatcgtctc cgacccagca aatgcctctg cttatgaatc agttgctgca | 120 |
| gaattgtctt caatgttgat cgaaaacaga caattcgcca tgatcgtaac tacatcaatc | 180 |
| gctgttttga tcggttgtat tgtcatgttg gtatggagaa gatccggtag tggtaattct | 240 |
| aaaagagtcg aacctttgaa accattagta attaagccaa gagaagaaga aatagatgac | 300 |
| ggtagaaaga aagttacaat attttttcggt acccaaactg gtacagctga aggttttgca | 360 |
| aaagccttag gtgaagaagc taaggcaaga tacgaaaaga ctagattcaa gatagtcgat | 420 |
| ttggatgact atgccgctga tgacgatgaa tacgaagaaa agttgaagaa gaagatgtt | 480 |
| gcattttctct ttttggcaac ctatggtgac ggtgaaccaa ctgacaatgc agccagattc | 540 |
| tacaaatggt ttacagaggg taatgatcgt ggtgaatggt tgaaaaactt aaagtacggt | 600 |
| gttttcggtt tgggtaacag acaatacgaa catttcaaca aagttgcaaa ggttgtcgac | 660 |
| gatatttttgg tcgaacaagg tgctcaaaga ttagtccaag taggtttggg tgacgatgac | 720 |
| caatgtatag aagatgactt tactgcctgg agagaagctt tgtggcctga attagacaca | 780 |
| atcttgagag aagaaggtga caccgccgtt gctaccccat atactgctgc agtattagaa | 840 |
| tacagagttt ccatccatga tagtgaagac gcaaagttta atgatatcac tttggccaat | 900 |
| ggtaacggtt atacagttttt cgatgcacaa caccccttaca aagctaacgt tgcagtcaag | 960 |
| agagaattac atacaccaga atccgacaga agttgtatac acttggaatt tgatatcgct | 1020 |
| ggttccggtt taaccatgaa gttgggtgac catgtaggtg ttttatgcga caatttgtct | 1080 |
| gaaactgttg atgaagcatt gagattgttg gatatgtccc ctgacactta ttttagtttg | 1140 |
| cacgctgaaa agaagatgg tacaccaatt tccagttctt taccacctcc attccctcca | 1200 |
| tgtaacttaa gaacagcctt gaccagatac gcttgcttgt tatcatcccc taaaaagtcc | 1260 |
| gccttggttg cttagccgc tcatgctagt gatcctactg aagcagaaag attgaaacac | 1320 |
| ttagcatctc cagccggtaa agatgaatat tcaaagtggg tagttgaatc tcaaagatca | 1380 |
| ttgttagaag ttatggcaga atttccatct gccaagcctc cattaggtgt cttctttgct | 1440 |
| ggtgtagcac ctagattgca accaagattc tactcaatca gttcttcacc taagatcgct | 1500 |
| gaaactagaa ttcatgttac atgtgcatta gtctacgaaa agatgccaac cggtagaatt | 1560 |
| cacaagggtg tatgctctac ttggatgaaa aatgctgttc cttacgaaaa atcagaaaag | 1620 |
| ttgttcttag gtagaccaat cttcgtaaga caatcaaact tcaagttgcc ttctgattca | 1680 |
| aaggttccaa taatcatgat aggtcctggt acaggtttag ccccattcag aggtttcttg | 1740 |
| caagaaagat tggctttagt tgaatctggt gtcgaattag gtccttcagt tttgttcttt | 1800 |
| ggttgtagaa acagaagaat ggatttcatc tatgaagaag aattgcaaag attcgtcgaa | 1860 |
| tctggtgcat tggccgaatt atctgtagct tttttcaagag aaggtccaac taaggaatac | 1920 |
| gttcaacata agatgatgga taaggcatcc gacatatgga acatgatcag tcaaggtgct | 1980 |
| tatttgtacg tttgcggtga cgcaaagggt atggccagag atgtcccatag atctttgcac | 2040 |
| acaattgctc aagaacaagg ttccatggat agtaccaaag ctgaaggttt cgtaaagaac | 2100 |
| ttacaaactt ccggtagata cttgagagat gtctggtga | 2139 |

TABLE 13-continued

Sequences disclosed herein.

SEQ ID NO: 52
```
atggcggaac aacaaaagat caagaaatca ccacacgttc tactcatccc attccctta      60
caaggccata taaacccttt catccagttt ggcaaacgat taatctccaa aggtgtcaaa     120
acaacacttg ttaccaccat ccacaccta aactcaaccc taaaccacag taacaccacc     180
accacctcca tcgaaatcca agcaatttcc gatggttgtg atgaaggcgg ttttatgagt     240
gcaggagaat catatttgga aacattcaaa caagttgggt ctaaatcact agctgactta     300
atcaagaagc ttcaaagtga aggaaccaca attgatgcaa tcatttatga ttctatgact     360
gaatgggttt tagatgttgc aattgagttt ggaatcgatg gtggttcgtt tttcactcaa     420
gcttgtgttg taaacagctt atattatcat gttcataagg gtttgatttc tttgccattg     480
ggtgaaactg tttcggttcc tggatttcca gtgcttcaac ggtgggagac accgttaatt     540
ttgcagaatc atgagcaaat acagagccct tggtctcaga tgttgtttgg tcagtttgct     600
aatattgatc aagcacgttg ggtcttcaca aatagttttt acaagctcga ggaagaggta     660
atagagtgga cgagaaagat atggaacttg aaggtaatcg gccaacact tccatccatg     720
taccttgaca aacgacttga tgatgataaa gataacggat taatctcta caaagcaaac     780
catcatgagt gcatgaactg gttagacgat aagccaaagg aatcagttgt ttacgtagca     840
tttggtagcc tggtgaaaca tggacccgaa caagtggaag aaatcacacg ggctttaata     900
gatagtgatg tcaacttctt gtgggttatc aaacataaag aagagggaaa gctcccagaa     960
aatctttcgg aagtaataaa aaccggaaag ggtttgattg tagcatggtg caaacaattg    1020
gatgtgttag cacacgaatc agtaggatgc tttgttacac attgtgggtt caactcaact    1080
cttgaagcaa taagtcttgg agtccccgtt gttgcaatgc ctcaatttc ggatcaaact    1140
acaaatgcca agcttctaga tgaaattttg ggtgttggag ttagagttaa ggctgatgag    1200
aatgggatag tgagaagagg aaatcttgcg tcatgtatta gatgattat ggaggaggaa    1260
agaggagtaa taatccgaaa gaatgcggta aaatggaagg attttggctaa agtagccgtt    1320
catgaaggtg gtagctcaga caatgatatt gtcgaatttg taagtgagct aattaaggct    1380
taaatttttg ttgctttgta ttttatgtgt tatggttttt tgatttagat gtattcaatt    1440
aatattgaat cataactaaa ttcaagatta ttgtttgtaa tattctttgt cctaaaattt    1500
tgcgacttaa aacctttagt ttataaaaag aaattagaaa atactattgc acgga          1555
```
SEQ ID NO: 53
```
atggaaaaca agaccgaaac aacagttaga cgtaggcgta gaatcattct gtttccagta      60
ccttttcaag ggcacatcaa tccaatacta caactagcca acgttttgta ctctaaaggt     120
ttttctatta caatctttca caccaatttc aacaaaccaa aaacatccaa ttacccacat     180
ttcacattca gattcatact tgataatgat ccacaagatg aacgtatttc aaacttacct     240
acccacggtc ctttagctgg aatgagaatt ccaatcatca atgaacatgg tgccgatgag     300
cttagaagag aattagagtt acttatgttg gcatccgaag aggacgagga agtctcttgt     360
ctgattactg acgctctatg gtactttgcc caatctgtgg ctgatagttt gaatttgagg     420
agattggtac taatgacatc cagtctgttt aactttcacg ctcatgttag tttaccacaa     480
tttgacgaat tgggatactt ggaccctgat gacaagacta ggttagagga acaggcctct     540
ggttttccta tgttgaaagt caaagatatc aagtctgcct attctaattg gcaaatcttg     600
aaagagatct taggaaagat gatcaaacag acaaaggctt catctggagt gatttggaac     660
agtttcaaag agttagaaga gtctgaattg gagactgtaa tcagagaaat tccagcacct     720
```

TABLE 13-continued

Sequences disclosed herein.

| | |
|---|---|
| tcattcctga taccattacc aaaacatttg actgcttcct cttcctcttt gttggatcat | 780 |
| gacagaacag ttttcaatg gttggaccaa caaccaccta gttctgtttt gtacgtgtca | 840 |
| tttggtagta cttctgaagt cgatgaaaag gacttccttg aaatcgcaag aggcttagtc | 900 |
| gatagtaagc agtcattcct ttgggtcgtg cgtccaggtt tcgtgaaagg ctcaacatgg | 960 |
| gtcgaaccac ttccagatgg ttttctaggc gaaagaggta gaatagtcaa atgggttcct | 1020 |
| caacaggaag ttttagctca tggcgctatt ggggcattct ggactcattc cggatggaat | 1080 |
| tcaactttag aatcagtatg cgaaggggta cctatgatct tttcagattt tggtcttgat | 1140 |
| caaccactga acgcaagata catgtctgat gttttgaaag tgggtgtata tctagaaaat | 1200 |
| ggctgggaaa ggggtgaaat agctaatgca ataagacgtg ttatggttga tgaagagggg | 1260 |
| gagtatatca gacaaaacgc aagagtgctg aagcaaaagg ccgacgtttc tctaatgaag | 1320 |
| ggaggctctt catacgaatc cttagaatct cttgtttcct acatttcatc actgtaa | 1377 |

SEQ ID NO: 54

| | |
|---|---|
| MDGVIDMQTI PLRTAIAIGG TAVALVVALY FWFLRSYASP SHHSNHLPPV PEVPGVPVLG | 60 |
| NLLQLKEKKP YMTFTKWAEM YGPIYSIRTG ATSMVVVSSN EIAKEVVVTR FPSISTRKLS | 120 |
| YALKVLTEDK SMVAMSDYHD YHKTVKRHIL TAVLGPNAQK KFRAHRDTMM ENVSNELHAF | 180 |
| FEKNPNQEVN LRKIFQSQLF GLAMKQALGK DVESIYVKDL ETTMKREEIF EVLVVDPMMG | 240 |
| AIEVDWRDFF PYLKWVPNKS FENIIHRMYT RREAVMKALI QEHKKRIASG ENLNSYIDYL | 300 |
| LSEAQTLTDK QLLMSLWEPI IESSDTTMVT TEWAMYELAK NPNMQDRLYE EIQSVCGSEK | 360 |
| ITEENLSQLP YLYAVFQETL RKHCPVPIMP LRYVHENTVL GGYHVPAGTE VAINIYGCNM | 420 |
| DKKVWENPEE WNPERFLSEK ESMDLYKTMA FGGGKRVCAG SLQAMVISCI GIGRLVQDFE | 480 |
| WKLKDDAEED VNTLGLTTQK LHPLLALINP RK | 512 |

SEQ ID NO: 55

| | |
|---|---|
| aagcttacta gtaaaatgga cggtgtcatc gatatgcaaa ccattccatt gagaaccgct | 60 |
| attgctattg gtggtactgc tgttgctttg gttgttgcat tatacttttg gttcttgaga | 120 |
| tcctacgctt ccccatctca tcattctaat catttgccac cagtacctga agttccaggt | 180 |
| gttccagttt tgggtaattt gttgcaattg aaagaaaaaa agccttacat gaccttcacc | 240 |
| aagtgggctg aaatgtatgg tccaatctac tctattagaa ctggtgctac ttccatggtt | 300 |
| gttgtctctt ctaacgaaat cgccaaagaa gttgttgtta ccagattccc atctatctct | 360 |
| accagaaaat tgtcttacgc cttgaaggtt ttgaccgaag ataagtctat ggttgccatg | 420 |
| tctgattatc acgattacca taagaccgtc aagagacata ttttgactgc tgttttgggt | 480 |
| ccaaacgccc aaaaaaagtt tagagcacat agagacacca tgatggaaaa cgtttccaat | 540 |
| gaattgcatg ccttcttcga aaagaaccca atcaagaag tcaacttgag aaagatcttc | 600 |
| caatcccaat tattcggttt ggctatgaag caagccttgg gtaaagatgt tgaatccatc | 660 |
| tacgttaagg atttggaaac caccatgaag agagaagaaa tcttcgaagt tttggttgtc | 720 |
| gatccaatga tgggtgctat tgaagttgat tggagagact ttttcccata cttgaaatgg | 780 |
| gttccaaaca gtccttcga aaacatcatc catagaatgt acactagaag agaagctgtt | 840 |
| atgaaggcct tgatccaaga acacaagaaa agaattgcct ccggtgaaaa cttgaactcc | 900 |
| tacattgatt acttgttgtc tgaagcccaa accttgaccg ataagcaatt attgatgtct | 960 |
| ttgtgggaac ctattatcga atcttctgat accactatgg ttactactga atgggctatg | 1020 |
| tacgaattgg ctaagaatcc aaacatgcaa gacagattat acgaagaaat ccaatccgtt | 1080 |

TABLE 13-continued

Sequences disclosed herein.

| | |
|---|---|
| tgcggttccg aaaagattac tgaagaaaac ttgtcccaat tgccatactt gtacgctgtt | 1140 |
| ttccaagaaa ctttgagaaa gcactgtcca gttcctatta tgccattgag atatgttcac | 1200 |
| gaaaacaccg ttttgggtgg ttatcatgtt ccagctggta ctgaagttgc tattaacatc | 1260 |
| tacggttgca acatggataa gaaggtctgg gaaaatccag aagaatggaa tccagaaaga | 1320 |
| ttcttgtccg aaaaagaatc catggacttg tacaaaacta tggcttttgg tggtggtaaa | 1380 |
| agagtttgcg ctggttcttt acaagccatg gttatttctt gcattggtat cggtagattg | 1440 |
| gtccaagatt ttgaatggaa gttgaaggat gatgccgaag aagatgttaa cactttgggt | 1500 |
| ttgactaccc aaaagttgca tccattattg gccttgatta acccaagaaa gtaactcgag | 1560 |
| ccgcgg | 1566 |

SEQ ID NO: 56

| | |
|---|---|
| atggccaccc tccttgagca tttccaagct atgcccttg ccatccctat tgcactggct | 60 |
| gctctgtctt ggctgttcct cttttacatc aaagtttcat tcttttccaa caagagtgct | 120 |
| caggctaagc tccctcctgt gccagtggtt cctgggctgc cggtgattgg gaatttactg | 180 |
| caactcaagg agaagaaacc ctaccagact tttacaaggt gggctgagga gtatggacca | 240 |
| atctattcta tcaggactgg tgcttccacc atggtcgttc tcaataccac ccaagttgca | 300 |
| aaagaggcca tggtgaccag atatttatcc atctcaacca gaaagctatc aaacgcacta | 360 |
| aagattctta ctgctgataa atgtatggtt gcaataagtg actacaacga ttttcacaag | 420 |
| atgataaagc gatacatact ctcaaatgtt cttggaccta gtgctcagaa gcgtcaccgg | 480 |
| agcaacagag ataccttgag agctaatgtc tgcagccgat gcattctca gtaaagaac | 540 |
| tctcctcgag aagctgtgaa tttcagaaga gttttgagt gggaactctt tggaattgca | 600 |
| ttgaagcaag cctttggaaa ggacatagaa aagcccattt atgtggagga acttggcact | 660 |
| acactgtcaa gagatgagat ctttaaggtt ctagtgcttg acataatgga gggtgcaatt | 720 |
| gaggttgatt ggagagattt cttcccttac ctgagatgga ttccgaatac gcgcatggaa | 780 |
| acaaaaattc agcgactcta tttccgcagg aaagcagtga tgactgccct gatcaacgag | 840 |
| cagaagaagc gaattgcttc aggagaggaa atcaactgtt atatcgactt cttgcttaag | 900 |
| gaagggaaga cactgacaat ggaccaaata agtatgttgc tttgggagac ggttattgaa | 960 |
| acagcagata ctacaatggt aacgacagaa tgggctatgt atgaagttgc taaagactca | 1020 |
| aagcgtcagg atcgtctcta tcaggaaatc caaaaggttt gtggatcgga gatggttaca | 1080 |
| gaggaatact tgtcccaact gccgtacctg aatgcagttt tccatgaaac gctaaggaag | 1140 |
| cacagtccgg ctgcgttagt tcctttaaga tatgcacatg aagatacccca actaggaggt | 1200 |
| tactacattc cagctggaac tgagattgct ataaacatat acgggtgtaa catggacaag | 1260 |
| catcaatggg aaagccctga ggaatggaaa ccggagagat ttttggaccc gaaatttgat | 1320 |
| cctatggatt tgtacaagac catggctttt ggggctggaa agagggtatg tgctggttct | 1380 |
| cttcaggcaa tgttaatagc gtcccgacg attggtaggc tggtgcagga gtttgagtgg | 1440 |
| aagctgagag atggagaaga agaaaatgta gatactgttg ggctcaccac tcacaaacgc | 1500 |
| tatccaatgc atgcaatcct gaagccaaga agtta | 1535 |

SEQ ID NO: 57

| | |
|---|---|
| aagcttacta gtaaaatggc ctccatcacc catttcttac aagattttca agctactcca | 60 |
| ttcgctactg cttttgctgt tggtggtgtt cttgttga tattcttctt cttcatccgt | 120 |
| ggtttccact ctactaagaa aaacgaatat tacaagttgc caccagttcc agttgttcca | 180 |

TABLE 13-continued

Sequences disclosed herein.

```
ggtttgccag ttgttggtaa tttgttgcaa ttgaaagaaa agaagccata caagactttc      240
ttgagatggg ctgaaattca tggtccaatc tactctatta gaactggtgc ttctaccatg      300
gttgttgtta actctactca tgttgccaaa gaagctatgg ttaccagatt ctcttcaatc      360
tctaccagaa agttgtccaa ggctttggaa ttattgacct ccaacaaatc tatggttgcc      420
acctctgatt acaacgaatt tcacaagatg gtcaagaagt acatcttggc cgaattattg      480
ggtgctaatg ctcaaaagag acacagaatt catagagaca ccttgatcga aaacgtcttg      540
aacaaattgc atgcccatac caagaattct ccattgcaag ctgttaactt cagaaagatc      600
ttcgaatctg aattattcgg tttggctatg aagcaagcct tgggttatga tgttgattcc      660
ttgttcgttg aagaatttgg gtactaccttg tccagaagaa aaatctacaa cgttttggtc      720
agtgacatgt tgaagggtgc tattgaagtt gattggagag acttttttccc atacttgaaa      780 tggatcccaa acaagtcctt cgaaatgaag attcaaagat tggcctctag aagacaagcc      840
gttatgaact ctattgtcaa agaacaaaag aagtccattg cctctggtaa gggtgaaaac      900
tgttacttga attacttgtt gtccgaagct aagactttga ccgaaaagca aatttccatt      960
ttggcctggg aaaccattat tgaaactgct gatacaactg ttgttaccac tgaatgggct     1020
atgtacgaat tggctaaaaa cccaaagcaa caagacagat tatacaacga atccaaaac     1080 gtctgcggta ctgataagat taccgaagaa catttgtcca agttgcctta cttgtctgct     1140 gttttttcacg aaaccttgag aaagtattct ccatctccat tggttccatt gagatacgct     1200
catgaagata ctcaattggg tggttattat gttccagccg gtactgaaat tgctgttaat     1260
atctacggtt gcaacatgga caagaatcaa tgggaaactc cagaagaatg gaagccagaa     1320 agattttttgg acgaaaagta cgatccaatg gacatgtaca agactatgtc ttttggttcc     1380
ggtaaaagag tttgcgctgg ttctttacaa gctagtttga ttgcttgtac ctccatcggt     1440
agattggttc aagaatttga atggagattg aaagacggtg aagttgaaaa cgttgatacc     1500
ttgggtttga ctacccataa gttgtatcca atgcaagcta tcttgcaacc tagaaactga     1560 ctcgagccgc                                                         99  1572
SEQ ID NO: 58
atgatttcct tgttgttggg ttttgttgtc tcctccttct tgtttatctt cttcttgaaa       60
aaattgttgt tcttcttcag tcgtcacaaa atgtccgaag tttctagatt gccatctgtt      120
ccagttccag gttttccatt gattggtaac ttgttgcaat tgaaagaaaa gaagccacac      180
aagactttca ccaagtggtc tgaattatat ggtccaatct actctatcaa gatgggttcc      240
tcttctttga tcgtcttgaa ctctattgaa accgccaaag aagctatggt cagtagattc      300
tcttcaatct ctaccagaaa gttgtctaac gctttgactg ttttgacctg caacaaatct      360
atggttgcta cctctgatta cgatgacttt cataagttcg tcaagagatg cttgttgaac      420
ggtttgttgg gtgctaatgc tcaagaagaa aaaagacatt acagagatgc cttgatcgaa      480
aacgttacct ctaaattgca tgcccatacc agaaatcatc cacaagaacc agttaacttc      540
agagccattt tcgaacacga attattcggt gttgctttga acaagccttt cggtaaagat      600
gtcgaatcca tctatgtaaa agaattgggt gtcaccttgt ccagagatga aatttttcaag      660 gttttggtcc acgacatgat ggaaggtgct attgatgttg attggagaga tttcttccca      720
tacttgaaat ggatcccaaa caactctttc gaagccagaa ttcaacaaaa gcacaagaga      780
agattggctg ttatgaacgc cttgatccaa gacagattga atcaaaacga ttccgaatcc      840
gatgatgact gctacttgaa ttttcttgatg tctgaagcta agaccttgac catggaacaa      900
```

TABLE 13-continued

Sequences disclosed herein.

```
attgctattt tggtttggga aaccattatc gaaactgctg ataccacttt ggttactact    960
gaatgggcta tgtacgaatt ggccaaacat caatctgttc aagatagatt attcaaagaa   1020
atccaatccg tctgcggtgg tgaaaagatc aagaagaac aattgccaag attgccttac    1080
gtcaatggtg tttttcacga aaccttgaga agtattctc cagctccatt ggttccaatt    1140
agatacgctc atgaagatac ccaaattggt ggttatcata ttccagccgg ttctgaaatt   1200
gccattaaca tctacggttg caacatggat aagaagagat gggaaagacc tgaagaatgg   1260
tggccagaaa gattttttgga agatagatac gaatcctccg acttgcataa gactatggct  1320
tttggtgctg gtaaaagagt ttgtgctggt gctttacaag ctagtttgat ggctggtatt   1380
gctatcggta gattggttca agaattcgaa tggaagttga gagatggtga agaagaaaac   1440
gttgatactt acggtttgac ctcccaaaag ttgtatccat tgatggccat tatcaaccca   1500
agaagatctt aa                                                       1512
```

SEQ ID NO: 59
```
atggatgctg tgacgggttt gttaactgtc ccagcaaccg ctataactat tggtggaact    60
gctgtagcat tggcggtagc gctaatcttt tggtacctga atcctacac atcagctaga    120 agatcccaat caaatcatct tccaagagtg cctgaagtcc caggtgttcc attgttagga   180
aatctgttac aattgaagga gaaaagcca tacatgactt ttacgagatg ggcagcgaca    240
tatggaccta tctatagtat caaaactggg gctacaagta tggttgtggt atcatctaat   300
gagatagcca aggaggcatt ggtgaccaga ttccaatcca tatctacaag gaacttatct   360
aaagccctga agtacttac agcagataag acaatggtcg caatgtcaga ttatgatgat    420
tatcataaaa cagttaagag acacatactg accgccgtct gggtcctaa tgcacagaaa   480 aagcatagaa ttcacagaga tatcatgatg gataacatat ctactcaact tcatgaattc   540
gtgaaaaaca acccagaaca ggaagaggta gaccttagaa aaatctttca atctgagtta   600
ttcggcttag ctatgagaca agccttagga aaggatgttg aaagtttgta cgttgaagac   660
ctgaaaatca ctatgaatag agacgaaatc tttcaagtcc ttgttgttga tccaatgatg    720
ggagcaatcg atgttgattg gagagacttc tttccatacc taaagtgggt cccaaacaaa   780
aagttcgaaa atactattca acaaatgtac atcagaagag aagctgttat gaaatcttta   840
atcaaagagc acaaaaagag aatagcgtca ggcgaaaagc taaatagtta tatcgattac   900
cttttatctg aagctcaaac tttaaccgat cagcaactat tgatgtcctt gtgggaacca   960
atcattgaat cttcagatac aacaatggtc acaacagaat gggcaatgta cgaattagct  1020
aaaaacccta aattgcaaga taggttgtac agagacatta agtccgtctg tggatctgaa  1080
aagataaccg aagagcatct atcacagctg ccttacatta cagctatttt ccacgaaaca  1140
ctgagaagac actcaccagt tcctatcatt cctctaagac atgtacatga agataccgtt  1200
ctaggcggct accatgttcc tgctggcaca gaacttgccg ttaacatcta cggttgcaac  1260
atggacaaaa acgtttggga aaatccagag gaatggaacc cagaaagatt catgaaagag  1320
aatgagacaa ttgattttca aaagacgatg gccttcggtg gtggtaagag agtttgtgct  1380
ggttccttgc aagcccttttt aactgcatct attgggattg ggagaatggt tcaagagttc  1440
gaatggaaac tgaaggatat gactcaagag gaagtgaaca cgataggcct aactacacaa   1500
atgttaagac cattgagagc tattatcaaa cctaggatct aa                     1542
```

TABLE 13-continued

Sequences disclosed herein.

SEQ ID NO: 60
```
aagcttacta gtaaaatgga catgatgggt attgaagctg ttccatttgc tactgctgtt      60
gttttgggtg gtatttcctt ggttgttttg atcttcatca gaagattcgt ttccaacaga     120
aagagatccg ttgaaggttt gccaccagtt ccagatattc caggtttacc attgattggt     180
aacttgttgc aattgaaaga aaagaagcca cataagacct tgctagatg ggctgaaact      240
tacggtccaa ttttctctat tagaactggt gcttctacca tgatcgtctt gaattcttct     300
gaagttgcca agaagctat ggtcactaga ttctcttcaa tctctaccag aaagttgtcc      360
aacgccttga agattttgac cttcgataag tgtatggttg ccacctctga ttacaacgat     420
tttcacaaaa tggtcaaggg tttcatcttg agaaacgttt taggtgctcc agcccaaaaa     480
agacatagat gtcatagaga taccttgatc gaaaacatct ctaagtactt gcatgcccat     540
gttaagactt ctccattgga accagttgtc ttgaagaaga ttttcgaatc cgaaattttc     600
ggtttggctt tgaaacaagc cttgggtaag gatatcgaat ccatctatgt tgaagaattg     660
ggtactacct tgtccagaga agaaattttt gccgttttgg ttgttgatcc aatggctggt     720
gctattgaag ttgattggag agattttttc ccatacttgt cctggattcc aaacaagtct     780
atggaaatga agatccaaag aatggatttt agaagaggtg ctttgatgaa ggccttgatt     840
ggtgaacaaa agaaaagaat cggttccggt gaagaaaaga actcctacat tgatttcttg     900
ttgtctgaag ctaccacttt gaccgaaaag caaattgcta tgttgatctg ggaaaccatc     960
atcgaaattt ccgatacaac tttggttacc tctgaatggg ctatgtacga attggctaaa    1020
gacccaaata gacaagaaat cttgtacaga gaaatccaca aggtttgcgg ttctaacaag    1080
ttgactgaag aaaacttgtc caagttgcca tacttgaact ctgttttcca cgaaaccttg    1140
agaaagtatt ctccagctcc aatggttcca gttagatatg ctcatgaaga tactcaattg    1200
ggtggttacc atattccagc tggttctcaa attgccatta acatctacgg ttgcaacatg    1260
aacaaaaagc aatgggaaaa tcctgaagaa tggaagccag aaagattctt ggacgaaaag    1320
tatgacttga tggacttgca taagactatg gcttttggtg gtggtaaaag agtttgtgct    1380
ggtgctttac aagcaatgtt gattgcttgc acttccatcg gtagattcgt tcaagaattt    1440
gaatggaagt tgatgggtgg tgaagaagaa aacgttgata ctgttgcttt gacctcccaa    1500
aaattgcatc caatgcaagc cattattaag gccagagaat gactcgagcc gcgg          1554
```

SEQ ID NO: 61
```
atgcaatcag attcagtcaa agtctctcca tttgatttgg tttccgctgc tatgaatggc      60
aaggcaatgg aaaagttgaa cgctagtgaa tctgaagatc aacaacatt gcctgcacta      120
aagatgctag ttgaaaatag agaattgttg acactgttca caacttcctt cgcagttctt     180
attgggtgtc ttgtatttct aatgtggaga cgttcatcct ctaaaaagct ggtacaagat     240
ccagttccac aagttatcgt tgtaaagaag aaagagaagg agtcagaggt tgatgacggg     300
aaaaagaaag tttctatttt ctacggcaca caaacaggaa ctgccgaagg ttttgctaaa     360
gcattagtcg aggaagcaaa agtgagatat gaaaagacct ctttcaaggt tatcgatcta     420
gatgactacg ctgcagatga tgatgaatat gaggaaaaac tgaaaaagga tccttagcc      480
ttcttcttct tggccacata cggtgatggt gaacctactg ataatgctgc taacttctac     540
aagtggttca cagaaggcga cgataaaggt gaatggctga aaagttaca atacggagta     600
tttggtttag gtaacagaca atatgaacat ttcaacaaga tcgctattgt agttgatgat     660
aaacttactg aaatgggagc caaaagatta gtaccagtag gattagggga tgatgatcag     720
```

| | |
|---|---:|
| tgtatagaag atgacttcac cgcctggaag gaattggtat ggccagaatt ggatcaactt | 780 |
| ttaagggacg aagatgatac ttctgtgact accccataca ctgcagccgt attggagtac | 840 |
| agagtggttt accatgataa accagcagac tcatatgctg aagatcaaac ccatacaaac | 900 |
| ggtcatgttg ttcatgatgc acagcatcct tcaagatcta atgtggcttt caaaaaggaa | 960 |
| ctacacacct ctcaatcaga taggtcttgt actcacttag aattcgatat ttctcacaca | 1020 |
| ggactgtctt acgaaactgg cgatcacgtt ggcgtttatt ccgagaactt gtccgaagtt | 1080 |
| gtcgatgaag cactaaaact gttagggtta tcaccagaca catacttctc agtccatgct | 1140 |
| gataaggagg atgggacacc tatcggtggt gcttcactac caccaccttt tcctccttgc | 1200 |
| acattgagag acgctctaac cagatacgca gatgtcttat cctcacctaa aaaggtagct | 1260 |
| ttgctggcat tggctgctca tgctagtgat cctagtgaag ccgataggtt aaagttcctg | 1320 |
| gcttcaccag ccgaaaaga tgaatatgca caatggatcg tcgccaacca acgttctttg | 1380 |
| ctagaagtga tgcaaagttt tccatctgcc aagcctccat taggtgtgtt cttcgcagca | 1440 |
| gtagctccac gtttacaacc aagatactac tctatcagtt catctcctaa gatgtctcct | 1500 |
| aacagaatac atgttacatg tgctttggtg tacgagacta ctccagcagg cagaattcac | 1560 |
| agaggattgt gttcaacctg gatgaaaaat gctgtcccctt taacagagtc acctgattgc | 1620 |
| tctcaagcat ccatttttcgt tagaacatca aatttcagac ttccagtgga tccaaaagtt | 1680 |
| ccagtcatta tgataggacc aggcactggt cttgccccat tcagggggctt tcttcaagag | 1740 |
| agattggcct tgaaggaatc tggtacagaa ttgggttctt ctatctttttt ctttggttgc | 1800 |
| cgtaatagaa aagttgactt tatctacgag gacgagctta acaattttgt tgagacagga | 1860 |
| gcattgtcag aattgatcgt cgcatttttca agagaaggga ctgccaaaga gtacgttcag | 1920 |
| cacaagatga gtcaaaaagc ctccgatata tggaaacttc taagtgaagg tgcctatctt | 1980 |
| tatgtctgtg gcgatgcaaa gggcatggcc aaggatgtcc atagaactct gcatacaatt | 2040 |
| gttcaggaac aagggagtct ggattcttcc aaggctgaat tgtacgtcaa aaacttacag | 2100 |
| atgtctggaa gatacttaag agatgtttgg taa | 2133 |
| SEQ ID NO: 62 | |
| atgaaggtca gtccattcga attcatgtcc gctattatca agggtagaat ggacccatct | 60 |
| aactcctcat ttgaatctac tggtgaagtt gcctccgtta tctttgaaaa cagagaattg | 120 |
| gttgccatct tgaccacttc tattgctgtt atgattggtt gcttcgttgt cttgatgtgg | 180 |
| agaagagctg gttctagaaa ggttaagaat gtcgaattgc caaagccatt gattgtccat | 240 |
| gaaccagaac ctgaagttga agatggtaag aagaaggttt ccatcttctt cggtactcaa | 300 |
| actggtactg ctgaaggttt tgctaaggct ttggctgatg aagctaaagc tagatacgaa | 360 |
| aaggctacct tcagagttgt tgatttggat gattatgctg ccgatgatga ccaatacgaa | 420 |
| gaaaaattga gaacgaatc cttcgccgtt ttcttgttgg ctacttatgg tgatggtgaa | 480 |
| cctactgata tgctgctag attttacaag tggttcgccg aagtaaaga aagaggtgaa | 540 |
| tggttgcaaa acttgcacta tgctgttttt ggtttgggta acagacaata cgaacacttc | 600 |
| aacaagattg ctaaggttgc cgacgaatta ttggaagctc aaggtggtaa tagattggtt | 660 |
| aaggttggtt taggtgatga cgatcaatgc atcgaagatg attttttctgc ttggagagaa | 720 |
| tcttttgtggc cagaattgga tatgttgttg agagatgaag atgatgctac tactgttact | 780 |
| actccatata ctgctgctgt cttggaatac agagttgtct ttcatgattc tgctgatgtt | 840 |
| gctgctgaag ataagtcttg gattaacgct aatggtcatg ctgttcatga tgctcaacat | 900 |

TABLE 13-continued

Sequences disclosed herein.

| | | | | |
|---|---|---|---|---|
| ccattcagat | ctaacgttgt | cgtcagaaaa | gaattgcata | cttctgcctc tgatagatcc | 960 |
| tgttctcatt | tggaattcaa | catttccggt | tccgctttga | attacgaaac tggtgatcat | 1020 |
| gttggtgtct | actgtgaaaa | cttgactgaa | actgttgatg | aagccttgaa cttgttgggt | 1080 |
| ttgtctccag | aaacttactt | ctctatctac | accgataacg | aagatggtac tccattgggt | 1140 |
| ggttcttcat | tgccaccacc | atttccatca | tgtactttga | aactgctttt gaccagatac | 1200 |
| gctgatttgt | tgaactctcc | aaaaaagtct | gctttgttgg | ctttagctgc tcatgcttct | 1260 |
| aatccagttg | aagctgatag | attgagatac | ttggcttctc | cagctggtaa agatgaatat | 1320 |
| gcccaatctg | ttatcggttc | ccaaaagtct | ttgttggaag | ttatggctga attcccatct | 1380 |
| gctaaaccac | cattaggtgt | tttttttgct | gctgttgctc | caagattgca acctagattc | 1440 |
| tactccattt | catcctctcc | aagaatggct | ccatctagaa | tccatgttac ttgtgctttg | 1500 |
| gtttacgata | agatgccaac | tggtagaatt | cataagggtg | tttgttctac ctggatgaag | 1560 |
| aattctgttc | caatggaaaa | gtcccatgaa | tgttcttggg | ctccaatttt cgttagacaa | 1620 |
| tccaattta | agttgccagc | cgaatccaag | gttccaatta | tcatggttgg tccaggtact | 1680 |
| ggtttggctc | cttttagagg | ttttttacaa | gaaagattgg | ccttgaaaga atccggtgtt | 1740 |
| gaattgggtc | catccatttt | gttttcggt | tgcagaaaca | gaagaatgga ttacatctac | 1800 |
| gaagatgaat | tgaacaactt | cgttgaaacc | ggtgctttgt | ccgaattggt tattgctttt | 1860 |
| tctagagaag | gtcctaccaa | agaatacgtc | caacataaga | tggctgaaaa ggcttctgat | 1920 |
| atctggaact | tgatttctga | aggtgcttac | ttgtacgttt | gtggtgatgc taaaggtatg | 1980 |
| gctaaggatg | ttcatagaac | cttgcatacc | atcatgcaag | aacaaggttc tttggattct | 2040 |
| tccaaagctg | aatccatggt | caagaacttg | caaatgaatg | tagatactt aagagatgtt | 2100 |
| tggtaa | | | | | 2106 |

SEQ ID NO: 63

| | | | | |
|---|---|---|---|---|
| aagcttaaaa | tgagtaagtc | taatagtatg | aattctacat | cacacgaaac ccttttcaa | 60 |
| caattggtct | tgggttttgga | ccgtatgcca | ttgatggatg | ttcactggtt gatctacgtt | 120 |
| gctttcggcg | catggttatg | ttcttatgtg | atacatgttt | tatcatcttc ctctacagta | 180 |
| aaagtgccag | ttgttggata | caggtctgta | ttcgaaccta | catggttgct tagacttaga | 240 |
| ttcgtctggg | aaggtggctc | tatcataggt | caagggtaca | ataagtttaa agactctatt | 300 |
| ttccaagtta | ggaaattggg | aactgatatt | gtcattatac | cacctaacta tattgatgaa | 360 |
| gtgagaaaat | tgtcacagga | caagactaga | tcagttgaac | ctttcattaa tgattttgca | 420 |
| ggtcaataca | caagaggcat | ggttttcttg | caatctgact | tacaaaaccg tgttatacaa | 480 |
| caaagactaa | ctccaaaatt | ggtttccttg | accaaggtca | tgaaggaaga gttggattat | 540 |
| gctttaacaa | aagagatgcc | tgatatgaaa | aatgacgaat | gggtagaagt agatatcagt | 600 |
| agtataatgg | tgagattgat | ttccaggatc | tccgccagag | tctttctagg gcctgaacac | 660 |
| tgtcgtaacc | aggaatggtt | gactactaca | gcagaatatt | cagaatcact tttcattaca | 720 |
| gggtttatct | taagagttgt | acctcatatc | ttaagaccat | tcatcgcccc tctattacct | 780 |
| tcatacagga | ctctacttag | aaacgtttca | agtggtagaa | gagtcatcgg tgacatcata | 840 |
| agatctcagc | aagggatgg | taacgaagat | atactttcct | ggatgagaga tgctgccaca | 900 |
| ggagaggaaa | agcaaatcga | taacattgct | cagagaatgt | taattctttc tttagcatca | 960 |
| atccacacta | ctgcgatgac | catgacacat | gccatgtacg | atctatgtgc ttgccctgag | 1020 |
| tacattgaac | cattaagaga | tgaagttaaa | tctgttgttg | gggcttctgg ctgggacaag | 1080 |

TABLE 13-continued

Sequences disclosed herein.

| | |
|---|---:|
| acagcgttaa acagatttca taagttggac tccttcctaa aagagtcaca aagattcaac | 1140 |
| ccagtattct tattgacatt caatagaatc taccatcaat ctatgacctt atcagatggc | 1200 |
| actaacattc catctggaac acgtattgct gttccatcac acgcaatgtt gcaagattct | 1260 |
| gcacatgtcc caggtccaac cccacctact gaatttgatg gattcagata tagtaagata | 1320 |
| cgttctgata gtaactacgc acaaaagtac ctattctcca tgaccgattc ttcaaacatg | 1380 |
| gctttcggat acggcaagta tgcttgtcca ggtagatttt acgcgtctaa tgagatgaaa | 1440 |
| ctaacattag ccattttgtt gctacaattt gagttcaaac taccagatgg taaaggtcgt | 1500 |
| cctagaaata tcactatcga ttctgatatg attccagacc caagagctag actttgcgtc | 1560 |
| agaaaaagat cacttagaga tgaatgaccg cgg | 1593 |

SEQ ID NO: 64

| | |
|---|---:|
| aagcttaaaa tggaagatcc tactgtctta tatgcttgtc ttgccattgc agttgcaact | 60 |
| ttcgttgtta gatggtacag agatccattg agatccatcc caacagttgg tggttccgat | 120 |
| ttgcctattc tatcttacat cggcgcacta agatggacaa gacgtggcag agagatactt | 180 |
| caagagggat atgatggcta cagaggatct acattcaaaa tcgcgatgtt agaccgttgg | 240 |
| atcgtgatcg caaatggtcc taaactagct gatgaagtca gacgtagacc agatgaagag | 300 |
| ttaaacttta tggacggatt aggagcattc gtccaaacta gtacaccttt aggtgaagct | 360 |
| attcataacg atccatacca tgtcgatatc ataagagaaa aactaacaag aggccttcca | 420 |
| gccgtgcttc ctgatgtcat tgaagagttg acacttgcgg ttagacagta cattccaaca | 480 |
| gaaggtgatg aatgggtgtc cgtaaactgt tcaaaggccg caagagatat tgttgctaga | 540 |
| gcttctaata gagtctttgt aggttttgcct gcttgcagaa accaaggtta cttagatttg | 600 |
| gcaatagact ttacattgtc tgttgtcaag gatagagcca tcatcaatat gtttccagaa | 660 |
| ttgttgaagc caatagttgg cagagttgta ggtaacgcca ccagaaatgt tcgtagagct | 720 |
| gttccttttg ttgctccatt ggtggaggaa agacgtagac ttatggaaga gtacggtgaa | 780 |
| gactggtctg aaaaacctaa tgatatgtta cagtggataa tggatgaagc tgcatccaga | 840 |
| gatagttcag tgaaggcaat cgcagagaga ttgttaatgg tgaacttcgc ggctattcat | 900 |
| acctcatcaa acactatcac tcatgctttg taccaccttg ccgaaatgcc tgaaactttg | 960 |
| caaccactta gagaagagat cgaaccatta gtcaaagagg agggctggac caaggctgct | 1020 |
| atgggaaaaa tgtggtggtt agattcattt ctaagagaat ctcaaagata caatggcatt | 1080 |
| aacatcgtat ctttaactag aatggctgac aaagatatta cattgagtga tggcacattt | 1140 |
| ttgccaaaag gtactctagt ggccgttcca gcgtattcta ctcatagaga tgatgctgtc | 1200 |
| tacgctgatg ccttagtatt cgatcctttc agattctcac gtatgagagc gagagaaggt | 1260 |
| gaaggtacaa agcaccagtt cgttaatact tcagtcgagt acgttccatt tggtcacgga | 1320 |
| aagcatgctt gtccaggaag attcttcgcc gcaaacgaat tgaaagcaat gttggcttac | 1380 |
| attgttctaa actatgatgt aaagttgcct ggtgacggta acgtccatt gaacatgtat | 1440 |
| tggggtccaa cagttttgcc tgcaccagca ggccaagtat tgttcagaaa gagacaagtt | 1500 |
| agtctataac cgcgg | 1515 |

SEQ ID NO: 65

| | |
|---|---:|
| atggctacct tgttggaaca ttttcaagct atgccattcg ctattccaat tgctttggct | 60 |
| gctttgtctt ggttgttttt gttctacatc aaggttcttt tcttctccaa caaatccgct | 120 |
| caagctaaat tgccaccagt tccagttgtt ccaggttttgc cagttattgg taatttgttg | 180 |

TABLE 13-continued

Sequences disclosed herein.

| | |
|---|---:|
| caattgaaag aaaagaagcc ataccaaacc ttcactagat gggctgaaga atatggtcca | 240 |
| atctactcta ttagaactgg tgcttctact atggttgtct tgaacactac tcaagttgcc | 300 |
| aaagaagcta tggttaccag atacttgtct atctctacca gaaagttgtc caacgccttg | 360 |
| aaaattttga ccgctgataa gtgcatggtt gccatttctg attacaacga tttccacaag | 420 |
| atgatcaaga gatatatctt gtctaacgtt ttgggtccat ctgcccaaaa aagacataga | 480 |
| tctaacagag ataccttgag agccaacgtt tgttctagat tgcattccca agttaagaac | 540 |
| tctccaagag aagctgtcaa ctttagaaga gttttcgaat gggaattatt cggtatcgct | 600 |
| ttgaaacaag ccttcggtaa ggatattgaa aagccaatct acgtcgaaga attgggtact | 660 |
| actttgtcca gagatgaaat cttcaaggtt ttggtcttgg acattatgga aggtgccatt | 720 |
| gaagttgatt ggagagattt tttcccatac ttgcgttgga ttccaaacac cagaatggaa | 780 |
| actaagatcc aaagattata ctttagaaga aaggccgtta tgaccgcctt gattaacgaa | 840 |
| caaaagaaaa gaattgcctc cggtgaagaa atcaactgct acatcgattt cttgttgaaa | 900 |
| gaaggtaaga ccttgaccat ggaccaaatc tctatgttgt tgtgggaaac cgttattgaa | 960 |
| actgctgata ccacaatggt tactactgaa tgggctatgt acgaagttgc taaggattct | 1020 |
| aaaagacaag acagattata ccaagaaatc caaaaggtct gcggttctga atggttaca | 1080 |
| gaagaatact tgtcccaatt gccatacttg aatgctgttt tccacgaaac tttgagaaaa | 1140 |
| cattctccag ctgctttggt tccattgaga tatgctcatg aagatactca attgggtggt | 1200 |
| tattacattc cagccggtac tgaaattgcc attaacatct acggttgcaa catggacaaa | 1260 |
| caccaatggg aatctccaga agaatggaag ccagaaagat ttttggatcc taagtttgac | 1320 |
| ccaatggact tgtacaaaac tatggctttt ggtgctggta aaagagtttg cgctggttct | 1380 |
| ttacaagcta tgttgattgc ttgtccaacc atcggtagat tggttcaaga atttgaatgg | 1440 |
| aagttgagag atggtgaaga agaaaacgtt gatactgttg gtttgaccac ccataagaga | 1500 |
| tatccaatgc atgctatttt gaagccaaga tcttaa | 1536 |
| SEQ ID NO: 66 | |
| atggcagaat tagatacact tgatatagta gtattaggtg ttatctttt gggtactgtg | 60 |
| gcatacttta ctaagggtaa attgtggggt gttaccaagg atccatacgc taacggattc | 120 |
| gctgcaggtg gtgcttccaa gcctggcaga actagaaaca tcgtcgaagc tatggaggaa | 180 |
| tcaggtaaaa actgtgttgt tttctacggc agtcaaacag gtacagcgga ggattacgca | 240 |
| tcaagacttg caaggaagg aaagtccaga ttcggttga acactatgat cgccgatcta | 300 |
| gaagattatg acttcgataa cttagacact gttccatctg ataacatcgt tatgtttgta | 360 |
| ttggctactt acggtgaagg cgaaccaaca gataacgccg tggatttcta tgagttcatt | 420 |
| actggcgaag atgcctcttt caatgagggc aacgatcctc cactaggtaa cttgaattac | 480 |
| gttgcgttcg gtctgggcaa caatacctac gaacactaca actcaatggt caggaacgtt | 540 |
| aacaaggctc tagaaaagtt aggagctcat agaattggag aagcaggtga gggtgacgac | 600 |
| ggagctggaa ctatggaaga ggactttta gcttggaaag atccaatgtg gaagccttg | 660 |
| gctaaaaaga tgggcttgga ggaaagagaa gctgtatatg aacctatttt cgctatcaat | 720 |
| gagagagatg atttgacccc tgaagcgaat gaggtatact gggagaacc taataagcta | 780 |
| cacttggaag gtacagcgaa aggtccattc aactcccaca acccatatat cgcaccaatt | 840 |
| gcagaatcat acgaactttt ctcagctaag gatagaaatt gtctgcatat ggaaattgat | 900 |
| atttctggta gtaatctaaa gtatgaaaca ggcgaccata tcgcgatctg gcctaccaac | 960 |

TABLE 13-continued

Sequences disclosed herein.

| | |
|---|---|
| ccaggtgaag aggtcaacaa atttcttgac attctagatc tgtctggtaa gcaacattcc | 1020 |
| gtcgtaacag tgaaagcctt agaacctaca gccaaagttc cttttccaaa tccaactacc | 1080 |
| tacgatgcta tattgagata ccatctggaa atatgcgctc cagtttctag acagtttgtc | 1140 |
| tcaactttag cagcattcgc ccctaatgat gatatcaaag ctgagatgaa ccgtttggga | 1200 |
| tcagacaaag attacttcca cgaaaagaca ggaccacatt actacaatat cgctagattt | 1260 |
| ttggcctcag tctctaaagg tgaaaaatgg acaaagatac cattttctgc tttcatagaa | 1320 |
| ggccttacaa aactacaacc aagatactat tctatctctt cctctagttt agttcagcct | 1380 |
| aaaaagatta gtattactgc tgttgtcgaa tctcagcaaa ttccaggtag agatgaccca | 1440 |
| ttcagaggtg tagcgactaa ctacttgttc gctttgaagc agaaacaaaa cggtgatcca | 1500 |
| aatccagctc cttttggcca atcatacgag ttgacaggac caaggaataa gtatgatggt | 1560 |
| atacatgttc cagtccatgt aagacattct aactttaagc taccatctga tccaggcaaa | 1620 |
| cctattatca tgatcggtcc aggtaccggt gttgcccctt ttagaggctt cgtccaagag | 1680 |
| agggcaaaac aagccagaga tggtgtagaa gttggtaaaa cactgctgtt ctttggatgt | 1740 |
| agaaagagta cagaagattt catgtatcaa aaagagtggc aagagtacaa ggaagctctt | 1800 |
| ggcgacaaat cgaaatgat tacagctttt tcaagagaag gatctaaaaa ggtttatgtt | 1860 |
| caacacagac tgaaggaaag atcaaaggaa gtttctgatc ttctatccca aaaagcatac | 1920 |
| ttctacgttt gcggagacgc cgcacatatg gcacgtgaag tgaacactgt gttagcacag | 1980 |
| atcatagcag aaggccgtgg tgtatcagaa gccaagggtg aggaaattgt caaaaacatg | 2040 |
| agatcagcaa atcaatacca agtgtgttct gatttcgtaa ctttacactg taaagagaca | 2100 |
| acatacgcga attcagaatt gcaagaggat gtctggagtt aa | 2142 |
| SEQ ID NO: 67 | |
| atggccgaat tggatacctt ggatatcgtt gttttgggtg ttatcttctt gggtactgtt | 60 |
| gcttacttca ccaaaggtaa attgtggggt gttactaagg atccatacgc taatggtttt | 120 |
| gctgctggtg gtgcttctaa accaggtaga actagaaata tcgttgaagc catggaagaa | 180 |
| tctggtaaga actgtgttgt tttctacggt tctcaaactg gtactgctga agattatgct | 240 |
| tccagattgg ctaaagaagg taagagtaga ttcggtttga acaccatgat tgccgatttg | 300 |
| gaagattacg atttcgataa cttggatacc gtcccatctg ataacatcgt tatgtttgtt | 360 |
| ttggctacct acggtgaagg tgaacctact gataatgctg ttgacttcta cgaattcatt | 420 |
| accggtgaag atgcttcttt caacgaaggt aatgatccac cattgggtaa cttgaattac | 480 |
| gttgcttttg gtttgggtaa caacacctac gaacattaca actccatggt tagaaacgtc | 540 |
| aacaaggctt tggaaaaatt gggtgctcat agaattggtg aagctggtga aggtgatgat | 600 |
| ggtgctggta ctatggaaga agattttttg gcttggaaag acccaatgtg gaagccttg | 660 |
| gctaaaaaga tgggtttgga agaaagagaa gctgtctacg aacctatttt cgccattaac | 720 |
| gaaagagatg atttgacccc tgaagccaat gaagtttatt gggtgaacc taacaagttg | 780 |
| cacttggaag gtactgctaa aggtccattc aattctcaca cccatatat tgctccaatc | 840 |
| gccgaatctt acgaattatt ctctgctaag gatagaaact gcttgcacat ggaaattgac | 900 |
| atctctggtt ctaatttgaa gtacgaaacc ggtgatcata ttgccatttg gccaactaat | 960 |
| ccaggtgaag aagttaacaa gttcttggac atcttggact tgtccggtaa acaacattct | 1020 |
| gttgttactg ttaaggcctt ggaacctaca gctaaagttc cttttccaaa tccaactacc | 1080 |
| tacgatgcca ttttgagata ccatttggaa atttgcgctc cagtctctag acaattcgtt | 1140 |

TABLE 13-continued

Sequences disclosed herein.

```
tctactttgg ctgcttttgc tccaaacgat gatattaagg ctgaaatgaa cagattgggt    1200
tccgataagg attacttcca cgaaaaaact ggtccacact actacaacat tgctagattt    1260
ttggcctctg tctctaaagg tgaaaagtgg actaagattc cattctccgc tttcattgaa    1320
ggtttgacta agttgcaacc tagatattac tccatctcct cctcatcttt ggttcaacct    1380
aagaagatct ctattaccgc cgttgttgaa tcccaacaaa ttccaggtag agatgatcct    1440
tttagaggtg ttgctaccaa ttacttgttc gccttgaaac aaaagcaaaa cggtgatcca    1500
aatcctgctc catttggtca atcttatgaa ttgactggtc aagaaacaa gtacgatggt     1560 attcatgttc cagttcacgt tagacactct aactttaagt tgccatctga tccaggtaag    1620
ccaattatca tgattggtcc aggtactggt gttgctccat tcagaggttt tgttcaagaa    1680
agagctaagc aagctagaga tggtgttgaa gttggtaaaa ccttgttgtt cttcggttgt    1740
agaaagtcca ctgaagattt catgtaccaa aaagaatggc aagaatacaa agaagcctta    1800
ggtgacaagt tcgaaatgat tactgccttc tcaagagaag ttctaagaa ggtttacgtc      1860 caacacagat tgaaagaaag atccaaagaa gtctccgatt tgttgtctca aaaggcctac    1920
ttttacgttt gtggtgatgc tgctcatatg gccagagaag ttaatactgt tttggcccaa    1980
attatcgctg aagtagagg tgtatctgaa gctaagggtg aagaaatcgt taagaacatg     2040
agatccgcca atcaatacca agtttgctct gattttgtta ccttgcactg taaagaaacc    2100
acctacgcta attccgaatt gcaagaagat gtttggtcct aa                       2142
```

SEQ ID NO: 68

```
MEASYLYISI LLLLASYLFT TQLRRKSANL PPTVFPSIPI IGHLYLLKKP LYRTLAKIAA     60

KYGPILQLQL GYRRVLVISS PSAAEECFTN NDVIFANRPK TLFGKIVGGT SLGSLSYGDQ    120

WRNLRRVASI EILSVHRLNE FHDIRVDENR LLIRKLRSSS SPVTLITVFY ALTLNVIMRM    180

ISGKRYFDSG DRELEEEGKR FREILDETLL LAGASNVGDY LPILNWLGVK SLEKKLIALQ    240

KKRDDFFQGL IEQVRKSRGA KVGKGRKTMI ELLLSLQESE PEYYTDAMIR SFVLGLLAAG    300

SDTSAGTMEW AMSLLVNHPH VLKKAQAEID RVIGNNRLID ESDIGNIPYI GCIINETLRL    360

YPAGPLLFPH ESSADCVISG YNIPRGTMLI VNQWAIHHDP KVWDDPETFK PERFQGLEGT    420

RDGFKLMPFG SGRRGCPGEG LAIRLLGMTL GSVIQCFDWE RVGDEMVDMT EGLGVTLPKA    480

VPLVAKCKPR SEMTNLLSEL                                                500
```

SEQ ID NO: 69

```
MQSESVEAST IDLMTAVLKD TVIDTANASD NGDSKMPPAL AMMFEIRDLL LILTTSVAVL     60

VGCFVVLVWK RSSGKKSGKE LEPPKIVVPK RRLEQEVDDG KKKVTIFFGT QTGTAEGFAK    120

ALFEEAKARY EKAAFKVIDL DDYAADLDEY AEKLKKETYA FFFLATYGDG EPTDNAAKFY    180

KWFTEGDEKG VWLQKLQYGV FGLGNRQYEH FNKIGIVVDD GLTEQGAKRI VPVGLGDDDQ    240

SIEDDFSAWK ELVWPELDLL LREDDDKAAA TPYTAAIPEY RVVFHDKPDA FSDDHTQTNG    300

HAVHDAQHPC RSNVAVKKEL HTPESDRSCT HLEFDISHTG LSYETGDHVG VYCENLIEVV    360

EEAGKLLGLS TDTYFSLHID NEDGSPLGGP SLQPPFPPCT LRKALTNYAD LLSSPKKSTL    420

LALAAHASDP TEADRLRFLA SREGKDEYAE WVVANQRSLL EVMEAFPSAR PPLGVFFAAV    480

APRLQPRYYS ISSSPKMEPN RIHVTCALVY EKTPAGRIHK GICSTWMKNA VPLTESQDCS    540

WAPIFVRTSN FRLPIDPKVP VIMIGPGTGL APFRGFLQER LALKESGTEL GSSILFFGCR    600

NRKVDYIYEN ELNNFVENGA LSELDVAFSR DGPTKEYVQH KMTQKASEIW NMLSEGAYLY    660

VCGDAKGMAK DVHRTLHTIV QEQGSLDSSK AELYVKNLQM SGRYLRDVW                709
```

TABLE 13-continued

Sequences disclosed herein.

```
SEQ ID NO: 70
MASITHFLQD FQATPFATAF AVGGVSLLIF FFFIRGFHST KKNEYYKLPP VPVVPGLPVV      60

GNLLQLKEKK PYKTFLRWAE IHGPIYSIRT GASTMVVVNS THVAKEAMVT RFSSISTRKL     120

SKALELLTSN KSMVATSDYN EFHKMVKKYI LAELLGANAQ KRHRIHRDTL IENVLNKLHA     180

HTKNSPLQAV NFRKIFESEL FGLAMKQALG YDVDSLFVEE LGTTLSREEI YNVLVSDMLK     240

GAIEVDWRDF FPYLKWIPNK SFEMKIQRLA SRRQAVMNSI VKEQKKSIAS GKGENCYLNY     300

LLSEAKTLTE KQISILAWET IIETADTTVV TTEWAMYELA KNPKQQDRLY NEIQNVCGTD     360

KITEEHLSKL PYLSAVFHET LRKYSPSPLV PLRYAHEDTQ LGGYYVPAGT EIAVNIYGCN     420

MDKNQWETPE EWKPERFLDE KYDPMDMYKT MSFGSGKRVC AGSLQASLIA CTSIGRLVQE     480

FEWRLKDGEV ENVDTLGLTT HKLYPMQAIL QPRN                                514

SEQ ID NO: 71
MASMISLLLG FVVSSFLFIF FLKKLLFFFS RHKMSEVSRL PSVPVPGFPL IGNLLQLKEK      60

KPHKTFTKWS ELYGPIYSIK MGSSSLIVLN SIETAKEAMV SRFSSISTRK LSNALTVLTC     120

NKSMVATSDY DDFHKFVKRC LLNGLLGANA QERKRHYRDA LIENVTSKLH AHTRNHPQEP     180

VNFRAIFEHE LFGVALKQAF GKDVESIYVK ELGVTLSRDE IFKVLVHDMM EGAIDVDWRD     240

FFPYLKWIPN NSFEARIQQK HKRRLAVMNA LIQDRLNQND SESDDDCYLN FLMSEAKTLT     300

MEQIAILVWE TIIETADTTL VTTEWAMYEL AKHQSVQDRL FKEIQSVCGG EKIKEEQLPR     360

LPYVNGVFHE TLRKYSPAPL VPIRYAHEDT QIGGYHIPAG SEIAINIYGC NMDKKRWERP     420

EEWWPERFLE DRYESSDLHK TMAFGAGKRV CAGALQASLM AGIAIGRLVQ EFEWKLRDGE     480

EENVDTYGLT SQKLYPLMAI INPRRS                                         506

SEQ ID NO: 72
MDMMGIEAVP FATAVVLGGI SLVVLIFIRR FVSNRKRSVE GLPPVPDIPG LPLIGNLLQL      60

KEKKPHKTFA RWAETYGPIF SIRTGASTMI VLNSSEVAKE AMVTRFSSIS TRKLSNALKI     120

LTFDKCMVAT SDYNDFHKMV KGFILRNVLG APAQKRHRCH RDTLIENISK YLHAHVKTSP     180

LEPVVLKKIF ESEIFGLALK QALGKDIESI YVEELGTTLS REEIFAVLVV DPMAGAIEVD     240

WRDFFPYLSW IPNKSMEMKI QRMDFRRGAL MKALIGEQKK RIGSGEEKNS YIDFLLSEAT     300

TLTEKQIAML IWETIIEISD TTLVTSEWAM YELAKDPNRQ EILYREIHKV CGSNKLTEEN     360

LSKLPYLNSV FHETLRKYSP APMVPVRYAH EDTQLGGYHI PAGSQIAINI YGCNMNKKQW     420

ENPEEWKPER FLDEKYDLMD LHKTMAFGGG KRVCAGALQA MLIACTSIGR FVQEFEWKLM     480

GGEEENVDTV ALTSQKLHPM QAIIKARE                                       508

SEQ ID NO: 73
MAELDTLDIV VLGVIFLGTV AYFTKGKLWG VTKDPYANGF AAGGASKPGR TRNIVEAMEE      60

SGKNCVVFYG SQTGTAEDYA SRLAKEGKSR FGLNTMIADL EDYDFDNLDT VPSDNIVMFV     120

LATYGEGEPT DNAVDFYEFI TGEDASFNEG NDPPLGNLNY VAFGLGNNTY EHYNSMVRNV     180

NKALEKLGAH RIGEAGEGDD GAGTMEEDFL AWKDPMWEAL AKKMGLEERE AVYEPIFAIN     240

ERDDLTPEAN EVYLGEPNKL HLEGTAKGPF NSHNPYIAPI AESYELFSAK DRNCLHMEID     300

ISGSNLKYET GDHIAIWPTN PGEEVNKFLD ILDLSGKQHS VVTVKALEPT AKVPFPNPTT     360

YDAILRYHLE ICAPVSRQFV STLAAFAPND DIKAEMNRLG SDKDYFHEKT GPHYYNIARF     420

LASVSKGEKW TKIPFSAFIE GLTKLQPRYY SISSSSLVQP KKISITAVVE SQQIPGRDDP     480

FRGVATNYLF ALKQKQNGDP NPAPFGQSYE LTGPRNKYDG IHVPVHVRHS NFKLPSDPGK     540

PIIMIGPGTG VAPFRGFVQE RAKQARDGVE VGKTLLFFGC RKSTEDFMYQ KEWQEYKEAL     600
```

TABLE 13-continued

Sequences disclosed herein.

```
GDKFEMITAF SREGSKKVYV QHRLKERSKE VSDLLSQKAY FYVCGDAAHM AREVNTVLAQ    660

IIAEGRGVSE AKGEEIVKNM RSANQYQVCS DFVTLHCKET TYANSELQED VWS           713

SEQ ID NO: 74
MKVSPFEFMS AIIKGRMDPS NSSFESTGEV ASVIFENREL VAILTTSIAV MIGCFVVLMW     60

RRAGSRKVKN VELPKPLIVH EPEPEVEDGK KKVSIFFGTQ TGTAEGFAKA LADEAKARYE    120

KATFRVVDLD DYAADDDQYE EKLKNESFAV FLLATYGDGE PTDNAARFYK WFAEGKERGE    180

WLQNLHYAVF GLGNRQYEHF NKIAKVADEL LEAQGGNRLV KVGLGDDDQC IEDDFSAWRE    240

SLWPELDMLL RDEDDATTVT TPYTAAVLEY RVVFHDSADV AAEDKSWINA NGHAVHDAQH    300

PFRSNVVVRK ELHTSASDRS CSHLEFNISG SALNYETGDH VGVYCENLTE TVDEALNLLG    360

LSPETYFSIY TDNEDGTPLG GSSLPPPFPS CTLRTALTRY ADLLNSPKKS ALLALAAHAS    420

NPVEADRLRY LASPAGKDEY AQSVIGSQKS LLEVMAEFPS AKPPLGVFFA AVAPRLQPRF    480

YSISSSPRMA PSRIHVTCAL VYDKMPTGRI HKGVCSTWMK NSVPMEKSHE CSWAPIFVRQ    540

SNFKLPAESK VPIIMVGPGT GLAPFRGFLQ ERLALKESGV ELGPSILFFG CRNRRMDYIY    600

EDELNNFVET GALSELVIAF SREGPTKEYV QHKMAEKASD IWNLISEGAY LYVCGDAKGM    660

AKDVHRTLHT IMQEQGSLDS SKAESMVKNL QMNGRYLRDV W                       701

SEQ ID NO: 75
MATLLEHFQA MPFAIPIALA ALSWLFLFYI KVSFFSNKSA QAKLPPVPVV PGLPVIGNLL     60

QLKEKKPYQT FTRWAEEYGP IYSIRTGAST MVVLNTTQVA KEAMVTRYLS ISTRKLSNAL    120

KILTADKCMV AISDYNDFHK MIKRYILSNV LGPSAQKRHR SNRDTLRANV CSRLHSQVKN    180

SPREAVNFRR VFEWELFGIA LKQAFGKDIE KPIYVEELGT TLSRDEIFKV LVLDIMEGAI    240

EVDWRDFFPY LRWIPNTRME TKIQRLYFRR KAVMTALINE QKKRIASGEE INCYIDFLLK    300

EGKTLTMDQI SMLLWETVIE TADTTMVTTE WAMYEVAKDS KRQDRLYQEI QKVCGSEMVT    360

EEYLSQLPYL NAVFHETLRK HSPAALVPLR YAHEDTQLGG YYIPAGTEIA INIYGCNMDK    420

HQWESPEEWK PERFLDPKFD PMDLYKTMAF GAGKRVCAGS LQAMLIACPT IGRLVQEFEW    480

KLRDGEEENV DTVGLTTHKR YPMHAILKPR S                                   511

SEQ ID NO: 76
MQSDSVKVSP FDLVSAAMNG KAMEKLNASE SEDPTTLPAL KMLVENRELL TLFTTSFAVL     60

IGCLVFLMWR RSSSKKLVQD PVPQVIVVKK KEKESEVDDG KKKVSIFYGT QTGTAEGFAK    120

ALVEEAKVRY EKTSFKVIDL DDYAADDDEY EEKLKKESLA FFFLATYGDG EPTDNAANFY    180

KWFTEGDDKG EWLKKLQYGV FGLGNRQYEH FNKIAIVVDD KLTEMGAKRL VPVGLGDDDQ    240

CIEDDFTAWK ELVWPELDQL LRDEDDTSVT TPYTAAVLEY RVVYHDKPAD SYAEDQTHTN    300

GHVVHDAQHP SRSNVAFKKE LHTSQSDRSC THLEFDISHT GLSYETGDHV GVYSENLSEV    360

VDEALKLLGL SPDTYFSVHA DKEDGTPIGG ASLPPPFPPC TLRDALTRYA DVLSSPKKVA    420

LLALAAHASD PSEADRLKFL ASPAGKDEYA QWIVANQRSL LEVMQSFPSA KPPLGVFFAA    480

VAPRLQPRYY SISSSPKMSP NRIHVTCALV YETTPAGRIH RGLCSTWMKN AVPLTESPDC    540

SQASIFVRTS NFRLPVDPKV PVIMIGPGTG LAPFRGFLQE RLALKESGTE LGSSIFFFGC    600

RNRKVDFIYE DELNNFVETG ALSELIVAFS REGTAKEYVQ HKMSQKASDI WKLLSEGAYL    660

YVCGDAKGMA KDVHRTLHTI VQEQGSLDSS KAELYVKNLQ MSGRYLRDVW              710

SEQ ID NO: 77
MSKSNSMNST SHETLFQQLV LGLDRMPLMD VHWLIYVAFG AWLCSYVIHV LSSSSTVKVP     60

VVGYRSVFEP TWLLRLRFVW EGGSIIGQGY NKFKDSIFQV RKLGTDIVII PPNYIDEVRK    120
```

TABLE 13-continued

Sequences disclosed herein.

| | | | | | |
|---|---|---|---|---|---|
| LSQDKTRSVE | PFINDFAGQY | TRGMVFLQSD | LQNRVIQQRL | TPKLVSLTKV | MKEELDYALT | 180 |
| KEMPDMKNDE | WVEVDISSIM | VRLISRISAR | VFLGPEHCRN | QEWLTTTAEY | SESLFITGFI | 240 |
| LRVVPHILRP | FIAPLLPSYR | TLLRNVSSGR | RVIGDIIRSQ | QGDGNEDILS | WMRDAATGEE | 300 |
| KQIDNIAQRM | LILSLASIHT | TAMTMTHAMY | DLCACPEYIE | PLRDEVKSVV | GASGWDKTAL | 360 |
| NRFHKLDSFL | KESQRFNPVF | LLTFNRIYHQ | SMTLSDGTNI | PSGTRIAVPS | HAMLQDSAHV | 420 |
| PGPTPPTEFD | GFRYSKIRSD | SNYAQKYLFS | MTDSSNMAFG | YGKYACPGRF | YASNEMKLTL | 480 |
| AILLLQFEFK | LPDGKGRPRN | ITIDSDMIPD | PRARLCVRKR | SLRDE | | 525 |

SEQ ID NO: 78

| | | | | | |
|---|---|---|---|---|---|
| MEDPTVLYAC | LAIAVATFVV | RWYRDPLRSI | PTVGGSDLPI | LSYIGALRWT | RRGREILQEG | 60 |
| YDGYRGSTFK | IAMLDRWIVI | ANGPKLADEV | RRRPDEELNF | MDGLGAFVQT | KYTLGEAIHN | 120 |
| DPYHVDIIRE | KLTRGLPAVL | PDVIEELTLA | VRQYIPTEGD | EWVSVNCSKA | ARDIVARASN | 180 |
| RVFVGLPACR | NQGYLDLAID | FTLSVVKDRA | IINMFPELLK | PIVGRVVGNA | TRNVRRAVPF | 240 |
| VAPLVEERRR | LMEEYGEDWS | EKPNDMLQWI | MDEAASRDSS | VKAIAERLLM | VNFAAIHTSS | 300 |
| NTITHALYHL | AEMPETLQPL | REEIEPLVKE | EGWTKAAMGK | MWWLDSFLRE | SQRYNGINIV | 360 |
| SLTRMADKDI | TLSDGTFLPK | GTLVAVPAYS | THRDDAVYAD | ALVFDPFRFS | RMRAREGEGT | 420 |
| KHQFVNTSVE | YVPFGHGKHA | CPGRFFAANE | LKAMLAYIVL | NYDVKLPGDG | KRPLNMYWGP | 480 |
| TVLPAPAGQV | LFRKRQVSL | | | | | 499 |

SEQ ID NO: 79

| | | | | | |
|---|---|---|---|---|---|
| MDAVTGLLTV | PATAITIGGT | AVALAVALIF | WYLKSYTSAR | RSQSNHLPRV | PEVPGVPLLG | 60 |
| NLLQLKEKKP | YMTFTRWAAT | YGPIYSIKTG | ATSMVVVSSN | EIAKEALVTR | FQSISTRNLS | 120 |
| KALKVLTADK | TMVAMSDYDD | YHKTVKRHIL | TAVLGPNAQK | KHRIHRDIMM | DNISTQLHEF | 180 |
| VKNNPEQEEV | DLRKIFQSEL | FGLAMRQALG | KDVESLYVED | LKITMNRDEI | FQVLVVDPMM | 240 |
| GAIDVDWRDF | FPYLKWVPNK | KFENTIQQMY | IRREAVMKSL | IKEHKKRIAS | GEKLNSYIDY | 300 |
| LLSEAQTLTD | QQLLMSLWEP | IIESSDTTMV | TTEWAMYELA | KNPKLQDRLY | RDIKSVCGSE | 360 |
| KITEEHLSQL | PYITAIFHET | LRRHSPVPII | PLRHVHEDTV | LGGYHVPAGT | ELAVNIYGCN | 420 |
| MDKNVWENPE | EWNPERFMKE | NETIDFQKTM | AFGGGKRVCA | GSLQALLTAS | IGIGRMVQEF | 480 |
| EWKLKDMTQE | EVNTIGLTTQ | MLRPLRAIIK | PRI | | | 513 |

SEQ ID NO: 80

| | | | | | |
|---|---|---|---|---|---|
| atggaagtaa | cagtagctag | tagtgtagcc | ctgagcctgg | tctttattag | catagtagta | 60 |
| agatgggcat | ggagtgtggt | gaattgggtg | tggtttaagc | cgaagaagct | ggaaagattt | 120 |
| ttgagggagc | aaggccttaa | aggcaattcc | tacaggtttt | tatatggaga | catgaaggag | 180 |
| aactctatcc | tgctcaaaca | agcaagatcc | aaacccatga | acctctccac | ctcccatgac | 240 |
| atagcacctc | aagtcacccc | ttttgtcgac | caaaccgtga | agcttacgg | taagaactct | 300 |
| tttaattggg | ttggccccat | accaagggtg | aacataatga | atccagaaga | tttgaaggac | 360 |
| gtcttaacaa | aaaatgttga | ctttgttaag | ccaatatcaa | acccacttat | caagttgcta | 420 |
| gctacaggta | ttgcaatcta | tgaaggtgag | aaatggacta | acacagaag | gattatcaac | 480 |
| ccaacattcc | attcggagag | gctaaagcgt | atgttacctt | catttcacca | aagttgtaat | 540 |
| gagatggtca | ggaatgggga | gagcttggtg | tcaaaagagg | gttcatcatg | tgagttggat | 600 |
| gtctggcctt | tcttgaaaaa | tatgtcggca | gatgtgatct | cgagaacagc | atttggaact | 660 |
| agctacaaaa | aaggacagaa | aatctttgaa | ctcttgagag | agcaagtaat | atatgtaacg | 720 |
| aaaggctttc | aaagttttta | cattccagga | tggaggtttc | tcccaactaa | gatgaacaag | 780 |

TABLE 13-continued

Sequences disclosed herein.

```
aggatgaatg agattaacga agaaataaaa ggattaatca ggggtattat aattgacaga    840
gagcaaatca ttaaggcagg tgaagaaacc aacgatgact tattaggtgc acttatggag    900
tcaaacttga aggacattcg ggaacatggg aaaaacaaca aaaatgttgg gatgagtatt    960
gaagatgtaa ttcaggagtg taagctgttt tactttgctg gcaagaaac cacttcagtg    1020 ttgctggctt ggacaatggt tttacttggt caaaatcaga actggcaaga tcgagcaaga   1080
caagaggttt tgcaagtctt tggaagcagc aagccagatt ttgatggtct agctcacctt   1140
aaagtcgtaa ccatgatttt gcttgaagtt cttcgattat acccaccagt cattgaactt   1200
attcgaacca ttcacaagaa aacacaactt gggaagctct cactaccaga aggagttgaa   1260
gtccgcttac caacactgct cattcaccat gacaaggaac tgtggggtga tgatgcaaac   1320
cagttcaatc cagagaggtt ttcggaagga gtttccaaag caacaaagaa ccgactctca   1380
ttcttcccct tcggagccgg tccacgcatt tgcattggac agaactttc tatgatggaa    1440 gcaaagttgg ccttagcatt gatcttgcaa cacttcacct ttgagctttc tccatctcat   1500
gcacatgctc cttcccatcg tataacccct caaccacagt atggtgttcg tatcatttta   1560
catcgacgtt ag                                                        1572

SEQ ID NO: 81
atggaagtca ctgtcgcctc ttctgtcgct ttatccttag tcttcatttc cattgtcgtc     60
agatgggctt ggtccgttgt caactgggtt tggttcaaac caagaagtt ggaaagattc     120 ttgagagagc aaggttttgaa gggtaattct tatagattct tgtacggtga catgaaggaa    180
aattctattt tgttgaagca agccagatcc aaaccaatga acttgtctac ctctcatgat    240
attgctccac aagttactcc attcgtcgat caaactgtta aagcctacgg taagaactct    300
ttcaattggg ttggtccaat tcctagagtt aacatcatga acccagaaga tttgaaggat    360
gtcttgacca agaacgttga cttcgttaag ccaatttcca acccattgat taaattgttg    420
gctactggta ttgccatttta cgaaggtgaa aagtggacta agcatagaag aatcatcaac    480
cctaccttcc actctgaaag attgaagaga atgttaccat cttccatca atcctgtaat    540 gaaatggtta aggaatggga atccttggtt tctaaagaag gttcttcttg cgaattggat    600
gtttggccat tcttggaaaa tatgtctgct gatgtcattt ccagaaccgc tttcggtacc    660
tcctacaaga agggtcaaaa gattttcgaa ttgttgagag agcaagttat ttacgttacc    720 aagggttttcc aatccttcta catcccaggt tggagattct tgccaactaa aatgaacaag    780
cgtatgaacg agatcaacga agaaattaaa ggtttgatca gaggtattat tatcgacaga    840
gaacaaatta ttaaagctgg tgaagaaacc aacgatgatt tgttgggtgc tttgatggag    900
tccaacttga aggatattag agaacatggt aagaacaaca gaatgttgg tatgtctatt    960 gaagatgtta ttcaagaatg taagttattc tacttcgctg gtcaagagac cacttctgtt   1020
ttgttagcct ggactatggt cttgttaggt caaaaccaaa attggcaaga tagagctaga   1080
caagaagttt tgcaagtctt cggttcttcc aagccagact ttgatggttt ggcccacttg   1140
aaggttgtta ctatgatttt gttagaagtt ttgagattgt acccaccagt cattgagtta   1200
atcagaacca ttcataaaaa gactcaattg ggtaaattat ctttgccaga aggtgttgaa   1260
gtcagattac aaccttgtt gattcaccac gataaggaat tatgggtga cgacgctaat    1320 caatttaatc cagaaagatt ttccgaaggt gtttccaagg ctaccaaaaa ccgtttgtcc   1380
ttcttcccat ttggtgctgg tccacgtatt tgtatcggtc aaaactttc catgatggaa    1440 gccaagttgg ctttggcttt aatcttgcaa cacttcactt tcgaattgtc tccatcccat   1500
```

TABLE 13-continued

Sequences disclosed herein.

```
gcccacgctc cttctcatag aatcacttta caaccacaat acggtgtcag aatcatctta        1560
cacagaagat aa                                                            1572

SEQ ID NO: 82
MEVTVASSVA LSLVFISIVV RWAWSVVNWV WFKPKKLERF LREQGLKGNS YRFLYGDMKE          60

NSILLKQARS KPMNLSTSHD IAPQVTPFVD QTVKAYGKNS FNWVGPIPRV NIMNPEDLKD         120

VLTKNVDFVK PISNPLIKLL ATGIAIYEGE KWTKHRRIIN PTFHSERLKR MLPSFHQSCN         180

EMVKEWESLV SKEGSSCELD VWPFLENMSA DVISRTAFGT SYKKGQKIFE LLREQVIYVT         240

KGFQSFYIPG WRFLPTKMNK RMNEINEEIK GLIRGIIIDR EQIIKAGEET NDDLLGALME         300

SNLKDIREHG KNNKNVGMSI EDVIQECKLF YFAGQETTSV LLAWTMVLLG QNQNWQDRAR         360

QEVLQVFGSS KPDFDGLAHL KVVTMILLEV LRLYPPVIEL IRTIHKKTQL GKLSLPEGVE         420

VRLPTLLIHH DKELWGDDAN QFNPERFSEG VSKATKNRLS FFPFGAGPRI CIGQNFSMME         480

AKLALALILQ HFTFELSPSH AHAPSHRITL QPQYGVRIIL HRR                          523

SEQ ID NO: 83
MENKTETTVR RRRIILFPV PFQGHINPIL QLANVLYSKG FSITIFHTNF NKPKTSNYPH           60

FTFRFILDND PQDERISNLP THGPLAGMRI PIINEHGADE LRRELELLML ASEEDEEVSC         120

LITDALWYFA QSVADSLNLR RLVLMTSSLF NFHAHVSLPQ FDELGYLDPD DKTRLEEQAS         180

GFPMLKVKDI KSAYSNWQIL KEILGKMIKQ TKASSGVIWN SFKELEESEL ETVIREIPAP         240

SFLIPLPKHL TASSSSLLDH DRTVFQWLDQ QPPSSVLYVS FGSTSEVDEK DFLEIARGLV         300

DSKQSFLWVV RPGFVKGSTW VEPLPDGFLG ERGRIVKWVP QQEVLAHGAI GAFWTHSGWN         360

STLESVCEGV PMIFSDFGLD QPLNARYMSD VLKVGVYLEN GWERGEIANA IRRVMVDEEG         420

EYIRQNARVL KQKADVSLMK GGSSYESLES LVSYISSL                                458

SEQ ID NO: 84
MDAMATTEKK PHVIFIPFPA QSHIKAMLKL AQLLHHKGLQ ITFVNTDFIH NQFLESSGPH          60

CLDGAPGFRF ETIPDGVSHS PEASIPIRES LLRSIETNFL DRFIDLVTKL PDPPTCIISD         120

GFLSVFTIDA AKKLGIPVMM YWTLAACGFM GFYHIHSLIE KGFAPLKDAS YLTNGYLDTV         180

IDWVPGMEGI RLKDFPLDWS TDLNDKVLMF TTEAPQRSHK VSHHIFHTFD ELEPSIIKTL         240

SLRYNHIYTI GPLQLLLDQI PEEKKQTGIT SLHGYSLVKE EPECFQWLQS KEPNSVVYVN         300

FGSTTVMSLE DMTEFGWGLA NSNHYFLWII RSNLVIGENA VLPPELEEHI KKRGFIASWC         360

SQEKVLKHPS VGGFLTHCGW GSTIESLSAG VPMICWPYSW DQLTNCRYIC KEWEVGLEMG         420

TKVKRDEVKR LVQELMGEGG HKMRNKAKDW KEKARIAIAP NGSSSLNIDK MVKEITVLAR         480

SEQ ID NO: 85
MATSDSIVDD RKQLHVATFP WLAFGHILPY LQLSKLIAEK GHKVSFLSTT RNIQRLSSHI          60

SPLINVVQLT LPRVQELPED AEATTDVHPE DIPYLKKASD GLQPEVTRFL EQHSPDWIIY         120

DYTHYWLPSI AASLGISRAH FSVTTPWAIA YMGPSADAMI NGSDGRTTVE DLTTPPKWFP         180

FPTKVCWRKH DLARLVPYKA PGISDGYRMG LVLKGSDCLL SKCYHEFGTQ WLPLLETLHQ         240

VPVVPVGLLP PEIPGDEKDE TWVSIKKWLD GKQKGSVVYV ALGSEVLVSQ TEVVELALGL         300

ELSGLPFVWA YRKPKGPAKS DSVELPDGFV ERTRDRGLVW TSWAPQLRIL SHESVCGFLT         360

HCGSGSIVEG LMFGHPLIML PIFGEIPRNE EDGCLTKESV ARSLRSVVVE KEGEIYKANA         420

RELSKIYNDT KVEKEYVSQF VDYLEKNARA VAIDHES                                 457

SEQ ID NO: 86
MDSGYSSSYA AAGMHVVIC PWLAFGHLLP CLDLAQRLAS RGHRVSFVST PRNISRLPPV           60

RPALAPLVAF VALPLPRVEG LPDGAESTND VPHDRPDMVE LHRRAFDGLA APFSEFLGTA         120
```

TABLE 13-continued

Sequences disclosed herein.

```
CADWVIVDVF HHWAAAAALE HKVPCAMMLL GSAHMIASIA DRRLERAETE SPAAAGQGRP    180

AAAPTFEVAR MKLIRTKGSS GMSLAERFSL TLSRSSLVVG RSCVEFEPET VPLLSTLRGK    240

PITFLGLMPP LHEGRREDGE DATVRWLDAQ PAKSVVYVAL GSEVPLGVEK VHELALGLEL    300

AGTRFLWALR KPTGVSDADL LPAGFEERTR GRGVVATRWV PQMSILAEAA VGAFLTHCGW    360

NSTIEGLMFG HPLIMLPIFG DQGPNARLIE AKNAGLQVAR NDGDGSFDRE GVAAAIRAVA    420

VEEESSKVFQ AKAKKLQEIV ADMACHERYI DGFIQQLRSY KD                       462

SEQ ID NO: 87
MSSSSSSSTS MIDLMAAIIK GEPVIVSDPA NASAYESVAA ELSSMLIENR QFAMIVTTSI     60

AVLIGCIVML VWRRSGSGNS KRVEPLKPLV IKPREEEIDD GRKKVTIFFG TQTGTAEGFA    120

KALGEEAKAR YEKTRFKIVD LDDYAADDDE YEEKLKKEDV AFFFLATYGD GEPTDNAARF    180

YKWFTEGNDR GEWLKNLKYG VFGLGNRQYE HFNKVAKVVD DILVEQGAQR LVQVGLGDDD    240

QCIEDDFTAW REALWPELDT ILREEGDTAV ATPYTAAVLE YRVSIHDSED AKFNDITLAN    300

GNGYTVFDAQ HPYKANVAVK RELHTPESDR SCIHLEFDIA GSGLTMKLGD HVGVLCDNLS    360

ETVDEALRLL DMSPDTYFSL HAEKEDGTPI SSSLPPPFPP CNLRTALTRY ACLLSSPKKS    420

ALVALAAEAS DPTEAERLKH LASPAGKDEY SKWVVESQRS LLEVMAEFPS AKPPLGVFFA    480

GVAPRLQPRF YSISSSPKIA ETRIHVTCAL VYEKMPTGRI HKGVCSTWMK NAVPYEKSEK    540

LFLGRPIFVR QSNFKLPSDS KVPIIMIGPG TGLAPFRGFL QERLALVESG VELGPSVLFF    600

GCRNRRMDFI YEEELQRFVE SGALAELSVA FSREGPTKEY VQHKMMDKAS DIWNMISQGA    660

YLYVCGDAKG MARDVHRSLH TIAQEQGSMD STKAEGFVKN LQTSGRYLRD VW            712

SEQ ID NO: 88
MATSDSIVDD RKQLHVATFP WLAFGHILPY LQLSKLIAEK GHKVSFLSTT RNIQRLSSHI     60

SPLINVVQLT LPRVQELPED AEATTDVHPE DIPYLKKASD GLQPEVTRFL EQHSPDWIIY    120

DYTHYWLPSI AASLGISRAH FSVTTPWAIA YMGPSADAMI NGSDGRTTVE DLTTPPKWFP    180

FPTKVCWRKH DLARLVPYKA PGISDGYRMG MVLKGSDCLL SKCYHEFGTQ WLPLLETLHQ    240

VPVVPVGLLP PEIPGDEKDE TWVSIKKWLD GKQKGSVVYV ALGSEALVSQ TEVVELALGL    300

ELSGLPFVWA YRKPKGPAKS DSVELPDGFV ERTRDRGLVW TSWAPQLRIL SHESVCGFLT    360

HCGSGSIVEG LMFGHPLIML PIFGDQPLNA RLLEDKQVGI EIPRNEEDGC LTKESVARSL    420

RSVVVEKEGE IYKANARELS KIYNDTKVEK EYVSQFVDYL EKNARAVAID HES           473

SEQ ID NO: 89
atggctactt ctgattccat cgttgacgat agaaagcaat gcatgttgc tacttttcca     60 tggttggctt tcggtcatat tttgccatac ttgcaattgt ccaagttgat tgctgaaaag    120
ggtcacaagg tttcattctt gtctaccacc agaaacatcc aaagattgtc ctctcatatc    180
tccccattga tcaacgttgt tcaattgact ttgccaagag tccaagaatt gccagaagat    240
gctgaagcta ctactgatgt tcatccagaa gatatccctt acttgaaaaa ggcttccgat    300
ggtttacaac agaagttac tagattcttg aacaacatt ccccagattg gatcatctac    360
gattatactc attactggtt gccatccatt gctgcttcat tgggtatttc tagagcccat    420
ttctctgtta ctactccatg ggctattgct tatatgggtc catctgctga tgctatgatt    480
aacggttctg atggtagaac taccgttgaa gatttgacta ctccaccaaa gtggtttcca    540
tttccaacaa aagtctgttg gagaaaacac gatttggcta gattggttcc atacaaagct    600 ccaggtatt ctgatggtta cagaatgggg atggttttga aaggtccga ttgcttgttg    660 tctaagtgct atcatgaatt cggtactcaa tggttgcctt tgttggaaac attgcatcaa    720
```

TABLE 13-continued

Sequences disclosed herein.

```
gttccagttg ttccagtagg tttgttgcca ccagaaattc caggtgacga aaaagacgaa    780
acttgggttt ccatcaaaaa gtggttggat ggtaagcaaa agggttctgt tgtttatgtt    840
gctttgggtt ccgaagcttt ggtttctcaa accgaagttg ttgaattggc tttgggtttg    900
gaattgtctg gtttgccatt tgtttgggct tacagaaaac ctaaaggtcc agctaagtct    960
gattctgtta aattgccaga tggtttcgtt gaaagaacta gagatagagg tttggtttgg   1020
acttcttggg ctccacaatt gagaattttg tctcatgaat ccgtctgtgg tttcttgact   1080
cattgtggtt ctggttctat cgttgaaggt ttgatgtttg gtcacccatt gattatgttg   1140
ccaatctttg gtgaccaacc attgaacgct agattattgg aagataagca agtcggtatc   1200
gaaatcccaa gaaatgaaga agatggttgc ttgaccaaag aatctgttgc tagatctttg   1260
agatccgttg tcgttgaaaa agaaggtgaa atctacaagg ctaacgctag agaattgtcc   1320
aagatctaca acgataccaa ggtcgaaaaa gaatacgttt cccaattcgt tgactacttg   1380
gaaaagaatg ctagagctgt tgccattgat catgaatctt ga                      1422
SEQ ID NO: 90
atggaagctt ctagagcatc ttgtgttgct ttgtgtgttg tttgggtttc catcgttatt     60
actttggctt ggagagtttt gaattgggtc tggttaagac caaaaaagtt ggaaagatgc    120
ttgagagaac aaggtttgac tggtaactct tacagattgt tgttcggtga taccaaggac    180
ttgtctaaga tgttggaaca aactcaatcc aagcctatca agttgtctac ctctcatgat    240
attgctccaa gagttactcc attcttccat agaactgtta actccaacgg taagaactct    300
tttgtttgga tgggtccaat tccaagagtc catattatga accctgaaga tttgaaggac    360
gctttcaaca gacatgatga tttccataag accgtcaaga acccaattat gaagtctcca    420
ccaccaggta tagttggtat tgaaggtgaa caatgggcca acatagaaa gattattaac     480
ccagccttcc acttggaaaa gttgaaaggt atggttccaa tcttctacca atcctgctct    540
gaaatgatta acaagtggga atccttggtt tccaaagaat cttcctgtga attggatgtc    600
tggccatatt tggaaaaactt cacctccgat gttatttcca gagctgcttt tggttcttct    660
tacgaagaag gtagaaagat cttccaatta ttgagagaag aagccaaggt ttactccgtt    720
gctttgagat ctgtttacat tccaggttgg agattcttgc caactaagca aaacaaaaag    780
accaaagaaa tccacaacga aatcaagggt ttgttgaagg gtatcatcaa caagagagaa    840
gaagctatga aggctggtga agctacaaaa gatgatttgt tgggtatctt gatggaatcc    900
aacttcagag aaatccaaga aacacggtaac aacaagaatg ccggtatgtc tattgaagat    960
gttatcggtg aatgcaagtt gttctacttt gctggtcaag aaactacctc cgttttgttg   1020
gtttggacca tgattttgtt gtcccaaaat caagattggc aagctagagc tagagaagaa   1080
gtcttgaaag ttttcggttc taacatccca acctacgaag aattgtctca cttgaaggtt   1140
gtcactatga tcttgttgga agtattgaga ttatacccat ccgttgttgc attgccaaga   1200
actactcata gaaaaactca attgggtaaa ttgtccttgc cagctggtgt tgaagtttct   1260
ttgccaattt tgttagtcca ccacgacaaa gaattgtggg gtgaagatgc taatgaattc   1320
aagccagaaa gattctccga aggtgttcct aaagctacca gaacaagtt cacttacttg   1380
ccatttggtg gtggtccaag aatatgtatt ggtcaaaatt cgctatggt cgaagctaaa   1440
ttggctttgg ctttgatctt gcaacatttc gctttcgaat tgtcaccatc ttatgctcat   1500
gctccatctg ctgttattac attgcaacca caatttggtg cccatatcat cttgcataag   1560
agataac                                                             1567
```

TABLE 13-continued

Sequences disclosed herein.

```
SEQ ID NO: 91
MEASRASCVA LCVVWVSIVI TLAWRVLNWV WLRPKKLERC LREQGLTGNS YRLLFGDTKD        60

LSKMLEQTQS KPIKLSTSHD IAPRVTPFFH RTVNSNGKNS FVWMGPIPRV HIMNPEDLKD       120

AFNRHDDFHK TVKNPIMKSP PPGIVGIEGE QWAKHRKIIN PAFHLEKLKG MVPIFYQSCS       180

EMINKWESLV SKESSCELDV WPYLENFTSD VISRAAFGSS YEEGRKIFQL LREEAKVYSV       240

ALRSVYIPGW RFLPTKQNKK TKEIHNEIKG LLKGIINKRE EAMKAGEATK DDLLGILMES       300

NFREIQEHGN NKNAGMSIED VIGECKLFYF AGQETTSVLL VWTMILLSQN QDWQARAREE       360

VLKVFGSNIP TYEELSHLKV VTMILLEVLR LYPSVVALPR TTHKKTQLGK LSLPAGVEVS       420

LPILLVHHDK ELWGEDANEF KPERFSEGVS KATKNKFTYL PFGGGPRICI GQNFAMVEAK       480

LALALILQHF AFELSPSYAH APSAVITLQP QFGAHIILHK R                          521

SEQ ID NO: 92
ASWVAVLSVV WVSMVIAWAW RVLNWVWLRP KKLEKCLREQ GLAGNSYRLL FGDTKDLSKM        60

LEQTQSKPIK LSTSHDIAPH VTPFFHQTVN SYGKNSFVWM GPIPRVHIMN PEDLKDTFNR       120

HDDFHKVVKN PIMKSLPQGI VGIEGEQWAK HRKIINPAFH LEKLKGMVPI FYRSCSEMIN       180

KWESLVSKES SCELDVWPYL ENFTSDVISR AAFGSSYEEG RKIFQLLREE AKIYTVAMRS       240

VYIPGWRFLP TKQNKKAKEI HNEIKGLLKG IINKREEAMK AGEATKDDLL GILMESNFRE       300

IQEHGNNKNA GMSIEDVIGE CKLFYFAGQE TTSVLLVWTM VLLSQNQDWQ ARAREEVLQV       360

FGSNIPTYEE LSQLKVVTMI LLEVLRLYPS VVALPRTTHK KTQLGKLSLP AGVEVSLPIL       420

LVHHDKELWG EDANEFKPER FSEGVSKATK NQFTYFPFGG GPRICIGQNF AMMEAKLALS       480

LILRHFALEL SPLYAHAPSV TITLQPQYGA HIILHKR                              517

SEQ ID NO: 93
MEASRPSCVA LSVVLVSIVI AWAWRVLNWV WLRPNKLERC LREQGLTGNS YRLLFGDTKE        60

ISMMVEQAQS KPIKLSTTHD IAPRVIPFSH QIVYTYGRNS FVWMGPTPRV TIMNPEDLKD       120

AFNKSDEFQR AISNPIVKSI SQGLSSLEGE KWAKHRKIIN PAFHLEKLKG MLPTFYQSCS       180

EMINKWESLV FKEGSREMDV WPYLENLTSD VISRAAFGSS YEEGRKIFQL LREEAKFYTI       240

AARSVYIPGW RFLPTKQNKR MKEIHKEVRG LLKGIINKRE DAIKAGEAAK GNLLGILMES       300

NFREIQEHGN NKNAGMSIED VIGECKLFYF AGQETTSVLL VWTLVLLSQN QDWQARAREE       360

VLQVFGTNIP TYDQLSHLKV VTMILLEVLR LYPAVVELPR TTYKKTQLGK FLLPAGVEVS       420

LHIMLAHHDK ELWGEDAKEF KPERFSEGVS KATKNQFTYF PFGAGPRICI GQNFAMLEAK       480

LALSLILQHF TFELSPSYAE APSVTITLHP QFGAHFILHK R                          521

SEQ ID NO: 94
CVALSVVLVS IVIAWAWRVL NWVWLRPNKL ERCLREQGLT GNSYRLLFGD TKEISMMVEQ        60

AQSKPIKLST THDIAPRVIP FSHQIVYTYG RNSFVWMGPT PRVTIMNPED LKDAFNKSDE       120

FQRAISNPIV KSISQGLSSL EGEKWAKHRK IINPAFHLEK LKGMLPTFYQ SCSEMINKWE       180

SLVFKEGSRE MDVWPYLENL TSDVISRAAF GSSYEEGRKI FQLLREEAKF YTIAARSVYI       240

PGWRFLPTKQ NKRMKEIHKE VRGLLKGIIN KREDAIKAGE AAKGNLLGIL MESNFREIQE       300

HGNNKNAGMS IEDVIGECKL FYFAGQETTS VLLVWTLVLL SQNQDWQARA REEVLQVFGT       360

NIPTYDQLSH LKVVTMILLE VLRLYPAVVE LPRTTYKKTQ LGKFLLPAGV EVSLHIMLAE       420

HDKELWGEDA KEFKPERFSE GVSKATKNQF TYFPFGAGPR ICIGQNFAML EAKLALSLIL       480

QHFTFELSPS YAHAPSVTIT LHPQFGAHFI LHKR                                  514
```

TABLE 13-continued

Sequences disclosed herein.

```
SEQ ID NO: 95
MGPIPRVHIM NPEDLKDTFN RHDDFHKVVK NPIMKSLPQG IVGIEGDQWA KHRKIINPAF        60

HLEKLKGMVP IFYQSCSEMI NIWKSLVSKE SSCELDVWPY LENFTSDVIS RAAFGSSYEE       120

GRKIFQLLRE EAKVYTVAVR SVYIPGWRFL PTKQNKKTKE IHNEIKGLLK GIINKREEAM       180

KAGEATKDDL LGILMESNFR EIQEHGNNKN AGMSIEDVIG ECKLFYFAGQ ETTSVLLVWT       240

MVLLSQNQDW QARAREEVLQ VFGSNIPTYE ELSHLKVVTM ILLEVLRLYP SVVALPRTTH       300

KKTQLGKLSL PAGVEVSLPI LLVHHDKELW GEDANEFKPE RFSEGVSKAT KNQFTYFPFG       360

GGPRICIGQN FAMMEAKLAL SLILQHFTFE LSPQYSHAPS VTITLQPQYG AHLILHKR        418

SEQ ID NO: 96
atggaagcat caagggctag ttgtgttgcg ctatgtgttg tttgggtgag catagtaatt        60
acattggcat ggagggtgct gaattgggtg tggttgaggc aaagaaaact agaaagatgc       120
ttgagggagc aaggccttac aggcaattct tacaggcttt tgtttggaga caccaaggat       180
ctctcgaaga tgctggaaca acacaatcc aaacccatca aactctccac ctcccatgat        240
atagcgccac gagtcacccc attttccat cgaactgtga actctaatgg caagaattct        300
tttgtttgga tgggccctat accaagagtg cacatcatga atccagaaga tttgaaagat       360
gccttcaaca gacatgatga ttttcataag acagtaaaaa atcctatcat gaagtctcca       420
ccaccgggca ttgtaggcat tgaaggtgag caatgggcta acacagaaa gattatcaac        480 ccagcattcc atttagagaa gctaaagggt atggtaccaa tattttacca agttgtagc        540 gagatgatta acaaatggga gagcttggtg tccaaagaga gttcatgtga gttggatgtg       600
tggccttatc ttgaaaattt taccagcgat gtgatttccc gagctgcatt tggaagtagc       660
tatgaagagg gaaggaaaat atttcaacta ctaagagagg aagcaaaagt ttattcggta       720
gctctacgaa gtgtttacat tccaggatgg aggtttctac caaccaagca gaacaagaag       780
acgaaggaaa ttcacaatga aattaaaggc ttacttaagg gcattataaa taaaagggaa       840
gaggcgatga aggcagggga agccactaaa gatgacttac taggaatact tatggagtcc       900
aacttcaggg aaattcagga acatgggaac aacaaaaatg ctggaatgag tattgaagat       960
gtaattggag agtgtaagtt gttttacttt gctgggcaag agaccacttc ggtgttgctt      1020
gtttggacaa tgattttact aagccaaaat caggattggc aagctcgtgc aagagaagag      1080
gtcttgaaag tctttggaag caacatccca acctatgaag agctaagtca cctaaaagtt      1140
gtgaccatga ttttacttga agttcttcga ttatacccat cagtcgttgc gcttcctcga      1200
accactcaca agaaaacaca gcttggaaaa ttatcattac cagctggagt ggaagtctcc      1260
ttgcccatac tgcttgttca ccatgacaaa gagttgtggg gtgaggatgc aaatgagttc      1320
aagccagaga ggttttcaga gggagtttca aaggcaacaa agaacaaatt tacatactta      1380
cctttcggag ggggtccaag gatttgcatt ggacaaaact tgccatggt ggaagctaaa       1440 ttggccttgg ccctgatttt acaacacttt gcctttgagc tttctccatc ctatgctcat      1500
gctccttctg cagttataac ccttcaacct caatttggtg ctcatatcat tttgcataaa      1560
cgttga                                                                1566

SEQ ID NO: 97
atgtcctcca actccgattt ggtcagaaga ttggaatctg ttttgggtgt ttctttcggt        60
ggttctgtta ctgattccgt tgttgttatt gctaccacct ctattgcttt ggttatcggt       120
gttttggttt tgttgtggag aagatcctct gacagatcta gaagagttaa gcaattggct       180
gttccaaagc cagttactat cgttgaagaa gaagatgaat tcgaagttgc ttctggtaag       240
```

TABLE 13-continued

Sequences disclosed herein.

```
accagagttt ctattttcta cggtactcaa actggtactg ctgaaggttt tgctaaggct    300
ttggctgaag aaatcaaagc cagatacgaa aaagctgccg ttaaggttat tgatttggat    360
gattacacag ccgaagatga caaatacggt gaaaagttga agaaagaaac tatggccttc    420
ttcatgttgg ctacttatgg tgatggtgaa cctactgata tgctgctag attttacaag     480 tggttcaccg aaggtactga tagaggtgtt tggttggaac atttgagata cggtgtattc    540
ggtttgggta acagacaata cgaacacttc aacaagattg ccaaggttgt tgatgatttg    600
ttggttgaac aaggtgccaa gagattggtt actgttggtt gggtgatga tgatcaatgc     660 atcgaagatg atttctccgc ttggaaagaa gccttgtggc agaattgga tcaattattg     720 caagatgata ccaacaccgt ttctactcca tacactgctg ttattccaga atacagagtt    780
gttatccacg atccatctgt tacctcttat gaagatccat actctaacat ggctaacggt    840
aatgcctctt acgatattca tcatccatgt agagctaacg ttgccgtcca aaaagaattg    900
cataagccag aatctgacag aagttgcatc catttggaat cgatatttt cgctactggt     960 ttgacttacg aaaccggtga tcatgttggt gtttacgctg ataattgtga tgatactgta   1020
gaagaagccg ctaagttgtt gggtcaacca ttggatttgt tgttctccat tcataccgat   1080
aacaacgacg gtacttcttt gggttcttct ttgccaccac catttccagg tccatgtact   1140
ttgagaactg ctttggctag atatgccgat tgttgaatc caccaaaaaa ggctgctttg    1200
attgctttag ctgctcatgc tgatgaacca tctgaagctg aaagattgaa gttcttgtca   1260
tctccacaag gtaaggacga atattctaaa tgggttgtcg gttcccaaag atccttggtt   1320
gaagttatgg ctgaatttcc atctgctaaa ccaccattgg gtgtattttt tgctgctgtt   1380
gttcctagat tgcaacctag atattactcc atctcttcca gtccaagatt tgctccacat   1440
agagttcatg ttacttgcgc tttggtttat ggtccaactc caactggtag aattcacaga   1500
ggtgtatgtt cattctggat gaagaatgtt gtcccattgg aaaagtctca aaactgttct   1560
tgggccccaa ttttcatcag acaatctaat ttcaagttgc cagccgatca ttctgttcca   1620
atagttatgg ttggtccagg tactggttta gctccttta gaggtttctt acaagaaaga   1680
ttggccttga agaagaagg tgctcaagtt ggtcctgctt tgttgttttt tggttgcaga   1740
aacagacaaa tggacttcat ctacgaagtc gaattgaaca actttgtcga acaaggtgct   1800
ttgtccgaat tgatcgttgc ttttcaaga gaaggtccat ccaagaata cgtccaacat    1860 aagatggtta aaaaggcagc ttacatgtgg aacttgattt ctcaaggtgg ttacttctac   1920
gtttgtggtg atgctaaagg tatggctaga gatgttcata gaacattgca taccatcgtc   1980
caacaagaag aaaaggttga ttctaccaag gccgaatcca tcgttaagaa attgcaaatg   2040
gacggtagat acttgagaga tgtttggtga                                    2070
```

SEQ ID NO: 98

```
MSSNSDLVRR LESVLGVSFG GSVTDSVVVI ATTSIALVIG VLVLLWRRSS DRSREVKQLA    60

VPKPVTIVEE EDEFEVASGK TRVSIFYGTQ TGTAEGFAKA LAEEIKARYE KAAVKVIDLD   120

DYTAEDDKYG EKLKKETMAF FMLATYGDGE PTDNAARFYK WFTEGTDRGV WLEHLRYGVF   180

GLGNRQYEHF NKIAKVVDDL LVEQGAKRLV TVGLGDDDQC IEDDFSAWKE ALWPELDQLL   240

QDDTNTVSTP YTAVIPEYRV VIHDPSVTSY EDPYSNMANG NASYDIHHPC RANVAVQKEL   300

HKPESDRSCI HLEFDIFATG LTYETGDHVG VYADNCDDTV EEAAKLLGQP LDLLFSIHTD   360

NNDGTSLGSS LPPPFPGPCT LRTALARYAD LLNPPKKAAL IALAAHADEP SEAERLKFLS   420

SPQGKDEYSK WVVGSQRSLV EVMAEFPSAK PPLGVFFAAV VPRLQPRYYS ISSSPRFAPH   480
```

TABLE 13-continued

Sequences disclosed herein.

```
RVHVTCALVY GPTPTGRIHR GVCSFWMKNV VPLEKSQNCS WAPIFIRQSN FKLPADHSVP        540

IVMVGPGTGL APFRGFLQER LALKEEGAQV GPALLFFGCR NRQMDFIYEV ELNNFVEQGA        600

LSELIVAFSR EGPSKEYVQH KMVEKAAYMW NLISQGGYFY VCGDAKGMAR DVHRTLHTIV        660

QQEEKVDSTK AESIVKKLQM DGRYLRDVW                                          689
```

SEQ ID NO: 99

```
atggatgctg tgacgggttt gttaactgtc ccagcaaccg ctataactat tggtggaact         60
gctgtagcat tggcggtagc gctaatcttt tggtacctga atcctacac atcagctaga         120
agatcccaat caaatcatct tccaagagtg cctgaagtcc caggtgttcc attgttagga        180
aatctgttac aattgaagga gaaaaagcca tacatgactt ttacgagatg ggcagcgaca        240
tatggaccta tctatagtat caaaactggg gctacaagta tggttgtggt atcatctaat        300
gagatagcca aggaggcatt ggtgaccaga ttccaatcca tatctacaag gaacttatct        360
aaagccctga agtacttac agcagataag acaatggtcg caatgtcaga ttatgatgat        420
tatcataaaa cagttaagag acacatactg accgccgtct gggtcctaa tgcacagaaa        480
aagcatagaa ttcacagaga tatcatgatg gataacatat ctactcaact tcatgaattc        540
gtgaaaaaca acccagaaca ggaagaggta gaccttagaa aaatctttca atctgagtta        600
ttcggcttag ctatgagaca agccttagga aaggatgttg aaagtttgta cgttgaagac        660
ctgaaaatca ctatgaatag agacgaaatc tttcaagtcc ttgttgttga tccaatgatg        720
ggagcaatcg atgttgattg gagagacttc tttccatacc taaagtgggt cccaaacaaa        780
aagttcgaaa atactattca acaaatgtac atcagaagag aagctgttat gaaatcttta        840
atcaaagagc acaaaaagag aatagcgtca ggcgaaaagc taaatagtta tatcgattac        900
cttttatctg aagctcaaac tttaaccgat cagcaactat tgatgtcctt gtgggaacca        960
atcattgaat cttcagatac aacaatggtc acaacagaat gggcaatgta cgaattagct       1020
aaaaacccta aattgcaaga taggttgtac agagacatta agtccgtctg tggatctgaa       1080
aagataaccg aagagcatct atcacagctg cctacattac agctatttt ccacgaaaca        1140
ctgagaagac actcaccagt tcctatcatt cctctaagac atgtacatga agataccgtt       1200
ctaggcggct accatgttcc tgctggcaca gaacttgccg ttaacatcta cggttgcaac       1260
atggacaaaa acgtttggga aaatccagag gaatggaacc cagaaagatt catgaaagag       1320
aatgagacaa ttgattttca aaagacgatg gccttcggtg gtggtaagag agtttgtgct       1380
ggttccttgc aagccctttt aactgcatct attgggattg ggagaatggt tcaagagttc       1440
gaatggaaac tgaaggatat gactcaagag gaagtgaaca cgataggcct aactacacaa       1500
atgttaagac cattgagagc tattatcaaa cctaggatcc catcaagacc aagtcctagt       1560
accgaacaat ctgcaaaaaa agttagaaaa aaagcagaaa atgcacacaa tactccattg       1620
ctagttcttt atggttctaa tatgggaaca gcggaaggaa cggccaggga tctagctgac       1680
atagctatgt ccaagggatt tgccccgcaa gtagcaaccc tggattccca tgcaggtaac       1740
ttgccaagag aaggtgctgt tctaatagtt accgctagct acaatgggca ccctccagat       1800
aatgcgaagc agttcgtcga ttggttagat caagcatcag cagatgaagt taagggtgtt       1860
agatactctg tttttggatg tggagataag aattgggcca ccacatatca gaaggttccg       1920
gctttcatcg atgaaatgct tgctgcaaaa ggggctgaaa atatagcaga tcgtggtgag       1980
gccgacgcaa gcgacgattt tgagggtacc tatgaggagt ggagagagca catgtggtct       2040
gatgttgccg cgtattttaa tctagacata gaaaattctg aagacaataa aagtgcctta       2100
```

TABLE 13-continued

Sequences disclosed herein.

| | | | | |
|---|---|---|---|---|
| cttcttcaat | tcgtcgatag | tgctgcggac | atgcccttag | caaagatgca tggagccttt | 2160 |
| tcaacgaacg | tagtagccag | taaggaactt | caacaaccag | gtagtgccag aagtacacgt | 2220 |
| cacttggaaa | ttgaattacc | aaaagaggca | tcctaccaag | aaggtgacca tcttggtgta | 2280 |
| atcccaagaa | actacgaagg | tatagtcaat | agggtaacgg | caagatttgg gctggatgca | 2340 |
| agccaacaga | taagactaga | agcagaagaa | gaaaaattgg | cgcaccttcc actagcgaag | 2400 |
| acagtatccg | ttgaagaatt | attgcaatac | gtggaattgc | aggatcccgt cactagaacg | 2460 |
| caattgagag | ctatggcagc | aaagactgtt | tgtccacctc | acaaggttga acttgaagct | 2520 |
| ctacttgaaa | aacaagcata | caaagagcaa | gtgctagcaa | agagactaac catgttagaa | 2580 |
| ttgctggaaa | ataccccggc | atgcgaaatg | gaattctccg | aatttatcgc gttgttgcca | 2640 |
| agtattcgtc | ccaggtatta | ctcaatttca | tcttcaccaa | gggttgacga gaaacaggca | 2700 |
| tctattaccg | tatctgtggt | ctctggagaa | gcttggagtg | gttacggaga atacaagggt | 2760 |
| attgcttcca | attatcttgc | agaactgcag | gaaggggata | caattacctg ctttatttct | 2820 |
| actcctcaat | cagaatttac | tcttccgaag | gatccagaaa | ctccgttaat tatggtaggt | 2880 |
| ccgggaacag | gagtcgcccc | tttcagaggc | tttgtgcaag | caaggaagca actaaaagaa | 2940 |
| cagggacaaa | gtctgggtga | ggcacatcta | tatttcggtt | gcagatcccc gcatgaggat | 3000 |
| tacttatacc | aagaagaact | tgaaaacgcc | aatcagaagg | gtattatcac cttgcatact | 3060 |
| gcattcagta | gaatgccaaa | ccagccgaaa | acttacgtac | agcatgttat ggagcaagat | 3120 |
| ggtaagaagt | taattgagct | tttggataag | ggcgcccact | tctacatttg cggcgacgga | 3180 |
| tcccaaatgg | cgcctgccgt | tgaagccacc | ttgatgaaat | catatgcaga tgttcatcaa | 3240 |
| gtttcagaag | cggacgcccg | tctttggtta | caacaactag | aggagaaagg aaggtatgca | 3300 |
| aaagatgttt | ggtaa | | | | 3315 |

SEQ ID NO: 100

| | | | | | |
|---|---|---|---|---|---|
| MDAVTGLLTV | PATAITIGGT | AVALAVALIF | WYLKSYTSAR | RSQSNHLPRV | PEVPGVPLLG | 60 |
| NLLQLKEKKP | YMTFTRWAAT | YGPIYSIKTG | ATSMVVVSSN | EIAKEALVTR | FQSISTRNLS | 120 |
| KALKVLTADK | TMVAMSDYDD | YHKTVKRHIL | TAVLGPNAQK | KHRIHRDIMM | DNISTQLHEF | 180 |
| VKNNPEQEEV | DLRKIFQSEL | FGLAMRQALG | KDVESLYVED | LKITMNRDEI | FQVLVVDPMM | 240 |
| GAIDVDWRDF | FPYLKWVPNK | KFENTIQQMY | IRREAVMKSL | IKEHKKRIAS | GEKLNSYIDY | 300 |
| LLSEAQTLTD | QQLLMSLWEP | IIESSDTTMV | TTEWAMYELA | KNPKLQDRLY | RDIKSVCGSE | 360 |
| KITEEHLSQL | PYITAIFHET | LRRHSPVPII | PLRHVHEDTV | LGGYHVPAGT | ELAVNIYGCN | 420 |
| MDKNVWENPE | EWNPERFMKE | NETIDFQKTM | AFGGGKRVCA | GSLQALLTAS | IGIGRMVQEF | 480 |
| EWKLKDMTQE | EVNTIGLTTQ | MLRPLRAIIK | PRIPSRPSPS | TEQSAKKVRK | KAENAHNTPL | 540 |
| LVLYGSNMGT | AEGTARDLAD | IAMSKGFAPQ | VATLDSHAGN | LPREGAVLIV | TASYNGHPPD | 600 |
| NAKQFVDWLD | QASADEVKGV | RYSVFGCGDK | NWATTYQKVP | AFIDEMLAAK | GAENIADRGE | 660 |
| ADASDDFEGT | YEEWREHMWS | DVAAYFNLDI | ENSEDNKSAL | LLQFVDSAAD | MPLAKMHGAF | 720 |
| STNVVASKEL | QQPGSARSTR | HLEIELPKEA | SYQEGDHLGV | IPRNYEGIVN | RVTARFGLDA | 780 |
| SQQIRLEAEE | EKLAHLPLAK | TVSVEELLQY | VELQDPVTRT | QLRAMAAKTV | CPPHKVELEA | 840 |
| LLEKQAYKEQ | VLAKRLTMLE | LLEKYPACEM | EFSEFIALLP | SIRPRYYSIS | SSPRVDEKQA | 900 |
| SITVSVVSGE | AWSGYGEYKG | IASNYLAELQ | EGDTITCFIS | TPQSEFTLPK | DPETPLIMVG | 960 |
| PGTGVAPFRG | FVQARKQLKE | QGQSLGEAHL | YFGCRSPHED | YLYQEELENA | QSEGIITLHT | 1020 |

TABLE 13-continued

Sequences disclosed herein.

| | | | | | |
|---|---|---|---|---|---|
| AFSRMPNQPK | TYVQHVMEQD | GKKLIELLDK | GAHFYICGDG | SQMAPAVEAT | LMKSYADVHQ | 1080 |
| VSEADARLWL | QQLEEKGRYA | KDVW | | | | 1104 |

SEQ ID NO: 101

| | | | | | |
|---|---|---|---|---|---|
| atggatgctg | tgacgggttt | gttaactgtc | ccagcaaccg | ctataactat | tggtggaact | 60 |
| gctgtagcat | tggcggtagc | gctaatcttt | tggtacctga | atcctacac | atcagctaga | 120 |
| agatcccaat | caaatcatct | tccaagagtg | cctgaagtcc | caggtgttcc | attgttagga | 180 |
| aatctgttac | aattgaagga | gaaaaagcca | tacatgactt | ttacgagatg | ggcagcgaca | 240 |
| tatggaccta | tctatagtat | caaaactggg | gctacaagta | tggttgtggt | atcatctaat | 300 |
| gagatagcca | aggaggcatt | ggtgaccaga | ttccaatcca | tatctacaag | gaacttatct | 360 |
| aaagccctga | agtacttac | agcagataag | acaatggtcg | caatgtcaga | ttatgatgat | 420 |
| tatcataaaa | cagttaagag | acacatactg | accgccgtct | gggtcctaa | tgcacagaaa | 480 |
| aagcatagaa | ttcacagaga | tatcatgatg | gataacatat | ctactcaact | tcatgaattc | 540 |
| gtgaaaaaca | acccagaaca | ggaagaggta | gaccttagaa | aaatctttca | atctgagtta | 600 |
| ttcggcttag | ctatgagaca | agccttagga | aaggatgttg | aaagtttgta | cgttgaagac | 660 |
| ctgaaaatca | ctatgaatag | agacgaaatc | tttcaagtcc | ttgttgttga | tccaatgatg | 720 |
| ggagcaatcg | atgttgattg | gagagacttc | tttccatacc | taaagtgggt | cccaaacaaa | 780 |
| aagttcgaaa | atactattca | acaaatgtac | atcagaagag | aagctgttat | gaaatcttta | 840 |
| atcaaagagc | acaaaaagag | aatagcgtca | ggcgaaaagc | taaatagtta | tatcgattac | 900 |
| cttttatctg | aagctcaaac | tttaaccgat | cagcaactat | tgatgtcctt | gtgggaacca | 960 |
| atcattgaat | cttcagatac | aacaatggtc | acaacagaat | gggcaatgta | cgaattagct | 1020 |
| aaaaaccta | aattgcaaga | taggttgtac | agagacatta | agtccgtctg | tggatctgaa | 1080 |
| aagataaccg | aagagcatct | atcacagctg | ccttacatta | cagctatttt | ccacgaaaca | 1140 |
| ctgagaagac | actcaccagt | tcctatcatt | cctctaagac | atgtacatga | agataccgtt | 1200 |
| ctaggcggct | accatgttcc | tgctggcaca | gaacttgccg | ttaacatcta | cggttgcaac | 1260 |
| atggacaaaa | acgtttggga | aaatccagag | gaatggaacc | cagaaagatt | catgaaagag | 1320 |
| aatgagacaa | ttgattttca | aaagacgatg | gccttcggtg | gtggtaagag | agtttgtgct | 1380 |
| ggttccttgc | aagccctttt | aactgcatct | attgggattg | ggagaatggt | tcaagagttc | 1440 |
| gaatggaaac | tgaaggatat | gactcaagag | gaagtgaaca | cgataggcct | aactacacaa | 1500 |
| atgttaagac | cattgagagc | tattatcaaa | cctaggatcc | catcaagacc | aagtcctagt | 1560 |
| accgaacaat | ctgcaaaaaa | agttagaaaa | aaagcagaaa | atgcacacaa | tactccattg | 1620 |
| ctagttcttt | atggttctaa | tatgggaaca | gcggaaggaa | cggccaggga | tctagctgac | 1680 |
| atagctatgt | ccaagggatt | tgccccgcaa | gtagcaaccc | tggattccca | tgcaggtaac | 1740 |
| ttgccaagag | aaggtgctgt | tctaatagtt | accgctagct | acaatgggca | ccctccagat | 1800 |
| aatgcgaagc | agttcgtcga | ttggttagat | caagcatcag | cagatgaagt | taagggtgtt | 1860 |
| agatactctg | tttttggatg | tggagataag | aattgggcca | ccacatatca | gaaggttccg | 1920 |
| gctttcatcg | atgaaatgct | tgctgcaaaa | ggggctgaaa | atatagcaga | tcgtggtgag | 1980 |
| gccgacgcaa | gcgacgattt | tgagggtacc | tatgaggagt | ggagagagca | catgtggtct | 2040 |
| gatgttgccg | cgtattttaa | tctagacata | gaaaattctg | aagacaataa | aagtgcctta | 2100 |
| cttcttcaat | tcgtcgatag | tgctgcggac | atgcccttag | caaagatgca | tggagccttt | 2160 |
| tcaacgaacg | tagtagccag | taaggaactt | caacaaccag | gtagtgccag | aagtacacgt | 2220 |

TABLE 13-continued

Sequences disclosed herein.

| | | | | | |
|---|---|---|---|---|---|
| cacttggaaa | ttgaattacc | aaaagaggca | tcctaccaag | aaggtgacca | tcttggtgta | 2280 |
| atcccaagaa | actacgaagg | tatagtcaat | agggtaacgg | caagatttgg | gctggatgca | 2340 |
| agccaacaga | taagactaga | agcagaagaa | gaaaaattgg | cgcaccttcc | actagcgaag | 2400 |
| acagtatccg | ttgaagaatt | attgcaatac | gtggaattgc | aggatcccgt | cactagaacg | 2460 |
| caattgagag | ctatggcagc | aaagactgtt | tgtccacctc | acaaggttga | acttgaagct | 2520 |
| ctacttgaaa | aacaagcata | caaagagcaa | gtgctagcaa | agagactaac | catgttagaa | 2580 |
| ttgctggaaa | ataccccggc | atgcgaaatg | gaattctccg | aatttatcgc | gttgttgcca | 2640 |
| agtattcgtc | ccaggtatta | ctcaatttca | tcttcaccaa | gggttgacga | gaaacaggca | 2700 |
| tctattaccg | tatctgtggt | ctctggagaa | gcttggagtg | gttacggaga | atacaagggt | 2760 |
| attgcttcca | attatcttgc | agaactgcag | gaaggggata | caattacctg | ctttatttct | 2820 |
| actcctcaat | cagaatttac | tcttccgaag | gatccagaaa | ctccgttaat | tatggtaggt | 2880 |
| ccgggaacag | gagtcgcccc | tttcagaggc | tttgtgcaag | caaggaagca | actaaaagaa | 2940 |
| cagggacaaa | gtctgggtga | ggcacatcta | tatttcggtt | gcagatcccc | gcatgaggat | 3000 |
| tacttatacc | aagaagaact | tgaaaacgcc | caatcagaag | gtattatcac | cttgcatact | 3060 |
| gcattcagta | gaatgccaaa | ccagccgaaa | acttacgtac | agcatgttat | ggagcaagat | 3120 |
| ggtaagaagt | taattgagct | tttggataag | ggcgcccact | tctacatttg | cggcgacgga | 3180 |
| tcccaaatgg | cgcctgccgt | tgaagccacc | ttgatgaaat | catatgcaga | tgttcatcaa | 3240 |
| gtttcagaag | cggacgcccg | tcttggtta | caacaactag | aggagaaagg | aaggtatgca | 3300 |
| aaagatgttg | cttaa | | | | | 3315 |

SEQ ID NO: 102

| | | | | | |
|---|---|---|---|---|---|
| MDAVTGLLTV | PATAITIGGT | AVALAVALIF | WYLKSYTSAR | RSQSNHLPRV | PEVPGVPLLG | 60 |
| NLLQLKEKKP | YMTFTRWAAT | YGPIYSIKTG | ATSMVVVSSN | EIAKEALVTR | FQSISTRNLS | 120 |
| KALKVLTADK | TMVAMSDYDD | YHKTVKRHIL | TAVLGPNAQK | KHRIHRDIMM | DNISTQLHEF | 180 |
| VKNNPEQEEV | DLRKIFQSEL | FGLAMRQALG | KDVESLYVED | LKITMNRDEI | FQVLVVDPMM | 240 |
| GAIDVDWRDF | FPYLKWVPNK | KFENTIQQMY | IRREAVMKSL | IKEHKKRIAS | GEKLNSYIDY | 300 |
| LLSEAQTLTD | QQLLMSLWEP | IIESSDTTMV | TTEWAMYELA | KNPKLQDRLY | RDIKSVCGSE | 360 |
| KITEEHLSQL | PYITAIFHET | LRRHSPVPII | PLRHVHEDTV | LGGYHVPAGT | ELAVNIYGCN | 420 |
| MDKNVWENPE | EWNPERFMKE | NETIDFQKTM | AFGGGKRVCA | GSLQALLTAS | IGIGRMVQEF | 480 |
| EWKLKDMTQE | EVNTIGLTTQ | MLRPLRAIIK | PRIPSRPSPS | TEQSAKKVRK | KAENAHNTPL | 540 |
| LVLYGSNMGT | AEGTARDLAD | IAMSKGFAPQ | VATLDSHAGN | LPREGAVLIV | TASYNGHPPD | 600 |
| NAKQFVDWLD | QASADEVKGV | RYSVFGCGDK | NWATTYQKVP | AFIDEMLAAK | GAENIADRGE | 660 |
| ADASDDFEGT | YEEWREHMWS | DVAAYFNLDI | ENSEDNKSAL | LLQFVDSAAD | MPLAKMHGAF | 720 |
| STNVVASKEL | QQPGSARSTR | HLEIELPKEA | SYQEGDHLGV | IPRNYEGIVN | RVTARFGLDA | 780 |
| SQQIRLEAEE | EKLAHLPLAK | TVSVEELLQY | VELQDPVTRT | QLRAMAAKTV | CPPHKVELEA | 840 |
| LLEKQAYKEQ | VLAKRLTMLE | LLEKYPACEM | EFSEFIALLP | SIRPRYYSIS | SSPRVDEKQA | 900 |
| SITVSVVSGE | AWSGYGEYKG | IASNYLAELQ | EGDTITCFIS | TPQSEFTLPK | DPETPLIMVG | 960 |
| PGTGVAPFRG | FVQARKQLKE | QGQSLGEAHL | YFGCRSPHED | YLYQEELENA | QSEGIITLHT | 1020 |
| AFSRMPNQPK | TYVQHVMEQD | GKKLIELLDK | GAHFYICGDG | SQMAPAVEAT | LMKSYADVHQ | 1080 |
| VSEADARLWL | QQLEEKGRYA | KDVA | | | | 1104 |

TABLE 13-continued

Sequences disclosed herein.

SEQ ID NO: 103

| | |
|---|---|
| atgccaagag tgcctgaagt cccaggtgtt ccattgttag gaaatctgtt acaattgaag | 60 |
| gagaaaaagc catacatgac ttttacgaga tgggcagcga catatggacc tatctatagt | 120 |
| atcaaaactg gggctacaag tatggttgtg gtatcatcta atgagatagc caaggaggca | 180 |
| ttggtgacca gattccaatc catatctaca aggaacttat ctaaagccct gaaagtactt | 240 |
| acagcagata agacaatggt cgcaatgtca gattatgatg attatcataa aacagttaag | 300 |
| agacacatac tgaccgccgt cttgggtcct aatgcacaga aaaagcatag aattcacaga | 360 |
| gatatcatga tggataacat atctactcaa cttcatgaat tcgtgaaaaa caacccagaa | 420 |
| caggaagagg tagaccttag aaaaatcttt caatctgagt tattcggctt agctatgaga | 480 |
| caagccttag gaaaggatgt tgaaagtttg tacgttgaag acctgaaaat cactatgaat | 540 |
| agagacgaaa tctttcaagt ccttgttgtt gatccaatga tgggagcaat cgatgttgat | 600 |
| tggagagact tctttccata cctaaagtgg gtcccaaaca aaaagttcga aaatactatt | 660 |
| caacaaatgt acatcagaag agaagctgtt atgaaatctt taatcaaaga gcacaaaaag | 720 |
| agaatagcgt caggcgaaaa gctaaatagt tatatcgatt accttttatc tgaagctcaa | 780 |
| actttaaccg atcagcaact attgatgtcc ttgtgggaac caatcattga atcttcagat | 840 |
| acaacaatgg tcacaacaga atgggcaatg tacgaattag ctaaaaaccc taaattgcaa | 900 |
| gataggttgt acagagacat taagtccgtc tgtggatctg aaaagataac cgaagagcat | 960 |
| ctatcacagc tgccttacat tacagctatt tccacgaaaa cactgagaag acactcacca | 1020 |
| gttcctatca ttcctctaag acatgtacat gaagataccg ttctaggcgg ctaccatgtt | 1080 |
| cctgctggca cagaacttgc cgttaacatc tacggttgca acatggacaa aaacgtttgg | 1140 |
| gaaaatccag aggaatggaa cccagaaaga ttcatgaaag agatgagaca aattgatttt | 1200 |
| caaaagacga tggccttcgg tggtggtaag agagtttgtg ctggttcctt gcaagccctt | 1260 |
| ttaactgcat ctattgggat tgggagaatg gttcaagagt tcgaatggaa actgaaggat | 1320 |
| atgactcaag aggaagtgaa cacgataggc ctaactacac aaatgttaag accattgaga | 1380 |
| gctattatca aacctaggat cccatcaaga ccaagtccta gtaccgaaca atctgcaaaa | 1440 |
| aaagttagaa aaaagcaga aatgcacac aatactccat tgctagttct ttatggttct | 1500 |
| aatatgggaa cagcggaagg aacggccagg gatctagctg acatagctat gtccaaggga | 1560 |
| tttgccccgc aagtagcaac cctggattcc catgcaggta acttgccaag agaaggtgct | 1620 |
| gttctaatag ttaccgctag ctacaatggg caccctccag ataatgcgaa gcagttcgtc | 1680 |
| gattggttag atcaagcatc agcagatgaa gttaagggtg ttagatactc tgttttttgga | 1740 |
| tgtggagata agaattgggc caccacatat cagaaggttc cggctttcat cgatgaaatg | 1800 |
| cttgctgcaa aaggggctga aaatatagca gatcgtggtg aggccgacgc aagcgacgat | 1860 |
| tttgagggta cctatgagga gtggagagag cacatgtggt ctgatgttgc cgcgtatttt | 1920 |
| aatctagaca tagaaaattc tgaagacaat aaaagtgcct tacttcttca attcgtcgat | 1980 |
| agtgctgcgg acatgcccct agcaaagatg catggagcct tttcaacgaa cgtagtagcc | 2040 |
| agtaaggaac ttcaacaacc aggtagtgcc agaagtacac gtcacttgga aattgaatta | 2100 |
| ccaaaagagg catcctacca agaaggtgac catcttggtg taatcccaag aaactacgaa | 2160 |
| ggtatagtca atagggtaac ggcaagattt gggctggatg caagccaaca gataagacta | 2220 |
| gaagcagaag aagaaaaatt ggcgcaccct tccactagcga agacagtatc cgttgaagaa | 2280 |
| ttattgcaat acgtggaatt gcaggatccc gtcactagaa cgcaattgag agctatggca | 2340 |

TABLE 13-continued

Sequences disclosed herein.

| | | | | | |
|---|---|---|---|---|---|
| gcaaagactg | tttgtccacc | tcacaaggtt | gaacttgaag | ctctacttga | aaaacaagca | 2400 |
| tacaaagagc | aagtgctagc | aaagagacta | accatgttag | aattgctgga | aaaatacccg | 2460 |
| gcatgcgaaa | tggaattctc | cgaatttatc | gcgttgttgc | caagtattcg | tcccaggtat | 2520 |
| tactcaattt | catcttcacc | aagggttgac | gagaaacagg | catctattac | cgtatctgtg | 2580 |
| gtctctggag | aagcttggag | tggttacgga | gaatacaagg | gtattgcttc | caattatctt | 2640 |
| gcagaactgc | aggaagggga | tacaattacc | tgctttattt | ctactcctca | atcagaattt | 2700 |
| actcttccga | aggatccaga | aactccgtta | attatggtag | gtccgggaac | aggagtcgcc | 2760 |
| cctttcagag | gctttgtgca | agcaaggaag | caactaaaag | aacagggaca | aagtctgggt | 2820 |
| gaggcacatc | tatatttcgg | ttgcagatct | ccgcatgagg | attacttata | ccaagaagaa | 2880 |
| cttgaaaacg | cccaatcaga | aggtattatc | accttgcata | ctgcattcag | tagaatgcca | 2940 |
| aaccagccga | aaacttacgt | acagcatgtt | atggagcaag | atggtaagaa | gttaattgag | 3000 |
| cttttggata | agggcgccca | cttctacatt | tgcggcgacg | gatcccaaat | ggcgcctgcc | 3060 |
| gttgaagcca | ccttgatgaa | atcatatgca | gatgttcatc | aagtttcaga | agcggacgcc | 3120 |
| cgtctttggt | tacaacaact | agaggagaaa | ggaaggtatg | caaaagatgt | ttggtaa | 3177 |

SEQ ID NO: 104

| | | | | | |
|---|---|---|---|---|---|
| MPRVPEVPGV | PLLGNLLQLK | EKKPYMTFTR | WAATYGPIYS | IKTGATSMVV | VSSNEIAKEA | 60 |
| LVTRFQSIST | RNLSKALKVL | TADKTMVAMS | DYDDYHKTVK | RHILTAVLGP | NAQKKHRIHR | 120 |
| DIMMDNISTQ | LHEFVKNNPE | QEEVDLRKIF | QSELFGLAMR | QALGKDVESL | YVEDLKITMN | 180 |
| RDEIFQVLVV | DPMMGAIDVD | WRDFFPYLKW | VPNKKFENTI | QQMYIRREAV | MKSLIKEHKK | 240 |
| RIASGEKLNS | YIDYLLSEAQ | TLTDQQLLMS | LWEPIIESSD | TTMVTTEWAM | YELAKNPKLQ | 300 |
| DRLYRDIKSV | CGSEKITEEH | LSQLPYITAI | FHETLRRHSP | VPIIPLRHVH | EDTVLGGYHV | 360 |
| PAGTELAVNI | YGCNMDKNVW | ENPEEWNPER | FMKENETIDF | QKTMAFGGGK | RVCAGSLQAL | 420 |
| LTASIGIGRM | VQEFEWKLKD | MTQEEVNTIG | LTTQMLRPLR | AIIKPRIPSR | PSPSTEQSAK | 480 |
| KVRKKAENAH | NTPLLVLYGS | NMGTAEGTAR | DLADIAMSKG | FAPQVATLDS | HAGNLPREGA | 540 |
| VLIVTASYNG | HPPDNAKQFV | DWLDQASADE | VKGVRYSVFG | CGDKNWATTY | QKVPAFIDEM | 600 |
| LAAKGAENIA | DRGEADASDD | FEGTYEEWRE | HMWSDVAAYF | NLDIENSEDN | KSALLLQFVD | 660 |
| SAADMPLAKM | HGAFSTNVVA | SKELQQPGSA | RSTRHLEIEL | PKEASYQEGD | HLGVIPRNYE | 720 |
| GIVNRVTARF | GLDASQQIRL | EAEEEKLAHL | PLAKTVSVEE | LLQYVELQDP | VTRTQLRAMA | 780 |
| AKTVCPPHKV | ELEALLEKQA | YKEQVLAKRL | TMLELLEKYP | ACEMEFSEFI | ALLPSIRPRY | 840 |
| YSISSSPRVD | EKQASITVSV | VSGEAWSGYG | EYKGIASNYL | AELQEGDTIT | CFISTPQSEF | 900 |
| TLPKDPETPL | IMVGPGTGVA | PFRGFVQARK | QLKEQGQSLG | EAHLYFGCRS | PHEDYLYQEE | 960 |
| LENAQSEGII | TLHTAFSRMP | NQPKTYVQHV | MEQDGKKLIE | LLDKGAHFYI | CGDGSQMAPA | 1020 |
| VEATLMKSYA | DVHQVSEADA | RLWLQQLEEK | GRYAKDVW | | | 1058 |

SEQ ID NO: 105

| | | | | | |
|---|---|---|---|---|---|
| atgccaagag | tgcctgaagt | cccaggtgtt | ccattgttag | gaaatctgtt | acaattgaag | 60 |
| gagaaaaagc | catacatgac | ttttacgaga | tgggcagcga | catatggacc | tatctatagt | 120 |
| atcaaaactg | gggctacaag | tatggttgtg | gtatcatcta | atgagatagc | caaggaggca | 180 |
| ttggtgacca | gattccaatc | catatctaca | aggaacttat | ctaaagccct | gaaagtactt | 240 |
| acagcagata | agacaatggt | cgcaatgtca | gattatgatg | attatcataa | aacagttaag | 300 |
| agacacatac | tgaccgccgt | cttgggtcct | aatgcacaga | aaaagcatag | aattcacaga | 360 |

TABLE 13-continued

Sequences disclosed herein.

```
gatatcatga tggataacat atctactcaa cttcatgaat tcgtgaaaaa caacccagaa    420
caggaagagg tagaccttag aaaaatcttt caatctgagt tattcggctt agctatgaga    480
caagccttag gaaaggatgt tgaaagtttg tacgttgaag acctgaaaat cactatgaat    540
agagacgaaa tctttcaagt ccttgttgtt gatccaatga tgggagcaat cgatgttgat    600
tggagagact tctttccata cctaaagtgg gtcccaaaca aaagttcga aaatactatt    660
caacaaatgt acatcagaag agaagctgtt atgaaatctt taatcaaaga gcacaaaaag    720
agaatagcgt caggcgaaaa gctaaatagt tatatcgatt acctttatc tgaagctcaa    780
actttaaccg atcagcaact attgatgtcc ttgtgggaac caatcattga atcttcagat    840
acaacaatgg tcacaacaga atgggcaatg tacgaattag ctaaaaaccc taaattgcaa    900
gataggttgt acagagacat taagtccgtc tgtggatctg aaaagataac cgaagagcat    960
ctatcacagc tgccttacat tacagctatt tccacgaaa cactgagaag acactcacca   1020
gttcctatca ttcctctaag acatgtacat gaagataccg ttctaggcgg ctaccatgtt   1080
cctgctggca cagaacttgc cgttaacatc tacggttgca acatggacaa aaacgtttgg   1140
gaaaatccag aggaatggaa cccagaaaga ttcatgaaag agaatgagac aattgatttt   1200
caaaagacga tggccttcgg tggtggtaag agagtttgtg ctggttcctt gcaagccctt   1260
ttaactgcat ctattgggat tgggagaatg gttcaagagt tcgaatggaa actgaaggat   1320
atgactcaag aggaagtgaa cacgataggc ctaactacac aaatgttaag accattgaga   1380
gctattatca aacctaggat cccatcaaga ccaagtccta gtaccgaaca atctgcaaaa   1440
aaagttagaa aaaaagcaga aaatgcacac aatactccat tgctagttct ttatggttct   1500
aatatgggaa cagcggaagg aacggccagg gatctagctg acatagctat gtccaaggga   1560
tttgccccgc aagtagcaac cctggattcc catgcaggta acttgccaag agaaggtgct   1620
gttctaatag ttaccgctag ctacaatggg caccctccag ataatgcgaa gcagttcgtc   1680
gattggttag atcaagcatc agcagatgaa gttaagggtg ttagatactc tgtttttgga   1740
tgtggagata agaattgggc caccacatat cagaaggttc cggctttcat cgatgaaatg   1800
cttgctgcaa agggctga aaatatagca gatcgtggtg aggccgacgc aagcgacgat   1860
tttgaggta cctatgagga gtggagagag cacatgtggt ctgatgttgc cgcgtatttt   1920
aatctagaca tagaaaattc tgaagacaat aaaagtgcct tacttcttca attcgtcgat   1980
agtgctgcgg acatgccctt agcaaagatg catggagcct tttcaacgaa cgtagtagcc   2040
agtaaggaac ttcaacaacc aggtagtgcc agaagtacac gtcacttgga aattgaatta   2100
ccaaaagagg catcctacca agaaggtgac catcttggtg taatcccaag aaactacgaa   2160
ggtatagtca atagggtaac ggcaagattt gggctggatg caagccaaca gataagacta   2220
gaagcagaag aagaaaaatt ggcgcaccct ccactagcga agacagtatc cgttgaagaa   2280
ttattgcaat acgtggaatt gcaggatccc gtcactagaa cgcaattgag agctatggca   2340
gcaaagactg tttgtccacc tcacaaggtt gaacttgaag ctctacttga aaaacaagca   2400
tacaaagagc aagtgctagc aaagagacta accatgttag aattgctgga aaatacccg   2460
gcatgcgaaa tggaattctc cgaatttatc gcgttgttgc caagtattcg tcccaggtat   2520
tactcaattt catcttcacc aagggttgac gagaaacagg catctattac cgtatctgtg   2580
gtctctggag aagcttggag tggttacgga gaatacaagg gtattgcttc caattatctt   2640
gcagaactgc aggaagggga tacaattacc tgctttattt ctactcctca atcagaattt   2700
```

TABLE 13-continued

Sequences disclosed herein.

| | |
|---|---|
| actcttccga aggatccaga aactccgtta attatggtag gtccgggaac aggagtcgcc | 2760 |
| cctttcagag gctttgtgca agcaaggaag caactaaaag aacagggaca aagtctgggt | 2820 |
| gaggcacatc tatatttcgg ttgcagatct ccgcatgagg attacttata ccaagaagaa | 2880 |
| cttgaaaacg cccaatcaga aggtattatc accttgcata ctgcattcag tagaatgcca | 2940 |
| aaccagccga aaacttacgt acagcatgtt atggagcaag atggtaagaa gttaattgag | 3000 |
| cttttggata agggcgccca cttctacatt tgcggcgacg gatcccaaat ggcgcctgcc | 3060 |
| gttgaagcca ccttgatgaa atcatatgca gatgttcatc aagtttcaga agcggacgcc | 3120 |
| cgtctttggt tacaacaact agaggagaaa ggaaggtatg caaaagatgt tgcttaa | 3177 |

SEQ ID NO: 106

| | |
|---|---|
| MPRVPEVPGV PLLGNLLQLK EKKPYMTFTR WAATYGPIYS IKTGATSMVV VSSNEIAKEA | 60 |
| LVTRFQSIST RNLSKALKVL TADKTMVAMS DYDDYHKTVK RHILTAVLGP NAQKKHRIHR | 120 |
| DIMMDNISTQ LHEFVKNNPE QEEVDLRKIF QSELFGLAMR QALGKDVESL YVEDLKITMN | 180 |
| RDEIFQVLVV DPMMGAIDVD WRDFFPYLKW VPNKKFENTI QQMYIRREAV MKSLIKEHKK | 240 |
| RIASGEKLNS YIDYLLSEAQ TLTDQQLLMS LWEPIIESSD TTMVTTEWAM YELAKNPKLQ | 300 |
| DRLYRDIKSV CGSEKITEEH LSQLPYITAI FHETLRRHSP VPIIPLRHVH EDTVLGGYHV | 360 |
| PAGTELAVNI YGCNMDKNVW ENPEEWNPER FMKENETIDF QKTMAFGGGK RVCAGSLQAL | 420 |
| LTASIGIGRM VQEFEWKLKD MTQEEVNTIG LTTQMLRPLR AIIKPRIPSR PSPSTEQSAK | 480 |
| KVRKKAENAH NTPLLVLYGS NMGTAEGTAR DLADIAMSKG FAPQVATLDS HAGNLPREGA | 540 |
| VLIVTASYNG HPPDNAKQFV DWLDQASADE VKGVRYSVFG CGDKNWATTY QKVPAFIDEM | 600 |
| LAAKGAENIA DRGEADASDD FEGTYEEWRE HMWSDVAAYF NLDIENSEDN KSALLLQFVD | 660 |
| SAADMPLAKM HGAFSTNVVA SKELQQPGSA RSTRHLEIEL PKEASYQEGD HLGVIPRNYE | 720 |
| GIVNRVTARF GLDASQQIRL EAEEEKLAHL PLAKTVSVEE LLQYVELQDP VTRTQLRAMA | 780 |
| AKTVCPPHKV ELEALLEKQA YKEQVLAKRL TMLELLEKYP ACEMEFSEFI ALLPSIRPRY | 840 |
| YSISSSPRVD EKQASITVSV VSGEAWSGYG EYKGIASNYL AELQEGDTIT CFISTPQSEF | 900 |
| TLPKDPETPL IMVGPGTGVA PFRGFVQARK QLKEQGQSLG EAHLYFGCRS PHEDYLYQEE | 960 |
| LENAQSEGII TLHTAFSRMP NQPKTYVQHV MEQDGKKLIE LLDKGAHFYI CGDGSQMAPA | 1020 |
| VEATLMKSYA DVHQVSEADA RLWLQQLEEK GRYAKDVA | 1058 |

SEQ ID NO: 107

| | |
|---|---|
| atggctacct tgttggaaca ttttcaagct atgccattcg ctattccaat tgctttggct | 60 |
| gctttgtctt ggttgttttt gttctacatc aaggtttctt tcttctccaa caaatccgct | 120 |
| caagctaaat tgccaccagt tccagttgtt ccaggttttgc cagttattgg taatttgttg | 180 |
| caattgaaag aaaagaagcc ataccaaacc ttcactagat gggctgaaga atatggtcca | 240 |
| atctactcta ttagaactgg tgcttctact atggttgtct tgaacactac tcaagttgcc | 300 |
| aaagaagcta tggttaccag atacttgtct atctctacca gaaagttgtc caacgccttg | 360 |
| aaaattttga ccgctgataa gtgcatggtt gccatttctg attacaacga tttccacaag | 420 |
| atgatcaaga gatatatctt gtctaacgtt ttgggtccat ctgcccaaaa aagacataga | 480 |
| tctaacagag ataccttgag agccaacgtt tgttctagat tgcattccca agttaagaac | 540 |
| tctccaagag aagctgtcaa ctttagaaga gttttcgaat gggaattatt cggtatcgct | 600 |
| ttgaaacaag cctccggtaa ggatattgaa aagccaatct acgtcgaaga attgggtact | 660 |
| actttgtcca gagatgaaat cttccaaggt ttggtcttgg acattatgga aggtgccatt | 720 |

TABLE 13-continued

Sequences disclosed herein.

```
gaagttgatt ggagagattt tttcccatac ttgcgttgga ttccaaacac cagaatggaa    780
actaagatcc aaagattata ctttagaaga aaggccgtta tgaccgcctt gattaacgaa    840
caaaagaaaa gaattgcctc cggtgaagaa atcaactgct acatcgattt cttgttgaaa    900
gaaggtaaga ccttgaccat ggaccaaatc tctatgttgt tgtgggaaac cgttattgaa    960
actgctgata ccacaatggt tactactgaa tgggctatgt acgaagttgc taaggattct   1020
aaaagacaag acagattata ccaagaaatc caaaaggtct gcggttctga aatggttaca   1080
gaagaatact tgtcccaatt gccatacttg aatgctgttt tccacgaaac tttgagaaaa   1140
cattctccag ctgctttggt tccattgaga tatgctcatg aagatactca attgggtggt   1200
tattacattc cagccggtac tgaaattgcc attaacatct acggttgcaa catggacaaa   1260
caccaatggg aatctccaga agaatggaag ccagaaagat ttttggatcc taagtttgac   1320
ccaatggact tgtacaaaac tatggctttt ggtgctggta aaagagtttg cgctggttct   1380
ttacaagcta tgttgattgc ttgtccaacc atcggtagat tggttcaaga atttgaatgg   1440
aagttgagag atggtgaaga agaaaacgtt gatactgttg gtttgaccac ccataagaga   1500
tatccaatgc atgctatttt gaagccaaga tctccatcaa gaccaagtcc tagtaccgaa   1560
caatctgcaa aaaagttag aaaaaagca gaaaatgcac acaatactcc attgctagtt   1620
ctttatggtt ctaatatggg aacagcggaa ggaacggcca gggatctagc tgacatagct   1680
atgtccaagg gatttgcccc gcaagtagca accctggatt cccatgcagg taacttgcca   1740
agagaaggtg ctgttctaat agttaccgct agctacaatg ggcaccctcc agataatgcg   1800
aagcagttcg tcgattggtt agatcaagca tcagcagatg aagttaaggg tgttagatac   1860
tctgtttttg gatgtggaga taagaattgg gccaccacat atcagaaggt tccggctttc   1920
atcgatgaaa tgcttgctgc aaaagggggct gaaaatatag cagatcgtgg tgaggccgac   1980
gcaagcgacg attttgaggg tacctatgag gagtggagag agcacatgtg gtctgatgtt   2040
gccgcgtatt ttaatctaga catagaaaat tctgaagaca ataaaagtgc cttacttctt   2100
caattcgtcg atagtgctgc ggacatgccc ttagcaaaga tgcatggagc cttttcaacg   2160
aacgtagtag ccagtaagga acttcaacaa ccaggtagtg ccagaagtac acgtcacttg   2220
gaaattgaat taccaaaaga ggcatcctac caagaaggtg accatcttgg tgtaatccca   2280
agaaactacg aaggtatagt caatagggta acggcaagat tgggctgga tgcaagccaa   2340
cagataagac tagaagcaga agaagaaaaa ttggcgcacc ttccactagc gaagacagta   2400
tccgttgaag aattattgca atacgtggaa ttgcaggatc ccgtcactag aacgcaattg   2460
agagctatgg cagcaaagac tgtttgtcca cctcacaagg ttgaacttga agctctactt   2520
gaaaaacaag catacaaaga gcaagtgcta gcaaagagac taaccatgtt agaattgctg   2580
gaaaaatacc cggcatgcga aatggaattc tccgaattta tcgcgttgtt gccaagtatt   2640
cgtcccaggt attactcaat ttcatcttca ccaagggttg acgagaaaca ggcatctatt   2700
accgtatctg tggtctctgg agaagcttgg agtggttacg gagaatacaa gggtattgct   2760
tccaattatc ttgcagaact gcaggaaggg gatacaatta cctgctttat ttctactcct   2820
caatcagaat ttactcttcc gaaggatcca gaaactccgt taattatggt aggtccggga   2880
acaggagtcg ccccttttcag aggctttgtg caagcaagga agcaactaaa agaacaggga   2940
caaagtctgg gtgaggcaca tctatatttc ggttgcagat ctccgcatga ggattactta   3000
taccaagaag aacttgaaaa cgcccaatca gaaggtatta tcaccttgca tactgcattc   3060
```

TABLE 13-continued

Sequences disclosed herein.

| | | | | |
|---|---|---|---|---|
| agtagaatgc | caaaccagcc | gaaaacttac | gtacagcatg | ttatggagca agatggtaag | 3120 |
| aagttaattg | agcttttgga | taagggcgcc | cacttctaca | tttgcggcga cggatcccaa | 3180 |
| atggcgcctg | ccgttgaagc | caccttgatg | aaatcatatg | cagatgttca tcaagtttca | 3240 |
| gaagcggacg | cccgtctttg | gttacaacaa | ctagaggaga | aggaaggta tgcaaaagat | 3300 |
| gtttggtaa | | | | | 3309 |

SEQ ID NO: 108
| | | | | | |
|---|---|---|---|---|---|
| MATLLEHFQA | MPFAIPIALA | ALSWLFLFYI | KVSFFSNKSA | QAKLPPVPVV | PGLPVIGNLL | 60 |
| QLKEKKPYQT | FTRWAEEYGP | IYSIRTGAST | MVVLNTTQVA | KEAMVTRYLS | ISTRKLSNAL | 120 |
| KILTADKCMV | AISDYNDFHK | MIKRYILSNV | LGPSAQKRHR | SNRDTLRANV | CSRLHSQVKN | 180 |
| SPREAVNFRR | VFEWELFGIA | LKQAFGKDIE | KPIYVEELGT | TLSRDEIFKV | LVLDIMEGAI | 240 |
| EVDWRDFFPY | LRWIPNTRME | TKIQRLYFRR | KAVMTALINE | QKKRIASGEE | INCYIDFLLK | 300 |
| EGKTLTMDQI | SMLLWETVIE | TADTTMVTTE | WAMYEVAKDS | KRQDRLYQEI | QKVCGSEMVT | 360 |
| EEYLSQLPYL | NAVFHETLRK | HSPAALVPLR | YAHEDTQLGG | YYIPAGTEIA | INIYGCNMDK | 420 |
| HQWESPEEWK | PERFLDPKFD | PMDLYKTMAF | GAGKRVCAGS | LQAMLIACPT | IGRLVQEFEW | 480 |
| KLRDGEEENV | DTVGLTTHKR | YPMHAILKPR | SPSRPSPSTE | QSAKKVRKKA | ENAHNTPLLV | 540 |
| LYGSNMGTAE | GTARDLADIA | MSKGFAPQVA | TLDSHAGNLP | REGAVLIVTA | SYNGHPPDNA | 600 |
| KQFVDWLDQA | SADEVKGVRY | SVFGCGDKNW | ATTYQKVPAF | IDEMLAAKGA | ENIADRGEAD | 660 |
| ASDDFEGTYE | EWREHMWSDV | AAYFNLDIEN | SEDNKSALLL | QFVDSAADMP | LAKMHGAFST | 720 |
| NVVASKELQQ | PGSARSTRHL | EIELPKEASY | QEGDHLGVIP | RNYEGIVNRV | TARFGLDASQ | 780 |
| QIRLEAEEEK | LAHLPLAKTV | SVEELLQYVE | LQDPVTRTQL | RAMAAKTVCP | PHKVELEALL | 840 |
| EKQAYKEQVL | AKRLTMLELL | EKYPACEMEF | SEFIALLPSI | RPRYYSISSS | PRVDEKQASI | 900 |
| TVSVVSGEAW | SGYGEYKGIA | SNYLAELQEG | DTITCFISTP | QSEFTLPKDP | ETPLIMVGPG | 960 |
| TGVAPFRGFV | QARKQLKEQG | QSLGEAHLYF | GCRSPHEDYL | YQEELENAQS | EGIITLHTAF | 1020 |
| SRMPNQPKTY | VQHVMEQDGK | KLIELLDKGA | HFYICGDGSQ | MAPAVEATLM | KSYADVHQVS | 1080 |
| EADARLWLQQ | LEEKGRYAKD | VW | | | | 1102 |

SEQ ID NO: 109
| | | | | | |
|---|---|---|---|---|---|
| atggctacct | tgttggaaca | ttttcaagct | atgccattcg | ctattccaat | tgctttggct | 60 |
| gctttgtctt | ggttgttttt | gttctacatc | aaggtttctt | tcttctccaa | caaatccgct | 120 |
| caagctaaat | tgccaccagt | tccagttgtt | ccaggtttgc | cagttattgg | taatttgttg | 180 |
| caattgaaag | aaaagaagcc | ataccaaacc | ttcactagat | gggctgaaga | atatggtcca | 240 |
| atctactcta | ttagaactgg | tgcttctact | atggttgtct | tgaacactac | tcaagttgcc | 300 |
| aaagaagcta | tggttaccag | atacttgtct | atctctacca | gaaagttgtc | caacgccttg | 360 |
| aaaattttga | ccgctgataa | gtgcatggtt | gccatttctg | attacaacga | tttccacaag | 420 |
| atgatcaaga | gatatatctt | gtctaacgtt | ttgggtccat | ctgcccaaaa | aagacataga | 480 |
| tctaacagag | ataccttgag | agccaacgtt | tgttctagat | gcattccca | agttaagaac | 540 |
| tctccaagag | aagctgtcaa | ctttagaaga | gttttcgaat | gggaattatt | cggtatcgct | 600 |
| ttgaaacaag | ccttcggtaa | ggatattgaa | aagccaatct | acgtcgaaga | attgggtact | 660 |
| actttgtcca | gagatgaaat | cttcaaggtt | ttggtcttgg | acattatgga | aggtgccatt | 720 |
| gaagttgatt | ggagagattt | ttttcccatac | ttgcgttgga | ttccaaacac | cagaatggaa | 780 |
| actaagatcc | aaagattata | ctttagaaga | aaggccgtta | tgaccgcctt | gattaacgaa | 840 |

TABLE 13-continued

Sequences disclosed herein.

```
caaaagaaaa gaattgcctc cggtgaagaa atcaactgct acatcgattt cttgttgaaa      900
gaaggtaaga ccttgaccat ggaccaaatc tctatgttgt tgtgggaaac cgttattgaa      960
actgctgata ccacaatggt tactactgaa tgggctatgt acgaagttgc taaggattct     1020
aaaagacaag acagattata ccaagaaatc caaaaggtct gcggttctga aatggttaca     1080
gaagaatact tgtcccaatt gccatacttg aatgctgttt ccacgaaac tttgagaaaa      1140 cattctccag ctgctttggt tccattgaga tatgctcatg aagatactca attgggtggt     1200
tattacattc cagccggtac tgaaattgcc attaacatct acggttgcaa catggacaaa     1260
caccaatggg aatctccaga agaatggaag ccagaaagat ttttggatcc taagtttgac     1320
ccaatggact tgtacaaaac tatggctttt ggtgctggta aaagagtttg cgctggttct     1380
ttacaagcta tgttgattgc ttgtccaacc atcggtagat tggttcaaga atttgaatgg     1440
aagttgagag atggtgaaga agaaaacgtt gatactgttg gtttgaccac ccataagaga     1500
tatccaatgc atgctatttt gaagccaaga tctccatcaa gaccaagtcc tagtaccgaa     1560
caatctgcaa aaaagttag aaaaaaagca gaaaatgcac acaatactcc attgctagtt     1620
ctttatggtt ctaatatggg aacagcggaa ggaacggcca gggatctagc tgacatagct     1680
atgtccaagg gatttgcccc gcaagtagca accctggatt cccatgcagg taacttgcca     1740
agagaaggtg ctgttctaat agttaccgct agctacaatg gcaccctcc agataatgcg      1800 aagcagttcg tcgattggtt agatcaagca tcagcagatg aagttaaggg tgttagatac     1860 tctgttttg gatgtggaga taagaattgg gccaccacat atcagaaggt tccggctttc      1920
atcgatgaaa tgcttgctgc aaaagggct gaaaatatag cagatcgtgg tgaggccgac      1980
gcaagcgacg attttgaggg tacctatgag gagtggagag agcacatgtg gtctgatgtt     2040
gccgcgtatt ttaatctaga catagaaaat tctgaagaca ataaaagtgc cttacttctt     2100
caattcgtcg atagtgctgc ggacatgccc ttagcaaaga tgcatggagc ctttttcaacg   2160 aacgtagtag ccagtaagga acttcaacaa ccaggtagtg ccagaagtac acgtcacttg     2220
gaaattgaat taccaaaaga ggcatcctac caagaaggtg accatcttgg tgtaatccca     2280
agaaactacg aaggtatagt caatagggta acggcaagat ttgggctgga tgcaagccaa     2340
cagataagac tagaagcaga agaagaaaaa ttggcgcacc ttccactagc gaagacagta     2400
tccgttgaag aattattgca atacgtggaa ttgcaggatc ccgtcactag aacgcaattg     2460
agagctatgg cagcaaagac tgtttgtcca cctcacaagg ttgaacttga agctctactt     2520
gaaaaacaag catacaaaga gcaagtgcta gcaaagagac taaccatgtt agaattgctg     2580
gaaaaatacc cggcatgcga aatggaattc tccgaattta tcgcgttgtt gccaagtatt     2640
cgtcccaggt attactcaat ttcatcttca ccaagggttg acgagaaaca ggcatctatt     2700
accgtatctg tggtctctgg agaagcttgg agtggttacg gagaatacaa gggtattgct     2760
tccaattatc ttgcagaact gcaggaaggg gatacaatta cctgctttat ttctactcct     2820
caatcagaat ttactcttcc gaaggatcca gaaactccgt taattatggt aggtccggga     2880
acaggagtcg ccccttttcag aggctttgtg caagcaagga agcaactaaa agaacaggga    2940
caaagtctgg gtgaggcaca tctatatttc ggttgcagat ctccgcatga ggattactta     3000
taccaagaag aacttgaaaa cgcccaatca gaaggtatta tcaccttgca tactgcattc     3060
agtagaatgc caaaccagcc gaaaacttac gtacagcatg ttatgagca agatggtaag      3120 aagttaattg agcttttgga taagggcgcc cacttctaca tttgcggcga cggatcccaa     3180
```

TABLE 13-continued

Sequences disclosed herein.

| | | | | | |
|---|---|---|---|---|---|
| atggcgcctg | ccgttgaagc | caccttgatg | aaatcatatg | cagatgttca | tcaagtttca | 3240 |
| gaagcggacg | cccgtctttg | gttacaacaa | ctagaggaga | aggaaggta | tgcaaaagat | 3300 |
| gttgcttaa | | | | | 3309 |

SEQ ID NO: 110
| | | | | | |
|---|---|---|---|---|---|
| MATLLEHFQA | MPFAIPIALA | ALSWLFLFYI | KVSFFSNKSA | QAKLPPVPVV | PGLPVIGNLL | 60 |
| QLKEKKPYQT | FTRWAEEYGP | IYSIRTGAST | MVVLNTTQVA | KEAMVTRYLS | ISTRKLSNAL | 120 |
| KILTADKCMV | AISDYNDFHK | MIKRYILSNV | LGPSAQKRHR | SNRDTLRANV | CSRLHSQVKN | 180 |
| SPREAVNFRR | VFEWELFGIA | LKQAFGKDIE | KPIYVEELGT | TLSRDEIFKV | LVLDIMEGAI | 240 |
| EVDWRDFFPY | LRWIPNTRME | TKIQRLYFRR | KAVMTALINE | QKKRIASGEE | INCYIDFLLK | 300 |
| EGKTLTMDQI | SMLLWETVIE | TADTTMVTTE | WAMYEVAKDS | KRQDRLYQEI | QKVCGSEMVT | 360 |
| EEYLSQLPYL | NAVFHETLRK | HSPAALVPLR | YAHEDTQLGG | YYIPAGTEIA | INIYGCNMDK | 420 |
| HQWESPEEWK | PERFLDPKFD | PMDLYKTMAF | GAGKRVCAGS | LQAMLIACPT | IGRLVQEFEW | 480 |
| KLRDGEEENV | DTVGLTTHKR | YPMHAILKPR | SPSRPSPSTE | QSAKKVRKKA | ENAHNTPLLV | 540 |
| LYGSNMGTAE | GTARDLADIA | MSKGFAPQVA | TLDSHAGNLP | REGAVLIVTA | SYNGHPPDNA | 600 |
| KQFVDWLDQA | SADEVKGVRY | SVFGCGDKNW | ATTYQKVPAF | IDEMLAAKGA | ENIADRGEAD | 660 |
| ASDDFEGTYE | EWREHMWSDV | AAYFNLDIEN | SEDNKSALLL | QFVDSAADMP | LAKMHGAFST | 720 |
| NVVASKELQQ | PGSARSTRHL | EIELPKEASY | QEGDHLGVIP | RNYEGIVNRV | TARFGLDASQ | 780 |
| QIRLEAEEEK | LAHLPLAKTV | SVEELLQYVE | LQDPVTRTQL | RAMAAKTVCP | PHKVELEALL | 840 |
| EKQAYKEQVL | AKRLTMLELL | EKYPACEMEF | SEFIALLPSI | RPRYYSISSS | PRVDEKQASI | 900 |
| TVSVVSGEAW | SGYGEYKGIA | SNYLAELQEG | DTITCFISTP | QSEFTLPKDP | ETPLIMVGPG | 960 |
| TGVAPFRGFV | QARKQLKEQG | QSLGEAHLYF | GCRSPHEDYL | YQEELENAQS | EGIITLHTAF | 1020 |
| SRMPNQPKTY | VQHVMEQDGK | KLIELLDKGA | HFYICGDGSQ | MAPAVEATLM | KSYADVHQVS | 1080 |
| EADARLWLQQ | LEEKGRYAKD | VA | | | 1102 |

SEQ ID NO: 111
| | | | | | |
|---|---|---|---|---|---|
| atggttccag | gtttgccagt | tattggtaat | ttgttgcaat | tgaaagaaaa | gaagccatac | 60 |
| caaaccttca | ctagatgggc | tgaagaatat | ggtccaatct | actctattag | aactggtgct | 120 |
| tctactatgg | ttgtcttgaa | cactactcaa | gttgccaaag | aagctatggt | taccagatac | 180 |
| ttgtctatct | ctaccagaaa | gttgtccaac | gccttgaaaa | ttttgaccgc | tgataagtgc | 240 |
| atggttgcca | tttctgatta | caacgatttc | cacaagatga | tcaagagata | tatcttgtct | 300 |
| aacgttttgg | gtccatctgc | ccaaaaaaga | catagatcta | acagagatac | cttgagagcc | 360 |
| aacgtttgtt | ctagattgca | tcccaagtt | aagaactctc | aagagaagc | tgtcaacttt | 420 |
| agaagagttt | tcgaatggga | attattcggt | atcgctttga | acaagccttt | cggtaaggat | 480 |
| attgaaaagc | caatctacgt | cgaagaattg | ggtactactt | tgtccagaga | tgaaatcttc | 540 |
| aaggttttgg | tcttggacat | tatggaaggt | gccattgaag | ttgattggag | agatttttc | 600 |
| ccatacttgc | gttggattcc | aaacaccaga | atggaaacta | gatccaaag | attatacttt | 660 |
| agaagaaagg | ccgttatgac | cgccttgatt | aacgaacaaa | agaaaagaat | tgcctccggt | 720 |
| gaagaaatca | actgctacat | cgatttcttg | ttgaaagaag | gtaagacctt | gaccatggac | 780 |
| caaatctcta | tgttgttgtg | ggaaaccgtt | attgaaactg | ctgataccac | aatggttact | 840 |
| actgaatggg | ctatgtacga | agttgctaag | gattctaaaa | gacaagacag | attataccaa | 900 |
| gaaatccaaa | aggtctgcgg | ttctgaaatg | gttacagaag | aatacttgtc | ccaattgcca | 960 |

TABLE 13-continued

Sequences disclosed herein.

```
tacttgaatg ctgttttcca cgaaactttg agaaaacatt ctccagctgc tttggttcca   1020
ttgagatatg ctcatgaaga tactcaattg ggtggttatt acattccagc cggtactgaa   1080
attgccatta acatctacgg ttgcaacatg gacaaacacc aatgggaatc tccagaagaa   1140
tggaagccag aaagattttt ggatcctaag tttgacccaa tggacttgta caaaactatg   1200 gctttggtg ctggtaaaag agtttgcgct ggttctttac aagctatgtt gattgcttgt    1260
ccaaccatcg gtagattggt tcaagaattt gaatggaagt tgagagatgg tgaagaagaa   1320
aacgttgata ctgttggttt gaccacccat aagagatatc caatgcatgc tattttgaag   1380
ccaagatctc catcaagacc aagtcctagt accgaacaat ctgcaaaaaa agttagaaaa   1440
aaagcagaaa atgcacacaa tactccattg ctagttcttt atggttctaa tatgggaaca   1500
gcggaaggaa cggccaggga tctagctgac atagctatgt ccaagggatt tgccccgcaa   1560
gtagcaaccc tggattccca tgcaggtaac ttgccaagag aaggtgctgt tctaatagtt   1620
accgctagct acaatgggca ccctccagat aatgcgaagc agttcgtcga ttggttagat   1680
caagcatcag cagatgaagt taagggtgtt agatactctg ttttttggatg tggagataag   1740 aattgggcca ccacatatca gaaggttccg gctttcatcg atgaaatgct tgctgcaaaa   1800
ggggctgaaa atatagcaga tcgtggtgag gccgacgcaa gcgacgattt tgagggtacc   1860
tatgaggagt ggagagagca catgtggtct gatgttgccg cgtattttaa tctagacata   1920
gaaaattctg aagacaataa aagtgcctta cttcttcaat tcgtcgatag tgctgcggac   1980
atgcccttag caaagatgca tggagccttt tcaacgaacg tagtagccag taaggaactt   2040
caacaaccag gtagtgccag aagtacacgt cacttggaaa ttgaattacc aaaagaggca   2100
tcctaccaag aaggtgacca tcttggtgta atcccaagaa actacgaagg tatagtcaat   2160
agggtaacgg caagatttgg gctggatgca agccaacaga taagactaga agcagaagaa   2220
gaaaaattgg cgcaccttcc actagcgaag acagtatccg ttgaagaatt attgcaatac   2280
gtggaattgc aggatcccgt cactagaacg caattgagag ctatggcagc aaagactgtt   2340
tgtccacctc acaaggttga acttgaagct ctacttgaaa aacaagcata caagagcaa    2400 gtgctagcaa agagactaac catgttagaa ttgctggaaa aatacccggc atgcgaaatg   2460
gaattctccg aatttatcgc gttgttgcca agtattcgtc ccaggtatta ctcaatttca   2520
tcttcaccaa gggttgacga gaaacaggca tctattaccg tatctgtggt ctctggagaa   2580
gcttggagtg gttacggaga atacaagggt attgcttcca attatcttgc agaactgcag   2640 gaagggata caattacctg ctttatttct actcctcaat cagaatttac tcttccgaag    2700
gatccagaaa ctccgttaat tatggtaggt ccgggaacag gagtcgcccc tttcagaggc   2760
tttgtgcaag caaggaagca actaaaagaa cagggacaaa gtctgggtga ggcacatcta   2820
tatttcggtt gcagatctcc gcatgaggat tacttatacc aagaagaact tgaaaacgcc   2880
caatcagaag gtattatcac cttgcatact gcattcagta gaatgccaaa ccagccgaaa   2940
acttacgtac agcatgttat ggagcaagat ggtaagaagt taattgagct tttggataag   3000
ggcgcccact tctacatttg cggcgacgga tcccaaatgg cgcctgccgt tgaagccacc   3060
ttgatgaaat catatgcaga tgttcatcaa gtttcagaag cggacgcccg tctttggtta   3120
caacaactag aggagaaagg aaggtatgca aaagatgttg cttaa                   3165
```

SEQ ID NO: 112
```
MVPGLPVIGN LLQLKEKKPY QTFTRWAEEY GPIYSIRTGA STMVVLNTTQ VAKEAMVTRY    60

LSISTRKLSN ALKILTADKC MVAISDYNDF HKMIKRYILS NVLGPSAQKR HRSNRDTLRA   120
```

TABLE 13-continued

Sequences disclosed herein.

| | | | | | |
|---|---|---|---|---|---|
| NVCSRLHSQV | KNSPREAVNF | RRVFEWELFG | IALKQAFGKD | IEKPIYVEEL | GTTLSRDEIF | 180 |
| KVLVLDIMEG | AIEVDWRDFF | PYLRWIPNTR | METKIQRLYF | RRKAVMTALI | NEQKKRIASG | 240 |
| EEINCYIDFL | LKEGKTLTMD | QISMLLWETV | IETADTTMVT | TEWAMYEVAK | DSKRQDRLYQ | 300 |
| EIQKVCGSEM | VTEEYLSQLP | YLNAVFHETL | RKHSPAALVP | LRYAHEDTQL | GGYYIPAGTE | 360 |
| IAINIYGCNM | DKHQWESPEE | WKPERFLDPK | FDPMDLYKTM | AFGAGKRVCA | GSLQAMLIAC | 420 |
| PTIGRLVQEF | EWKLRDGEEE | NVDTVGLTTH | KRYPMHAILK | PRSPSRPSPS | TEQSAKKVRK | 480 |
| KAENAHNTPL | LVLYGSNMGT | AEGTARDLAD | IAMSKGFAPQ | VATLDSHAGN | LPREGAVLIV | 540 |
| TASYNGHPPD | NAKQFVDWLD | QASADEVKGV | RYSVFGCGDK | NWATTYQKVP | AFIDEMLAAK | 600 |
| GAENIADRGE | ADASDDFEGT | YEEWREHMWS | DVAAYFNLDI | ENSEDNKSAL | LLQFVDSAAD | 660 |
| MPLAKMHGAF | STNVVASKEL | QQPGSARSTR | HLEIELPKEA | SYQEGDHLGV | IPRNYEGIVN | 720 |
| RVTARFGLDA | SQQIRLEAEE | EKLAHLPLAK | TVSVEELLQY | VELQDPVTRT | QLRAMAAKTV | 780 |
| CPPHKVELEA | LLEKQAYKEQ | VLAKRLTMLE | LLEKYPACEM | EFSEFIALLP | SIRPRYYSIS | 840 |
| SSPRVDEKQA | SITVSVVSGE | AWSGYGEYKG | IASNYLAELQ | EGDTITCFIS | TPQSEFTLPK | 900 |
| DPETPLIMVG | PGTGVAPFRG | FVQARKQLKE | QGQSLGEAHL | YFGCRSPHED | YLYQEELENA | 960 |
| QSEGIITLHT | AFSRMPNQPK | TYVQHVMEQD | GKKLIELLDK | GAHFYICGDG | SQMAPAVEAT | 1020 |
| LMKSYADVHQ | VSEADARLWL | QQLEEKGRYA | KDVA | | | 1054 |

SEQ ID NO: 113

| | | | | | |
|---|---|---|---|---|---|
| atgaccagtt | tgtccaaaag | cttcatgcag | agtggacgaa | tctgcgcagc | atgtttctat | 60 |
| ctgttattca | cactactttc | aattccaatc | tcgtttaaag | ttggtggttt | ggaatgcggg | 120 |
| ctttccttca | cggtgacact | gttcacttta | tatttcataa | ctacgactct | taacgtgttg | 180 |
| gcaagacgac | atggaggaag | actatacatt | tttttttacca | actgtctgta | ttactcacaa | 240 |
| cattttatca | ttgcatcttt | gctatacctg | tttttgtctg | gattttctaa | tgatgagttg | 300 |
| ggaaacgttc | tgaaaaataa | atataatgag | tcggagtcgt | tcctggaagc | tttgaaaaat | 360 |
| agcttgaatt | ccaatcaaat | taactacgtc | ttatattatt | actactatcg | atttgttgta | 420 |
| caaccgtggc | aattcgtgct | taccaagtcc | acacctttt | ttactctatc | ggaaggtttt | 480 |
| ttcactattt | tagccattca | ggccgtcggg | gaaactaata | tgatggttatc | aaatgacttg | 540 |
| aattcaaaca | cgtggattat | ttcctcattg | ttaacctccg | gaggtgtgat | taccgcatcg | 600 |
| ctgtactatt | tgtatcggat | ttatgtcacc | cccatatggc | cgttatccat | ccaaacggcg | 660 |
| tccttattag | gacttgtttt | gtctatggta | tgtggactgg | ggttgtatgg | tattgtgagt | 720 |
| caaaaaggat | ccgtcataga | gagctcttta | ttttttgcgt | atattgttcg | ttgtatttat | 780 |
| gaaatttccc | ccaaattagc | tactaccgcg | actgatgaaa | ttttaaattt | gttcaaagac | 840 |
| gtctggcaga | aacatcaaag | aaatctgccc | acagctgaca | atcttttgtg | ctactttcat | 900 |
| aatgtcatat | tgaaaaatgc | agaggtgtta | tgggggtcct | ttattcctag | aggaagaaag | 960 |
| aaaaccggtg | attttcatga | taaactcatt | agcattctat | cattcgaaaa | agtatccttg | 1020 |
| atatctaaac | cattttggaa | atttttcaag | aatttcacct | ttagtgttcc | gctatccatt | 1080 |
| aatgaatttt | gtcaagttac | aattaagatg | gcaagcgaat | cagtttcccc | agctatagta | 1140 |
| atcaatttat | gctttagagt | tctgatgttt | tactcggcaa | cgaggattat | tccagcatta | 1200 |
| caaagaaaaa | atgacaaaca | gttgcgcaag | agtcgcagga | tcatgaaggg | attgtattgg | 1260 |
| tacagtcctt | gcatattaat | tgctatgtat | actcacctga | ttttacaata | ttcaggtgag | 1320 |
| ctaaagaaag | acctgtgcat | atggggttgc | agtgaaaagt | ggtttggcgt | agatcaacca | 1380 |

TABLE 13-continued

Sequences disclosed herein.

| | | | | |
|---|---|---|---|---|
| gaaattatag | tagattcatg | gggattttgg | aactggtgca | acattttctg | tactattttg | 1440 |
| gtatacgcta | cagaattaat | aggttctggt | agttga | | | 1476 |

SEQ ID NO: 114
| | | | | | |
|---|---|---|---|---|---|
| MTSLSKSFMQ | SGRICAACFY | LLFTLLSIPI | SFKVGGLECG | LSFTVTLFTL | YFITTTLNVL | 60 |
| ARRHGGRLYI | FFTSCLYYSQ | HFIIASLLYL | FLSGFSNDEL | GNVLKNKYNE | SESFLEALKN | 120 |
| SLNSNQINYV | LYYYYYRFVV | QPWQFVLTKS | TPFFTLSEGF | FTILAIQAVG | ETNRWLSNDL | 180 |
| NSNTWIISSL | LTSGGVITAS | LYYLYRIYVT | PIWPLSIQTA | SLLGFVLSMV | CGLGLYGIVS | 240 |
| QKGSVIESSL | FFAYIVRCIY | EISPKLATTA | TDEILNLFKD | VWQKHQRNLP | TADNLLCYFH | 300 |
| NVILKNAEVL | WGSFIPRGRK | KTGDFHDKLI | SILSFEKVSL | ISKPFWKFFK | NFTFSVPLSI | 360 |
| NEFCQVTIKM | ASESVSPAIV | INLCFRVLMF | YSATRIIPAL | QRKNDKQLRK | SRRIMKGLYW | 420 |
| YSPCILIAMY | THLILQYSGE | LKKDLCIWGC | SEKWFGVDQP | EIIVDSWGFW | NWCNIFCTIL | 480 |
| VYATELIGSG | S | | | | | 491 |

SEQ ID NO: 115
| | | | | |
|---|---|---|---|---|
| agatctttat | gaagacatag | ctgcagaaga | aaaagcaaga | gctacatatc | aatggttaat | 60 |
| tgatatatca | gatgatcccg | atttaaacga | cagcttacga | tttttacgag | aaagagagat | 120 |
| tgttcactca | cagcggttcc | gcgaggccgt | ggagatttta | aaagatgaca | gagacaggaa | 180 |
| gaaaatcttt | taactagtaa | aaaaacatcc | cccttggcga | atgcaaacga | aaggagggat | 240 |
| gtttttttgtt | gtgactgcgt | tgattatgcg | ctagaactgc | agtgacaaga | aacaaccttt | 300 |
| aatttcccttt | caacatcttt | ccaaactcgc | gtataactgt | attcacctcc | aatagattca | 360 |
| ccggttgcca | gtgccccatt | taacgctact | tttgtaacgg | taacggcaag | ttcttgaaac | 420 |
| agtttaactt | cttgttccaa | cacttccatg | cccgctatat | caagactttt | tgaacgatga | 480 |
| acatttatat | cttcttcttt | tgacaaccat | tgcccaaggt | gattcacaaa | ataagctca | 540 |
| tctgaaagta | attcttctaa | tagctctatg | ttattagaaa | gcatggctga | gcgaagcatt | 600 |
| tcttcgtatt | ctataactct | tgcttgattc | attttttaatc | ctcctttacg | ccttgtgtaa | 660 |
| ctcttttcta | tttccacgtt | gcttttcctt | taaacttctt | tcattaataa | ttcgtgctaa | 720 |
| attatgttaa | tagaggggat | aagtggacta | attttctgta | agcactaaat | attctgaaat | 780 |
| actctgttaa | ttaccttttaa | atggtataaa | attagaatga | agaaccttt | tctttccact | 840 |
| tttctagtta | tctttttact | attaagatgc | agttttttat | acttgtaatt | gtagcggaat | 900 |
| gaacgttcat | tccgtttttg | aaaagaggtg | ataaagtgga | atctactcca | acaaaacaaa | 960 |
| aagcgatttt | ttctgcttcg | cttctgctgt | ttgcagaaag | agggtttgat | gcaaccacga | 1020 |
| tgccaatgat | tgcagagaat | gccaaagtag | gagcaggaac | aatttatcgc | tactttaaaa | 1080 |
| ataaagaaag | ccttgtaaat | gaattattcc | aacagcacgt | aaacgagttt | ttacagtgca | 1140 |
| ttgaaagcgg | tctggcaaac | gagagagatg | gataccgaga | tgggtttcat | catatctttg | 1200 |
| aaggtatggt | gacatttact | aaaaaccatc | ctcgtgctct | tggatttatt | aaaactcata | 1260 |
| gccaaggaac | ttttttaaca | gaagagagcc | gcttagcata | tcaaaagctg | gtggaatttg | 1320 |
| tttgtacgtt | cttcagagaa | ggacaaaagc | aaggtgtgat | tagaaatctt | cctgaaaatg | 1380 |
| cgctaattgc | tatttttattt | ggaagtttca | tggaagtata | tgaaatgatt | gaaaatgact | 1440 |
| acttatcttt | aactgatgaa | cttcttaccg | gtgtagaaga | gagtctgtgg | gcagcactta | 1500 |
| gcagacaatc | atgaaactta | acaagtgaaa | gagggataac | atgacaatta | agaaatgcc | 1560 |
| tcagccaaaa | acgtttggag | agcttaaaaa | tttaccgtta | ttaaacacag | ataaaccggt | 1620 |

TABLE 13-continued

Sequences disclosed herein.

```
tcaagctttg atgaaaattg cggatgaatt aggagaaatc tttaaattcg aggcgcctgg    1680
tcgtgtaacg cgctacttat caagtcagcg tctaattaaa gaagcatgcg atgaatcacg    1740
ctttgataaa aacttaagtc aagcgcttaa atttgtacgt gattttgcag gagacgggtt    1800
atttacaagc tggacgcatg aaaaaaattg gaaaaaagcg cataatatct tacttccaag    1860
cttcagtcag caggcaatga aaggctatca tgcgatgatg gtcgatatcg ccgtgcagct    1920
tgttcaaaag tgggagcgtc taaatgcaga tgagcatatt gaagtaccgg aagacatgac    1980
acgtttaacg cttgatacaa ttggtctttg cggctttaac tatcgcttta acagctttta    2040
ccgagatcag cctcatccat ttattacaag tatggtccgt gcactggatg aagcaatgaa    2100
caagctgcag cgagcaaatc cagacgaccc agcttatgat gaaaacaagc gccagtttca    2160
agaagatatc aaggtgatga cgacctagt agataaaatt attgcagatc gcaaagcaag    2220
cggtgaacaa agcgatgatt tattaacgca tatgctaaac ggaaaagatc cagaaacggg    2280
tgagccgctt gatgacgaga acattcgcta tcaaattatt acattcttaa ttgcgggaca    2340
cgaaacaaca agtggtcttt tatcatttgc gctgtatttc ttagtgaaaa atccacatgt    2400
attacaaaaa gcagcagaag aagcagcacg agttctagta gatcctgttc caagctacaa    2460
acaagtcaaa cagcttaaat atgtcggcat ggtcttaaac gaagcgctgc gcttatggcc    2520
aactgctcct gcgttttccc tatatgcaaa agaagatacg gtgcttggag gagaatatcc    2580
tttagaaaaa ggcgacgaac taatggttct gattcctcag cttaccgtg ataaaacaat    2640
ttggggagac gatgtggaag agttccgtcc agagcgtttt gaaaatccaa gtgcgattcc    2700
gcagcatgcg tttaaaccgt ttggaaacgg tcagcgtgcg tgtatcggtc agcagttcgc    2760
tcttcatgaa gcaacgctgg tacttggtat gatgctaaaa cactttgact ttgaagatca    2820
tacaaactac gagctggata ttaaagaaac tttaacgtta aaacctgaag ctttgtggt    2880
aaaagcaaaa tcgaaaaaaa ttccgcttgg cggtattcct tcacctagca ctgaacagtc    2940
tgctaaaaaa gtacgcaaaa aggcagaaaa cgctcataat acgccgctgc ttgtgctata    3000
cggttcaaat atgggaacag ctgaaggaac ggcgcgtgat ttagcagata ttgcaatgag    3060
caaaggattt gcaccgcagg tcgcaacgct tgattcacac gccggaaatc ttccgcgcga    3120
aggagctgta ttaattgtaa cggcgtctta taacggtcat ccgcctgata acgcaaagca    3180
atttgtcgac tggttagacc aagcgtctgc tgatgaagta aaaggcgttc gctactccgt    3240
atttggatgc ggcgataaaa actgggctac tacgtatcaa aaagtgcctg cttttatcga    3300
tgaaacgctt gccgctaaag gggcagaaaa catcgctgac cgcggtgaag cagatgcaag    3360
cgacgacttt gaaggcacat atgaagaatg gcgtgaacat atgtggagtg acgtagcagc    3420
ctactttaac ctcgacattg aaaacagtga agataataaa tctactcttt cacttcaatt    3480
tgtcgacagc gccgcggata tgccgcttgc gaaaatgcac ggtgcgtttt caacgaacgt    3540
cgtagcaagc aaagaacttc aacagccagg cagtgcacga agcacgcgac atcttgaaat    3600
tgaacttcca aaagaagctt cttatcaaga aggagatcat ttaggtgtta ttcctcgcaa    3660
ctatgaagga atagtaaacc gtgtaacagc aaggttcggc ctagatgcat cacagcaaat    3720
ccgtctggaa gcagaagaag aaaaattagc tcatttgcca ctcgctaaaa cagtatccgt    3780
agaagagctt ctgcaatacg tggagcttca agatcctgtt acgcgcacgc agcttcgcgc    3840
aatggctgct aaaacggtct gcccgccgca taaagtagag cttgaagcct tgcttgaaaa    3900
gcaagcctac aaagaacaag tgctggcaaa acgtttaaca atgcttgaac tgcttgaaaa    3960
```

TABLE 13-continued

Sequences disclosed herein.

| | | | | | |
|---|---|---|---|---|---|
| ataccggcg | tgtgaaatga | aattcagcga | atttatcgcc | cttctgccaa | gcatacgccc | 4020 |
| gcgctattac | tcgatttctt | catcacctcg | tgtcgatgaa | aaacaagcaa | gcatcacggt | 4080 |
| cagcgttgtc | tcaggagaag | cgtggagcgg | atatggagaa | tataaaggaa | ttgcgtcgaa | 4140 |
| ctatcttgcc | gagctgcaag | aaggagatac | gattacgtgc | tttatttcca | caccgcagtc | 4200 |
| agaatttacg | ctgccaaaag | accctgaaac | gccgcttatc | atggtcggac | cgggaacagg | 4260 |
| cgtcgcgccg | tttagaggct | ttgtgcaggc | gcgcaaacag | ctaaaagaac | aaggacagtc | 4320 |
| acttggagaa | gcacatttat | acttcggctg | ccgttcacct | catgaagact | atctgtatca | 4380 |
| agaagagctt | gaaaacgccc | aaagcgaagg | catcattacg | cttcataccg | cttttctcg | 4440 |
| catgccaaat | cagccgaaaa | catacgttca | gcacgtaatg | gaacaagacg | gcaagaaatt | 4500 |
| gattgaactt | cttgatcaag | gagcgcactt | ctatatttgc | ggagacggaa | gccaaatggc | 4560 |
| acctgccgtt | gaagcaacgc | ttatgaaaag | ctatgctgac | gttcaccaag | tgagtgaagc | 4620 |
| agacgctcgc | ttatggctgc | agcagctaga | agaaaaaggc | cgatacgcaa | agacgtgtg | 4680 |
| ggctgggtaa | attaaaaaga | ggctaggata | aaagtagttt | agttggttga | aggaagatcc | 4740 |
| gaacgatgaa | tcgttcggat | cttttttattg | gtagagtaaa | cgtagatttc | atctatttag | 4800 |
| tgacttgtag | cggttgattg | gagggcaagg | tgaagactcc | aatcaaccgc | ggtgtcacat | 4860 |
| gcaagccata | cgaaattcat | ttctcccatt | tattcgtctt | ttgtcccac | ttaattttta | 4920 |
| tagcgcctta | acgtttcttc | tgcgtgacag | cagatct | | | 4957 |

SEQ ID NO: 116
| | | | | | |
|---|---|---|---|---|---|
| MTIKEMPQPK | TFGELKNLPL | LNTDKPVQAL | MKIADELGEI | FKFEAPGRVT | RYLSSQRLIK | 60 |
| EACDESRFDK | NLSQALKFVR | DFAGDGLFTS | WTHEKNWKKA | HNILLPSFSQ | QAMKGYHAMM | 120 |
| VDIAVQLVQK | WERLNADEHI | EVPEDMTRLT | LDTIGLCGFN | YRFNSFYRDQ | PHPFITSMVR | 180 |
| ALDEAMNKLQ | RANPDDPAYD | ENKRQFQEDI | KVMNDLVDKI | IADRKASGEQ | SDDLLTHMLN | 240 |
| GKDPETGEPL | DDENIRYQII | TFLIAGHETT | SGLLSFALYF | LVKNPHVLQK | AAEEAARVLV | 300 |
| DPVPSYKQVK | QLKYVGMVLN | EALRLWPTAP | AFSLYAKEDT | VLGGEYPLEK | GDELMVLIPQ | 360 |
| LHRDKTIWGD | DVEEFRPERF | ENPSAIPQHA | FKPFGNGQRA | CIGQQFALHE | ATLVLGMMLK | 420 |
| HFDFEDHTNY | ELDIKETLTL | KPEGFVVKAK | SKKIPLGGIP | SPSTEQSAKK | VRKKAENAHN | 480 |
| TPLLVLYGSN | MGTAEGTARD | LADIAMSKGF | APQVATLDSH | AGNLPREGAV | LIVTASYNGH | 540 |
| PPDNAKQFVD | WLDQASADEV | KGVRYSVFGC | GDKNWATTYQ | KVPAFIDETL | AAKGAENIAD | 600 |
| RGEADASDDF | EGTYEEWREH | MWSDVAAYFN | LDIENSEDNK | STLSLQFVDS | AADMPLAKMH | 660 |
| GAFSTNVVAS | KELQQPGSAR | STRHLEIELP | KEASYQEGDH | LGVIPRNYEG | IVNRVTARFG | 720 |
| LDASQQIRLE | AEEEKLAHLP | LAKTVSVEEL | LQYVELQDPV | TRTQLRAMAA | KTVCPPHKVE | 780 |
| LEALLEKQAY | KEQVLAKRLT | MLELLEKYPA | CEMKFSEFIA | LLPSIRPRYY | SISSSPRVDE | 840 |
| KQASITVSVV | SGEAWSGYGE | YKGIASNYLA | ELQEGDTITC | FISTPQSEFT | LPKDPETPLI | 900 |
| MVGPGTGVAP | FRGFVQARKQ | LKEQGQSLGE | AHLYFGCRSP | HEDYLYQEEL | ENAQSEGIIT | 960 |
| LHTAFSRMPN | QPKTYVQHVM | EQDGKKLIEL | LDQGAHFYIC | GDGSQMAPAV | EATLMKSYAD | 1020 |
| VHQVSEADAR | LWLQQLEEKG | RYAKDVWAG | | | | 1049 |

SEQ ID NO: 117
| | | | | | |
|---|---|---|---|---|---|
| ccaagtccta | gtaccgaaca | atctgcaaaa | aagttagaa | aaaaagcaga | aaatgcacac | 60 |
| aatactccat | tgctagttct | ttatggttct | aatatgggaa | cagcggaagg | aacggccagg | 120 |
| gatctagctg | acatagctat | gtccaaggga | tttgccccgc | aagtagcaac | cctggattcc | 180 |

TABLE 13-continued

Sequences disclosed herein.

```
catgcaggta acttgccaag agaaggtgct gttctaatag ttaccgctag ctacaatggg      240
caccctccag ataatgcgaa gcagttcgtc gattggttag atcaagcatc agcagatgaa      300
gttaagggtg ttagatactc tgtttttgga tgtggagata agaattgggc caccacatat      360
cagaaggttc cggctttcat cgatgaaatg cttgctgcaa aggggctga aatatagca       420 gatcgtggtg aggccgacgc aagcgacgat tttgagggta cctatgagga gtggagagag      480
cacatgtggt ctgatgttgc cgcgtatttt aatctagaca tagaaaattc tgaagacaat      540
aaaagtgcct tacttcttca attcgtcgat agtgctgcgg acatgcccct agcaaagatg      600
catggagcct tttcaacgaa cgtagtagcc agtaaggaac ttcaacaacc aggtagtgcc      660
agaagtacac gtcacttgga aattgaatta ccaaaagagg catcctacca agaaggtgac      720
catcttggtg taatcccaag aaactacgaa ggtatagtca atagggtaac ggcaagattt      780
gggctggatg caagccaaca gataagacta gaagcagaag aagaaaaatt ggcgcacctt      840
ccactagcga agacagtatc cgttgaagaa ttattgcaat acgtggaatt gcaggatccc      900
gtcactagaa cgcaattgag agctatggca gcaaagactg tttgtccacc tcacaaggtt      960
gaacttgaag ctctacttga aaaacaagca tacaaagagc aagtgctagc aaagagacta     1020
accatgttag aattgctgga aaaatacccg gcatgcgaaa tggaattctc cgaatttatc     1080
gcgttgttgc caagtattcg tcccaggtat tactcaattt catcttcacc aagggttgac     1140
gagaaacagg catctattac cgtatctgtg gtctctggag aagcttggag tggttacgga     1200
gaatacaagg gtattgcttc caattatctt gcagaactgc aggaagggga tacaattacc     1260
tgctttattt ctactcctca atcagaattt actcttccga aggatccaga aactccgtta     1320
attatggtag gtccgggaac aggagtcgcc cctttcagag gctttgtgca agcaaggaag     1380
caactaaaag aacagggaca aagtctgggt gaggcacatc tatatttcgg ttgcagatct     1440
ccgcatgagg attacttata ccaagaagaa cttgaaaacg cccaatcaga aggtattatc     1500
accttgcata ctgcattcag tagaatgcca aaccagccga aaacttacgt acagcatgtt     1560
atggagcaag atggtaagaa gttaattgag cttttggata agggcgccca cttctacatt     1620
tgcggcgacg gatcccaaat ggcgcctgcc gttgaagcca ccttgatgaa atcatatgca     1680
gatgttcatc aagtttcaga agcggacgcc cgtctttggt tacaacaact agaggagaaa     1740
ggaaggtatg caaaagatgt ttggtaa                                        1767

SEQ ID NO: 118
PSPSTEQSAK KVRKKAENAH NTPLLVLYGS NMGTAEGTAR DLADIAMSKG FAPQVATLDS       60

HAGNLPREGA VLIVTASYNG HPPDNAKQFV DWLDQASADE VKGVRYSVFG CGDKNWATTY      120

QKVPAFIDEM LAAKGAENIA DRGEADASDD FEGTYEEWRE HMWSDVAAYF NLDIENSEDN      180

KSALLLQFVD SAADMPLAKM HGAFSTNVVA SKELQQPGSA RSTRHLEIEL PKEASYQEGD      240

HLGVIPRNYE GIVNRVTARF GLDASQQIRL EAEEEKLAHL PLAKTVSVEE LLQYVELQDP      300

VTRTQLRAMA AKTVCPPHKV ELEALLEKQA YKEQVLAKRL TMLELLEKYP ACEMEFSEFI      360

ALLPSIRPRY YSISSSPRVD EKQASITVSV VSGEAWSGYG EYKGIASNYL AELQEGDTIT      420

CFISTPQSEF TLPKDPETPL IMVGPGTGVA PFRGFVQARK QLKEQGQSLG EAHLYFGCRS      480

PHEDYLYQEE LENAQSEGII TLHTAFSRMP NQPKTYVQHV MEQDGKKLIE LLDKGAHFYI      540

CGDGSQMAPA VEATLMKSYA DVHQVSEADA RLWLQQLEEK GRYAKDVW                  588
```

TABLE 13-continued

Sequences disclosed herein.

SEQ ID NO: 119

| | | | | | |
|---|---|---|---|---|---|
| ccaagtccta | gtaccgaaca | atctgcaaaa | aaagttagaa | aaaaagcaga | aaatgcacac | 60 |
| aatactccat | tgctagttct | ttatggttct | aatatgggaa | cagcggaagg | aacggccagg | 120 |
| gatctagctg | acatagctat | gtccaaggga | tttgccccgc | aagtagcaac | cctggattcc | 180 |
| catgcaggta | acttgccaag | agaaggtgct | gttctaatag | ttaccgctag | ctacaatggg | 240 |
| caccctccag | ataatgcgaa | gcagttcgtc | gattggttag | atcaagcatc | agcagatgaa | 300 |
| gttaagggtg | ttagatactc | tgttttttgga | tgtggagata | agaattgggc | caccacatat | 360 |
| cagaaggttc | cggctttcat | cgatgaaatg | cttgctgcaa | aggggctga | aaatatagca | 420 |
| gatcgtggtg | aggccgacgc | aagcgacgat | tttgagggta | cctatgagga | gtggagagag | 480 |
| cacatgtggt | ctgatgttgc | cgcgtatttt | aatctagaca | tagaaaattc | tgaagacaat | 540 |
| aaaagtgcct | tacttcttca | attcgtcgat | agtgctgcgg | acatgccctt | agcaaagatg | 600 |
| catggagcct | tttcaacgaa | cgtagtagcc | agtaaggaac | ttcaacaacc | aggtagtgcc | 660 |
| agaagtacac | gtcacttgga | aattgaatta | ccaaaagagg | catcctacca | gaaggtgac | 720 |
| catcttggtg | taatcccaag | aaactacgaa | ggtatagtca | atagggtaac | ggcaagattt | 780 |
| gggctggatg | caagccaaca | gataagacta | gaagcagaag | aagaaaaatt | ggcgcacctt | 840 |
| ccactagcga | agacagtatc | cgttgaagaa | ttattgcaat | acgtggaatt | gcaggatccc | 900 |
| gtcactagaa | cgcaattgag | agctatggca | gcaaagactg | tttgtccacc | tcacaaggtt | 960 |
| gaacttgaag | ctctacttga | aaacaagca | tacaaagagc | aagtgctagc | aaagagacta | 1020 |
| accatgttag | aattgctgga | aaaatacccg | gcatgcgaaa | tggaattctc | cgaatttatc | 1080 |
| gcgttgttgc | caagtattcg | tcccaggtat | tactcaattt | catcttcacc | aagggttgac | 1140 |
| gagaaacagg | catctattac | cgtatctgtg | gtctctggag | aagcttggag | tggttacgga | 1200 |
| gaatacaagg | gtattgcttc | caattatctt | gcagaactgc | aggaagggga | tacaattacc | 1260 |
| tgctttattt | ctactcctca | atcagaattt | actcttccga | aggatccaga | aactccgtta | 1320 |
| attatggtag | gtccgggaac | aggagtcgcc | cctttcagag | gctttgtgca | agcaaggaag | 1380 |
| caactaaaag | aacagggaca | aagtctgggt | gaggcacatc | tatatttcgg | ttgcagatct | 1440 |
| ccgcatgagg | attacttata | ccaagaagaa | cttgaaaacg | cccaatcaga | aggtattatc | 1500 |
| accttgcata | ctgcattcag | tagaatgcca | aaccagccga | aaacttacgt | acagcatgtt | 1560 |
| atggagcaag | atggtaagaa | gttaattgag | cttttggata | agggcgccca | cttctacatt | 1620 |
| tgcggcgacg | gatcccaaat | ggcgcctgcc | gttgaagcca | ccttgatgaa | atcatatgca | 1680 |
| gatgttcatc | aagtttcaga | agcggacgcc | cgtctttggt | acaacaact | agaggagaaa | 1740 |
| ggaaggtatg | caaaagatgt | tgcttaa | | | | 1767 |

SEQ ID NO: 120

| | | | | | |
|---|---|---|---|---|---|
| PSPSTEQSAK | KVRKKAENAH | NTPLLVLYGS | NMGTAEGTAR | DLADIAMSKG | FAPQVATLDS | 60 |
| HAGNLPREGA | VLIVTASYNG | HPPDNAKQFV | DWLDQASADE | VKGVRYSVFG | CGDKNWATTY | 120 |
| QKVPAFIDEM | LAAKGAENIA | DRGEADASDD | FEGTYEEWRE | HMWSDVAAYF | NLDIENSEDN | 180 |
| KSALLLQFVD | SAADMPLAKM | HGAFSTNVVA | SKELQQPGSA | RSTRHLEIEL | PKEASYQEGD | 240 |
| HLGVIPRNYE | GIVNRVTARF | GLDASQQIRL | EAEEEKLAHL | PLAKTVSVEE | LLQYVELQDP | 300 |
| VTRTQLRAMA | AKTVCPPHKV | ELEALLEKQA | YKEQVLAKRL | TMLELLEKYP | ACEMEFSEFI | 360 |
| ALLPSIRPRY | YSISSSPRVD | EKQASITVSV | VSGEAWSGYG | EYKGIASNYL | AELQEGDTIT | 420 |
| CFISTPQSEF | TLPKDPETPL | IMVGPGTGVA | PFRGFVQARK | QLKEQGQSLG | EAHLYFGCRS | 480 |

TABLE 13-continued

Sequences disclosed herein.

| | |
|---|---|
| PHEDYLYQEE LENAQSEGII TLHTAFSRMP NQPKTYVQHV MEQDGKKLIE LLDKGAHFYI | 540 |
| CGDGSQMAPA VEATLMKSYA DVHQVSEADA RLWLQQLEEK GRYAKDVA | 588 |
| SEQ ID NO: 121 ccatcaaga | 9 |
| SEQ ID NO: 122 PSR | 3 |

The invention claimed is:
1. A recombinant host cell that produces a steviol glycoside precursor and/or one or more steviol glycosides in a cell culture, comprising:
(a) a gene encoding a polypeptide that synthesizes geranylgeranyl pyrophosphate (GGPP) from farnesyl diphosphate (FPP) and isopentenyl diphosphate (IPP);
(b) a gene encoding a polypeptide that synthesizes ent-copalyl diphosphate from GGPP;
(c) a gene encoding a polypeptide that synthesizes ent-kaurene from ent-copalyl diphosphate; and
(d) a gene encoding a polypeptide that reduces cytochrome P450 complex;
wherein the polypeptide that reduces cytochrome P450 complex comprises a polypeptide having at least 90% sequence identity to the amino acid sequence set forth in SEQ ID NO:28;
and further comprising:
(e) a gene encoding a polypeptide that synthesizes ent-kaurenoic acid from ent-kaurene;
wherein the polypeptide that synthesizes ent-kaurenoic acid from ent-kaurene comprises a polypeptide having at least 90% sequence identity to the amino acid sequence set forth in SEQ ID NO:79; or
(f) a gene encoding a polypeptide that synthesizes steviol from ent-kaurenoic acid;
wherein the polypeptide that synthesizes steviol from ent-kaurenoic acid comprises a polypeptide having at least 90% sequence identity to the amino acid sequence set forth in SEQ ID NO:68;
wherein at least one of the genes is a recombinant gene; and
wherein the recombinant host cell is a fungal cell.
2. A recombinant host that produces a steviol glycoside precursor in a cell culture, comprising:
(a) a gene encoding a polypeptide that synthesizes ent-kaurenoic acid from ent-kaurene;
wherein the polypeptide that synthesizes ent-kaurenoic acid from ent-kaurene comprises a polypeptide having at least 90% sequence identity to the amino acid sequence set forth in SEQ ID NO:79;
(b) a gene encoding a polypeptide that reduces cytochrome P450 complex;
wherein the polypeptide that reduces cytochrome P450 complex comprises a polypeptide having at least 90% identity to the amino acid sequence set forth in SEQ ID NO:28; and/or
(c) a gene encoding a polypeptide that synthesizes steviol from ent-kaurenoic acid;
wherein the polypeptide that synthesizes steviol from ent-kaurenoic acid comprises a polypeptide having at least 90% identity to the amino acid sequence set forth in SEQ ID NO:68; and
wherein at least one of the genes is a recombinant gene.
3. The recombinant host of claim 2, further comprising:
(d) a gene encoding a polypeptide that synthesizes geranylgeranyl pyrophosphate (GGPP) from farnesyl diphosphate (FPP) and isopentenyl diphosphate (IPP);
(e) a gene encoding a polypeptide that synthesizes ent-copalyl diphosphate from GGPP; and/or
(f) a gene encoding a polypeptide that synthesizes ent-kaurene from ent-copalyl diphosphate.
4. The recombinant host of claim 1, wherein:
(a) the gene encoding a polypeptide that synthesizes geranylgeranyl pyrophosphate (GGPP) from farnesyl diphosphate (FPP) and isopentenyl diphosphate (IPP) comprising a polypeptide having at least 90% sequence identity to the amino acid sequence set forth in SEQ ID NO:49;
(b) the gene encoding a polypeptide that synthesizes ent-copalyl diphosphate from GGPP comprising a polypeptide having at least 90% sequence identity to the amino acid sequence set forth in SEQ ID NO:37; and/or
(c) the gene encoding a polypeptide that synthesizes ent-kaurene from ent-copalyl pyrophosphate comprising a polypeptide having at least 90% sequence identity to the amino acid sequence set forth in SEQ ID NO:6.
5. The recombinant host of claim 1, wherein the polypeptide that synthesizes ent-kaurenoic acid from ent-kaurene is a fusion construct.
6. The recombinant host of claim 1, further comprising:
(a) a gene encoding a polypeptide that glycosylates steviol or a steviol glycoside at its C-13 hydroxyl group thereof;
(b) a gene encoding a polypeptide that beta 1,3 glycosylates the C3' of the 13-O-glucose, 19-O-glucose, or both 13-O-glucose and 19-O-glucose of a steviol glycoside;
(c) a gene encoding a polypeptide that glycosylates steviol or a steviol glycoside at its C-19 carboxyl group thereof;
(d) a first gene encoding a first polypeptide that beta 1,2 glycosylates the C2' of the 13-O-glucose, 19-O-glucose, or both 13-O-glucose and 19-O-glucose of a steviol glycoside; and/or
(e) a second gene encoding a second polypeptide that beta 1,2 glycosylates the C2' of the 13-O-glucose, 19-O-glucose, or both 13-O-glucose and 19-O-glucose of a steviol glycoside;
wherein at least one of the genes is a recombinant gene; and
wherein the host is producing the one or more steviol glycosides.
7. The recombinant host of claim 6, wherein:
(a) the polypeptide that glycosylates steviol or the steviol glycoside at its C-13 hydroxyl group thereof comprises a polypeptide having at least 90% sequence identity to the amino acid sequence set forth in SEQ ID NO:30;
(b) the polypeptide that beta 1,3 glycosylates the C3' of the 13-O-glucose, 19-O-glucose, or both 13-O-glucose and 19-O-glucose of the steviol glycoside comprises a polypeptide having at least 90% sequence identity to the amino acid sequence set forth in SEQ ID NO:83;
(c) the polypeptide that glycosylates steviol or the steviol glycoside at its C-19 carboxyl group comprises a polypeptide having at least 90% sequence identity to the amino acid sequence set forth in SEQ ID NO:29;
(d) the first polypeptide that beta 1,2 glycosylates the C2' of the 13-O-glucose, 19-O-glucose, or both 13-O-glucose and 19-O-glucose of the steviol glycoside comprises a polypeptide having at least 90% sequence identity to the amino acid sequence set forth in SEQ ID NO:84; and/or
(e) the second polypeptide that beta 1,2 glycosylates the C2' of the 13-O-glucose, 19-O-glucose, or both 13-O-glucose and 19-O-glucose of the steviol glycoside comprises a polypeptide having at least 90% sequence identity to the amino acid sequence set forth in SEQ ID NO:86.
8. The recombinant host of claim 6, wherein the one or more steviol glycosides comprises steviol-13-O-glucoside (13-SMG), steviol-1,2-bioside, steviol-1,3-bioside, steviol-

19-O-glucoside (19-SMG), stevioside, 1,3-stevioside, rubusoside, Rebaudioside A (RebA), Rebaudioside B (RebB), Rebaudioside C (RebC), Rebaudioside D (RebD), Rebaudioside E (RebE), Rebaudioside F (RebF), Rebaudioside M (RebM), Rebaudioside Q (RebQ), Rebaudioside I (RebI), dulcoside A, di-glycosylated steviol, tri-glycosylated steviol, tetra-glycosylated steviol, penta-glycosylated steviol, hexa-glycosylated steviol, hepta-glycosylated steviol, or isomers thereof.

9. The recombinant host of claim 8, wherein an amount of 13-SMG produced by the host is increased by at least 2-fold relative to a corresponding host lacking the one or more recombinant genes.

10. The recombinant host of claim 8, wherein a total amount of 13-SMG, steviol-1,2-bioside, rubusoside, RebB, RebA, RebD, and RebM produced by the host is increased by at least about 10% relative to a corresponding host lacking the one or more recombinant genes.

11. The recombinant host of claim 1, wherein the fungal cell comprises a yeast cell.

12. The recombinant host of claim 11, wherein the yeast cell is a cell from *Saccharomyces cerevisiae*.

13. A cell culture, comprising the recombinant host of claim 1 and the steviol glycoside precursor or the one or more steviol glycosides produced by the host, the cell culture further comprising:
    (a) glucose, fructose, sucrose, xylose, rhamnose, UDP-glucose, UDP-rhamnose, UDP-xylose, and/or N-acetyl-glucosamine; and
    (b) supplemental nutrients comprising trace metals, vitamins, salts, YNB, and/or amino acids;
    wherein the steviol glycoside precursor or the one or more steviol glycosides is present at a concentration of at least 1 mg/liter of the cell culture; and
    wherein the cell culture is enriched for the steviol glycoside precursor or the one or more steviol glycosides relative to a steviol glycoside composition from a *Stevia* plant and has a reduced level of *Stevia* plant-derived components relative to a plant-derived *Stevia* extract.

14. A cell lysate from the cell culture comprising the host of claim 1 and the steviol glycoside precursor or the one or more steviol glycosides produced by the host, comprising:
    (a) glucose, fructose, sucrose, xylose, rhamnose, UDP-glucose, UDP-rhamnose, UDP-xylose, and/or N-acetyl-glucosamine; and/or
    (b) supplemental nutrients comprising trace metals, vitamins, salts, yeast nitrogen base YNB, and/or amino acids;
    wherein the steviol glycoside precursor or the one or more steviol glycosides produced by the host is present at a concentration of at least 1 mg/liter of the cell culture.

15. A method of producing a steviol glycoside precursor in a cell culture, comprising culturing the recombinant host of claim 1 under conditions in which the genes are expressed, and wherein the steviol glycoside precursor is produced by the recombinant host.

16. A method of producing one or more steviol glycosides in a cell culture, comprising culturing the recombinant host of claim 6 under conditions in which the genes are expressed, and wherein the one or more steviol glycosides are produced by the recombinant host.

* * * * *

SEQUENCE LISTING

<160> NUMBER OF SEQ ID NOS: 122

<210> SEQ ID NO 1
<211> LENGTH: 784
<212> TYPE: PRT
<213> ORGANISM: Stevia rebaudiana

<400> SEQUENCE: 1

```
Met Asn Leu Ser Leu Cys Ile Ala Ser Pro Leu Leu Thr Lys Ser Asn
1               5                   10                  15

Arg Pro Ala Ala Leu Ser Ala Ile His Thr Ala Ser Thr Ser His Gly
            20                  25                  30

Gly Gln Thr Asn Pro Thr Asn Leu Ile Ile Asp Thr Thr Lys Glu Arg
        35                  40                  45

Ile Gln Lys Gln Phe Lys Asn Val Glu Ile Ser Val Ser Ser Tyr Asp
    50                  55                  60

Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
    130                 135                 140

Glu Ser Asn Leu Ala Ser Ala Thr Glu Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190

Lys Arg Glu Leu Glu Gln Lys Arg Cys His Ser Asn Glu Met Asp Gly
        195                 200                 205

Tyr Leu Ala Tyr Ile Ser Glu Gly Leu Gly Asn Leu Tyr Asp Trp Asn
    210                 215                 220

Met Val Lys Lys Tyr Gln Met Lys Asn Gly Ser Val Phe Asn Ser Pro
225                 230                 235                 240

Ser Ala Thr Ala Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
            260                 265                 270
```

```
Val Tyr Pro His Asp Leu Phe Ile Arg Leu Ser Met Val Asp Thr Ile
        275                 280                 285

Glu Arg Leu Gly Ile Ser His His Phe Arg Val Glu Ile Lys Asn Val
        290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile Asn
                325                 330                 335

Gly Tyr Glu Val Ser Pro Asp Pro Leu Ala Glu Ile Thr Asn Glu Leu
                340                 345                 350

Ala Leu Lys Asp Glu Tyr Ala Ala Leu Glu Thr Tyr His Ala Ser His
        355                 360                 365

Ile Leu Tyr Gln Glu Asp Leu Ser Ser Gly Lys Gln Ile Leu Lys Ser
        370                 375                 380

Ala Asp Phe Leu Lys Glu Ile Ile Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
        420                 425                 430

Val Asp Asn Thr Arg Ile Leu Lys Thr Thr Tyr His Ser Ser Asn Ile
        435                 440                 445

Ser Asn Thr Asp Tyr Leu Arg Leu Ala Val Glu Asp Phe Tyr Thr Cys
        450                 455                 460

Gln Ser Ile Tyr Arg Glu Glu Leu Lys Gly Leu Glu Arg Trp Val Val
465                 470                 475                 480

Glu Asn Lys Leu Asp Gln Leu Lys Phe Ala Arg Gln Lys Thr Ala Tyr
                485                 490                 495

Cys Tyr Phe Ser Val Ala Ala Thr Leu Ser Ser Pro Glu Leu Ser Asp
                500                 505                 510

Ala Arg Ile Ser Trp Ala Lys Asn Gly Ile Leu Thr Thr Val Val Asp
        515                 520                 525

Asp Phe Phe Asp Ile Gly Gly Thr Ile Asp Glu Leu Thr Asn Leu Ile
        530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
                565                 570                 575

Ile Gly Asp Glu Ala Phe Lys Trp Gln Ala Arg Asp Val Thr Ser His
                580                 585                 590

Val Ile Gln Thr Trp Leu Glu Leu Met Asn Ser Met Leu Arg Glu Ala
        595                 600                 605

Ile Trp Thr Arg Asp Ala Tyr Val Pro Thr Leu Asn Glu Tyr Met Glu
        610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Ile Val Glu Ser Ser Glu
                645                 650                 655

Tyr His Asn Leu Phe Lys Leu Met Ser Thr Gln Gly Arg Leu Leu Asn
                660                 665                 670

Asp Ile His Ser Phe Lys Arg Glu Phe Lys Glu Gly Lys Leu Asn Ala
        675                 680                 685

Val Ala Leu His Leu Ser Asn Gly Glu Ser Gly Lys Val Glu Glu Glu
```

```
                    690                 695                 700
Val Val Glu Glu Met Met Met Met Ile Lys Asn Lys Arg Lys Glu Leu
705                 710                 715                 720

Met Lys Leu Ile Phe Glu Glu Asn Gly Ser Ile Val Pro Arg Ala Cys
                    725                 730                 735

Lys Asp Ala Phe Trp Asn Met Cys His Val Leu Asn Phe Phe Tyr Ala
                    740                 745                 750

Asn Asp Asp Gly Phe Thr Gly Asn Thr Ile Leu Asp Thr Val Lys Asp
                    755                 760                 765

Ile Ile Tyr Asn Pro Leu Val Leu Val Asn Glu Asn Glu Glu Gln Arg
770                 775                 780

<210> SEQ ID NO 2
<211> LENGTH: 784
<212> TYPE: PRT
<213> ORGANISM: Stevia rebaudiana

<400> SEQUENCE: 2

Met Asn Leu Ser Leu Cys Ile Ala Ser Pro Leu Leu Thr Lys Ser Ser
1               5                   10                  15

Arg Pro Thr Ala Leu Ser Ala Ile His Thr Ala Ser Thr Ser His Gly
                20                  25                  30

Gly Gln Thr Asn Pro Thr Asn Leu Ile Ile Asp Thr Thr Lys Glu Arg
            35                  40                  45

Ile Gln Lys Leu Phe Lys Asn Val Glu Ile Ser Val Ser Ser Tyr Asp
    50                  55                  60

Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
    130                 135                 140

Glu Ser Asn Leu Ala Ser Ala Thr Asp Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190

Lys Arg Glu Leu Glu Gln Lys Arg Cys His Ser Asn Glu Ile Asp Gly
        195                 200                 205

Tyr Leu Ala Tyr Ile Ser Glu Gly Leu Gly Asn Leu Tyr Asp Trp Asn
    210                 215                 220

Met Val Lys Lys Tyr Gln Met Lys Asn Gly Ser Val Phe Asn Ser Pro
225                 230                 235                 240

Ser Ala Thr Ala Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
            260                 265                 270

Val Tyr Pro Leu Asp Leu Tyr Ile Arg Leu Ser Met Val Asp Thr Ile
        275                 280                 285
```

-continued

Glu Arg Leu Gly Ile Ser His His Phe Arg Val Glu Ile Lys Asn Val
    290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile His
                325                 330                 335

Gly Tyr Lys Val Ser Pro Asp Gln Leu Ala Glu Ile Thr Asn Glu Leu
            340                 345                 350

Ala Phe Lys Asp Glu Tyr Ala Ala Leu Glu Thr Tyr His Ala Ser Gln
        355                 360                 365

Ile Leu Tyr Gln Glu Asp Leu Ser Ser Gly Lys Gln Ile Leu Lys Ser
    370                 375                 380

Ala Asp Phe Leu Lys Gly Ile Leu Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
            420                 425                 430

Val Asp Asn Thr Arg Ile Leu Lys Thr Thr Tyr His Ser Ser Asn Ile
        435                 440                 445

Ser Asn Thr Tyr Tyr Leu Arg Leu Ala Val Glu Asp Phe Tyr Thr Cys
    450                 455                 460

Gln Ser Ile Tyr Arg Glu Leu Lys Gly Leu Glu Arg Trp Val Val
465                 470                 475                 480

Gln Asn Lys Leu Asp Gln Leu Lys Phe Ala Arg Gln Lys Thr Ala Tyr
                485                 490                 495

Cys Tyr Phe Ser Val Ala Ala Thr Leu Ser Ser Pro Glu Leu Ser Asp
            500                 505                 510

Ala Arg Ile Ser Trp Ala Lys Asn Gly Ile Leu Thr Thr Val Val Asp
        515                 520                 525

Asp Phe Phe Asp Ile Gly Gly Thr Ile Asp Glu Leu Thr Asn Leu Ile
    530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
                565                 570                 575

Ile Gly Asp Glu Ala Phe Lys Trp Gln Ala Arg Asp Val Thr Ser His
            580                 585                 590

Val Ile Gln Thr Trp Leu Glu Leu Met Asn Ser Met Leu Arg Glu Ala
        595                 600                 605

Ile Trp Thr Arg Asp Ala Tyr Val Pro Thr Leu Asn Glu Tyr Met Glu
    610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
                645                 650                 655

Tyr His Asn Leu Phe Lys Leu Met Ser Thr Gln Gly Arg Leu Leu Asn
            660                 665                 670

Asp Ile His Ser Phe Lys Arg Glu Phe Lys Glu Gly Lys Leu Asn Ala
        675                 680                 685

Val Ala Leu His Leu Ser Asn Gly Glu Ser Gly Lys Val Glu Glu Glu
    690                 695                 700

Val Val Glu Glu Met Met Met Met Ile Lys Asn Lys Arg Lys Glu Leu

```
                705                 710                 715                 720
Met Lys Leu Ile Phe Glu Glu Asn Gly Ser Ile Val Pro Arg Ala Cys
                    725                 730                 735
Lys Asp Ala Phe Trp Asn Met Cys His Val Leu Asn Phe Phe Tyr Ala
                    740                 745                 750
Asn Asp Asp Gly Phe Thr Gly Asn Thr Ile Leu Asp Thr Val Lys Asp
                    755                 760                 765
Ile Ile Tyr Asn Pro Leu Val Leu Val Asn Glu Asn Glu Glu Gln Arg
                    770                 775                 780

<210> SEQ ID NO 3
<211> LENGTH: 590
<212> TYPE: PRT
<213> ORGANISM: Zea mays

<400> SEQUENCE: 3

Met Ala Met Pro Val Lys Leu Thr Pro Ala Ser Leu Ser Leu Lys Ala
1               5                   10                  15
Val Cys Cys Arg Phe Ser Ser Gly Gly His Ala Leu Arg Phe Gly Ser
                    20                  25                  30
Ser Leu Pro Cys Trp Arg Arg Thr Pro Thr Gln Arg Ser Thr Ser Ser
                    35                  40                  45
Ser Thr Thr Arg Pro Ala Ala Glu Val Ser Ser Gly Lys Ser Lys Gln
            50                  55                  60
His Asp Gln Glu Ala Ser Glu Ala Thr Ile Arg Gln Leu Gln Leu
65                  70                  75                  80
Val Asp Val Leu Glu Asn Met Gly Ile Ser Arg His Phe Ala Ala Glu
                    85                  90                  95
Ile Lys Cys Ile Leu Asp Arg Thr Tyr Arg Ser Trp Leu Gln Arg His
                    100                 105                 110
Glu Glu Ile Met Leu Asp Thr Met Thr Cys Ala Met Ala Phe Arg Ile
                    115                 120                 125
Leu Arg Leu Asn Gly Tyr Asn Val Ser Ser Asp Glu Leu Tyr His Val
            130                 135                 140
Val Glu Ala Ser Gly Leu His Asn Ser Leu Gly Gly Tyr Leu Asn Asp
145                 150                 155                 160
Thr Arg Thr Leu Leu Glu Leu His Lys Ala Ser Thr Val Ser Ile Ser
                    165                 170                 175
Glu Asp Glu Ser Ile Leu Asp Ser Ile Gly Ser Arg Ser Arg Thr Leu
                    180                 185                 190
Leu Arg Glu Gln Leu Glu Ser Gly Gly Ala Leu Arg Lys Pro Ser Leu
                    195                 200                 205
Phe Lys Glu Val Glu His Ala Leu Asp Gly Pro Phe Tyr Thr Thr Leu
            210                 215                 220
Asp Arg Leu His His Arg Trp Asn Ile Glu Asn Phe Asn Ile Ile Glu
225                 230                 235                 240
Gln His Met Leu Glu Thr Pro Tyr Leu Ser Asn Gln His Thr Ser Arg
                    245                 250                 255
Asp Ile Leu Ala Leu Ser Ile Arg Asp Phe Ser Ser Ser Gln Phe Thr
                    260                 265                 270
Tyr Gln Gln Glu Leu Gln His Leu Glu Ser Trp Val Lys Glu Cys Arg
                    275                 280                 285
Leu Asp Gln Leu Gln Phe Ala Arg Gln Lys Leu Ala Tyr Phe Tyr Leu
            290                 295                 300
```

```
Ser Ala Ala Gly Thr Met Phe Ser Pro Glu Leu Ser Asp Ala Arg Thr
305                 310                 315                 320

Leu Trp Ala Lys Asn Gly Val Leu Thr Thr Ile Val Asp Asp Phe Phe
                325                 330                 335

Asp Val Ala Gly Ser Lys Glu Glu Leu Glu Asn Leu Val Met Leu Val
            340                 345                 350

Glu Met Trp Asp Glu His His Lys Val Glu Phe Tyr Ser Glu Gln Val
        355                 360                 365

Glu Ile Ile Phe Ser Ser Ile Tyr Asp Ser Val Asn Gln Leu Gly Glu
    370                 375                 380

Lys Ala Ser Leu Val Gln Asp Arg Ser Ile Thr Lys His Leu Val Glu
385                 390                 395                 400

Ile Trp Leu Asp Leu Leu Lys Ser Met Met Thr Glu Val Glu Trp Arg
                405                 410                 415

Leu Ser Lys Tyr Val Pro Thr Glu Lys Glu Tyr Met Ile Asn Ala Ser
            420                 425                 430

Leu Ile Phe Gly Leu Gly Pro Ile Val Leu Pro Ala Leu Tyr Phe Val
        435                 440                 445

Gly Pro Lys Ile Ser Glu Ser Ile Val Lys Asp Pro Glu Tyr Asp Glu
    450                 455                 460

Leu Phe Lys Leu Met Ser Thr Cys Gly Arg Leu Leu Asn Asp Val Gln
465                 470                 475                 480

Thr Phe Glu Arg Glu Tyr Asn Glu Gly Lys Leu Asn Ser Val Ser Leu
                485                 490                 495

Leu Val Leu His Gly Gly Pro Met Ser Ile Ser Asp Ala Lys Arg Lys
            500                 505                 510

Leu Gln Lys Pro Ile Asp Thr Cys Arg Arg Asp Leu Leu Ser Leu Val
        515                 520                 525

Leu Arg Glu Glu Ser Val Val Pro Arg Pro Cys Lys Glu Leu Phe Trp
    530                 535                 540

Lys Met Cys Lys Val Cys Tyr Phe Phe Tyr Ser Thr Thr Asp Gly Phe
545                 550                 555                 560

Ser Ser Gln Val Glu Arg Ala Lys Glu Val Asp Ala Val Ile Asn Glu
                565                 570                 575

Pro Leu Lys Leu Gln Gly Ser His Thr Leu Val Ser Asp Val
            580                 585                 590

<210> SEQ ID NO 4
<211> LENGTH: 775
<212> TYPE: PRT
<213> ORGANISM: Populus trichocarpa

<400> SEQUENCE: 4

Met Ser Cys Ile Arg Pro Trp Phe Cys Pro Ser Ser Ile Ser Ala Thr
1               5                   10                  15

Leu Thr Asp Pro Ala Ser Lys Leu Val Thr Gly Glu Phe Lys Thr Thr
            20                  25                  30

Ser Leu Asn Phe His Gly Thr Lys Glu Arg Ile Lys Lys Met Phe Asp
        35                  40                  45

Lys Ile Glu Leu Ser Val Ser Tyr Asp Thr Ala Trp Val Ala Met
    50                  55                  60

Val Pro Ser Pro Asp Cys Pro Glu Thr Pro Cys Phe Pro Glu Cys Thr
65                  70                  75                  80

Lys Trp Ile Leu Glu Asn Gln Leu Gly Asp Gly Ser Trp Ser Leu Pro
                85                  90                  95
```

```
His Gly Asn Pro Leu Leu Val Lys Asp Ala Leu Ser Ser Thr Leu Ala
            100                 105                 110

Cys Ile Leu Ala Leu Lys Arg Trp Gly Ile Gly Glu Glu Gln Ile Asn
            115                 120                 125

Lys Gly Leu Arg Phe Ile Glu Leu Asn Ser Ala Ser Val Thr Asp Asn
            130                 135                 140

Glu Gln His Lys Pro Ile Gly Phe Asp Ile Ile Phe Pro Gly Met Ile
145                 150                 155                 160

Glu Tyr Ala Lys Asp Leu Asp Leu Asn Leu Pro Leu Lys Pro Thr Asp
            165                 170                 175

Ile Asn Ser Met Leu His Arg Arg Ala Leu Glu Leu Thr Ser Gly Gly
            180                 185                 190

Gly Lys Asn Leu Glu Gly Arg Arg Ala Tyr Leu Ala Tyr Val Ser Glu
            195                 200                 205

Gly Ile Gly Lys Leu Gln Asp Trp Glu Met Ala Met Lys Tyr Gln Arg
            210                 215                 220

Lys Asn Gly Ser Leu Phe Asn Ser Pro Ser Thr Thr Ala Ala Ala Phe
225                 230                 235                 240

Ile His Ile Gln Asp Ala Glu Cys Leu His Tyr Ile Arg Ser Leu Leu
            245                 250                 255

Gln Lys Phe Gly Asn Ala Val Pro Thr Ile Tyr Pro Leu Asp Ile Tyr
            260                 265                 270

Ala Arg Leu Ser Met Val Asp Ala Leu Glu Arg Leu Gly Ile Asp Arg
            275                 280                 285

His Phe Arg Lys Glu Arg Lys Phe Val Leu Asp Glu Thr Tyr Arg Phe
            290                 295                 300

Trp Leu Gln Gly Glu Glu Ile Phe Ser Asp Asn Ala Thr Cys Ala
305                 310                 315                 320

Leu Ala Phe Arg Ile Leu Arg Leu Asn Gly Tyr Asp Val Ser Leu Glu
            325                 330                 335

Asp His Phe Ser Asn Ser Leu Gly Gly Tyr Leu Lys Asp Ser Gly Ala
            340                 345                 350

Ala Leu Glu Leu Tyr Arg Ala Leu Gln Leu Ser Tyr Pro Asp Glu Ser
            355                 360                 365

Leu Leu Glu Lys Gln Asn Ser Arg Thr Ser Tyr Phe Leu Lys Gln Gly
            370                 375                 380

Leu Ser Asn Val Ser Leu Cys Gly Asp Arg Leu Arg Lys Asn Ile Ile
385                 390                 395                 400

Gly Glu Val His Asp Ala Leu Asn Phe Pro Asp His Ala Asn Leu Gln
            405                 410                 415

Arg Leu Ala Ile Arg Arg Ile Lys His Tyr Ala Thr Asp Asp Thr
            420                 425                 430

Arg Ile Leu Lys Thr Ser Tyr Arg Cys Ser Thr Ile Gly Asn Gln Asp
            435                 440                 445

Phe Leu Lys Leu Ala Val Glu Asp Phe Asn Ile Cys Gln Ser Ile Gln
            450                 455                 460

Arg Glu Glu Phe Lys His Ile Glu Arg Trp Val Val Glu Arg Leu
465                 470                 475                 480

Asp Lys Leu Lys Phe Ala Arg Gln Lys Glu Ala Tyr Cys Tyr Phe Ser
            485                 490                 495

Ala Ala Ala Thr Leu Phe Ala Pro Glu Leu Ser Asp Ala Arg Met Ser
            500                 505                 510
```

```
Trp Ala Lys Asn Gly Val Leu Thr Val Val Asp Asp Phe Phe Asp
            515                 520                 525

Val Gly Gly Ser Glu Glu Glu Leu Val Asn Leu Ile Glu Leu Ile Glu
        530                 535                 540

Arg Trp Asp Val Asn Gly Ser Ala Asp Phe Cys Ser Glu Glu Val Glu
545                 550                 555                 560

Ile Ile Tyr Ser Ala Ile His Ser Thr Ile Ser Glu Ile Gly Asp Lys
                565                 570                 575

Ser Phe Gly Trp Gln Gly Arg Asp Val Lys Ser His Val Ile Lys Ile
            580                 585                 590

Trp Leu Asp Leu Leu Lys Ser Met Leu Thr Glu Ala Gln Trp Ser Ser
        595                 600                 605

Asn Lys Ser Val Pro Thr Leu Asp Glu Tyr Met Thr Thr Ala His Val
    610                 615                 620

Ser Phe Ala Leu Gly Pro Ile Val Leu Pro Ala Leu Tyr Phe Val Gly
625                 630                 635                 640

Pro Lys Leu Ser Glu Glu Val Ala Gly His Pro Glu Leu Leu Asn Leu
                645                 650                 655

Tyr Lys Val Met Ser Thr Cys Gly Arg Leu Leu Asn Asp Trp Arg Ser
            660                 665                 670

Phe Lys Arg Glu Ser Glu Glu Gly Lys Leu Asn Ala Ile Ser Leu Tyr
        675                 680                 685

Met Ile His Ser Gly Gly Ala Ser Thr Glu Glu Thr Ile Glu His
    690                 695                 700

Phe Lys Gly Leu Ile Asp Ser Gln Arg Arg Gln Leu Leu Gln Leu Val
705                 710                 715                 720

Leu Gln Glu Lys Asp Ser Ile Ile Pro Arg Pro Cys Lys Asp Leu Phe
                725                 730                 735

Trp Asn Met Ile Lys Leu Leu His Thr Phe Tyr Met Lys Asp Asp Gly
            740                 745                 750

Phe Thr Ser Asn Glu Met Arg Asn Val Val Lys Ala Ile Ile Asn Glu
        755                 760                 765

Pro Ile Ser Leu Asp Glu Leu
    770                 775

<210> SEQ ID NO 5
<211> LENGTH: 2506
<212> TYPE: DNA
<213> ORGANISM: Arabidopsis thaliana

<400> SEQUENCE: 5
cgtcagtcat caaggctaat tcgtcgcgag ttgctacgac gccgtttcgg ttgcttctgg      60
tttctttatg tctatcaacc ttcgctcctc cggttgttcg tctccgatct cagctacttt     120
ggaacgagga ttggactcag aagtacagac aagagctaac aatgtgagct tgagcaaac      180 aaaggagaag attaggaaga tgttggagaa agtggagctt tctgtttcgg cctacgatac     240
tagttgggta gcaatggttc catcaccgag ctcccaaaat gctccacttt tcccacagtg     300
tgtgaaatgg ttattggata atcaacatga agatggatct tggggacttg ataaccatga     360
ccatcaatct cttaagaagg atgtgttatc atctacactg gctagtatcc tcgcgttaaa     420
gaagtgggga attggtgaaa gacaaataaa caagggtctc cagtttattg agctgaattc     480
tgcattagtc actgatgaaa ccatacagaa accaacaggg tttgatatta tatttcctgg     540
gatgattaaa tatgctagag atttgaatct gacgattcca ttgggctcag aagtggtgga     600
```

| | |
|---|---|
| tgacatgata cgaaaaagag atctggatct taaatgtgat agtgaaaagt tttcaaaggg | 660 |
| aagagaagca tatctggcct atgttttaga ggggacaaga aacctaaaag attgggattt | 720 |
| gatagtcaaa tatcaaagga aaaatgggtc actgtttgat tctccagcca caacagcagc | 780 |
| tgcttttact cagtttggga atgatggttg tctccgttat ctctgttctc tccttcagaa | 840 |
| attcgaggct gcagttcctt cagtttatcc atttgatcaa tatgcacgcc ttagtataat | 900 |
| tgtcactctt gaaagcttag gaattgatag agatttcaaa accgaaatca aaagcatatt | 960 |
| ggatgaaacc tatagatatt ggcttcgtgg ggatgaagaa atatgtttgg acttggccac | 1020 |
| ttgtgctttg gctttccgat tattgcttgc tcatggctat gatgtgtctt acgatccgct | 1080 |
| aaaaccattt gcagaagaat ctggtttctc tgatactttg gaaggatatg ttaagaatac | 1140 |
| gttttctgtg ttagaattat ttaaggctgc tcaaagttat ccacatgaat cagctttgaa | 1200 |
| gaagcagtgt tgttggacta acaatatct ggagatggaa ttgtccagct gggttaagac | 1260 |
| ctctgttcga gataaatacc tcaagaaaga ggtcgaggat gctcttgctt ttccctccta | 1320 |
| tgcaagccta gaaagatcag atcacaggag aaaaatactc aatggttctg ctgtggaaaa | 1380 |
| caccagagtt acaaaaacct catatcgttt gcacaatatt tgcacctctg atatcctgaa | 1440 |
| gttagctgtg gatgacttca atttctgcca gtccatacac cgtgaagaaa tggaacgtct | 1500 |
| tgataggtgg attgtggaga atagattgca ggaactgaaa tttgccagac agaagctggc | 1560 |
| ttactgttat ttctctgggg ctgcaacttt attttctcca gaactatctg atgctcgtat | 1620 |
| atcgtgggcc aaaggtggag tacttacaac ggttgtagac gacttctttg atgttggagg | 1680 |
| gtccaaagaa gaactggaaa acctcataca cttggtcgaa aagtgggatt tgaacggtgt | 1740 |
| tcctgagtac agctcagaac atgttgagat catattctca gttctaaggg acaccattct | 1800 |
| cgaaacagga gacaaagcat tcacctatca aggacgcaat gtgacacacc acattgtgaa | 1860 |
| aatttggttg gatctgctca gtctatgtt gagagaagcc gagtggtcca gtgacaagtc | 1920 |
| aacaccaagc ttgaaggatt acatggaaaa tgcgtacata tcatttgcat taggaccaat | 1980 |
| tgtcctccca gctacctatc tgatcggacc tccacttcca gagaagacag tcgatagcca | 2040 |
| ccaatataat cagctctaca agctcgtgag cactatgggt cgtcttctaa atgcatacat | 2100 |
| aggttttaag agagaaagcg cggaagggaa gctgaatgcg gtttcattgc acatgaaaca | 2160 |
| cgagagagac aatcgcagca aagaagtgat catagaatcg atgaaaggtt tagcagagag | 2220 |
| aaagagggaa gaattgcata agctagtttt ggaggagaaa ggaagtgtgg ttccaaggga | 2280 |
| atgcaaagaa gcgttcttga aaatgagcaa agtgttgaac ttattttaca ggaaggacga | 2340 |
| tggattcaca tcaaatgatc tgatgagtct tgttaaatca gtgatctacg agcctgttag | 2400 |
| cttacagaaa gaatctttaa cttgatccaa gttgatctgg caggtaaact cagtaaatga | 2460 |
| aaataagact ttggtcttct tctttgttgc ttcagaacaa gaagag | 2506 |

<210> SEQ ID NO 6
<211> LENGTH: 785
<212> TYPE: PRT
<213> ORGANISM: Arabidopsis thaliana

<400> SEQUENCE: 6

Met Ser Ile Asn Leu Arg Ser Ser Gly Cys Ser Ser Pro Ile Ser Ala
1               5                   10                  15

Thr Leu Glu Arg Gly Leu Asp Ser Glu Val Gln Thr Arg Ala Asn Asn
            20                  25                  30

Val Ser Phe Glu Gln Thr Lys Glu Lys Ile Arg Lys Met Leu Glu Lys

```
            35                  40                  45
Val Glu Leu Ser Val Ser Ala Tyr Asp Thr Ser Trp Val Ala Met Val
 50                  55                  60

Pro Ser Pro Ser Ser Gln Asn Ala Pro Leu Phe Pro Gln Cys Val Lys
 65                  70                  75                  80

Trp Leu Leu Asp Asn Gln His Glu Asp Gly Ser Trp Gly Leu Asp Asn
                 85                  90                  95

His Asp His Gln Ser Leu Lys Lys Asp Val Leu Ser Ser Thr Leu Ala
                100                 105                 110

Ser Ile Leu Ala Leu Lys Lys Trp Gly Ile Gly Glu Arg Gln Ile Asn
            115                 120                 125

Lys Gly Leu Gln Phe Ile Glu Leu Asn Ser Ala Leu Val Thr Asp Glu
130                 135                 140

Thr Ile Gln Lys Pro Thr Gly Phe Asp Ile Ile Phe Pro Gly Met Ile
145                 150                 155                 160

Lys Tyr Ala Arg Asp Leu Asn Leu Thr Ile Pro Leu Gly Ser Glu Val
                165                 170                 175

Val Asp Asp Met Ile Arg Lys Arg Asp Leu Asp Leu Lys Cys Asp Ser
                180                 185                 190

Glu Lys Phe Ser Lys Gly Arg Glu Ala Tyr Leu Ala Tyr Val Leu Glu
            195                 200                 205

Gly Thr Arg Asn Leu Lys Asp Trp Asp Leu Ile Val Lys Tyr Gln Arg
210                 215                 220

Lys Asn Gly Ser Leu Phe Asp Ser Pro Ala Thr Thr Ala Ala Ala Phe
225                 230                 235                 240

Thr Gln Phe Gly Asn Asp Gly Cys Leu Arg Tyr Leu Cys Ser Leu Leu
                245                 250                 255

Gln Lys Phe Glu Ala Ala Val Pro Ser Val Tyr Pro Phe Asp Gln Tyr
            260                 265                 270

Ala Arg Leu Ser Ile Ile Val Thr Leu Glu Ser Leu Gly Ile Asp Arg
275                 280                 285

Asp Phe Lys Thr Glu Ile Lys Ser Ile Leu Asp Glu Thr Tyr Arg Tyr
290                 295                 300

Trp Leu Arg Gly Asp Glu Glu Ile Cys Leu Asp Leu Ala Thr Cys Ala
305                 310                 315                 320

Leu Ala Phe Arg Leu Leu Leu Ala His Gly Tyr Asp Val Ser Tyr Asp
                325                 330                 335

Pro Leu Lys Pro Phe Ala Glu Glu Ser Gly Phe Ser Asp Thr Leu Glu
            340                 345                 350

Gly Tyr Val Lys Asn Thr Phe Ser Val Leu Glu Leu Phe Lys Ala Ala
            355                 360                 365

Gln Ser Tyr Pro His Glu Ser Ala Leu Lys Lys Gln Cys Cys Trp Thr
            370                 375                 380

Lys Gln Tyr Leu Glu Met Glu Leu Ser Ser Trp Val Lys Thr Ser Val
385                 390                 395                 400

Arg Asp Lys Tyr Leu Lys Lys Glu Val Glu Asp Ala Leu Ala Phe Pro
                405                 410                 415

Ser Tyr Ala Ser Leu Glu Arg Ser Asp His Arg Lys Ile Leu Asn
            420                 425                 430

Gly Ser Ala Val Glu Asn Thr Arg Val Thr Lys Thr Ser Tyr Arg Leu
            435                 440                 445

His Asn Ile Cys Thr Ser Asp Ile Leu Lys Leu Ala Val Asp Asp Phe
450                 455                 460
```

```
Asn Phe Cys Gln Ser Ile His Arg Glu Glu Met Glu Arg Leu Asp Arg
465                 470                 475                 480

Trp Ile Val Glu Asn Arg Leu Gln Glu Leu Lys Phe Ala Arg Gln Lys
            485                 490                 495

Leu Ala Tyr Cys Tyr Phe Ser Gly Ala Ala Thr Leu Phe Ser Pro Glu
        500                 505                 510

Leu Ser Asp Ala Arg Ile Ser Trp Ala Lys Gly Gly Val Leu Thr Thr
    515                 520                 525

Val Val Asp Asp Phe Phe Asp Val Gly Gly Ser Lys Glu Glu Leu Glu
530                 535                 540

Asn Leu Ile His Leu Val Glu Lys Trp Asp Leu Asn Gly Val Pro Glu
545                 550                 555                 560

Tyr Ser Ser Glu His Val Glu Ile Ile Phe Ser Val Leu Arg Asp Thr
                565                 570                 575

Ile Leu Glu Thr Gly Asp Lys Ala Phe Thr Tyr Gln Gly Arg Asn Val
            580                 585                 590

Thr His His Ile Val Lys Ile Trp Leu Asp Leu Leu Lys Ser Met Leu
        595                 600                 605

Arg Glu Ala Glu Trp Ser Ser Asp Lys Ser Thr Pro Ser Leu Glu Asp
    610                 615                 620

Tyr Met Glu Asn Ala Tyr Ile Ser Phe Ala Leu Gly Pro Ile Val Leu
625                 630                 635                 640

Pro Ala Thr Tyr Leu Ile Gly Pro Pro Leu Pro Glu Lys Thr Val Asp
                645                 650                 655

Ser His Gln Tyr Asn Gln Leu Tyr Lys Leu Val Ser Thr Met Gly Arg
            660                 665                 670

Leu Leu Asn Asp Ile Gln Gly Phe Lys Arg Glu Ser Ala Glu Gly Lys
        675                 680                 685

Leu Asn Ala Val Ser Leu His Met Lys His Glu Arg Asp Asn Arg Ser
    690                 695                 700

Lys Glu Val Ile Ile Glu Ser Met Lys Gly Leu Ala Glu Arg Lys Arg
705                 710                 715                 720

Glu Glu Leu His Lys Leu Val Leu Glu Glu Lys Gly Ser Val Val Pro
                725                 730                 735

Arg Glu Cys Lys Glu Ala Phe Leu Lys Met Ser Lys Val Leu Asn Leu
            740                 745                 750

Phe Tyr Arg Lys Asp Asp Gly Phe Thr Ser Asn Asp Leu Met Ser Leu
        755                 760                 765

Val Lys Ser Val Ile Tyr Glu Pro Val Ser Leu Gln Lys Glu Ser Leu
    770                 775                 780

Thr
785

<210> SEQ ID NO 7
<211> LENGTH: 513
<212> TYPE: PRT
<213> ORGANISM: Arabidopsis thaliana

<400> SEQUENCE: 7

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
```

-continued

```
                35                  40                  45
Arg Val Pro Glu Val Pro Gly Val Pro Leu Leu Gly Asn Leu Leu Gln
 50                  55                  60

Leu Lys Glu Lys Lys Pro Tyr Met Thr Phe Thr Arg Trp Ala Ala Thr
 65                  70                  75                  80

Tyr Gly Pro Ile Tyr Ser Ile Lys Thr Gly Ala Thr Ser Met Val Val
                     85                  90                  95

Val Ser Ser Asn Glu Ile Ala Lys Glu Ala Leu Val Thr Arg Phe Gln
                100                 105                 110

Ser Ile Ser Thr Arg Asn Leu Ser Lys Ala Leu Lys Val Leu Thr Ala
                115                 120                 125

Asp Lys Thr Met Val Ala Met Ser Asp Tyr Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                    165                 170                 175

Leu His Glu Phe Val Lys Asn Asn Pro Glu Gln Glu Glu Val Asp Leu
                180                 185                 190

Arg Lys Ile Phe Gln Ser Glu Leu Phe Gly Leu Ala Met Arg Gln Ala
                195                 200                 205

Leu Gly Lys Asp Val Glu Ser Leu Tyr Val Glu Asp Leu Lys Ile Thr
210                 215                 220

Met Asn Arg Asp Glu Ile Phe Gln Val Leu Val Asp Pro Met Met
225                 230                 235                 240

Gly Ala Ile Asp Val Asp Trp Arg Asp Phe Phe Pro Tyr Leu Lys Trp
                    245                 250                 255

Val Pro Asn Lys Lys Phe Glu Asn Thr Ile Gln Gln Met Tyr Ile Arg
                260                 265                 270

Arg Glu Ala Val Met Lys Ser Leu Ile Lys Glu His Lys Lys Arg Ile
                275                 280                 285

Ala Ser Gly Glu Lys Leu Asn Ser Tyr Ile Asp Tyr Leu Leu Ser Glu
290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                    325                 330                 335

Tyr Glu Leu Ala Lys Asn Pro Lys Leu Gln Asp Arg Leu Tyr Arg Asp
                340                 345                 350

Ile Lys Ser Val Cys Gly Ser Glu Lys Ile Thr Glu Glu His Leu Ser
                355                 360                 365

Gln Leu Pro Tyr Ile Thr Ala Ile Phe His Glu Thr Leu Arg Arg His
                370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                    405                 410                 415

Tyr Gly Cys Asn Met Asp Lys Asn Val Trp Glu Asn Pro Glu Glu Trp
                420                 425                 430

Asn Pro Glu Arg Phe Met Lys Glu Asn Glu Thr Ile Asp Phe Gln Lys
                435                 440                 445

Thr Met Ala Phe Gly Gly Gly Lys Arg Val Cys Ala Gly Ser Leu Gln
                450                 455                 460
```

```
Ala Leu Leu Thr Ala Ser Ile Gly Ile Gly Arg Met Val Gln Glu Phe
465                 470                 475                 480

Glu Trp Lys Leu Lys Asp Met Thr Gln Glu Val Asn Thr Ile Gly
                485                 490                 495

Leu Thr Thr Gln Met Leu Arg Pro Leu Arg Ala Ile Ile Lys Pro Arg
                500                 505                 510

Ile
```

<210> SEQ ID NO 8
<211> LENGTH: 509
<212> TYPE: PRT
<213> ORGANISM: Arabidopsis thaliana

<400> SEQUENCE: 8

```
Met Ala Phe Phe Ser Met Ile Ser Ile Leu Leu Gly Phe Val Ile Ser
1               5                   10                  15

Ser Phe Ile Phe Ile Phe Phe Lys Lys Leu Leu Ser Phe Ser Arg
                20                  25                  30

Lys Asn Met Ser Glu Val Ser Thr Leu Pro Ser Val Pro Val Val Pro
                35                  40                  45

Gly Phe Pro Val Ile Gly Asn Leu Leu Gln Leu Lys Glu Lys Lys Pro
50                  55                  60

His Lys Thr Phe Thr Arg Trp Ser Glu Ile Tyr Gly Pro Ile Tyr Ser
65                  70                  75                  80

Ile Lys Met Gly Ser Ser Ser Leu Ile Val Leu Asn Ser Thr Glu Thr
                85                  90                  95

Ala Lys Glu Ala Met Val Thr Arg Phe Ser Ser Ile Ser Thr Arg Lys
                100                 105                 110

Leu Ser Asn Ala Leu Thr Val Leu Thr Cys Asp Lys Ser Met Val Ala
                115                 120                 125

Thr Ser Asp Tyr Asp Asp Phe His Lys Leu Val Lys Arg Cys Leu Leu
130                 135                 140

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
                180                 185                 190

Leu Phe Gly Val Ala Leu Lys Gln Ala Phe Gly Lys Asp Val Glu Ser
                195                 200                 205

Ile Tyr Val Lys Glu Leu Gly Val Thr Leu Ser Lys Asp Glu Ile Phe
                210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
                260                 265                 270

Leu Ile Gln Asp Arg Leu Lys Gln Asn Gly Ser Glu Ser Asp Asp
                275                 280                 285

Cys Tyr Leu Asn Phe Leu Met Ser Glu Ala Lys Thr Leu Thr Lys Glu
                290                 295                 300

Gln Ile Ala Ile Leu Val Trp Glu Thr Ile Ile Glu Thr Ala Asp Thr
305                 310                 315                 320
```

```
Thr Leu Val Thr Thr Glu Trp Ala Ile Tyr Glu Leu Ala Lys His Pro
                325                 330                 335

Ser Val Gln Asp Arg Leu Cys Lys Glu Ile Gln Asn Val Cys Gly Gly
            340                 345                 350

Glu Lys Phe Lys Glu Glu Gln Leu Ser Gln Val Pro Tyr Leu Asn Gly
        355                 360                 365

Val Phe His Glu Thr Leu Arg Lys Tyr Ser Ala Pro Leu Val Pro
    370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
                405                 410                 415

Lys Arg Trp Glu Arg Pro Glu Asp Trp Trp Pro Glu Arg Phe Leu Asp
            420                 425                 430

Asp Gly Lys Tyr Glu Thr Ser Asp Leu His Lys Thr Met Ala Phe Gly
        435                 440                 445

Ala Gly Lys Arg Val Cys Ala Gly Ala Leu Gln Ala Ser Leu Met Ala
    450                 455                 460

Gly Ile Ala Ile Gly Arg Leu Val Gln Glu Phe Glu Trp Lys Leu Arg
465                 470                 475                 480

Asp Gly Glu Glu Asn Val Asp Thr Tyr Gly Leu Thr Ser Gln Lys
                485                 490                 495

Leu Tyr Pro Leu Met Ala Ile Ile Asn Pro Arg Arg Ser
            500                 505

<210> SEQ ID NO 9
<211> LENGTH: 525
<212> TYPE: PRT
<213> ORGANISM: Fusarium fujikuroi

<400> SEQUENCE: 9

Met Ser Lys Ser Asn Ser Met Asn Ser Thr Ser His Glu Thr Leu Phe
1               5                   10                  15

Gln Gln Leu Val Leu Gly Leu Asp Arg Met Pro Leu Met Asp Val His
            20                  25                  30

Trp Leu Ile Tyr Val Ala Phe Gly Ala Trp Leu Cys Ser Tyr Val Ile
        35                  40                  45

His Val Leu Ser Ser Ser Thr Val Lys Val Pro Val Val Gly Tyr
    50                  55                  60

Arg Ser Val Phe Glu Pro Thr Trp Leu Leu Arg Leu Arg Phe Val Trp
65                  70                  75                  80

Glu Gly Gly Ser Ile Ile Gly Gln Gly Tyr Asn Lys Phe Lys Asp Ser
                85                  90                  95

Ile Phe Gln Val Arg Lys Leu Gly Thr Asp Ile Val Ile Pro Pro
            100                 105                 110

Asn Tyr Ile Asp Glu Val Arg Lys Leu Ser Gln Asp Lys Thr Arg Ser
        115                 120                 125

Val Glu Pro Phe Ile Asn Asp Phe Ala Gly Gln Tyr Thr Arg Gly Met
    130                 135                 140

Val Phe Leu Gln Ser Asp Leu Gln Asn Arg Val Ile Gln Gln Arg Leu
145                 150                 155                 160

Thr Pro Lys Leu Val Ser Leu Thr Lys Val Met Lys Glu Glu Leu Asp
                165                 170                 175

Tyr Ala Leu Thr Lys Glu Met Pro Asp Met Lys Asn Asp Glu Trp Val
```

```
                180             185             190
Glu Val Asp Ile Ser Ser Ile Met Val Arg Leu Ile Ser Arg Ile Ser
            195                 200                 205
Ala Arg Val Phe Leu Gly Pro Glu His Cys Arg Asn Gln Glu Trp Leu
        210                 215                 220
Thr Thr Thr Ala Glu Tyr Ser Glu Ser Leu Phe Ile Thr Gly Phe Ile
225                 230                 235                 240
Leu Arg Val Val Pro His Ile Leu Arg Pro Phe Ile Ala Pro Leu Leu
                245                 250                 255
Pro Ser Tyr Arg Thr Leu Leu Arg Asn Val Ser Ser Gly Arg Arg Val
            260                 265                 270
Ile Gly Asp Ile Ile Arg Ser Gln Gln Gly Asp Gly Asn Glu Asp Ile
        275                 280                 285
Leu Ser Trp Met Arg Asp Ala Ala Thr Gly Glu Glu Lys Gln Ile Asp
        290                 295                 300
Asn Ile Ala Gln Arg Met Leu Ile Leu Ser Leu Ala Ser Ile His Thr
305                 310                 315                 320
Thr Ala Met Thr Met Thr His Ala Met Tyr Asp Leu Cys Ala Cys Pro
                325                 330                 335
Glu Tyr Ile Glu Pro Leu Arg Asp Glu Val Lys Ser Val Val Gly Ala
            340                 345                 350
Ser Gly Trp Asp Lys Thr Ala Leu Asn Arg Phe His Lys Leu Asp Ser
        355                 360                 365
Phe Leu Lys Glu Ser Gln Arg Phe Asn Pro Val Phe Leu Leu Thr Phe
        370                 375                 380
Asn Arg Ile Tyr His Gln Ser Met Thr Leu Ser Asp Gly Thr Asn Ile
385                 390                 395                 400
Pro Ser Gly Thr Arg Ile Ala Val Pro Ser His Ala Met Leu Gln Asp
                405                 410                 415
Ser Ala His Val Pro Gly Pro Thr Pro Thr Glu Phe Asp Gly Phe
            420                 425                 430
Arg Tyr Ser Lys Ile Arg Ser Asp Ser Asn Tyr Ala Gln Lys Tyr Leu
        435                 440                 445
Phe Ser Met Thr Asp Ser Ser Asn Met Ala Phe Gly Tyr Gly Lys Tyr
        450                 455                 460
Ala Cys Pro Gly Arg Phe Tyr Ala Ser Asn Glu Met Lys Leu Thr Leu
465                 470                 475                 480
Ala Ile Leu Leu Leu Gln Phe Glu Phe Lys Leu Pro Asp Gly Lys Gly
                485                 490                 495
Arg Pro Arg Asn Ile Thr Ile Asp Ser Asp Met Ile Pro Asp Pro Arg
            500                 505                 510
Ala Arg Leu Cys Val Arg Lys Arg Ser Leu Arg Asp Glu
        515                 520                 525

<210> SEQ ID NO 10
<211> LENGTH: 499
<212> TYPE: PRT
<213> ORGANISM: Trametes versicolor

<400> SEQUENCE: 10

Met Glu Asp Pro Thr Val Leu Tyr Ala Cys Leu Ala Ile Ala Val Ala
1               5                   10                  15
Thr Phe Val Val Arg Trp Tyr Arg Asp Pro Leu Arg Ser Ile Pro Thr
            20                  25                  30
```

-continued

```
Val Gly Gly Ser Asp Leu Pro Ile Leu Ser Tyr Ile Gly Ala Leu Arg
            35                  40                  45
Trp Thr Arg Arg Gly Arg Glu Ile Leu Gln Glu Gly Tyr Asp Gly Tyr
 50                  55                  60
Arg Gly Ser Thr Phe Lys Ile Ala Met Leu Asp Arg Trp Ile Val Ile
 65                  70                  75                  80
Ala Asn Gly Pro Lys Leu Ala Asp Glu Val Arg Arg Pro Asp Glu
                    85                  90                  95
Glu Leu Asn Phe Met Asp Gly Leu Gly Ala Phe Val Gln Thr Lys Tyr
                100                 105                 110
Thr Leu Gly Glu Ala Ile His Asn Asp Pro Tyr His Val Asp Ile Ile
            115                 120                 125
Arg Glu Lys Leu Thr Arg Gly Leu Pro Ala Val Leu Pro Asp Val Ile
            130                 135                 140
Glu Glu Leu Thr Leu Ala Val Arg Gln Tyr Ile Pro Thr Glu Gly Asp
145                 150                 155                 160
Glu Trp Val Ser Val Asn Cys Ser Lys Ala Ala Arg Asp Ile Val Ala
                165                 170                 175
Arg Ala Ser Asn Arg Val Phe Val Gly Leu Pro Ala Cys Arg Asn Gln
                180                 185                 190
Gly Tyr Leu Asp Leu Ala Ile Asp Phe Thr Leu Ser Val Val Lys Asp
            195                 200                 205
Arg Ala Ile Ile Asn Met Phe Pro Glu Leu Leu Lys Pro Ile Val Gly
            210                 215                 220
Arg Val Val Gly Asn Ala Thr Arg Asn Val Arg Arg Ala Val Pro Phe
225                 230                 235                 240
Val Ala Pro Leu Val Glu Glu Arg Arg Leu Met Glu Glu Tyr Gly
                245                 250                 255
Glu Asp Trp Ser Glu Lys Pro Asn Asp Met Leu Gln Trp Ile Met Asp
                260                 265                 270
Glu Ala Ala Ser Arg Asp Ser Ser Val Lys Ala Ile Ala Glu Arg Leu
            275                 280                 285
Leu Met Val Asn Phe Ala Ala Ile His Thr Ser Ser Asn Thr Ile Thr
290                 295                 300
His Ala Leu Tyr His Leu Ala Glu Met Pro Glu Thr Leu Gln Pro Leu
305                 310                 315                 320
Arg Glu Glu Ile Glu Pro Leu Val Lys Glu Glu Gly Trp Thr Lys Ala
                325                 330                 335
Ala Met Gly Lys Met Trp Trp Leu Asp Ser Phe Leu Arg Glu Ser Gln
                340                 345                 350
Arg Tyr Asn Gly Ile Asn Ile Val Ser Leu Thr Arg Met Ala Asp Lys
            355                 360                 365
Asp Ile Thr Leu Ser Asp Gly Thr Phe Leu Pro Lys Gly Thr Leu Val
            370                 375                 380
Ala Val Pro Ala Tyr Ser Thr His Arg Asp Ala Val Tyr Ala Asp
385                 390                 395                 400
Ala Leu Val Phe Asp Pro Phe Arg Phe Ser Arg Met Arg Ala Arg Glu
                405                 410                 415
Gly Glu Gly Thr Lys His Gln Phe Val Asn Thr Ser Val Glu Tyr Val
            420                 425                 430
Pro Phe Gly His Gly Lys His Ala Cys Pro Gly Arg Phe Phe Ala Ala
            435                 440                 445
Asn Glu Leu Lys Ala Met Leu Ala Tyr Ile Val Leu Asn Tyr Asp Val
```

Lys Leu Pro Gly Asp Gly Lys Arg Pro Leu Asn Met Tyr Trp Gly Pro
465                 470                 475                 480

Thr Val Leu Pro Ala Pro Ala Gly Gln Val Leu Phe Arg Lys Arg Gln
                485                 490                 495

Val Ser Leu

<210> SEQ ID NO 11
<211> LENGTH: 1678
<212> TYPE: DNA
<213> ORGANISM: Stevia rebaudiana

<400> SEQUENCE: 11

```
aaacaaagaa tgattcaagt tctaacaccg atccttctct tcctcatttt cttcgttttc    60
tggaaggttt acaagcacca gaaaaccaaa atcaatcttc caccgggaag cttcggatgg   120
ccatttctgg gcgaaactct ggcactccta cgtgcaggtt gggactcaga gccggagaga   180
tttgttcgtg aacggatcaa gaaacacgga agtcctctag tgtttaagac gtcgttgttt   240
ggcgaccgtt ttgcggtgtt gtgtggacct gccggaaaca agttcctgtt ctgcaacgag   300
aacaagctgg tggcgtcgtg gtggccggtt ccggtgagga agcttttcgg caagtctctg   360
ctcacgattc gtggtgatga agctaagtgg atgaggaaga tgttgttatc gtatctcggt   420
cctgatgctt tcgcaactca ttatgccgtc accatggacg tcgtcacccg tcggcatatc   480
gacgttcatt ggcgagggaa ggaagaggtg aacgtattcc aaaccgttaa gttatatgcc   540
tttgagcttg catgtcgttt attcatgaac ctagacgacc caaaccacat tgcaaaactc   600
ggttccttgt tcaacatttt cttgaaaggc atcattgagc ttccaatcga cgtcccaggg   660
acacgatttt atagctccaa aaaagcagca gcagctatca ggattgaact aaaaaaattg   720
attaaagcaa gaaaactgga actgaaagaa gggaaggcat catcttcaca agacctctta   780
tcacatttgc ttcacatctcc agatgaaaat ggtatgtttc taaccgaaga agagattgta   840
gacaacatct tgttactact ctttgcgggt catgataccct cggctctttc aatcactttg   900
ctcatgaaga ctcttggcga acattctgat gtttatgaca aggtgttaaa agagcaacta   960
gagatatcga agacgaaaga agcatgggag tccctgaaat gggaggacat acaaaagatg  1020
aaatactcct ggagtgttat atgtgaagtc atgagactaa atccacctgt tataggaacc  1080
tatagagagg cccttgtgga tattgattat gcgggttata ccatccccaa aggatggaag  1140
ctgcactgga gtgctgtatc gacacaaagg gacgaggcta actttgaaga cgtaacacgt  1200
tttgacccat cacggtttga aggcgcagga ccgactccat tcacctttgt tccgtttgga  1260
gggggggccta gaatgtgttt agggaaagaa tttgctcgat tggaagtact tgcgtttctt  1320
cacaatattg tcaccaattt caaatgggac ctgttgatac ctgatgagaa aatagaatat  1380
gatcccatgg ctaccccagc aaaggggctt ccaattcgtc ttcatcccca tcaagtttga  1440
ttacttcaag catgaatcag tgatgtgaag gtaaaccata atggatctta ttggtagtta  1500
cagattatgt gttttttatgg catgaagaag ttatgataaa taaaattgtg ttattctaca  1560
acttatgtaa tttgtgcctg taagtaactg aatctattaa tgttttatgt gacatgaaac  1620
ataaatgtat aattagtaaa ttttctgctc aaaaaaaaaa aaaaaaaaaa aaaaaaa     1678
```

<210> SEQ ID NO 12
<211> LENGTH: 476
<212> TYPE: PRT
<213> ORGANISM: Stevia rebaudiana

<400> SEQUENCE: 12

```
Met Ile Gln Val Leu Thr Pro Ile Leu Leu Phe Leu Ile Phe Phe Val
1               5                   10                  15

Phe Trp Lys Val Tyr Lys His Gln Lys Thr Lys Ile Asn Leu Pro Pro
            20                  25                  30

Gly Ser Phe Gly Trp Pro Phe Leu Gly Glu Thr Leu Ala Leu Leu Arg
        35                  40                  45

Ala Gly Trp Asp Ser Glu Pro Glu Arg Phe Val Arg Glu Arg Ile Lys
    50                  55                  60

Lys His Gly Ser Pro Leu Val Phe Lys Thr Ser Leu Phe Gly Asp Arg
65                  70                  75                  80

Phe Ala Val Leu Cys Gly Pro Ala Gly Asn Lys Phe Leu Phe Cys Asn
                85                  90                  95

Glu Asn Lys Leu Val Ala Ser Trp Trp Pro Val Pro Val Arg Lys Leu
            100                 105                 110

Phe Gly Lys Ser Leu Leu Thr Ile Arg Gly Asp Glu Ala Lys Trp Met
        115                 120                 125

Arg Lys Met Leu Leu Ser Tyr Leu Gly Pro Asp Ala Phe Ala Thr His
    130                 135                 140

Tyr Ala Val Thr Met Asp Val Val Thr Arg Arg His Ile Asp Val His
145                 150                 155                 160

Trp Arg Gly Lys Glu Glu Val Asn Val Phe Gln Thr Val Lys Leu Tyr
                165                 170                 175

Ala Phe Glu Leu Ala Cys Arg Leu Phe Met Asn Leu Asp Asp Pro Asn
            180                 185                 190

His Ile Ala Lys Leu Gly Ser Leu Phe Asn Ile Phe Leu Lys Gly Ile
        195                 200                 205

Ile Glu Leu Pro Ile Asp Val Pro Gly Thr Arg Phe Tyr Ser Ser Lys
    210                 215                 220

Lys Ala Ala Ala Ile Arg Ile Glu Leu Lys Lys Leu Ile Lys Ala
225                 230                 235                 240

Arg Lys Leu Glu Leu Lys Glu Gly Lys Ala Ser Ser Ser Gln Asp Leu
                245                 250                 255

Leu Ser His Leu Leu Thr Ser Pro Asp Glu Asn Gly Met Phe Leu Thr
            260                 265                 270

Glu Glu Glu Ile Val Asp Asn Ile Leu Leu Leu Leu Phe Ala Gly His
        275                 280                 285

Asp Thr Ser Ala Leu Ser Ile Thr Leu Leu Met Lys Thr Leu Gly Glu
    290                 295                 300

His Ser Asp Val Tyr Asp Lys Val Leu Lys Glu Gln Leu Glu Ile Ser
305                 310                 315                 320

Lys Thr Lys Glu Ala Trp Glu Ser Leu Lys Trp Glu Asp Ile Gln Lys
                325                 330                 335

Met Lys Tyr Ser Trp Ser Val Ile Cys Glu Val Met Arg Leu Asn Pro
            340                 345                 350

Pro Val Ile Gly Thr Tyr Arg Glu Ala Leu Val Asp Ile Asp Tyr Ala
        355                 360                 365

Gly Tyr Thr Ile Pro Lys Gly Trp Lys Leu His Trp Ser Ala Val Ser
    370                 375                 380

Thr Gln Arg Asp Glu Ala Asn Phe Glu Asp Val Thr Arg Phe Asp Pro
385                 390                 395                 400

Ser Arg Phe Glu Gly Ala Gly Pro Thr Pro Phe Thr Phe Val Pro Phe
```

```
                    405                 410                 415
Gly Gly Gly Pro Arg Met Cys Leu Gly Lys Glu Phe Ala Arg Leu Glu
            420                 425                 430

Val Leu Ala Phe Leu His Asn Ile Val Thr Asn Phe Lys Trp Asp Leu
            435                 440                 445

Leu Ile Pro Asp Glu Lys Ile Glu Tyr Asp Pro Met Ala Thr Pro Ala
    450                 455                 460

Lys Gly Leu Pro Ile Arg Leu His Pro His Gln Val
465                 470                 475

<210> SEQ ID NO 13
<211> LENGTH: 522
<212> TYPE: PRT
<213> ORGANISM: Stevia rebaudiana

<400> SEQUENCE: 13

Met Gly Leu Phe Pro Leu Glu Asp Ser Tyr Ala Leu Val Phe Glu Gly
1               5                   10                  15

Leu Ala Ile Thr Leu Ala Leu Tyr Tyr Leu Leu Ser Phe Ile Tyr Lys
            20                  25                  30

Thr Ser Lys Lys Thr Cys Thr Pro Pro Lys Ala Ser Gly Glu His Pro
        35                  40                  45

Ile Thr Gly His Leu Asn Leu Leu Ser Gly Ser Gly Leu Pro His His
    50                  55                  60

Leu Ala Leu Ala Ser Leu Ala Asp Arg Cys Gly Pro Ile Phe Thr Ile
65                  70                  75                  80

Arg Leu Gly Ile Arg Arg Val Leu Val Val Ser Asn Trp Glu Ile Ala
                85                  90                  95

Lys Glu Ile Phe Thr Thr His Asp Leu Ile Val Ser Asn Arg Pro Lys
            100                 105                 110

Tyr Leu Ala Ala Lys Ile Leu Gly Phe Asn Tyr Val Ser Phe Ser Phe
        115                 120                 125

Ala Pro Tyr Gly Pro Tyr Trp Val Gly Ile Arg Lys Ile Ile Ala Thr
    130                 135                 140

Lys Leu Met Ser Ser Arg Leu Gln Lys Leu Gln Phe Val Arg Val
145                 150                 155                 160

Phe Glu Leu Glu Asn Ser Met Lys Ser Ile Arg Glu Ser Trp Lys Glu
                165                 170                 175

Lys Lys Asp Glu Glu Gly Lys Val Leu Val Glu Met Lys Lys Trp Phe
            180                 185                 190

Trp Glu Leu Asn Met Asn Ile Val Leu Arg Thr Val Ala Gly Lys Gln
        195                 200                 205

Tyr Thr Gly Thr Val Asp Asp Ala Asp Ala Lys Arg Ile Ser Glu Leu
    210                 215                 220

Phe Arg Glu Trp Phe His Tyr Thr Gly Arg Phe Val Val Gly Asp Ala
225                 230                 235                 240

Phe Pro Phe Leu Gly Trp Leu Asp Leu Gly Gly Tyr Lys Lys Thr Met
                245                 250                 255

Glu Leu Val Ala Ser Arg Leu Asp Ser Met Val Ser Lys Trp Leu Asp
            260                 265                 270

Glu His Arg Lys Lys Gln Ala Asn Asp Asp Lys Lys Glu Asp Met Asp
        275                 280                 285

Phe Met Asp Ile Met Ile Ser Met Thr Glu Ala Asn Ser Pro Leu Glu
    290                 295                 300
```

Gly Tyr Gly Thr Asp Thr Ile Ile Lys Thr Thr Cys Met Thr Leu Ile
305                 310                 315                 320

Val Ser Gly Val Asp Thr Thr Ser Ile Val Leu Thr Trp Ala Leu Ser
            325                 330                 335

Leu Leu Leu Asn Asn Arg Asp Thr Leu Lys Lys Ala Gln Glu Glu Leu
            340                 345                 350

Asp Met Cys Val Gly Lys Gly Arg Gln Val Asn Glu Ser Asp Leu Val
            355                 360                 365

Asn Leu Ile Tyr Leu Glu Ala Val Leu Lys Glu Ala Leu Arg Leu Tyr
    370                 375                 380

Pro Ala Ala Phe Leu Gly Gly Pro Arg Ala Phe Leu Glu Asp Cys Thr
385                 390                 395                 400

Val Ala Gly Tyr Arg Ile Pro Lys Gly Thr Cys Leu Leu Ile Asn Met
                405                 410                 415

Trp Lys Leu His Arg Asp Pro Asn Ile Trp Ser Asp Pro Cys Glu Phe
                420                 425                 430

Lys Pro Glu Arg Phe Leu Thr Pro Asn Gln Lys Asp Val Asp Val Ile
            435                 440                 445

Gly Met Asp Phe Glu Leu Ile Pro Phe Gly Ala Gly Arg Arg Tyr Cys
450                 455                 460

Pro Gly Thr Arg Leu Ala Leu Gln Met Leu His Ile Val Leu Ala Thr
465                 470                 475                 480

Leu Leu Gln Asn Phe Glu Met Ser Thr Pro Asn Asp Ala Pro Val Asp
                485                 490                 495

Met Thr Ala Ser Val Gly Met Thr Asn Ala Lys Ala Ser Pro Leu Glu
            500                 505                 510

Val Leu Leu Ser Pro Arg Val Lys Trp Ser
            515                 520

<210> SEQ ID NO 14
<211> LENGTH: 476
<212> TYPE: PRT
<213> ORGANISM: Stevia rebaudiana

<400> SEQUENCE: 14

Met Ile Gln Val Leu Thr Pro Ile Leu Leu Phe Leu Ile Phe Phe Val
1               5                   10                  15

Phe Trp Lys Val Tyr Lys His Gln Lys Thr Lys Ile Asn Leu Pro Pro
            20                  25                  30

Gly Ser Phe Gly Trp Pro Phe Leu Gly Glu Thr Leu Ala Leu Leu Arg
        35                  40                  45

Ala Gly Trp Asp Ser Glu Pro Glu Arg Phe Val Arg Glu Arg Ile Lys
    50                  55                  60

Lys His Gly Ser Pro Leu Val Phe Lys Thr Ser Leu Phe Gly Asp Arg
65                  70                  75                  80

Phe Ala Val Leu Cys Gly Pro Ala Gly Asn Lys Phe Leu Phe Cys Asn
                85                  90                  95

Glu Asn Lys Leu Val Ala Ser Trp Trp Pro Val Pro Val Arg Lys Leu
            100                 105                 110

Phe Gly Lys Ser Leu Leu Thr Ile Arg Gly Asp Glu Ala Lys Trp Met
        115                 120                 125

Arg Lys Met Leu Leu Ser Tyr Leu Gly Pro Asp Ala Phe Ala Thr His
    130                 135                 140

Tyr Ala Val Thr Met Asp Val Val Thr Arg Arg His Ile Asp Val His
145                 150                 155                 160

```
Trp Arg Gly Lys Glu Glu Val Asn Val Phe Gln Thr Val Lys Leu Tyr
                165                 170                 175

Ala Phe Glu Leu Ala Cys Arg Leu Phe Met Asn Leu Asp Asp Pro Asn
            180                 185                 190

His Ile Ala Lys Leu Gly Ser Leu Phe Asn Ile Phe Leu Lys Gly Ile
        195                 200                 205

Ile Glu Leu Pro Ile Asp Val Pro Gly Thr Arg Phe Tyr Ser Ser Lys
    210                 215                 220

Lys Ala Ala Ala Ile Arg Ile Glu Leu Lys Lys Leu Ile Lys Ala
225                 230                 235                 240

Arg Lys Leu Glu Leu Lys Glu Gly Lys Ala Ser Ser Ser Gln Asp Leu
                245                 250                 255

Leu Ser His Leu Leu Thr Ser Pro Asp Glu Asn Gly Met Phe Leu Thr
            260                 265                 270

Glu Glu Glu Ile Val Asp Asn Ile Leu Leu Leu Phe Ala Gly His
        275                 280                 285

Asp Thr Ser Ala Leu Ser Ile Thr Leu Leu Met Lys Thr Leu Gly Glu
    290                 295                 300

His Ser Asp Val Tyr Asp Lys Val Leu Glu Gln Leu Glu Ile Ser
305                 310                 315                 320

Lys Thr Lys Glu Ala Trp Glu Ser Leu Lys Trp Glu Asp Ile Gln Lys
                325                 330                 335

Met Lys Tyr Ser Trp Ser Val Ile Cys Glu Val Met Arg Leu Asn Pro
            340                 345                 350

Pro Val Ile Gly Thr Tyr Arg Glu Ala Leu Val Asp Ile Asp Tyr Ala
    355                 360                 365

Gly Tyr Thr Ile Pro Lys Gly Trp Lys Leu His Trp Ser Ala Val Ser
    370                 375                 380

Thr Gln Arg Asp Glu Ala Asn Phe Glu Asp Val Thr Arg Phe Asp Pro
385                 390                 395                 400

Ser Arg Phe Glu Gly Ala Gly Pro Thr Pro Phe Thr Phe Val Pro Phe
                405                 410                 415

Gly Gly Gly Pro Arg Met Cys Leu Gly Lys Glu Phe Ala Arg Leu Glu
            420                 425                 430

Val Leu Ala Phe Leu His Asn Ile Val Thr Asn Phe Lys Trp Asp Leu
    435                 440                 445

Leu Ile Pro Asp Glu Lys Ile Glu Tyr Asp Pro Met Ala Thr Pro Ala
    450                 455                 460

Lys Gly Leu Pro Ile Arg Leu His Pro His Gln Val
465                 470                 475

<210> SEQ ID NO 15
<211> LENGTH: 525
<212> TYPE: PRT
<213> ORGANISM: Arabidopsis thaliana

<400> SEQUENCE: 15

Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
            20                  25                  30

Val Glu Gln Trp Arg Met Arg Arg Ser Leu Lys Leu Gln Gly Val Lys
        35                  40                  45

Gly Pro Pro Pro Ser Ile Phe Asn Gly Asn Val Ser Glu Met Gln Arg
```

```
            50                  55                  60
Ile Gln Ser Glu Ala Lys His Cys Ser Gly Asp Asn Ile Ile Ser His
 65                  70                  75                  80

Asp Tyr Ser Ser Ser Leu Phe Pro His Phe Asp His Trp Arg Lys Gln
                     85                  90                  95

Tyr Gly Arg Ile Tyr Thr Tyr Ser Thr Gly Leu Lys Gln His Leu Tyr
                100                 105                 110

Ile Asn His Pro Glu Met Val Lys Glu Leu Ser Gln Thr Asn Thr Leu
                115                 120                 125

Asn Leu Gly Arg Ile Thr His Ile Thr Lys Arg Leu Asn Pro Ile Leu
            130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Ile Lys Gly Met Val
                165                 170                 175

Gly Leu Met Val Glu Ser Ala Met Pro Met Leu Asn Lys Trp Glu Glu
                180                 185                 190

Met Val Lys Arg Gly Gly Glu Met Gly Cys Asp Ile Arg Val Asp Glu
                195                 200                 205

Asp Leu Lys Asp Val Ser Ala Asp Val Ile Ala Lys Ala Cys Phe Gly
210                 215                 220

Ser Ser Phe Ser Lys Gly Lys Ala Ile Phe Ser Met Ile Arg Asp Leu
225                 230                 235                 240

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
                260                 265                 270

Ala Leu Glu Met Glu Leu Glu Ser Ser Ile Trp Glu Thr Val Lys Glu
                275                 280                 285

Arg Glu Ile Glu Cys Lys Asp Thr His Lys Lys Asp Leu Met Gln Leu
                290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
                325                 330                 335

Ala Gly His Asp Ser Thr Ala Val Ser Val Ser Trp Cys Leu Met Leu
                340                 345                 350

Leu Ala Leu Asn Pro Ser Trp Gln Val Lys Ile Arg Asp Glu Ile Leu
                355                 360                 365

Ser Ser Cys Lys Asn Gly Ile Pro Asp Ala Glu Ser Ile Pro Asn Leu
370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
                405                 410                 415

Leu Val Val Pro Lys Gly Val Cys Ile Trp Thr Leu Ile Pro Ala Leu
                420                 425                 430

His Arg Asp Pro Glu Ile Trp Gly Pro Asp Ala Asn Asp Phe Lys Pro
                435                 440                 445

Glu Arg Phe Ser Glu Gly Ile Ser Lys Ala Cys Lys Tyr Pro Gln Ser
                450                 455                 460

Tyr Ile Pro Phe Gly Leu Gly Pro Arg Thr Cys Val Gly Lys Asn Phe
465                 470                 475                 480
```

Gly Met Met Glu Val Lys Val Leu Val Ser Leu Ile Val Ser Lys Phe
                485                 490                 495

Ser Phe Thr Leu Ser Pro Thr Tyr Gln His Ser Pro Ser His Lys Leu
            500                 505                 510

Leu Val Glu Pro Gln His Gly Val Val Ile Arg Val Val
        515                 520                 525

<210> SEQ ID NO 16
<211> LENGTH: 526
<212> TYPE: PRT
<213> ORGANISM: Vitis vinifera

<400> SEQUENCE: 16

Met Tyr Phe Leu Leu Gln Tyr Leu Asn Ile Thr Thr Val Gly Val Phe
1               5                   10                  15

Ala Thr Leu Phe Leu Ser Tyr Cys Leu Leu Trp Arg Ser Arg Ala
            20                  25                  30

Gly Asn Lys Lys Ile Ala Pro Glu Ala Ala Ala Trp Pro Ile Ile
        35                  40                  45

Gly His Leu His Leu Leu Ala Gly Ser His Gln Leu Pro His Ile
    50                  55                  60

Thr Leu Gly Asn Met Ala Asp Lys Tyr Gly Pro Val Phe Thr Ile Arg
65                  70                  75                  80

Ile Gly Leu His Arg Ala Val Val Val Ser Trp Glu Met Ala Lys
                85                  90                  95

Glu Cys Ser Thr Ala Asn Asp Gln Val Ser Ser Arg Pro Glu Leu
            100                 105                 110

Leu Ala Ser Lys Leu Leu Gly Tyr Asn Tyr Ala Met Phe Gly Phe Ser
            115                 120                 125

Pro Tyr Gly Ser Tyr Trp Arg Glu Met Arg Lys Ile Ile Ser Leu Glu
    130                 135                 140

Leu Leu Ser Asn Ser Arg Leu Glu Leu Leu Lys Asp Val Arg Ala Ser
145                 150                 155                 160

Glu Val Val Thr Ser Ile Lys Glu Leu Tyr Lys Leu Trp Ala Glu Lys
                165                 170                 175

Lys Asn Glu Ser Gly Leu Val Ser Val Glu Met Lys Gln Trp Phe Gly
            180                 185                 190

Asp Leu Thr Leu Asn Val Ile Leu Arg Met Val Ala Gly Lys Arg Tyr
        195                 200                 205

Phe Ser Ala Ser Asp Ala Ser Glu Asn Lys Gln Ala Gln Arg Cys Arg
210                 215                 220

Arg Val Phe Arg Glu Phe Phe His Leu Ser Gly Leu Phe Val Val Ala
225                 230                 235                 240

Asp Ala Ile Pro Phe Leu Gly Trp Leu Asp Trp Gly Arg His Glu Lys
                245                 250                 255

Thr Leu Lys Lys Thr Ala Ile Glu Met Asp Ser Ile Ala Gln Glu Trp
            260                 265                 270

Leu Glu Glu His Arg Arg Arg Lys Asp Ser Gly Asp Asp Asn Ser Thr
        275                 280                 285

Gln Asp Phe Met Asp Val Met Gln Ser Val Leu Asp Gly Lys Asn Leu
    290                 295                 300

Gly Gly Tyr Asp Ala Asp Thr Ile Asn Lys Ala Thr Cys Leu Thr Leu
305                 310                 315                 320

Ile Ser Gly Gly Ser Asp Thr Thr Val Val Ser Leu Thr Trp Ala Leu

-continued

```
                325                 330                 335
Ser Leu Val Leu Asn Asn Arg Asp Thr Leu Lys Lys Ala Gln Glu Glu
            340                 345                 350
Leu Asp Ile Gln Val Gly Lys Glu Arg Leu Val Asn Glu Gln Asp Ile
        355                 360                 365
Ser Lys Leu Val Tyr Leu Gln Ala Ile Val Lys Glu Thr Leu Arg Leu
    370                 375                 380
Tyr Pro Pro Gly Pro Leu Gly Gly Leu Arg Gln Phe Thr Glu Asp Cys
385                 390                 395                 400
Thr Leu Gly Gly Tyr His Val Ser Lys Gly Thr Arg Leu Ile Met Asn
                405                 410                 415
Leu Ser Lys Ile Gln Lys Asp Pro Arg Ile Trp Ser Asp Pro Thr Glu
            420                 425                 430
Phe Gln Pro Glu Arg Phe Leu Thr Thr His Lys Asp Val Asp Pro Arg
        435                 440                 445
Gly Lys His Phe Glu Phe Ile Pro Phe Gly Ala Gly Arg Arg Ala Cys
    450                 455                 460
Pro Gly Ile Thr Phe Gly Leu Gln Val Leu His Leu Thr Leu Ala Ser
465                 470                 475                 480
Phe Leu His Ala Phe Glu Phe Ser Thr Pro Ser Asn Glu Gln Val Asn
                485                 490                 495
Met Arg Glu Ser Leu Gly Leu Thr Asn Met Lys Ser Thr Pro Leu Glu
            500                 505                 510
Val Leu Ile Ser Pro Arg Leu Ser Ser Cys Ser Leu Tyr Asn
        515                 520                 525
```

<210> SEQ ID NO 17
<211> LENGTH: 479
<212> TYPE: PRT
<213> ORGANISM: Medicago truncatula

<400> SEQUENCE: 17

```
Met Glu Pro Asn Phe Tyr Leu Ser Leu Leu Leu Phe Val Thr Phe
1               5                   10                  15
Ile Ser Leu Ser Leu Phe Phe Ile Phe Tyr Lys Gln Lys Ser Pro Leu
            20                  25                  30
Asn Leu Pro Pro Gly Lys Met Gly Tyr Pro Ile Ile Gly Glu Ser Leu
        35                  40                  45
Glu Phe Leu Ser Thr Gly Trp Lys Gly His Pro Glu Lys Phe Ile Phe
    50                  55                  60
Asp Arg Met Arg Lys Tyr Ser Ser Glu Leu Phe Lys Thr Ser Ile Val
65                  70                  75                  80
Gly Glu Ser Thr Val Val Cys Cys Gly Ala Ala Ser Asn Lys Phe Leu
                85                  90                  95
Phe Ser Asn Glu Asn Lys Leu Val Thr Ala Trp Trp Pro Asp Ser Val
            100                 105                 110
Asn Lys Ile Phe Pro Thr Thr Ser Leu Asp Ser Asn Leu Lys Glu Glu
        115                 120                 125
Ser Ile Lys Met Arg Lys Leu Leu Pro Gln Phe Phe Lys Pro Glu Ala
    130                 135                 140
Leu Gln Arg Tyr Val Gly Val Met Asp Val Ile Ala Gln Arg His Phe
145                 150                 155                 160
Val Thr His Trp Asp Asn Lys Asn Glu Ile Thr Val Tyr Pro Leu Ala
                165                 170                 175
```

-continued

```
Lys Arg Tyr Thr Phe Leu Leu Ala Cys Arg Leu Phe Met Ser Val Glu
            180                 185                 190

Asp Glu Asn His Val Ala Lys Phe Ser Asp Pro Phe Gln Leu Ile Ala
        195                 200                 205

Ala Gly Ile Ile Ser Leu Pro Ile Asp Leu Pro Gly Thr Pro Phe Asn
    210                 215                 220

Lys Ala Ile Lys Ala Ser Asn Phe Ile Arg Lys Glu Leu Ile Lys Ile
225                 230                 235                 240

Ile Lys Gln Arg Arg Val Asp Leu Ala Glu Gly Thr Ala Ser Pro Thr
                245                 250                 255

Gln Asp Ile Leu Ser His Met Leu Leu Thr Ser Asp Glu Asn Gly Lys
            260                 265                 270

Ser Met Asn Glu Leu Asn Ile Ala Asp Lys Ile Leu Gly Leu Leu Ile
        275                 280                 285

Gly Gly His Asp Thr Ala Ser Val Ala Cys Thr Phe Leu Val Lys Tyr
    290                 295                 300

Leu Gly Glu Leu Pro His Ile Tyr Asp Lys Val Tyr Gln Glu Gln Met
305                 310                 315                 320

Glu Ile Ala Lys Ser Lys Pro Ala Gly Glu Leu Leu Asn Trp Asp Asp
                325                 330                 335

Leu Lys Lys Met Lys Tyr Ser Trp Asn Val Ala Cys Glu Val Met Arg
            340                 345                 350

Leu Ser Pro Pro Leu Gln Gly Phe Arg Glu Ala Ile Thr Asp Phe
        355                 360                 365

Met Phe Asn Gly Phe Ser Ile Pro Lys Gly Trp Lys Leu Tyr Trp Ser
    370                 375                 380

Ala Asn Ser Thr His Lys Asn Ala Glu Cys Phe Pro Met Pro Glu Lys
385                 390                 395                 400

Phe Asp Pro Thr Arg Phe Glu Gly Asn Gly Pro Ala Pro Tyr Thr Phe
                405                 410                 415

Val Pro Phe Gly Gly Gly Pro Arg Met Cys Pro Gly Lys Glu Tyr Ala
            420                 425                 430

Arg Leu Glu Ile Leu Val Phe Met His Asn Leu Val Lys Arg Phe Lys
        435                 440                 445

Trp Glu Lys Val Ile Pro Asp Glu Lys Ile Ile Val Asp Pro Phe Pro
    450                 455                 460

Ile Pro Ala Lys Asp Leu Pro Ile Arg Leu Tyr Pro His Lys Ala
465                 470                 475
```

<210> SEQ ID NO 18
<211> LENGTH: 1503
<212> TYPE: DNA
<213> ORGANISM: Artificial Sequence
<220> FEATURE:
<223> OTHER INFORMATION: Codon-optimized Stevia rebaudiana KAHe1

<400> SEQUENCE: 18

```
atggaagcct cttacctata catttctatt tgcttttac tggcatcata cctgttcacc      60
actcaactta gaaggaagag cgctaatcta ccaccaaccg tgtttccatc aataccaatc     120
attggacact tatacttact caaaaagcct ctttatagaa ctttagcaaa aattgccgct     180
aagtacggac caatactgca attacaactc ggctacagac gtgttctggt gatttcctca     240
ccatcagcag cagaagagtg ctttaccaat aacgatgtaa tcttcgcaaa tagacctaag     300
acattgtttg gcaaaatagt gggtggaaca tcccttggca gttatcccta cggcgatcaa     360
```

```
tggcgtaatc taaggagagt agcttctatc gaaatcctat cagttcatag gttgaacgaa    420
tttcatgata tcagagtgga tgagaacaga ttgttaatta gaaaacttag aagttcatct    480
tctcctgtta ctcttataac agtctttat gctctaacat tgaacgtcat tatgagaatg    540
atctctggca aaagatattt cgacagtggg gatagagaat ggaggagga aggtaagaga    600 tttcgagaaa tcttagacga aacgttgctt ctagccggtg cttctaatgt tggcgactac    660
ttaccaatat tgaactggtt gggagttaag tctcttgaaa agaaattgat cgctttgcag    720
aaaaagagag atgactttt ccagggtttg attgaacagg ttagaaaatc tcgtggtgct    780
aaagtaggca aagtagaaa aacgatgatc gaactcttat tatctttgca agagtcagaa    840
cctgagtact atacagatgc tatgataaga tcttttgtcc taggtctgct ggctgcaggt    900
agtgatactt cagcgggcac tatggaatgg gccatgagct tactggtcaa tcacccacat    960
gtattgaaga aagctcaagc tgaaatcgat agagttatcg gtaataacag attgattgac   1020
gagtcagaca ttggaaatat cccttacatc gggtgtatta tcaatgaaac tctaagactc   1080
tatccagcag ggccattgtt gttcccacat gaaagttctg ccgactgcgt tatttccggt   1140
tacaatatac ctagaggtac aatgttaatc gtaaaccaat gggcgattca tcacgatcct   1200
aaagtctggg atgatcctga aacctttaaa cctgaaagat ttcaaggatt agaaggaact   1260
agagatggtt tcaaacttat gccattcggt tctgggagaa aggatgtcc aggtgaaggt   1320 ttggcaataa ggctgttagg gatgacacta ggctcagtga tccaatgttt tgattgggag   1380
agagtaggag atgagatggt tgacatgaca gaaggtttgg gtgtcacact tcctaaggcc   1440
gttccattag ttgccaaatg taagccacgt tccgaaatga ctaatctcct atccgaactt   1500
taa                                                                 1503
```

<210> SEQ ID NO 19
<211> LENGTH: 500
<212> TYPE: PRT
<213> ORGANISM: Stevia rebaudiana

<400> SEQUENCE: 19

```
Met Glu Ala Ser Tyr Leu Tyr Ile Ser Ile Leu Leu Leu Ala Ser
1               5                   10                  15

Tyr Leu Phe Thr Thr Gln Leu Arg Arg Lys Ser Ala Asn Leu Pro Pro
            20                  25                  30

Thr Val Phe Pro Ser Ile Pro Ile Ile Gly His Leu Tyr Leu Leu Lys
        35                  40                  45

Lys Pro Leu Tyr Arg Thr Leu Ala Lys Ile Ala Ala Lys Tyr Gly Pro
    50                  55                  60

Ile Leu Gln Leu Gln Leu Gly Tyr Arg Arg Val Leu Val Ile Ser Ser
65                  70                  75                  80

Pro Ser Ala Ala Glu Glu Cys Phe Thr Asn Asn Asp Val Ile Phe Ala
                85                  90                  95

Asn Arg Pro Lys Thr Leu Phe Gly Lys Ile Val Gly Gly Thr Ser Leu
            100                 105                 110

Gly Ser Leu Ser Tyr Gly Asp Gln Trp Arg Asn Leu Arg Arg Val Ala
        115                 120                 125

Ser Ile Glu Ile Leu Ser Val His Arg Leu Asn Glu Phe His Asp Ile
    130                 135                 140

Arg Val Asp Glu Asn Arg Leu Leu Ile Arg Lys Leu Arg Ser Ser Ser
145                 150                 155                 160

Ser Pro Val Thr Leu Ile Thr Val Phe Tyr Ala Leu Thr Leu Asn Val
```

|     |     |     |     |     |     |     |     |     |     |     |
| --- | --- | --- | --- | --- | --- | --- | --- | --- | --- | --- |
|     |     |     | 165 |     |     | 170 |     |     | 175 |     |

Ile Met Arg Met Ile Ser Gly Lys Arg Tyr Phe Asp Ser Gly Asp Arg
                180                 185                 190

Glu Leu Glu Glu Glu Gly Lys Arg Phe Arg Glu Ile Leu Asp Glu Thr
            195                 200                 205

Leu Leu Leu Ala Gly Ala Ser Asn Val Gly Asp Tyr Leu Pro Ile Leu
        210                 215                 220

Asn Trp Leu Gly Val Lys Ser Leu Glu Lys Lys Leu Ile Ala Leu Gln
225                 230                 235                 240

Lys Lys Arg Asp Asp Phe Phe Gln Gly Leu Ile Glu Gln Val Arg Lys
                245                 250                 255

Ser Arg Gly Ala Lys Val Gly Lys Gly Arg Lys Thr Met Ile Glu Leu
            260                 265                 270

Leu Leu Ser Leu Gln Glu Ser Glu Pro Glu Tyr Tyr Thr Asp Ala Met
        275                 280                 285

Ile Arg Ser Phe Val Leu Gly Leu Leu Ala Ala Gly Ser Asp Thr Ser
        290                 295                 300

Ala Gly Thr Met Glu Trp Ala Met Ser Leu Leu Val Asn His Pro His
305                 310                 315                 320

Val Leu Lys Lys Ala Gln Ala Glu Ile Asp Arg Val Ile Gly Asn Asn
                325                 330                 335

Arg Leu Ile Asp Glu Ser Asp Ile Gly Asn Ile Pro Tyr Ile Gly Cys
            340                 345                 350

Ile Ile Asn Glu Thr Leu Arg Leu Tyr Pro Ala Gly Pro Leu Leu Phe
        355                 360                 365

Pro His Glu Ser Ser Ala Asp Cys Val Ile Ser Gly Tyr Asn Ile Pro
        370                 375                 380

Arg Gly Thr Met Leu Ile Val Asn Gln Trp Ala Ile His His Asp Pro
385                 390                 395                 400

Lys Val Trp Asp Asp Pro Glu Thr Phe Lys Pro Glu Arg Phe Gln Gly
                405                 410                 415

Leu Glu Gly Thr Arg Asp Gly Phe Lys Leu Met Pro Phe Gly Ser Gly
            420                 425                 430

Arg Arg Gly Cys Pro Gly Glu Gly Leu Ala Ile Arg Leu Leu Gly Met
        435                 440                 445

Thr Leu Gly Ser Val Ile Gln Cys Phe Asp Trp Glu Arg Val Gly Asp
        450                 455                 460

Glu Met Val Asp Met Thr Glu Gly Leu Gly Val Thr Leu Pro Lys Ala
465                 470                 475                 480

Val Pro Leu Val Ala Lys Cys Lys Pro Arg Ser Glu Met Thr Asn Leu
                485                 490                 495

Leu Ser Glu Leu
            500

<210> SEQ ID NO 20
<211> LENGTH: 710
<212> TYPE: PRT
<213> ORGANISM: Stevia rebaudiana

<400> SEQUENCE: 20

Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
            20                  25                  30

-continued

```
Asp Pro Thr Thr Leu Pro Ala Leu Lys Met Leu Val Glu Asn Arg Glu
        35                  40                  45

Leu Leu Thr Leu Phe Thr Thr Ser Phe Ala Val Leu Ile Gly Cys Leu
 50                  55                  60

Val Phe Leu Met Trp Arg Arg Ser Ser Lys Lys Leu Val Gln Asp
 65                  70                  75                  80

Pro Val Pro Gln Val Ile Val Lys Lys Lys Glu Lys Glu Ser Glu
                     85                  90                  95

Val Asp Asp Gly Lys Lys Lys Val Ser Ile Phe Gly Thr Gln Thr
                100                 105                 110

Gly Thr Ala Glu Gly Phe Ala Lys Ala Leu Val Glu Glu Ala Lys Val
            115                 120                 125

Arg Tyr Glu Lys Thr Ser Phe Lys Val Ile Asp Leu Asp Asp Tyr Ala
    130                 135                 140

Ala Asp Asp Asp Glu Tyr Glu Glu Lys Leu Lys Lys Glu Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Asp Lys Gly Glu Trp
                180                 185                 190

Leu Lys Lys Leu Gln Tyr Gly Val Phe Gly Leu Gly Asn Arg Gln Tyr
            195                 200                 205

Glu His Phe Asn Lys Ile Ala Ile Val Val Asp Asp Lys Leu Thr Glu
    210                 215                 220

Met Gly Ala Lys Arg Leu Val Pro Val Gly Leu Gly Asp Asp Gln
225                 230                 235                 240

Cys Ile Glu Asp Asp Phe Thr Ala Trp Lys Glu Leu Val Trp Pro Glu
                245                 250                 255

Leu Asp Gln Leu Leu Arg Asp Glu Asp Asp Thr Ser Val Thr Thr Pro
                260                 265                 270

Tyr Thr Ala Ala Val Leu Glu Tyr Arg Val Val Tyr His Asp Lys Pro
            275                 280                 285

Ala Asp Ser Tyr Ala Glu Asp Gln Thr His Thr Asn Gly His Val Val
    290                 295                 300

His Asp Ala Gln His Pro Ser Arg Ser Asn Val Ala Phe Lys Lys Glu
305                 310                 315                 320

Leu His Thr Ser Gln Ser Asp Arg Ser Cys Thr His Leu Glu Phe Asp
                325                 330                 335

Ile Ser His Thr Gly Leu Ser Tyr Glu Thr Gly Asp His Val Gly Val
                340                 345                 350

Tyr Ser Glu Asn Leu Ser Glu Val Val Asp Glu Ala Leu Lys Leu Leu
            355                 360                 365

Gly Leu Ser Pro Asp Thr Tyr Phe Ser Val His Ala Asp Lys Glu Asp
    370                 375                 380

Gly Thr Pro Ile Gly Gly Ala Ser Leu Pro Pro Phe Pro Pro Cys
385                 390                 395                 400

Thr Leu Arg Asp Ala Leu Thr Arg Tyr Ala Asp Val Leu Ser Ser Pro
                405                 410                 415

Lys Lys Val Ala Leu Leu Ala Leu Ala Ala His Ala Ser Asp Pro Ser
                420                 425                 430

Glu Ala Asp Arg Leu Lys Phe Leu Ala Ser Pro Ala Gly Lys Asp Glu
            435                 440                 445

Tyr Ala Gln Trp Ile Val Ala Asn Gln Arg Ser Leu Leu Glu Val Met
```

```
                450                 455                 460
Gln Ser Phe Pro Ser Ala Lys Pro Pro Leu Gly Val Phe Ala Ala
465                 470                 475                 480

Val Ala Pro Arg Leu Gln Pro Arg Tyr Tyr Ser Ile Ser Ser Pro
                485                 490                 495

Lys Met Ser Pro Asn Arg Ile His Val Thr Cys Ala Leu Val Tyr Glu
                500                 505                 510

Thr Thr Pro Ala Gly Arg Ile His Arg Gly Leu Cys Ser Thr Trp Met
                515                 520                 525

Lys Asn Ala Val Pro Leu Thr Glu Ser Pro Asp Cys Ser Gln Ala Ser
                530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
                580                 585                 590

Ser Ser Ile Phe Phe Phe Gly Cys Arg Asn Arg Lys Val Asp Phe Ile
                595                 600                 605

Tyr Glu Asp Glu Leu Asn Asn Phe Val Glu Thr Gly Ala Leu Ser Glu
                610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
                660                 665                 670

Val His Arg Thr Leu His Thr Ile Val Gln Glu Gln Gly Ser Leu Asp
                675                 680                 685

Ser Ser Lys Ala Glu Leu Tyr Val Lys Asn Leu Gln Met Ser Gly Arg
                690                 695                 700

Tyr Leu Arg Asp Val Trp
705                 710

<210> SEQ ID NO 21
<211> LENGTH: 692
<212> TYPE: PRT
<213> ORGANISM: Arabidopsis thaliana

<400> SEQUENCE: 21

Met Thr Ser Ala Leu Tyr Ala Ser Asp Leu Phe Lys Gln Leu Lys Ser
1               5                   10                  15

Ile Met Gly Thr Asp Ser Leu Ser Asp Val Val Leu Val Ile Ala
                20                  25                  30

Thr Thr Ser Leu Ala Leu Val Ala Gly Phe Val Val Leu Leu Trp Lys
            35                  40                  45

Lys Thr Thr Ala Asp Arg Ser Gly Glu Leu Lys Pro Leu Met Ile Pro
        50                  55                  60

Lys Ser Leu Met Ala Lys Asp Glu Asp Asp Leu Asp Leu Gly Ser
65                  70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
                100                 105                 110
```

```
Lys Ala Ala Val Lys Val Ile Asp Leu Asp Asp Tyr Ala Asp Asp
            115                 120                 125

Asp Gln Tyr Glu Glu Lys Leu Lys Lys Glu Thr Leu Ala Phe Phe Cys
        130                 135                 140

Val Ala Thr Tyr Gly Asp Gly Glu Pro Thr Asp Asn Ala Ala Arg Phe
145                 150                 155                 160

Tyr Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
            180                 185                 190

Asn Lys Ile Gly Ile Val Leu Asp Glu Leu Cys Lys Lys Gly Ala
        195                 200                 205

Lys Arg Leu Ile Glu Val Gly Leu Gly Asp Asp Gln Ser Ile Glu
    210                 215                 220

Asp Asp Phe Asn Ala Trp Lys Glu Ser Leu Trp Ser Glu Leu Asp Lys
225                 230                 235                 240

Leu Leu Lys Asp Glu Asp Asp Lys Ser Val Ala Thr Pro Tyr Thr Ala
                245                 250                 255

Val Ile Pro Glu Tyr Arg Val Val Thr His Asp Pro Arg Phe Thr Thr
            260                 265                 270

Gln Lys Ser Met Glu Ser Asn Val Ala Asn Gly Asn Thr Thr Ile Asp
        275                 280                 285

Ile His His Pro Cys Arg Val Asp Val Ala Val Gln Lys Glu Leu His
    290                 295                 300

Thr His Glu Ser Asp Arg Ser Cys Ile His Leu Glu Phe Asp Ile Ser
305                 310                 315                 320

Arg Thr Gly Ile Thr Tyr Glu Thr Gly Asp His Val Gly Val Tyr Ala
                325                 330                 335

Glu Asn His Val Glu Ile Val Glu Glu Ala Gly Lys Leu Leu Gly His
            340                 345                 350

Ser Leu Asp Leu Val Phe Ser Ile His Ala Asp Lys Glu Asp Gly Ser
        355                 360                 365

Pro Leu Glu Ser Ala Val Pro Pro Pro Phe Pro Gly Pro Cys Thr Leu
    370                 375                 380

Gly Thr Gly Leu Ala Arg Tyr Ala Asp Leu Leu Asn Pro Pro Arg Lys
385                 390                 395                 400

Ser Ala Leu Val Ala Leu Ala Ala Tyr Ala Thr Glu Pro Ser Glu Ala
                405                 410                 415

Glu Lys Leu Lys His Leu Thr Ser Pro Asp Gly Lys Asp Glu Tyr Ser
            420                 425                 430

Gln Trp Ile Val Ala Ser Gln Arg Ser Leu Leu Glu Val Met Ala Ala
        435                 440                 445

Phe Pro Ser Ala Lys Pro Pro Leu Gly Val Phe Phe Ala Ala Ile Ala
    450                 455                 460

Pro Arg Leu Gln Pro Arg Tyr Tyr Ser Ile Ser Ser Ser Pro Arg Leu
465                 470                 475                 480

Ala Pro Ser Arg Val His Val Thr Ser Ala Leu Val Tyr Gly Pro Thr
                485                 490                 495

Pro Thr Gly Arg Ile His Lys Gly Val Cys Ser Thr Trp Met Lys Asn
            500                 505                 510

Ala Val Pro Ala Glu Lys Ser His Glu Cys Ser Gly Ala Pro Ile Phe
        515                 520                 525

Ile Arg Ala Ser Asn Phe Lys Leu Pro Ser Asn Pro Ser Thr Pro Ile
```

```
              530                 535                 540
Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Leu Gly Ser Ser
                565                 570                 575

Leu Leu Phe Phe Gly Cys Arg Asn Arg Gln Met Asp Phe Ile Tyr Glu
                580                 585                 590

Asp Glu Leu Asn Asn Phe Val Asp Gln Gly Val Ile Ser Glu Leu Ile
                595                 600                 605

Met Ala Phe Ser Arg Glu Gly Ala Gln Lys Glu Tyr Val Gln His Lys
                610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Glu Gln Glu Gly Val Ser Ser Ser
                660                 665                 670

Glu Ala Glu Ala Ile Val Lys Lys Leu Gln Thr Glu Gly Arg Tyr Leu
                675                 680                 685

Arg Asp Val Trp
            690

<210> SEQ ID NO 22
<211> LENGTH: 713
<212> TYPE: PRT
<213> ORGANISM: Fusarium fujikuroi

<400> SEQUENCE: 22

Met Ala Glu Leu Asp Thr Leu Asp Ile Val Val Leu Gly Val Ile Phe
1               5                   10                  15

Leu Gly Thr Val Ala Tyr Phe Thr Lys Gly Lys Leu Trp Gly Val Thr
                20                  25                  30

Lys Asp Pro Tyr Ala Asn Gly Phe Ala Ala Gly Gly Ala Ser Lys Pro
                35                  40                  45

Gly Arg Thr Arg Asn Ile Val Glu Ala Met Glu Glu Ser Gly Lys Asn
            50                  55                  60

Cys Val Val Phe Tyr Gly Ser Gln Thr Gly Thr Ala Glu Asp Tyr Ala
65                  70                  75                  80

Ser Arg Leu Ala Lys Glu Gly Lys Ser Arg Phe Gly Leu Asn Thr Met
                85                  90                  95

Ile Ala Asp Leu Glu Asp Tyr Asp Phe Asp Asn Leu Asp Thr Val Pro
                100                 105                 110

Ser Asp Asn Ile Val Met Phe Val Leu Ala Thr Tyr Gly Glu Gly Glu
                115                 120                 125

Pro Thr Asp Asn Ala Val Asp Phe Tyr Glu Phe Ile Thr Gly Glu Asp
                130                 135                 140

Ala Ser Phe Asn Glu Gly Asn Asp Pro Pro Leu Gly Asn Leu Asn Tyr
145                 150                 155                 160

Val Ala Phe Gly Leu Gly Asn Asn Thr Tyr Glu His Tyr Asn Ser Met
                165                 170                 175

Val Arg Asn Val Asn Lys Ala Leu Glu Lys Leu Gly Ala His Arg Ile
                180                 185                 190

Gly Glu Ala Gly Glu Gly Asp Asp Gly Ala Gly Thr Met Glu Glu Asp
                195                 200                 205
```

```
Phe Leu Ala Trp Lys Asp Pro Met Trp Glu Ala Leu Ala Lys Lys Met
    210                 215                 220

Gly Leu Glu Glu Arg Glu Ala Val Tyr Glu Pro Ile Phe Ala Ile Asn
225                 230                 235                 240

Glu Arg Asp Asp Leu Thr Pro Glu Ala Asn Glu Val Tyr Leu Gly Glu
                245                 250                 255

Pro Asn Lys Leu His Leu Glu Gly Thr Ala Lys Gly Pro Phe Asn Ser
            260                 265                 270

His Asn Pro Tyr Ile Ala Pro Ala Glu Ser Tyr Glu Leu Phe Ser
            275                 280                 285

Ala Lys Asp Arg Asn Cys Leu His Met Glu Ile Asp Ile Ser Gly Ser
290                 295                 300

Asn Leu Lys Tyr Glu Thr Gly Asp His Ile Ala Ile Trp Pro Thr Asn
305                 310                 315                 320

Pro Gly Glu Glu Val Asn Lys Phe Leu Asp Ile Leu Asp Leu Ser Gly
                325                 330                 335

Lys Gln His Ser Val Val Thr Val Lys Ala Leu Glu Pro Thr Ala Lys
            340                 345                 350

Val Pro Phe Pro Asn Pro Thr Thr Tyr Asp Ala Ile Leu Arg Tyr His
            355                 360                 365

Leu Glu Ile Cys Ala Pro Val Ser Arg Gln Phe Val Ser Thr Leu Ala
    370                 375                 380

Ala Phe Ala Pro Asn Asp Ile Lys Ala Glu Met Asn Arg Leu Gly
385                 390                 395                 400

Ser Asp Lys Asp Tyr Phe His Glu Lys Thr Gly Pro His Tyr Tyr Asn
                405                 410                 415

Ile Ala Arg Phe Leu Ala Ser Val Ser Lys Gly Glu Lys Trp Thr Lys
                420                 425                 430

Ile Pro Phe Ser Ala Phe Ile Glu Gly Leu Thr Lys Leu Gln Pro Arg
            435                 440                 445

Tyr Tyr Ser Ile Ser Ser Ser Leu Val Gln Pro Lys Lys Ile Ser
    450                 455                 460

Ile Thr Ala Val Val Glu Ser Gln Gln Ile Pro Gly Arg Asp Asp Pro
465                 470                 475                 480

Phe Arg Gly Val Ala Thr Asn Tyr Leu Phe Ala Leu Lys Gln Lys Gln
                485                 490                 495

Asn Gly Asp Pro Asn Pro Ala Pro Phe Gly Gln Ser Tyr Glu Leu Thr
            500                 505                 510

Gly Pro Arg Asn Lys Tyr Asp Gly Ile His Val Pro Val His Val Arg
            515                 520                 525

His Ser Asn Phe Lys Leu Pro Ser Asp Pro Gly Lys Pro Ile Ile Met
    530                 535                 540

Ile Gly Pro Gly Thr Gly Val Ala Pro Phe Arg Gly Phe Val Gln Glu
545                 550                 555                 560

Arg Ala Lys Gln Ala Arg Asp Gly Val Glu Val Gly Lys Thr Leu Leu
                565                 570                 575

Phe Phe Gly Cys Arg Lys Ser Thr Glu Asp Phe Met Tyr Gln Lys Glu
            580                 585                 590

Trp Gln Glu Tyr Lys Glu Ala Leu Gly Asp Lys Phe Glu Met Ile Thr
            595                 600                 605

Ala Phe Ser Arg Glu Gly Ser Lys Lys Val Tyr Val Gln His Arg Leu
    610                 615                 620

Lys Glu Arg Ser Lys Glu Val Ser Asp Leu Leu Ser Gln Lys Ala Tyr
```

```
                625                 630                 635                 640
Phe Tyr Val Cys Gly Asp Ala Ala His Met Ala Arg Glu Val Asn Thr
                    645                 650                 655

Val Leu Ala Gln Ile Ile Ala Glu Gly Arg Gly Val Ser Glu Ala Lys
                660                 665                 670

Gly Glu Glu Ile Val Lys Asn Met Arg Ser Ala Asn Gln Tyr Gln Val
            675                 680                 685

Cys Ser Asp Phe Val Thr Leu His Cys Lys Glu Thr Thr Tyr Ala Asn
        690                 695                 700

Ser Glu Leu Gln Glu Asp Val Trp Ser
705                 710

<210> SEQ ID NO 23
<211> LENGTH: 2130
<212> TYPE: DNA
<213> ORGANISM: Stevia rebaudiana

<400> SEQUENCE: 23
atgcaatcgg aatccgttga agcatcgacg attgatttga tgactgctgt tttgaaggac        60
acagtgatcg atacagcgaa cgcatctgat aacggagact caaagatgcc gccggcgttg       120
gcgatgatgt tcgaaattcg tgatctgttg ctgattttga ctacgtcagt tgctgttttg       180
gtcggatgtt tcgttgtttt ggtgtggaag agatcgtccg ggaagaagtc cggcaaggaa       240
ttggagccgc cgaagatcgt tgtgccgaag aggcggctgg agcaggaggt tgatgatggt       300
aagaagaagg ttacgatttt cttcggaaca caaactggaa cggctgaagg tttcgctaag       360
gcacttttcg aagaagcgaa agcgcgatat gaaaaggcag cgtttaaagt gattgatttg       420
gatgattatg ctgctgattt ggatgagtat gcagagaagc tgaagaagga acatatgct        480 ttcttcttct tggctacata tggagatggt gagccaactg ataatgctgc caaatttat       540 aaatggttta ctgagggaga cgagaaaggc gtttggcttc aaaaacttca atatggagta       600
tttggtcttg gcaacagaca atatgaacat tcaacaagaa ttggaatagt ggttgatgat       660
ggtctcaccg agcagggtgc aaaacgcatt gttcccgttg gtcttggaga cgacgatcaa       720
tcaattgaag acgatttttc ggcatggaaa gagttagtgt ggcccgaatt ggatctattg       780
cttcgcgatg aagatgacaa agctgctgca actccttaca cagctgcaat ccctgaatac       840
cgcgtcgtat tcatgacaa acccgatgcg ttttctgatg atcatactca aaccaatggt       900
catgctgttc atgatgctca acatccatgc agatccaatg tggctgttaa aaaagagctt       960
catactcctg aatccgatcg ttcatgcaca tcttgaat ttgacatttc tcacactgga      1020
ttatcttatg aaactgggga tcatgttggt gtatactgtg aaaacctaat gaagtagtg      1080 gaagaagctg ggaaattgtt aggattatca acagatactt atttctcgtt acatattgat      1140
aacgaagatg gttcaccact tggtggacct tcattacaac ctccttttcc tccttgtact      1200
ttaagaaaag cattgactaa ttatgcagat ctgttaagct ctcccaaaaa gtcaactttg      1260
cttgctctag ctgctcatgc ttccgatccc actgaagctg atcgtttaag atttcttgca      1320
tctcgcgagg gcaaggatga atatgctgaa tgggttgttg caaaccaaag aagtcttctt      1380
gaagtcatgg aagctttccc gtcagctaga ccgccacttg gtgttttctt tgcagcggtt      1440
gcaccgcgtt tacagcctcg ttactactct atttcttcct ccccaaagat ggaaccaaac      1500
aggattcatg ttacttgcgc gttggtttat gaaaaaactc ccgcaggtcg tatccacaaa      1560
ggaatctgct caacctggat gaagaacgct gtaccttga ccgaaagtca agattgcagt       1620
```

```
tgggcaccga ttttgttag aacatcaaac ttcagacttc caattgaccc gaaagtcccg    1680
gttatcatga ttggtcctgg aaccggggttg gctccattta ggggttttct tcaagaaaga    1740
ttggctctta aagaatccgg aaccgaactc gggtcatcta tttattctt cggttgtaga    1800 aaccgcaaag tggattacat atatgagaat gaactcaaca actttgttga aaatggtgcg    1860
ctttctgagc ttgatgttgc tttctcccgc gatggcccga cgaaagaata cgtgcaacat    1920
aaaatgaccc aaaaggcttc tgaaatatgg aatatgcttt ctgagggagc atatttatat    1980
gtatgtggtg atgctaaagg catggctaaa gatgtacacc gtacacttca caccattgtg    2040
caagaacagg gaagtttgga ctcgtctaaa gcggagttgt atgtgaagaa tctacaaatg    2100
tcaggaagat acctccgtga tgtttggtaa                                    2130

<210> SEQ ID NO 24
<211> LENGTH: 2124
<212> TYPE: DNA
<213> ORGANISM: Stevia rebaudiana

<400> SEQUENCE: 24
atgcaatcta actccgtgaa gatttcgccg cttgatctgg taactgcgct gtttagcggc      60
aaggttttgg acacatcgaa cgcatcggaa tcgggagaat ctgctatgct gccgactata     120
gcgatgatta tggagaatcg tgagctgttg atgatactca caacgtcggt tgctgtattg     180
atcggatgcg ttgtcgtttt ggtgtggcgg agatcgtcta cgaagaagtc ggcgttggag     240
ccaccggtga ttgtggttcc gaagagagtg caagaggagg aagttgatga tggtaagaag     300
aaagttacgg ttttcttcgg caccaaact ggaacagctg aaggcttcgc taaggcactt     360
gttgaggaag ctaaagctcg atatgaaaag gctgtcttta agtaattga tttggatgat     420 tatgctgctg atgacgatga gtatgaggag aaactaaaga aagaatcttt ggccttttc      480 tttttggcta cgtatggaga tggtgagcca acagataatg ctgccagatt ttataaatgg     540
tttactgagg gagatgcgaa aggagaatgg cttaataagc ttcaatatgg agtatttggt     600
ttgggtaaca gacaatatga acattttaac aagatcgcaa agtggttga tgatggtctt     660 gtagaacagg gtgcaaagcg tcttgttcct gttggacttg gagatgatga tcaatgtatt     720
gaagatgact tcaccgcatg gaaagagtta gtatggccgg agttggatca attacttcgt     780
gatgaggatg cacaactgt tgctactcca tacacagctg ctgttgcaga atatcgcgtt     840 gttttcatg aaaaaccaga cgcgcttcct gaagattata gttatacaaa tggccatgct     900
gttcatgatg ctcaacatcc atgcagatcc aacgtggctg tcaaaaagga acttcatagt     960
cctgaatctg accggtcttg cactcatctt gaatttgaca tctcgaacac cggactatca    1020
tatgaaactg gggaccatgt tggagtttac tgtgaaaact tgagtgaagt tgtgaatgat    1080
gctgaaagat tagtaggatt accaccagac acttactcct ccatccacac tgatagtgaa    1140
gacgggtcgc cacttggcgg agcctcattg ccgcctcctt tcccgccatg cactttaagg    1200
aaagcattga cgtgttatgc tgatgttttg agttctccca gaagtcggc tttgcttgca    1260 ctagctgctc atgccaccga tcccagtgaa gctgatagat tgaaatttct tgcatccccc    1320
gccgaaaagg atgaatattc tcaatggata gttgcaagcc aaagaagtct ccttgaagtc    1380
atggaagcat tcccgtcagc taagccttca cttggtgttt tcttttgcatc tgttgccccg    1440 cgcttacaac caagatacta ctctatttct tcctcaccca agatggcacc ggataggatt    1500
catgttacat gtgcattagt ctatgagaaa acacctgcag gccgcatcca caagggagtt    1560
tgttcaactt ggatgaagaa cgcagtgcct atgaccgaga gtcaagattg cagttgggcc    1620
```

-continued

```
ccaatatacg tccgaacatc caatttcaga ctaccatctg accctaaggt cccggttatc    1680
atgattggac ctggcactgg tttggctcct tttagaggtt ccttcaaga gcggttagct     1740 ttaaaggaag ccggaactga cctcggttta ccattttat tcttcggatg taggaatcgc    1800
aaagtggatt tcatatatga aaacgagctt aacaactttg tggagactgg tgctctttct    1860
gagcttattg ttgctttctc ccgtgaaggc ccgactaagg aatatgtgca acacaagatg    1920
agtgagaagg cttcggatat ctggaacttg ctttctgaag gagcatattt atacgtatgt    1980
ggtgatgcca aaggcatggc caaagatgta catcgaaccc tccacacaat tgtgcaagaa    2040
cagggatctc ttgactcgtc aaaggcagaa ctctacgtga agaatctaca aatgtcagga    2100
agatacctcc gtgacgtttg gtaa                                          2124
```

<210> SEQ ID NO 25
<211> LENGTH: 692
<212> TYPE: PRT
<213> ORGANISM: Arabidopsis thaliana

<400> SEQUENCE: 25

```
Met Thr Ser Ala Leu Tyr Ala Ser Asp Leu Phe Lys Gln Leu Lys Ser
1               5                   10                  15

Ile Met Gly Thr Asp Ser Leu Ser Asp Asp Val Val Leu Val Ile Ala
                20                  25                  30

Thr Thr Ser Leu Ala Leu Val Ala Gly Phe Val Val Leu Leu Trp Lys
            35                  40                  45

Lys Thr Thr Ala Asp Arg Ser Gly Glu Leu Lys Pro Leu Met Ile Pro
    50                  55                  60

Lys Ser Leu Met Ala Lys Asp Glu Asp Asp Leu Asp Leu Gly Ser
65                  70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
            100                 105                 110

Lys Ala Val Lys Val Ile Asp Leu Asp Asp Tyr Ala Ala Asp Asp
        115                 120                 125

Asp Gln Tyr Glu Glu Lys Leu Lys Lys Glu Thr Leu Ala Phe Phe Cys
    130                 135                 140

Val Ala Thr Tyr Gly Asp Gly Glu Pro Thr Asp Asn Ala Ala Arg Phe
145                 150                 155                 160

Tyr Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
            180                 185                 190

Asn Lys Ile Gly Ile Val Leu Asp Glu Glu Leu Cys Lys Lys Gly Ala
        195                 200                 205

Lys Arg Leu Ile Glu Val Gly Leu Gly Asp Asp Gln Ser Ile Glu
    210                 215                 220

Asp Asp Phe Asn Ala Trp Lys Glu Ser Leu Trp Ser Glu Leu Asp Lys
225                 230                 235                 240

Leu Leu Lys Asp Glu Asp Asp Lys Ser Val Ala Thr Pro Tyr Thr Ala
                245                 250                 255

Val Ile Pro Glu Tyr Arg Val Val Thr His Asp Pro Arg Phe Thr Thr
            260                 265                 270

Gln Lys Ser Met Glu Ser Asn Val Ala Asn Gly Asn Thr Thr Ile Asp
```

```
            275                 280                 285
Ile His His Pro Cys Arg Val Asp Val Ala Val Gln Lys Glu Leu His
            290                 295                 300
Thr His Glu Ser Asp Arg Ser Cys Ile His Leu Glu Phe Asp Ile Ser
305                 310                 315                 320
Arg Thr Gly Ile Thr Tyr Glu Thr Gly Asp His Val Gly Val Tyr Ala
                325                 330                 335
Glu Asn His Val Glu Ile Val Glu Ala Gly Lys Leu Leu Gly His
            340                 345                 350
Ser Leu Asp Leu Val Phe Ser Ile His Ala Asp Lys Glu Asp Gly Ser
            355                 360                 365
Pro Leu Glu Ser Ala Val Pro Pro Phe Pro Gly Pro Cys Thr Leu
    370                 375                 380
Gly Thr Gly Leu Ala Arg Tyr Ala Asp Leu Leu Asn Pro Pro Arg Lys
385                 390                 395                 400
Ser Ala Leu Val Ala Leu Ala Ala Tyr Ala Thr Glu Pro Ser Glu Ala
                405                 410                 415
Glu Lys Leu Lys His Leu Thr Ser Pro Asp Gly Lys Asp Glu Tyr Ser
            420                 425                 430
Gln Trp Ile Val Ala Ser Gln Arg Ser Leu Leu Glu Val Met Ala Ala
            435                 440                 445
Phe Pro Ser Ala Lys Pro Pro Leu Gly Val Phe Phe Ala Ala Ile Ala
    450                 455                 460
Pro Arg Leu Gln Pro Arg Tyr Tyr Ser Ile Ser Ser Pro Arg Leu
465                 470                 475                 480
Ala Pro Ser Arg Val His Val Thr Ser Ala Leu Val Tyr Gly Pro Thr
                485                 490                 495
Pro Thr Gly Arg Ile His Lys Gly Val Cys Ser Thr Trp Met Lys Asn
            500                 505                 510
Ala Val Pro Ala Glu Lys Ser His Glu Cys Ser Gly Ala Pro Ile Phe
            515                 520                 525
Ile Arg Ala Ser Asn Phe Lys Leu Pro Ser Asn Pro Ser Thr Pro Ile
    530                 535                 540
Val Met Val Gly Pro Gly Thr Gly Leu Ala Pro Phe Arg Gly Phe Leu
545                 550                 555                 560
Gln Glu Arg Met Ala Leu Lys Glu Asp Gly Glu Glu Leu Gly Ser Ser
                565                 570                 575
Leu Leu Phe Phe Gly Cys Arg Asn Arg Gln Met Asp Phe Ile Tyr Glu
            580                 585                 590
Asp Glu Leu Asn Asn Phe Val Asp Gln Gly Val Ile Ser Glu Leu Ile
            595                 600                 605
Met Ala Phe Ser Arg Glu Gly Ala Gln Lys Glu Tyr Val Gln His Lys
    610                 615                 620
Met Met Glu Lys Ala Ala Gln Val Trp Asp Leu Ile Lys Glu Gly
625                 630                 635                 640
Tyr Leu Tyr Val Cys Gly Asp Ala Lys Gly Met Ala Arg Asp Val His
                645                 650                 655
Arg Thr Leu His Thr Ile Val Gln Glu Gln Gly Val Ser Ser Ser
            660                 665                 670
Glu Ala Glu Ala Ile Val Lys Lys Leu Gln Thr Glu Gly Arg Tyr Leu
            675                 680                 685
Arg Asp Val Trp
    690
```

```
<210> SEQ ID NO 26
<211> LENGTH: 712
<212> TYPE: PRT
<213> ORGANISM: Arabidopsis thaliana

<400> SEQUENCE: 26

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
                20                  25                  30

Ser Ala Tyr Glu Ser Val Ala Ala Glu Leu Ser Ser Met Leu Ile Glu
            35                  40                  45

Asn Arg Gln Phe Ala Met Ile Val Thr Thr Ser Ile Ala Val Leu Ile
        50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
                100                 105                 110

Thr Gly Thr Ala Glu Gly Phe Ala Lys Ala Leu Gly Glu Glu Ala Lys
            115                 120                 125

Ala Arg Tyr Glu Lys Thr Arg Phe Lys Ile Val Asp Leu Asp Asp Tyr
        130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Thr Leu Ala Asn Gly Asn Gly Tyr
    290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Met Lys Leu Gly Asp His Val
            340                 345                 350

Gly Val Leu Cys Asp Asn Leu Ser Glu Thr Val Asp Glu Ala Leu Arg
        355                 360                 365

Leu Leu Asp Met Ser Pro Asp Thr Tyr Phe Ser Leu His Ala Glu Lys
```

```
                370                 375                 380
Glu Asp Gly Thr Pro Ile Ser Ser Leu Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
            420                 425                 430

Thr Glu Ala Glu Arg Leu Lys His Leu Ala Ser Pro Ala Gly Lys Asp
        435                 440                 445

Glu Tyr Ser Lys Trp Val Val Glu Ser Gln Arg Ser Leu Leu Glu Val
450                 455                 460

Met Ala Glu Phe Pro Ser Ala Lys Pro Pro Leu Gly Val Phe Phe Ala
465                 470                 475                 480

Gly Val Ala Pro Arg Leu Gln Pro Arg Phe Tyr Ser Ile Ser Ser Ser
                485                 490                 495

Pro Lys Ile Ala Glu Thr Arg Ile His Val Thr Cys Ala Leu Val Tyr
            500                 505                 510

Glu Lys Met Pro Thr Gly Arg Ile His Lys Gly Val Cys Ser Thr Trp
        515                 520                 525

Met Lys Asn Ala Val Pro Tyr Glu Lys Ser Glu Lys Leu Phe Leu Gly
530                 535                 540

Arg Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
            580                 585                 590

Leu Gly Pro Ser Val Leu Phe Phe Gly Cys Arg Asn Arg Arg Met Asp
        595                 600                 605

Phe Ile Tyr Glu Glu Glu Leu Gln Arg Phe Val Glu Ser Gly Ala Leu
610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
        675                 680                 685

Met Asp Ser Thr Lys Ala Glu Gly Phe Val Lys Asn Leu Gln Thr Ser
690                 695                 700

Gly Arg Tyr Leu Arg Asp Val Trp
705                 710

<210> SEQ ID NO 27
<211> LENGTH: 709
<212> TYPE: PRT
<213> ORGANISM: Stevia rebaudiana

<400> SEQUENCE: 27

Met Gln Ser Glu Ser Val Glu Ala Ser Thr Ile Asp Leu Met Thr Ala
1               5                   10                  15

Val Leu Lys Asp Thr Val Ile Asp Thr Ala Asn Ala Ser Asp Asn Gly
            20                  25                  30
```

-continued

Asp Ser Lys Met Pro Pro Ala Leu Ala Met Met Phe Glu Ile Arg Asp
         35                  40                  45

Leu Leu Leu Ile Leu Thr Thr Ser Val Ala Val Leu Val Gly Cys Phe
 50                      55                  60

Val Val Leu Val Trp Lys Arg Ser Ser Gly Lys Lys Ser Gly Lys Glu
 65                  70                  75                  80

Leu Glu Pro Pro Lys Ile Val Pro Lys Arg Leu Glu Gln Glu
                 85                  90                  95

Val Asp Asp Gly Lys Lys Val Thr Ile Phe Phe Gly Thr Gln Thr
             100                 105                 110

Gly Thr Ala Glu Gly Phe Ala Lys Ala Leu Phe Glu Glu Ala Lys Ala
             115                 120                 125

Arg Tyr Glu Lys Ala Ala Phe Lys Val Ile Asp Leu Asp Asp Tyr Ala
 130                 135                 140

Ala Asp Leu Asp Glu Tyr Ala Glu Lys Leu Lys Lys Glu Thr Tyr Ala
145                 150                 155                 160

Phe Phe Phe Leu Ala Thr Tyr Gly Asp Gly Glu Pro Thr Asp Asn Ala
                 165                 170                 175

Ala Lys Phe Tyr Lys Trp Phe Thr Glu Gly Asp Glu Lys Gly Val Trp
             180                 185                 190

Leu Gln Lys Leu Gln Tyr Gly Val Phe Gly Leu Gly Asn Arg Gln Tyr
             195                 200                 205

Glu His Phe Asn Lys Ile Gly Ile Val Val Asp Asp Gly Leu Thr Glu
             210                 215                 220

Gln Gly Ala Lys Arg Ile Val Pro Val Gly Leu Gly Asp Asp Asp Gln
225                 230                 235                 240

Ser Ile Glu Asp Asp Phe Ser Ala Trp Lys Glu Leu Val Trp Pro Glu
                 245                 250                 255

Leu Asp Leu Leu Leu Arg Asp Glu Asp Asp Lys Ala Ala Ala Thr Pro
             260                 265                 270

Tyr Thr Ala Ala Ile Pro Glu Tyr Arg Val Val Phe His Asp Lys Pro
             275                 280                 285

Asp Ala Phe Ser Asp Asp His Thr Gln Thr Asn Gly His Ala Val His
             290                 295                 300

Asp Ala Gln His Pro Cys Arg Ser Asn Val Ala Val Lys Lys Glu Leu
305                 310                 315                 320

His Thr Pro Glu Ser Asp Arg Ser Cys Thr His Leu Glu Phe Asp Ile
                 325                 330                 335

Ser His Thr Gly Leu Ser Tyr Glu Thr Gly Asp His Val Gly Val Tyr
             340                 345                 350

Cys Glu Asn Leu Ile Glu Val Val Glu Glu Ala Gly Lys Leu Leu Gly
             355                 360                 365

Leu Ser Thr Asp Thr Tyr Phe Ser Leu His Ile Asp Asn Glu Asp Gly
 370                 375                 380

Ser Pro Leu Gly Gly Pro Ser Leu Gln Pro Pro Phe Pro Pro Cys Thr
385                 390                 395                 400

Leu Arg Lys Ala Leu Thr Asn Tyr Ala Asp Leu Leu Ser Ser Pro Lys
             405                 410                 415

Lys Ser Thr Leu Leu Ala Leu Ala Ala His Ala Ser Asp Pro Thr Glu
             420                 425                 430

Ala Asp Arg Leu Arg Phe Leu Ala Ser Arg Glu Gly Lys Asp Glu Tyr
             435                 440                 445

Ala Glu Trp Val Val Ala Asn Gln Arg Ser Leu Leu Glu Val Met Glu

```
                450                 455                 460
Ala Phe Pro Ser Ala Arg Pro Pro Leu Gly Val Phe Ala Ala Val
465                 470                 475                 480

Ala Pro Arg Leu Gln Pro Arg Tyr Tyr Ser Ile Ser Ser Pro Lys
                485                 490                 495

Met Glu Pro Asn Arg Ile His Val Thr Cys Ala Leu Val Tyr Glu Lys
                500                 505                 510

Thr Pro Ala Gly Arg Ile His Lys Gly Ile Cys Ser Thr Trp Met Lys
                515                 520                 525

Asn Ala Val Pro Leu Thr Glu Ser Gln Asp Cys Ser Trp Ala Pro Ile
530                 535                 540

Phe Val Arg Thr Ser Asn Phe Arg Leu Pro Ile Asp Pro Lys Val Pro
545                 550                 555                 560

Val Ile Met Ile Gly Pro Gly Thr Gly Leu Ala Pro Phe Arg Gly Phe
                565                 570                 575

Leu Gln Glu Arg Leu Ala Leu Lys Glu Ser Gly Thr Glu Leu Gly Ser
                580                 585                 590

Ser Ile Leu Phe Phe Gly Cys Arg Asn Arg Lys Val Asp Tyr Ile Tyr
                595                 600                 605

Glu Asn Glu Leu Asn Asn Phe Val Glu Asn Gly Ala Leu Ser Glu Leu
                610                 615                 620

Asp Val Ala Phe Ser Arg Asp Gly Pro Thr Lys Glu Tyr Val Gln His
625                 630                 635                 640

Lys Met Thr Gln Lys Ala Ser Glu Ile Trp Asn Met Leu Ser Glu Gly
                645                 650                 655

Ala Tyr Leu Tyr Val Cys Gly Asp Ala Lys Gly Met Ala Lys Asp Val
                660                 665                 670

His Arg Thr Leu His Thr Ile Val Gln Glu Gly Ser Leu Asp Ser
                675                 680                 685

Ser Lys Ala Glu Leu Tyr Val Lys Asn Leu Gln Met Ser Gly Arg Tyr
                690                 695                 700

Leu Arg Asp Val Trp
705

<210> SEQ ID NO 28
<211> LENGTH: 707
<212> TYPE: PRT
<213> ORGANISM: Stevia rebaudiana

<400> SEQUENCE: 28

Met Gln Ser Asn Ser Val Lys Ile Ser Pro Leu Asp Leu Val Thr Ala
1                   5                   10                  15

Leu Phe Ser Gly Lys Val Leu Asp Thr Ser Asn Ala Ser Glu Ser Gly
                20                  25                  30

Glu Ser Ala Met Leu Pro Thr Ile Ala Met Ile Met Glu Asn Arg Glu
            35                  40                  45

Leu Leu Met Ile Leu Thr Thr Ser Val Ala Val Leu Ile Gly Cys Val
        50                  55                  60

Val Val Leu Val Trp Arg Arg Ser Ser Thr Lys Lys Ser Ala Leu Glu
65                  70                  75                  80

Pro Pro Val Ile Val Pro Lys Arg Val Gln Glu Glu Glu Val Asp
                85                  90                  95

Asp Gly Lys Lys Lys Val Thr Val Phe Phe Gly Thr Gln Thr Gly Thr
                100                 105                 110
```

Ala Glu Gly Phe Ala Lys Ala Leu Val Glu Ala Lys Ala Arg Tyr
            115                 120                 125

Glu Lys Ala Val Phe Lys Val Ile Asp Leu Asp Asp Tyr Ala Ala Asp
        130                 135                 140

Asp Asp Glu Tyr Glu Glu Lys Leu Lys Lys Glu Ser Leu Ala Phe Phe
145                 150                 155                 160

Phe Leu Ala Thr Tyr Gly Asp Gly Glu Pro Thr Asp Asn Ala Ala Arg
                165                 170                 175

Phe Tyr Lys Trp Phe Thr Glu Gly Asp Ala Lys Gly Glu Trp Leu Asn
            180                 185                 190

Lys Leu Gln Tyr Gly Val Phe Gly Leu Gly Asn Arg Gln Tyr Glu His
        195                 200                 205

Phe Asn Lys Ile Ala Lys Val Val Asp Asp Gly Leu Val Glu Gln Gly
210                 215                 220

Ala Lys Arg Leu Val Pro Val Gly Leu Gly Asp Asp Gln Cys Ile
225                 230                 235                 240

Glu Asp Asp Phe Thr Ala Trp Lys Glu Leu Val Trp Pro Glu Leu Asp
                245                 250                 255

Gln Leu Leu Arg Asp Glu Asp Thr Thr Val Ala Thr Pro Tyr Thr
            260                 265                 270

Ala Ala Val Ala Glu Tyr Arg Val Val Phe His Glu Lys Pro Asp Ala
        275                 280                 285

Leu Ser Glu Asp Tyr Ser Tyr Thr Asn Gly His Ala Val His Asp Ala
290                 295                 300

Gln His Pro Cys Arg Ser Asn Val Ala Val Lys Lys Glu Leu His Ser
305                 310                 315                 320

Pro Glu Ser Asp Arg Ser Cys Thr His Leu Glu Phe Asp Ile Ser Asn
                325                 330                 335

Thr Gly Leu Ser Tyr Glu Thr Gly Asp His Val Gly Val Tyr Cys Glu
            340                 345                 350

Asn Leu Ser Glu Val Val Asn Asp Ala Glu Arg Leu Val Gly Leu Pro
        355                 360                 365

Pro Asp Thr Tyr Ser Ser Ile His Thr Asp Ser Glu Asp Gly Ser Pro
370                 375                 380

Leu Gly Gly Ala Ser Leu Pro Pro Phe Pro Pro Cys Thr Leu Arg
385                 390                 395                 400

Lys Ala Leu Thr Cys Tyr Ala Asp Val Leu Ser Ser Pro Lys Lys Ser
                405                 410                 415

Ala Leu Leu Ala Leu Ala Ala His Ala Thr Asp Pro Ser Glu Ala Asp
            420                 425                 430

Arg Leu Lys Phe Leu Ala Ser Pro Ala Gly Lys Asp Glu Tyr Ser Gln
        435                 440                 445

Trp Ile Val Ala Ser Gln Arg Ser Leu Leu Glu Val Met Glu Ala Phe
450                 455                 460

Pro Ser Ala Lys Pro Ser Leu Gly Val Phe Phe Ala Ser Val Ala Pro
465                 470                 475                 480

Arg Leu Gln Pro Arg Tyr Tyr Ser Ile Ser Ser Ser Pro Lys Met Ala
                485                 490                 495

Pro Asp Arg Ile His Val Thr Cys Ala Leu Val Tyr Glu Lys Thr Pro
            500                 505                 510

Ala Gly Arg Ile His Lys Gly Val Cys Ser Thr Trp Met Lys Asn Ala
        515                 520                 525

Val Pro Met Thr Glu Ser Gln Asp Cys Ser Trp Ala Pro Ile Tyr Val

```
                    530                 535                 540
Arg Thr Ser Asn Phe Arg Leu Pro Ser Asp Pro Lys Val Pro Val Ile
545                 550                 555                 560

Met Ile Gly Pro Gly Thr Gly Leu Ala Pro Phe Arg Gly Phe Leu Gln
                565                 570                 575

Glu Arg Leu Ala Leu Lys Glu Ala Gly Thr Asp Leu Gly Leu Ser Ile
                580                 585                 590

Leu Phe Phe Gly Cys Arg Asn Arg Lys Val Asp Phe Ile Tyr Glu Asn
                595                 600                 605

Glu Leu Asn Asn Phe Val Glu Thr Gly Ala Leu Ser Glu Leu Ile Val
                610                 615                 620

Ala Phe Ser Arg Glu Gly Pro Thr Lys Glu Tyr Val Gln His Lys Met
625                 630                 635                 640

Ser Glu Lys Ala Ser Asp Ile Trp Asn Leu Leu Ser Glu Gly Ala Tyr
                645                 650                 655

Leu Tyr Val Cys Gly Asp Ala Lys Gly Met Ala Lys Asp Val His Arg
                660                 665                 670

Thr Leu His Thr Ile Val Gln Glu Gln Gly Ser Leu Asp Ser Ser Lys
                675                 680                 685

Ala Glu Leu Tyr Val Lys Asn Leu Gln Met Ser Gly Arg Tyr Leu Arg
                690                 695                 700

Asp Val Trp
705

<210> SEQ ID NO 29
<211> LENGTH: 460
<212> TYPE: PRT
<213> ORGANISM: Stevia rebaudiana

<400> SEQUENCE: 29

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
                20                  25                  30

Arg Leu Ile Ser Lys Gly Val Lys Thr Thr Leu Val Thr Thr Ile His
                35                  40                  45

Thr Leu Asn Ser Thr Leu Asn His Ser Asn Thr Thr Thr Thr Ser Ile
            50                  55                  60

Glu Ile Gln Ala Ile Ser Asp Gly Cys Asp Glu Gly Gly Phe Met Ser
65              70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
                100                 105                 110

Ala Ile Ile Tyr Asp Ser Met Thr Glu Trp Val Leu Asp Val Ala Ile
                115                 120                 125

Glu Phe Gly Ile Asp Gly Gly Ser Phe Phe Thr Gln Ala Cys Val Val
                130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
                180                 185                 190
```

-continued

Gln Met Leu Phe Gly Gln Phe Ala Asn Ile Asp Gln Ala Arg Trp Val
            195                 200                 205

Phe Thr Asn Ser Phe Tyr Lys Leu Glu Glu Val Ile Glu Trp Thr
210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
            245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
            275                 280                 285

Pro Glu Gln Val Glu Glu Ile Thr Arg Ala Leu Ile Asp Ser Asp Val
            290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
                340                 345                 350

Thr His Cys Gly Phe Asn Ser Thr Leu Glu Ala Ile Ser Leu Gly Val
            355                 360                 365

Pro Val Val Ala Met Pro Gln Phe Ser Asp Gln Thr Thr Asn Ala Lys
            370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
                420                 425                 430

Lys Asp Leu Ala Lys Val Ala Val His Glu Gly Gly Ser Ser Asp Asn
            435                 440                 445

Asp Ile Val Glu Phe Val Ser Glu Leu Ile Lys Ala
            450                 455                 460

<210> SEQ ID NO 30
<211> LENGTH: 481
<212> TYPE: PRT
<213> ORGANISM: Stevia rebaudiana

<400> SEQUENCE: 30

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
                20                  25                  30

Leu Leu His His Lys Gly Leu Gln Ile Thr Phe Val Asn Thr Asp Phe
            35                  40                  45

Ile His Asn Gln Phe Leu Glu Ser Ser Gly Pro His Cys Leu Asp Gly
        50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
                180                 185                 190

Lys Asp Phe Pro Leu Asp Trp Ser Thr Asp Leu Asn Asp Lys Val Leu
                195                 200                 205

Met Phe Thr Thr Glu Ala Pro Gln Arg Ser His Lys Val Ser His His
210                 215                 220

Ile Phe His Thr Phe Asp Glu Leu Glu Pro Ser Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
                260                 265                 270

His Gly Tyr Ser Leu Val Lys Glu Glu Pro Glu Cys Phe Gln Trp Leu
                275                 280                 285

Gln Ser Lys Glu Pro Asn Ser Val Val Tyr Val Asn Phe Gly Ser Thr
                290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
                340                 345                 350

Arg Gly Phe Ile Ala Ser Trp Cys Ser Gln Glu Lys Val Leu Lys His
                355                 360                 365

Pro Ser Val Gly Gly Phe Leu Thr His Cys Gly Trp Gly Ser Thr Ile
                370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
                420                 425                 430

Gln Glu Leu Met Gly Glu Gly His Lys Met Arg Asn Lys Ala Lys
                435                 440                 445

Asp Trp Lys Glu Lys Ala Arg Ile Ala Ile Ala Pro Asn Gly Ser Ser
                450                 455                 460

Ser Leu Asn Ile Asp Lys Met Val Lys Glu Ile Thr Val Leu Ala Arg
465                 470                 475                 480

Asn

<210> SEQ ID NO 31
<211> LENGTH: 1586
<212> TYPE: DNA
<213> ORGANISM: Stevia rebaudiana

<400> SEQUENCE: 31

```
atggatgcaa tggctacaac tgagaagaaa ccacacgtca tcttcatacc atttccagca      60
caaagccaca ttaaagccat gctcaaacta gcacaacttc tccaccacaa aggactccag     120
ataaccttcg tcaacaccga cttcatccac aaccagtttc ttgaatcatc gggcccacat     180
tgtctagacg gtgcaccggg tttccggttc gaaaccattc cggatggtgt ttctcacagt     240
ccggaagcga gcatcccaat cagagaatca ctcttgagat ccattgaaac caacttcttg     300
gatcgtttca ttgatcttgt aaccaaactt ccggatcctc cgacttgtat tatctcagat     360
gggttcttgt cggttttcac aattgacgct gcaaaaaagc ttggaattcc ggtcatgatg     420
tattggacac ttgctgcctg tgggttcatg gttttttacc atattcattc tctcattgag     480
aaaggatttg caccacttaa agatgcaagt acttgacaa tgggtatttt ggacaccgtc     540
attgattggg ttccgggaat ggaaggcatc cgtctcaagg atttcccgct ggactggagc     600
actgacctca atgacaaagt tttgatgttc actacggaag ctcctcaaag gtcacacaag     660
gtttcacatc atattttcca cacgttcgat gagttggagc ctagtattat aaaaactttg     720
tcattgaggt ataatcacat ttacaccatc ggcccactgc aattacttct tgatcaaata     780
cccgaagaga aaaagcaaac tggaattacg agtctccatg gatacagttt agtaaaagaa     840
gaaccagagt gtttccagtg gcttcagtct aaagaaccaa attccgtcgt ttatgtaaat     900
tttggaagta ctacagtaat gtctttagaa gacatgacgg aatttggttg gggacttgct     960
aatagcaacc attatttcct ttggatcatc cgatcaaact ggtgataggg gaaaatgca    1020
gttttgcccc ctgaacttga ggaacatata agaaaagag ctttattgc tagctggtgt    1080
tcacaagaaa aggtcttgaa gcacccttcg gttggagggt tcttgactca ttgtgggtgg    1140
ggatcgacca tcgagagctt gtctgctggg gtgccaatga tatgctggcc ttattcgtgg    1200
gaccagctga ccaactgtag gtatatatgc aaagaatggg aggttgggct cgagatggga    1260
accaaagtga aacgagatga agtcaagagg cttgtacaag agttgatggg agaaggaggt    1320
cacaaaatga ggaacaaggc taaagattgg aaagaaaagg ctcgcattgc aatagctcct    1380
aacggttcat cttctttgaa catagacaaa atggtcaagg aaatcaccgt gctagcaaga    1440
aactagttac aaagttgttt cacattgtgc tttctattta agatgtaact tgttctaat    1500
ttaatattgt ctagatgtat tgaaccataa gtttagttgg tctcaggaat tgattttaa    1560
tgaaataatg gtcattaggg gtgagt                                        1586
```

<210> SEQ ID NO 32
<211> LENGTH: 1446
<212> TYPE: DNA
<213> ORGANISM: Artificial Sequence
<220> FEATURE:
<223> OTHER INFORMATION: Codon optimized nucleotide sequence encoding
      Stevia rebaudiana UGT85C2

<400> SEQUENCE: 32

```
atggatgcaa tggcaactac tgagaaaaag cctcatgtga tcttcattcc atttcctgca      60
caatctcaca taaaggcaat gctaaagtta gcacaactat acaccataa gggattacag     120
ataacttcg tgaataccga cttcatccat aatcaatttc tggaatctag tggccctcat     180
tgtttggacg gagccccagg gtttagattc gaaacaattc ctgacggtgt tcacattcc     240
ccagaggcct ccatcccaat aagagagagt ttactgaggt caatagaaac caactttttg     300
gatcgtttca ttgacttggt cacaaaactt ccagacccac caacttgcat aatctctgat     360
ggctttctgt cagtgtttac tatcgacgct gccaaaaagt tgggtatccc agttatgatg     420
```

```
tactggactc ttgctgcatg cggtttcatg ggtttctatc acatccattc tcttatcgaa      480
aagggttttg ctccactgaa agatgcatca tacttaacca acggctacct ggatactgtt      540
attgactggg taccaggtat ggaaggtata agacttaaag attttccttt ggattggtct      600
acagacctta atgataaagt attgatgttt actacagaag ctccacaaag atctcataag      660
gtttcacatc atatctttca cacctttgat gaattggaac catcaatcat caaaaccttg      720
tctctaagat acaatcatat ctacactatt ggtccattac aattacttct agatcaaatt      780
cctgaagaga aaaagcaaac tggtattaca tccttacacg gctactcttt agtgaaagag      840
gaaccagaat gttttcaatg ctacaaagt aaagagccta attctgtggt ctacgtcaac      900
ttcggaagta caacagtcat gtccttggaa gatatgactg aatttggttg gggccttgct      960
aattcaaatc attactttct atggattatc aggtccaatt tggtaatagg ggaaaacgcc     1020
gtattacctc cagaattgga ggaacacatc aaaagagag gtttcattgc ttcctggtgt     1080
tctcaggaaa aggtattgaa acatccttct gttggtggtt tccttactca ttgcggttgg     1140
ggctctacaa tcgaatcact aagtgcagga gttccaatga tttgttggcc atattcatgg     1200
gaccaactta caaattgtag gtatatctgt aaagagtggg aagttggatt agaaatggga     1260
acaaaggtta aacgtgatga agtgaaaaga ttggttcagg agttgatggg ggaaggtggc     1320
cacaagatga gaaacaaggc caagattgg aaggaaaaag ccagaattgc tattgctcct     1380
aacgggtcat cctctctaaa cattgataag atggtcaaag agattacagt cttagccaga     1440
aactaa                                                                1446
```

<210> SEQ ID NO 33
<211> LENGTH: 787
<212> TYPE: PRT
<213> ORGANISM: Stevia rebaudiana

<400> SEQUENCE: 33

```
Met Lys Thr Gly Phe Ile Ser Pro Ala Thr Val Phe His His Arg Ile
1               5                   10                  15

Ser Pro Ala Thr Thr Phe Arg His His Leu Ser Pro Ala Thr Thr Asn
            20                  25                  30

Ser Thr Gly Ile Val Ala Leu Arg Asp Ile Asn Phe Arg Cys Lys Ala
        35                  40                  45

Val Ser Lys Glu Tyr Ser Asp Leu Leu Gln Lys Asp Glu Ala Ser Phe
    50                  55                  60

Thr Lys Trp Asp Asp Lys Val Lys Asp His Leu Asp Thr Asn Lys
65                  70                  75                  80

Asn Leu Tyr Pro Asn Asp Glu Ile Lys Glu Phe Val Glu Ser Val Lys
                85                  90                  95

Ala Met Phe Gly Ser Met Asn Asp Gly Glu Ile Asn Val Ser Ala Tyr
            100                 105                 110

Asp Thr Ala Trp Val Ala Leu Val Gln Asp Val Asp Gly Ser Gly Ser
        115                 120                 125

Pro Gln Phe Pro Ser Ser Leu Glu Trp Ile Ala Asn Asn Gln Leu Ser
    130                 135                 140

Asp Gly Ser Trp Gly Asp His Leu Leu Phe Ser Ala His Asp Arg Ile
145                 150                 155                 160

Ile Asn Thr Leu Ala Cys Val Ile Ala Leu Thr Ser Trp Asn Val His
                165                 170                 175

Pro Ser Lys Cys Glu Lys Gly Leu Asn Phe Leu Arg Glu Asn Ile Cys
```

```
            180                 185                 190
Lys Leu Glu Asp Glu Asn Ala Glu His Met Pro Ile Gly Phe Glu Val
            195                 200                 205
Thr Phe Pro Ser Leu Ile Asp Ile Ala Lys Lys Leu Asn Ile Glu Val
            210                 215                 220
Pro Glu Asp Thr Pro Ala Leu Lys Glu Ile Tyr Ala Arg Arg Asp Ile
225                 230                 235                 240
Lys Leu Thr Lys Ile Pro Met Glu Val Leu His Lys Val Pro Thr Thr
                245                 250                 255
Leu Leu His Ser Leu Glu Gly Met Pro Asp Leu Glu Trp Glu Lys Leu
            260                 265                 270
Leu Lys Leu Gln Cys Lys Asp Gly Ser Phe Leu Phe Ser Pro Ser Ser
            275                 280                 285
Thr Ala Phe Ala Leu Met Gln Thr Lys Asp Glu Lys Cys Leu Gln Tyr
            290                 295                 300
Leu Thr Asn Ile Val Thr Lys Phe Asn Gly Gly Val Pro Asn Val Tyr
305                 310                 315                 320
Pro Val Asp Leu Phe Glu His Ile Trp Val Val Asp Arg Leu Gln Arg
                325                 330                 335
Leu Gly Ile Ala Arg Tyr Phe Lys Ser Glu Ile Lys Asp Cys Val Glu
            340                 345                 350
Tyr Ile Asn Lys Tyr Trp Thr Lys Asn Gly Ile Cys Trp Ala Arg Asn
            355                 360                 365
Thr His Val Gln Asp Ile Asp Asp Thr Ala Met Gly Phe Arg Val Leu
            370                 375                 380
Arg Ala His Gly Tyr Asp Val Thr Pro Asp Val Phe Arg Gln Phe Glu
385                 390                 395                 400
Lys Asp Gly Lys Phe Val Cys Phe Ala Gly Gln Ser Thr Gln Ala Val
                405                 410                 415
Thr Gly Met Phe Asn Val Tyr Arg Ala Ser Gln Met Leu Phe Pro Gly
            420                 425                 430
Glu Arg Ile Leu Glu Asp Ala Lys Lys Phe Ser Tyr Asn Tyr Leu Lys
            435                 440                 445
Glu Lys Gln Ser Thr Asn Glu Leu Leu Asp Lys Trp Ile Ile Ala Lys
            450                 455                 460
Asp Leu Pro Gly Glu Val Gly Tyr Ala Leu Asp Ile Pro Trp Tyr Ala
465                 470                 475                 480
Ser Leu Pro Arg Leu Glu Thr Arg Tyr Tyr Leu Glu Gln Tyr Gly Gly
                485                 490                 495
Glu Asp Asp Val Trp Ile Gly Lys Thr Leu Tyr Arg Met Gly Tyr Val
            500                 505                 510
Ser Asn Asn Thr Tyr Leu Glu Met Ala Lys Leu Asp Tyr Asn Asn Tyr
            515                 520                 525
Val Ala Val Leu Gln Leu Glu Trp Tyr Thr Ile Gln Gln Trp Tyr Val
            530                 535                 540
Asp Ile Gly Ile Glu Lys Phe Glu Ser Asp Asn Ile Lys Ser Val Leu
545                 550                 555                 560
Val Ser Tyr Tyr Leu Ala Ala Ala Ser Ile Phe Glu Pro Glu Arg Ser
                565                 570                 575
Lys Glu Arg Ile Ala Trp Ala Lys Thr Thr Ile Leu Val Asp Lys Ile
            580                 585                 590
Thr Ser Ile Phe Asp Ser Ser Gln Ser Ser Lys Glu Asp Ile Thr Ala
            595                 600                 605
```

```
Phe Ile Asp Lys Phe Arg Asn Lys Ser Ser Lys Lys His Ser Ile
    610                 615                 620

Asn Gly Glu Pro Trp His Glu Val Met Val Ala Leu Lys Lys Thr Leu
625                 630                 635                 640

His Gly Phe Ala Leu Asp Ala Leu Met Thr His Ser Gln Asp Ile His
                645                 650                 655

Pro Gln Leu His Gln Ala Trp Glu Met Trp Leu Thr Lys Leu Gln Asp
            660                 665                 670

Gly Val Asp Val Thr Ala Glu Leu Met Val Gln Met Ile Asn Met Thr
        675                 680                 685

Ala Gly Arg Trp Val Ser Lys Glu Leu Leu Thr His Pro Gln Tyr Gln
    690                 695                 700

Arg Leu Ser Thr Val Thr Asn Ser Val Cys His Asp Ile Thr Lys Leu
705                 710                 715                 720

His Asn Phe Lys Glu Asn Ser Thr Thr Val Asp Ser Lys Val Gln Glu
                725                 730                 735

Leu Val Gln Leu Val Phe Ser Asp Thr Pro Asp Asp Leu Asp Gln Asp
            740                 745                 750

Met Lys Gln Thr Phe Leu Thr Val Met Lys Thr Phe Tyr Tyr Lys Ala
        755                 760                 765

Trp Cys Asp Pro Asn Thr Ile Asn Asp His Ile Ser Lys Val Phe Glu
770                 775                 780

Ile Val Ile
785

<210> SEQ ID NO 34
<211> LENGTH: 527
<212> TYPE: PRT
<213> ORGANISM: Streptomyces clavuligerus

<400> SEQUENCE: 34

Met Pro Asp Ala His Asp Ala Pro Pro Gln Ile Arg Gln Arg Thr
1               5                   10                  15

Leu Val Asp Glu Ala Thr Gln Leu Leu Thr Glu Ser Ala Glu Asp Ala
                20                  25                  30

Trp Gly Glu Val Ser Val Ser Glu Tyr Glu Thr Ala Arg Leu Val Ala
            35                  40                  45

His Ala Thr Trp Leu Gly Gly His Ala Thr Arg Val Ala Phe Leu Leu
        50                  55                  60

Glu Arg Gln His Glu Asp Gly Ser Trp Gly Pro Pro Gly Gly Tyr Arg
65                  70                  75                  80

Leu Val Pro Thr Leu Ser Ala Val His Ala Leu Leu Thr Cys Leu Ala
                85                  90                  95

Ser Pro Ala Gln Asp His Gly Val Pro His Asp Arg Leu Leu Arg Ala
            100                 105                 110

Val Asp Ala Gly Leu Thr Ala Leu Arg Arg Leu Gly Thr Ser Asp Ser
        115                 120                 125

Pro Pro Asp Thr Ile Ala Val Glu Leu Val Ile Pro Ser Leu Leu Glu
    130                 135                 140

Gly Ile Gln His Leu Leu Asp Pro Ala His Pro His Ser Arg Pro Ala
145                 150                 155                 160

Phe Ser Gln His Arg Gly Ser Leu Val Cys Pro Gly Gly Leu Asp Gly
                165                 170                 175

Arg Thr Leu Gly Ala Leu Arg Ser His Ala Ala Ala Gly Thr Pro Val
```

```
            180                 185                 190
Pro Gly Lys Val Trp His Ala Ser Glu Thr Leu Gly Leu Ser Thr Glu
        195                 200                 205

Ala Ala Ser His Leu Gln Pro Ala Gln Gly Ile Ile Gly Gly Ser Ala
    210                 215                 220

Ala Ala Thr Ala Thr Trp Leu Thr Arg Val Ala Pro Ser Gln Gln Ser
225                 230                 235                 240

Asp Ser Ala Arg Arg Tyr Leu Glu Glu Leu Gln His Arg Tyr Ser Gly
                245                 250                 255

Pro Val Pro Ser Ile Thr Pro Ile Thr Tyr Phe Glu Arg Ala Trp Leu
            260                 265                 270

Leu Asn Asn Phe Ala Ala Gly Val Pro Cys Glu Ala Pro Ala Ala
                275                 280                 285

Leu Leu Asp Ser Leu Glu Ala Ala Leu Thr Pro Gln Gly Ala Pro Ala
            290                 295                 300

Gly Ala Gly Leu Pro Pro Asp Ala Asp Asp Thr Ala Ala Val Leu Leu
305                 310                 315                 320

Ala Leu Ala Thr His Gly Arg Gly Arg Arg Pro Glu Val Leu Met Asp
                325                 330                 335

Tyr Arg Thr Asp Gly Tyr Phe Gln Cys Phe Ile Gly Glu Arg Thr Pro
            340                 345                 350

Ser Ile Ser Thr Asn Ala His Val Leu Glu Thr Leu Gly His His Val
            355                 360                 365

Ala Gln His Pro Gln Asp Arg Ala Arg Tyr Gly Ser Ala Met Asp Thr
        370                 375                 380

Ala Ser Ala Trp Leu Leu Ala Ala Gln Lys Gln Asp Gly Ser Trp Leu
385                 390                 395                 400

Asp Lys Trp His Ala Ser Pro Tyr Tyr Ala Thr Val Cys Cys Thr Gln
                405                 410                 415

Ala Leu Ala Ala His Ala Ser Pro Ala Thr Ala Pro Ala Arg Gln Arg
            420                 425                 430

Ala Val Arg Trp Val Leu Ala Thr Gln Arg Ser Asp Gly Gly Trp Gly
        435                 440                 445

Leu Trp His Ser Thr Val Glu Glu Thr Ala Tyr Ala Leu Gln Ile Leu
    450                 455                 460

Ala Pro Pro Ser Gly Gly Gly Asn Ile Pro Val Gln Gln Ala Leu Thr
465                 470                 475                 480

Arg Gly Arg Ala Arg Leu Cys Gly Ala Leu Pro Leu Thr Pro Leu Trp
                485                 490                 495

His Asp Lys Asp Leu Tyr Thr Pro Val Arg Val Arg Ala Ala Arg
            500                 505                 510

Ala Ala Ala Leu Tyr Thr Thr Arg Asp Leu Leu Leu Pro Pro Leu
        515                 520                 525

<210> SEQ ID NO 35
<211> LENGTH: 516
<212> TYPE: PRT
<213> ORGANISM: Bradyrhizobium diazoefficiens

<400> SEQUENCE: 35

Met Asn Ala Leu Ser Glu His Ile Leu Ser Glu Leu Arg Arg Leu Leu
1               5                   10                  15

Ser Glu Met Ser Asp Gly Gly Ser Val Gly Pro Ser Val Tyr Asp Thr
            20                  25                  30
```

-continued

```
Ala Gln Ala Leu Arg Phe His Gly Asn Val Thr Gly Arg Gln Asp Ala
         35                  40                  45

Tyr Ala Trp Leu Ile Ala Gln Gln Ala Asp Gly Gly Trp Gly Ser
 50                  55                  60

Ala Asp Phe Pro Leu Phe Arg His Ala Pro Thr Trp Ala Ala Leu Leu
 65              70                  75                  80

Ala Leu Gln Arg Ala Asp Pro Leu Pro Gly Ala Ala Asp Ala Val Gln
                 85                  90                  95

Thr Ala Thr Arg Phe Leu Gln Arg Gln Pro Asp Pro Tyr Ala His Ala
            100                 105                 110

Val Pro Glu Asp Ala Pro Ile Gly Ala Glu Leu Ile Leu Pro Gln Phe
        115                 120                 125

Cys Gly Glu Ala Ala Trp Leu Leu Gly Gly Val Ala Phe Pro Arg His
    130                 135                 140

Pro Ala Leu Leu Pro Leu Arg Gln Ala Cys Leu Val Lys Leu Gly Ala
145                 150                 155                 160

Val Ala Met Leu Pro Ser Gly His Pro Leu Leu His Ser Trp Glu Ala
                165                 170                 175

Trp Gly Thr Ser Pro Thr Thr Ala Cys Pro Asp Asp Gly Ser Ile
                180                 185                 190

Gly Ile Ser Pro Ala Ala Thr Ala Ala Trp Arg Ala Gln Ala Val Thr
            195                 200                 205

Arg Gly Ser Thr Pro Gln Val Gly Arg Ala Asp Ala Tyr Leu Gln Met
    210                 215                 220

Ala Ser Arg Ala Thr Arg Ser Gly Ile Glu Gly Val Phe Pro Asn Val
225                 230                 235                 240

Trp Pro Ile Asn Val Phe Glu Pro Cys Trp Ser Leu Tyr Thr Leu His
                245                 250                 255

Leu Ala Gly Leu Phe Ala His Pro Ala Leu Ala Glu Ala Val Arg Val
            260                 265                 270

Ile Val Ala Gln Leu Glu Ala Arg Leu Gly Val His Gly Leu Gly Pro
        275                 280                 285

Ala Leu His Phe Ala Ala Asp Ala Asp Thr Ala Val Ala Leu Cys
    290                 295                 300

Val Leu His Leu Ala Gly Arg Asp Pro Ala Val Asp Ala Leu Arg His
305                 310                 315                 320

Phe Glu Ile Gly Glu Leu Phe Val Thr Phe Pro Gly Glu Arg Asn Ala
                325                 330                 335

Ser Val Ser Thr Asn Ile His Ala Leu His Ala Leu Arg Leu Leu Gly
            340                 345                 350

Lys Pro Ala Ala Gly Ala Ser Ala Tyr Val Glu Ala Asn Arg Asn Pro
        355                 360                 365

His Gly Leu Trp Asp Asn Glu Lys Trp His Val Ser Trp Leu Tyr Pro
    370                 375                 380

Thr Ala His Ala Val Ala Ala Leu Ala Gln Gly Lys Pro Gln Trp Arg
385                 390                 395                 400

Asp Glu Arg Ala Leu Ala Ala Leu Leu Gln Ala Gln Arg Asp Asp Gly
                405                 410                 415

Gly Trp Gly Ala Gly Arg Gly Ser Thr Phe Glu Thr Ala Tyr Ala
            420                 425                 430

Leu Phe Ala Leu His Val Met Asp Gly Ser Glu Glu Ala Thr Gly Arg
        435                 440                 445

Arg Arg Ile Ala Gln Val Val Ala Arg Ala Leu Glu Trp Met Leu Ala
```

```
                450           455           460
Arg His Ala Ala His Gly Leu Pro Gln Thr Pro Leu Trp Ile Gly Lys
465                 470               475                 480

Glu Leu Tyr Cys Pro Thr Arg Val Val Arg Val Ala Glu Leu Ala Gly
                485               490               495

Leu Trp Leu Ala Leu Arg Trp Gly Arg Arg Val Leu Ala Glu Gly Ala
            500               505               510

Gly Ala Ala Pro
        515

<210> SEQ ID NO 36
<211> LENGTH: 4577
<212> TYPE: DNA
<213> ORGANISM: Zea mays

<400> SEQUENCE: 36
gacctgacca ccaccccccg gccggcccctt tcattctttc cttactttct tcctcctgct      60
gctcttgccg tttcagtgat tattagctgc tgtacgtgcg tgcgtacatt gttctctctg     120
ctgacaccca tacacgctgt agcttctaca cataccagtt cgatcgcaag ctatagcatg     180
gggcttcaat catcgcccat gctgctgcca gcgccgacgg caacggcggc cggcagcggg     240
tcacagtggc gcacggctgt ggcgggtaat ggtaactcgt ttatcttctt ctacacgtaa     300
tctctattat atacctagat tttctccaca ggcagatcag attctttaca cagctgtatt     360
ctcaaaaaaa actcatagaa aaaaagaaa aaactaaacc aaaggagcga cctcaacctg      420
taccagtgcc cctgctagca gtagcttcgt tctgtcccctt ttttttcatt tggatcctct    480
acataaatgc tgggtggtgg tgtcctttca cgcacacatc cgcagatagc gccccagcag    540
catttatgtg gggacgacgg ctctgaaatg aattactagt cagtttcatg cgtttcagtg    600
cgagtattat agtagtagat ctcttctccg atatatccgg ccaaaggaag aagagaagag    660
aaaccacaca tctcattctc aactagtagt agaaaagtaa aaacgtacta caagcgcaag    720
cgcaaagatg gttctttcat cgtcttgcac aacagttcct cacctttctt cccttgcggt    780
cgttcaacta ggcccatgga gttcccgcat caagaagaag acggatacag tcgccgtccc    840
cgcggccgcc ggccggtgga ggagggcact ggcgcgggcc cagcacacca gcgaatccgc    900
cgccgtcgcc aaaggtacgg gtgatcgcta gctttgatag ctccaaatct gagcagcaaa    960
ttaaatagct aggtttgtaa cgcacgcacg catgcaggtt cgtccctaac gcccatcgtg   1020
agaaccgatg ccgaaagccg ccgcacgaga tggcctacgg acgacgacga cgctgagccg   1080
ctggtcgacg agatcagggc aatgctgacg tcgatgagcg acgggacat cagcgtgtcg    1140 gcgtacgaca ccgcctgggt gggtcttgtg cccaggctgg acggcggcga gggcccgcag    1200
ttcccggccg ccgtgcggtg gatccggaac aaccagctcc ccgacggctc gtggggcgac   1260
gcggccctgt tctccgcgta cgaccgcctg atcaacacgc tggcgtgcgt cgtcacgctc   1320
accaggtggt cgctggagcc cgagatgcgc ggcagaggta cgtaattact gtgtgctggc   1380
cgatcgagag aacacacgac ggcagtgtac ctcgacagaa acgggcgtt gctgaagact    1440 caagtgtgtg tgtgtgtgtg ttcacagggc tctctttcct cggccggaac atgtggaagc   1500
tagcgacgga ggacgaggag tccatgccga tagggttcga gctcgcgttc ccttctctca   1560
tcgaactagc caagagtctg gcgtccacg acttcccgta cgaccaccag gctctgcagg    1620
gaatatactc gagcagggag atcaagatga agaggattcc taaggaagtg atgcacacgg   1680
ttcccacatc cattctccac agcctggaag ggatgcccgg gctagactgg gcgaagctgc   1740
```

```
tgaaactgca gtcgagcgac gggtccttcc tcttctctcc cgcggccacc gcgtacgctc    1800
tcatgaacac cggcgacgac aggtgcttca gctacatcga caggacagtc aagaaattca    1860
acggaggagg tacgcaagca gtagcgtaga tacatgggca tagcatgcat gcatgcaatg    1920
cagcgttgcc cactgcatgc gccttccttc cttccttctc gtctcttcaa cggttcgtct    1980
tctctcgccg tttctcgcag tgcccaacgt ctaccccgtg gaccttttcg agcacatatg    2040
ggctgtcgat cgcctggagc gtctcgggat ctcccgctac ttccagaaag agattgagca    2100
gtgcatggac tacgtgaaca ggcactggac tgaggacggg atctgctggg cgaggaactc    2160
cgacgtgaag gaggtggacg acacggccat ggctttccgc ctgctacggc tgcacggata    2220
cagcgtctcg ccaggtacgt aacaaacaca aaaaaaaaaa acgcgcagac aacagagatc    2280
gtcacgtcat acacacgcgt gtcctgaaca tttttcattt ggtctcccac ccatcgtacg    2340
taataataat aaaaaaaaac gtgcttctgc cctgcctgtg tacgtgtaga tgtgttcaag    2400
aacttcgaga aggacgggga gttcttcgcc ttcgtggggc agtcgaacca ggcggtgacg    2460
gggatgtaca acctcaacag ggcctcccag ataagcttcc cggggagga cgtcctgcac    2520 cgtgcagggg ctttctcgta cgagtttctc aggcggaaag aggccgaggg agcgctccgt    2580
gacaaatgga tcatatctaa ggacctgcct ggggaggtag tgtacaccct ggacttccct    2640
tggtatggga acctgccgcg cgtggaggcg agagactatc tggaacagta cggcggcggc    2700
gacgatgtct ggatcgggaa gacgctctac aggtagatag atcttttttag ctattaattg    2760 gtttcagatc gaccagataa aatttgcatt attggttctt ttgatgcatg taattgaaag    2820
ccaataaata acctcagtat gcgtgatggc tgacttttgc attggcagga tgcctcttgt    2880
gaataacgat gtgtatcttg agctggctag gatggacttc aaccattgcc aagccctaca    2940
tcagcttgag tggcaaggcc tgaaaaggta tgtatgttac tatatatata cagcccggtt    3000
gttgagtttt ttttttattt tattttttc gcgattacca tttcttctcg atgcaaaata    3060
aatctgcaca gatcatcata tatatccttg atgatatata agggcttctc gtatatatat    3120
cttatcacct atatatacat aggtggtaca ctgagaaccg gctcatggat ttcggagtgg    3180
cgcaagagga tgctctgcga gcgtatttcc tggccgccgc ttccgtctac gagccgtgcc    3240
gagccgcgga gcggcttgcg tgggccagag cggcgatact tgccaacgcc gtctctaccc    3300
atctccgtaa cagcccctca ttcagagaac gcttggaaca ctccttgcgt tgccgcccca    3360
gtgaagaaac ggatggatca tggtaataag ctgatcgatg ggaaattaaa aatttaagtt    3420 tttttttttct ttttttgttgc cattatctga gaccaatgca atgtggtgca tatatatcca    3480
ggttcaactc atcaagtgga agtgacgctg ttcttgtgaa ggcagttctg cggcttaccg    3540
actcgttagc gcgagaagcg cagccgattc atggcggtga tccggaggac atcatccaca    3600
agctactgag atcagctgta agttaaacgt aacgttcaga agaagatttt ttttttttttt    3660 tgcagttaac aagtactacg acatctatcg tttttgttca gcatgcacag tcatcctagc    3720
tactaatacc attattcttc tgtgaacttg tgtagtgggc tgaatgggtc agggagaagg    3780
cagatgcagc agacagcgtg tgtaatggat ccagtgctgt ggaacaagaa gggtcgcgca    3840
tggttcatga caagcaaacg tgtctgcttt tagctcgaat gatcgagatc agcgctgggc    3900
gagctgcagg tgaggctgcg agcgaagatg gtgaccgtcg gattatccag ctcactgggt    3960
ctatatgtga cagtctcaag cagaagatgc tagtatctca ggtatagcac atatatacta    4020
cagaaagttt gtgcgtagtt attatttccc ttttttcatg tgacgaacat gatgacctga    4080
```

-continued

```
tgatgcatgt atatggcttc ataggacc ccgagaagaa cgaagagatg atgagccatg    4140
tcgatgacga attgaagctg cgtatacgag agttcgttca gtatcttctg agactcggtg    4200
agaagaaaac cggcagcagc gagacaaggc agacctttct gagcatcgtg aaaagctgtt    4260
actacgctgc tcactgcccg ccgcatgtgg tagacaggca tatttccaga gttattttg     4320 aacctgtttc cgccgcaaaa taatggtaat ggtagatgtg aatgtgatat ggagataaga    4380
gagagagaaa atgttgatag tggaaattgg cgttgatgtc gcctccacat tctttacgca    4440
aaagtagcgt ctgttttgga taaaaaaat ccagtttctg taaattatag aataaatcaa     4500
tcgctgtgtc ccaaactcta aaatgttatt ctgtgaagta tggaataaat cggtcactat    4560
acctatcttg tggatgc                                                    4577
```

<210> SEQ ID NO 37
<211> LENGTH: 827
<212> TYPE: PRT
<213> ORGANISM: Zea mays

<400> SEQUENCE: 37

```
Met Val Leu Ser Ser Cys Thr Thr Val Pro His Leu Ser Ser Leu
1               5                   10                  15

Ala Val Val Gln Leu Gly Pro Trp Ser Ser Arg Ile Lys Lys Lys Thr
            20                  25                  30

Asp Thr Val Ala Val Pro Ala Ala Ala Gly Arg Trp Arg Arg Ala Leu
        35                  40                  45

Ala Arg Ala Gln His Thr Ser Glu Ser Ala Ala Val Ala Lys Gly Ser
    50                  55                  60

Ser Leu Thr Pro Ile Val Arg Thr Asp Ala Glu Ser Arg Arg Thr Arg
65                  70                  75                  80

Trp Pro Thr Asp Asp Asp Ala Glu Pro Leu Val Asp Glu Ile Arg
                85                  90                  95

Ala Met Leu Thr Ser Met Ser Asp Gly Asp Ile Ser Val Ser Ala Tyr
            100                 105                 110

Asp Thr Ala Trp Val Gly Leu Val Pro Arg Leu Asp Gly Gly Glu Gly
        115                 120                 125

Pro Gln Phe Pro Ala Ala Val Arg Trp Ile Arg Asn Asn Gln Leu Pro
    130                 135                 140

Asp Gly Ser Trp Gly Asp Ala Ala Leu Phe Ser Ala Tyr Asp Arg Leu
145                 150                 155                 160

Ile Asn Thr Leu Ala Cys Val Val Thr Leu Thr Arg Trp Ser Leu Glu
                165                 170                 175

Pro Glu Met Arg Gly Arg Gly Leu Ser Phe Leu Gly Arg Asn Met Trp
            180                 185                 190

Lys Leu Ala Thr Glu Asp Glu Ser Met Pro Ile Gly Phe Glu Leu
        195                 200                 205

Ala Phe Pro Ser Leu Ile Glu Leu Ala Lys Ser Leu Gly Val His Asp
    210                 215                 220

Phe Pro Tyr Asp His Gln Ala Leu Gln Gly Ile Tyr Ser Ser Arg Glu
225                 230                 235                 240

Ile Lys Met Lys Arg Ile Pro Lys Glu Val Met His Thr Val Pro Thr
                245                 250                 255

Ser Ile Leu His Ser Leu Glu Gly Met Pro Gly Leu Asp Trp Ala Lys
            260                 265                 270

Leu Leu Lys Leu Gln Ser Ser Asp Gly Ser Phe Leu Phe Ser Pro Ala
        275                 280                 285
```

-continued

```
Ala Thr Ala Tyr Ala Leu Met Asn Thr Gly Asp Asp Arg Cys Phe Ser
            290                 295                 300
Tyr Ile Asp Arg Thr Val Lys Lys Phe Asn Gly Gly Val Pro Asn Val
305                 310                 315                 320
Tyr Pro Val Asp Leu Phe Glu His Ile Trp Ala Val Asp Arg Leu Glu
                    325                 330                 335
Arg Leu Gly Ile Ser Arg Tyr Phe Gln Lys Glu Ile Glu Gln Cys Met
                340                 345                 350
Asp Tyr Val Asn Arg His Trp Thr Glu Asp Gly Ile Cys Trp Ala Arg
            355                 360                 365
Asn Ser Asp Val Lys Glu Val Asp Asp Thr Ala Met Ala Phe Arg Leu
370                 375                 380
Leu Arg Leu His Gly Tyr Ser Val Ser Pro Asp Val Phe Lys Asn Phe
385                 390                 395                 400
Glu Lys Asp Gly Glu Phe Phe Ala Phe Val Gly Gln Ser Asn Gln Ala
                405                 410                 415
Val Thr Gly Met Tyr Asn Leu Asn Arg Ala Ser Gln Ile Ser Phe Pro
                420                 425                 430
Gly Glu Asp Val Leu His Arg Ala Gly Ala Phe Ser Tyr Glu Phe Leu
            435                 440                 445
Arg Arg Lys Glu Ala Glu Gly Ala Leu Arg Asp Lys Trp Ile Ile Ser
450                 455                 460
Lys Asp Leu Pro Gly Glu Val Val Tyr Thr Leu Asp Phe Pro Trp Tyr
465                 470                 475                 480
Gly Asn Leu Pro Arg Val Glu Ala Arg Asp Tyr Leu Glu Gln Tyr Gly
                485                 490                 495
Gly Gly Asp Asp Val Trp Ile Gly Lys Thr Leu Tyr Arg Met Pro Leu
            500                 505                 510
Val Asn Asn Asp Val Tyr Leu Glu Leu Ala Arg Met Asp Phe Asn His
            515                 520                 525
Cys Gln Ala Leu His Gln Leu Glu Trp Gln Gly Leu Lys Arg Trp Tyr
530                 535                 540
Thr Glu Asn Arg Leu Met Asp Phe Gly Val Ala Gln Glu Asp Ala Leu
545                 550                 555                 560
Arg Ala Tyr Phe Leu Ala Ala Ser Val Tyr Glu Pro Cys Arg Ala
                565                 570                 575
Ala Glu Arg Leu Ala Trp Ala Arg Ala Ala Ile Leu Ala Asn Ala Val
                580                 585                 590
Ser Thr His Leu Arg Asn Ser Pro Ser Phe Arg Glu Arg Leu Glu His
            595                 600                 605
Ser Leu Arg Cys Arg Pro Ser Glu Glu Thr Asp Gly Ser Trp Phe Asn
610                 615                 620
Ser Ser Ser Gly Ser Asp Ala Val Leu Val Lys Ala Val Leu Arg Leu
625                 630                 635                 640
Thr Asp Ser Leu Ala Arg Glu Ala Gln Pro Ile His Gly Gly Asp Pro
                645                 650                 655
Glu Asp Ile Ile His Lys Leu Leu Arg Ser Ala Trp Ala Glu Trp Val
                660                 665                 670
Arg Glu Lys Ala Asp Ala Ala Asp Ser Val Cys Asn Gly Ser Ser Ala
            675                 680                 685
Val Glu Gln Glu Gly Ser Arg Met Val His Asp Lys Gln Thr Cys Leu
690                 695                 700
```

```
Leu Leu Ala Arg Met Ile Glu Ile Ser Ala Gly Arg Ala Ala Gly Glu
705                 710                 715                 720

Ala Ala Ser Glu Asp Gly Asp Arg Arg Ile Ile Gln Leu Thr Gly Ser
                725                 730                 735

Ile Cys Asp Ser Leu Lys Gln Lys Met Leu Val Ser Gln Asp Pro Glu
            740                 745                 750

Lys Asn Glu Glu Met Met Ser His Val Asp Asp Glu Leu Lys Leu Arg
        755                 760                 765

Ile Arg Glu Phe Val Gln Tyr Leu Leu Arg Leu Gly Lys Lys Thr
    770                 775                 780

Gly Ser Ser Glu Thr Arg Gln Thr Phe Leu Ser Ile Val Lys Ser Cys
785                 790                 795                 800

Tyr Tyr Ala Ala His Cys Pro Pro His Val Val Asp Arg His Ile Ser
                805                 810                 815

Arg Val Ile Phe Glu Pro Val Ser Ala Ala Lys
            820                 825
```

<210> SEQ ID NO 38
<211> LENGTH: 2570
<212> TYPE: DNA
<213> ORGANISM: Arabidopsis thaliana

<400> SEQUENCE: 38

```
cttcttcact aaatacttag acagagaaaa cagagctttt taaagccatg tctcttcagt     60
atcatgttct aaactccatt ccaagtacaa cctttctcag ttctactaaa acaacaatat    120
cttcttcttt ccttaccatc tcaggatctc ctctcaatgt cgctagagac aaatccagaa    180
gcggttccat acattgttca agcttcgaa ctcaagaata cattaattct caagaggttc    240
aacatgattt gcctctaata catgagtggc aacagcttca aggagaagat gctcctcaga    300
ttagtgttgg aagtaatagt aatgcattca agaagcagt gaagagtgtg aaaacgatct    360
tgagaaacct aacggacggg gaaattacga tatcggctta cgatacagct gggttgcat    420
tgatcgatgc cggagataaa actccggcgt ttccctccgc cgtgaaatgg atcgccgaga    480
accaactttc cgatggttct tggggagatg cgtatctctt ctcttatcat gatcgtctca    540
tcaataccct tgcatgcgtc gttgctctaa gatcatggaa tctctttcct catcaatgca    600
acaaaggaat cacgttttc cgggaaaata ttgggaagct agaagacgaa atgatgagc    660
atatgccaat cggattcgaa gtagcattcc catcgttgct tgagatagct cgaggaataa    720
acattgatgt accgtacgat tctccggtct taaaagatat atacgccaag aaagagctaa    780
agcttacaag gataccaaaa gagataatgc acaagatacc aacaacattg ttgcatagtt    840
tggaggggat gcgtgattta gattgggaaa agctcttgaa acttcaatct caagacggat    900
ctttcctctt ctctccttcc tctaccgctt ttgcattcat gcagaccga gacagtaact    960
gcctcgagta tttgcgaaat gccgtcaaac gtttcaatgg aggagttccc aatgtctttc   1020
ccgtggatct tttcgagcac atatggatag tggatcggtt acaacgttta gggatatcga   1080
gatactttga agaagagatt aaagagtgtc ttgactatgt ccacagatat ggaccgaca   1140
atggcatatg ttgggctaga tgttcccatg tccaagacat cgatgataca gccatggcat   1200
ttaggctctt aagacaacat ggataccaag tgtccgcaga tgtattcaag aactttgaga   1260
aagagggaga gttttctgc tttgtggggc aatcaaacca agcagtaacc ggtatgttca   1320
acctataccg ggcatcacaa ttggcgtttc caagggaaga gatattgaaa aacgccaaag   1380
agttttctta taattatctg ctagaaaaac gggagagaga ggagttgatt gataagtgga   1440
```

```
ttataatgaa agacttacct ggcgagattg ggtttgcgtt agagattcca tggtacgcaa   1500
gcttgcctcg agtagagacg agattctata ttgatcaata tggtggagaa aacgacgttt   1560
ggattggcaa gactctttat aggatgccat acgtgaacaa taatggatat ctggaattag   1620
caaaacaaga ttacaacaat tgccaagctc agcatcagct cgaatgggac atattccaaa   1680
agtggtatga agaaaatagg ttaagtgagt ggggtgtgcg cagaagtgag cttctcgagt   1740
gttactactt agcggctgca actatatttg aatcagaaag gtcacatgag agaatggttt   1800
gggctaagtc aagtgtattg gttaaagcca tttcttcttc ttttggggaa tcctctgact   1860
ccagaagaag cttctccgat cagtttcatg aatacattgc caatgctcga cgaagtgatc   1920
atcactttaa tgacaggaac atgagattgg accgaccagg atcggttcag gccagtcggc   1980
ttgccggagt gttaatcggg actttgaatc aaatgtcttt tgacctttc atgtctcatg    2040 gccgtgacgt taacaatctc ctctatctat cgtggggaga ttggatggaa aaatggaaac   2100
tatatggaga tgaaggagaa ggagagctca tggtgaagat gataattcta atgaagaaca   2160
atgacctaac taacttcttc acccacactc acttcgttcg tctcgcggaa atcatcaatc   2220
gaatctgtct tcctcgccaa tacttaaagg caaggagaaa cgatgagaag gagaagacaa   2280
taaagagtat ggagaaggag atggggaaaa tggttgagtt agcattgtcg gagagtgaca   2340
catttcgtga cgtcagcatc acgtttcttg atgtagcaaa agcatttac tactttgctt    2400 tatgtggcga tcatctccaa actcacatct ccaaagtctt gtttcaaaaa gtctagtaac   2460
ctcatcatca tcatcgatcc attaacaatc agtggatcga tgtatccata gatgcgtgaa   2520
taatatttca tgtagagaag gagaacaaat tagatcatgt agggttatca               2570
```

<210> SEQ ID NO 39
<211> LENGTH: 802
<212> TYPE: PRT
<213> ORGANISM: Arabidopsis thaliana

<400> SEQUENCE: 39

```
Met Ser Leu Gln Tyr His Val Leu Asn Ser Ile Pro Ser Thr Thr Phe
1               5                   10                  15

Leu Ser Ser Thr Lys Thr Thr Ile Ser Ser Phe Leu Thr Ile Ser
                20                  25                  30

Gly Ser Pro Leu Asn Val Ala Arg Asp Lys Ser Arg Ser Gly Ser Ile
            35                  40                  45

His Cys Ser Lys Leu Arg Thr Gln Glu Tyr Ile Asn Ser Gln Glu Val
        50                  55                  60

Gln His Asp Leu Pro Leu Ile His Glu Trp Gln Gln Leu Gln Gly Glu
65                  70                  75                  80

Asp Ala Pro Gln Ile Ser Val Gly Ser Asn Ser Asn Ala Phe Lys Glu
                85                  90                  95

Ala Val Lys Ser Val Lys Thr Ile Leu Arg Asn Leu Thr Asp Gly Glu
            100                 105                 110

Ile Thr Ile Ser Ala Tyr Asp Thr Ala Trp Val Ala Leu Ile Asp Ala
        115                 120                 125

Gly Asp Lys Thr Pro Ala Phe Pro Ser Ala Val Lys Trp Ile Ala Glu
    130                 135                 140

Asn Gln Leu Ser Asp Gly Ser Trp Gly Asp Ala Tyr Leu Phe Ser Tyr
145                 150                 155                 160

His Asp Arg Leu Ile Asn Thr Leu Ala Cys Val Val Ala Leu Arg Ser
                165                 170                 175
```

```
Trp Asn Leu Phe Pro His Gln Cys Asn Lys Gly Ile Thr Phe Phe Arg
        180                 185                 190
Glu Asn Ile Gly Lys Leu Glu Asp Glu Asn Asp Glu His Met Pro Ile
            195                 200                 205
Gly Phe Glu Val Ala Phe Pro Ser Leu Leu Glu Ile Ala Arg Gly Ile
210                 215                 220
Asn Ile Asp Val Pro Tyr Asp Ser Pro Val Leu Lys Asp Ile Tyr Ala
225                 230                 235                 240
Lys Lys Glu Leu Lys Leu Thr Arg Ile Pro Lys Glu Ile Met His Lys
                245                 250                 255
Ile Pro Thr Thr Leu Leu His Ser Leu Glu Gly Met Arg Asp Leu Asp
            260                 265                 270
Trp Glu Lys Leu Leu Lys Leu Gln Ser Gln Asp Gly Ser Phe Leu Phe
        275                 280                 285
Ser Pro Ser Ser Thr Ala Phe Ala Phe Met Gln Thr Arg Asp Ser Asn
    290                 295                 300
Cys Leu Glu Tyr Leu Arg Asn Ala Val Lys Arg Phe Asn Gly Gly Val
305                 310                 315                 320
Pro Asn Val Phe Pro Val Asp Leu Phe Glu His Ile Trp Ile Val Asp
                325                 330                 335
Arg Leu Gln Arg Leu Gly Ile Ser Arg Tyr Phe Glu Glu Ile Lys
            340                 345                 350
Glu Cys Leu Asp Tyr Val His Arg Tyr Trp Thr Asp Asn Gly Ile Cys
        355                 360                 365
Trp Ala Arg Cys Ser His Val Gln Asp Ile Asp Asp Thr Ala Met Ala
    370                 375                 380
Phe Arg Leu Leu Arg Gln His Gly Tyr Gln Val Ser Ala Asp Val Phe
385                 390                 395                 400
Lys Asn Phe Glu Lys Glu Gly Glu Phe Phe Cys Phe Val Gly Gln Ser
                405                 410                 415
Asn Gln Ala Val Thr Gly Met Phe Asn Leu Tyr Arg Ala Ser Gln Leu
            420                 425                 430
Ala Phe Pro Arg Glu Glu Ile Leu Lys Asn Ala Lys Glu Phe Ser Tyr
        435                 440                 445
Asn Tyr Leu Leu Glu Lys Arg Glu Arg Glu Glu Leu Ile Asp Lys Trp
    450                 455                 460
Ile Ile Met Lys Asp Leu Pro Gly Glu Ile Gly Phe Ala Leu Glu Ile
465                 470                 475                 480
Pro Trp Tyr Ala Ser Leu Pro Arg Val Glu Thr Arg Phe Tyr Ile Asp
                485                 490                 495
Gln Tyr Gly Gly Glu Asn Asp Val Trp Ile Gly Lys Thr Leu Tyr Arg
            500                 505                 510
Met Pro Tyr Val Asn Asn Asn Gly Tyr Leu Glu Leu Ala Lys Gln Asp
        515                 520                 525
Tyr Asn Asn Cys Gln Ala Gln His Gln Leu Glu Trp Asp Ile Phe Gln
    530                 535                 540
Lys Trp Tyr Glu Glu Asn Arg Leu Ser Glu Trp Gly Val Arg Arg Ser
545                 550                 555                 560
Glu Leu Leu Glu Cys Tyr Tyr Leu Ala Ala Ala Thr Ile Phe Glu Ser
                565                 570                 575
Glu Arg Ser His Glu Arg Met Val Trp Ala Lys Ser Ser Val Leu Val
            580                 585                 590
```

-continued

Lys Ala Ile Ser Ser Ser Phe Gly Glu Ser Ser Asp Ser Arg Arg Ser
            595                 600                 605

Phe Ser Asp Gln Phe His Glu Tyr Ile Ala Asn Ala Arg Arg Ser Asp
    610                 615                 620

His His Phe Asn Asp Arg Asn Met Arg Leu Asp Arg Pro Gly Ser Val
625                 630                 635                 640

Gln Ala Ser Arg Leu Ala Gly Val Leu Ile Gly Thr Leu Asn Gln Met
                645                 650                 655

Ser Phe Asp Leu Phe Met Ser His Gly Arg Asp Val Asn Asn Leu Leu
                660                 665                 670

Tyr Leu Ser Trp Gly Asp Trp Met Glu Lys Trp Lys Leu Tyr Gly Asp
            675                 680                 685

Glu Gly Glu Gly Glu Leu Met Val Lys Met Ile Ile Leu Met Lys Asn
690                 695                 700

Asn Asp Leu Thr Asn Phe Phe Thr His Thr His Phe Val Arg Leu Ala
705                 710                 715                 720

Glu Ile Ile Asn Arg Ile Cys Leu Pro Arg Gln Tyr Leu Lys Ala Arg
                725                 730                 735

Arg Asn Asp Glu Lys Glu Lys Thr Ile Lys Ser Met Glu Lys Glu Met
            740                 745                 750

Gly Lys Met Val Glu Leu Ala Leu Ser Glu Ser Asp Thr Phe Arg Asp
        755                 760                 765

Val Ser Ile Thr Phe Leu Asp Val Ala Lys Ala Phe Tyr Tyr Phe Ala
    770                 775                 780

Leu Cys Gly Asp His Leu Gln Thr His Ile Ser Lys Val Leu Phe Gln
785                 790                 795                 800

Lys Val

<210> SEQ ID NO 40
<211> LENGTH: 983
<212> TYPE: PRT
<213> ORGANISM: Diaporthe amygdali

<400> SEQUENCE: 40

Met Glu Phe Asp Glu Pro Leu Val Asp Glu Ala Arg Ser Leu Val Gln
1               5                   10                  15

Arg Thr Leu Gln Asp Tyr Asp Asp Arg Tyr Gly Phe Gly Thr Met Ser
            20                  25                  30

Cys Ala Ala Tyr Asp Thr Ala Trp Val Ser Leu Val Thr Lys Thr Val
        35                  40                  45

Asp Gly Arg Lys Gln Trp Leu Phe Pro Glu Cys Phe Glu Phe Leu Leu
    50                  55                  60

Glu Thr Gln Ser Asp Ala Gly Gly Trp Glu Ile Gly Asn Ser Ala Pro
65                  70                  75                  80

Ile Asp Gly Ile Leu Asn Thr Ala Ala Ser Leu Leu Ala Leu Lys Arg
                85                  90                  95

His Val Gln Thr Glu Gln Ile Ile Gln Pro Gln His Asp His Lys Asp
            100                 105                 110

Leu Ala Gly Arg Ala Glu Arg Ala Ala Ala Ser Leu Arg Ala Gln Leu
        115                 120                 125

Ala Ala Leu Asp Val Ser Thr Thr Glu His Val Gly Phe Glu Ile Ile
    130                 135                 140

Val Pro Ala Met Leu Asp Pro Leu Glu Ala Glu Asp Pro Ser Leu Val
145                 150                 155                 160

```
Phe Asp Phe Pro Ala Arg Lys Pro Leu Met Lys Ile His Asp Ala Lys
            165                 170                 175

Met Ser Arg Phe Arg Pro Glu Tyr Leu Tyr Gly Lys Gln Pro Met Thr
            180                 185                 190

Ala Leu His Ser Leu Glu Ala Phe Ile Gly Lys Ile Asp Phe Asp Lys
            195                 200                 205

Val Arg His His Arg Thr His Gly Ser Met Met Gly Ser Pro Ser Ser
            210                 215                 220

Thr Ala Ala Tyr Leu Met His Ala Ser Gln Trp Asp Gly Asp Ser Glu
225                 230                 235                 240

Ala Tyr Leu Arg His Val Ile Lys His Ala Ala Gly Gln Gly Thr Gly
            245                 250                 255

Ala Val Pro Ser Ala Phe Pro Ser Thr His Phe Glu Ser Ser Trp Ile
            260                 265                 270

Leu Thr Thr Leu Phe Arg Ala Gly Phe Ser Ala Ser His Leu Ala Cys
            275                 280                 285

Asp Glu Leu Asn Lys Leu Val Glu Ile Leu Gly Ser Phe Glu Lys
            290                 295                 300

Glu Gly Gly Ala Ile Gly Tyr Ala Pro Gly Phe Gln Ala Asp Val Asp
305                 310                 315                 320

Asp Thr Ala Lys Thr Ile Ser Thr Leu Ala Val Leu Gly Arg Asp Ala
            325                 330                 335

Thr Pro Arg Gln Met Ile Lys Val Phe Glu Ala Asn Thr His Phe Arg
            340                 345                 350

Thr Tyr Pro Gly Glu Arg Asp Pro Ser Leu Thr Ala Asn Cys Asn Ala
            355                 360                 365

Leu Ser Ala Leu Leu His Gln Pro Asp Ala Ala Met Tyr Gly Ser Gln
            370                 375                 380

Ile Gln Lys Ile Thr Lys Phe Val Cys Asp Tyr Trp Trp Lys Ser Asp
385                 390                 395                 400

Gly Lys Ile Lys Asp Lys Trp Asn Thr Cys Tyr Leu Tyr Pro Ser Val
            405                 410                 415

Leu Leu Val Glu Val Leu Val Asp Leu Val Ser Leu Leu Glu Gln Gly
            420                 425                 430

Lys Leu Pro Asp Val Leu Asp Gln Glu Leu Gln Tyr Arg Val Ala Ile
            435                 440                 445

Thr Leu Phe Gln Ala Cys Leu Arg Pro Leu Leu Asp Gln Asp Ala Glu
            450                 455                 460

Gly Ser Trp Asn Lys Ser Ile Glu Ala Thr Ala Tyr Gly Ile Leu Ile
465                 470                 475                 480

Leu Thr Glu Ala Arg Arg Val Cys Phe Phe Asp Arg Leu Ser Glu Pro
            485                 490                 495

Leu Asn Glu Ala Ile Arg Arg Gly Ile Ala Phe Ala Asp Ser Met Ser
            500                 505                 510

Gly Thr Glu Ala Gln Leu Asn Tyr Ile Trp Ile Glu Lys Val Ser Tyr
            515                 520                 525

Ala Pro Ala Leu Leu Thr Lys Ser Tyr Leu Leu Ala Ala Arg Trp Ala
            530                 535                 540

Ala Lys Ser Pro Leu Gly Ala Ser Val Gly Ser Ser Leu Trp Thr Pro
545                 550                 555                 560

Pro Arg Glu Gly Leu Asp Lys His Val Arg Leu Phe His Gln Ala Glu
            565                 570                 575

Leu Phe Arg Ser Leu Pro Glu Trp Glu Leu Arg Ala Ser Met Ile Glu
```

```
            580                 585                 590
Ala Ala Leu Phe Thr Pro Leu Leu Arg Ala His Arg Leu Asp Val Phe
        595                 600                 605

Pro Arg Gln Asp Val Gly Glu Asp Lys Tyr Leu Asp Val Val Pro Phe
610                 615                 620

Phe Trp Thr Ala Ala Asn Asn Arg Asp Arg Thr Tyr Ala Ser Thr Leu
625                 630                 635                 640

Phe Leu Tyr Asp Met Cys Phe Ile Ala Met Leu Asn Phe Gln Leu Asp
                645                 650                 655

Glu Phe Met Glu Ala Thr Ala Gly Ile Leu Phe Arg Asp His Met Asp
            660                 665                 670

Asp Leu Arg Gln Leu Ile His Asp Leu Leu Ala Glu Lys Thr Ser Pro
        675                 680                 685

Lys Ser Ser Gly Arg Ser Gln Gly Thr Lys Asp Ala Asp Ser Gly
    690                 695                 700

Ile Glu Glu Asp Val Ser Met Ser Asp Ser Ala Ser Asp Ser Gln Asp
705                 710                 715                 720

Arg Ser Pro Glu Tyr Asp Leu Val Phe Ser Ala Leu Ser Thr Phe Thr
                725                 730                 735

Lys His Val Leu Gln His Pro Ser Ile Gln Ser Ala Ser Val Trp Asp
            740                 745                 750

Arg Lys Leu Leu Ala Arg Glu Met Lys Ala Tyr Leu Leu Ala His Ile
        755                 760                 765

Gln Gln Ala Glu Asp Ser Thr Pro Leu Ser Glu Leu Lys Asp Val Pro
    770                 775                 780

Gln Lys Thr Asp Val Thr Arg Val Ser Thr Ser Thr Thr Thr Phe Phe
785                 790                 795                 800

Asn Trp Val Arg Thr Thr Ser Ala Asp His Ile Ser Cys Pro Tyr Ser
                805                 810                 815

Phe His Phe Val Ala Cys His Leu Gly Ala Ala Leu Ser Pro Lys Gly
            820                 825                 830

Ser Asn Gly Asp Cys Tyr Pro Ser Ala Gly Glu Lys Phe Leu Ala Ala
        835                 840                 845

Ala Val Cys Arg His Leu Ala Thr Met Cys Arg Met Tyr Asn Asp Leu
    850                 855                 860

Gly Ser Ala Glu Arg Asp Ser Asp Glu Gly Asn Leu Asn Ser Leu Asp
865                 870                 875                 880

Phe Pro Glu Phe Ala Asp Ser Ala Gly Asn Gly Gly Ile Glu Ile Gln
                885                 890                 895

Lys Ala Ala Leu Leu Arg Leu Ala Glu Phe Glu Arg Asp Ser Tyr Leu
            900                 905                 910

Glu Ala Phe Arg Arg Leu Gln Asp Glu Ser Asn Arg Val His Gly Pro
        915                 920                 925

Ala Gly Gly Asp Glu Ala Arg Leu Ser Arg Arg Met Ala Ile Leu
    930                 935                 940

Glu Phe Phe Ala Gln Gln Val Asp Leu Tyr Gly Gln Val Tyr Val Ile
945                 950                 955                 960

Arg Asp Ile Ser Ala Arg Ile Pro Lys Asn Glu Val Glu Lys Lys Arg
                965                 970                 975

Lys Leu Asp Asp Ala Phe Asn
            980

<210> SEQ ID NO 41
```

```
<211> LENGTH: 881
<212> TYPE: PRT
<213> ORGANISM: Physcomitrella patens

<400> SEQUENCE: 41
```

| | | | | | | | | | | | | | | |
|---|---|---|---|---|---|---|---|---|---|---|---|---|---|---|
|Met|Ala|Ser|Ser|Thr|Leu|Ile|Gln|Asn|Arg|Ser|Cys|Gly|Val|Thr|Ser|
|1| | | |5| | | | |10| | | | |15| |
|Ser|Met|Ser|Ser|Phe|Gln|Ile|Phe|Arg|Gly|Gln|Pro|Leu|Arg|Phe|Pro|
| | | |20| | | | |25| | | | |30| | |
|Gly|Thr|Arg|Thr|Pro|Ala|Ala|Val|Gln|Cys|Leu|Lys|Lys|Arg|Arg|Cys|
| | |35| | | | |40| | | | |45| | | |
|Leu|Arg|Pro|Thr|Glu|Ser|Val|Leu|Glu|Ser|Ser|Pro|Gly|Ser|Gly|Ser|
| |50| | | | |55| | | | |60| | | | |
|Tyr|Arg|Ile|Val|Thr|Gly|Pro|Ser|Gly|Ile|Asn|Pro|Ser|Ser|Asn|Gly|
|65| | | | |70| | | | |75| | | | |80|
|His|Leu|Gln|Glu|Gly|Ser|Leu|Thr|His|Arg|Leu|Pro|Ile|Pro|Met|Glu|
| | | | |85| | | | |90| | | | |95| |
|Lys|Ser|Ile|Asp|Asn|Phe|Gln|Ser|Thr|Leu|Tyr|Val|Ser|Asp|Ile|Trp|
| | | |100| | | | |105| | | | |110| | |
|Ser|Glu|Thr|Leu|Gln|Arg|Thr|Glu|Cys|Leu|Leu|Gln|Val|Thr|Glu|Asn|
| | |115| | | | |120| | | | |125| | | |
|Val|Gln|Met|Asn|Glu|Trp|Ile|Glu|Glu|Ile|Arg|Met|Tyr|Phe|Arg|Asn|
| |130| | | | |135| | | | |140| | | | |
|Met|Thr|Leu|Gly|Glu|Ile|Ser|Met|Ser|Pro|Tyr|Asp|Thr|Ala|Trp|Val|
|145| | | | |150| | | | |155| | | | |160|
|Ala|Arg|Val|Pro|Ala|Leu|Asp|Gly|Ser|His|Gly|Pro|Gln|Phe|His|Arg|
| | | | |165| | | | |170| | | | |175| | |
|Ser|Leu|Gln|Trp|Ile|Ile|Asp|Asn|Gln|Leu|Pro|Asp|Gly|Asp|Trp|Gly|
| | | |180| | | | |185| | | | |190| | | |
|Glu|Pro|Ser|Leu|Phe|Leu|Gly|Tyr|Asp|Arg|Val|Cys|Asn|Thr|Leu|Ala|
| | |195| | | | |200| | | | |205| | | |
|Cys|Val|Ile|Ala|Leu|Lys|Thr|Trp|Gly|Val|Gly|Ala|Gln|Asn|Val|Glu|
| |210| | | | |215| | | | |220| | | | |
|Arg|Gly|Ile|Gln|Phe|Leu|Gln|Ser|Asn|Ile|Tyr|Lys|Met|Glu|Glu|Asp|
|225| | | | |230| | | | |235| | | | |240|
|Asp|Ala|Asn|His|Met|Pro|Ile|Gly|Phe|Glu|Ile|Val|Phe|Pro|Ala|Met|
| | | | |245| | | | |250| | | | |255| | |
|Met|Glu|Asp|Ala|Lys|Ala|Leu|Gly|Leu|Asp|Leu|Pro|Tyr|Asp|Ala|Thr|
| | | |260| | | | |265| | | | |270| | | |
|Ile|Leu|Gln|Gln|Ile|Ser|Ala|Glu|Arg|Glu|Lys|Lys|Met|Lys|Lys|Ile|
| | |275| | | | |280| | | | |285| | | | |
|Pro|Met|Ala|Met|Val|Tyr|Lys|Tyr|Pro|Thr|Thr|Leu|Leu|His|Ser|Leu|
| |290| | | | |295| | | | |300| | | | |
|Glu|Gly|Leu|His|Arg|Glu|Val|Asp|Trp|Asn|Lys|Leu|Leu|Gln|Leu|Gln|
|305| | | | |310| | | | |315| | | | |320|
|Ser|Glu|Asn|Gly|Ser|Phe|Leu|Tyr|Ser|Pro|Ala|Ser|Thr|Ala|Cys|Ala|
| | | | |325| | | | |330| | | | |335| | |
|Leu|Met|Tyr|Thr|Lys|Asp|Val|Lys|Cys|Phe|Asp|Tyr|Leu|Asn|Gln|Leu|
| | | |340| | | | |345| | | | |350| | | |
|Leu|Ile|Lys|Phe|Asp|His|Ala|Cys|Pro|Asn|Val|Tyr|Pro|Val|Asp|Leu|
| | |355| | | | |360| | | | |365| | | | |
|Phe|Glu|Arg|Leu|Trp|Met|Val|Asp|Arg|Leu|Gln|Arg|Leu|Gly|Ile|Ser|
| |370| | | | |375| | | | |380| | | | |
|Arg|Tyr|Phe|Glu|Arg|Glu|Ile|Arg|Asp|Cys|Leu|Gln|Tyr|Val|Tyr|Arg|

```
            385                 390                 395                 400
Tyr Trp Lys Asp Cys Gly Ile Gly Trp Ala Ser Asn Ser Ser Val Gln
                405                 410                 415

Asp Val Asp Asp Thr Ala Met Ala Phe Arg Leu Leu Arg Thr His Gly
                420                 425                 430

Phe Asp Val Lys Glu Asp Cys Phe Arg Gln Phe Lys Asp Gly Glu
                435                 440                 445

Phe Phe Cys Phe Ala Gly Gln Ser Ser Gln Ala Val Thr Gly Met Phe
    450                 455                 460

Asn Leu Ser Arg Ala Ser Gln Thr Leu Phe Pro Gly Glu Ser Leu Leu
465                 470                 475                 480

Lys Lys Ala Arg Thr Phe Ser Arg Asn Phe Leu Arg Thr Lys His Glu
                485                 490                 495

Asn Asn Glu Cys Phe Asp Lys Trp Ile Ile Thr Lys Asp Leu Ala Gly
                500                 505                 510

Glu Val Glu Tyr Asn Leu Thr Phe Pro Trp Tyr Ala Ser Leu Pro Arg
                515                 520                 525

Leu Glu His Arg Thr Tyr Leu Asp Gln Tyr Gly Ile Asp Asp Ile Trp
    530                 535                 540

Ile Gly Lys Ser Leu Tyr Lys Met Pro Ala Val Thr Asn Glu Val Phe
545                 550                 555                 560

Leu Lys Leu Ala Lys Ala Asp Phe Asn Met Cys Gln Ala Leu His Lys
                565                 570                 575

Lys Glu Leu Glu Gln Val Ile Lys Trp Asn Ala Ser Cys Gln Phe Arg
                580                 585                 590

Asp Leu Glu Phe Ala Arg Gln Lys Ser Val Glu Cys Tyr Phe Ala Gly
                595                 600                 605

Ala Ala Thr Met Phe Glu Pro Glu Met Val Gln Ala Arg Leu Val Trp
                610                 615                 620

Ala Arg Cys Cys Val Leu Thr Thr Val Leu Asp Asp Tyr Phe Asp His
625                 630                 635                 640

Gly Thr Pro Val Glu Glu Leu Arg Val Phe Val Gln Ala Val Arg Thr
                645                 650                 655

Trp Asn Pro Glu Leu Ile Asn Gly Leu Pro Glu Gln Ala Lys Ile Leu
                660                 665                 670

Phe Met Gly Leu Tyr Lys Thr Val Asn Thr Ile Ala Glu Glu Ala Phe
                675                 680                 685

Met Ala Gln Lys Arg Asp Val His His Leu Lys His Tyr Trp Asp
    690                 695                 700

Lys Leu Ile Thr Ser Ala Leu Lys Glu Ala Glu Trp Ala Glu Ser Gly
705                 710                 715                 720

Tyr Val Pro Thr Phe Asp Glu Tyr Met Glu Val Ala Glu Ile Ser Val
                725                 730                 735

Ala Leu Glu Pro Ile Val Cys Ser Thr Leu Phe Phe Ala Gly His Arg
                740                 745                 750

Leu Asp Glu Asp Val Leu Asp Ser Tyr Asp Tyr His Leu Val Met His
    755                 760                 765

Leu Val Asn Arg Val Gly Arg Ile Leu Asn Asp Ile Gln Gly Met Lys
770                 775                 780

Arg Glu Ala Ser Gln Gly Lys Ile Ser Ser Val Gln Ile Tyr Met Glu
785                 790                 795                 800

Glu His Pro Ser Val Pro Ser Glu Ala Met Ala Ile Ala His Leu Gln
                805                 810                 815
```

-continued

```
Glu Leu Val Asp Asn Ser Met Gln Gln Leu Thr Tyr Glu Val Leu Arg
                820                 825                 830

Phe Thr Ala Val Pro Lys Ser Cys Lys Arg Ile His Leu Asn Met Ala
        835                 840                 845

Lys Ile Met His Ala Phe Tyr Lys Asp Thr Asp Gly Phe Ser Ser Leu
850                 855                 860

Thr Ala Met Thr Gly Phe Val Lys Lys Val Leu Phe Glu Pro Val Pro
865                 870                 875                 880

Glu

<210> SEQ ID NO 42
<211> LENGTH: 952
<212> TYPE: PRT
<213> ORGANISM: Fusarium fujikuroi

<400> SEQUENCE: 42

Met Pro Gly Lys Ile Glu Asn Gly Thr Pro Lys Asp Leu Lys Thr Gly
1               5                   10                  15

Asn Asp Phe Val Ser Ala Ala Lys Ser Leu Leu Asp Arg Ala Phe Lys
                20                  25                  30

Ser His His Ser Tyr Tyr Gly Leu Cys Ser Thr Ser Cys Gln Val Tyr
            35                  40                  45

Asp Thr Ala Trp Val Ala Met Ile Pro Lys Thr Arg Asp Asn Val Lys
    50                  55                  60

Gln Trp Leu Phe Pro Glu Cys Phe His Tyr Leu Leu Lys Thr Gln Ala
65                  70                  75                  80

Ala Asp Gly Ser Trp Gly Ser Leu Pro Thr Thr Gln Thr Ala Gly Ile
                85                  90                  95

Leu Asp Thr Ala Ser Ala Val Leu Ala Leu Leu Cys His Ala Gln Glu
            100                 105                 110

Pro Leu Gln Ile Leu Asp Val Ser Pro Asp Glu Met Gly Leu Arg Ile
        115                 120                 125

Glu His Gly Val Thr Ser Leu Lys Arg Gln Leu Ala Val Trp Asn Asp
    130                 135                 140

Val Glu Asp Thr Asn His Ile Gly Val Glu Phe Ile Ile Pro Ala Leu
145                 150                 155                 160

Leu Ser Met Leu Glu Lys Glu Leu Asp Val Pro Ser Phe Glu Phe Pro
                165                 170                 175

Cys Arg Ser Ile Leu Glu Arg Met His Gly Glu Lys Leu Gly His Phe
            180                 185                 190

Asp Leu Glu Gln Val Tyr Gly Lys Pro Ser Ser Leu Leu His Ser Leu
        195                 200                 205

Glu Ala Phe Leu Gly Lys Leu Asp Phe Asp Arg Leu Ser His His Leu
    210                 215                 220

Tyr His Gly Ser Met Met Ala Ser Pro Ser Ser Thr Ala Ala Tyr Leu
225                 230                 235                 240

Ile Gly Ala Thr Lys Trp Asp Asp Glu Ala Glu Asp Tyr Leu Arg His
                245                 250                 255

Val Met Arg Asn Gly Ala Gly His Gly Asn Gly Gly Ile Ser Gly Thr
            260                 265                 270

Phe Pro Thr Thr His Phe Glu Cys Ser Trp Ile Ile Ala Thr Leu Leu
        275                 280                 285

Lys Val Gly Phe Thr Leu Lys Gln Ile Asp Gly Asp Gly Leu Arg Gly
    290                 295                 300
```

-continued

```
Leu Ser Thr Ile Leu Leu Glu Ala Leu Arg Asp Glu Asn Gly Val Ile
305                 310                 315                 320

Gly Phe Ala Pro Arg Thr Ala Asp Val Asp Asp Thr Ala Lys Ala Leu
                325                 330                 335

Leu Ala Leu Ser Leu Val Asn Gln Pro Val Ser Pro Asp Ile Met Ile
            340                 345                 350

Lys Val Phe Glu Gly Lys Asp His Phe Thr Thr Phe Gly Ser Glu Arg
        355                 360                 365

Asp Pro Ser Leu Thr Ser Asn Leu His Val Leu Leu Ser Leu Leu Lys
370                 375                 380

Gln Ser Asn Leu Ser Gln Tyr His Pro Gln Ile Leu Lys Thr Thr Leu
385                 390                 395                 400

Phe Thr Cys Arg Trp Trp Trp Gly Ser Asp His Cys Val Lys Asp Lys
                405                 410                 415

Trp Asn Leu Ser His Leu Tyr Pro Thr Met Leu Leu Val Glu Ala Phe
            420                 425                 430

Thr Glu Val Leu His Leu Ile Asp Gly Gly Glu Leu Ser Ser Leu Phe
        435                 440                 445

Asp Glu Ser Phe Lys Cys Lys Ile Gly Leu Ser Ile Phe Gln Ala Val
450                 455                 460

Leu Arg Ile Ile Leu Thr Gln Asp Asn Asp Gly Ser Trp Arg Gly Tyr
465                 470                 475                 480

Arg Glu Gln Thr Cys Tyr Ala Ile Leu Ala Leu Val Gln Ala Arg His
                485                 490                 495

Val Cys Phe Phe Thr His Met Val Asp Arg Leu Gln Ser Cys Val Asp
            500                 505                 510

Arg Gly Phe Ser Trp Leu Lys Ser Cys Ser Phe His Ser Gln Asp Leu
        515                 520                 525

Thr Trp Thr Ser Lys Thr Ala Tyr Glu Val Gly Phe Val Ala Glu Ala
530                 535                 540

Tyr Lys Leu Ala Ala Leu Gln Ser Ala Ser Leu Glu Val Pro Ala Ala
545                 550                 555                 560

Thr Ile Gly His Ser Val Thr Ser Ala Val Pro Ser Ser Asp Leu Glu
                565                 570                 575

Lys Tyr Met Arg Leu Val Arg Lys Thr Ala Leu Phe Ser Pro Leu Asp
            580                 585                 590

Glu Trp Gly Leu Met Ala Ser Ile Ile Glu Ser Ser Phe Phe Val Pro
        595                 600                 605

Leu Leu Gln Ala Gln Arg Val Glu Ile Tyr Pro Arg Asp Asn Ile Lys
            610                 615                 620

Val Asp Glu Asp Lys Tyr Leu Ser Ile Ile Pro Phe Thr Trp Val Gly
625                 630                 635                 640

Cys Asn Asn Arg Ser Arg Thr Phe Ala Ser Asn Arg Trp Leu Tyr Asp
                645                 650                 655

Met Met Tyr Leu Ser Leu Leu Gly Tyr Gln Thr Asp Glu Tyr Met Glu
            660                 665                 670

Ala Val Ala Gly Pro Val Phe Gly Asp Val Ser Leu Leu His Gln Thr
        675                 680                 685

Ile Asp Lys Val Ile Asp Asn Thr Met Gly Asn Leu Ala Arg Ala Asn
            690                 695                 700

Gly Thr Val His Ser Gly Asn Gly His Gln His Glu Ser Pro Asn Ile
705                 710                 715                 720
```

-continued

Gly Gln Val Glu Asp Thr Leu Thr Arg Phe Thr Asn Ser Val Leu Asn
                    725                 730                 735

His Lys Asp Val Leu Asn Ser Ser Ser Asp Gln Ser Thr Leu Arg
            740                 745                 750

Arg Glu Phe Arg Thr Phe Met His Ala His Ile Thr Gln Ile Glu Asp
        755                 760                 765

Asn Ser Arg Phe Ser Lys Gln Ala Ser Ser Asp Ala Phe Ser Ser Pro
    770                 775                 780

Glu Gln Ser Tyr Phe Gln Trp Val Asn Ser Thr Gly Gly Ser His Val
785                 790                 795                 800

Ala Cys Ala Tyr Ser Phe Ala Phe Ser Asn Cys Leu Met Ser Ala Asn
                805                 810                 815

Leu Leu Gln Gly Lys Asp Ala Phe Pro Ser Gly Thr Gln Lys Tyr Leu
            820                 825                 830

Ile Ser Ser Val Met Arg His Ala Thr Asn Met Cys Arg Met Tyr Asn
        835                 840                 845

Asp Phe Gly Ser Ile Ala Arg Asp Asn Ala Glu Arg Asn Val Asn Ser
    850                 855                 860

Ile His Phe Pro Glu Phe Thr Leu Cys Asn Gly Thr Ser Gln Asn Leu
865                 870                 875                 880

Asp Glu Arg Lys Glu Arg Leu Leu Lys Ile Ala Thr Tyr Glu Gln Gly
                885                 890                 895

Tyr Leu Asp Arg Ala Leu Glu Ala Leu Glu Arg Gln Ser Arg Asp Asp
            900                 905                 910

Ala Gly Asp Arg Ala Gly Ser Lys Asp Met Arg Lys Leu Lys Ile Val
        915                 920                 925

Lys Leu Phe Cys Asp Val Thr Asp Leu Tyr Asp Gln Leu Tyr Val Ile
    930                 935                 940

Lys Asp Leu Ser Ser Ser Met Lys
945                 950

<210> SEQ ID NO 43
<211> LENGTH: 361
<212> TYPE: PRT
<213> ORGANISM: Stevia rebaudiana

<400> SEQUENCE: 43

Met Ala Leu Val Asn Pro Thr Ala Leu Phe Tyr Gly Thr Ser Ile Arg
1               5                   10                  15

Thr Arg Pro Thr Asn Leu Leu Asn Pro Thr Gln Lys Leu Arg Pro Val
                20                  25                  30

Ser Ser Ser Ser Leu Pro Ser Phe Ser Ser Val Ser Ala Ile Leu Thr
            35                  40                  45

Glu Lys His Gln Ser Asn Pro Ser Glu Asn Asn Leu Gln Thr His
        50                  55                  60

Leu Glu Thr Pro Phe Asn Phe Asp Ser Tyr Met Leu Glu Lys Val Asn
65                  70                  75                  80

Met Val Asn Glu Ala Leu Asp Ala Ser Val Pro Leu Lys Asp Pro Ile
                85                  90                  95

Lys Ile His Glu Ser Met Arg Tyr Ser Leu Leu Ala Gly Gly Lys Arg
            100                 105                 110

Ile Arg Pro Met Met Cys Ile Ala Ala Cys Glu Ile Val Gly Gly Asn
        115                 120                 125

Ile Leu Asn Ala Met Pro Ala Ala Cys Ala Val Glu Met Ile His Thr
    130                 135                 140

Met Ser Leu Val His Asp Asp Leu Pro Cys Met Asn Asp Asp Phe
145                 150                 155                 160

Arg Arg Gly Lys Pro Ile Ser His Lys Val Tyr Gly Glu Glu Met Ala
                165                 170                 175

Val Leu Thr Gly Asp Ala Leu Leu Ser Leu Ser Phe Glu His Ile Ala
            180                 185                 190

Thr Ala Thr Lys Gly Val Ser Lys Asp Arg Ile Val Arg Ala Ile Gly
        195                 200                 205

Glu Leu Ala Arg Ser Val Gly Ser Glu Gly Leu Val Ala Gly Gln Val
    210                 215                 220

Val Asp Ile Leu Ser Glu Gly Ala Asp Val Gly Leu Asp His Leu Glu
225                 230                 235                 240

Tyr Ile His Ile His Lys Thr Ala Met Leu Leu Glu Ser Ser Val Val
                245                 250                 255

Ile Gly Ala Ile Met Gly Gly Gly Ser Asp Gln Gln Ile Glu Lys Leu
            260                 265                 270

Arg Lys Phe Ala Arg Ser Ile Gly Leu Leu Phe Gln Val Val Asp Asp
        275                 280                 285

Ile Leu Asp Val Thr Lys Ser Thr Glu Glu Leu Gly Lys Thr Ala Gly
    290                 295                 300

Lys Asp Leu Leu Thr Asp Lys Thr Thr Tyr Pro Lys Leu Leu Gly Ile
305                 310                 315                 320

Glu Lys Ser Arg Glu Phe Ala Glu Lys Leu Asn Lys Glu Ala Gln Glu
                325                 330                 335

Gln Leu Ser Gly Phe Asp Arg Arg Lys Ala Ala Pro Leu Ile Ala Leu
            340                 345                 350

Ala Asn Tyr Asn Ala Tyr Arg Gln Asn
            355                 360

<210> SEQ ID NO 44
<211> LENGTH: 342
<212> TYPE: PRT
<213> ORGANISM: Fusarium fujikuroi

<400> SEQUENCE: 44

Met Ala Glu Gln Gln Ile Ser Asn Leu Leu Ser Met Phe Asp Ala Ser
1               5                   10                  15

His Ala Ser Gln Lys Leu Glu Ile Thr Val Gln Met Met Asp Thr Tyr
                20                  25                  30

His Tyr Arg Glu Thr Pro Pro Asp Ser Ser Ser Glu Gly Gly Ser
            35                  40                  45

Leu Ser Arg Tyr Asp Glu Arg Arg Val Ser Leu Pro Leu Ser His Asn
    50                  55                  60

Ala Ala Ser Pro Asp Ile Val Ser Gln Leu Cys Phe Ser Thr Ala Met
65                  70                  75                  80

Ser Ser Glu Leu Asn His Arg Trp Lys Ser Gln Arg Leu Lys Val Ala
                85                  90                  95

Asp Ser Pro Tyr Asn Tyr Ile Leu Thr Leu Pro Ser Lys Gly Ile Arg
            100                 105                 110

Gly Ala Phe Ile Asp Ser Leu Asn Val Trp Leu Glu Val Pro Glu Asp
        115                 120                 125

Glu Thr Ser Val Ile Lys Glu Val Ile Gly Met Leu His Asn Ser Ser
    130                 135                 140

Leu Ile Ile Asp Asp Phe Gln Asp Asn Ser Pro Leu Arg Arg Gly Lys

```
                145                 150                 155                 160
Pro Ser Thr His Thr Val Phe Gly Pro Ala Gln Ala Ile Asn Thr Ala
                    165                 170                 175

Thr Tyr Val Ile Val Lys Ala Ile Glu Lys Ile Gln Asp Ile Val Gly
                    180                 185                 190

His Asp Ala Leu Ala Asp Val Thr Gly Thr Ile Thr Thr Ile Phe Gln
                    195                 200                 205

Gly Gln Ala Met Asp Leu Trp Trp Thr Ala Asn Ala Ile Val Pro Ser
                210                 215                 220

Ile Gln Glu Tyr Leu Leu Met Val Asn Asp Lys Thr Gly Ala Leu Phe
225                 230                 235                 240

Arg Leu Ser Leu Glu Leu Leu Ala Leu Asn Ser Glu Ala Ser Ile Ser
                    245                 250                 255

Asp Ser Ala Leu Glu Ser Leu Ser Ser Ala Val Ser Leu Leu Gly Gln
                    260                 265                 270

Tyr Phe Gln Ile Arg Asp Asp Tyr Met Asn Leu Ile Asp Asn Lys Tyr
                    275                 280                 285

Thr Asp Gln Lys Gly Phe Cys Glu Asp Leu Asp Glu Gly Lys Tyr Ser
                290                 295                 300

Leu Thr Leu Ile His Ala Leu Gln Thr Asp Ser Ser Asp Leu Leu Thr
305                 310                 315                 320

Asn Ile Leu Ser Met Arg Arg Val Gln Gly Lys Leu Thr Ala Gln Lys
                    325                 330                 335

Arg Cys Trp Phe Trp Lys
                    340

<210> SEQ ID NO 45
<211> LENGTH: 300
<212> TYPE: PRT
<213> ORGANISM: Mus musculus

<400> SEQUENCE: 45

Met Glu Lys Thr Lys Glu Lys Ala Glu Arg Ile Leu Leu Glu Pro Tyr
1               5                   10                  15

Arg Tyr Leu Leu Gln Leu Pro Gly Lys Gln Val Arg Ser Lys Leu Ser
                20                  25                  30

Gln Ala Phe Asn His Trp Leu Lys Val Pro Glu Asp Lys Leu Gln Ile
                35                  40                  45

Ile Ile Glu Val Thr Glu Met Leu His Asn Ala Ser Leu Leu Ile Asp
            50                  55                  60

Asp Ile Glu Asp Ser Ser Lys Leu Arg Arg Gly Phe Pro Val Ala His
65                  70                  75                  80

Ser Ile Tyr Gly Val Pro Ser Val Ile Asn Ser Ala Asn Tyr Val Tyr
                85                  90                  95

Phe Leu Gly Leu Glu Lys Val Leu Thr Leu Asp His Pro Asp Ala Val
                100                 105                 110

Lys Leu Phe Thr Arg Gln Leu Leu Glu Leu His Gln Gly Gln Gly Leu
                115                 120                 125

Asp Ile Tyr Trp Arg Asp Thr Tyr Thr Cys Pro Thr Glu Glu Glu Tyr
                130                 135                 140

Lys Ala Met Val Leu Gln Lys Thr Gly Gly Leu Phe Gly Leu Ala Val
145                 150                 155                 160

Gly Leu Met Gln Leu Phe Ser Asp Tyr Lys Glu Asp Leu Lys Pro Leu
                165                 170                 175
```

```
Leu Asp Thr Leu Gly Leu Phe Phe Gln Ile Arg Asp Asp Tyr Ala Asn
            180                 185                 190

Leu His Ser Lys Glu Tyr Ser Glu Asn Lys Ser Phe Cys Glu Asp Leu
            195                 200                 205

Thr Glu Gly Lys Phe Ser Phe Pro Thr Ile His Ala Ile Trp Ser Arg
            210                 215                 220

Pro Glu Ser Thr Gln Val Gln Asn Ile Leu Arg Gln Arg Thr Glu Asn
225                 230                 235                 240

Ile Asp Ile Lys Lys Tyr Cys Val Gln Tyr Leu Glu Asp Val Gly Ser
            245                 250                 255

Phe Ala Tyr Thr Arg His Thr Leu Arg Glu Leu Glu Ala Lys Ala Tyr
            260                 265                 270

Lys Gln Ile Glu Ala Cys Gly Gly Asn Pro Ser Leu Val Ala Leu Val
            275                 280                 285

Lys His Leu Ser Lys Met Phe Thr Glu Glu Asn Lys
            290                 295                 300

<210> SEQ ID NO 46
<211> LENGTH: 339
<212> TYPE: PRT
<213> ORGANISM: Thalassiosira pseudonana

<400> SEQUENCE: 46

Met Ala Arg Phe Tyr Phe Leu Asn Ala Leu Leu Met Val Ile Ser Leu
1               5                   10                  15

Gln Ser Thr Thr Ala Phe Thr Pro Ala Lys Leu Ala Tyr Pro Thr Thr
            20                  25                  30

Thr Thr Ala Leu Asn Val Ala Ser Ala Glu Thr Ser Phe Ser Leu Asp
            35                  40                  45

Glu Tyr Leu Ala Ser Lys Ile Gly Pro Ile Glu Ser Ala Leu Glu Ala
        50                  55                  60

Ser Val Lys Ser Arg Ile Pro Gln Thr Asp Lys Ile Cys Glu Ser Met
65                  70                  75                  80

Ala Tyr Ser Leu Met Ala Gly Gly Lys Arg Ile Arg Pro Val Leu Cys
            85                  90                  95

Ile Ala Ala Cys Glu Met Phe Gly Gly Ser Gln Asp Val Ala Met Pro
            100                 105                 110

Thr Ala Val Ala Leu Glu Met Ile His Thr Met Ser Leu Ile His Asp
            115                 120                 125

Asp Leu Pro Ser Met Asp Asn Asp Asp Leu Arg Arg Gly Lys Pro Thr
            130                 135                 140

Asn His Val Val Phe Gly Glu Asp Val Ala Ile Leu Ala Gly Asp Ser
145                 150                 155                 160

Leu Leu Ser Thr Ser Phe Glu His Val Ala Arg Glu Thr Lys Gly Val
            165                 170                 175

Ser Ala Glu Lys Ile Val Asp Val Ile Ala Arg Leu Gly Lys Ser Val
            180                 185                 190

Gly Ala Glu Gly Leu Ala Gly Gly Gln Val Met Asp Leu Glu Cys Glu
            195                 200                 205

Ala Lys Pro Gly Thr Thr Leu Asp Asp Leu Lys Trp Ile His Ile His
            210                 215                 220

Lys Thr Ala Thr Leu Leu Gln Val Ala Val Ala Ser Gly Ala Val Leu
225                 230                 235                 240

Gly Gly Ala Thr Pro Glu Glu Val Ala Ala Cys Glu Leu Phe Ala Met
            245                 250                 255
```

```
Asn Ile Gly Leu Ala Phe Gln Val Ala Asp Ile Leu Asp Val Thr
            260                 265                 270

Ala Ser Ser Glu Asp Leu Gly Lys Thr Ala Gly Lys Asp Glu Ala Thr
275                 280                 285

Asp Lys Thr Thr Tyr Pro Lys Leu Leu Gly Leu Glu Glu Ser Lys Ala
        290                 295                 300

Tyr Ala Arg Gln Leu Ile Asp Glu Ala Lys Glu Ser Leu Ala Pro Phe
305                 310                 315                 320

Gly Asp Arg Ala Ala Pro Leu Leu Ala Ile Ala Asp Phe Ile Ile Asp
                325                 330                 335

Arg Lys Asn

<210> SEQ ID NO 47
<211> LENGTH: 355
<212> TYPE: PRT
<213> ORGANISM: Streptomyces clavuligerus

<400> SEQUENCE: 47

Met His Leu Ala Pro Arg Arg Val Pro Arg Gly Arg Ser Pro Pro
1               5                   10                  15

Asp Arg Val Pro Glu Arg Gln Gly Ala Leu Gly Arg Arg Gly Ala
                20                  25                  30

Gly Ser Thr Gly Cys Ala Arg Ala Ala Gly Val His Arg Arg Arg
            35                  40                  45

Gly Gly Gly Glu Ala Asp Pro Ser Ala Ala Val His Arg Gly Trp Gln
        50                  55                  60

Ala Gly Gly Gly Thr Gly Leu Pro Asp Glu Val Val Ser Thr Ala Ala
65                  70                  75                  80

Ala Leu Glu Met Phe His Ala Phe Ala Leu Ile His Asp Ile Met
                85                  90                  95

Asp Asp Ser Ala Thr Arg Arg Gly Ser Pro Thr Val His Arg Ala Leu
            100                 105                 110

Ala Asp Arg Leu Gly Ala Ala Leu Asp Pro Asp Gln Ala Gly Gln Leu
        115                 120                 125

Gly Val Ser Thr Ala Ile Leu Val Gly Asp Leu Ala Leu Thr Trp Ser
    130                 135                 140

Asp Glu Leu Leu Tyr Ala Pro Leu Thr Pro His Arg Leu Ala Ala Val
145                 150                 155                 160

Leu Pro Leu Val Thr Ala Met Arg Ala Glu Thr Val His Gly Gln Tyr
                165                 170                 175

Leu Asp Ile Thr Ser Ala Arg Arg Pro Gly Thr Asp Thr Ser Leu Ala
            180                 185                 190

Leu Arg Ile Ala Arg Tyr Lys Thr Ala Ala Tyr Thr Met Glu Arg Pro
        195                 200                 205

Leu His Ile Gly Ala Ala Leu Ala Gly Ala Arg Pro Glu Leu Leu Ala
    210                 215                 220

Gly Leu Ser Ala Tyr Ala Leu Pro Ala Gly Glu Ala Phe Gln Leu Ala
225                 230                 235                 240

Asp Asp Leu Leu Gly Val Phe Gly Asp Pro Arg Arg Thr Gly Lys Pro
                245                 250                 255

Asp Leu Asp Asp Leu Arg Gly Gly Lys His Thr Val Leu Val Ala Leu
            260                 265                 270

Ala Arg Glu His Ala Thr Pro Glu Gln Arg His Thr Leu Asp Thr Leu
        275                 280                 285
```

```
Leu Gly Thr Pro Gly Leu Asp Arg Gln Gly Ala Ser Arg Leu Arg Cys
        290                 295                 300

Val Leu Val Ala Thr Gly Ala Arg Ala Glu Ala Glu Arg Leu Ile Thr
305                 310                 315                 320

Glu Arg Arg Asp Gln Ala Leu Thr Ala Leu Asn Ala Leu Thr Leu Pro
                325                 330                 335

Pro Pro Leu Ala Glu Ala Leu Ala Arg Leu Thr Leu Gly Ser Thr Ala
                340                 345                 350

His Pro Ala
        355

<210> SEQ ID NO 48
<211> LENGTH: 330
<212> TYPE: PRT
<213> ORGANISM: Sulfolobus acidocaldarius

<400> SEQUENCE: 48

Met Ser Tyr Phe Asp Asn Tyr Phe Asn Glu Ile Val Asn Ser Val Asn
1               5                   10                  15

Asp Ile Ile Lys Ser Tyr Ile Ser Gly Asp Val Pro Lys Leu Tyr Glu
            20                  25                  30

Ala Ser Tyr His Leu Phe Thr Ser Gly Gly Lys Arg Leu Arg Pro Leu
        35                  40                  45

Ile Leu Thr Ile Ser Ser Asp Leu Phe Gly Gly Gln Arg Glu Arg Ala
50                  55                  60

Tyr Tyr Ala Gly Ala Ala Ile Glu Val Leu His Thr Phe Thr Leu Val
65                  70                  75                  80

His Asp Asp Ile Met Asp Gln Asp Asn Ile Arg Arg Gly Leu Pro Thr
                85                  90                  95

Val His Val Lys Tyr Gly Leu Pro Leu Ala Ile Leu Ala Gly Asp Leu
            100                 105                 110

Leu His Ala Lys Ala Phe Gln Leu Leu Thr Gln Ala Leu Arg Gly Leu
        115                 120                 125

Pro Ser Glu Thr Ile Ile Lys Ala Phe Asp Ile Phe Thr Arg Ser Ile
130                 135                 140

Ile Ile Ile Ser Glu Gly Gln Ala Val Asp Met Glu Phe Glu Asp Arg
145                 150                 155                 160

Ile Asp Ile Lys Glu Gln Glu Tyr Leu Asp Met Ile Ser Arg Lys Thr
                165                 170                 175

Ala Ala Leu Phe Ser Ala Ser Ser Ile Gly Ala Leu Ile Ala Gly
            180                 185                 190

Ala Asn Asp Asn Asp Val Arg Leu Met Ser Asp Phe Gly Thr Asn Leu
        195                 200                 205

Gly Ile Ala Phe Gln Ile Val Asp Asp Ile Leu Gly Leu Thr Ala Asp
210                 215                 220

Glu Lys Glu Leu Gly Lys Pro Val Phe Ser Asp Ile Arg Glu Gly Lys
225                 230                 235                 240

Lys Thr Ile Leu Val Ile Lys Thr Leu Glu Leu Cys Lys Glu Asp Glu
                245                 250                 255

Lys Lys Ile Val Leu Lys Ala Leu Gly Asn Lys Ser Ala Ser Lys Glu
            260                 265                 270

Glu Leu Met Ser Ser Ala Asp Ile Ile Lys Lys Tyr Ser Leu Asp Tyr
        275                 280                 285

Ala Tyr Asn Leu Ala Glu Lys Tyr Tyr Lys Asn Ala Ile Asp Ser Leu
```

```
                290                 295                 300
Asn Gln Val Ser Ser Lys Ser Asp Ile Pro Gly Lys Ala Leu Lys Tyr
305                 310                 315                 320

Leu Ala Glu Phe Thr Ile Arg Arg Lys
                325                 330
```

<210> SEQ ID NO 49
<211> LENGTH: 297
<212> TYPE: PRT
<213> ORGANISM: Synechococcus sp.

<400> SEQUENCE: 49

```
Met Val Ala Gln Thr Phe Asn Leu Asp Thr Tyr Leu Ser Gln Arg Gln
1               5                   10                  15

Gln Gln Val Glu Glu Ala Leu Ser Ala Ala Leu Val Pro Ala Tyr Pro
                20                  25                  30

Glu Arg Ile Tyr Glu Ala Met Arg Tyr Ser Leu Leu Ala Gly Gly Lys
            35                  40                  45

Arg Leu Arg Pro Ile Leu Cys Leu Ala Ala Cys Glu Leu Ala Gly Gly
        50                  55                  60

Ser Val Glu Gln Ala Met Pro Thr Ala Cys Ala Leu Glu Met Ile His
65                  70                  75                  80

Thr Met Ser Leu Ile His Asp Asp Leu Pro Ala Met Asp Asn Asp Asp
                85                  90                  95

Phe Arg Arg Gly Lys Pro Thr Asn His Lys Val Phe Gly Glu Asp Ile
            100                 105                 110

Ala Ile Leu Ala Gly Asp Ala Leu Leu Ala Tyr Ala Phe Glu His Ile
        115                 120                 125

Ala Ser Gln Thr Arg Gly Val Pro Pro Gln Leu Val Leu Gln Val Ile
130                 135                 140

Ala Arg Ile Gly His Ala Val Ala Ala Thr Gly Leu Val Gly Gly Gln
145                 150                 155                 160

Val Val Asp Leu Glu Ser Glu Gly Lys Ala Ile Ser Leu Glu Thr Leu
                165                 170                 175

Glu Tyr Ile His Ser His Lys Thr Gly Ala Leu Leu Glu Ala Ser Val
            180                 185                 190

Val Ser Gly Gly Ile Leu Ala Gly Ala Asp Glu Glu Leu Leu Ala Arg
        195                 200                 205

Leu Ser His Tyr Ala Arg Asp Ile Gly Leu Ala Phe Gln Ile Val Asp
210                 215                 220

Asp Ile Leu Asp Val Thr Ala Thr Ser Glu Gln Leu Gly Lys Thr Ala
225                 230                 235                 240

Gly Lys Asp Gln Ala Ala Ala Lys Ala Thr Tyr Pro Ser Leu Leu Gly
                245                 250                 255

Leu Glu Ala Ser Arg Gln Lys Ala Glu Leu Ile Gln Ser Ala Lys
            260                 265                 270

Glu Ala Leu Arg Pro Tyr Gly Ser Gln Ala Glu Pro Leu Leu Ala Leu
        275                 280                 285

Ala Asp Phe Ile Thr Arg Arg Gln His
    290                 295
```

<210> SEQ ID NO 50
<211> LENGTH: 371
<212> TYPE: PRT
<213> ORGANISM: Arabidopsis thaliana

<400> SEQUENCE: 50

```
Met Ala Ser Val Thr Leu Gly Ser Trp Ile Val His His Asn
1               5                   10                  15

His His His Pro Ser Ser Ile Leu Thr Lys Ser Arg Ser Arg Ser Cys
                20                  25                  30

Pro Ile Thr Leu Thr Lys Pro Ile Ser Phe Arg Ser Lys Arg Thr Val
            35                  40                  45

Ser Ser Ser Ser Ser Ile Val Ser Ser Val Val Thr Lys Glu Asp
    50                  55                  60

Asn Leu Arg Gln Ser Glu Pro Ser Ser Phe Asp Phe Met Ser Tyr Ile
65                  70                  75                  80

Ile Thr Lys Ala Glu Leu Val Asn Lys Ala Leu Asp Ser Ala Val Pro
                85                  90                  95

Leu Arg Glu Pro Leu Lys Ile His Glu Ala Met Arg Tyr Ser Leu Leu
            100                 105                 110

Ala Gly Gly Lys Arg Val Arg Pro Val Leu Cys Ile Ala Ala Cys Glu
            115                 120                 125

Leu Val Gly Gly Glu Glu Ser Thr Ala Met Pro Ala Ala Cys Ala Val
130                 135                 140

Glu Met Ile His Thr Met Ser Leu Ile His Asp Asp Leu Pro Cys Met
145                 150                 155                 160

Asp Asn Asp Asp Leu Arg Arg Gly Lys Pro Thr Asn His Lys Val Phe
                165                 170                 175

Gly Glu Asp Val Ala Val Leu Ala Gly Asp Ala Leu Leu Ser Phe Ala
            180                 185                 190

Phe Glu His Leu Ala Ser Ala Thr Ser Ser Asp Val Val Ser Pro Val
            195                 200                 205

Arg Val Val Arg Ala Val Gly Glu Leu Ala Lys Ala Ile Gly Thr Glu
210                 215                 220

Gly Leu Val Ala Gly Gln Val Val Asp Ile Ser Ser Glu Gly Leu Asp
225                 230                 235                 240

Leu Asn Asp Val Gly Leu Glu His Leu Glu Phe Ile His Leu His Lys
                245                 250                 255

Thr Ala Ala Leu Leu Glu Ala Ser Ala Val Leu Gly Ala Ile Val Gly
            260                 265                 270

Gly Gly Ser Asp Asp Glu Ile Glu Arg Leu Arg Lys Phe Ala Arg Cys
        275                 280                 285

Ile Gly Leu Leu Phe Gln Val Val Asp Asp Ile Leu Asp Val Thr Lys
290                 295                 300

Ser Ser Lys Glu Leu Gly Lys Thr Ala Gly Lys Asp Leu Ile Ala Asp
305                 310                 315                 320

Lys Leu Thr Tyr Pro Lys Ile Met Gly Leu Glu Lys Ser Arg Glu Phe
                325                 330                 335

Ala Glu Lys Leu Asn Arg Glu Ala Arg Asp Gln Leu Leu Gly Phe Asp
            340                 345                 350

Ser Asp Lys Val Ala Pro Leu Leu Ala Leu Ala Asn Tyr Ile Ala Tyr
            355                 360                 365

Arg Gln Asn
370
```

<210> SEQ ID NO 51
<211> LENGTH: 2139
<212> TYPE: DNA
<213> ORGANISM: Artificial Sequence
<220> FEATURE:
<223> OTHER INFORMATION: Codon optimized nucleotide seqeunce encoding A. thaliana ATR2

<400> SEQUENCE: 51

```
atgtcttcct cttcctcttc cagtacctct atgattgatt tgatggctgc tattattaaa      60
ggtgaaccag ttatcgtctc cgacccagca aatgcctctg cttatgaatc agttgctgca     120
gaattgtctt caatgttgat cgaaaacaga caattcgcca tgatcgtaac tacatcaatc     180
gctgttttga tcggttgtat tgtcatgttg gtatggagaa gatccggtag tggtaattct     240
aaaagagtcg aacctttgaa accattagta attaagccaa gagaagaaga aatagatgac     300
ggtagaaaga aagttacaat attttttcggt acccaaactg gtacagctga aggttttgca     360
aaagccttag gtgaagaagc taaggcaaga tacgaaaaga ctagattcaa gatagtcgat     420
ttggatgact atgccgctga tgacgatgaa tacgaagaaa agttgaagaa agaagatgtt     480
gcattttttct ttttggcaac ctatggtgac ggtgaaccaa ctgacaatgc agccagattc     540
tacaaatggt ttacagaggg taatgatcgt ggtgaatggt tgaaaaactt aaagtacggt     600
gttttcggtt tgggtaacag acaatacgaa catttcaaca agttgcaaa ggttgtcgac     660
gatattttgg tcgaacaagg tgctcaaaga ttagtccaag taggtttggg tgacgatgac     720
caatgtatag aagatgactt tactgcctgg agagaagctt gtggcctga attagacaca     780
atcttgagag aagaaggtga caccgccgtt gctaccccat atactgctgc agtattagaa     840
tacagagttt ccatccatga tagtgaagac gcaaagttta atgatatcac tttggccaat     900
ggtaacggtt atacagtttt cgatgcacaa caccccttaca aagctaacgt tgcagtcaag     960
agagaattac atacaccaga atccgacaga agttgtatac acttggaatt tgatatcgct    1020
ggttccggtt taaccatgaa gttgggtgac catgtaggtg ttttatgcga caatttgtct    1080
gaaactgttg atgaagcatt gagattgttg atatgtcccc tgacactta ttttagtttg    1140
cacgctgaaa aagaagatgg tacaccaatt tccagttctt taccacctcc attccctcca    1200
tgtaacttaa gaacagcctt gaccagatac gcttgcttgt tatcatcccc taaaaagtcc    1260
gccttggttg ctttagccgc tcatgctagt gatcctactg aagcagaaag attgaaacac    1320
ttagcatctc cagccggtaa agatgaatat tcaaagtggg tagttgaatc tcaaagatca    1380
ttgttagaag ttatggcaga atttccatct gccaagcctc cattaggtgt cttctttgct    1440
ggtgtagcac ctagattgca accaagattc tactcaatca gttcttcacc taagatcgct    1500
gaaactagaa ttcatgttac atgtgcatta gtctacgaaa agatgccaac cggtagaatt    1560
cacaagggtg tatgctctac ttggatgaaa aatgctgttc cttacgaaaa atcagaaaag    1620
ttgttcttag gtagaccaat cttcgtaaga caatcaaact tcaagttgcc ttctgattca    1680
aaggttccaa taatcatgat aggtcctggt acaggtttag ccccattcag aggtttcttg    1740
caagaaagat tggctttagt tgaatctggt gtcgaattag gtccttcagt tttgttcttt    1800
ggttgtagaa acagaagaat ggatttcatc tatgaagaag aattgcaaag attcgtcgaa    1860
tctggtgcat tggccgaatt atctgtagct ttttcaagag aaggtccaac taaggaatac    1920
gttcaacata tagatgatgga taaggcatcc gacatatgga acatgatcag tcaaggtgct    1980
tatttgtacg tttgcggtga cgcaaagggt atggccagag atgtccatag atctttgcac    2040
acaattgctc aagaacaagg ttccatggat agtaccaaag ctgaaggttt cgtaaagaac    2100
ttacaaactt ccggtagata cttgagagat gtctggtga                           2139
```

<210> SEQ ID NO 52
<211> LENGTH: 1555
<212> TYPE: DNA
<213> ORGANISM: Stevia rebaudiana

<400> SEQUENCE: 52

| | | | | | |
|---|---|---|---|---|---|
| atggcggaac | aacaaaagat | caagaaatca | ccacacgttc | tactcatccc | attcccttta | 60 |
| caaggccata | taaacccttt | catccagttt | ggcaaacgat | taatctccaa | aggtgtcaaa | 120 |
| acaacacttg | ttaccaccat | ccacaccttA | aactcaaccc | taaccacag | taacaccacc | 180 |
| accacctcca | tcgaaatcca | agcaatttcc | gatggttgtg | atgaaggcgg | ttttatgagt | 240 |
| gcaggagaat | catatttgga | aacattcaaa | caagttgggt | ctaaatcact | agctgactta | 300 |
| atcaagaagc | ttcaaagtga | aggaaccaca | attgatgcaa | tcatttatga | ttctatgact | 360 |
| gaatgggttt | tagatgttgc | aattgagttt | ggaatcgatg | gtggttcgtt | tttcactcaa | 420 |
| gcttgtgttg | taaacagctt | atattatcat | gttcataagg | gtttgatttc | tttgccattg | 480 |
| ggtgaaactg | tttcggttcc | tggatttcca | gtgcttcaac | ggtgggagac | accgttaatt | 540 |
| ttgcagaatc | atgagcaaat | acagagccct | tggtctcaga | tgttgtttgg | tcagtttgct | 600 |
| aatattgatc | aagcacgttg | ggtcttcaca | aatagttttt | acaagctcga | ggaagaggta | 660 |
| atagagtgga | cgagaaagat | atggaacttg | aaggtaatcg | gccaacact | tccatccatg | 720 |
| taccttgaca | aacgacttga | tgatgataaa | gataacggat | taatctctA | caaagcaaac | 780 |
| catcatgagt | gcatgaactg | gttagacgat | aagccaaagg | aatcagttgt | ttacgtagca | 840 |
| tttggtagcc | tggtgaaaca | tggacccgaa | caagtggaag | aaatcacacg | ggctttaata | 900 |
| gatagtgatg | tcaacttctt | gtgggttatc | aaacataaag | aagagggaaa | gctcccagaa | 960 |
| aatctttcgg | aagtaataaa | aaccggaaag | ggtttgattg | tagcatggtg | caaacaattg | 1020 |
| gatgtgttag | cacacgaatc | agtaggatgc | tttgttacac | attgtgggtt | caactcaact | 1080 |
| cttgaagcaa | taagtcttgg | agtccccgtt | gttgcaatgc | ctcaatttc | ggatcaaact | 1140 |
| acaaatgcca | agcttctaga | tgaaattttg | ggtgttggag | ttagagttaa | ggctgatgag | 1200 |
| aatgggatag | tgagaagagg | aaatcttgcg | tcatgtatta | agatgattat | ggaggaggaa | 1260 |
| agaggagtaa | taatccgaaa | gaatgcggta | aaatggaagg | atttggctaa | agtagccgtt | 1320 |
| catgaaggtg | gtagctcaga | caatgatatt | gtcgaatttg | taagtgagct | aattaaggct | 1380 |
| taaattttg | ttgctttgta | ttttatgtgt | tatggttttt | tgatttagat | gtattcaatt | 1440 |
| aatattgaat | cataactaaa | ttcaagatta | ttgtttgtaa | tattctttgt | cctaaaattt | 1500 |
| tgcgacttaa | aacctttagt | ttataaaaag | aaattagaaa | atactattgc | acgga | 1555 |

<210> SEQ ID NO 53
<211> LENGTH: 1377
<212> TYPE: DNA
<213> ORGANISM: Artificial Sequence
<220> FEATURE:
<223> OTHER INFORMATION: Codon-optimized S. rebaudiana UGT76G1

<400> SEQUENCE: 53

| | | | | | |
|---|---|---|---|---|---|
| atggaaaaca | agaccgaaac | aacagttaga | cgtaggcgta | gaatcattct | gtttccagta | 60 |
| cctttttcaag | ggcacatcaa | tccaatacta | caactagcca | acgttttgta | ctctaaaggt | 120 |
| ttttctatta | caatctttca | caccaatttc | aacaaaccaa | aacatccaa | ttacccacat | 180 |
| ttcacattca | gattcatact | tgataatgat | ccacaagatg | aacgtatttc | aaacttacct | 240 |
| acccacggtc | ctttagctgg | aatgagaatt | ccaatcatca | atgaacatgg | tgccgatgag | 300 |

```
cttagaagag aattagagtt acttatgttg gcatccgaag aggacgagga agtctcttgt    360
ctgattactg acgctctatg gtactttgcc caatctgtgg ctgatagttt gaatttgagg    420
agattggtac taatgacatc cagtctgttt aactttcacg ctcatgttag tttaccacaa    480
tttgacgaat tgggatactt ggaccctgat gacaagacta ggttagagga acaggcctct    540
ggttttccta tgttgaaagt caaagatatc aagtctgcct attctaattg gcaaatcttg    600
aaagagatct taggaaagat gatcaaacag acaaaggctt catctggagt gatttggaac    660
agtttcaaag agttagaaga gtctgaattg gagactgtaa tcagagaaat tccagcacct    720
tcattcctga taccattacc aaaacatttg actgcttcct cttcctcttt gttggatcat    780
gacagaacag ttttcaatg gttggaccaa caaccaccta gttctgtttt gtacgtgtca    840
tttggtagta cttctgaagt cgatgaaaag gacttccttg aaatcgcaag aggcttagtc    900
gatagtaagc agtcattcct ttgggtcgtg cgtccaggtt tcgtgaaagg ctcaacatgg    960
gtcgaaccac ttccagatgg ttttctaggc gaaagaggta gaatagtcaa atgggttcct   1020
caacaggaag ttttagctca tggcgctatt ggggcattct ggactcattc cggatggaat   1080
tcaactttag aatcagtatg cgaagggta cctatgatct tttcagattt tggtcttgat   1140
caaccactga acgcaagata catgtctgat gttttgaaag tgggtgtata tctagaaaat   1200
ggctgggaaa ggggtgaaat agctaatgca ataagacgtg ttatggttga tgaagagggg   1260
gagtatatca gacaaaacgc aagagtgctg aagcaaaagg ccgacgtttc tctaatgaag   1320
ggaggctctt catacgaatc cttagaatct cttgtttcct acatttcatc actgtaa      1377

<210> SEQ ID NO 54
<211> LENGTH: 512
<212> TYPE: PRT
<213> ORGANISM: Lactuca sativa

<400> SEQUENCE: 54

Met Asp Gly Val Ile Asp Met Gln Thr Ile Pro Leu Arg Thr Ala Ile
1               5                   10                  15

Ala Ile Gly Gly Thr Ala Val Ala Leu Val Val Ala Leu Tyr Phe Trp
            20                  25                  30

Phe Leu Arg Ser Tyr Ala Ser Pro Ser His His Ser Asn His Leu Pro
        35                  40                  45

Pro Val Pro Glu Val Pro Gly Val Pro Val Leu Gly Asn Leu Leu Gln
    50                  55                  60

Leu Lys Glu Lys Lys Pro Tyr Met Thr Phe Thr Lys Trp Ala Glu Met
65                  70                  75                  80

Tyr Gly Pro Ile Tyr Ser Ile Arg Thr Gly Ala Thr Ser Met Val Val
                85                  90                  95

Val Ser Ser Asn Glu Ile Ala Lys Glu Val Val Thr Arg Phe Pro
            100                 105                 110

Ser Ile Ser Thr Arg Lys Leu Ser Tyr Ala Leu Lys Val Leu Thr Glu
        115                 120                 125

Asp Lys Ser Met Val Ala Met Ser Asp Tyr His Asp Tyr His Lys Thr
    130                 135                 140

Val Lys Arg His Ile Leu Thr Ala Val Leu Gly Pro Asn Ala Gln Lys
145                 150                 155                 160

Lys Phe Arg Ala His Arg Asp Thr Met Met Glu Asn Val Ser Asn Glu
                165                 170                 175

Leu His Ala Phe Phe Glu Lys Asn Pro Asn Gln Glu Val Asn Leu Arg
            180                 185                 190
```

Lys Ile Phe Gln Ser Gln Leu Phe Gly Leu Ala Met Lys Gln Ala Leu
        195                 200                 205

Gly Lys Asp Val Glu Ser Ile Tyr Val Lys Asp Leu Glu Thr Thr Met
    210                 215                 220

Lys Arg Glu Glu Ile Phe Glu Val Leu Val Asp Pro Met Met Gly
225                 230                 235                 240

Ala Ile Glu Val Asp Trp Arg Asp Phe Phe Pro Tyr Leu Lys Trp Val
                245                 250                 255

Pro Asn Lys Ser Phe Glu Asn Ile Ile His Arg Met Tyr Thr Arg Arg
            260                 265                 270

Glu Ala Val Met Lys Ala Leu Ile Gln Glu His Lys Lys Arg Ile Ala
        275                 280                 285

Ser Gly Glu Asn Leu Asn Ser Tyr Ile Asp Tyr Leu Leu Ser Glu Ala
    290                 295                 300

Gln Thr Leu Thr Asp Lys Gln Leu Leu Met Ser Leu Trp Glu Pro Ile
305                 310                 315                 320

Ile Glu Ser Ser Asp Thr Thr Met Val Thr Thr Glu Trp Ala Met Tyr
                325                 330                 335

Glu Leu Ala Lys Asn Pro Asn Met Gln Asp Arg Leu Tyr Glu Glu Ile
            340                 345                 350

Gln Ser Val Cys Gly Ser Glu Lys Ile Thr Glu Glu Asn Leu Ser Gln
        355                 360                 365

Leu Pro Tyr Leu Tyr Ala Val Phe Gln Glu Thr Leu Arg Lys His Cys
    370                 375                 380

Pro Val Pro Ile Met Pro Leu Arg Tyr Val His Glu Asn Thr Val Leu
385                 390                 395                 400

Gly Gly Tyr His Val Pro Ala Gly Thr Glu Val Ala Ile Asn Ile Tyr
                405                 410                 415

Gly Cys Asn Met Asp Lys Lys Val Trp Glu Asn Pro Glu Glu Trp Asn
            420                 425                 430

Pro Glu Arg Phe Leu Ser Glu Lys Glu Ser Met Asp Leu Tyr Lys Thr
        435                 440                 445

Met Ala Phe Gly Gly Lys Arg Val Cys Ala Gly Ser Leu Gln Ala
    450                 455                 460

Met Val Ile Ser Cys Ile Gly Ile Gly Arg Leu Val Gln Asp Phe Glu
465                 470                 475                 480

Trp Lys Leu Lys Asp Asp Ala Glu Glu Asp Val Asn Thr Leu Gly Leu
                485                 490                 495

Thr Thr Gln Lys Leu His Pro Leu Leu Ala Leu Ile Asn Pro Arg Lys
            500                 505                 510

<210> SEQ ID NO 55
<211> LENGTH: 1566
<212> TYPE: DNA
<213> ORGANISM: Artificial Sequence
<220> FEATURE:
<223> OTHER INFORMATION: Codon-optimized KO

<400> SEQUENCE: 55
aagcttacta gtaaaatgga cggtgtcatc gatatgcaaa ccattccatt gagaaccgct      60
attgctattg gtggtactgc tgttgctttg gttgttgcat tatacttttg gttcttgaga     120
tcctacgctt ccccatctca tcattctaat catttgccac cagtacctga agttccaggt     180
gttccagttt tgggtaattt gttgcaattg aaagaaaaaa agccttacat gaccttcacc     240

```
aagtgggctg aaatgtatgg tccaatctac tctattagaa ctggtgctac ttccatggtt      300
gttgtctctt ctaacgaaat cgccaaagaa gttgttgtta ccagattccc atctatctct      360
accagaaaat tgtcttacgc cttgaaggtt ttgaccgaag ataagtctat ggttgccatg      420
tctgattatc acgattacca taagaccgtc aagagacata ttttgactgc tgttttgggt      480
ccaaacgccc aaaaaagtt tagagcacat agagacacca tgatggaaaa cgtttccaat       540
gaattgcatg ccttcttcga aaagaaccca aatcaagaag tcaacttgag aaagatcttc      600
caatcccaat tattcggttt ggctatgaag caagccttgg gtaaagatgt tgaatccatc      660
tacgttaagg atttggaaac caccatgaag agagaagaaa tcttcgaagt tttggttgtc      720
gatccaatga tgggtgctat tgaagttgat tggagagact ttttcccata cttgaaatgg      780
gttccaaaca agtccttcga aaacatcatc catagaatgt acactagaag agaagctgtt      840
atgaaggcct tgatccaaga acacaagaaa agaattgcct ccggtgaaaa cttgaactcc      900
tacattgatt acttgttgtc tgaagcccaa accttgaccg ataagcaatt attgatgtct      960
ttgtgggaac ctattatcga atcttctgat accactatgg ttactactga atgggctatg     1020
tacgaattgg ctaagaatcc aaacatgcaa gacagattat acgaagaaat ccaatccgtt     1080
tgcggttccg aaaagattac tgaagaaaac ttgtcccaat gccatacttt gtacgctgtt     1140
ttccaagaaa cttttgagaaa gcactgtcca gttcctatta tgccattgag atatgttcac     1200
gaaaacaccg ttttgggtgg ttatcatgtt ccagctggta ctgaagttgc tattaacatc     1260
tacggttgca acatggataa gaaggtctgg gaaaatccag aagaatggaa tccagaaaga     1320
ttcttgtccg aaaagaatc catggacttg tacaaaacta tggcttttgg tggtggtaaa     1380
agagtttgcg ctggttcttt acaagccatg gttatttctt gcattggtat cggtagattg     1440
gtccaagatt ttgaatggaa gttgaaggat gatgccgaag aagatgttaa cacttttggg     1500
ttgactaccc aaaagttgca tccattattg gccttgatta cccaagaaa gtaactcgag     1560 ccgcgg                                                                1566

<210> SEQ ID NO 56
<211> LENGTH: 1535
<212> TYPE: DNA
<213> ORGANISM: Rubus suavissimus

<400> SEQUENCE: 56
atggccaccc tccttgagca tttccaagct atgccctttg ccatccctat tgcactggct       60
gctctgtctt ggctgttcct cttttacatc aaagtttcat tcttttccaa caagagtgct     120
caggctaagc tccctcctgt gccagtggtt cctgggctgc cggtgattgg gaatttactg     180
caactcaagg agaagaaacc ctaccagact tttacaaggt gggctgagga gtatggacca     240
atctattcta tcaggactgg tgcttccacc atggtcgttc tcaataccac ccaagttgca     300
aaagaggcca tggtgaccag atatttatcc atctcaacca gaaagctatc aaacgcacta     360
aagattctta ctgctgataa atgtatggtt gcaataagtg actacaacga ttttcacaag     420
atgataaagc gatacatact ctcaaatgtt cttggaccta gtgctcagaa gcgtcaccgg     480
agcaacagag ataccttgag agctaatgtc tgcagccgat tgcattctca gtaaagaac      540 tctcctcgag aagctgtgaa tttcagaaga gttttttgagt gggaactctt tggaattgca    600
ttgaagcaag cctttggaaa ggacatagaa aagcccattt atgtgggaagga acttggcact  660 acactgtcaa gagatgagat ctttaaggtt ctagtgcttg acataatgga gggtgcaatt    720
gaggttgatt ggagagattt cttcccttac ctgagatgga ttccgaatac gcgcatggaa    780
```

```
acaaaaattc agcgactcta tttccgcagg aaagcagtga tgactgccct gatcaacgag      840
cagaagaagc gaattgcttc aggagaggaa atcaactgtt atatcgactt cttgcttaag      900
gaagggaaga cactgacaat ggaccaaata agtatgttgc tttgggagac ggttattgaa      960
acagcagata ctacaatggt aacgacagaa tgggctatgt atgaagttgc taaagactca     1020
aagcgtcagg atcgtctcta tcaggaaatc caaaaggttt gtggatcgga tggttaca      1080 gaggaatact tgtcccaact gccgtacctg aatgcagttt ccatgaaaac gctaaggaag     1140
cacagtccgg ctgcgttagt tcctttaaga tatgcacatg aagatacccca actaggaggt     1200 tactacattc cagctggaac tgagattgct ataaacatat acgggtgtaa catggacaag     1260
catcaatggg aaagccctga ggaatggaaa ccggagagat ttttggaccc gaaatttgat     1320
cctatggatt tgtacaagac catggctttt ggggctggaa agagggtatg tgctggttct     1380
cttcaggcaa tgttaatagc gtgcccgacg attggtaggc tggtgcagga gtttgagtgg     1440
aagctgagag atggagaaga agaaaatgta gatactgttg ggctcaccac tcacaaacgc     1500
tatccaatgc atgcaatcct gaagccaaga agtta                                1535

<210> SEQ ID NO 57
<211> LENGTH: 1572
<212> TYPE: DNA
<213> ORGANISM: Artificial Sequence
<220> FEATURE:
<223> OTHER INFORMATION: Codon-optimized KO

<400> SEQUENCE: 57
aagcttacta gtaaaatggc ctccatcacc catttcttac aagattttca agctactcca       60
ttcgctactg cttttgctgt tggtggtgtt tctttgttga tattcttctt cttcatccgt      120
ggtttccact ctactaagaa aaacgaatat acaagttgc caccagttcc agttgttcca      180
ggtttgccag ttgttggtaa tttgttgcaa ttgaaagaaa agaagccata caagactttc      240
ttgagatggg ctgaaattca tggtccaatc tactctatta gaactggtgc ttctaccatg      300
gttgttgtta actctactca tgttgccaaa gaagctatgg ttaccagatt ctcttcaatc      360
tctaccagaa agttgtccaa ggcttttgaa ttattgaccc caacaaatc tatggttgcc      420 acctctgatt acaacgaatt tcacaagatg gtcaagaagt acatcttggc cgaattattg      480
ggtgctaatg ctcaaaagag acacagaatt catagagaca ccttgatcga aacgtcttg      540 aacaaattgc atgcccatac caagaattct ccattgcaag ctgttaactt cagaaagatc      600
ttcgaatctg aattattcgg tttggctatg aagcaagcct ggggtatga tgttgattcc      660 ttgttcgttg aagaattggg tactaccttg tccagagaag aaatctacaa cgttttggtc      720
agtgacatgt gaagggtgc tattgaagtt gattggagag acttttttcc atacttgaaa      780
tggatcccaa acaagtcctt cgaaatgaag attcaaagat ggcctctag aagacaagcc      840 gttatgaact ctattgtcaa agaacaaaag aagtccattg cctctggtaa gggtgaaaac      900
tgttacttga attacttgtt gtccgaagct aagactttga ccgaaaagca aatttccatt      960
ttggcctggg aaaccattat tgaaactgct gatacaactg ttgttaccac tgaatgggct     1020
atgtacgaat ggctaaaaa cccaaagcaa caagacagat tatacaacga aatccaaaac     1080
gtctgcggta ctgataagat taccgaagaa catttgtcca agttgcctta cttgtctgct     1140
gtttttcacg aaaaccttgag aaagtattct ccatctccat tggttccatt gagatacgct     1200
catgaagata ctcaattggg tggttattat gttccagccg gtactgaaat tgctgttaat     1260
```

```
atctacggtt gcaacatgga caagaatcaa tgggaaactc agaagaatg gaagccagaa      1320 agatttttgg acgaaaagta cgatccaatg gacatgtaca agactatgtc ttttggttcc      1380
ggtaaaagag tttgcgctgg ttctttacaa gctagtttga ttgcttgtac ctccatcggt      1440
agattggttc aagaatttga atggagattg aaagacggtg aagttgaaaa cgttgatacc      1500
ttgggtttga ctacccataa gttgtatcca atgcaagcta tcttgcaacc tagaaactga      1560
ctcgagccgc gg                                                          1572

<210> SEQ ID NO 58
<211> LENGTH: 1512
<212> TYPE: DNA
<213> ORGANISM: Artificial Sequence
<220> FEATURE:
<223> OTHER INFORMATION: Codon-optimized KO

<400> SEQUENCE: 58
atgatttcct tgttgttggg ttttgttgtc tcctccttct tgtttatctt cttcttgaaa       60
aaattgttgt tcttcttcag tcgtcacaaa atgtccgaag tttctagatt gccatctgtt      120
ccagttccag gttttccatt gattggtaac ttgttgcaat tgaaagaaaa gaagccacac      180
aagactttca ccaagtggtc tgaattatat ggtccaatct actctatcaa gatgggttcc      240
tcttctttga tcgtcttgaa ctctattgaa accgccaaag aagctatggt cagtagattc      300
tcttcaatct ctaccagaaa gttgtctaac gctttgactg ttttgacctg caacaaatct      360
atggttgcta cctctgatta cgatgacttt cataagttcg tcaagagatg cttgttgaac      420
ggtttgttgg gtgctaatgc tcaagaaaga aaaagacatt acagagatgc cttgatcgaa      480
aacgttacct ctaaattgca tgcccatacc agaaatcatc acaagaacc agttaacttc       540 agagccattt tcgaacacga attattcggt gttgctttga acaagccttt cggtaaagat      600
gtcgaatcca tctatgtaaa agaattgggt gtcaccttgt ccagagatga atttttcaag      660
gttttggtcc acgacatgat ggaaggtgct attgatgttg attggagaga ttttcttccca     720 tacttgaaat ggatcccaaa caactctttc gaagccagaa ttcaacaaaa gcacaagaga      780
agattggctg ttatgaacgc cttgatccaa gacagattga atcaaaacga ttccgaatcc      840
gatgatgact gctacttgaa tttcttgatg tctgaagcta gaccttgac catggaacaa       900 attgctattt tggtttggga aaccattatc gaaactgctg ataccacttt ggttactact      960
gaatgggcta tgtacgaatt ggccaaacat caatctgttc aagatagatt attcaaagaa     1020
atccaatccg tctgcggtgg tgaaaagatc aagaagaac aattgccaag attgccttac      1080
gtcaatggtg tttttcacga aaccttgaga agtattctc cagctccatt ggttccaatt      1140
agatacgctc atgaagatac ccaaattggt ggttatcata ttccagccgg ttctgaaatt     1200
gccattaaca tctacggttg caacatggat aagaagagat gggaaagacc tgaagaatgg     1260
tggccagaaa gatttttgga agatagatac gaatcctccg acttgcataa gactatggct     1320
tttggtgctg gtaaaagagt ttgtgctggt gctttacaag ctagtttgat ggctggtatt     1380
gctatcggta gattggttca agaattcgaa tggaagttga gagatggtga agaagaaaac     1440
gttgatactt acggtttgac ctcccaaaag ttgtatccat tgatggccat tatcaaccca     1500
agaagatctt aa                                                         1512

<210> SEQ ID NO 59
<211> LENGTH: 1542
<212> TYPE: DNA
<213> ORGANISM: Artificial Sequence
```

<220> FEATURE:
<223> OTHER INFORMATION: Codon-optimized KO

<400> SEQUENCE: 59

```
atggatgctg tgacgggttt gttaactgtc ccagcaaccg ctataactat tggtggaact      60
gctgtagcat tggcggtagc gctaatcttt tggtacctga atcctacac atcagctaga     120
agatcccaat caaatcatct tccaagagtg cctgaagtcc caggtgttcc attgttagga     180
aatctgttac aattgaagga gaaaaagcca tacatgactt ttacgagatg ggcagcgaca     240
tatggaccta tctatagtat caaaactggg gctacaagta tggttgtggt atcatctaat     300
gagatagcca aggaggcatt ggtgaccaga ttccaatcca tatctacaag gaacttatct     360
aaagccctga agtacttac agcagataag acaatggtcg caatgtcaga ttatgatgat     420
tatcataaaa cagttaagag acacatactg accgccgtct gggtcctaa tgcacagaaa     480
aagcatagaa ttcacagaga tatcatgatg gataacatat ctactcaact tcatgaattc     540
gtgaaaaaca acccgaaaca ggaagaggta gaccttagaa aaatctttca atctgagtta     600
ttcggcttag ctatgagaca agccttagga aaggatgttg aaagtttgta cgttgaagac     660
ctgaaaatca ctatgaatag agacgaaatc tttcaagtcc ttgttgttga tccaatgatg     720
ggagcaatcg atgttgattg gagagacttc tttccatacc taaagtgggt cccaaacaaa     780
aagttcgaaa atactattca acaaatgtac atcagaagag aagctgttat gaaatcttta     840
atcaaagagc acaaaaagag aatagcgtca ggcgaaaagc taaatagtta tatcgattac     900
cttttatctg aagctcaaac tttaaccgat cagcaactat tgatgtcctt gtgggaacca     960
atcattgaat cttcagatac aacaatggtc acaacagaat gggcaatgta cgaattagct    1020
aaaaaccta aattgcaaga taggttgtac agagacatta agtccgtctg tggatctgaa    1080
aagataaccg aagagcatct atcacagctg ccttacatta cagctatttt ccacgaaaca    1140
ctgagaagac actcaccagt tcctatcatt cctctaagac atgtacatga agataccgtt    1200
ctaggcggct accatgttcc tgctggcaca gaacttgccg ttaacatcta cggttgcaac    1260
atggacaaaa acgtttggga aaatccagag gaatggaacc cagaaagatt catgaaagag    1320
aatgagacaa ttgattttca aaagacgatg gccttcggtg gtggtaagag agtttgtgct    1380
ggttccttgc aagcccttt aactgcatct attgggattg ggagaatggt tcaagagttc    1440
gaatggaaac tgaaggatat gactcaagag gaagtgaaca cgataggcct aactacacaa    1500
atgttaagac cattgagagc tattatcaaa cctaggatct aa                        1542
```

<210> SEQ ID NO 60
<211> LENGTH: 1554
<212> TYPE: DNA
<213> ORGANISM: Artificial Sequence
<220> FEATURE:
<223> OTHER INFORMATION: Codon-optimized KO

<400> SEQUENCE: 60

```
aagcttacta gtaaaatgga catgatgggt attgaagctg ttccatttgc tactgctgtt      60
gttttgggtg gtatttcctt ggttgttttg atcttcatca gaagattcgt ttccaacaga     120
aagagatccg ttgaaggttt gccaccagtt ccagatattc aggtttacc attgattggt     180
aacttgttgc aattgaaaga aaagaagcca cataagacct tgctagatg ggctgaaact     240
tacggtccaa ttttctctat tagaactggt gcttctacca tgatcgtctt gaattcttct     300
gaagttgcca agaagctat ggtcactaga ttctcttcaa tctctaccag aaagttgtcc     360
```

```
aacgccttga agattttgac cttcgataag tgtatggttg ccacctctga ttacaacgat    420
tttcacaaaa tggtcaaggg tttcatcttg agaaacgttt taggtgctcc agcccaaaaa    480
agacatagat gtcatagaga taccttgatc gaaaacatct ctaagtactt gcatgcccat    540
gttaagactt ctccattgga accagttgtc ttgaagaaga ttttcgaatc cgaaattttc    600
ggtttggctt tgaaacaagc cttgggtaag gatatcgaat ccatctatgt tgaagaattg    660
ggtactacct tgtccagaga agaaattttt gccgttttgg ttgttgatcc aatggctggt    720
gctattgaag ttgattggag agattttttc ccatacttgt cctggattcc aaacaagtct    780
atggaaatga agatccaaag aatggatttt agaagaggtg ctttgatgaa ggccttgatt    840
ggtgaacaaa agaaaagaat cggttccggt gaagaaaaga actcctacat tgatttcttg    900
ttgtctgaag ctaccacttt gaccgaaaag caaattgcta tgttgatctg gaaaccatc     960 atcgaaattt ccgatacaac tttggttacc tctgaatggg ctatgtacga attggctaaa   1020
gacccaaata gacaagaaat cttgtacaga gaaatccaca aggtttgcgg ttctaacaag   1080
ttgactgaag aaaacttgtc caagttgcca tacttgaact ctgttttcca cgaaaccttg   1140
agaaagtatt ctccagctcc aatggttcca gttagatatg ctcatgaaga tactcaattg   1200
ggtggttacc atattccagc tggttctcaa attgccatta acatctacgg ttgcaacatg   1260
aacaaaaagc aatgggaaaa tcctgaagaa tggaagccag aaagattctt ggacgaaaag   1320
tatgacttga tggacttgca taagactatg gcttttggtg gtggtaaaag agtttgtgct   1380
ggtgctttac aagcaatgtt gattgcttgc acttccatcg gtagattcgt tcaagaattt   1440
gaatggaagt tgatgggtgg tgaagaagaa acgttgata ctgttgcttt gacctcccaa    1500
aaattgcatc caatgcaagc cattattaag gccagagaat gactcgagcc gcgg         1554

<210> SEQ ID NO 61
<211> LENGTH: 2133
<212> TYPE: DNA
<213> ORGANISM: Artificial Sequence
<220> FEATURE:
<223> OTHER INFORMATION: Codon-optimized CPR

<400> SEQUENCE: 61
atgcaatcag attcagtcaa agtctctcca tttgatttgg tttccgctgc tatgaatggc     60
aaggcaatgg aaaagttgaa cgctagtgaa tctgaagatc caacaacatt gcctgcacta    120 agatgctag ttgaaaatag agaattgttg acactgttca caacttcctt cgcagttctt     180
attgggtgtc ttgtatttct aatgtggaga cgttcatcct ctaaaaagct ggtacaagat    240
ccagttccac aagttatcgt tgtaaagaag aaagagaagg agtcagaggt tgatgacggg    300
aaaaagaaag tttctatttt ctacggcaca caaacaggaa ctgccgaagg ttttgctaaa    360
gcattagtcg aggaagcaaa agtgagatat gaaaagacct cttccaaggt tatcgatcta    420
gatgactacg ctgcagatga tgatgaatat gaggaaaaac tgaaaaggga tccttagcc     480 ttcttcttct tggccacata cggtgatggt gaacctactg ataatgctgc taacttctac    540
aagtggttca cagaaggcga cgataaaggt gaatggctga aaagttaca atacggagta    600 tttggtttag gtaacagaca atatgaacat ttcaacaaga tcgctattgt agttgatgat    660
aaacttactg aaatgggagc caaaagatta gtaccagtag gattagggga tgatgatcag    720
tgtatagaag atgacttcac cgcctggaag gaattggtat ggccagaatt ggatcaactt    780
ttaagggacg aagatgatac ttctgtgact accccataca ctgcagccgt attggagtac    840
agagtggttt accatgataa accagcagac tcatatgctg aagatcaaac ccatacaaac    900
```

```
ggtcatgttg ttcatgatgc acagcatcct tcaagatcta atgtggcttt caaaaaggaa      960
ctacacacct ctcaatcaga taggtcttgt actcacttag aattcgatat ttctcacaca     1020
ggactgtctt acgaaactgg cgatcacgtt ggcgtttatt ccgagaactt gtccgaagtt     1080
gtcgatgaag cactaaaact gttagggtta tcaccagaca catacttctc agtccatgct     1140
gataaggagg atgggacacc tatcggtggt gcttcactac caccaccttt tcctccttgc     1200
acattgagag acgctctaac cagatacgca gatgtcttat cctcacctaa aaaggtagct     1260
ttgctggcat tggctgctca tgctagtgat cctagtgaag ccgataggtt aaagttcctg     1320
gcttcaccag ccgaaaaaga tgaatatgca caatggatcg tcgccaacca acgttctttg     1380
ctagaagtga tgcaaagttt tccatctgcc aagcctccat aggtgtgtt cttcgcagca     1440
gtagctccac gttacaacc aagatactac tctatcagtt catctcctaa gatgtctcct     1500
aacagaatac atgttacatg tgctttggtg tacgagacta ctccagcagg cagaattcac     1560
agaggattgt gttcaacctg gatgaaaaat gctgtcccct taacagagtc acctgattgc     1620
tctcaagcat ccattttcgt tagaacatca aatttcagac ttccagtgga tccaaaagtt     1680
ccagtcatta tgataggacc aggcactggt cttgccccat tcaggggctt tcttcaagag     1740
agattggcct tgaaggaatc tggtacagaa ttgggttctt ctatcttttt ctttggttgc     1800
cgtaatagaa aagttgactt tatctacgag gacgagctta acaattttgt tgagacagga     1860
gcattgtcag aattgatcgt cgcattttca agagaaggga ctgccaaaga gtacgttcag     1920
cacaagatga gtcaaaaagc ctccgatata tggaaacttc taagtgaagg tgcctatctt     1980
tatgtctgtg gcgatgcaaa gggcatggcc aaggatgtcc atagaactct gcatacaatt     2040
gttcaggaac aagggagtct ggattcttcc aaggctgaat tgtacgtcaa aaacttacag     2100
atgtctggaa gatacttaag agatgtttgg taa                                 2133
```

<210> SEQ ID NO 62
<211> LENGTH: 2106
<212> TYPE: DNA
<213> ORGANISM: Siraitia grosvenorii

<400> SEQUENCE: 62

```
atgaaggtca gtccattcga attcatgtcc gctattatca agggtagaat ggacccatct      60
aactcctcat ttgaatctac tggtgaagtt gcctccgtta tctttgaaaa cagagaattg     120
gttgccatct tgaccacttc tattgctgtt atgattggtt gcttcgttgt cttgatgtgg     180
agaagagctg ttctagaaa ggttaagaat gtcgaattgc caaagccatt gattgtccat     240
gaaccagaac ctgaagttga agatggtaag aagaaggttt ccatcttctt cggtactcaa     300
actggtactg ctgaaggttt tgctaaggct ttggctgatg aagctaaagc tagatacgaa     360
aaggctacct tcagagttgt tgatttggat gattatgctg ccgatgatga ccaatacgaa     420
gaaaaattga gaacgaatc cttcgccgtt ttccttgttgg ctacttatgg tgatggtgaa     480
cctactgata atgctgctag attttacaag tggttcgccg aaggtaaaga agaggtgaa     540
tggttgcaaa acttgcacta tgctgttttt ggtttgggta acagacaata cgaacacttc     600
aacaagattg ctaaggttgc cgacgaatta ttggaagctc aaggtggtaa tagattggtt     660
aaggttggtt taggtgatga cgatcaatgc atcgaagatg atttttctgc ttggagagaa     720
tctttgtggc cagaattgga tatgttgttg agagatgaag atgatgctac tactgttact     780
actccatata ctgctgctgt cttggaatac agagttgtct ttcatgattc tgctgatgtt     840
```

```
gctgctgaag ataagtcttg gattaacgct aatggtcatg ctgttcatga tgctcaacat    900
ccattcagat ctaacgttgt cgtcagaaaa gaattgcata cttctgcctc tgatagatcc    960
tgttctcatt tggaattcaa catttccggt tccgctttga attacgaaac tggtgatcat   1020
gttggtgtct actgtgaaaa cttgactgaa actgttgatg aagccttgaa cttgttgggt   1080
ttgtctccag aaacttactt ctctatctac accgataacg aagatggtac tccattgggt   1140
ggttcttcat tgccaccacc atttccatca tgtactttga aactgctttt gaccagatac   1200
gctgatttgt tgaactctcc aaaaaagtct gctttgttgg ctttagctgc tcatgcttct   1260
aatccagttg aagctgatag attgagatac ttggcttctc cagctggtaa agatgaatat   1320
gcccaatctg ttatcggttc ccaaaagtct tgttggaag ttatggctga attcccatct    1380
gctaaaccac cattaggtgt tttttttgct gctgttgctc caagattgca acctagattc   1440
tactccattt catcctctcc aagaatggct ccatctagaa tccatgttac ttgtgctttg   1500
gtttacgata agatgccaac tggtagaatt cataagggtg tttgttctac ctggatgaag   1560
aattctgttc aatggaaaaa gtcccatgaa tgttcttggg ctccaatttt cgttagacaa   1620
tccaattta agttgccagc cgaatccaag gttccaatta tcatggttgg tccaggtact   1680
ggtttggctc cttttagagg ttttttacaa gaaagattgg ccttgaaaga tccggtgtt    1740
gaattgggtc catccatttt gttttttcggt tgcagaaaca gaagaatgga ttacatctac   1800
gaagatgaat tgaacaactt cgttgaaacc ggtgctttgt ccgaattggt tattgctttt   1860
tctagagaag gtcctaccaa agaatacgtc aacataaga tggctgaaaa ggcttctgat    1920
atctggaact tgatttctga aggtgcttac ttgtacgttt gtgtgatgc taaaggtatg    1980
gctaaggatg ttcatagaac cttgcatacc atcatgcaag aacaaggttc tttggattct   2040
tccaaagctg aatccatggt caagaacttg caaatgaatg gtagatactt aagagatgtt   2100
tggtaa                                                               2106
```

<210> SEQ ID NO 63
<211> LENGTH: 1593
<212> TYPE: DNA
<213> ORGANISM: Artificial Sequence
<220> FEATURE:
<223> OTHER INFORMATION: Codon-optimized KO

<400> SEQUENCE: 63

```
aagcttaaaa tgagtaagtc taatagtatg aattctacat cacacgaaac ccttttttcaa    60
caattggtct tgggttttgga ccgtatgcca ttgatggatg ttcactggtt gatctacgtt   120
gctttcggcg catggttatg ttcttatgtg atacatgttt tatcatcttc ctctacagta   180
aaagtgccag ttgttggata caggtctgta ttcgaaccta catggttgct tagacttaga   240
ttcgtctggg aaggtggctc tatcataggt caagggtaca ataagtttaa agactctatt   300
ttccaagtta ggaaattggg aactgatatt gtcattatac cacctaacta tattgatgaa   360
gtgagaaaat tgtcacagga caagactaga tcagttgaac ctttcattaa tgattttgca   420
ggtcaataca caagaggcat ggttttcttg caatctgact tacaaaaccg tgttatacaa   480
caaagactaa ctccaaaatt ggtttccttg accaaggtca tgaaggaaga gttggattat   540
gctttaacaa aagagatgcc tgatatgaaa aatgacgaat gggtagaagt agatatcagt   600
agtataatgg tgagattgat ttccaggatc tccgccagag tctttctagg gcctgaacac   660
tgtcgtaacc aggaatggtt gactactaca gcagaatatt cagaatcact tttcattaca   720
gggtttatct taagagttgt acctcatatc ttaagaccat tcatcgcccc tctattacct   780
```

```
tcatacagga ctctacttag aaacgtttca agtggtagaa gagtcatcgg tgacatcata    840
agatctcagc aagggatgg taacgaagat atactttcct ggatgagaga tgctgccaca     900
ggagaggaaa agcaaatcga taacattgct cagagaatgt taattctttc tttagcatca    960
atccacacta ctgcgatgac catgacacat gccatgtacg atctatgtgc ttgccctgag   1020
tacattgaac cattaagaga tgaagttaaa tctgttgttg gggcttctgg ctgggacaag   1080
acagcgttaa acagatttca taagttggac tccttcctaa aagagtcaca aagattcaac   1140
ccagtattct tattgacatt caatagaatc taccatcaat ctatgacctt atcagatggc   1200
actaacattc catctggaac acgtattgct gttccatcac acgcaatgtt gcaagattct   1260
gcacatgtcc caggtccaac cccacctact gaatttgatg gattcagata tagtaagata   1320
cgttctgata gtaactacgc acaaaagtac ctattctcca tgaccgattc ttcaaacatg   1380
gctttcggat acggcaagta tgcttgtcca ggtagatttt acgcgtctaa tgagatgaaa   1440
ctaacattag ccattttgtt gctacaattt gagttcaaac taccagatgg taaaggtcgt   1500
cctagaaata tcactatcga ttctgatatg attccagacc caagagctag actttgcgtc   1560
agaaaaagat cacttagaga tgaatgaccg cgg                                 1593

<210> SEQ ID NO 64
<211> LENGTH: 1515
<212> TYPE: DNA
<213> ORGANISM: Artificial Sequence
<220> FEATURE:
<223> OTHER INFORMATION: Codon-optimized KO

<400> SEQUENCE: 64
aagcttaaaa tggaagatcc tactgtctta tatgcttgtc ttgccattgc agttgcaact     60
ttcgttgtta gatggtacag agatccattg agatccatcc aacagttgg tggttccgat    120
ttgcctattc tatcttacat cggcgcacta agatggacaa gacgtggcag agagatactt    180
caagagggat atgatggcta cagaggatct acattcaaaa tcgcgatgtt agaccgttgg    240
atcgtgatcg caaatggtcc taaactagct gatgaagtca gacgtagacc agatgaagag    300
ttaaacttta tggacggatt aggagcattc gtccaaacta gtacacctt aggtgaagct    360
attcataacg atccataccā tgtcgatatc ataagagaaa aactaacaag aggccttcca    420
gccgtgcttc ctgatgtcat tgaagagttg acacttgcgg ttagacagta cattccaaca    480
gaaggtgatg aatgggtgtc cgtaaactgt tcaaaggccg caagagatat tgttgctaga    540
gcttctaata gagtctttgt aggtttgcct gcttgcagaa accaaggtta cttagatttg    600
gcaatagact ttacattgtc tgttgtcaag gatagagcca tcatcaatat gtttccagaa    660
ttgttgaagc caatagttgg cagagttgta ggtaacgcca ccagaaatgt tcgtagagct    720
gttcctttg ttgctccatt ggtggaggaa agacgtagac ttatggaaga gtacggtgaa    780
gactggtctg aaaaacctaa tgatatgtta cagtggataa tggatgaagc tgcatccaga    840
gatagttcag tgaaggcaat cgcagagaga ttgttaatgg tgaacttcgc ggctattcat    900
acctcatcaa acactatcac tcatgctttg taccaccttg ccgaaatgcc tgaaactttg    960
caaccactta gagaagagat cgaaccatta gtcaaagagg agggctggac caaggctgct   1020
atgggaaaaa tgtggtggtt agattcattt ctaagagaat ctcaaagata caatggcatt   1080
aacatcgtat ctttaactag aatggctgac aaagatatta cattgagtga tggcacattt   1140
ttgccaaaag gtactctagt ggccgttcca gcgtattcta ctcatagaga tgatgctgtc   1200
```

```
tacgctgatg ccttagtatt cgatcctttc agattctcac gtatgagagc gagagaaggt   1260
gaaggtacaa agcaccagtt cgttaatact tcagtcgagt acgttccatt tggtcacgga   1320
aagcatgctt gtccaggaag attcttcgcc gcaaacgaat tgaaagcaat gttggcttac   1380
attgttctaa actatgatgt aaagttgcct ggtgacggta acgtccatt gaacatgtat    1440 tggggtccaa cagttttgcc tgcaccagca ggccaagtat tgttcagaaa gagacaagtt   1500
agtctataac cgcgg                                                    1515

<210> SEQ ID NO 65
<211> LENGTH: 1536
<212> TYPE: DNA
<213> ORGANISM: Artificial Sequence
<220> FEATURE:
<223> OTHER INFORMATION: Codon-optimized KO

<400> SEQUENCE: 65
atggctacct tgttggaaca ttttcaagct atgccattcg ctattccaat tgctttggct     60
gctttgtctt ggttgttttt gttctacatc aaggtttctt tcttctccaa caaatccgct    120
caagctaaat tgccaccagt tccagttgtt ccaggtttgc cagttattgg taatttgttg    180
caattgaaag aaaagaagcc ataccaaacc ttcactagat gggctgaaga atatggtcca    240
atctactcta ttagaactgg tgcttctact atggttgtct tgaacactac tcaagttgcc    300
aaagaagcta tggttaccag atacttgtct atctctacca gaaagttgtc caacgccttg    360
aaaattttga ccgctgataa gtgcatggtt gccatttctg attacaacga tttccacaag    420
atgatcaaga gatatatctt gtctaacgtt ttgggtccat ctgcccaaaa agacataga    480 tctaacagag ataccttgag agccaacgtt tgttctagat gcattcccca agttaagaac    540
tctccaagag aagctgtcaa ctttagaaga gttttcgaat gggaattatt cggtatcgct    600
ttgaaacaag ccttcggtaa ggatattgaa aagccaatct acgtcgaaga attgggtact    660
actttgtcca gagatgaaat cttcaaggtt ttggtcttgg acattatgga aggtgccatt    720
gaagttgatt ggagagattt ttttcccatac ttgcgttgga ttccaaacac cagaatggaa    780
actaagatcc aaagattata ctttagaaga aaggccgtta tgaccgcctt gattaacgaa    840
caaaagaaaa gaattgcctc cggtgaagaa atcaactgct acatcgattt cttgttgaaa    900
gaaggtaaga ccttgaccat ggaccaaatc tctatgttgt tgtgggaaac cgttattgaa    960
actgctgata ccacaatggt tactactgaa tgggctatgt acgaagttgc taaggattct   1020
aaaagacaag acagattata ccaagaaatc caaaaggtct gcggttctga atggttaca    1080 gaagaatact tgtcccaatt gccatacttg aatgctgttt tccacgaaac tttgagaaaa   1140
cattctccag ctgctttggt tccattgaga tatgctcatg aagatactca attgggtggt   1200
tattacattc cagccggtac tgaaattgcc attaacatct acggttgcaa catggacaaa   1260
caccaatggg aatctccaga gaatggaag ccagaaagat ttttggatcc taagtttgac   1320
ccaatggact tgtacaaaac tatggctttt ggtgctggta aaagagtttg cgctggttct   1380
ttacaagcta tgttgattgc ttgtccaacc atcggtagat tggttcaaga atttgaatgg   1440
aagttgagag atggtgaaga agaaaacgtt gatactgttg gtttgaccac ccataagaga   1500
tatccaatgc atgctatttt gaagccaaga tcttaa                              1536

<210> SEQ ID NO 66
<211> LENGTH: 2142
<212> TYPE: DNA
<213> ORGANISM: Artificial Sequence
```

<220> FEATURE:
<223> OTHER INFORMATION: Codon-optimized CPR

<400> SEQUENCE: 66

```
atggcagaat tagatacact tgatatagta gtattaggtg ttatctttt gggtactgtg      60
gcatacttta ctaagggtaa attgtggggt gttaccaagg atccatacgc taacggattc    120
gctgcaggtg gtgcttccaa gcctggcaga actagaaaca tcgtcgaagc tatggaggaa    180
tcaggtaaaa actgtgttgt tttctacggc agtcaaacag gtacagcgga ggattacgca    240
tcaagacttg caaaggaagg aaagtccaga ttcggtttga acactatgat cgccgatcta    300
gaagattatg acttcgataa cttagacact gttccatctg ataacatcgt tatgtttgta    360
ttggctactt acggtgaagg cgaaccaaca gataacgccg tggatttcta tgagttcatt    420
actggcgaag atgcctcttt caatgagggc aacgatcctc cactaggtaa cttgaattac    480
gttgcgttcg gtctgggcaa caatacctac gaacactaca actcaatggt caggaacgtt    540
aacaaggctc tagaaaagtt aggagctcat agaattggag aagcaggtga gggtgacgac    600
ggagctggaa ctatggaaga ggactttta gcttggaaag atccaatgtg gaagccttg    660
gctaaaaaga tgggcttgga ggaaagagaa gctgtatatg aacctatttt cgctatcaat    720
gagagagatg atttgacccc tgaagcgaat gaggtatact gggagaaacc taataagcta    780
cacttggaag gtacagcgaa aggtccattc aactcccaca acccatatat cgcaccaatt    840
gcagaatcat acgaactttt ctcagctaag gatagaaatt gtctgcatat ggaaattgat    900
atttctggta gtaatctaaa gtatgaaaca ggcgaccata tcgcgatctg gcctaccaac    960
ccaggtgaag aggtcaacaa atttcttgac attctagatc tgtctggtaa gcaacattcc   1020
gtcgtaacag tgaaagcctt agaacctaca gccaaagttc cttttccaaa tccaactacc   1080
tacgatgcta tattgagata ccatctggaa atatgcgctc agtttctag acagtttgtc   1140
tcaactttag cagcattcgc ccctaatgat gatatcaaag ctgagatgaa ccgtttggga   1200
tcagacaaag attacttcca cgaaaagaca ggaccacatt actacaatat cgctagattt   1260
ttggcctcag tctctaaagg tgaaaaatgg acaaagatac cattttctgc tttcatagaa   1320
ggccttacaa aactacaacc aagatactat tctatctctt cctctagtttt agttcagcct   1380
aaaaagatta gtattactgc tgttgtcgaa tctcagcaaa ttccaggtag agatgaccca   1440
ttcagaggtg tagcgactaa ctacttgttc gctttgaagc agaaacaaaa cggtgatcca   1500
aatccagctc cttttggcca atcatacgag ttgacaggac caaggaataa gtatgatggt   1560
atacatgttc cagtccatgt aagacattct aactttaagc taccatctga tccaggcaaa   1620
cctattatca tgatcggtcc aggtaccggt gttgcccctt ttagaggctt cgtccaagag   1680
agggcaaaac aagccagaga tggtgtagaa gttggtaaaa cactgctgtt ctttggatgt   1740
agaaagagta cagaagattt catgtatcaa aaagagtggc aagagtacaa ggaagctctt   1800
ggcgacaaat cgaaatgat tacagctttt tcaagagaag gatctaaaaa ggtttatgtt   1860
caacacagac tgaaggaaag atcaaaggaa gtttctgatc ttctatccca aaaagcatac   1920
ttctacgttt gcggagacgc cgcacatatg gcacgtgaag tgaacactgt gttagcacag   1980
atcatagcag aaggccgtgg tgtatcagaa gccaagggtg aggaaattgt caaaaacatg   2040
agatcagcaa tcaatacca agtgtgttct gatttcgtaa ctttacactg taaagagaca   2100
acatacgcga attcagaatt gcaagaggat gtctggagtt aa                     2142
```

<210> SEQ ID NO 67

<211> LENGTH: 2142
<212> TYPE: DNA
<213> ORGANISM: Artificial Sequence
<220> FEATURE:
<223> OTHER INFORMATION: Codon-optimized CPR

<400> SEQUENCE: 67

| | | | | | |
|---|---|---|---|---|---|
| atggccgaat | tggatacctt | ggatatcgtt | gttttgggtg | ttatcttctt | gggtactgtt | 60 |
| gcttacttca | ccaaaggtaa | attgtggggt | gttactaagg | atccatacgc | taatggtttt | 120 |
| gctgctggtg | gtgcttctaa | accaggtaga | actagaaata | tcgttgaagc | catggaagaa | 180 |
| tctggtaaga | actgtgttgt | tttctacggt | tctcaaactg | gtactgctga | agattatgct | 240 |
| tccagattgg | ctaaagaagg | taagagtaga | ttcggtttga | acaccatgat | tgccgatttg | 300 |
| gaagattacg | atttcgataa | cttggatacc | gtcccatctg | ataacatcgt | tatgtttgtt | 360 |
| ttggctacct | acggtgaagg | tgaacctact | gataatgctg | ttgacttcta | cgaattcatt | 420 |
| accggtgaag | atgcttcttt | caacgaaggt | aatgatccac | cattgggtaa | cttgaattac | 480 |
| gttgcttttg | gtttgggtaa | caacacctac | gaacattaca | actccatggt | tagaaacgtc | 540 |
| aacaaggctt | tggaaaaatt | gggtgctcat | agaattggtg | aagctggtga | aggtgatgat | 600 |
| ggtgctggta | ctatggaaga | agatttttg | gcttggaaag | acccaatgtg | ggaagccttg | 660 |
| gctaaaaaga | tgggtttgga | agaaagagaa | gctgtctacg | aacctatttt | cgccattaac | 720 |
| gaaagagatg | atttgacccc | tgaagccaat | gaagtttatt | ggggtgaacc | taacaagttg | 780 |
| cacttggaag | gtactgctaa | aggtccattc | aattctcaca | cccatatatg | tgctccaatc | 840 |
| gccgaatctt | acgaattatt | ctctgctaag | gatagaaact | gcttgcacat | ggaaattgac | 900 |
| atctctggtt | ctaatttgaa | gtacgaaacc | ggtgatcata | ttgccatttg | gccaactaat | 960 |
| ccaggtgaag | aagttaacaa | gttcttggac | atcttggact | tgtccggtaa | caacacattct | 1020 |
| gttgttactg | ttaaggcctt | ggaacctaca | gctaaagttc | cttttccaaa | tccaactacc | 1080 |
| tacgatgcca | ttttgagata | ccatttggaa | atttgcgctc | cagtctctag | acaattcgtt | 1140 |
| tctactttgg | ctgcttttgc | tccaaacgat | gatattaagg | ctgaaatgaa | cagattgggt | 1200 |
| tccgataagg | attacttcca | cgaaaaaact | ggtccacact | actacaacat | tgctagattt | 1260 |
| ttggcctctg | tctctaaagg | tgaaaagtgg | actaagattc | cattctccgc | tttcattgaa | 1320 |
| ggtttgacta | agttgcaacc | tagatattac | tccatctcct | cctcatcttt | ggttcaacct | 1380 |
| aagaagatct | ctattaccgc | cgttgttgaa | tcccaacaaa | ttccaggtag | agatgatcct | 1440 |
| tttagaggtg | ttgctaccaa | ttacttgttc | gccttgaaac | aaaagcaaaa | cggtgatcca | 1500 |
| aatcctgctc | catttggtca | atcttatgaa | ttgactggtc | caagaaacaa | gtacgatggt | 1560 |
| attcatgttc | cagttcacgt | tagacactct | aactttaagt | tgccatctga | tccaggtaag | 1620 |
| ccaattatca | tgattggtcc | aggtactggt | gttgctccat | tcagaggttt | tgttcaagaa | 1680 |
| agagctaagc | aagctagaga | tggtgttgaa | gttggtaaaa | ccttgttgtt | cttcggttgt | 1740 |
| agaaagtcca | ctgaagattt | catgtaccaa | aaagaatggc | aagaatacaa | agaagcctta | 1800 |
| ggtgacaagt | tcgaaatgat | tactgccttc | tcaagagaag | ttctaagaa | ggtttacgtc | 1860 |
| caacacagat | tgaaagaaag | atccaaagaa | gtctccgatt | tgttgtctca | aaaggcctac | 1920 |
| ttttacgttt | gtggtgatgc | tgctcatatg | gccgagaaag | ttaatactgt | tttggcccaa | 1980 |
| attatcgctg | aaggtagagg | tgtatctgaa | gctaagggtg | aagaaatcgt | taagaacatg | 2040 |
| agatccgcca | atcaataccaaa | gtttgctct | gattttgtta | ccttgcactg | taaagaaacc | 2100 |
| acctacgcta | attccgaatt | gcaagaagat | gtttggtcct | aa | | 2142 |

<210> SEQ ID NO 68
<211> LENGTH: 500
<212> TYPE: PRT
<213> ORGANISM: Stevia rebaudiana

<400> SEQUENCE: 68

```
Met Glu Ala Ser Tyr Leu Tyr Ile Ser Ile Leu Leu Leu Ala Ser
1               5                   10                  15

Tyr Leu Phe Thr Thr Gln Leu Arg Arg Lys Ser Ala Asn Leu Pro Pro
            20                  25                  30

Thr Val Phe Pro Ser Ile Pro Ile Ile Gly His Leu Tyr Leu Leu Lys
                35                  40                  45

Lys Pro Leu Tyr Arg Thr Leu Ala Lys Ile Ala Ala Lys Tyr Gly Pro
    50                  55                  60

Ile Leu Gln Leu Gln Leu Gly Tyr Arg Arg Val Leu Val Ile Ser Ser
65                  70                  75                  80

Pro Ser Ala Ala Glu Glu Cys Phe Thr Asn Asn Asp Val Ile Phe Ala
                85                  90                  95

Asn Arg Pro Lys Thr Leu Phe Gly Lys Ile Val Gly Gly Thr Ser Leu
            100                 105                 110

Gly Ser Leu Ser Tyr Gly Asp Gln Trp Arg Asn Leu Arg Arg Val Ala
        115                 120                 125

Ser Ile Glu Ile Leu Ser Val His Arg Leu Asn Glu Phe His Asp Ile
    130                 135                 140

Arg Val Asp Glu Asn Arg Leu Leu Ile Arg Lys Leu Arg Ser Ser Ser
145                 150                 155                 160

Ser Pro Val Thr Leu Ile Thr Val Phe Tyr Ala Leu Thr Leu Asn Val
                165                 170                 175

Ile Met Arg Met Ile Ser Gly Lys Arg Tyr Phe Asp Ser Gly Asp Arg
            180                 185                 190

Glu Leu Glu Glu Glu Gly Lys Arg Phe Arg Glu Ile Leu Asp Glu Thr
        195                 200                 205

Leu Leu Leu Ala Gly Ala Ser Asn Val Gly Asp Tyr Leu Pro Ile Leu
    210                 215                 220

Asn Trp Leu Gly Val Lys Ser Leu Glu Lys Lys Leu Ile Ala Leu Gln
225                 230                 235                 240

Lys Lys Arg Asp Asp Phe Phe Gln Gly Leu Ile Glu Gln Val Arg Lys
                245                 250                 255

Ser Arg Gly Ala Lys Val Gly Lys Gly Arg Lys Thr Met Ile Glu Leu
            260                 265                 270

Leu Leu Ser Leu Gln Glu Ser Glu Pro Glu Tyr Tyr Thr Asp Ala Met
        275                 280                 285

Ile Arg Ser Phe Val Leu Gly Leu Leu Ala Ala Gly Ser Asp Thr Ser
    290                 295                 300

Ala Gly Thr Met Glu Trp Ala Met Ser Leu Leu Val Asn His Pro His
305                 310                 315                 320

Val Leu Lys Lys Ala Gln Ala Glu Ile Asp Arg Val Ile Gly Asn Asn
                325                 330                 335

Arg Leu Ile Asp Glu Ser Asp Ile Gly Asn Ile Pro Tyr Ile Gly Cys
            340                 345                 350

Ile Ile Asn Glu Thr Leu Arg Leu Tyr Pro Ala Gly Pro Leu Leu Phe
        355                 360                 365

Pro His Glu Ser Ser Ala Asp Cys Val Ile Ser Gly Tyr Asn Ile Pro
```

```
            370                 375                 380
Arg Gly Thr Met Leu Ile Val Asn Gln Trp Ala Ile His His Asp Pro
385                 390                 395                 400

Lys Val Trp Asp Asp Pro Glu Thr Phe Lys Pro Glu Arg Phe Gln Gly
                405                 410                 415

Leu Glu Gly Thr Arg Asp Gly Phe Lys Leu Met Pro Phe Gly Ser Gly
                420                 425                 430

Arg Arg Gly Cys Pro Gly Glu Gly Leu Ala Ile Arg Leu Leu Gly Met
                435                 440                 445

Thr Leu Gly Ser Val Ile Gln Cys Phe Asp Trp Glu Arg Val Gly Asp
                450                 455                 460

Glu Met Val Asp Met Thr Glu Gly Leu Gly Val Thr Leu Pro Lys Ala
465                 470                 475                 480

Val Pro Leu Val Ala Lys Cys Lys Pro Arg Ser Glu Met Thr Asn Leu
                485                 490                 495

Leu Ser Glu Leu
                500

<210> SEQ ID NO 69
<211> LENGTH: 709
<212> TYPE: PRT
<213> ORGANISM: Stevia rebaudiana

<400> SEQUENCE: 69

Met Gln Ser Glu Ser Val Glu Ala Ser Thr Ile Asp Leu Met Thr Ala
1               5                   10                  15

Val Leu Lys Asp Thr Val Ile Asp Thr Ala Asn Ala Ser Asp Asn Gly
                20                  25                  30

Asp Ser Lys Met Pro Pro Ala Leu Ala Met Met Phe Glu Ile Arg Asp
            35                  40                  45

Leu Leu Leu Ile Leu Thr Thr Ser Val Ala Val Leu Val Gly Cys Phe
50                  55                  60

Val Val Leu Val Trp Lys Arg Ser Ser Gly Lys Lys Ser Gly Lys Glu
65                  70                  75                  80

Leu Glu Pro Pro Lys Ile Val Val Pro Lys Arg Leu Glu Gln Glu
                85                  90                  95

Val Asp Asp Gly Lys Lys Lys Val Thr Ile Phe Phe Gly Thr Gln Thr
                100                 105                 110

Gly Thr Ala Glu Gly Phe Ala Lys Ala Leu Phe Glu Glu Ala Lys Ala
            115                 120                 125

Arg Tyr Glu Lys Ala Ala Phe Lys Val Ile Asp Leu Asp Asp Tyr Ala
130                 135                 140

Ala Asp Leu Asp Glu Tyr Ala Glu Lys Leu Lys Lys Glu Thr Tyr Ala
145                 150                 155                 160

Phe Phe Phe Leu Ala Thr Tyr Gly Asp Gly Glu Pro Thr Asp Asn Ala
                165                 170                 175

Ala Lys Phe Tyr Lys Trp Phe Thr Glu Gly Asp Glu Lys Gly Val Trp
                180                 185                 190

Leu Gln Lys Leu Gln Tyr Gly Val Phe Gly Leu Gly Asn Arg Gln Tyr
            195                 200                 205

Glu His Phe Asn Lys Ile Gly Ile Val Val Asp Asp Gly Leu Thr Glu
        210                 215                 220

Gln Gly Ala Lys Arg Ile Val Pro Val Gly Leu Gly Asp Asp Asp Gln
225                 230                 235                 240
```

-continued

```
Ser Ile Glu Asp Asp Phe Ser Ala Trp Lys Glu Leu Val Trp Pro Glu
            245                 250                 255

Leu Asp Leu Leu Leu Arg Asp Glu Asp Lys Ala Ala Ala Thr Pro
        260                 265                 270

Tyr Thr Ala Ala Ile Pro Glu Tyr Arg Val Val Phe His Asp Lys Pro
        275                 280                 285

Asp Ala Phe Ser Asp Asp His Thr Gln Thr Asn Gly His Ala Val His
    290                 295                 300

Asp Ala Gln His Pro Cys Arg Ser Asn Val Ala Val Lys Lys Glu Leu
305                 310                 315                 320

His Thr Pro Glu Ser Asp Arg Ser Cys Thr His Leu Glu Phe Asp Ile
            325                 330                 335

Ser His Thr Gly Leu Ser Tyr Glu Thr Gly Asp His Val Gly Val Tyr
            340                 345                 350

Cys Glu Asn Leu Ile Glu Val Val Glu Ala Gly Lys Leu Leu Gly
        355                 360                 365

Leu Ser Thr Asp Thr Tyr Phe Ser Leu His Ile Asp Asn Glu Asp Gly
    370                 375                 380

Ser Pro Leu Gly Gly Pro Ser Leu Gln Pro Pro Phe Pro Pro Cys Thr
385                 390                 395                 400

Leu Arg Lys Ala Leu Thr Asn Tyr Ala Asp Leu Leu Ser Ser Pro Lys
            405                 410                 415

Lys Ser Thr Leu Leu Ala Leu Ala Ala His Ala Ser Asp Pro Thr Glu
            420                 425                 430

Ala Asp Arg Leu Arg Phe Leu Ala Ser Arg Glu Gly Lys Asp Glu Tyr
        435                 440                 445

Ala Glu Trp Val Val Ala Asn Gln Arg Ser Leu Leu Glu Val Met Glu
    450                 455                 460

Ala Phe Pro Ser Ala Arg Pro Pro Leu Gly Val Phe Phe Ala Ala Val
465                 470                 475                 480

Ala Pro Arg Leu Gln Pro Arg Tyr Tyr Ser Ile Ser Ser Ser Pro Lys
            485                 490                 495

Met Glu Pro Asn Arg Ile His Val Thr Cys Ala Leu Val Tyr Glu Lys
            500                 505                 510

Thr Pro Ala Gly Arg Ile His Lys Gly Ile Cys Ser Thr Trp Met Lys
        515                 520                 525

Asn Ala Val Pro Leu Thr Glu Ser Gln Asp Cys Ser Trp Ala Pro Ile
    530                 535                 540

Phe Val Arg Thr Ser Asn Phe Arg Leu Pro Ile Asp Pro Lys Val Pro
545                 550                 555                 560

Val Ile Met Ile Gly Pro Gly Thr Gly Leu Ala Pro Phe Arg Gly Phe
            565                 570                 575

Leu Gln Glu Arg Leu Ala Leu Lys Glu Ser Gly Thr Glu Leu Gly Ser
            580                 585                 590

Ser Ile Leu Phe Phe Gly Cys Arg Asn Arg Lys Val Asp Tyr Ile Tyr
        595                 600                 605

Glu Asn Glu Leu Asn Asn Phe Val Glu Asn Gly Ala Leu Ser Glu Leu
    610                 615                 620

Asp Val Ala Phe Ser Arg Asp Gly Pro Thr Lys Glu Tyr Val Gln His
625                 630                 635                 640

Lys Met Thr Gln Lys Ala Ser Glu Ile Trp Asn Met Leu Ser Glu Gly
            645                 650                 655

Ala Tyr Leu Tyr Val Cys Gly Asp Ala Lys Gly Met Ala Lys Asp Val
```

```
                     660                 665                 670
His Arg Thr Leu His Thr Ile Val Gln Glu Gln Gly Ser Leu Asp Ser
            675                 680                 685

Ser Lys Ala Glu Leu Tyr Val Lys Asn Leu Gln Met Ser Gly Arg Tyr
        690                 695                 700

Leu Arg Asp Val Trp
705

<210> SEQ ID NO 70
<211> LENGTH: 514
<212> TYPE: PRT
<213> ORGANISM: Castanea mollissima

<400> SEQUENCE: 70

Met Ala Ser Ile Thr His Phe Leu Gln Asp Phe Gln Ala Thr Pro Phe
1               5                  10                  15

Ala Thr Ala Phe Ala Val Gly Gly Val Ser Leu Leu Ile Phe Phe Phe
            20                  25                  30

Phe Ile Arg Gly Phe His Ser Thr Lys Lys Asn Glu Tyr Tyr Lys Leu
        35                  40                  45

Pro Pro Val Pro Val Val Pro Gly Leu Pro Val Val Gly Asn Leu Leu
    50                  55                  60

Gln Leu Lys Glu Lys Lys Pro Tyr Lys Thr Phe Leu Arg Trp Ala Glu
65                  70                  75                  80

Ile His Gly Pro Ile Tyr Ser Ile Arg Thr Gly Ala Ser Thr Met Val
                85                  90                  95

Val Val Asn Ser Thr His Val Ala Lys Glu Ala Met Val Thr Arg Phe
            100                 105                 110

Ser Ser Ile Ser Thr Arg Lys Leu Ser Lys Ala Leu Glu Leu Leu Thr
        115                 120                 125

Ser Asn Lys Ser Met Val Ala Thr Ser Asp Tyr Asn Glu Phe His Lys
    130                 135                 140

Met Val Lys Lys Tyr Ile Leu Ala Glu Leu Leu Gly Ala Asn Ala Gln
145                 150                 155                 160

Lys Arg His Arg Ile His Arg Asp Thr Leu Ile Glu Asn Val Leu Asn
                165                 170                 175

Lys Leu His Ala His Thr Lys Asn Ser Pro Leu Gln Ala Val Asn Phe
            180                 185                 190

Arg Lys Ile Phe Glu Ser Glu Leu Phe Gly Leu Ala Met Lys Gln Ala
        195                 200                 205

Leu Gly Tyr Asp Val Asp Ser Leu Phe Val Glu Glu Leu Gly Thr Thr
    210                 215                 220

Leu Ser Arg Glu Glu Ile Tyr Asn Val Leu Val Ser Asp Met Leu Lys
225                 230                 235                 240

Gly Ala Ile Glu Val Asp Trp Arg Asp Phe Phe Pro Tyr Leu Lys Trp
                245                 250                 255

Ile Pro Asn Lys Ser Phe Glu Met Lys Ile Gln Arg Leu Ala Ser Arg
            260                 265                 270

Arg Gln Ala Val Met Asn Ser Ile Val Lys Glu Gln Lys Lys Ser Ile
        275                 280                 285

Ala Ser Gly Lys Gly Glu Asn Cys Tyr Leu Asn Tyr Leu Leu Ser Glu
    290                 295                 300

Ala Lys Thr Leu Thr Glu Lys Gln Ile Ser Ile Leu Ala Trp Glu Thr
305                 310                 315                 320
```

```
Ile Ile Glu Thr Ala Asp Thr Thr Val Val Thr Glu Trp Ala Met
                325                 330                 335

Tyr Glu Leu Ala Lys Asn Pro Lys Gln Gln Asp Arg Leu Tyr Asn Glu
            340                 345                 350

Ile Gln Asn Val Cys Gly Thr Asp Lys Ile Thr Glu Glu His Leu Ser
            355                 360                 365

Lys Leu Pro Tyr Leu Ser Ala Val Phe His Glu Thr Leu Arg Lys Tyr
        370                 375                 380

Ser Pro Ser Pro Leu Val Pro Leu Arg Tyr Ala His Glu Asp Thr Gln
385                 390                 395                 400

Leu Gly Gly Tyr Tyr Val Pro Ala Gly Thr Glu Ile Ala Val Asn Ile
                405                 410                 415

Tyr Gly Cys Asn Met Asp Lys Asn Gln Trp Glu Thr Pro Glu Glu Trp
            420                 425                 430

Lys Pro Glu Arg Phe Leu Asp Glu Lys Tyr Asp Pro Met Asp Met Tyr
        435                 440                 445

Lys Thr Met Ser Phe Gly Ser Gly Lys Arg Val Cys Ala Gly Ser Leu
        450                 455                 460

Gln Ala Ser Leu Ile Ala Cys Thr Ser Ile Gly Arg Leu Val Gln Glu
465                 470                 475                 480

Phe Glu Trp Arg Leu Lys Asp Gly Glu Val Glu Asn Val Asp Thr Leu
                485                 490                 495

Gly Leu Thr Thr His Lys Leu Tyr Pro Met Gln Ala Ile Leu Gln Pro
            500                 505                 510

Arg Asn

<210> SEQ ID NO 71
<211> LENGTH: 506
<212> TYPE: PRT
<213> ORGANISM: Eutrema halophilum

<400> SEQUENCE: 71

Met Ala Ser Met Ile Ser Leu Leu Leu Gly Phe Val Val Ser Ser Phe
1               5                   10                  15

Leu Phe Ile Phe Phe Leu Lys Lys Leu Leu Phe Phe Ser Arg His
            20                  25                  30

Lys Met Ser Glu Val Ser Arg Leu Pro Ser Val Pro Val Pro Gly Phe
        35                  40                  45

Pro Leu Ile Gly Asn Leu Leu Gln Leu Lys Glu Lys Pro His Lys
50                  55                  60

Thr Phe Thr Lys Trp Ser Glu Leu Tyr Gly Pro Ile Tyr Ser Ile Lys
65                  70                  75                  80

Met Gly Ser Ser Ser Leu Ile Val Leu Asn Ser Ile Glu Thr Ala Lys
                85                  90                  95

Glu Ala Met Val Ser Arg Phe Ser Ser Ile Ser Thr Arg Lys Leu Ser
            100                 105                 110

Asn Ala Leu Thr Val Leu Thr Cys Asn Lys Ser Met Val Ala Thr Ser
        115                 120                 125

Asp Tyr Asp Asp Phe His Lys Phe Val Lys Arg Cys Leu Leu Asn Gly
        130                 135                 140

Leu Leu Gly Ala Asn Ala Gln Glu Arg Lys Arg His Tyr Arg Asp Ala
145                 150                 155                 160

Leu Ile Glu Asn Val Thr Ser Lys Leu His Ala His Thr Arg Asn His
                165                 170                 175
```

Pro Gln Glu Pro Val Asn Phe Arg Ala Ile Phe Glu His Glu Leu Phe
                180                 185                 190

Gly Val Ala Leu Lys Gln Ala Phe Gly Lys Asp Val Glu Ser Ile Tyr
            195                 200                 205

Val Lys Glu Leu Gly Val Thr Leu Ser Arg Asp Glu Ile Phe Lys Val
210                 215                 220

Leu Val His Asp Met Met Glu Gly Ala Ile Asp Val Asp Trp Arg Asp
225                 230                 235                 240

Phe Phe Pro Tyr Leu Lys Trp Ile Pro Asn Asn Ser Phe Glu Ala Arg
                245                 250                 255

Ile Gln Gln Lys His Lys Arg Arg Leu Ala Val Met Asn Ala Leu Ile
            260                 265                 270

Gln Asp Arg Leu Asn Gln Asn Asp Ser Glu Asp Asp Cys Tyr
        275                 280                 285

Leu Asn Phe Leu Met Ser Glu Ala Lys Thr Leu Thr Met Glu Gln Ile
        290                 295                 300

Ala Ile Leu Val Trp Glu Thr Ile Ile Glu Thr Ala Asp Thr Thr Leu
305                 310                 315                 320

Val Thr Thr Glu Trp Ala Met Tyr Glu Leu Ala Lys His Gln Ser Val
                325                 330                 335

Gln Asp Arg Leu Phe Lys Glu Ile Gln Ser Val Cys Gly Gly Glu Lys
            340                 345                 350

Ile Lys Glu Glu Gln Leu Pro Arg Leu Pro Tyr Val Asn Gly Val Phe
        355                 360                 365

His Glu Thr Leu Arg Lys Tyr Ser Pro Ala Pro Leu Val Pro Ile Arg
        370                 375                 380

Tyr Ala His Glu Asp Thr Gln Ile Gly Gly Tyr His Ile Pro Ala Gly
385                 390                 395                 400

Ser Glu Ile Ala Ile Asn Ile Tyr Gly Cys Asn Met Asp Lys Lys Arg
                405                 410                 415

Trp Glu Arg Pro Glu Glu Trp Trp Pro Glu Arg Phe Leu Glu Asp Arg
            420                 425                 430

Tyr Glu Ser Ser Asp Leu His Lys Thr Met Ala Phe Gly Ala Gly Lys
        435                 440                 445

Arg Val Cys Ala Gly Ala Leu Gln Ala Ser Leu Met Ala Gly Ile Ala
    450                 455                 460

Ile Gly Arg Leu Val Gln Glu Phe Glu Trp Lys Leu Arg Asp Gly Glu
465                 470                 475                 480

Glu Glu Asn Val Asp Thr Tyr Gly Leu Thr Ser Gln Lys Leu Tyr Pro
                485                 490                 495

Leu Met Ala Ile Ile Asn Pro Arg Arg Ser
            500                 505

<210> SEQ ID NO 72
<211> LENGTH: 508
<212> TYPE: PRT
<213> ORGANISM: Vitis vinifera

<400> SEQUENCE: 72

Met Asp Met Met Gly Ile Glu Ala Val Pro Phe Ala Thr Ala Val Val
1               5                   10                  15

Leu Gly Gly Ile Ser Leu Val Val Leu Ile Phe Ile Arg Arg Phe Val
            20                  25                  30

Ser Asn Arg Lys Arg Ser Val Glu Gly Leu Pro Pro Val Pro Asp Ile
        35                  40                  45

```
Pro Gly Leu Pro Leu Ile Gly Asn Leu Leu Gln Leu Lys Glu Lys Lys
    50                  55                  60

Pro His Lys Thr Phe Ala Arg Trp Ala Glu Thr Tyr Gly Pro Ile Phe
65                  70                  75                  80

Ser Ile Arg Thr Gly Ala Ser Thr Met Ile Val Leu Asn Ser Ser Glu
                85                  90                  95

Val Ala Lys Glu Ala Met Val Thr Arg Phe Ser Ser Ile Ser Thr Arg
                100                 105                 110

Lys Leu Ser Asn Ala Leu Lys Ile Leu Thr Phe Asp Lys Cys Met Val
            115                 120                 125

Ala Thr Ser Asp Tyr Asn Asp Phe His Lys Met Val Lys Gly Phe Ile
        130                 135                 140

Leu Arg Asn Val Leu Gly Ala Pro Ala Gln Lys Arg His Arg Cys His
145                 150                 155                 160

Arg Asp Thr Leu Ile Glu Asn Ile Ser Lys Tyr Leu His Ala His Val
                165                 170                 175

Lys Thr Ser Pro Leu Glu Pro Val Val Leu Lys Lys Ile Phe Glu Ser
                180                 185                 190

Glu Ile Phe Gly Leu Ala Leu Lys Gln Ala Leu Gly Lys Asp Ile Glu
        195                 200                 205

Ser Ile Tyr Val Glu Glu Leu Gly Thr Thr Leu Ser Arg Glu Glu Ile
    210                 215                 220

Phe Ala Val Leu Val Val Asp Pro Met Ala Gly Ala Ile Glu Val Asp
225                 230                 235                 240

Trp Arg Asp Phe Phe Pro Tyr Leu Ser Trp Ile Pro Asn Lys Ser Met
                245                 250                 255

Glu Met Lys Ile Gln Arg Met Asp Phe Arg Arg Gly Ala Leu Met Lys
                260                 265                 270

Ala Leu Ile Gly Glu Gln Lys Lys Arg Ile Gly Ser Gly Glu Glu Lys
            275                 280                 285

Asn Ser Tyr Ile Asp Phe Leu Leu Ser Glu Ala Thr Thr Leu Thr Glu
        290                 295                 300

Lys Gln Ile Ala Met Leu Ile Trp Glu Thr Ile Glu Ile Ser Asp
305                 310                 315                 320

Thr Thr Leu Val Thr Ser Glu Trp Ala Met Tyr Glu Leu Ala Lys Asp
                325                 330                 335

Pro Asn Arg Gln Glu Ile Leu Tyr Arg Glu Ile His Lys Val Cys Gly
                340                 345                 350

Ser Asn Lys Leu Thr Glu Glu Asn Leu Ser Lys Leu Pro Tyr Leu Asn
            355                 360                 365

Ser Val Phe His Glu Thr Leu Arg Lys Tyr Ser Pro Ala Pro Met Val
        370                 375                 380

Pro Val Arg Tyr Ala His Glu Asp Thr Gln Leu Gly Gly Tyr His Ile
385                 390                 395                 400

Pro Ala Gly Ser Gln Ile Ala Ile Asn Ile Tyr Gly Cys Asn Met Asn
                405                 410                 415

Lys Lys Gln Trp Glu Asn Pro Glu Glu Trp Lys Pro Glu Arg Phe Leu
                420                 425                 430

Asp Glu Lys Tyr Asp Leu Met Asp Leu His Lys Thr Met Ala Phe Gly
            435                 440                 445

Gly Gly Lys Arg Val Cys Ala Gly Ala Leu Gln Ala Met Leu Ile Ala
        450                 455                 460
```

```
Cys Thr Ser Ile Gly Arg Phe Val Gln Glu Phe Glu Trp Lys Leu Met
465                 470                 475                 480

Gly Gly Glu Glu Glu Asn Val Asp Thr Val Ala Leu Thr Ser Gln Lys
                485                 490                 495

Leu His Pro Met Gln Ala Ile Ile Lys Ala Arg Glu
                500                 505

<210> SEQ ID NO 73
<211> LENGTH: 713
<212> TYPE: PRT
<213> ORGANISM: Fusarium fujikuroi

<400> SEQUENCE: 73

Met Ala Glu Leu Asp Thr Leu Asp Ile Val Val Leu Gly Val Ile Phe
1               5                   10                  15

Leu Gly Thr Val Ala Tyr Phe Thr Lys Gly Lys Leu Trp Gly Val Thr
                20                  25                  30

Lys Asp Pro Tyr Ala Asn Gly Phe Ala Ala Gly Gly Ala Ser Lys Pro
            35                  40                  45

Gly Arg Thr Arg Asn Ile Val Glu Ala Met Glu Glu Ser Gly Lys Asn
        50                  55                  60

Cys Val Val Phe Tyr Gly Ser Gln Thr Gly Thr Ala Glu Asp Tyr Ala
65                  70                  75                  80

Ser Arg Leu Ala Lys Glu Gly Lys Ser Arg Phe Gly Leu Asn Thr Met
                85                  90                  95

Ile Ala Asp Leu Glu Asp Tyr Asp Phe Asp Asn Leu Asp Thr Val Pro
                100                 105                 110

Ser Asp Asn Ile Val Met Phe Val Leu Ala Thr Tyr Gly Glu Gly Glu
            115                 120                 125

Pro Thr Asp Asn Ala Val Asp Phe Tyr Glu Phe Ile Thr Gly Glu Asp
        130                 135                 140

Ala Ser Phe Asn Glu Gly Asn Asp Pro Pro Leu Gly Asn Leu Asn Tyr
145                 150                 155                 160

Val Ala Phe Gly Leu Gly Asn Asn Thr Tyr Glu His Tyr Asn Ser Met
                165                 170                 175

Val Arg Asn Val Asn Lys Ala Leu Glu Lys Leu Gly Ala His Arg Ile
                180                 185                 190

Gly Glu Ala Gly Glu Gly Asp Asp Gly Ala Gly Thr Met Glu Glu Asp
            195                 200                 205

Phe Leu Ala Trp Lys Asp Pro Met Trp Glu Ala Leu Ala Lys Lys Met
        210                 215                 220

Gly Leu Glu Glu Arg Glu Ala Val Tyr Glu Pro Ile Phe Ala Ile Asn
225                 230                 235                 240

Glu Arg Asp Asp Leu Thr Pro Glu Ala Asn Glu Val Tyr Leu Gly Glu
                245                 250                 255

Pro Asn Lys Leu His Leu Glu Gly Thr Ala Lys Gly Pro Phe Asn Ser
                260                 265                 270

His Asn Pro Tyr Ile Ala Pro Ile Ala Glu Ser Tyr Glu Leu Phe Ser
            275                 280                 285

Ala Lys Asp Arg Asn Cys Leu His Met Glu Ile Asp Ile Ser Gly Ser
        290                 295                 300

Asn Leu Lys Tyr Glu Thr Gly Asp His Ile Ala Ile Trp Pro Thr Asn
305                 310                 315                 320

Pro Gly Glu Glu Val Asn Lys Phe Leu Asp Ile Leu Asp Leu Ser Gly
                325                 330                 335
```

Lys Gln His Ser Val Val Thr Val Lys Ala Leu Glu Pro Thr Ala Lys
                340                 345                 350

Val Pro Phe Pro Asn Pro Thr Thr Tyr Asp Ala Ile Leu Arg Tyr His
            355                 360                 365

Leu Glu Ile Cys Ala Pro Val Ser Arg Gln Phe Val Ser Thr Leu Ala
370                 375                 380

Ala Phe Ala Pro Asn Asp Asp Ile Lys Ala Glu Met Asn Arg Leu Gly
385                 390                 395                 400

Ser Asp Lys Asp Tyr Phe His Glu Lys Thr Gly Pro His Tyr Tyr Asn
                405                 410                 415

Ile Ala Arg Phe Leu Ala Ser Val Ser Lys Gly Glu Lys Trp Thr Lys
            420                 425                 430

Ile Pro Phe Ser Ala Phe Ile Glu Gly Leu Thr Lys Leu Gln Pro Arg
        435                 440                 445

Tyr Tyr Ser Ile Ser Ser Ser Leu Val Gln Pro Lys Lys Ile Ser
450                 455                 460

Ile Thr Ala Val Val Glu Ser Gln Gln Ile Pro Gly Arg Asp Asp Pro
465                 470                 475                 480

Phe Arg Gly Val Ala Thr Asn Tyr Leu Phe Ala Leu Lys Gln Lys Gln
                485                 490                 495

Asn Gly Asp Pro Asn Pro Ala Pro Phe Gly Gln Ser Tyr Glu Leu Thr
            500                 505                 510

Gly Pro Arg Asn Lys Tyr Asp Gly Ile His Val Pro Val His Val Arg
        515                 520                 525

His Ser Asn Phe Lys Leu Pro Ser Asp Pro Gly Lys Pro Ile Ile Met
    530                 535                 540

Ile Gly Pro Gly Thr Gly Val Ala Pro Phe Arg Gly Phe Val Gln Glu
545                 550                 555                 560

Arg Ala Lys Gln Ala Arg Asp Gly Val Glu Val Gly Lys Thr Leu Leu
                565                 570                 575

Phe Phe Gly Cys Arg Lys Ser Thr Glu Asp Phe Met Tyr Gln Lys Glu
            580                 585                 590

Trp Gln Glu Tyr Lys Glu Ala Leu Gly Asp Lys Phe Glu Met Ile Thr
        595                 600                 605

Ala Phe Ser Arg Glu Gly Ser Lys Lys Val Tyr Val Gln His Arg Leu
    610                 615                 620

Lys Glu Arg Ser Lys Glu Val Ser Asp Leu Leu Ser Gln Lys Ala Tyr
625                 630                 635                 640

Phe Tyr Val Cys Gly Asp Ala Ala His Met Ala Arg Glu Val Asn Thr
                645                 650                 655

Val Leu Ala Gln Ile Ile Ala Glu Gly Arg Gly Val Ser Glu Ala Lys
            660                 665                 670

Gly Glu Glu Ile Val Lys Asn Met Arg Ser Ala Asn Gln Tyr Gln Val
        675                 680                 685

Cys Ser Asp Phe Val Thr Leu His Cys Lys Glu Thr Thr Tyr Ala Asn
    690                 695                 700

Ser Glu Leu Gln Glu Asp Val Trp Ser
705                 710

<210> SEQ ID NO 74
<211> LENGTH: 701
<212> TYPE: PRT
<213> ORGANISM: Siraitia grosvenorii

```
<400> SEQUENCE: 74

Met Lys Val Ser Pro Phe Glu Phe Met Ser Ala Ile Ile Lys Gly Arg
1               5                   10                  15

Met Asp Pro Ser Asn Ser Ser Phe Glu Ser Thr Gly Glu Val Ala Ser
            20                  25                  30

Val Ile Phe Glu Asn Arg Glu Leu Val Ala Ile Leu Thr Ser Ile
        35                  40                  45

Ala Val Met Ile Gly Cys Phe Val Val Leu Met Trp Arg Arg Ala Gly
        50                  55                  60

Ser Arg Lys Val Lys Asn Val Glu Leu Pro Lys Pro Leu Ile Val His
65                  70                  75                  80

Glu Pro Glu Pro Glu Val Glu Asp Gly Lys Lys Val Ser Ile Phe
                85                  90                  95

Phe Gly Thr Gln Thr Gly Thr Ala Glu Gly Phe Ala Lys Ala Leu Ala
                100                 105                 110

Asp Glu Ala Lys Ala Arg Tyr Glu Lys Ala Thr Phe Arg Val Val Asp
        115                 120                 125

Leu Asp Asp Tyr Ala Ala Asp Asp Gln Tyr Glu Glu Lys Leu Lys
130                 135                 140

Asn Glu Ser Phe Ala Val Phe Leu Leu Ala Thr Tyr Gly Asp Gly Glu
145                 150                 155                 160

Pro Thr Asp Asn Ala Ala Arg Phe Tyr Lys Trp Phe Ala Glu Gly Lys
                165                 170                 175

Glu Arg Gly Glu Trp Leu Gln Asn Leu His Tyr Ala Val Phe Gly Leu
            180                 185                 190

Gly Asn Arg Gln Tyr Glu His Phe Asn Lys Ile Ala Lys Val Ala Asp
        195                 200                 205

Glu Leu Leu Glu Ala Gln Gly Gly Asn Arg Leu Val Lys Val Gly Leu
210                 215                 220

Gly Asp Asp Asp Gln Cys Ile Glu Asp Phe Ser Ala Trp Arg Glu
225                 230                 235                 240

Ser Leu Trp Pro Glu Leu Asp Met Leu Leu Arg Asp Glu Asp Asp Ala
                245                 250                 255

Thr Thr Val Thr Thr Pro Tyr Thr Ala Ala Val Leu Glu Tyr Arg Val
            260                 265                 270

Val Phe His Asp Ser Ala Asp Val Ala Ala Glu Asp Lys Ser Trp Ile
        275                 280                 285

Asn Ala Asn Gly His Ala Val His Asp Ala Gln His Pro Phe Arg Ser
290                 295                 300

Asn Val Val Arg Lys Glu Leu His Thr Ser Ala Ser Asp Arg Ser
305                 310                 315                 320

Cys Ser His Leu Glu Phe Asn Ile Ser Gly Ser Ala Leu Asn Tyr Glu
                325                 330                 335

Thr Gly Asp His Val Gly Val Tyr Cys Glu Asn Leu Thr Glu Thr Val
            340                 345                 350

Asp Glu Ala Leu Asn Leu Leu Gly Leu Ser Pro Glu Thr Tyr Phe Ser
        355                 360                 365

Ile Tyr Thr Asp Asn Glu Asp Gly Thr Pro Leu Gly Gly Ser Ser Leu
    370                 375                 380

Pro Pro Pro Phe Pro Ser Cys Thr Leu Arg Thr Ala Leu Thr Arg Tyr
385                 390                 395                 400

Ala Asp Leu Leu Asn Ser Pro Lys Lys Ser Ala Leu Leu Ala Leu Ala
                405                 410                 415
```

```
Ala His Ala Ser Asn Pro Val Glu Ala Asp Arg Leu Arg Tyr Leu Ala
            420                 425                 430

Ser Pro Ala Gly Lys Asp Glu Tyr Ala Gln Ser Val Ile Gly Ser Gln
            435                 440                 445

Lys Ser Leu Leu Glu Val Met Ala Glu Phe Pro Ser Ala Lys Pro Pro
            450                 455                 460

Leu Gly Val Phe Phe Ala Ala Val Ala Pro Arg Leu Gln Pro Arg Phe
465                 470                 475                 480

Tyr Ser Ile Ser Ser Ser Pro Arg Met Ala Pro Ser Arg Ile His Val
            485                 490                 495

Thr Cys Ala Leu Val Tyr Asp Lys Met Pro Thr Gly Arg Ile His Lys
            500                 505                 510

Gly Val Cys Ser Thr Trp Met Lys Asn Ser Val Pro Met Glu Lys Ser
            515                 520                 525

His Glu Cys Ser Trp Ala Pro Ile Phe Val Arg Gln Ser Asn Phe Lys
            530                 535                 540

Leu Pro Ala Glu Ser Lys Val Pro Ile Ile Met Val Gly Pro Gly Thr
545                 550                 555                 560

Gly Leu Ala Pro Phe Arg Gly Phe Leu Gln Glu Arg Leu Ala Leu Lys
            565                 570                 575

Glu Ser Gly Val Glu Leu Gly Pro Ser Ile Leu Phe Phe Gly Cys Arg
            580                 585                 590

Asn Arg Arg Met Asp Tyr Ile Tyr Glu Asp Glu Leu Asn Asn Phe Val
            595                 600                 605

Glu Thr Gly Ala Leu Ser Glu Leu Val Ile Ala Phe Ser Arg Glu Gly
            610                 615                 620

Pro Thr Lys Glu Tyr Val Gln His Lys Met Ala Glu Lys Ala Ser Asp
625                 630                 635                 640

Ile Trp Asn Leu Ile Ser Glu Gly Ala Tyr Leu Tyr Val Cys Gly Asp
            645                 650                 655

Ala Lys Gly Met Ala Lys Asp Val His Arg Thr Leu His Thr Ile Met
            660                 665                 670

Gln Glu Gln Gly Ser Leu Asp Ser Ser Lys Ala Glu Ser Met Val Lys
            675                 680                 685

Asn Leu Gln Met Asn Gly Arg Tyr Leu Arg Asp Val Trp
            690                 695                 700

<210> SEQ ID NO 75
<211> LENGTH: 511
<212> TYPE: PRT
<213> ORGANISM: Rubus suavissimus

<400> SEQUENCE: 75

Met Ala Thr Leu Leu Glu His Phe Gln Ala Met Pro Phe Ala Ile Pro
1               5                   10                  15

Ile Ala Leu Ala Ala Leu Ser Trp Leu Phe Leu Phe Tyr Ile Lys Val
            20                  25                  30

Ser Phe Phe Ser Asn Lys Ser Ala Gln Ala Lys Leu Pro Pro Val Pro
            35                  40                  45

Val Val Pro Gly Leu Pro Val Ile Gly Asn Leu Leu Gln Leu Lys Glu
            50                  55                  60

Lys Lys Pro Tyr Gln Thr Phe Thr Arg Trp Ala Glu Glu Tyr Gly Pro
65                  70                  75                  80

Ile Tyr Ser Ile Arg Thr Gly Ala Ser Thr Met Val Val Leu Asn Thr
```

-continued

```
                85                  90                  95
Thr Gln Val Ala Lys Glu Ala Met Val Thr Arg Tyr Leu Ser Ile Ser
            100                 105                 110
Thr Arg Lys Leu Ser Asn Ala Leu Lys Ile Leu Thr Ala Asp Lys Cys
            115                 120                 125
Met Val Ala Ile Ser Asp Tyr Asn Asp Phe His Lys Met Ile Lys Arg
130                 135                 140
Tyr Ile Leu Ser Asn Val Leu Gly Pro Ser Ala Gln Lys Arg His Arg
145                 150                 155                 160
Ser Asn Arg Asp Thr Leu Arg Ala Asn Val Cys Ser Arg Leu His Ser
            165                 170                 175
Gln Val Lys Asn Ser Pro Arg Glu Ala Val Asn Phe Arg Arg Val Phe
            180                 185                 190
Glu Trp Glu Leu Phe Gly Ile Ala Leu Lys Gln Ala Phe Gly Lys Asp
            195                 200                 205
Ile Glu Lys Pro Ile Tyr Val Glu Glu Leu Gly Thr Thr Leu Ser Arg
            210                 215                 220
Asp Glu Ile Phe Lys Val Leu Val Leu Asp Ile Met Glu Gly Ala Ile
225                 230                 235                 240
Glu Val Asp Trp Arg Asp Phe Phe Pro Tyr Leu Arg Trp Ile Pro Asn
            245                 250                 255
Thr Arg Met Glu Thr Lys Ile Gln Arg Leu Tyr Phe Arg Arg Lys Ala
            260                 265                 270
Val Met Thr Ala Leu Ile Asn Glu Gln Lys Lys Arg Ile Ala Ser Gly
            275                 280                 285
Glu Glu Ile Asn Cys Tyr Ile Asp Phe Leu Leu Lys Glu Gly Lys Thr
            290                 295                 300
Leu Thr Met Asp Gln Ile Ser Met Leu Leu Trp Glu Thr Val Ile Glu
305                 310                 315                 320
Thr Ala Asp Thr Thr Met Val Thr Thr Glu Trp Ala Met Tyr Glu Val
            325                 330                 335
Ala Lys Asp Ser Lys Arg Gln Asp Arg Leu Tyr Gln Glu Ile Gln Lys
            340                 345                 350
Val Cys Gly Ser Glu Met Val Thr Glu Glu Tyr Leu Ser Gln Leu Pro
            355                 360                 365
Tyr Leu Asn Ala Val Phe His Glu Thr Leu Arg Lys His Ser Pro Ala
            370                 375                 380
Ala Leu Val Pro Leu Arg Tyr Ala His Glu Asp Thr Gln Leu Gly Gly
385                 390                 395                 400
Tyr Tyr Ile Pro Ala Gly Thr Glu Ile Ala Ile Asn Ile Tyr Gly Cys
            405                 410                 415
Asn Met Asp Lys His Gln Trp Glu Ser Pro Glu Glu Trp Lys Pro Glu
            420                 425                 430
Arg Phe Leu Asp Pro Lys Phe Asp Pro Met Asp Leu Tyr Lys Thr Met
            435                 440                 445
Ala Phe Gly Ala Gly Lys Arg Val Cys Ala Gly Ser Leu Gln Ala Met
            450                 455                 460
Leu Ile Ala Cys Pro Thr Ile Gly Arg Leu Val Gln Glu Phe Glu Trp
465                 470                 475                 480
Lys Leu Arg Asp Gly Glu Glu Glu Asn Val Asp Thr Val Gly Leu Thr
            485                 490                 495
Thr His Lys Arg Tyr Pro Met His Ala Ile Leu Lys Pro Arg Ser
            500                 505                 510
```

<210> SEQ ID NO 76
<211> LENGTH: 710
<212> TYPE: PRT
<213> ORGANISM: Stevia rebaudiana

<400> SEQUENCE: 76

```
Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
            20                  25                  30

Asp Pro Thr Thr Leu Pro Ala Leu Lys Met Leu Val Glu Asn Arg Glu
        35                  40                  45

Leu Leu Thr Leu Phe Thr Thr Ser Phe Ala Val Leu Ile Gly Cys Leu
    50                  55                  60

Val Phe Leu Met Trp Arg Arg Ser Ser Lys Lys Leu Val Gln Asp
65                  70                  75                  80

Pro Val Pro Gln Val Ile Val Lys Lys Glu Lys Glu Ser Glu
                85                  90                  95

Val Asp Asp Gly Lys Lys Val Ser Ile Phe Tyr Gly Thr Gln Thr
            100                 105                 110

Gly Thr Ala Glu Gly Phe Ala Lys Ala Leu Val Glu Glu Ala Lys Val
            115                 120                 125

Arg Tyr Glu Lys Thr Ser Phe Lys Val Ile Asp Leu Asp Asp Tyr Ala
    130                 135                 140

Ala Asp Asp Asp Glu Tyr Glu Glu Lys Leu Lys Lys Glu Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Asp Lys Gly Glu Trp
            180                 185                 190

Leu Lys Lys Leu Gln Tyr Gly Val Phe Gly Leu Gly Asn Arg Gln Tyr
        195                 200                 205

Glu His Phe Asn Lys Ile Ala Ile Val Val Asp Asp Lys Leu Thr Glu
    210                 215                 220

Met Gly Ala Lys Arg Leu Val Pro Val Gly Leu Gly Asp Asp Gln
225                 230                 235                 240

Cys Ile Glu Asp Asp Phe Thr Ala Trp Lys Glu Leu Val Trp Pro Glu
                245                 250                 255

Leu Asp Gln Leu Leu Arg Asp Glu Asp Asp Thr Ser Val Thr Thr Pro
            260                 265                 270

Tyr Thr Ala Ala Val Leu Glu Tyr Arg Val Val Tyr His Asp Lys Pro
        275                 280                 285

Ala Asp Ser Tyr Ala Glu Asp Gln Thr His Thr Asn Gly His Val Val
    290                 295                 300

His Asp Ala Gln His Pro Ser Arg Ser Asn Val Ala Phe Lys Lys Glu
305                 310                 315                 320

Leu His Thr Ser Gln Ser Asp Arg Ser Cys Thr His Leu Glu Phe Asp
                325                 330                 335

Ile Ser His Thr Gly Leu Ser Tyr Glu Thr Gly Asp His Val Gly Val
            340                 345                 350

Tyr Ser Glu Asn Leu Ser Glu Val Val Asp Glu Ala Leu Lys Leu Leu
        355                 360                 365

Gly Leu Ser Pro Asp Thr Tyr Phe Ser Val His Ala Asp Lys Glu Asp
```

Gly Thr Pro Ile Gly Gly Ala Ser Leu Pro Pro Phe Pro Pro Cys
385                 390                 395                 400

Thr Leu Arg Asp Ala Leu Thr Arg Tyr Ala Asp Val Leu Ser Ser Pro
                405                 410                 415

Lys Lys Val Ala Leu Leu Ala Leu Ala Ala His Ala Ser Asp Pro Ser
            420                 425                 430

Glu Ala Asp Arg Leu Lys Phe Leu Ala Ser Pro Ala Gly Lys Asp Glu
        435                 440                 445

Tyr Ala Gln Trp Ile Val Ala Asn Gln Arg Ser Leu Leu Glu Val Met
    450                 455                 460

Gln Ser Phe Pro Ser Ala Lys Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
            500                 505                 510

Thr Thr Pro Ala Gly Arg Ile His Arg Gly Leu Cys Ser Thr Trp Met
        515                 520                 525

Lys Asn Ala Val Pro Leu Thr Glu Ser Pro Asp Cys Ser Gln Ala Ser
530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Phe Phe Gly Cys Arg Asn Arg Lys Val Asp Phe Ile
        595                 600                 605

Tyr Glu Asp Glu Leu Asn Asn Phe Val Glu Thr Gly Ala Leu Ser Glu
    610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
            660                 665                 670

Val His Arg Thr Leu His Thr Ile Val Gln Glu Gln Gly Ser Leu Asp
        675                 680                 685

Ser Ser Lys Ala Glu Leu Tyr Val Lys Asn Leu Gln Met Ser Gly Arg
    690                 695                 700

Tyr Leu Arg Asp Val Trp
705                 710

<210> SEQ ID NO 77
<211> LENGTH: 525
<212> TYPE: PRT
<213> ORGANISM: Fusarium fujikuroi

<400> SEQUENCE: 77

Met Ser Lys Ser Asn Ser Met Asn Ser Thr Ser His Glu Thr Leu Phe
1               5                   10                  15

Gln Gln Leu Val Leu Gly Leu Asp Arg Met Pro Leu Met Asp Val His
            20                  25                  30

```
Trp Leu Ile Tyr Val Ala Phe Gly Ala Trp Leu Cys Ser Tyr Val Ile
         35                  40                  45

His Val Leu Ser Ser Ser Thr Val Lys Val Pro Val Val Gly Tyr
 50                  55                  60

Arg Ser Val Phe Glu Pro Thr Trp Leu Leu Arg Leu Arg Phe Val Trp
 65                  70                  75                  80

Glu Gly Gly Ser Ile Ile Gly Gln Gly Tyr Asn Lys Phe Lys Asp Ser
                 85                  90                  95

Ile Phe Gln Val Arg Lys Leu Gly Thr Asp Ile Val Ile Ile Pro Pro
                100                 105                 110

Asn Tyr Ile Asp Glu Val Arg Lys Leu Ser Gln Asp Lys Thr Arg Ser
             115                 120                 125

Val Glu Pro Phe Ile Asn Asp Phe Ala Gly Gln Tyr Thr Arg Gly Met
 130                 135                 140

Val Phe Leu Gln Ser Asp Leu Gln Asn Arg Val Ile Gln Gln Arg Leu
 145                 150                 155                 160

Thr Pro Lys Leu Val Ser Leu Thr Lys Val Met Lys Glu Glu Leu Asp
                165                 170                 175

Tyr Ala Leu Thr Lys Glu Met Pro Asp Met Lys Asn Asp Glu Trp Val
             180                 185                 190

Glu Val Asp Ile Ser Ser Ile Met Val Arg Leu Ile Ser Arg Ile Ser
 195                 200                 205

Ala Arg Val Phe Leu Gly Pro Glu His Cys Arg Asn Gln Glu Trp Leu
 210                 215                 220

Thr Thr Thr Ala Glu Tyr Ser Glu Ser Leu Phe Ile Thr Gly Phe Ile
225                 230                 235                 240

Leu Arg Val Val Pro His Ile Leu Arg Pro Phe Ile Ala Pro Leu Leu
                245                 250                 255

Pro Ser Tyr Arg Thr Leu Leu Arg Asn Val Ser Ser Gly Arg Arg Val
             260                 265                 270

Ile Gly Asp Ile Ile Arg Ser Gln Gln Gly Asp Gly Asn Glu Asp Ile
 275                 280                 285

Leu Ser Trp Met Arg Asp Ala Ala Thr Gly Glu Glu Lys Gln Ile Asp
 290                 295                 300

Asn Ile Ala Gln Arg Met Leu Ile Leu Ser Leu Ala Ser Ile His Thr
305                 310                 315                 320

Thr Ala Met Thr Met Thr His Ala Met Tyr Asp Leu Cys Ala Cys Pro
                325                 330                 335

Glu Tyr Ile Glu Pro Leu Arg Asp Glu Val Lys Ser Val Val Gly Ala
             340                 345                 350

Ser Gly Trp Asp Lys Thr Ala Leu Asn Arg Phe His Lys Leu Asp Ser
 355                 360                 365

Phe Leu Lys Glu Ser Gln Arg Phe Asn Pro Val Phe Leu Leu Thr Phe
 370                 375                 380

Asn Arg Ile Tyr His Gln Ser Met Thr Leu Ser Asp Gly Thr Asn Ile
385                 390                 395                 400

Pro Ser Gly Thr Arg Ile Ala Val Pro Ser His Ala Met Leu Gln Asp
                405                 410                 415

Ser Ala His Val Pro Gly Pro Thr Pro Thr Glu Phe Asp Gly Phe
             420                 425                 430

Arg Tyr Ser Lys Ile Arg Ser Asp Ser Asn Tyr Ala Gln Lys Tyr Leu
 435                 440                 445

Phe Ser Met Thr Asp Ser Ser Asn Met Ala Phe Gly Tyr Gly Lys Tyr
```

-continued

```
            450                 455                 460
Ala Cys Pro Gly Arg Phe Tyr Ala Ser Asn Glu Met Lys Leu Thr Leu
465                 470                 475                 480

Ala Ile Leu Leu Leu Gln Phe Glu Phe Lys Leu Pro Asp Gly Lys Gly
                485                 490                 495

Arg Pro Arg Asn Ile Thr Ile Asp Ser Asp Met Ile Pro Asp Pro Arg
                500                 505                 510

Ala Arg Leu Cys Val Arg Lys Arg Ser Leu Arg Asp Glu
                515                 520                 525

<210> SEQ ID NO 78
<211> LENGTH: 499
<212> TYPE: PRT
<213> ORGANISM: Trametes versicolor

<400> SEQUENCE: 78

Met Glu Asp Pro Thr Val Leu Tyr Ala Cys Leu Ala Ile Ala Val Ala
1               5                   10                  15

Thr Phe Val Val Arg Trp Tyr Arg Asp Pro Leu Arg Ser Ile Pro Thr
                20                  25                  30

Val Gly Gly Ser Asp Leu Pro Ile Leu Ser Tyr Ile Gly Ala Leu Arg
            35                  40                  45

Trp Thr Arg Arg Gly Arg Glu Ile Leu Gln Glu Gly Tyr Asp Gly Tyr
50                  55                  60

Arg Gly Ser Thr Phe Lys Ile Ala Met Leu Asp Arg Trp Ile Val Ile
65                  70                  75                  80

Ala Asn Gly Pro Lys Leu Ala Asp Glu Val Arg Arg Pro Asp Glu
                85                  90                  95

Glu Leu Asn Phe Met Asp Gly Leu Gly Ala Phe Val Gln Thr Lys Tyr
                100                 105                 110

Thr Leu Gly Glu Ala Ile His Asn Asp Pro Tyr His Val Asp Ile Ile
            115                 120                 125

Arg Glu Lys Leu Thr Arg Gly Leu Pro Ala Val Leu Pro Asp Val Ile
130                 135                 140

Glu Glu Leu Thr Leu Ala Val Arg Gln Tyr Ile Pro Thr Glu Gly Asp
145                 150                 155                 160

Glu Trp Val Ser Val Asn Cys Ser Lys Ala Ala Arg Asp Ile Val Ala
                165                 170                 175

Arg Ala Ser Asn Arg Val Phe Val Gly Leu Pro Ala Cys Arg Asn Gln
                180                 185                 190

Gly Tyr Leu Asp Leu Ala Ile Asp Phe Thr Leu Ser Val Val Lys Asp
            195                 200                 205

Arg Ala Ile Ile Asn Met Phe Pro Glu Leu Leu Lys Pro Ile Val Gly
210                 215                 220

Arg Val Val Gly Asn Ala Thr Arg Asn Val Arg Arg Ala Val Pro Phe
225                 230                 235                 240

Val Ala Pro Leu Val Glu Glu Arg Arg Leu Met Glu Glu Tyr Gly
                245                 250                 255

Glu Asp Trp Ser Glu Lys Pro Asn Asp Met Leu Gln Trp Ile Met Asp
                260                 265                 270

Glu Ala Ala Ser Arg Asp Ser Ser Val Lys Ala Ile Ala Glu Arg Leu
            275                 280                 285

Leu Met Val Asn Phe Ala Ala Ile His Thr Ser Ser Asn Thr Ile Thr
290                 295                 300
```

His Ala Leu Tyr His Leu Ala Glu Met Pro Glu Thr Leu Gln Pro Leu
305                 310                 315                 320

Arg Glu Glu Ile Glu Pro Leu Val Lys Glu Glu Gly Trp Thr Lys Ala
            325                 330                 335

Ala Met Gly Lys Met Trp Trp Leu Asp Ser Phe Leu Arg Glu Ser Gln
            340                 345                 350

Arg Tyr Asn Gly Ile Asn Ile Val Ser Leu Thr Arg Met Ala Asp Lys
            355                 360                 365

Asp Ile Thr Leu Ser Asp Gly Thr Phe Leu Pro Lys Gly Thr Leu Val
            370                 375                 380

Ala Val Pro Ala Tyr Ser Thr His Arg Asp Asp Ala Val Tyr Ala Asp
385                 390                 395                 400

Ala Leu Val Phe Asp Pro Phe Arg Phe Ser Arg Met Arg Ala Arg Glu
            405                 410                 415

Gly Glu Gly Thr Lys His Gln Phe Val Asn Thr Ser Val Glu Tyr Val
            420                 425                 430

Pro Phe Gly His Gly Lys His Ala Cys Pro Gly Arg Phe Phe Ala Ala
            435                 440                 445

Asn Glu Leu Lys Ala Met Leu Ala Tyr Ile Val Leu Asn Tyr Asp Val
450                 455                 460

Lys Leu Pro Gly Asp Gly Lys Arg Pro Leu Asn Met Tyr Trp Gly Pro
465                 470                 475                 480

Thr Val Leu Pro Ala Pro Gly Gln Val Leu Phe Arg Lys Arg Gln
            485                 490                 495

Val Ser Leu

<210> SEQ ID NO 79
<211> LENGTH: 513
<212> TYPE: PRT
<213> ORGANISM: Stevia rebaudiana

<400> SEQUENCE: 79

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

| | | | | | | | | | | |
|---|---|---|---|---|---|---|---|---|---|---|
| Leu | His | Glu | Phe | Val | Lys | Asn | Asn | Pro | Glu | Gln | Glu | Glu | Val | Asp | Leu |
| | | | 180 | | | | | 185 | | | | | 190 | | |

Arg Lys Ile Phe Gln Ser Glu Leu Phe Gly Leu Ala Met Arg Gln Ala
         195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Asp Pro Met Met
225                 230                 235                 240

Gly Ala Ile Asp Val Asp Trp Arg Asp Phe Phe Pro Tyr Leu Lys Trp
            245                 250                 255

Val Pro Asn Lys Lys Phe Glu Asn Thr Ile Gln Gln Met Tyr Ile Arg
        260                 265                 270

Arg Glu Ala Val Met Lys Ser Leu Ile Lys Glu His Lys Lys Arg Ile
    275                 280                 285

Ala Ser Gly Glu Lys Leu Asn Ser Tyr Ile Asp Tyr Leu Leu Ser Glu
290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Arg His
    370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Gly Lys Arg Val Cys Ala Gly Ser Leu Gln
450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
            500                 505                 510

Ile

<210> SEQ ID NO 80
<211> LENGTH: 1572
<212> TYPE: DNA
<213> ORGANISM: Rubus suavissimus

<400> SEQUENCE: 80
atggaagtaa cagtagctag tagtgtagcc ctgagcctgg tctttattag catagtagta      60
agatgggcat ggagtgtggt gaattgggtg tggtttaagc cgaagaagct ggaaagattt     120
ttgagggagc aaggccttaa aggcaattcc tacaggtttt tatatggaga catgaaggag     180

| | |
|---|---|
| aactctatcc tgctcaaaca agcaagatcc aaacccatga acctctccac ctcccatgac | 240 |
| atagcacctc aagtcacccc ttttgtcgac caaaccgtga aagcttacgg taagaactct | 300 |
| tttaattggg ttggccccat accaagggtg aacataatga atccagaaga tttgaaggac | 360 |
| gtcttaacaa aaaatgttga ctttgttaag ccaatatcaa acccacttat caagttgcta | 420 |
| gctacaggta ttgcaatcta tgaaggtgag aaatggacta acacagaag gattatcaac | 480 |
| ccaacattcc attcggagag gctaaagcgt atgttacctt catttcacca aagttgtaat | 540 |
| gagatggtca aggaatggga gagcttggtg tcaaaagagg gttcatcatg tgagttggat | 600 |
| gtctggcctt ttcttgaaaa tatgtcggca gatgtgatct cgagaacagc atttggaact | 660 |
| agctacaaaa aaggacagaa aatctttgaa ctcttgagag agcaagtaat atatgtaacg | 720 |
| aaaggctttc aaagttttta cattccagga tggaggtttc tcccaactaa gatgaacaag | 780 |
| aggatgaatg agattaacga agaaataaaa ggattaatca ggggtattat aattgacaga | 840 |
| gagcaaatca ttaaggcagg tgaagaaacc aacgatgact tattaggtgc acttatggag | 900 |
| tcaaacttga aggacattcg ggaacatggg aaaaacaaca aaaatgttgg gatgagtatt | 960 |
| gaagatgtaa ttcaggagtg taagctgttt tactttgctg ggcaagaaac cacttcagtg | 1020 |
| ttgctggctt ggacaatggt tttacttggt caaaatcaga actggcaaga tcgagcaaga | 1080 |
| caagaggttt tgcaagtctt tggaagcagc aagccagatt ttgatggtct agctcaccctt | 1140 |
| aaagtcgtaa ccatgatttt gcttgaagtt cttcgattat acccaccagt cattgaactt | 1200 |
| attcgaacca ttcacaagaa aacacaactt gggaagctct cactaccaga aggagttgaa | 1260 |
| gtccgcttac caacactgct cattcaccat gacaaggaac tgtggggtga tgatgcaaac | 1320 |
| cagttcaatc cagagaggtt ttcggaagga gtttccaaag caacaaagaa ccgactctca | 1380 |
| ttcttcccct tcggagccgg tccacgcatt tgcattggac agaactttc tatgatggaa | 1440 |
| gcaaagttgg ccttagcatt gatcttgcaa cacttcacct ttgagctttc tccatctcat | 1500 |
| gcacatgctc cttcccatcg tataaccct caaccacagt atggtgttcg tatcatttta | 1560 |
| catcgacgtt ag | 1572 |

<210> SEQ ID NO 81
<211> LENGTH: 1572
<212> TYPE: DNA
<213> ORGANISM: Artificial Sequence
<220> FEATURE:
<223> OTHER INFORMATION: Codon-optimized KAH

<400> SEQUENCE: 81

| | |
|---|---|
| atggaagtca ctgtcgcctc ttctgtcgct ttatccttag tcttcatttc cattgtcgtc | 60 |
| agatgggctt ggtccgttgt caactgggtt tggttcaaac caagaagtt ggaaagattc | 120 |
| ttgagagagc aaggtttgaa gggtaattct tatagattct tgtacggtga catgaaggaa | 180 |
| aattctattt tgttgaagca agccagatcc aaaccaatga acttgtctac ctctcatgat | 240 |
| attgctccac aagttactcc attcgtcgat caaactgtta aagcctacgg taagaactct | 300 |
| ttcaattggg ttggtccaat tcctagagtt aacatcatga acccagaaga tttgaaggat | 360 |
| gtcttgacca gaacgttga cttcgttaag ccaatttcca acccattgat taaattgttg | 420 |
| gctactggta ttgccatttta cgaaggtgaa agtggactaa gcatagaag aatcatcaac | 480 |
| cctaccttcc actctgaaag attgaagaga atgttaccat ctttccatca atcctgtaat | 540 |
| gaaatggtta aggaatggga atccttggtt tctaaagaag gttcttcttg cgaattggat | 600 |
| gtttggccat tcttggaaaa tatgtctgct gatgtcattt ccagaaccgc tttcggtacc | 660 |

-continued

```
tcctacaaga agggtcaaaa gattttcgaa ttgttgagag agcaagttat ttacgttacc    720
aagggtttcc aatccttcta catcccaggt tggagattct tgccaactaa aatgaacaag    780
cgtatgaacg agatcaacga agaaattaaa ggtttgatca gaggtattat tatcgacaga    840
gaacaaatta ttaaagctgg tgaagaaacc aacgatgatt tgttgggtgc tttgatggag    900
tccaacttga aggatattag agaacatggt aagaacaaca agaatgttgg tatgtctatt    960
gaagatgtta ttcaagaatg taagttattc tacttcgctg gtcaagagac cacttctgtt   1020
ttgttagcct ggactatggt cttgttaggt caaaaccaaa attggcaaga tagagctaga   1080
caagaagttt tgcaagtctt cggttcttcc aagccagact ttgatggttt ggcccacttg   1140
aaggttgtta ctatgatttt gttagaagtt ttgagattgt acccaccagt cattgagtta   1200
atcagaacca ttcataaaaa gactcaattg ggtaaattat ctttgccaga aggtgttgaa   1260
gtcagattac caaccttgtt gattcaccac gataaggaat tatggggtga cgacgctaat   1320
caatttaatc cagaaagatt ttccgaaggt gtttccaagg ctaccaaaaa ccgtttgtcc   1380
ttcttcccat ttggtgctgg tccacgtatt tgtatcggtc aaaacttttc catgatggaa   1440
gccaagttgg ctttggcttt aatcttgcaa cacttcactt tcgaattgtc tccatcccat   1500
gcccacgctc cttctcatag aatcacttta caaccacaat acggtgtcag aatcatctta   1560
cacagaagat aa                                                       1572
```

<210> SEQ ID NO 82
<211> LENGTH: 523
<212> TYPE: PRT
<213> ORGANISM: Rubus suavissimus

<400> SEQUENCE: 82

```
Met Glu Val Thr Val Ala Ser Ser Val Ala Leu Ser Leu Val Phe Ile
1               5                  10                  15

Ser Ile Val Arg Trp Ala Trp Ser Val Val Asn Trp Val Trp Phe
            20                  25                  30

Lys Pro Lys Lys Leu Glu Arg Phe Leu Arg Glu Gln Gly Leu Lys Gly
        35                  40                  45

Asn Ser Tyr Arg Phe Leu Tyr Gly Asp Met Lys Glu Asn Ser Ile Leu
    50                  55                  60

Leu Lys Gln Ala Arg Ser Lys Pro Met Asn Leu Ser Thr Ser His Asp
65                  70                  75                  80

Ile Ala Pro Gln Val Thr Pro Phe Val Asp Gln Thr Val Lys Ala Tyr
                85                  90                  95

Gly Lys Asn Ser Phe Asn Trp Val Gly Pro Ile Pro Arg Val Asn Ile
            100                 105                 110

Met Asn Pro Glu Asp Leu Lys Asp Val Leu Thr Lys Asn Val Asp Phe
        115                 120                 125

Val Lys Pro Ile Ser Asn Pro Leu Ile Lys Leu Leu Ala Thr Gly Ile
    130                 135                 140

Ala Ile Tyr Glu Gly Glu Lys Trp Thr Lys His Arg Arg Ile Ile Asn
145                 150                 155                 160

Pro Thr Phe His Ser Glu Arg Leu Lys Arg Met Leu Pro Ser Phe His
                165                 170                 175

Gln Ser Cys Asn Glu Met Val Lys Glu Trp Glu Ser Leu Val Ser Lys
            180                 185                 190

Glu Gly Ser Ser Cys Glu Leu Asp Val Trp Pro Phe Leu Glu Asn Met
        195                 200                 205
```

Ser Ala Asp Val Ile Ser Arg Thr Ala Phe Gly Thr Ser Tyr Lys Lys
        210                 215                 220

Gly Gln Lys Ile Phe Glu Leu Leu Arg Glu Gln Val Ile Tyr Val Thr
225                 230                 235                 240

Lys Gly Phe Gln Ser Phe Tyr Ile Pro Gly Trp Arg Phe Leu Pro Thr
                245                 250                 255

Lys Met Asn Lys Arg Met Asn Glu Ile Asn Glu Glu Ile Lys Gly Leu
            260                 265                 270

Ile Arg Gly Ile Ile Ile Asp Arg Glu Gln Ile Ile Lys Ala Gly Glu
        275                 280                 285

Glu Thr Asn Asp Asp Leu Leu Gly Ala Leu Met Glu Ser Asn Leu Lys
    290                 295                 300

Asp Ile Arg Glu His Gly Lys Asn Asn Lys Asn Val Gly Met Ser Ile
305                 310                 315                 320

Glu Asp Val Ile Gln Glu Cys Lys Leu Phe Tyr Phe Ala Gly Gln Glu
                325                 330                 335

Thr Thr Ser Val Leu Leu Ala Trp Thr Met Val Leu Leu Gly Gln Asn
            340                 345                 350

Gln Asn Trp Gln Asp Arg Ala Arg Gln Glu Val Leu Gln Val Phe Gly
        355                 360                 365

Ser Ser Lys Pro Asp Phe Asp Gly Leu Ala His Leu Lys Val Val Thr
370                 375                 380

Met Ile Leu Leu Glu Val Leu Arg Leu Tyr Pro Pro Val Ile Glu Leu
385                 390                 395                 400

Ile Arg Thr Ile His Lys Lys Thr Gln Leu Gly Lys Leu Ser Leu Pro
                405                 410                 415

Glu Gly Val Glu Val Arg Leu Pro Thr Leu Leu Ile His His Asp Lys
            420                 425                 430

Glu Leu Trp Gly Asp Asp Ala Asn Gln Phe Asn Pro Glu Arg Phe Ser
        435                 440                 445

Glu Gly Val Ser Lys Ala Thr Lys Asn Arg Leu Ser Phe Phe Pro Phe
450                 455                 460

Gly Ala Gly Pro Arg Ile Cys Ile Gly Gln Asn Phe Ser Met Met Glu
465                 470                 475                 480

Ala Lys Leu Ala Leu Ala Leu Ile Leu Gln His Phe Thr Phe Glu Leu
                485                 490                 495

Ser Pro Ser His Ala His Ala Pro Ser His Arg Ile Thr Leu Gln Pro
            500                 505                 510

Gln Tyr Gly Val Arg Ile Ile Leu His Arg Arg
        515                 520

<210> SEQ ID NO 83
<211> LENGTH: 458
<212> TYPE: PRT
<213> ORGANISM: Stevia rebaudiana

<400> SEQUENCE: 83

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg

```
            50                  55                  60
Phe Ile Leu Asp Asn Asp Pro Gln Asp Glu Arg Ile Ser Asn Leu Pro
 65                  70                  75                  80

Thr His Gly Pro Leu Ala Gly Met Arg Ile Pro Ile Ile Asn Glu His
                 85                  90                  95

Gly Ala Asp Glu Leu Arg Arg Glu Leu Leu Leu Met Leu Ala Ser
            100                 105                 110

Glu Glu Asp Glu Glu Val Ser Cys Leu Ile Thr Asp Ala Leu Trp Tyr
            115                 120                 125

Phe Ala Gln Ser Val Ala Asp Ser Leu Asn Leu Arg Arg Leu Val Leu
            130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
            195                 200                 205

Lys Gln Thr Lys Ala Ser Ser Gly Val Ile Trp Asn Ser Phe Lys Glu
210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
            275                 280                 285

Glu Lys Asp Phe Leu Glu Ile Ala Arg Gly Leu Val Asp Ser Lys Gln
            290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
                355                 360                 365

Gly Val Pro Met Ile Phe Ser Asp Phe Gly Leu Asp Gln Pro Leu Asn
            370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
450                 455

<210> SEQ ID NO 84
```

```
<211> LENGTH: 480
<212> TYPE: PRT
<213> ORGANISM: Stevia rebaudiana

<400> SEQUENCE: 84

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
```

```
                385                 390                 395                 400
Asp Gln Leu Thr Asn Cys Arg Tyr Ile Cys Lys Glu Trp Glu Val Gly
                    405                 410                 415

Leu Glu Met Gly Thr Lys Val Lys Arg Asp Glu Val Lys Arg Leu Val
            420                 425                 430

Gln Glu Leu Met Gly Glu Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

<210> SEQ ID NO 85
<211> LENGTH: 457
<212> TYPE: PRT
<213> ORGANISM: Stevia rebaudiana

<400> SEQUENCE: 85

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Val Leu Val
        275                 280                 285
```

```
Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
                340                 345                 350

Glu Ser Val Cys Gly Phe Leu Thr His Cys Gly Ser Gly Ser Ile Val
                355                 360                 365

Glu Gly Leu Met Phe Gly His Pro Leu Ile Met Leu Pro Ile Phe Gly
                370                 375                 380

Glu Ile Pro Arg Asn Glu Glu Asp Gly Cys Leu Thr Lys Glu Ser Val
385                 390                 395                 400

Ala Arg Ser Leu Arg Ser Val Val Glu Lys Gly Glu Ile Tyr
                405                 410                 415

Lys Ala Asn Ala Arg Glu Leu Ser Lys Ile Tyr Asn Asp Thr Lys Val
                420                 425                 430

Glu Lys Glu Tyr Val Ser Gln Phe Val Asp Tyr Leu Glu Lys Asn Ala
                435                 440                 445

Arg Ala Val Ala Ile Asp His Glu Ser
    450                 455

<210> SEQ ID NO 86
<211> LENGTH: 462
<212> TYPE: PRT
<213> ORGANISM: Oryza sativa

<400> SEQUENCE: 86

Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
                20                  25                  30

Asp Leu Ala Gln Arg Leu Ala Ser Arg Gly His Arg Val Ser Phe Val
                35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
                100                 105                 110

Phe Ser Glu Phe Leu Gly Thr Ala Cys Ala Asp Trp Val Ile Val Asp
                115                 120                 125

Val Phe His His Trp Ala Ala Ala Ala Ala Leu Glu His Lys Val Pro
                130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
                165                 170                 175

Gln Gly Arg Pro Ala Ala Ala Pro Thr Phe Glu Val Ala Arg Met Lys
                180                 185                 190

Leu Ile Arg Thr Lys Gly Ser Ser Gly Met Ser Leu Ala Glu Arg Phe
                195                 200                 205
```

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
        275                 280                 285

Glu Lys Val His Glu Leu Ala Leu Gly Leu Glu Leu Ala Gly Thr Arg
    290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
                325                 330                 335

Thr Arg Trp Val Pro Gln Met Ser Ile Leu Ala His Ala Ala Val Gly
            340                 345                 350

Ala Phe Leu Thr His Cys Gly Trp Asn Ser Thr Ile Glu Gly Leu Met
        355                 360                 365

Phe Gly His Pro Leu Ile Met Leu Pro Ile Phe Gly Asp Gln Gly Pro
    370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
                405                 410                 415

Arg Ala Val Ala Val Glu Glu Ser Ser Lys Val Phe Gln Ala Lys
            420                 425                 430

Ala Lys Lys Leu Gln Glu Ile Val Ala Asp Met Ala Cys His Glu Arg
        435                 440                 445

Tyr Ile Asp Gly Phe Ile Gln Gln Leu Arg Ser Tyr Lys Asp
    450                 455                 460

<210> SEQ ID NO 87
<211> LENGTH: 712
<212> TYPE: PRT
<213> ORGANISM: Arabidopsis thaliana

<400> SEQUENCE: 87

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys

```
            115                 120                 125
Ala Arg Tyr Glu Lys Thr Arg Phe Lys Ile Val Asp Leu Asp Tyr
    130                 135                 140
Ala Ala Asp Asp Glu Tyr Glu Glu Lys Leu Lys Lys Glu Asp Val
145                 150                 155                 160
Ala Phe Phe Phe Leu Ala Thr Tyr Gly Asp Gly Glu Pro Thr Asp Asn
                165                 170                 175
Ala Ala Arg Phe Tyr Lys Trp Phe Thr Glu Gly Asn Asp Arg Gly Glu
            180                 185                 190
Trp Leu Lys Asn Leu Lys Tyr Gly Val Phe Gly Leu Gly Asn Arg Gln
            195                 200                 205
Tyr Glu His Phe Asn Lys Val Ala Lys Val Val Asp Asp Ile Leu Val
    210                 215                 220
Glu Gln Gly Ala Gln Arg Leu Val Gln Val Gly Leu Gly Asp Asp Asp
225                 230                 235                 240
Gln Cys Ile Glu Asp Asp Phe Thr Ala Trp Arg Glu Ala Leu Trp Pro
                245                 250                 255
Glu Leu Asp Thr Ile Leu Arg Glu Gly Asp Thr Ala Val Ala Thr
                260                 265                 270
Pro Tyr Thr Ala Ala Val Leu Glu Tyr Arg Val Ser Ile His Asp Ser
            275                 280                 285
Glu Asp Ala Lys Phe Asn Asp Ile Thr Leu Ala Asn Gly Asn Gly Tyr
    290                 295                 300
Thr Val Phe Asp Ala Gln His Pro Tyr Lys Ala Asn Val Ala Val Lys
305                 310                 315                 320
Arg Glu Leu His Thr Pro Glu Ser Asp Arg Ser Cys Ile His Leu Glu
                325                 330                 335
Phe Asp Ile Ala Gly Ser Gly Leu Thr Met Lys Leu Gly Asp His Val
            340                 345                 350
Gly Val Leu Cys Asp Asn Leu Ser Glu Thr Val Asp Glu Ala Leu Arg
            355                 360                 365
Leu Leu Asp Met Ser Pro Asp Thr Tyr Phe Ser Leu His Ala Glu Lys
    370                 375                 380
Glu Asp Gly Thr Pro Ile Ser Ser Ser Leu Pro Pro Pro Phe Pro Pro
385                 390                 395                 400
Cys Asn Leu Arg Thr Ala Leu Thr Arg Tyr Ala Cys Leu Leu Ser Ser
                405                 410                 415
Pro Lys Lys Ser Ala Leu Val Ala Leu Ala His Ala Ser Asp Pro
            420                 425                 430
Thr Glu Ala Glu Arg Leu Lys His Leu Ala Ser Pro Ala Gly Lys Asp
            435                 440                 445
Glu Tyr Ser Lys Trp Val Val Glu Ser Gln Arg Ser Leu Leu Glu Val
    450                 455                 460
Met Ala Glu Phe Pro Ser Ala Lys Pro Pro Leu Gly Val Phe Phe Ala
465                 470                 475                 480
Gly Val Ala Pro Arg Leu Gln Pro Arg Phe Tyr Ser Ile Ser Ser Ser
                485                 490                 495
Pro Lys Ile Ala Glu Thr Arg Ile His Val Thr Cys Ala Leu Val Tyr
            500                 505                 510
Glu Lys Met Pro Thr Gly Arg Ile His Lys Gly Val Cys Ser Thr Trp
    515                 520                 525
Met Lys Asn Ala Val Pro Tyr Glu Lys Ser Glu Lys Leu Phe Leu Gly
    530                 535                 540
```

```
Arg Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
            580                 585                 590

Leu Gly Pro Ser Val Leu Phe Phe Gly Cys Arg Asn Arg Arg Met Asp
        595                 600                 605

Phe Ile Tyr Glu Glu Glu Leu Gln Arg Phe Val Glu Ser Gly Ala Leu
    610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
        675                 680                 685

Met Asp Ser Thr Lys Ala Glu Gly Phe Val Lys Asn Leu Gln Thr Ser
    690                 695                 700

Gly Arg Tyr Leu Arg Asp Val Trp
705                 710

<210> SEQ ID NO 88
<211> LENGTH: 473
<212> TYPE: PRT
<213> ORGANISM: Artificial Sequence
<220> FEATURE:
<223> OTHER INFORMATION: Synthetic polypeptide

<400> SEQUENCE: 88

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
                20                  25                  30

Leu Ser Lys Leu Ile Ala Glu Lys Gly His Lys Val Ser Phe Leu Ser
            35                  40                  45

Thr Thr Arg Asn Ile Gln Arg Leu Ser Ser His Ile Ser Pro Leu Ile
        50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190
```

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
    210                 215                 220

His Glu Phe Gly Thr Gln Trp Leu Pro Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Ala Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Glu Lys Glu Gly Glu Ile Tyr
            420                 425                 430

Lys Ala Asn Ala Arg Glu Leu Ser Lys Ile Tyr Asn Asp Thr Lys Val
        435                 440                 445

Glu Lys Glu Tyr Val Ser Gln Phe Val Asp Tyr Leu Gly Lys Asn Ala
    450                 455                 460

Arg Ala Val Ala Ile Asp His Glu Ser
465                 470

<210> SEQ ID NO 89
<211> LENGTH: 1422
<212> TYPE: DNA
<213> ORGANISM: Artificial Sequence
<220> FEATURE:
<223> OTHER INFORMATION: Synthetic oligonucleotide

<400> SEQUENCE: 89
atggctactt ctgattccat cgttgacgat agaaagcaat tgcatgttgc tactttccca      60
tggttggctt tcggtcatat tttgccatac ttgcaattgt ccaagttgat tgctgaaaag     120
ggtcacaagg tttcattctt gtctaccacc agaaacatcc aaagattgtc ctctcatatc     180
tccccattga tcaacgttgt tcaattgact ttgccaagag tccaagaatt gccagaagat     240
gctgaagcta ctactgatgt tcatccagaa gatatccctt acttgaaaaa ggcttccgat     300
ggtttacaac cagaagttac tagattcttg aacaacatt cccagattg atcatctac       360 gattatactc attactggtt gccatccatt gctgcttcat tgggtatttc tagagcccat     420

```
ttctctgtta ctactccatg ggctattgct tatatgggtc catctgctga tgctatgatt        480
aacggttctg atggtagaac taccgttgaa gatttgacta ctccaccaaa gtggtttcca        540
tttccaacaa aagtctgttg gagaaaacac gatttggcta gattggttcc atacaaagct        600
ccaggtattt ctgatggtta cagaatgggt atggttttga aaggttccga ttgcttgttg        660
tctaagtgct atcatgaatt cggtactcaa tggttgcctt tgttggaaac attgcatcaa        720
gttccagttg tttccagtagg tttgttgcca ccagaaattc caggtgacga aaaagacgaa       780 actgggttt ccatcaaaaa gtggttggat ggtaagcaaa agggttctgt tgtttatgtt         840
gctttgggtt ccgaagcttt ggtttctcaa accgaagttg ttgaattggc tttgggtttg        900
gaattgtctg gtttgccatt tgtttgggct tacagaaaac ctaaaggtcc agctaagtct        960
gattctgttg aattgccaga tggtttcgtt gaaagaacta gagatagagg tttggtttgg       1020
acttcttggg ctccacaatt gagaattttg tctcatgaat ccgtctgtgg tttcttgact       1080
cattgtggtt ctggttctat cgttgaaggt ttgatgtttg gtcacccatt gattatgttg       1140
ccaatctttg gtgaccaacc attgaacgct agattattgg aagataagca agtcggtatc      1200
gaaatcccaa gaaatgaaga agatggttgc ttgaccaaag aatctgttgc tagatctttg      1260
agatccgttg tcgttgaaaa agaaggtgaa atctacaagg ctaacgctag agaattgtcc       1320
aagatctaca acgataccaa ggtcgaaaaa gaatacgttt cccaattcgt tgactacttg       1380
gaaaagaatg ctagagctgt tgccattgat catgaatctt ga                         1422
```

<210> SEQ ID NO 90
<211> LENGTH: 1567
<212> TYPE: DNA
<213> ORGANISM: Artificial Sequence
<220> FEATURE:
<223> OTHER INFORMATION: Synthetic oligonucleotide

<400> SEQUENCE: 90

```
atggaagctt ctagagcatc ttgtgttgct ttgtgtgttg tttgggtttc catcgttatt         60
actttggctt ggagagtttt gaattgggtc tggttaagac caaaaaagtt ggaaagatgc       120
ttgagagaac aaggttttgac tggtaactct tacagattgt tgttcggtga taccaaggac       180
ttgtctaaga tgttggaaca aactcaatcc aagcctatca agttgtctac ctctcatgat       240
attgctccaa gagttactcc attcttccat agaactgtta actccaacgg taagaactct       300 tttgttgga tgggtccaat tccaagagtc catattatga accctgaaga tttgaaggac        360
gctttcaaca gacatgatga tttccataag accgtcaaga acccaattat gaagtctcca      420
ccaccaggta tagttggtat tgaaggtgaa caatgggcca acatagaaa gattattaac       480 ccagccttcc acttggaaaa gttgaaaggt atggttccaa tcttctacca atcctgctct      540
gaaatgatta acaagtggga atccttggtt tccaaagaat cttcctgtga attggatgtc      600
tggccatatt tggaaaactt cacctccgat gttatttcca gagctgcttt tggttcttct      660
tacgaagaag gtagaaagat cttccaatta ttgagagaag aagccaaggt ttactccgtt      720
gctttgagat ctgtttacat tccaggttgg agattcttgc caactaagca aaacaaaaag     780
accaaagaaa tccacaacga aatcaagggt tgttgaagg gtatcatcaa caagagagaa      840
gaagctatga aggctggtga agctacaaaa gatgatttgt tgggtatctt gatggaatcc      900
aacttcagag aaatccaaga acacggtaac aacaagaatg ccggtatgtc tattgaagat      960
gttatcggtg aatgcaagtt gttctacttt gctggtcaag aaactacctc cgttttgttg     1020
gtttggacca tgatttttgtt gtcccaaaat caagattggc aagctagagc tagagaagaa    1080
```

```
gtcttgaaag ttttcggttc taacatccca acctacgaag aattgtctca cttgaaggtt    1140
gtcactatga tcttgttgga agtattgaga ttatacccat ccgttgttgc attgccaaga    1200
actactcata agaaaactca attgggtaaa ttgtccttgc cagctggtgt tgaagtttct    1260
ttgccaattt tgttagtcca ccacgacaaa gaattgtggg gtgaagatgc taatgaattc    1320
aagccagaaa gattctccga aggtgtttct aaagctacca gaacaagtt cacttacttg     1380 ccatttggtg gtggtccaag aatatgtatt ggtcaaaatt tcgctatggt cgaagctaaa    1440
ttggctttgg ctttgatctt gcaacatttc gctttcgaat tgtcaccatc ttatgctcat    1500
gctccatctg ctgttattac attgcaacca caatttggtg cccatatcat cttgcataag    1560
agataac                                                              1567
```

<210> SEQ ID NO 91
<211> LENGTH: 521
<212> TYPE: PRT
<213> ORGANISM: Prunus avium

<400> SEQUENCE: 91

```
Met Glu Ala Ser Arg Ala Ser Cys Val Ala Leu Cys Val Val Trp Val
1               5                   10                  15

Ser Ile Val Ile Thr Leu Ala Trp Arg Val Leu Asn Trp Val Trp Leu
            20                  25                  30

Arg Pro Lys Leu Glu Arg Cys Leu Arg Glu Gln Gly Leu Thr Gly
        35                  40                  45

Asn Ser Tyr Arg Leu Leu Phe Gly Asp Thr Lys Asp Leu Ser Lys Met
    50                  55                  60

Leu Glu Gln Thr Gln Ser Lys Pro Ile Lys Leu Ser Thr Ser His Asp
65                  70                  75                  80

Ile Ala Pro Arg Val Thr Pro Phe Phe His Arg Thr Val Asn Ser Asn
                85                  90                  95

Gly Lys Asn Ser Phe Val Trp Met Gly Pro Ile Pro Arg Val His Ile
            100                 105                 110

Met Asn Pro Glu Asp Leu Lys Asp Ala Phe Asn Arg His Asp Asp Phe
        115                 120                 125

His Lys Thr Val Lys Asn Pro Ile Met Lys Ser Pro Pro Gly Ile
    130                 135                 140

Val Gly Ile Glu Gly Glu Gln Trp Ala Lys His Arg Lys Ile Ile Asn
145                 150                 155                 160

Pro Ala Phe His Leu Glu Lys Leu Lys Gly Met Val Pro Ile Phe Tyr
                165                 170                 175

Gln Ser Cys Ser Glu Met Ile Asn Lys Trp Glu Ser Leu Val Ser Lys
            180                 185                 190

Glu Ser Ser Cys Glu Leu Asp Val Trp Pro Tyr Leu Glu Asn Phe Thr
        195                 200                 205

Ser Asp Val Ile Ser Arg Ala Ala Phe Gly Ser Ser Tyr Glu Glu Gly
    210                 215                 220

Arg Lys Ile Phe Gln Leu Leu Arg Glu Glu Ala Lys Val Tyr Ser Val
225                 230                 235                 240

Ala Leu Arg Ser Val Tyr Ile Pro Gly Trp Arg Phe Leu Pro Thr Lys
                245                 250                 255

Gln Asn Lys Lys Thr Lys Glu Ile His Asn Glu Ile Lys Gly Leu Leu
            260                 265                 270

Lys Gly Ile Ile Asn Lys Arg Glu Glu Ala Met Lys Ala Gly Glu Ala
```

```
                275                 280                 285
Thr Lys Asp Asp Leu Leu Gly Ile Leu Met Glu Ser Asn Phe Arg Glu
290                 295                 300

Ile Gln Glu His Gly Asn Asn Lys Asn Ala Gly Met Ser Ile Glu Asp
305                 310                 315                 320

Val Ile Gly Glu Cys Lys Leu Phe Tyr Phe Ala Gly Gln Glu Thr Thr
                325                 330                 335

Ser Val Leu Leu Val Trp Thr Met Ile Leu Leu Ser Gln Asn Gln Asp
            340                 345                 350

Trp Gln Ala Arg Ala Arg Glu Glu Val Leu Lys Val Phe Gly Ser Asn
        355                 360                 365

Ile Pro Thr Tyr Glu Glu Leu Ser His Leu Lys Val Val Thr Met Ile
370                 375                 380

Leu Leu Glu Val Leu Arg Leu Tyr Pro Ser Val Val Ala Leu Pro Arg
385                 390                 395                 400

Thr Thr His Lys Lys Thr Gln Leu Gly Lys Leu Ser Leu Pro Ala Gly
                405                 410                 415

Val Glu Val Ser Leu Pro Ile Leu Leu Val His His Asp Lys Glu Leu
            420                 425                 430

Trp Gly Glu Asp Ala Asn Glu Phe Lys Pro Glu Arg Phe Ser Glu Gly
        435                 440                 445

Val Ser Lys Ala Thr Lys Asn Lys Phe Thr Tyr Leu Pro Phe Gly Gly
450                 455                 460

Gly Pro Arg Ile Cys Ile Gly Gln Asn Phe Ala Met Val Glu Ala Lys
465                 470                 475                 480

Leu Ala Leu Ala Leu Ile Leu Gln His Phe Ala Phe Glu Leu Ser Pro
                485                 490                 495

Ser Tyr Ala His Ala Pro Ser Ala Val Ile Thr Leu Gln Pro Gln Phe
            500                 505                 510

Gly Ala His Ile Ile Leu His Lys Arg
        515                 520

<210> SEQ ID NO 92
<211> LENGTH: 517
<212> TYPE: PRT
<213> ORGANISM: Prunus mume

<400> SEQUENCE: 92

Ala Ser Trp Val Ala Val Leu Ser Val Val Trp Val Ser Met Val Ile
1               5                   10                  15

Ala Trp Ala Trp Arg Val Leu Asn Trp Val Trp Leu Arg Pro Lys Lys
            20                  25                  30

Leu Glu Lys Cys Leu Arg Glu Gln Gly Leu Ala Gly Asn Ser Tyr Arg
        35                  40                  45

Leu Leu Phe Gly Asp Thr Lys Asp Leu Ser Lys Met Leu Glu Gln Thr
50                  55                  60

Gln Ser Lys Pro Ile Lys Leu Ser Thr Ser His Asp Ile Ala Pro His
65                  70                  75                  80

Val Thr Pro Phe Phe His Gln Thr Val Asn Ser Tyr Gly Lys Asn Ser
                85                  90                  95

Phe Val Trp Met Gly Pro Ile Pro Arg Val His Ile Met Asn Pro Glu
            100                 105                 110

Asp Leu Lys Asp Thr Phe Asn Arg His Asp Phe His Lys Val Val
        115                 120                 125
```

Lys Asn Pro Ile Met Lys Ser Leu Pro Gln Gly Ile Val Gly Ile Glu
            130                 135                 140

Gly Glu Gln Trp Ala Lys His Arg Lys Ile Ile Asn Pro Ala Phe His
145                 150                 155                 160

Leu Glu Lys Leu Lys Gly Met Val Pro Ile Phe Tyr Arg Ser Cys Ser
                165                 170                 175

Glu Met Ile Asn Lys Trp Glu Ser Leu Val Ser Lys Glu Ser Ser Cys
            180                 185                 190

Glu Leu Asp Val Trp Pro Tyr Leu Glu Asn Phe Thr Ser Asp Val Ile
        195                 200                 205

Ser Arg Ala Ala Phe Gly Ser Ser Tyr Glu Glu Gly Arg Lys Ile Phe
    210                 215                 220

Gln Leu Leu Arg Glu Glu Ala Lys Ile Tyr Thr Val Ala Met Arg Ser
225                 230                 235                 240

Val Tyr Ile Pro Gly Trp Arg Phe Leu Pro Thr Lys Gln Asn Lys Lys
                245                 250                 255

Ala Lys Glu Ile His Asn Glu Ile Lys Gly Leu Leu Lys Gly Ile Ile
            260                 265                 270

Asn Lys Arg Glu Glu Ala Met Lys Ala Gly Glu Ala Thr Lys Asp Asp
        275                 280                 285

Leu Leu Gly Ile Leu Met Glu Ser Asn Phe Arg Glu Ile Gln Glu His
    290                 295                 300

Gly Asn Asn Lys Asn Ala Gly Met Ser Ile Glu Asp Val Ile Gly Glu
305                 310                 315                 320

Cys Lys Leu Phe Tyr Phe Ala Gly Gln Glu Thr Thr Ser Val Leu Leu
                325                 330                 335

Val Trp Thr Met Val Leu Leu Ser Gln Asn Gln Asp Trp Gln Ala Arg
            340                 345                 350

Ala Arg Glu Glu Val Leu Gln Val Phe Gly Ser Asn Ile Pro Thr Tyr
        355                 360                 365

Glu Glu Leu Ser Gln Leu Lys Val Val Thr Met Ile Leu Leu Glu Val
    370                 375                 380

Leu Arg Leu Tyr Pro Ser Val Val Ala Leu Pro Arg Thr Thr His Lys
385                 390                 395                 400

Lys Thr Gln Leu Gly Lys Leu Ser Leu Pro Ala Gly Val Glu Val Ser
                405                 410                 415

Leu Pro Ile Leu Leu Val His His Asp Lys Glu Leu Trp Gly Glu Asp
            420                 425                 430

Ala Asn Glu Phe Lys Pro Glu Arg Phe Ser Glu Gly Val Ser Lys Ala
        435                 440                 445

Thr Lys Asn Gln Phe Thr Tyr Phe Pro Phe Gly Gly Gly Pro Arg Ile
    450                 455                 460

Cys Ile Gly Gln Asn Phe Ala Met Met Glu Ala Lys Leu Ala Leu Ser
465                 470                 475                 480

Leu Ile Leu Arg His Phe Ala Leu Glu Leu Ser Pro Leu Tyr Ala His
                485                 490                 495

Ala Pro Ser Val Thr Ile Thr Leu Gln Pro Gln Tyr Gly Ala His Ile
            500                 505                 510

Ile Leu His Lys Arg
            515

<210> SEQ ID NO 93
<211> LENGTH: 521
<212> TYPE: PRT

<213> ORGANISM: Prunus mume

<400> SEQUENCE: 93

| | | | | | | | | | | | | | | |
|---|---|---|---|---|---|---|---|---|---|---|---|---|---|---|
| Met | Glu | Ala | Ser | Arg | Pro | Ser | Cys | Val | Ala | Leu | Ser | Val | Val | Leu | Val |
| 1 | | | | 5 | | | | | 10 | | | | | 15 | |
| Ser | Ile | Val | Ile | Ala | Trp | Ala | Trp | Arg | Val | Leu | Asn | Trp | Val | Trp | Leu |
| | | | 20 | | | | | 25 | | | | | 30 | | |
| Arg | Pro | Asn | Lys | Leu | Glu | Arg | Cys | Leu | Arg | Glu | Gln | Gly | Leu | Thr | Gly |
| | | | 35 | | | | 40 | | | | | 45 | | | |
| Asn | Ser | Tyr | Arg | Leu | Leu | Phe | Gly | Asp | Thr | Lys | Glu | Ile | Ser | Met | Met |
| | 50 | | | | | 55 | | | | | 60 | | | | |
| Val | Glu | Gln | Ala | Gln | Ser | Lys | Pro | Ile | Lys | Leu | Ser | Thr | Thr | His | Asp |
| 65 | | | | | 70 | | | | | 75 | | | | | 80 |
| Ile | Ala | Pro | Arg | Val | Ile | Pro | Phe | Ser | His | Gln | Ile | Val | Tyr | Thr | Tyr |
| | | | | 85 | | | | | 90 | | | | | 95 | |
| Gly | Arg | Asn | Ser | Phe | Val | Trp | Met | Gly | Pro | Thr | Pro | Arg | Val | Thr | Ile |
| | | | 100 | | | | | 105 | | | | | 110 | | |
| Met | Asn | Pro | Glu | Asp | Leu | Lys | Asp | Ala | Phe | Asn | Lys | Ser | Asp | Glu | Phe |
| | | | 115 | | | | | 120 | | | | | 125 | | |
| Gln | Arg | Ala | Ile | Ser | Asn | Pro | Ile | Val | Lys | Ser | Ile | Ser | Gln | Gly | Leu |
| | 130 | | | | | 135 | | | | | 140 | | | | |
| Ser | Ser | Leu | Glu | Gly | Glu | Lys | Trp | Ala | Lys | His | Arg | Lys | Ile | Ile | Asn |
| 145 | | | | | 150 | | | | | 155 | | | | | 160 |
| Pro | Ala | Phe | His | Leu | Glu | Lys | Leu | Lys | Gly | Met | Leu | Pro | Thr | Phe | Tyr |
| | | | | 165 | | | | | 170 | | | | | 175 | |
| Gln | Ser | Cys | Ser | Glu | Met | Ile | Asn | Lys | Trp | Glu | Ser | Leu | Val | Phe | Lys |
| | | | 180 | | | | | 185 | | | | | 190 | | |
| Glu | Gly | Ser | Arg | Glu | Met | Asp | Val | Trp | Pro | Tyr | Leu | Glu | Asn | Leu | Thr |
| | | | 195 | | | | | 200 | | | | | 205 | | |
| Ser | Asp | Val | Ile | Ser | Arg | Ala | Ala | Phe | Gly | Ser | Ser | Tyr | Glu | Glu | Gly |
| | 210 | | | | | 215 | | | | | 220 | | | | |
| Arg | Lys | Ile | Phe | Gln | Leu | Leu | Arg | Glu | Glu | Ala | Lys | Phe | Tyr | Thr | Ile |
| 225 | | | | | 230 | | | | | 235 | | | | | 240 |
| Ala | Ala | Arg | Ser | Val | Tyr | Ile | Pro | Gly | Trp | Arg | Phe | Leu | Pro | Thr | Lys |
| | | | | 245 | | | | | 250 | | | | | 255 | |
| Gln | Asn | Lys | Arg | Met | Lys | Glu | Ile | His | Lys | Glu | Val | Arg | Gly | Leu | Leu |
| | | | 260 | | | | | 265 | | | | | 270 | | |
| Lys | Gly | Ile | Ile | Asn | Lys | Arg | Glu | Asp | Ala | Ile | Lys | Ala | Gly | Glu | Ala |
| | 275 | | | | | 280 | | | | | 285 | | | | |
| Ala | Lys | Gly | Asn | Leu | Leu | Gly | Ile | Leu | Met | Glu | Ser | Asn | Phe | Arg | Glu |
| | 290 | | | | | 295 | | | | | 300 | | | | |
| Ile | Gln | Glu | His | Gly | Asn | Asn | Lys | Asn | Ala | Gly | Met | Ser | Ile | Glu | Asp |
| 305 | | | | | 310 | | | | | 315 | | | | | 320 |
| Val | Ile | Gly | Glu | Cys | Lys | Leu | Phe | Tyr | Phe | Ala | Gly | Gln | Glu | Thr | Thr |
| | | | | 325 | | | | | 330 | | | | | 335 | |
| Ser | Val | Leu | Leu | Val | Trp | Thr | Leu | Val | Leu | Leu | Ser | Gln | Asn | Gln | Asp |
| | | | 340 | | | | | 345 | | | | | 350 | | |
| Trp | Gln | Ala | Arg | Ala | Arg | Glu | Glu | Val | Leu | Gln | Val | Phe | Gly | Thr | Asn |
| | | | 355 | | | | | 360 | | | | | 365 | | |
| Ile | Pro | Thr | Tyr | Asp | Gln | Leu | Ser | His | Leu | Lys | Val | Val | Thr | Met | Ile |
| | 370 | | | | | 375 | | | | | 380 | | | | |
| Leu | Leu | Glu | Val | Leu | Arg | Leu | Tyr | Pro | Ala | Val | Val | Glu | Leu | Pro | Arg |
| 385 | | | | | 390 | | | | | 395 | | | | | 400 |

Thr Thr Tyr Lys Lys Thr Gln Leu Gly Lys Phe Leu Leu Pro Ala Gly
            405                 410                 415

Val Glu Val Ser Leu His Ile Met Leu Ala His His Asp Lys Glu Leu
            420                 425                 430

Trp Gly Glu Asp Ala Lys Glu Phe Lys Pro Glu Arg Phe Ser Glu Gly
            435                 440                 445

Val Ser Lys Ala Thr Lys Asn Gln Phe Thr Tyr Phe Pro Phe Gly Ala
            450                 455                 460

Gly Pro Arg Ile Cys Ile Gly Gln Asn Phe Ala Met Leu Glu Ala Lys
465                 470                 475                 480

Leu Ala Leu Ser Leu Ile Leu Gln His Phe Thr Phe Glu Leu Ser Pro
            485                 490                 495

Ser Tyr Ala His Ala Pro Ser Val Thr Ile Thr Leu His Pro Gln Phe
            500                 505                 510

Gly Ala His Phe Ile Leu His Lys Arg
            515                 520

<210> SEQ ID NO 94
<211> LENGTH: 514
<212> TYPE: PRT
<213> ORGANISM: Prunus mume

<400> SEQUENCE: 94

Cys Val Ala Leu Ser Val Val Leu Val Ser Ile Val Ile Ala Trp Ala
1               5                   10                  15

Trp Arg Val Leu Asn Trp Val Trp Leu Arg Pro Asn Lys Leu Glu Arg
            20                  25                  30

Cys Leu Arg Glu Gln Gly Leu Thr Gly Asn Ser Tyr Arg Leu Leu Phe
        35                  40                  45

Gly Asp Thr Lys Glu Ile Ser Met Met Val Glu Gln Ala Gln Ser Lys
    50                  55                  60

Pro Ile Lys Leu Ser Thr Thr His Asp Ile Ala Pro Arg Val Ile Pro
65                  70                  75                  80

Phe Ser His Gln Ile Val Tyr Thr Tyr Gly Arg Asn Ser Phe Val Trp
                85                  90                  95

Met Gly Pro Thr Pro Arg Val Thr Ile Met Asn Pro Glu Asp Leu Lys
            100                 105                 110

Asp Ala Phe Asn Lys Ser Asp Glu Phe Gln Arg Ala Ile Ser Asn Pro
        115                 120                 125

Ile Val Lys Ser Ile Ser Gln Gly Leu Ser Ser Leu Glu Gly Glu Lys
    130                 135                 140

Trp Ala Lys His Arg Lys Ile Ile Asn Pro Ala Phe His Leu Glu Lys
145                 150                 155                 160

Leu Lys Gly Met Leu Pro Thr Phe Tyr Gln Ser Cys Ser Glu Met Ile
                165                 170                 175

Asn Lys Trp Glu Ser Leu Val Phe Lys Glu Gly Ser Arg Glu Met Asp
            180                 185                 190

Val Trp Pro Tyr Leu Glu Asn Leu Thr Ser Asp Val Ile Ser Arg Ala
        195                 200                 205

Ala Phe Gly Ser Ser Tyr Glu Glu Gly Arg Lys Ile Phe Gln Leu Leu
    210                 215                 220

Arg Glu Glu Ala Lys Phe Tyr Thr Ile Ala Ala Arg Ser Val Tyr Ile
225                 230                 235                 240

Pro Gly Trp Arg Phe Leu Pro Thr Lys Gln Asn Lys Arg Met Lys Glu
                245                 250                 255

```
Ile His Lys Glu Val Arg Gly Leu Leu Lys Gly Ile Ile Asn Lys Arg
            260                 265                 270

Glu Asp Ala Ile Lys Ala Gly Glu Ala Lys Gly Asn Leu Leu Gly
            275                 280                 285

Ile Leu Met Glu Ser Asn Phe Arg Glu Ile Gln Glu His Gly Asn Asn
            290                 295                 300

Lys Asn Ala Gly Met Ser Ile Glu Asp Val Ile Gly Glu Cys Lys Leu
305                 310                 315                 320

Phe Tyr Phe Ala Gly Gln Glu Thr Thr Ser Val Leu Val Trp Thr
                325                 330                 335

Leu Val Leu Leu Ser Gln Asn Gln Asp Trp Gln Ala Arg Ala Arg Glu
            340                 345                 350

Glu Val Leu Gln Val Phe Gly Thr Asn Ile Pro Thr Tyr Asp Gln Leu
            355                 360                 365

Ser His Leu Lys Val Val Thr Met Ile Leu Glu Val Leu Arg Leu
            370                 375                 380

Tyr Pro Ala Val Val Glu Leu Pro Arg Thr Thr Tyr Lys Lys Thr Gln
385                 390                 395                 400

Leu Gly Lys Phe Leu Leu Pro Ala Gly Val Glu Val Ser Leu His Ile
                405                 410                 415

Met Leu Ala His His Asp Lys Glu Leu Trp Gly Glu Asp Ala Lys Glu
            420                 425                 430

Phe Lys Pro Glu Arg Phe Ser Glu Gly Val Ser Lys Ala Thr Lys Asn
            435                 440                 445

Gln Phe Thr Tyr Phe Pro Phe Gly Ala Gly Pro Arg Ile Cys Ile Gly
450                 455                 460

Gln Asn Phe Ala Met Leu Glu Ala Lys Leu Ala Leu Ser Leu Ile Leu
465                 470                 475                 480

Gln His Phe Thr Phe Glu Leu Ser Pro Ser Tyr Ala His Ala Pro Ser
            485                 490                 495

Val Thr Ile Thr Leu His Pro Gln Phe Gly Ala His Phe Ile Leu His
            500                 505                 510

Lys Arg

<210> SEQ ID NO 95
<211> LENGTH: 418
<212> TYPE: PRT
<213> ORGANISM: Prunus persica

<400> SEQUENCE: 95

Met Gly Pro Ile Pro Arg Val His Ile Met Asn Pro Glu Asp Leu Lys
1               5                   10                  15

Asp Thr Phe Asn Arg His Asp Asp Phe His Lys Val Val Lys Asn Pro
            20                  25                  30

Ile Met Lys Ser Leu Pro Gln Gly Ile Val Gly Ile Glu Gly Asp Gln
            35                  40                  45

Trp Ala Lys His Arg Lys Ile Ile Asn Pro Ala Phe His Leu Glu Lys
        50                  55                  60

Leu Lys Gly Met Val Pro Ile Phe Tyr Gln Ser Cys Ser Glu Met Ile
65              70                  75                  80

Asn Ile Trp Lys Ser Leu Val Ser Lys Glu Ser Ser Cys Glu Leu Asp
            85                  90                  95

Val Trp Pro Tyr Leu Glu Asn Phe Thr Ser Asp Val Ile Ser Arg Ala
            100                 105                 110
```

Ala Phe Gly Ser Ser Tyr Glu Glu Gly Arg Lys Ile Phe Gln Leu Leu
            115                 120                 125

Arg Glu Glu Ala Lys Val Tyr Thr Val Ala Val Arg Ser Val Tyr Ile
130                 135                 140

Pro Gly Trp Arg Phe Leu Pro Thr Lys Gln Asn Lys Lys Thr Lys Glu
145                 150                 155                 160

Ile His Asn Glu Ile Lys Gly Leu Leu Lys Gly Ile Ile Asn Lys Arg
                165                 170                 175

Glu Glu Ala Met Lys Ala Gly Glu Ala Thr Lys Asp Asp Leu Leu Gly
            180                 185                 190

Ile Leu Met Glu Ser Asn Phe Arg Glu Ile Gln Glu His Gly Asn Asn
        195                 200                 205

Lys Asn Ala Gly Met Ser Ile Glu Asp Val Ile Gly Glu Cys Lys Leu
    210                 215                 220

Phe Tyr Phe Ala Gly Gln Glu Thr Thr Ser Val Leu Leu Val Trp Thr
225                 230                 235                 240

Met Val Leu Leu Ser Gln Asn Gln Asp Trp Gln Ala Arg Ala Arg Glu
                245                 250                 255

Glu Val Leu Gln Val Phe Gly Ser Asn Ile Pro Thr Tyr Glu Glu Leu
            260                 265                 270

Ser His Leu Lys Val Val Thr Met Ile Leu Leu Glu Val Leu Arg Leu
        275                 280                 285

Tyr Pro Ser Val Val Ala Leu Pro Arg Thr Thr His Lys Lys Thr Gln
    290                 295                 300

Leu Gly Lys Leu Ser Leu Pro Ala Gly Val Glu Val Ser Leu Pro Ile
305                 310                 315                 320

Leu Leu Val His His Asp Lys Glu Leu Trp Gly Glu Asp Ala Asn Glu
                325                 330                 335

Phe Lys Pro Glu Arg Phe Ser Glu Gly Val Ser Lys Ala Thr Lys Asn
            340                 345                 350

Gln Phe Thr Tyr Phe Pro Phe Gly Gly Gly Pro Arg Ile Cys Ile Gly
        355                 360                 365

Gln Asn Phe Ala Met Met Glu Ala Lys Leu Ala Leu Ser Leu Ile Leu
    370                 375                 380

Gln His Phe Thr Phe Glu Leu Ser Pro Gln Tyr Ser His Ala Pro Ser
385                 390                 395                 400

Val Thr Ile Thr Leu Gln Pro Gln Tyr Gly Ala His Leu Ile Leu His
                405                 410                 415

Lys Arg

<210> SEQ ID NO 96
<211> LENGTH: 1566
<212> TYPE: DNA
<213> ORGANISM: Prunus avium

<400> SEQUENCE: 96
atggaagcat caagggctag ttgtgttgcg ctatgtgttg tttgggtgag catagtaatt      60
acattggcat ggagggtgct gaattgggtg tggttgaggc aaagaaaact agaaagatgc     120
ttgagggagc aaggccttac aggcaattct acaggctttt gtttggaga caccaaggat      180 ctctcgaaga tgctggaaca acacaatcc aaacccatca aactctccac ctcccatgat     240
atagcgccac gagtcacccc atttttccat cgaactgtga actctaatgg caagaattct     300
tttgtttgga tgggccctat accaagagtg cacatcatga atccagaaga tttgaaagat     360

```
gccttcaaca gacatgatga ttttcataag acagtaaaaa atcctatcat gaagtctcca      420
ccaccgggca ttgtaggcat tgaaggtgag caatgggcta acacagaaa gattatcaac       480 ccagcattcc atttagagaa gctaaagggt atggtaccaa tattttacca aagttgtagc      540
gagatgatta acaaatggga gagcttggtg tccaaagaga gttcatgtga gttggatgtg      600
tggccttatc ttgaaaattt taccagcgat gtgatttccc gagctgcatt tggaagtagc      660
tatgaagagg gaaggaaaat atttcaacta ctaagagagg aagcaaaagt ttattcggta      720
gctctacgaa gtgtttacat tccaggatgg aggtttctac caaccaagca gaacaagaag      780
acgaaggaaa ttcacaatga aattaaaggc ttacttaagg gcattataaa taaaagggaa      840
gaggcgatga aggcagggga agccactaaa gatgacttac taggaatact tatggagtcc      900
aacttcaggg aaattcagga acatgggaac aacaaaaatg ctggaatgag tattgaagat      960
gtaattggag agtgtaagtt gttttacttt gctgggcaag agaccacttc ggtgttgctt     1020
gtttggacaa tgattttact aagccaaaat caggattggc aagctcgtgc aagagaagag     1080
gtcttgaaag tctttggaag caacatccca acctatgaag agctaagtca cctaaaagtt     1140
gtgaccatga ttttacttga agttcttcga ttatacccat cagtcgttgc gcttcctcga     1200
accactcaca agaaaacaca gcttggaaaa ttatcattac cagctggagt ggaagtctcc     1260
ttgcccatac tgcttgttca ccatgacaaa gagttgtggg gtgaggatgc aaatgagttc     1320
aagccagaga ggttttcaga gggagtttca aaggcaacaa gaacaaaatt tacatactta     1380
cctttcggag ggggtccaag gatttgcatt ggacaaaact ttgccatggt ggaagctaaa     1440
ttggccttgg ccctgatttt acaacacttt gcctttgagc tttctccatc ctatgctcat     1500
gctccttctg cagttataac ccttcaacct caatttggtg ctcatatcat tttgcataaa     1560
cgttga                                                                 1566

<210> SEQ ID NO 97
<211> LENGTH: 2070
<212> TYPE: DNA
<213> ORGANISM: Artificial Sequence
<220> FEATURE:
<223> OTHER INFORMATION: Synthetic oligonucleotide

<400> SEQUENCE: 97
atgtcctcca actccgattt ggtcagaaga ttggaatctg ttttgggtgt ttctttcggt       60
ggttctgtta ctgattccgt tgttgttatt gctaccacct ctattgcttt ggttatcggt      120
gttttggttt tgttgtggag aagatcctct gacagatcta gagaagttaa gcaattggct      180
gttccaaagc cagttactat cgttgaagaa gaagatgaat tcgaagttgc ttctggtaag      240
accagagttt ctattttcta cggtactcaa actggtactg ctgaaggttt tgctaaggct      300
ttggctgaag aaatcaaagc cagatacgaa aaagctgccg ttaaggttat tgatttggat      360
gattacacag ccgaagatga caaatacggt gaaaagttga agaaagaaac tatggccttc      420
ttcatgttgg ctacttatgg tgatggtgaa cctactgata tgctgctagt attttacaag      480
tggttcaccg aaggtactga tagaggtgtt tggttggaac atttgagata cggtgtattc      540
ggtttgggta acagacaata cgaacacttc aacaagattg ccaaggttgt tgatgatttg      600
ttggttgaac aaggtgccaa gagattggtt actgttggtt gggtgatga tgatcaatgc      660 atcgaagatg atttctccgc ttggaaagaa gccttgtggc cagaattgga tcaattattg      720
caagatgata ccaacaccgt ttctactcca tacactgctg ttattccaga atacagagtt      780
```

```
gttatccacg atccatctgt tacctcttat gaagatccat actctaacat ggctaacggt    840
aatgcctctt acgatattca tcatccatgt agagctaacg ttgccgtcca aaaagaattg    900
cataagccag aatctgacag aagttgcatc catttggaat tcgatatttt cgctactggt    960
ttgacttacg aaaccggtga tcatgttggt gtttacgctg ataattgtga tgatactgta   1020
gaagaagccg ctaagttgtt gggtcaacca ttggatttgt tgttctccat tcataccgat   1080
aacaacgacg gtacttcttt gggttcttct ttgccaccac catttccagg tccatgtact   1140
ttgagaactg ctttggctag atatgccgat tgttgaatc caccaaaaaa ggctgctttg   1200
attgctttag ctgctcatgc tgatgaacca tctgaagctg aaagattgaa gttcttgtca   1260
tctccacaag gtaaggacga atattctaaa tgggttgtcg gttcccaaag atccttggtt   1320
gaagttatgg ctgaatttcc atctgctaaa ccaccattgg gtgtattttt tgctgctgtt   1380
gttcctagat tgcaacctag atattactcc atctcttcca gtccaagatt tgctccacat   1440
agagttcatg ttacttgcgc tttggtttat ggtccaactc caactggtag aattcacaga   1500
ggtgtatgtt cattctggat gaagaatgtt gtcccattgg aaaagtctca aaactgttct   1560
tgggccccaa ttttcatcag acaatctaat ttcaagttgc cagccgatca ttctgttcca   1620
atagttatgg ttggtccagg tactggttta gctccttta gaggtttctt acaagaaaga   1680
ttggccttga agaagaagg tgctcaagtt ggtcctgctt tgttgttttt tggttgcaga   1740
aacagacaaa tggacttcat ctacgaagtc gaattgaaca actttgtcga acaaggtgct   1800
ttgtccgaat tgatcgttgc tttttcaaga gaaggtccat ccaagaata cgtccaacat   1860
aagatggttg aaaaggcagc ttacatgtgg aacttgattt ctcaaggtgg ttacttctac   1920
gtttgtggtg atgctaaagg tatggctaga gatgttcata gaacattgca taccatcgtc   1980
caacaagaag aaaaggttga ttctaccaag gccgaatcca tcgttaagaa attgcaaatg   2040
gacggtagat acttgagaga tgtttggtga                                    2070
```

<210> SEQ ID NO 98
<211> LENGTH: 689
<212> TYPE: PRT
<213> ORGANISM: Rubus suavissimus

<400> SEQUENCE: 98

```
Met Ser Ser Asn Ser Asp Leu Val Arg Arg Leu Glu Ser Val Leu Gly
 1               5                  10                  15

Val Ser Phe Gly Gly Ser Val Thr Asp Ser Val Val Ile Ala Thr
             20                  25                  30

Thr Ser Ile Ala Leu Val Ile Gly Val Leu Val Leu Leu Trp Arg Arg
         35                  40                  45

Ser Ser Asp Arg Ser Arg Glu Val Lys Gln Leu Ala Val Pro Lys Pro
     50                  55                  60

Val Thr Ile Val Glu Glu Glu Asp Glu Phe Glu Val Ala Ser Gly Lys
 65                  70                  75                  80

Thr Arg Val Ser Ile Phe Tyr Gly Thr Gln Thr Gly Thr Ala Glu Gly
                 85                  90                  95

Phe Ala Lys Ala Leu Ala Glu Glu Ile Lys Ala Arg Tyr Glu Lys Ala
            100                 105                 110

Ala Val Lys Val Ile Asp Leu Asp Asp Tyr Thr Ala Glu Asp Asp Lys
        115                 120                 125

Tyr Gly Glu Lys Leu Lys Lys Glu Thr Met Ala Phe Phe Met Leu Ala
    130                 135                 140
```

Thr Tyr Gly Asp Gly Glu Pro Thr Asp Asn Ala Ala Arg Phe Tyr Lys
145                 150                 155                 160

Trp Phe Thr Glu Gly Thr Asp Arg Gly Val Trp Leu Glu His Leu Arg
            165                 170                 175

Tyr Gly Val Phe Gly Leu Gly Asn Arg Gln Tyr Glu His Phe Asn Lys
            180                 185                 190

Ile Ala Lys Val Val Asp Asp Leu Val Glu Gln Gly Ala Lys Arg
            195                 200                 205

Leu Val Thr Val Gly Leu Gly Asp Asp Gln Cys Ile Glu Asp Asp
            210                 215                 220

Phe Ser Ala Trp Lys Glu Ala Leu Trp Pro Glu Leu Asp Gln Leu Leu
225                 230                 235                 240

Gln Asp Asp Thr Asn Thr Val Ser Thr Pro Tyr Thr Ala Val Ile Pro
            245                 250                 255

Glu Tyr Arg Val Val Ile His Asp Pro Ser Val Thr Ser Tyr Glu Asp
            260                 265                 270

Pro Tyr Ser Asn Met Ala Asn Gly Asn Ala Ser Tyr Asp Ile His His
            275                 280                 285

Pro Cys Arg Ala Asn Val Ala Val Gln Lys Glu Leu His Lys Pro Glu
            290                 295                 300

Ser Asp Arg Ser Cys Ile His Leu Glu Phe Asp Ile Phe Ala Thr Gly
305                 310                 315                 320

Leu Thr Tyr Glu Thr Gly Asp His Val Gly Val Tyr Ala Asp Asn Cys
            325                 330                 335

Asp Asp Thr Val Glu Glu Ala Ala Lys Leu Leu Gly Gln Pro Leu Asp
            340                 345                 350

Leu Leu Phe Ser Ile His Thr Asp Asn Asn Asp Gly Thr Ser Leu Gly
            355                 360                 365

Ser Ser Leu Pro Pro Pro Phe Pro Gly Pro Cys Thr Leu Arg Thr Ala
370                 375                 380

Leu Ala Arg Tyr Ala Asp Leu Leu Asn Pro Pro Lys Lys Ala Ala Leu
385                 390                 395                 400

Ile Ala Leu Ala Ala His Ala Asp Glu Pro Ser Glu Ala Glu Arg Leu
            405                 410                 415

Lys Phe Leu Ser Ser Pro Gln Gly Lys Asp Glu Tyr Ser Lys Trp Val
            420                 425                 430

Val Gly Ser Gln Arg Ser Leu Val Glu Val Met Ala Glu Phe Pro Ser
            435                 440                 445

Ala Lys Pro Pro Leu Gly Val Phe Phe Ala Ala Val Pro Arg Leu
            450                 455                 460

Gln Pro Arg Tyr Tyr Ser Ile Ser Ser Ser Pro Arg Phe Ala Pro His
465                 470                 475                 480

Arg Val His Val Thr Cys Ala Leu Val Tyr Gly Pro Thr Pro Thr Gly
            485                 490                 495

Arg Ile His Arg Gly Val Cys Ser Phe Trp Met Lys Asn Val Val Pro
            500                 505                 510

Leu Glu Lys Ser Gln Asn Cys Ser Trp Ala Pro Ile Phe Ile Arg Gln
            515                 520                 525

Ser Asn Phe Lys Leu Pro Ala Asp His Ser Val Pro Ile Val Met Val
            530                 535                 540

Gly Pro Gly Thr Gly Leu Ala Pro Phe Arg Gly Phe Leu Gln Glu Arg
545                 550                 555                 560

Leu Ala Leu Lys Glu Glu Gly Ala Gln Val Gly Pro Ala Leu Leu Phe

```
                565                 570                 575
Phe Gly Cys Arg Asn Arg Gln Met Asp Phe Ile Tyr Glu Val Glu Leu
            580                 585                 590

Asn Asn Phe Val Glu Gln Gly Ala Leu Ser Glu Leu Ile Val Ala Phe
            595                 600                 605

Ser Arg Glu Gly Pro Ser Lys Glu Tyr Val Gln His Lys Met Val Glu
    610                 615                 620

Lys Ala Ala Tyr Met Trp Asn Leu Ile Ser Gln Gly Gly Tyr Phe Tyr
625                 630                 635                 640

Val Cys Gly Asp Ala Lys Gly Met Ala Arg Asp Val His Arg Thr Leu
                645                 650                 655

His Thr Ile Val Gln Gln Glu Glu Lys Val Asp Ser Thr Lys Ala Glu
            660                 665                 670

Ser Ile Val Lys Lys Leu Gln Met Asp Gly Arg Tyr Leu Arg Asp Val
        675                 680                 685

Trp

<210> SEQ ID NO 99
<211> LENGTH: 3315
<212> TYPE: DNA
<213> ORGANISM: Artificial Sequence
<220> FEATURE:
<223> OTHER INFORMATION: KO-BMR fusion construct

<400> SEQUENCE: 99
atggatgctg tgacgggttt gttaactgtc ccagcaaccg ctataactat tggtggaact      60
gctgtagcat tggcggtagc gctaatcttt tggtacctga atcctacac atcagctaga     120
agatcccaat caaatcatct tccaagagtg cctgaagtcc caggtgttcc attgttagga     180
aatctgttac aattgaagga gaaaaagcca tacatgactt ttacgagatg ggcagcgaca     240
tatggaccta tctatagtat caaaactggg gctacaagta tggttgtggt atcatctaat     300
gagatagcca aggaggcatt ggtgaccaga ttccaatcca tatctacaag gaacttatct     360
aaagccctga agtacttac agcagataag acaatggtcg caatgtcaga ttatgatgat     420
tatcataaaa cagttaagag acacatactg accgccgtct gggtcctaa tgcacagaaa     480
aagcatagaa ttcacagaga tatcatgatg gataacatat ctactcaact tcatgaattc     540
gtgaaaaaca cccagaaca ggaagaggta gaccttagaa aaatctttca atctgagtta     600
ttcggcttag ctatgagaca agccttagga aaggatgttg aaagtttgta cgttgaagac     660
ctgaaaatca ctatgaatag agacgaaatc tttcaagtcc ttgttgttga tccaatgatg     720
ggagcaatcg atgttgattg gagagacttc tttccatacc taaagtgggt cccaaacaaa     780
aagttcgaaa atactattca acaaatgtac atcagaagag aagctgttat gaaatcttta     840
atcaaagagc acaaaagag aatagcgtca ggcgaaaagc taaatagtta tatcgattac     900
cttttatctg aagctcaaac tttaaccgat cagcaactat tgatgtcctt gtgggaacca     960
atcattgaat cttcagatac aacaatggtc acaacagaat gggcaatgta cgaattagct    1020
aaaaaccta aattgcaaga taggttgtac agagacatta agtccgtctg tggatctgaa    1080
aagataaccg aagagcatct atcacagctg ccttacatta cagctatttt ccacgaaaca    1140
ctgagaagac actcaccagt tcctatcatt cctctaagac atgtacatga agataccgtt    1200
ctaggcggct accatgttcc tgctggcaca gaacttgccg ttaacatcta cggttgcaac    1260
atggacaaaa acgtttggga aaatccagag gaatggaacc cagaaagatt catgaaagag    1320
```

```
aatgagacaa ttgattttca aaagacgatg gccttcggtg gtggtaagag agtttgtgct   1380
ggttccttgc aagccctttt aactgcatct attgggattg ggagaatggt tcaagagttc   1440
gaatggaaac tgaaggatat gactcaagag gaagtgaaca cgataggcct aactacacaa   1500
atgttaagac cattgagagc tattatcaaa cctaggatcc catcaagacc aagtcctagt   1560
accgaacaat ctgcaaaaaa agttagaaaa aaagcagaaa atgcacacaa tactccattg   1620
ctagttcttt atggttctaa tatgggaaca gcggaaggaa cggccaggga tctagctgac   1680
atagctatgt ccaagggatt tgccccgcaa gtagcaaccc tggattccca tgcaggtaac   1740
ttgccaagag aaggtgctgt tctaatagtt accgctagct acaatgggca ccctccagat   1800
aatgcgaagc agttcgtcga ttggttagat caagcatcag cagatgaagt taagggtgtt   1860
agatactctg tttttggatg tggagataag aattgggcca ccacatatca gaaggttccg   1920
gctttcatcg atgaaatgct tgctgcaaaa ggggctgaaa atatagcaga tcgtggtgag   1980
gccgacgcaa gcgacgattt tgagggtacc tatgaggagt ggagagagca catgtggtct   2040
gatgttgccg cgtattttaa tctagacata gaaaattctg aagacaataa aagtgcctta   2100
cttcttcaat tcgtcgatag tgctgcggac atgcccttag caaagatgca tggagccttt   2160
tcaacgaacg tagtagccag taaggaactt caacaaccag gtagtgccag aagtacacgt   2220
cacttggaaa ttgaattacc aaaagaggca tcctaccaag aaggtgacca tcttggtgta   2280
atcccaagaa actacgaagg tatagtcaat agggtaacgg caagatttgg gctggatgca   2340
agccaacaga taagactaga agcagaagaa gaaaaattgg cgcaccttcc actagcgaag   2400
acagtatccg ttgaagaatt attgcaatac gtggaattgc aggatcccgt cactagaacg   2460
caattgagag ctatggcagc aaagactgtt tgtccacctc acaaggttga acttgaagct   2520
ctacttgaaa acaagcata caaagagcaa gtgctagcaa agagactaac catgttagaa   2580
ttgctggaaa ataccccggc atgcgaaatg gaattctccg aatttatcgc gttgttgcca   2640
agtattcgtc ccaggtatta ctcaatttca tcttccaccaa gggttgacga gaaacaggca   2700
tctattaccg tatctgtggt ctctggagaa gcttggagtg gttacggaga atacaagggt   2760
attgcttcca attatcttgc agaactgcag gaaggggata caattacctg ctttatttct   2820
actcctcaat cagaatttac tcttccgaag gatccagaaa ctccgttaat tatggtaggt   2880
ccggaacag gagtcgcccc tttcagaggc tttgtgcaag caaggaagca actaaaagaa   2940
cagggacaaa gtctgggtga ggcacatcta tatttcggtt gcagatctcc gcatgaggat   3000
tacttatacc aagaagaact tgaaaacgcc caatcgaag gtattatcac cttgcatact   3060
gcattcagta gaatgccaaa ccagccgaaa acttacgtac agcatgttat ggagcaagat   3120
ggtaagaagt taattgagct tttggataag ggcgcccact tctacatttg cggcgacgga   3180
tcccaaatgg cgcctgccgt tgaagccacc ttgatgaaat catatgcaga tgttcatcaa   3240
gtttcagaag cggacgcccg tctttggtta caacaactag aggagaaagg aaggtatgca   3300
aaagatgttt ggtaa                                                    3315
```

<210> SEQ ID NO 100
<211> LENGTH: 1104
<212> TYPE: PRT
<213> ORGANISM: Artificial Sequence
<220> FEATURE:
<223> OTHER INFORMATION: KO-BMR fusion construct

<400> SEQUENCE: 100

Met Asp Ala Val Thr Gly Leu Leu Thr Val Pro Ala Thr Ala Ile Thr

-continued

```
1               5                   10                  15
Ile Gly Gly Thr Ala Val Ala Leu Ala Val Ala Leu Ile Phe Trp Tyr
                20                  25                  30
Leu Lys Ser Tyr Thr Ser Ala Arg Arg Ser Gln Ser Asn His Leu Pro
                35                  40                  45
Arg Val Pro Glu Val Pro Gly Val Pro Leu Leu Gly Asn Leu Leu Gln
 50                  55                  60
Leu Lys Glu Lys Pro Tyr Met Thr Phe Thr Arg Trp Ala Ala Thr
 65                  70                  75                  80
Tyr Gly Pro Ile Tyr Ser Ile Lys Thr Gly Ala Thr Ser Met Val Val
                85                  90                  95
Val Ser Ser Asn Glu Ile Ala Lys Glu Ala Leu Val Thr Arg Phe Gln
                100                 105                 110
Ser Ile Ser Thr Arg Asn Leu Ser Lys Ala Leu Lys Val Leu Thr Ala
                115                 120                 125
Asp Lys Thr Met Val Ala Met Ser Asp Tyr Asp Tyr His Lys Thr
 130                 135                 140
Val Lys Arg His Ile Leu Thr Ala Val Leu Gly Pro Asn Ala Gln Lys
 145                 150                 155                 160
Lys His Arg Ile His Arg Asp Ile Met Met Asp Asn Ile Ser Thr Gln
                165                 170                 175
Leu His Glu Phe Val Lys Asn Asn Pro Glu Gln Glu Val Asp Leu
                180                 185                 190
Arg Lys Ile Phe Gln Ser Glu Leu Phe Gly Leu Ala Met Arg Gln Ala
                195                 200                 205
Leu Gly Lys Asp Val Glu Ser Leu Tyr Val Glu Asp Leu Lys Ile Thr
 210                 215                 220
Met Asn Arg Asp Glu Ile Phe Gln Val Leu Val Asp Pro Met Met
 225                 230                 235                 240
Gly Ala Ile Asp Val Asp Trp Arg Asp Phe Phe Pro Tyr Leu Lys Trp
                245                 250                 255
Val Pro Asn Lys Lys Phe Glu Asn Thr Ile Gln Gln Met Tyr Ile Arg
                260                 265                 270
Arg Glu Ala Val Met Lys Ser Leu Ile Lys Glu His Lys Lys Arg Ile
                275                 280                 285
Ala Ser Gly Glu Lys Leu Asn Ser Tyr Ile Asp Tyr Leu Leu Ser Glu
                290                 295                 300
Ala Gln Thr Leu Thr Asp Gln Gln Leu Leu Met Ser Leu Trp Glu Pro
 305                 310                 315                 320
Ile Ile Glu Ser Ser Asp Thr Thr Met Val Thr Thr Glu Trp Ala Met
                325                 330                 335
Tyr Glu Leu Ala Lys Asn Pro Lys Leu Gln Asp Arg Leu Tyr Arg Asp
                340                 345                 350
Ile Lys Ser Val Cys Gly Ser Glu Lys Ile Thr Glu Glu His Leu Ser
                355                 360                 365
Gln Leu Pro Tyr Ile Thr Ala Ile Phe His Glu Thr Leu Arg Arg His
                370                 375                 380
Ser Pro Val Pro Ile Ile Pro Leu Arg His Val His Glu Asp Thr Val
 385                 390                 395                 400
Leu Gly Gly Tyr His Val Pro Ala Gly Thr Glu Leu Ala Val Asn Ile
                405                 410                 415
Tyr Gly Cys Asn Met Asp Lys Asn Val Trp Glu Asn Pro Glu Glu Trp
                420                 425                 430
```

```
Asn Pro Glu Arg Phe Met Lys Glu Asn Glu Thr Ile Asp Phe Gln Lys
        435                 440                 445

Thr Met Ala Phe Gly Gly Lys Arg Val Cys Ala Gly Ser Leu Gln
450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
                500                 505                 510

Ile Pro Ser Arg Pro Ser Pro Ser Thr Glu Gln Ser Ala Lys Lys Val
        515                 520                 525

Arg Lys Lys Ala Glu Asn Ala His Asn Thr Pro Leu Leu Val Leu Tyr
530                 535                 540

Gly Ser Asn Met Gly Thr Ala Glu Gly Thr Ala Arg Asp Leu Ala Asp
545                 550                 555                 560

Ile Ala Met Ser Lys Gly Phe Ala Pro Gln Val Ala Thr Leu Asp Ser
                565                 570                 575

His Ala Gly Asn Leu Pro Arg Glu Gly Ala Val Leu Ile Val Thr Ala
                580                 585                 590

Ser Tyr Asn Gly His Pro Pro Asp Asn Ala Lys Gln Phe Val Asp Trp
        595                 600                 605

Leu Asp Gln Ala Ser Ala Asp Glu Val Lys Gly Val Arg Tyr Ser Val
610                 615                 620

Phe Gly Cys Gly Asp Lys Asn Trp Ala Thr Thr Tyr Gln Lys Val Pro
625                 630                 635                 640

Ala Phe Ile Asp Glu Met Leu Ala Ala Lys Gly Ala Glu Asn Ile Ala
                645                 650                 655

Asp Arg Gly Glu Ala Asp Ala Ser Asp Asp Phe Glu Gly Thr Tyr Glu
                660                 665                 670

Glu Trp Arg Glu His Met Trp Ser Asp Val Ala Ala Tyr Phe Asn Leu
            675                 680                 685

Asp Ile Glu Asn Ser Glu Asp Asn Lys Ser Ala Leu Leu Leu Gln Phe
    690                 695                 700

Val Asp Ser Ala Ala Asp Met Pro Leu Ala Lys Met His Gly Ala Phe
705                 710                 715                 720

Ser Thr Asn Val Val Ala Ser Lys Glu Leu Gln Gln Pro Gly Ser Ala
                725                 730                 735

Arg Ser Thr Arg His Leu Glu Ile Glu Leu Pro Lys Glu Ala Ser Tyr
                740                 745                 750

Gln Glu Gly Asp His Leu Gly Val Ile Pro Arg Asn Tyr Glu Gly Ile
            755                 760                 765

Val Asn Arg Val Thr Ala Arg Phe Gly Leu Asp Ala Ser Gln Gln Ile
770                 775                 780

Arg Leu Glu Ala Glu Glu Lys Leu Ala His Leu Pro Leu Ala Lys
785                 790                 795                 800

Thr Val Ser Val Glu Glu Leu Leu Gln Tyr Val Glu Leu Gln Asp Pro
                805                 810                 815

Val Thr Arg Thr Gln Leu Arg Ala Met Ala Ala Lys Thr Val Cys Pro
            820                 825                 830

Pro His Lys Val Glu Leu Glu Ala Leu Leu Glu Lys Gln Ala Tyr Lys
        835                 840                 845
```

Glu Gln Val Leu Ala Lys Arg Leu Thr Met Leu Glu Leu Leu Glu Lys
850                 855                 860

Tyr Pro Ala Cys Glu Met Glu Phe Ser Glu Phe Ile Ala Leu Leu Pro
865                 870                 875                 880

Ser Ile Arg Pro Arg Tyr Tyr Ser Ile Ser Ser Ser Pro Arg Val Asp
            885                 890                 895

Glu Lys Gln Ala Ser Ile Thr Val Ser Val Val Ser Gly Glu Ala Trp
                900                 905                 910

Ser Gly Tyr Gly Glu Tyr Lys Gly Ile Ala Ser Asn Tyr Leu Ala Glu
            915                 920                 925

Leu Gln Glu Gly Asp Thr Ile Thr Cys Phe Ile Ser Thr Pro Gln Ser
930                 935                 940

Glu Phe Thr Leu Pro Lys Asp Pro Glu Thr Pro Leu Ile Met Val Gly
945                 950                 955                 960

Pro Gly Thr Gly Val Ala Pro Phe Arg Gly Phe Val Gln Ala Arg Lys
                965                 970                 975

Gln Leu Lys Glu Gln Gly Gln Ser Leu Gly Glu Ala His Leu Tyr Phe
            980                 985                 990

Gly Cys Arg Ser Pro His Glu Asp Tyr Leu Tyr Gln Glu Glu Leu Glu
            995                 1000                1005

Asn Ala Gln Ser Glu Gly Ile Ile Thr Leu His Thr Ala Phe Ser
    1010                1015                1020

Arg Met Pro Asn Gln Pro Lys Thr Tyr Val Gln His Val Met Glu
    1025                1030                1035

Gln Asp Gly Lys Lys Leu Ile Glu Leu Leu Asp Lys Gly Ala His
    1040                1045                1050

Phe Tyr Ile Cys Gly Asp Gly Ser Gln Met Ala Pro Ala Val Glu
    1055                1060                1065

Ala Thr Leu Met Lys Ser Tyr Ala Asp Val His Gln Val Ser Glu
    1070                1075                1080

Ala Asp Ala Arg Leu Trp Leu Gln Gln Leu Glu Glu Lys Gly Arg
    1085                1090                1095

Tyr Ala Lys Asp Val Trp
    1100

<210> SEQ ID NO 101
<211> LENGTH: 3315
<212> TYPE: DNA
<213> ORGANISM: Artificial Sequence
<220> FEATURE:
<223> OTHER INFORMATION: KO-BMR fusion construct

<400> SEQUENCE: 101
atggatgctg tgacgggttt gttaactgtc ccagcaaccg ctataactat tggtggaact    60
gctgtagcat tggcggtagc gctaatcttt tggtacctga atcctacac atcagctaga    120 agatcccaat caaatcatct tccaagagtg cctgaagtcc caggtgttcc attgttagga    180
aatctgttac aattgaagga gaaaaagcca tacatgactt ttacgagatg ggcagcgaca    240
tatggaccta tctatagtat caaaactggg gctacaagta tggttgtggt atcatctaat    300
gagatagcca aggaggcatt ggtgaccaga ttccaatcca tatctacaag gaacttatct    360
aaagccctga agtacttac agcagataag acaatggtcg caatgtcaga ttatgatgat    420
tatcataaaa cagttaagag acacatactg accgccgtct gggtcctaa tgcacagaaa    480 aagcatagaa ttcacagaga tatcatgatg gataacatat ctactcaact tcatgaattc    540

```
gtgaaaaaca acccagaaca ggaagaggta gaccttagaa aaatctttca atctgagtta      600
ttcggcttag ctatgagaca agccttagga aaggatgttg aaagtttgta cgttgaagac      660
ctgaaaatca ctatgaatag agacgaaatc tttcaagtcc ttgttgttga tccaatgatg      720
ggagcaatcg atgttgattg gagagacttc tttccatacc taaagtgggt cccaaacaaa      780
aagttcgaaa atactattca acaaatgtac atcagaagag aagctgttat gaaatcttta      840
atcaaagagc acaaaaagag aatagcgtca ggcgaaaagc taaatagtta tatcgattac      900
cttttatctg aagctcaaac tttaaccgat cagcaactat tgatgtcctt gtgggaacca      960
atcattgaat cttcagatac aacaatggtc acaacagaat gggcaatgta cgaattagct     1020
aaaaaccta aattgcaaga taggttgtac agagacatta agtccgtctg tggatctgaa      1080
aagataaccg aagagcatct atcacagctg ccttacatta cagctatttt ccacgaaaca     1140
ctgagaagac actcaccagt tcctatcatt cctctaagac atgtacatga agataccgtt     1200
ctaggcggct accatgttcc tgctggcaca gaacttgccg ttaacatcta cggttgcaac     1260
atggacaaaa acgtttggga aaatccagag gaatggaacc cagaaagatt catgaaagag     1320
aatgagacaa ttgatttttca aaagacgatg gccttcggtg gtggtaagag agtttgtgct    1380
ggttccttgc aagccctttt aactgcatct attgggattg ggagaatggt tcaagagttc     1440
gaatggaaac tgaaggatat gactcaagag gaagtgaaca cgataggcct aactacacaa     1500
atgttaagac cattgagagc tattatcaaa cctaggatcc catcaagacc aagtcctagt     1560
accgaacaat ctgcaaaaaa agttagaaaa aaagcagaaa atgcacacaa tactccattg     1620
ctagttcttt atggttctaa tatgggaaca gcggaaggaa cggccaggga tctagctgac     1680
atagctatgt ccaagggatt tgccccgcaa gtagcaaccc tggattccca tgcaggtaac     1740
ttgccaagag aaggtgctgt tctaatagtt accgctagct acaatgggca ccctccagat     1800
aatgcgaagc agttcgtcga ttggttagat caagcatcag cagatgaagt taagggtgtt     1860
agatactctg tttttggatg tggagataag aattgggcca ccacatatca gaaggttccg     1920
gctttcatcg atgaaatgct tgctgcaaaa ggggctgaaa atatagcaga tcgtggtgag     1980
gccgacgcaa gcgacgattt tgagggtacc tatgaggagt ggagagagca catgtggtct     2040
gatgttgccg cgtattttaa tctagacata gaaaattctg aagacaataa aagtgcctta     2100
cttcttcaat tcgtcgatag tgctgcggac atgcccttag caaagatgca tggagccttt     2160
tcaacgaacg tagtagccag taaggaactt caacaaccag gtagtgccag aagtacacgt     2220
cacttggaaa ttgaattacc aaaagaggca tcctaccaag aaggtgacca tcttggtgta     2280
atcccaagaa actacgaagg tatagtcaat agggtaacgg caagatttgg gctggatgca     2340
agccaacaga taagactaga agcagaagaa gaaaaattgg cgcaccttcc actagcgaag     2400
acagtatccg ttgaagaatt attgcaatac gtggaattgc aggatcccgt cactagaacg     2460
caattgagag ctatgcagc aaagactgtt tgtccacctc acaaggttga acttgaagct     2520
ctacttgaaa aacaagcata caaagagcaa gtgctagcaa agagactaac catgttagaa     2580
ttgctggaaa ataccccggc atgcgaaatg gaattctccg aatttatcgc gttgttgcca     2640
agtattcgtc ccaggtatta ctcaatttca tcttcaccaa gggttgacga gaaacaggca     2700
tctattaccg tatctgtggt ctctggagaa gcttggagtg gttacggaga atacaagggt     2760
attgcttcca attatcttgc agaactgcag gaagggggata caattacctg ctttatttct     2820
actcctcaat cagaatttac tcttccgaag gatccagaaa ctccgttaat tatggtaggt     2880
ccgggaacag gagtcgcccc tttcagaggc tttgtgcaag caaggaagca actaaaagaa     2940
```

-continued

```
cagggacaaa gtctgggtga ggcacatcta tatttcggtt gcagatctcc gcatgaggat    3000
tacttatacc aagaagaact tgaaaacgcc caatcagaag gtattatcac cttgcatact    3060
gcattcagta gaatgccaaa ccagccgaaa acttacgtac agcatgttat ggagcaagat    3120
ggtaagaagt taattgagct tttggataag ggcgcccact tctacatttg cggcgacgga    3180
tcccaaatgg cgcctgccgt tgaagccacc ttgatgaaat catatgcaga tgttcatcaa    3240
gtttcagaag cggacgcccg tctttggtta caacaactag aggagaaagg aaggtatgca    3300
aaagatgttg cttaa                                                    3315
```

<210> SEQ ID NO 102
<211> LENGTH: 1104
<212> TYPE: PRT
<213> ORGANISM: Artificial Sequence
<220> FEATURE:
<223> OTHER INFORMATION: KO-BMR fusion construct

<400> SEQUENCE: 102

```
Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
                20                  25                  30

Leu Lys Ser Tyr Thr Ser Ala Arg Arg Ser Gln Ser Asn His Leu Pro
            35                  40                  45

Arg Val Pro Glu Val Pro Gly Val Pro Leu Leu Gly Asn Leu Leu Gln
        50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
                100                 105                 110

Ser Ile Ser Thr Arg Asn Leu Ser Lys Ala Leu Lys Val Leu Thr Ala
            115                 120                 125

Asp Lys Thr Met Val Ala Met Ser Asp Tyr Asp Tyr His Lys Thr
        130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Pro Glu Gln Glu Glu Val Asp Leu
                180                 185                 190

Arg Lys Ile Phe Gln Ser Glu Leu Phe Gly Leu Ala Met Arg Gln Ala
            195                 200                 205

Leu Gly Lys Asp Val Glu Ser Leu Tyr Val Glu Asp Leu Lys Ile Thr
        210                 215                 220

Met Asn Arg Asp Glu Ile Phe Gln Val Leu Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285
```

```
Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu His Leu Ser
        355                 360                 365

Gln Leu Pro Tyr Ile Thr Ala Ile Phe His Glu Thr Leu Arg Arg His
    370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Lys Arg Val Cys Ala Gly Ser Leu Gln
    450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
            500                 505                 510

Ile Pro Ser Arg Pro Ser Pro Ser Thr Glu Gln Ser Ala Lys Lys Val
        515                 520                 525

Arg Lys Lys Ala Glu Asn Ala His Asn Thr Pro Leu Leu Val Leu Tyr
    530                 535                 540

Gly Ser Asn Met Gly Thr Ala Glu Gly Thr Ala Arg Asp Leu Ala Asp
545                 550                 555                 560

Ile Ala Met Ser Lys Gly Phe Ala Pro Gln Val Ala Thr Leu Asp Ser
                565                 570                 575

His Ala Gly Asn Leu Pro Arg Glu Gly Ala Val Leu Ile Val Thr Ala
            580                 585                 590

Ser Tyr Asn Gly His Pro Pro Asp Asn Ala Lys Gln Phe Val Asp Trp
        595                 600                 605

Leu Asp Gln Ala Ser Ala Asp Glu Val Lys Gly Val Arg Tyr Ser Val
    610                 615                 620

Phe Gly Cys Gly Asp Lys Asn Trp Ala Thr Thr Tyr Gln Lys Val Pro
625                 630                 635                 640

Ala Phe Ile Asp Glu Met Leu Ala Ala Lys Gly Ala Glu Asn Ile Ala
                645                 650                 655

Asp Arg Gly Glu Ala Asp Ala Ser Asp Phe Glu Gly Thr Tyr Glu
            660                 665                 670

Glu Trp Arg Glu His Met Trp Ser Asp Val Ala Ala Tyr Phe Asn Leu
        675                 680                 685

Asp Ile Glu Asn Ser Glu Asp Asn Lys Ser Ala Leu Leu Leu Gln Phe
    690                 695                 700

Val Asp Ser Ala Ala Asp Met Pro Leu Ala Lys Met His Gly Ala Phe
```

```
              705                 710                 715                 720
       Ser Thr Asn Val Val Ala Ser Lys Glu Leu Gln Gln Pro Gly Ser Ala
                       725                 730                 735

Arg Ser Thr Arg His Leu Glu Ile Glu Leu Pro Lys Glu Ala Ser Tyr
                       740                 745                 750

Gln Glu Gly Asp His Leu Gly Val Ile Pro Arg Asn Tyr Glu Gly Ile
                       755                 760                 765

Val Asn Arg Val Thr Ala Arg Phe Gly Leu Asp Ala Ser Gln Gln Ile
               770                 775                 780

Arg Leu Glu Ala Glu Glu Lys Leu Ala His Leu Pro Leu Ala Lys
       785                 790                 795                 800

Thr Val Ser Val Glu Glu Leu Leu Gln Tyr Val Glu Leu Gln Asp Pro
                       805                 810                 815

Val Thr Arg Thr Gln Leu Arg Ala Met Ala Ala Lys Thr Val Cys Pro
                       820                 825                 830

Pro His Lys Val Glu Leu Glu Ala Leu Leu Glu Lys Gln Ala Tyr Lys
                       835                 840                 845

Glu Gln Val Leu Ala Lys Arg Leu Thr Met Leu Glu Leu Leu Glu Lys
               850                 855                 860

Tyr Pro Ala Cys Glu Met Glu Phe Ser Glu Phe Ile Ala Leu Leu Pro
       865                 870                 875                 880

Ser Ile Arg Pro Arg Tyr Tyr Ser Ile Ser Ser Ser Pro Arg Val Asp
                       885                 890                 895

Glu Lys Gln Ala Ser Ile Thr Val Ser Val Val Ser Gly Glu Ala Trp
                       900                 905                 910

Ser Gly Tyr Gly Glu Tyr Lys Gly Ile Ala Ser Asn Tyr Leu Ala Glu
                       915                 920                 925

Leu Gln Glu Gly Asp Thr Ile Thr Cys Phe Ile Ser Thr Pro Gln Ser
               930                 935                 940

Glu Phe Thr Leu Pro Lys Asp Pro Glu Thr Pro Leu Ile Met Val Gly
       945                 950                 955                 960

Pro Gly Thr Gly Val Ala Pro Phe Arg Gly Phe Val Gln Ala Arg Lys
                       965                 970                 975

Gln Leu Lys Glu Gln Gly Gln Ser Leu Gly Glu Ala His Leu Tyr Phe
                       980                 985                 990

Gly Cys Arg Ser Pro His Glu Asp Tyr Leu Tyr Gln Glu Glu Leu Glu
                       995                1000                1005

Asn Ala Gln Ser Glu Gly Ile Ile Thr Leu His Thr Ala Phe Ser
              1010                1015                1020

Arg Met Pro Asn Gln Pro Lys Thr Tyr Val Gln His Val Met Glu
              1025                1030                1035

Gln Asp Gly Lys Lys Leu Ile Glu Leu Leu Asp Lys Gly Ala His
              1040                1045                1050

Phe Tyr Ile Cys Gly Asp Gly Ser Gln Met Ala Pro Ala Val Glu
              1055                1060                1065

Ala Thr Leu Met Lys Ser Tyr Ala Asp Val His Gln Val Ser Glu
              1070                1075                1080

Ala Asp Ala Arg Leu Trp Leu Gln Gln Leu Glu Glu Lys Gly Arg
              1085                1090                1095

Tyr Ala Lys Asp Val Ala
              1100

<210> SEQ ID NO 103
```

<211> LENGTH: 3177
<212> TYPE: DNA
<213> ORGANISM: Artificial Sequence
<220> FEATURE:
<223> OTHER INFORMATION: KO-BMR fusion construct

<400> SEQUENCE: 103

| | | | | | |
|---|---|---|---|---|---|
| atgccaagag | tgcctgaagt | cccaggtgtt | ccattgttag | gaaatctgtt | acaattgaag | 60 |
| gagaaaaagc | atacatgac | ttttacgaga | tgggcagcga | catatggacc | tatctatagt | 120 |
| atcaaaactg | gggctacaag | tatggttgtg | gtatcatcta | atgagatagc | caaggaggca | 180 |
| ttggtgacca | gattccaatc | catatctaca | aggaacttat | ctaaagccct | gaaagtactt | 240 |
| acagcagata | agacaatggt | cgcaatgtca | gattatgatg | attatcataa | aacagttaag | 300 |
| agacacatac | tgaccgccgt | cttgggtcct | aatgcacaga | aaaagcatag | aattcacaga | 360 |
| gatatcatga | tggataacat | atctactcaa | cttcatgaat | tcgtgaaaaa | caacccagaa | 420 |
| caggaagagg | tagaccttag | aaaaatcttt | caatctgagt | tattcggctt | agctatgaga | 480 |
| caagccttag | gaaaggatgt | tgaaagtttg | tacgttgaag | acctgaaaat | cactatgaat | 540 |
| agagacgaaa | tctttcaagt | ccttgttgtt | gatccaatga | tgggagcaat | cgatgttgat | 600 |
| tggagagact | tctttccata | cctaaagtgg | gtcccaaaca | aaaagttcga | aaatactatt | 660 |
| caacaaatgt | acatcagaag | agaagctgtt | atgaaatctt | taatcaaaga | gcacaaaaag | 720 |
| agaatagcgt | caggcgaaaa | gctaaatagt | tatatcgatt | accttttatc | tgaagctcaa | 780 |
| actttaaccg | atcagcaact | attgatgtcc | ttgtgggaac | caatcattga | atcttcagat | 840 |
| acaacaatgt | tcacaacaga | tgggcaatg | tacgaattag | ctaaaaaccc | taaattgcaa | 900 |
| gataggttgt | acagagacat | taagtccgtc | tgtggatctg | aaaagataac | cgaagagcat | 960 |
| ctatcacagc | tgccttacat | tacagctatt | ttccacgaaa | cactgagaag | acactccacca | 1020 |
| gttcctatca | ttcctctaag | acatgtacat | gaagataccg | ttctaggcgg | ctaccatgtt | 1080 |
| cctgctggca | cagaacttgc | cgttaacatc | tacggttgca | acatggacaa | aaacgtttgg | 1140 |
| gaaaatccag | aggaatggaa | cccagaaaga | ttcatgaaag | agaatgagac | aattgatttt | 1200 |
| caaaagacga | tggccttcgg | tggtggtaag | agagtttgtg | ctggttcctt | gcaagccctt | 1260 |
| ttaactgcat | ctattgggat | tgggagaatg | gttcaagagt | tcgaatggaa | actgaaggat | 1320 |
| atgactcaag | aggaagtgaa | cacgataggc | ctaactacac | aaatgttaag | accattgaga | 1380 |
| gctattatca | aacctaggat | cccatcaaga | ccaagtccta | gtaccgaaca | atctgcaaaa | 1440 |
| aaagttagaa | aaaaagcaga | aaatgcacac | aatactccat | tgctagttct | ttatggttct | 1500 |
| aatatgggaa | cagcggaagg | aacggccagg | gatctagctg | acatagctat | gtccaaggga | 1560 |
| tttgccccgc | aagtagcaac | cctggattcc | catgcaggta | acttgccaag | agaaggtgct | 1620 |
| gttctaatag | ttaccgctag | ctacaatggg | caccctccag | ataatgcgaa | gcagttcgtc | 1680 |
| gattggttag | atcaagcatc | agcagatgaa | gttaagggtg | ttagatactc | tgttttttgga | 1740 |
| tgtggagata | agaattgggc | caccacatat | cagaaggttc | cggctttcat | cgatgaaatg | 1800 |
| cttgctgcaa | aggggctga | aaatatagca | gatcgtggtg | aggccgacgc | aagcgacgat | 1860 |
| tttgagggta | cctatgagga | gtggagagag | cacatgtggt | ctgatgttgc | cgcgtatttt | 1920 |
| aatctagaca | tagaaaattc | tgaagacaat | aaaagtgcct | acttcttcca | attcgtcgat | 1980 |
| agtgctgcgg | acatgccctt | agcaaagatg | catggagcct | tttcaacgaa | cgtagtagcc | 2040 |
| agtaaggaac | ttcaacaacc | aggtagtgcc | agaagtacac | gtcacttgga | aattgaatta | 2100 |
| ccaaaagagg | catcctacca | agaaggtgac | catcttggtg | taatcccaag | aaactacgaa | 2160 |

```
ggtatagtca atagggtaac ggcaagattt gggctggatg caagccaaca gataagacta    2220
gaagcagaag aagaaaaatt ggcgcacctt ccactagcga agacagtatc cgttgaagaa    2280
ttattgcaat acgtggaatt gcaggatccc gtcactagaa cgcaattgag agctatggca    2340
gcaaagactg tttgtccacc tcacaaggtt gaacttgaag ctctacttga aaacaagca    2400 tacaaagagc aagtgctagc aaagagacta accatgttag aattgctgga aaaatacccg    2460
gcatgcgaaa tggaattctc cgaatttatc gcgttgttgc caagtattcg tcccaggtat    2520
tactcaattt catcttcacc aagggttgac gagaaacagg catctattac cgtatctgtg    2580
gtctctggag aagcttggag tggttacgga gaatacaagg gtattgcttc caattatctt    2640
gcagaactgc aggaagggga tacaattacc tgctttattt ctactcctca atcagaattt    2700
actcttccga aggatccaga aactccgtta attatggtag gtccgggaac aggagtcgcc    2760
cctttcagag gctttgtgca agcaaggaag caactaaaag aacagggaca agtctgggt    2820 gaggcacatc tatatttcgg ttgcagatct ccgcatgagg attacttata ccaagaagaa    2880
cttgaaaacg cccaatcaga aggtattatc accttgcata ctgcattcag tagaatgcca    2940
aaccagccga aaacttacgt acagcatgtt atggagcaag atggtaagaa gttaattgag    3000
cttttggata agggcgccca cttctacatt tgcggcgacg atcccaaat ggcgcctgcc    3060 gttgaagcca ccttgatgaa atcatatgca gatgttcatc aagtttcaga gcggacgcc    3120 cgtctttggt tacaacaact agaggagaaa ggaaggtatg caaaagatgt ttggtaa       3177

<210> SEQ ID NO 104
<211> LENGTH: 1058
<212> TYPE: PRT
<213> ORGANISM: Artificial Sequence
<220> FEATURE:
<223> OTHER INFORMATION: KO-BMR fusion construct

<400> SEQUENCE: 104

Met Pro Arg Val Pro Glu Val Pro Gly Val Pro Leu Leu Gly Asn Leu
1               5                   10                  15

Leu Gln Leu Lys Glu Lys Pro Tyr Met Thr Phe Thr Arg Trp Ala
            20                  25                  30

Ala Thr Tyr Gly Pro Ile Tyr Ser Ile Lys Thr Gly Ala Thr Ser Met
        35                  40                  45

Val Val Val Ser Ser Asn Glu Ile Ala Lys Glu Ala Leu Val Thr Arg
    50                  55                  60

Phe Gln Ser Ile Ser Thr Arg Asn Leu Ser Lys Ala Leu Lys Val Leu
65                  70                  75                  80

Thr Ala Asp Lys Thr Met Val Ala Met Ser Asp Tyr Asp Asp Tyr His
                85                  90                  95

Lys Thr Val Lys Arg His Ile Leu Thr Ala Val Leu Gly Pro Asn Ala
            100                 105                 110

Gln Lys Lys His Arg Ile His Arg Asp Ile Met Met Asp Asn Ile Ser
        115                 120                 125

Thr Gln Leu His Glu Phe Val Lys Asn Asn Pro Glu Gln Glu Glu Val
    130                 135                 140

Asp Leu Arg Lys Ile Phe Gln Ser Glu Leu Phe Gly Leu Ala Met Arg
145                 150                 155                 160

Gln Ala Leu Gly Lys Asp Val Glu Ser Leu Tyr Val Glu Asp Leu Lys
                165                 170                 175

Ile Thr Met Asn Arg Asp Glu Ile Phe Gln Val Leu Val Val Asp Pro
```

-continued

```
                180                 185                 190
Met Met Gly Ala Ile Asp Val Asp Trp Arg Asp Phe Phe Pro Tyr Leu
            195                 200                 205
Lys Trp Val Pro Asn Lys Lys Phe Glu Asn Thr Ile Gln Gln Met Tyr
            210                 215                 220
Ile Arg Arg Glu Ala Val Met Lys Ser Leu Ile Lys Glu His Lys Lys
225                 230                 235                 240
Arg Ile Ala Ser Gly Glu Lys Leu Asn Ser Tyr Ile Asp Tyr Leu Leu
            245                 250                 255
Ser Glu Ala Gln Thr Leu Thr Asp Gln Gln Leu Leu Met Ser Leu Trp
            260                 265                 270
Glu Pro Ile Ile Glu Ser Ser Asp Thr Thr Met Val Thr Thr Glu Trp
            275                 280                 285
Ala Met Tyr Glu Leu Ala Lys Asn Pro Lys Leu Gln Asp Arg Leu Tyr
            290                 295                 300
Arg Asp Ile Lys Ser Val Cys Gly Ser Glu Lys Ile Thr Glu Glu His
305                 310                 315                 320
Leu Ser Gln Leu Pro Tyr Ile Thr Ala Ile Phe His Glu Thr Leu Arg
            325                 330                 335
Arg His Ser Pro Val Pro Ile Ile Pro Leu Arg His Val His Glu Asp
            340                 345                 350
Thr Val Leu Gly Gly Tyr His Val Pro Ala Gly Thr Glu Leu Ala Val
            355                 360                 365
Asn Ile Tyr Gly Cys Asn Met Asp Lys Asn Val Trp Glu Asn Pro Glu
            370                 375                 380
Glu Trp Asn Pro Glu Arg Phe Met Lys Glu Asn Glu Thr Ile Asp Phe
385                 390                 395                 400
Gln Lys Thr Met Ala Phe Gly Gly Gly Lys Arg Val Cys Ala Gly Ser
            405                 410                 415
Leu Gln Ala Leu Leu Thr Ala Ser Ile Gly Ile Gly Arg Met Val Gln
            420                 425                 430
Glu Phe Glu Trp Lys Leu Lys Asp Met Thr Gln Glu Glu Val Asn Thr
            435                 440                 445
Ile Gly Leu Thr Thr Gln Met Leu Arg Pro Leu Arg Ala Ile Ile Lys
            450                 455                 460
Pro Arg Ile Pro Ser Arg Pro Ser Pro Ser Thr Glu Gln Ser Ala Lys
465                 470                 475                 480
Lys Val Arg Lys Lys Ala Glu Asn Ala His Asn Thr Pro Leu Leu Val
            485                 490                 495
Leu Tyr Gly Ser Asn Met Gly Thr Ala Glu Gly Thr Ala Arg Asp Leu
            500                 505                 510
Ala Asp Ile Ala Met Ser Lys Gly Phe Ala Pro Gln Val Ala Thr Leu
            515                 520                 525
Asp Ser His Ala Gly Asn Leu Pro Arg Glu Gly Ala Val Leu Ile Val
            530                 535                 540
Thr Ala Ser Tyr Asn Gly His Pro Pro Asp Asn Ala Lys Gln Phe Val
545                 550                 555                 560
Asp Trp Leu Asp Gln Ala Ser Ala Asp Glu Val Lys Gly Val Arg Tyr
            565                 570                 575
Ser Val Phe Gly Cys Gly Asp Lys Asn Trp Ala Thr Thr Tyr Gln Lys
            580                 585                 590
Val Pro Ala Phe Ile Asp Glu Met Leu Ala Ala Lys Gly Ala Glu Asn
            595                 600                 605
```

```
Ile Ala Asp Arg Gly Glu Ala Asp Ala Ser Asp Asp Phe Glu Gly Thr
        610                 615                 620

Tyr Glu Glu Trp Arg Glu His Met Trp Ser Asp Val Ala Ala Tyr Phe
625                 630                 635                 640

Asn Leu Asp Ile Glu Asn Ser Glu Asp Asn Lys Ser Ala Leu Leu Leu
                645                 650                 655

Gln Phe Val Asp Ser Ala Ala Asp Met Pro Leu Ala Lys Met His Gly
            660                 665                 670

Ala Phe Ser Thr Asn Val Val Ala Ser Lys Glu Leu Gln Gln Pro Gly
        675                 680                 685

Ser Ala Arg Ser Thr Arg His Leu Glu Ile Glu Leu Pro Lys Glu Ala
    690                 695                 700

Ser Tyr Gln Glu Gly Asp His Leu Gly Val Ile Pro Arg Asn Tyr Glu
705                 710                 715                 720

Gly Ile Val Asn Arg Val Thr Ala Arg Phe Gly Leu Asp Ala Ser Gln
                725                 730                 735

Gln Ile Arg Leu Glu Ala Glu Glu Lys Leu Ala His Leu Pro Leu
            740                 745                 750

Ala Lys Thr Val Ser Val Glu Glu Leu Leu Gln Tyr Val Glu Leu Gln
        755                 760                 765

Asp Pro Val Thr Arg Thr Gln Leu Arg Ala Met Ala Ala Lys Thr Val
    770                 775                 780

Cys Pro Pro His Lys Val Glu Leu Glu Ala Leu Leu Glu Lys Gln Ala
785                 790                 795                 800

Tyr Lys Glu Gln Val Leu Ala Lys Arg Leu Thr Met Leu Glu Leu Leu
                805                 810                 815

Glu Lys Tyr Pro Ala Cys Glu Met Glu Phe Ser Glu Phe Ile Ala Leu
            820                 825                 830

Leu Pro Ser Ile Arg Pro Arg Tyr Tyr Ser Ile Ser Ser Ser Pro Arg
        835                 840                 845

Val Asp Glu Lys Gln Ala Ser Ile Thr Val Ser Val Ser Gly Glu
    850                 855                 860

Ala Trp Ser Gly Tyr Gly Glu Tyr Lys Gly Ile Ala Ser Asn Tyr Leu
865                 870                 875                 880

Ala Glu Leu Gln Glu Gly Asp Thr Ile Thr Cys Phe Ile Ser Thr Pro
                885                 890                 895

Gln Ser Glu Phe Thr Leu Pro Lys Asp Pro Glu Thr Pro Leu Ile Met
            900                 905                 910

Val Gly Pro Gly Thr Gly Val Ala Pro Phe Arg Gly Phe Val Gln Ala
        915                 920                 925

Arg Lys Gln Leu Lys Glu Gln Gly Gln Ser Leu Gly Glu Ala His Leu
    930                 935                 940

Tyr Phe Gly Cys Arg Ser Pro His Glu Asp Tyr Leu Tyr Gln Glu Glu
945                 950                 955                 960

Leu Glu Asn Ala Gln Ser Glu Gly Ile Ile Thr Leu His Thr Ala Phe
                965                 970                 975

Ser Arg Met Pro Asn Gln Pro Lys Thr Tyr Val Gln His Val Met Glu
            980                 985                 990

Gln Asp Gly Lys Lys Leu Ile Glu Leu Leu Asp Lys Gly Ala His Phe
        995                 1000                1005

Tyr Ile Cys Gly Asp Gly Ser Gln Met Ala Pro Ala Val Glu Ala
    1010                1015                1020
```

```
Thr Leu Met Lys Ser Tyr Ala Asp Val His Gln Val Ser Glu Ala
    1025                1030                1035

Asp Ala Arg Leu Trp Leu Gln Gln Leu Glu Glu Lys Gly Arg Tyr
    1040                1045                1050

Ala Lys Asp Val Trp
    1055

<210> SEQ ID NO 105
<211> LENGTH: 3177
<212> TYPE: DNA
<213> ORGANISM: Artificial Sequence
<220> FEATURE:
<223> OTHER INFORMATION: KO-BMR fusion construct

<400> SEQUENCE: 105
atgccaagag tgcctgaagt cccaggtgtt ccattgttag gaaatctgtt acaattgaag      60
gagaaaaagc catacatgac ttttacgaga tgggcagcga catatggacc tatctatagt    120
atcaaaactg gggctacaag tatggttgtg gtatcatcta atgagatagc caaggaggca    180
ttggtgacca gattccaatc catatctaca aggaacttat ctaaagccct gaaagtactt    240
acagcagata agacaatggt cgcaatgtca gattatgatg attatcataa acagttaag     300 agacacatac tgaccgccgt cttgggtcct aatgcacaga aaaagcatag aattcacaga    360
gatatcatga tggataacat atctactcaa cttcatgaat cgtgaaaaaa caacccagaa    420
caggaagagg tagaccttag aaaaatcttt caatctgagt tattcggctt agctatgaga    480
caagccttag gaaaggatgt tgaaagttg tacgttgaag acctgaaaat cactatgaat     540
agagacgaaa tctttcaagt ccttgttgtt gatccaatga tgggagcaat cgatgttgat    600
tggagagact tctttccata cctaaagtgg gtcccaaaca aaaagttcga aaatactatt    660
caacaaatgt acatcagaag agaagctgtt atgaaatctt aatcaaaga gcacaaaaag    720 agaatagcgt caggcgaaaa gctaaatagt tatatcgatt acctttatc tgaagctcaa     780 actttaaccg atcagcaact attgatgtcc ttgtgggaac caatcattga atcttcagat    840
acaacaatgg tcacaacaga atgggcaatg tacgaattag ctaaaaaccc taaattgcaa    900
gataggttgt acagagacat taagtccgtc tgtggatctg aaaagataac cgaagagcat    960
ctatcacagc tgccttacat tacagctatt ttccacgaaa cactgagaag acactcacca   1020
gttcctatca ttcctctaag acatgtacat gaagataccg ttctaggcgg ctaccatgtt   1080
cctgctggca cagaacttgc cgttaacatc tacggttgca acatggacaa aaacgttgg    1140 gaaaatccag aggaatggaa cccagaaaga ttcatgaaag agaatgagac aattgatttt   1200
caaaagacga tggccttcgg tggtggtaag agagtttgtg ctggttcctt gcaagccctt   1260
ttaactgcat ctattgggat tgggagaatg gttcaagagt tcgaatggaa actgaaggat   1320
atgactcaag aggaagtgaa cacgataggc ctaactacac aaatgttaag accattgaga   1380
gctattatca aacctaggat cccatcaaga ccaagtccta gtaccgaaca atctgcaaaa   1440
aaagttagaa aaaaagcaga aaatgcacac aatactccat tgctagttct ttatggttct   1500
aatatgggaa cagcggaagg aacggccagg atctagctg acatagctat gtccaaggga    1560
tttgccccgc aagtagcaac cctggattcc catgcaggta acttgccaag agaaggtgct   1620
gttctaatag ttaccgctag ctacaatggg caccctccag ataatgcgaa gcagttcgtc   1680
gattggttag atcaagcatc agcagatgaa gttaagggtg ttagatactc tgttttttgga   1740 tgtggagata agaattgggc caccacatat cagaaggttc cggctttcat cgatgaaatg   1800
```

```
cttgctgcaa aagggctga aaatatagca gatcgtggtg aggccgacgc aagcgacgat    1860
tttgagggta cctatgagga gtggagagag cacatgtggt ctgatgttgc cgcgtatttt    1920
aatctagaca tagaaaattc tgaagacaat aaaagtgcct tacttcttca attcgtcgat    1980
agtgctgcgg acatgccctt agcaaagatg catggagcct tttcaacgaa cgtagtagcc    2040
agtaaggaac ttcaacaacc aggtagtgcc agaagtacac gtcacttgga aattgaatta    2100
ccaaaagagg catcctacca agaaggtgac catcttggtg taatcccaag aaactacgaa    2160
ggtatagtca ataggtaac ggcaagattt gggctggatg caagccaaca gataagacta    2220
gaagcagaag aagaaaaatt ggcgcacctt ccactagcga agacagtatc cgttgaagaa    2280
ttattgcaat acgtggaatt gcaggatccc gtcactagaa cgcaattgag agctatggca    2340
gcaaagactg tttgtccacc tcacaaggtt gaacttgaag ctctacttga aaacaagca    2400 tacaaagagc aagtgctagc aaagagacta accatgttag aattgctgga aaatacccg    2460 gcatgcgaaa tggaattctc cgaatttatc gcgttgttgc caagtattcg tcccaggtat    2520
tactcaattt catcttcacc aagggttgac gagaaacagg catctattac cgtatctgtg    2580
gtctctggag aagcttggag tggttacgga gaatacaagg gtattgcttc caattatctt    2640
gcagaactgc aggaagggga tacaattacc tgctttattt ctactcctca atcagaattt    2700
actcttccga aggatccaga aactccgtta attatggtag gtccgggaac aggagtcgcc    2760
cctttcagag gctttgtgca agcaaggaag caactaaaag aacagggaca aagtctgggt    2820
gaggcacatc tatatttcgg ttgcagatct ccgcatgagg attacttata ccaagaagaa    2880
cttgaaaacg cccaatcaga aggtattatc accttgcata ctgcattcag tagaatgcca    2940
aaccagccga aaacttacgt acagcatgtt atggagcaag atggtaagaa gttaattgag    3000
cttttggata agggcgccca cttctacatt tgcggcgacg gatcccaaat ggcgcctgcc    3060
gttgaagcca ccttgatgaa atcatatgca gatgttcatc aagtttcaga agcggacgcc    3120
cgtctttggt tacaacaact agaggagaaa ggaaggtatg caaaagatgt tgcttaa       3177
```

<210> SEQ ID NO 106
<211> LENGTH: 1058
<212> TYPE: PRT
<213> ORGANISM: Artificial Sequence
<220> FEATURE:
<223> OTHER INFORMATION: KO-BMR fusion construct

<400> SEQUENCE: 106

```
Met Pro Arg Val Pro Glu Val Pro Gly Val Pro Leu Leu Gly Asn Leu
1               5                   10                  15

Leu Gln Leu Lys Glu Lys Lys Pro Tyr Met Thr Phe Thr Arg Trp Ala
            20                  25                  30

Ala Thr Tyr Gly Pro Ile Tyr Ser Ile Lys Thr Gly Ala Thr Ser Met
        35                  40                  45

Val Val Val Ser Ser Asn Glu Ile Ala Lys Glu Ala Leu Val Thr Arg
    50                  55                  60

Phe Gln Ser Ile Ser Thr Arg Asn Leu Ser Lys Ala Leu Lys Val Leu
65                  70                  75                  80

Thr Ala Asp Lys Thr Met Val Ala Met Ser Asp Tyr Asp Asp Tyr His
                85                  90                  95

Lys Thr Val Lys Arg His Ile Leu Thr Ala Val Leu Gly Pro Asn Ala
            100                 105                 110

Gln Lys Lys His Arg Ile His Arg Asp Ile Met Met Asp Asn Ile Ser
        115                 120                 125
```

```
Thr Gln Leu His Glu Phe Val Lys Asn Asn Pro Gln Glu Glu Val
    130                 135                 140

Asp Leu Arg Lys Ile Phe Gln Ser Glu Leu Phe Gly Leu Ala Met Arg
145                 150                 155                 160

Gln Ala Leu Gly Lys Asp Val Glu Ser Leu Tyr Val Glu Asp Leu Lys
                165                 170                 175

Ile Thr Met Asn Arg Asp Glu Ile Phe Gln Val Leu Val Asp Pro
                180                 185                 190

Met Met Gly Ala Ile Asp Val Asp Trp Arg Asp Phe Phe Pro Tyr Leu
            195                 200                 205

Lys Trp Val Pro Asn Lys Lys Phe Glu Asn Thr Ile Gln Gln Met Tyr
    210                 215                 220

Ile Arg Arg Glu Ala Val Met Lys Ser Leu Ile Lys Glu His Lys Lys
225                 230                 235                 240

Arg Ile Ala Ser Gly Glu Lys Leu Asn Ser Tyr Ile Asp Tyr Leu Leu
                245                 250                 255

Ser Glu Ala Gln Thr Leu Thr Asp Gln Gln Leu Leu Met Ser Leu Trp
            260                 265                 270

Glu Pro Ile Ile Glu Ser Ser Asp Thr Thr Met Val Thr Thr Glu Trp
    275                 280                 285

Ala Met Tyr Glu Leu Ala Lys Asn Pro Lys Leu Gln Asp Arg Leu Tyr
    290                 295                 300

Arg Asp Ile Lys Ser Val Cys Gly Ser Glu Lys Ile Thr Glu Glu His
305                 310                 315                 320

Leu Ser Gln Leu Pro Tyr Ile Thr Ala Ile Phe His Glu Thr Leu Arg
                325                 330                 335

Arg His Ser Pro Val Pro Ile Ile Pro Leu Arg His Val His Glu Asp
            340                 345                 350

Thr Val Leu Gly Gly Tyr His Val Pro Ala Gly Thr Glu Leu Ala Val
    355                 360                 365

Asn Ile Tyr Gly Cys Asn Met Asp Lys Asn Val Trp Glu Asn Pro Glu
    370                 375                 380

Glu Trp Asn Pro Glu Arg Phe Met Lys Glu Asn Glu Thr Ile Asp Phe
385                 390                 395                 400

Gln Lys Thr Met Ala Phe Gly Gly Gly Lys Arg Val Cys Ala Gly Ser
                405                 410                 415

Leu Gln Ala Leu Leu Thr Ala Ser Ile Gly Ile Gly Arg Met Val Gln
            420                 425                 430

Glu Phe Glu Trp Lys Leu Lys Asp Met Thr Gln Glu Glu Val Asn Thr
    435                 440                 445

Ile Gly Leu Thr Thr Gln Met Leu Arg Pro Leu Arg Ala Ile Ile Lys
    450                 455                 460

Pro Arg Ile Pro Ser Arg Pro Ser Pro Ser Thr Glu Gln Ser Ala Lys
465                 470                 475                 480

Lys Val Arg Lys Lys Ala Glu Asn Ala His Asn Thr Pro Leu Leu Val
                485                 490                 495

Leu Tyr Gly Ser Asn Met Gly Thr Ala Glu Gly Thr Ala Arg Asp Leu
            500                 505                 510

Ala Asp Ile Ala Met Ser Lys Gly Phe Ala Pro Gln Val Ala Thr Leu
    515                 520                 525

Asp Ser His Ala Gly Asn Leu Pro Arg Glu Gly Ala Val Leu Ile Val
530                 535                 540
```

-continued

```
Thr Ala Ser Tyr Asn Gly His Pro Asp Asn Ala Lys Gln Phe Val
545                 550                 555                 560

Asp Trp Leu Asp Gln Ala Ser Ala Asp Glu Val Lys Gly Val Arg Tyr
            565                 570                 575

Ser Val Phe Gly Cys Gly Asp Lys Asn Trp Ala Thr Thr Tyr Gln Lys
                580                 585                 590

Val Pro Ala Phe Ile Asp Glu Met Leu Ala Ala Lys Gly Ala Glu Asn
            595                 600                 605

Ile Ala Asp Arg Gly Glu Ala Asp Ser Asp Phe Glu Gly Thr
610                 615                 620

Tyr Glu Glu Trp Arg Glu His Met Trp Ser Asp Val Ala Ala Tyr Phe
625                 630                 635                 640

Asn Leu Asp Ile Glu Asn Ser Glu Asp Asn Lys Ser Ala Leu Leu Leu
            645                 650                 655

Gln Phe Val Asp Ser Ala Ala Asp Met Pro Leu Ala Lys Met His Gly
                660                 665                 670

Ala Phe Ser Thr Asn Val Val Ala Ser Lys Glu Leu Gln Gln Pro Gly
            675                 680                 685

Ser Ala Arg Ser Thr Arg His Leu Glu Ile Glu Leu Pro Lys Glu Ala
690                 695                 700

Ser Tyr Gln Glu Gly Asp His Leu Gly Val Ile Pro Arg Asn Tyr Glu
705                 710                 715                 720

Gly Ile Val Asn Arg Val Thr Ala Arg Phe Gly Leu Asp Ala Ser Gln
            725                 730                 735

Gln Ile Arg Leu Glu Ala Glu Glu Lys Leu Ala His Leu Pro Leu
                740                 745                 750

Ala Lys Thr Val Ser Val Glu Glu Leu Leu Gln Tyr Val Glu Leu Gln
            755                 760                 765

Asp Pro Val Thr Arg Thr Gln Leu Arg Ala Met Ala Ala Lys Thr Val
770                 775                 780

Cys Pro Pro His Lys Val Glu Leu Glu Ala Leu Leu Glu Lys Gln Ala
785                 790                 795                 800

Tyr Lys Glu Gln Val Leu Ala Lys Arg Leu Thr Met Leu Glu Leu Leu
            805                 810                 815

Glu Lys Tyr Pro Ala Cys Glu Met Glu Phe Ser Glu Phe Ile Ala Leu
                820                 825                 830

Leu Pro Ser Ile Arg Pro Arg Tyr Ser Ile Ser Ser Pro Arg
            835                 840                 845

Val Asp Glu Lys Gln Ala Ser Ile Thr Val Ser Val Val Ser Gly Glu
850                 855                 860

Ala Trp Ser Gly Tyr Gly Glu Tyr Lys Gly Ile Ala Ser Asn Tyr Leu
865                 870                 875                 880

Ala Glu Leu Gln Glu Gly Asp Thr Ile Thr Cys Phe Ile Ser Thr Pro
            885                 890                 895

Gln Ser Glu Phe Thr Leu Pro Lys Asp Pro Glu Thr Pro Leu Ile Met
                900                 905                 910

Val Gly Pro Gly Thr Gly Val Ala Pro Phe Arg Gly Phe Val Gln Ala
            915                 920                 925

Arg Lys Gln Leu Lys Glu Gln Gly Gln Ser Leu Gly Glu Ala His Leu
930                 935                 940

Tyr Phe Gly Cys Arg Ser Pro His Glu Asp Tyr Leu Tyr Gln Glu Glu
945                 950                 955                 960

Leu Glu Asn Ala Gln Ser Glu Gly Ile Ile Thr Leu His Thr Ala Phe
```

```
                965                 970                 975
Ser Arg Met Pro Asn Gln Pro Lys Thr Tyr Val Gln His Val Met Glu
                    980                 985                 990
Gln Asp Gly Lys Lys Leu Ile Glu Leu Leu Asp Lys Gly Ala His Phe
                    995                1000                1005
Tyr Ile Cys Gly Asp Gly Ser Gln Met Ala Pro Ala Val Glu Ala
    1010                1015                1020
Thr Leu Met Lys Ser Tyr Ala Asp Val His Gln Val Ser Glu Ala
    1025                1030                1035
Asp Ala Arg Leu Trp Leu Gln Gln Leu Glu Glu Lys Gly Arg Tyr
    1040                1045                1050
Ala Lys Asp Val Ala
    1055

<210> SEQ ID NO 107
<211> LENGTH: 3309
<212> TYPE: DNA
<213> ORGANISM: Artificial Sequence
<220> FEATURE:
<223> OTHER INFORMATION: KO-BMR fusion construct

<400> SEQUENCE: 107
```

| | | |
|---|---|---|
| atggctacct tgttggaaca ttttcaagct atgccattcg ctattccaat tgctttggct | 60 |
| gctttgtctt ggttgttttt gttctacatc aaggtttctt tcttctccaa caaatccgct | 120 |
| caagctaaat tgccaccagt tccagttgtt ccaggtttgc cagttattgg taatttgttg | 180 |
| caattgaaag aaaagaagcc ataccaaacc ttcactagat gggctgaaga atatggtcca | 240 |
| atctactcta ttagaactgg tgcttctact atggttgtct tgaacactac tcaagttgcc | 300 |
| aaagaagcta tggttaccag atacttgtct atctctacca gaaagttgtc caacgccttg | 360 |
| aaaattttga ccgctgataa gtgcatggtt gccatttctg attacaacga tttccacaag | 420 |
| atgatcaaga gatatatctt gtctaacgtt ttgggtccat ctgcccaaaa agacatagaa | 480 |
| tctaacagag ataccttgag agccaacgtt tgttctagat tgcattccca gttaagaac | 540 |
| tctccaagag aagctgtcaa ctttagaaga gttttcgaat gggaattatt cggtatcgct | 600 |
| ttgaaacaag ccttcggtaa ggatattgaa agccaatct acgtcgaaga attgggtact | 660 |
| actttgtcca gagatgaaat cttcaaggtt ttggtcttgg acattatgga aggtgccatt | 720 |
| gaagttgatt ggagagattt tttcccatac ttgcgttgga ttccaaacac cagaatggaa | 780 |
| actaagatcc aaagattata ctttagaaga aaggccgtta tgaccgcctt gattaacgaa | 840 |
| caaaagaaaa gaattgcctc cggtgaagaa atcaactgct acatcgattt cttgttgaaa | 900 |
| gaaggtaaga ccttgaccat ggaccaaatc tctatgttgt tgtgggaaac cgttattgaa | 960 |
| actgctgata ccacaatggt tactactgaa tgggctatgt acgaagttgc taaggattct | 1020 |
| aaaagacaag acagattata ccaagaaatc caaaaggtct gcggttctga atggttaca | 1080 |
| gaagaatact tgtcccaatt gccatacttg aatgctgttt ccacgaaac tttgagaaaa | 1140 |
| cattctccag ctgctttggt tccattgaga tatgctcatg aagatactca attgggtggt | 1200 |
| tattacattc cagccggtac tgaaattgcc attaacatct acggttgcaa catggacaaa | 1260 |
| caccaatggg aatctccaga agaatggaag ccagaaagat ttttggatcc taagtttgac | 1320 |
| ccaatggact gtacaaaac tatgctttt ggtgctggta aaagagttg cgctggttct | 1380 |
| ttacaagcta tgttgattgc ttgtccaacc atcggtagat ggttcaaga atttgaatgg | 1440 |
| aagttgagag atggtgaaga agaaaacgtt gatactgttg gtttgaccac ccataagaga | 1500 |

```
tatccaatgc atgctatttt gaagccaaga tctccatcaa gaccaagtcc tagtaccgaa    1560
caatctgcaa aaaagttag aaaaaaagca gaaaatgcac acaatactcc attgctagtt    1620
ctttatggtt ctaatatggg aacagcggaa ggaacggcca gggatctagc tgacatagct    1680
atgtccaagg gatttgcccc gcaagtagca accctggatt cccatgcagg taacttgcca    1740
agagaaggtg ctgttctaat agttaccgct agctacaatg gcaccctcc agataatgcg    1800 aagcagttcg tcgattggtt agatcaagca tcagcagatt aagttaaggg tgttagatac    1860 tctgttttg gatgtggaga taagaattgg gccaccacat atcagaaggt tccggctttc    1920
atcgatgaaa tgcttgctgc aaaagggct gaaaatatag cagatcgtgg tgaggccgac    1980
gcaagcgacg attttgaggg tacctatgag gagtggagag agcacatgtg gtctgatgtt    2040
gccgcgtatt ttaatctaga catagaaaat tctgaagaca ataaaagtgc cttacttctt    2100
caattcgtcg atagtgctgc ggacatgccc ttagcaaaga tgcatggagc cttttcaacg    2160
aacgtagtag ccagtaagga acttcaacaa ccaggtagtg ccagaagtac acgtcacttg    2220
gaaattgaat taccaaaaga ggcatcctac caagaaggtg accatcttgg tgtaatccca    2280
agaaactacg aaggtatagt caataggtta acggcaagat ttgggctgga tgcaagccaa    2340
cagataagac tagaagcaga agaagaaaaa ttggcgcacc ttccactagc gaagacagta    2400
tccgttgaag aattattgca atacgtggaa ttgcaggatc ccgtcactag aacgcaattg    2460
agagctatgg cagcaaagac tgtttgtcca cctcacaagg ttgaacttga agctctactt    2520
gaaaaacaag catacaaaga gcaagtgcta gcaaagagac taaccatgtt agaattgctg    2580
gaaaaatacc cggcatgcga aatggaattc tccgaattta tcgcgttgtt gccaagtatt    2640
cgtcccaggt attactcaat ttcatcttca ccaagggttg acgagaaaca ggcatctatt    2700
accgtatctg tggtctctgg agaagcttgg agtggttacg gagaatacaa gggtattgct    2760
tccaattatc ttgcagaact gcaggaaggg gatacaatta cctgctttat ttctactcct    2820
caatcagaat ttactcttcc gaaggatcca gaaactccgt taattatggt aggtccggga    2880
acaggagtcg cccctttcag aggctttgtg caagcaagga agcaactaaa agaacaggga    2940
caaagtctgg gtgaggcaca tctatatttc ggttgcagat ctccgcatga ggattactta    3000
taccaagaag aacttgaaaa cgcccaatca gaaggtatta tcaccttgca tactgcattc    3060
agtagaatgc caaccagcc gaaaacttac gtacagcatg ttatggagca agatggtaag    3120
aagttaattg agcttttgga taaggcgcc cacttctaca tttgcggcga cggatcccaa    3180
atggcgcctg ccgttgaagc caccttgatg aaatcatatg cagatgttca tcaagtttca    3240
gaagcggacg cccgtctttg gttacaacaa ctagaggaga aaggaaggta tgcaaaagat    3300
gtttggtaa                                                          3309
```

<210> SEQ ID NO 108
<211> LENGTH: 1102
<212> TYPE: PRT
<213> ORGANISM: Artificial Sequence
<220> FEATURE:
<223> OTHER INFORMATION: KO-BMR fusion construct

<400> SEQUENCE: 108

Met Ala Thr Leu Leu Glu His Phe Gln Ala Met Pro Phe Ala Ile Pro
1               5                   10                  15

Ile Ala Leu Ala Ala Leu Ser Trp Leu Phe Leu Phe Tyr Ile Lys Val
            20                  25                  30

-continued

Ser Phe Phe Ser Asn Lys Ser Ala Gln Ala Lys Leu Pro Val Pro
                35                  40                  45

Val Val Pro Gly Leu Pro Val Ile Gly Asn Leu Leu Gln Leu Lys Glu
 50                  55                  60

Lys Lys Pro Tyr Gln Thr Phe Thr Arg Trp Ala Glu Glu Tyr Gly Pro
 65                  70                  75                  80

Ile Tyr Ser Ile Arg Thr Gly Ala Ser Thr Met Val Val Leu Asn Thr
                 85                  90                  95

Thr Gln Val Ala Lys Glu Ala Met Val Thr Arg Tyr Leu Ser Ile Ser
                100                 105                 110

Thr Arg Lys Leu Ser Asn Ala Leu Lys Ile Leu Thr Ala Asp Lys Cys
            115                 120                 125

Met Val Ala Ile Ser Asp Tyr Asn Asp Phe His Lys Met Ile Lys Arg
        130                 135                 140

Tyr Ile Leu Ser Asn Val Leu Gly Pro Ser Ala Gln Lys Arg His Arg
145                 150                 155                 160

Ser Asn Arg Asp Thr Leu Arg Ala Asn Val Cys Ser Arg Leu His Ser
                165                 170                 175

Gln Val Lys Asn Ser Pro Arg Glu Ala Val Asn Phe Arg Arg Val Phe
            180                 185                 190

Glu Trp Glu Leu Phe Gly Ile Ala Leu Lys Gln Ala Phe Gly Lys Asp
        195                 200                 205

Ile Glu Lys Pro Ile Tyr Val Glu Leu Gly Thr Thr Leu Ser Arg
210                 215                 220

Asp Glu Ile Phe Lys Val Leu Val Leu Asp Ile Met Glu Gly Ala Ile
225                 230                 235                 240

Glu Val Asp Trp Arg Asp Phe Phe Pro Tyr Leu Arg Trp Ile Pro Asn
                245                 250                 255

Thr Arg Met Glu Thr Lys Ile Gln Arg Leu Tyr Phe Arg Arg Lys Ala
            260                 265                 270

Val Met Thr Ala Leu Ile Asn Glu Gln Lys Lys Arg Ile Ala Ser Gly
        275                 280                 285

Glu Glu Ile Asn Cys Tyr Ile Asp Phe Leu Leu Lys Glu Gly Lys Thr
    290                 295                 300

Leu Thr Met Asp Gln Ile Ser Met Leu Leu Trp Glu Thr Val Ile Glu
305                 310                 315                 320

Thr Ala Asp Thr Thr Met Val Thr Thr Glu Trp Ala Met Tyr Glu Val
                325                 330                 335

Ala Lys Asp Ser Lys Arg Gln Asp Arg Leu Tyr Gln Glu Ile Gln Lys
            340                 345                 350

Val Cys Gly Ser Glu Met Val Thr Glu Glu Tyr Leu Ser Gln Leu Pro
        355                 360                 365

Tyr Leu Asn Ala Val Phe His Glu Thr Leu Arg Lys His Ser Pro Ala
370                 375                 380

Ala Leu Val Pro Leu Arg Tyr Ala His Glu Asp Thr Gln Leu Gly Gly
385                 390                 395                 400

Tyr Tyr Ile Pro Ala Gly Thr Glu Ile Ala Ile Asn Ile Tyr Gly Cys
                405                 410                 415

Asn Met Asp Lys His Gln Trp Glu Ser Pro Glu Glu Trp Lys Pro Glu
            420                 425                 430

Arg Phe Leu Asp Pro Lys Phe Asp Pro Met Asp Leu Tyr Lys Thr Met
        435                 440                 445

Ala Phe Gly Ala Gly Lys Arg Val Cys Ala Gly Ser Leu Gln Ala Met

```
                450                 455                 460
Leu Ile Ala Cys Pro Thr Ile Gly Arg Leu Val Gln Glu Phe Glu Trp
465                 470                 475                 480

Lys Leu Arg Asp Gly Glu Glu Asn Val Asp Thr Val Gly Leu Thr
                485                 490                 495

Thr His Lys Arg Tyr Pro Met His Ala Ile Leu Lys Pro Arg Ser Pro
                500                 505                 510

Ser Arg Pro Ser Pro Ser Thr Glu Gln Ser Ala Lys Lys Val Arg Lys
                515                 520                 525

Lys Ala Glu Asn Ala His Asn Thr Pro Leu Leu Val Leu Tyr Gly Ser
                530                 535                 540

Asn Met Gly Thr Ala Glu Gly Thr Ala Arg Asp Leu Ala Asp Ile Ala
545                 550                 555                 560

Met Ser Lys Gly Phe Ala Pro Gln Val Ala Thr Leu Asp Ser His Ala
                565                 570                 575

Gly Asn Leu Pro Arg Glu Gly Ala Val Leu Ile Val Thr Ala Ser Tyr
                580                 585                 590

Asn Gly His Pro Pro Asp Asn Ala Lys Gln Phe Val Asp Trp Leu Asp
                595                 600                 605

Gln Ala Ser Ala Asp Glu Val Lys Gly Val Arg Tyr Ser Val Phe Gly
                610                 615                 620

Cys Gly Asp Lys Asn Trp Ala Thr Thr Tyr Gln Lys Val Pro Ala Phe
625                 630                 635                 640

Ile Asp Glu Met Leu Ala Ala Lys Gly Ala Glu Asn Ile Ala Asp Arg
                645                 650                 655

Gly Glu Ala Asp Ala Ser Asp Asp Phe Glu Gly Thr Tyr Glu Glu Trp
                660                 665                 670

Arg Glu His Met Trp Ser Asp Val Ala Ala Tyr Phe Asn Leu Asp Ile
                675                 680                 685

Glu Asn Ser Glu Asp Asn Lys Ser Ala Leu Leu Leu Gln Phe Val Asp
                690                 695                 700

Ser Ala Ala Asp Met Pro Leu Ala Lys Met His Gly Ala Phe Ser Thr
705                 710                 715                 720

Asn Val Val Ala Ser Lys Glu Leu Gln Gln Pro Gly Ser Ala Arg Ser
                725                 730                 735

Thr Arg His Leu Glu Ile Glu Leu Pro Lys Glu Ala Ser Tyr Gln Glu
                740                 745                 750

Gly Asp His Leu Gly Val Ile Pro Arg Asn Tyr Glu Gly Ile Val Asn
                755                 760                 765

Arg Val Thr Ala Arg Phe Gly Leu Asp Ala Ser Gln Gln Ile Arg Leu
                770                 775                 780

Glu Ala Glu Glu Glu Lys Leu Ala His Leu Pro Leu Ala Lys Thr Val
785                 790                 795                 800

Ser Val Glu Glu Leu Leu Gln Tyr Val Glu Leu Gln Asp Pro Val Thr
                805                 810                 815

Arg Thr Gln Leu Arg Ala Met Ala Ala Lys Thr Val Cys Pro Pro His
                820                 825                 830

Lys Val Glu Leu Glu Ala Leu Leu Glu Lys Gln Ala Tyr Lys Glu Gln
                835                 840                 845

Val Leu Ala Lys Arg Leu Thr Met Leu Glu Leu Leu Glu Lys Tyr Pro
                850                 855                 860

Ala Cys Glu Met Glu Phe Ser Glu Phe Ile Ala Leu Leu Pro Ser Ile
865                 870                 875                 880
```

Arg Pro Arg Tyr Tyr Ser Ile Ser Ser Pro Arg Val Asp Glu Lys
            885                 890                 895

Gln Ala Ser Ile Thr Val Ser Val Val Ser Gly Glu Ala Trp Ser Gly
            900                 905                 910

Tyr Gly Glu Tyr Lys Gly Ile Ala Ser Asn Tyr Leu Ala Glu Leu Gln
            915                 920                 925

Glu Gly Asp Thr Ile Thr Cys Phe Ile Ser Thr Pro Gln Ser Glu Phe
    930                 935                 940

Thr Leu Pro Lys Asp Pro Glu Thr Pro Leu Ile Met Val Gly Pro Gly
945                 950                 955                 960

Thr Gly Val Ala Pro Phe Arg Gly Phe Val Gln Ala Arg Lys Gln Leu
            965                 970                 975

Lys Glu Gln Gly Gln Ser Leu Gly Glu Ala His Leu Tyr Phe Gly Cys
            980                 985                 990

Arg Ser Pro His Glu Asp Tyr Leu Tyr Gln Glu Glu Leu Glu Asn Ala
            995                1000                1005

Gln Ser Glu Gly Ile Ile Thr Leu His Thr Ala Phe Ser Arg Met
    1010                1015                1020

Pro Asn Gln Pro Lys Thr Tyr Val Gln His Val Met Glu Gln Asp
    1025                1030                1035

Gly Lys Lys Leu Ile Glu Leu Leu Asp Lys Gly Ala His Phe Tyr
    1040                1045                1050

Ile Cys Gly Asp Gly Ser Gln Met Ala Pro Ala Val Glu Ala Thr
    1055                1060                1065

Leu Met Lys Ser Tyr Ala Asp Val His Gln Val Ser Glu Ala Asp
    1070                1075                1080

Ala Arg Leu Trp Leu Gln Gln Leu Glu Glu Lys Gly Arg Tyr Ala
    1085                1090                1095

Lys Asp Val Trp
    1100

<210> SEQ ID NO 109
<211> LENGTH: 3309
<212> TYPE: DNA
<213> ORGANISM: Artificial Sequence
<220> FEATURE:
<223> OTHER INFORMATION: KO-BMR fusion construct

<400> SEQUENCE: 109
atggctacct tgttggaaca ttttcaagct atgccattcg ctattccaat tgctttggct      60
gctttgtctt ggttgttttt gttctacatc aaggtttctt tcttctccaa caaatccgct     120
caagctaaat tgccaccagt tccagttgtt ccaggtttgc cagttattgg taatttgttg     180
caattgaaag aaaagaagcc ataccaaacc ttcactagat gggctgaaga atatggtcca     240
atctactcta ttagaactgg tgcttctact atggttgtct tgaacactac tcaagttgcc     300
aaagaagcta tggttaccag atacttgtct atctctacca gaaagttgtc caacgccttg     360
aaaattttga ccgctgataa gtgcatggtt gccatttctg attacaacga tttccacaag     420
atgatcaaga gatatatctt gtctaacgtt tgggtccat ctgcccaaaa agacataga      480 tctaacagag ataccttgag agccaacgtt tgttctagat gcattcccca gttaagaac      540 tctccaagag aagctgtcaa ctttagaaga gttttcgaat gggaattatt cggtatcgct     600
ttgaaacaag ccttcggtaa ggatattgaa aagccaatct acgtcgaaga attgggtact     660
actttgtcca gagatgaaat cttcaaggtt ttggtcttgg acattatgga aggtgccatt     720

```
gaagttgatt ggagagattt tttcccatac ttgcgttgga ttccaaacac cagaatggaa      780
actaagatcc aaagattata ctttagaaga aaggccgtta tgaccgcctt gattaacgaa      840
caaaagaaaa gaattgcctc cggtgaagaa atcaactgct acatcgattt cttgttgaaa      900
gaaggtaaga ccttgaccat ggaccaaatc tctatgttgt tgtgggaaac cgttattgaa      960
actgctgata ccacaatggt tactactgaa tgggctatgt acgaagttgc taaggattct     1020
aaaagacaag acagattata ccaagaaatc caaaaggtct gcggttctga aatggttaca     1080
gaagaatact tgtcccaatt gccatacttg aatgctgttt ccacgaaac tttgagaaaa      1140 cattctccag ctgctttggt tccattgaga tatgctcatg aagatactca attgggtggt     1200
tattacattc cagccggtac tgaaattgcc attaacatct acggttgcaa catggacaaa     1260
caccaatggg aatctccaga gaatggaag ccagaaagat ttttggatcc taagtttgac      1320
ccaatggact tgtacaaaac tatggctttt ggtgctggta aaagagtttg cgctggttct     1380
ttacaagcta tgttgattgc ttgtccaacc atcggtagat tggttcaaga atttgaatgg     1440
aagttgagag atggtgaaga agaaaacgtt gatactgttg gtttgaccac ccataagaga     1500
tatccaatgc atgctatttt gaagccaaga tctccatcaa gaccaagtcc tagtaccgaa     1560
caatctgcaa aaaagttag aaaaaaagca gaaaatgcac acaatactcc attgctagtt      1620
ctttatggtt ctaatatggg aacagcggaa ggaacggcca gggatctagc tgacatagct     1680
atgtccaagg gatttgcccc gcaagtagca accctggatt cccatgcagg taacttgcca     1740
agagaaggtg ctgttctaat agttaccgct agctacaatg gcaccctcc agataatgcg      1800 aagcagttcg tcgattggtt agatcaagca tcagcagatg aagttaaggg tgttagatac     1860 tctgttttg gatgtggaga taagaattgg ccaccacat atcagaaggt tccggctttc       1920
atcgatgaaa tgcttgctgc aaaaggggct gaaaatatag cagatcgtgg tgaggccgac     1980
gcaagcgacg atttttgaggg tacctatgag gagtggagag agcacatgtg gtctgatgtt     2040
gccgcgtatt ttaatctaga catagaaaat tctgaagaca ataaaagtgc cttacttctt     2100
caattcgtcg atagtgctgc ggacatgccc ttagcaaaga tgcatggagc cttttcaacg     2160
aacgtagtag ccagtaagga acttcaacaa ccaggtagtg ccagaagtac acgtcacttg     2220
gaaattgaat taccaaaaga ggcatcctac caagaaggtg accatcttgg tgtaatccca     2280
agaaactacg aaggtatagt caatagggta acggcaagat ttgggctgga tgcaagccaa     2340
cagataagac tagaagcaga agaagaaaaa ttggcgcacc ttccactagc gaagacagta     2400
tccgttgaag aattattgca atacgtggaa ttgcaggatc ccgtcactag aacgcaattg     2460
agagctatgg cagcaaagac tgtttgtcca cctcacaagg ttgaacttga agctctactt     2520
gaaaaacaag catacaaaga gcaagtgcta gcaaagagac taaccatgtt agaattgctg     2580
gaaaaatacc cggcatgcga aatggaattc tccgaattta tcgcgttgtt gccaagtatt     2640
cgtcccaggt attactcaat ttcatcttca ccaaggggttg acgagaaaca ggcatctatt     2700
accgtatctg tggtctctgg agaagcttgg agtggttacg gagaatacaa gggtattgct     2760
tccaattatc ttgcagaact gcaggaaggg gatacaatta cctgctttat ttctactcct     2820
caatcagaat ttactcttcc gaaggatcca gaaactccgt taattatggt aggtccggga     2880
acaggagtcg cccctttcag aggctttgtg caagcaagga agcaactaaa agaacaggga     2940
caaagtctgg gtgaggcaca tctatatttc ggttgcagat ctccgcatga ggattactta     3000
taccaagaag aacttgaaaa cgcccaatca gaaggtatta tcaccttgca tactgcattc     3060
```

-continued

```
agtagaatgc caaaccagcc gaaaacttac gtacagcatg ttatggagca agatggtaag    3120
aagttaattg agcttttgga taagggcgcc cacttctaca tttgcggcga cggatcccaa    3180
atggcgcctg ccgttgaagc caccttgatg aaatcatatg cagatgttca tcaagtttca    3240
gaagcggacg cccgtctttg gttacaacaa ctagaggaga aaggaaggta tgcaaaagat    3300
gttgcttaa                                                            3309
```

<210> SEQ ID NO 110
<211> LENGTH: 1102
<212> TYPE: PRT
<213> ORGANISM: Artificial Sequence
<220> FEATURE:
<223> OTHER INFORMATION: KO-BMR fusion construct

<400> SEQUENCE: 110

```
Met Ala Thr Leu Leu Glu His Phe Gln Ala Met Pro Phe Ala Ile Pro
1               5                   10                  15

Ile Ala Leu Ala Ala Leu Ser Trp Leu Phe Leu Phe Tyr Ile Lys Val
            20                  25                  30

Ser Phe Phe Ser Asn Lys Ser Ala Gln Ala Lys Leu Pro Pro Val Pro
        35                  40                  45

Val Val Pro Gly Leu Pro Val Ile Gly Asn Leu Leu Gln Leu Lys Glu
    50                  55                  60

Lys Lys Pro Tyr Gln Thr Phe Thr Arg Trp Ala Glu Glu Tyr Gly Pro
65                  70                  75                  80

Ile Tyr Ser Ile Arg Thr Gly Ala Ser Thr Met Val Val Leu Asn Thr
                85                  90                  95

Thr Gln Val Ala Lys Glu Ala Met Val Thr Arg Tyr Leu Ser Ile Ser
            100                 105                 110

Thr Arg Lys Leu Ser Asn Ala Leu Lys Ile Leu Thr Ala Asp Lys Cys
        115                 120                 125

Met Val Ala Ile Ser Asp Tyr Asn Asp Phe His Lys Met Ile Lys Arg
    130                 135                 140

Tyr Ile Leu Ser Asn Val Leu Gly Pro Ser Ala Gln Lys Arg His Arg
145                 150                 155                 160

Ser Asn Arg Asp Thr Leu Arg Ala Asn Val Cys Ser Arg Leu His Ser
                165                 170                 175

Gln Val Lys Asn Ser Pro Arg Glu Ala Val Asn Phe Arg Arg Val Phe
            180                 185                 190

Glu Trp Glu Leu Phe Gly Ile Ala Leu Lys Gln Ala Phe Gly Lys Asp
        195                 200                 205

Ile Glu Lys Pro Ile Tyr Val Glu Glu Leu Gly Thr Thr Leu Ser Arg
    210                 215                 220

Asp Glu Ile Phe Lys Val Leu Val Leu Asp Ile Met Glu Gly Ala Ile
225                 230                 235                 240

Glu Val Asp Trp Arg Asp Phe Phe Pro Tyr Leu Arg Trp Ile Pro Asn
                245                 250                 255

Thr Arg Met Glu Thr Lys Ile Gln Arg Leu Tyr Phe Arg Arg Lys Ala
            260                 265                 270

Val Met Thr Ala Leu Ile Asn Glu Gln Lys Lys Arg Ile Ala Ser Gly
        275                 280                 285

Glu Glu Ile Asn Cys Tyr Ile Asp Phe Leu Leu Lys Glu Gly Lys Thr
    290                 295                 300

Leu Thr Met Asp Gln Ile Ser Met Leu Leu Trp Glu Thr Val Ile Glu
305                 310                 315                 320
```

```
Thr Ala Asp Thr Thr Met Val Thr Thr Glu Trp Ala Met Tyr Glu Val
                    325                 330                 335

Ala Lys Asp Ser Lys Arg Gln Asp Arg Leu Tyr Gln Glu Ile Gln Lys
                340                 345                 350

Val Cys Gly Ser Glu Met Val Thr Glu Glu Tyr Leu Ser Gln Leu Pro
                355                 360                 365

Tyr Leu Asn Ala Val Phe His Glu Thr Leu Arg Lys His Ser Pro Ala
            370                 375                 380

Ala Leu Val Pro Leu Arg Tyr Ala His Glu Asp Thr Gln Leu Gly Gly
385                 390                 395                 400

Tyr Tyr Ile Pro Ala Gly Thr Glu Ile Ala Ile Asn Ile Tyr Gly Cys
                405                 410                 415

Asn Met Asp Lys His Gln Trp Glu Ser Pro Glu Glu Trp Lys Pro Glu
                420                 425                 430

Arg Phe Leu Asp Pro Lys Phe Asp Pro Met Asp Leu Tyr Lys Thr Met
            435                 440                 445

Ala Phe Gly Ala Gly Lys Arg Val Cys Ala Gly Ser Leu Gln Ala Met
450                 455                 460

Leu Ile Ala Cys Pro Thr Ile Gly Arg Leu Val Gln Glu Phe Glu Trp
465                 470                 475                 480

Lys Leu Arg Asp Gly Glu Glu Glu Asn Val Asp Thr Val Gly Leu Thr
                485                 490                 495

Thr His Lys Arg Tyr Pro Met His Ala Ile Leu Lys Pro Arg Ser Pro
                500                 505                 510

Ser Arg Pro Ser Pro Ser Thr Glu Gln Ser Ala Lys Lys Val Arg Lys
            515                 520                 525

Lys Ala Glu Asn Ala His Asn Thr Pro Leu Leu Val Leu Tyr Gly Ser
530                 535                 540

Asn Met Gly Thr Ala Glu Gly Thr Ala Arg Asp Leu Ala Asp Ile Ala
545                 550                 555                 560

Met Ser Lys Gly Phe Ala Pro Gln Val Ala Thr Leu Asp Ser His Ala
                565                 570                 575

Gly Asn Leu Pro Arg Glu Gly Ala Val Leu Ile Val Thr Ala Ser Tyr
                580                 585                 590

Asn Gly His Pro Pro Asp Asn Ala Lys Gln Phe Val Asp Trp Leu Asp
            595                 600                 605

Gln Ala Ser Ala Asp Glu Val Lys Gly Val Arg Tyr Ser Val Phe Gly
610                 615                 620

Cys Gly Asp Lys Asn Trp Ala Thr Thr Tyr Gln Lys Val Pro Ala Phe
625                 630                 635                 640

Ile Asp Glu Met Leu Ala Ala Lys Gly Ala Glu Asn Ile Ala Asp Arg
                645                 650                 655

Gly Glu Ala Asp Ala Ser Asp Asp Phe Glu Gly Thr Tyr Glu Glu Trp
                660                 665                 670

Arg Glu His Met Trp Ser Asp Val Ala Ala Tyr Phe Asn Leu Asp Ile
            675                 680                 685

Glu Asn Ser Glu Asp Asn Lys Ser Ala Leu Leu Gln Phe Val Asp
690                 695                 700

Ser Ala Ala Asp Met Pro Leu Ala Lys Met His Gly Ala Phe Ser Thr
705                 710                 715                 720

Asn Val Val Ala Ser Lys Glu Leu Gln Gln Pro Gly Ser Ala Arg Ser
                725                 730                 735
```

Thr Arg His Leu Glu Ile Glu Leu Pro Lys Glu Ala Ser Tyr Gln Glu
            740                 745                 750

Gly Asp His Leu Gly Val Ile Pro Arg Asn Tyr Glu Gly Ile Val Asn
        755                 760                 765

Arg Val Thr Ala Arg Phe Gly Leu Asp Ala Ser Gln Gln Ile Arg Leu
    770                 775                 780

Glu Ala Glu Glu Lys Leu Ala His Leu Pro Leu Ala Lys Thr Val
785                 790                 795                 800

Ser Val Glu Glu Leu Leu Gln Tyr Val Glu Leu Gln Asp Pro Val Thr
                805                 810                 815

Arg Thr Gln Leu Arg Ala Met Ala Ala Lys Thr Val Cys Pro Pro His
            820                 825                 830

Lys Val Glu Leu Glu Ala Leu Leu Glu Lys Gln Ala Tyr Lys Glu Gln
        835                 840                 845

Val Leu Ala Lys Arg Leu Thr Met Leu Glu Leu Leu Glu Lys Tyr Pro
    850                 855                 860

Ala Cys Glu Met Glu Phe Ser Glu Phe Ile Ala Leu Leu Pro Ser Ile
865                 870                 875                 880

Arg Pro Arg Tyr Tyr Ser Ile Ser Ser Ser Pro Arg Val Asp Glu Lys
                885                 890                 895

Gln Ala Ser Ile Thr Val Ser Val Val Ser Gly Glu Ala Trp Ser Gly
            900                 905                 910

Tyr Gly Glu Tyr Lys Gly Ile Ala Ser Asn Tyr Leu Ala Glu Leu Gln
        915                 920                 925

Glu Gly Asp Thr Ile Thr Cys Phe Ile Ser Thr Pro Gln Ser Glu Phe
    930                 935                 940

Thr Leu Pro Lys Asp Pro Glu Thr Pro Leu Ile Met Val Gly Pro Gly
945                 950                 955                 960

Thr Gly Val Ala Pro Phe Arg Gly Phe Val Gln Ala Arg Lys Gln Leu
                965                 970                 975

Lys Glu Gln Gly Gln Ser Leu Gly Glu Ala His Leu Tyr Phe Gly Cys
            980                 985                 990

Arg Ser Pro His Glu Asp Tyr Leu Tyr Gln Glu Glu Leu Glu Asn Ala
        995                 1000                1005

Gln Ser Glu Gly Ile Ile Thr Leu His Thr Ala Phe Ser Arg Met
    1010                1015                1020

Pro Asn Gln Pro Lys Thr Tyr Val Gln His Val Met Glu Gln Asp
    1025                1030                1035

Gly Lys Lys Leu Ile Glu Leu Leu Asp Lys Gly Ala His Phe Tyr
    1040                1045                1050

Ile Cys Gly Asp Gly Ser Gln Met Ala Pro Ala Val Glu Ala Thr
    1055                1060                1065

Leu Met Lys Ser Tyr Ala Asp Val His Gln Val Ser Glu Ala Asp
    1070                1075                1080

Ala Arg Leu Trp Leu Gln Gln Leu Glu Glu Lys Gly Arg Tyr Ala
    1085                1090                1095

Lys Asp Val Ala
    1100

<210> SEQ ID NO 111
<211> LENGTH: 3165
<212> TYPE: DNA
<213> ORGANISM: Artificial Sequence
<220> FEATURE:
<223> OTHER INFORMATION: KO-BMR fusion construct

<400> SEQUENCE: 111

```
atggttccag gtttgccagt tattggtaat ttgttgcaat tgaaagaaaa gaagccatac      60
caaaccttca ctagatgggc tgaagaatat ggtccaatct actctattag aactggtgct     120
tctactatgg ttgtcttgaa cactactcaa gttgccaaag aagctatggt taccagatac     180
ttgtctatct ctaccagaaa gttgtccaac gccttgaaaa ttttgaccgc tgataagtgc     240
atggttgcca tttctgatta caacgatttc cacaagatga tcaagagata tatcttgtct     300
aacgttttgg gtccatctgc ccaaaaaaga catagatcta acagagatac cttgagagcc     360
aacgtttgtt ctagattgca ttcccaagtt aagaactctc aagagaagc tgtcaacttt     420
agaagagttt tcgaatggga attattcggt atcgctttga acaagccctt cggtaaggat     480
attgaaaagc caatctacgt cgaagaattg ggtactactt tgtccagaga tgaaatcttc     540
aaggttttgg tcttggacat tatggaaggt gccattgaag ttgattggag agatttttc     600
ccatacttgc gttggattcc aaacaccaga atggaaacta agatccaaag attatacttt     660
agaagaaagg ccgttatgac cgccttgatt aacgaacaaa agaaaagaat tgcctccggt     720
gaagaaatca actgctacat cgatttcttg ttgaaagaag gtaagacctt gaccatggac     780
caaatctcta tgttgttgtg ggaaaccgtt attgaaactg ctgataccac aatggttact     840
actgaatggg ctatgtacga agttgctaag gattctaaaa gacaagacag attataccaa     900
gaaatccaaa aggtctgcgg ttctgaaatg gttacagaag aatacttgtc ccaattgcca     960
tacttgaatg ctgttttcca cgaaactttg agaaaacatt ctccagctgc tttggttcca    1020
ttgagatatg ctcatgaaga tactcaattg ggtggttatt acattccagc cggtactgaa    1080
attgccatta acatctacgg ttgcaacatg gacaaacacc aatgggaatc tccagaagaa    1140
tggaagccag aaagatttt ggatcctaag tttgacccaa tggacttgta caaaactatg    1200
gcttttggtg ctggtaaaag agtttgcgct ggttctttac aagctatgtt gattgcttgt    1260
ccaaccatcg gtagattggt tcaagaattt gaatggaagt tgagagatgg tgaagaagaa    1320
aacgttgata ctgttggttt gaccacccat aagagatatc caatgcatgc tattttgaag    1380
ccaagatctc catcaagacc aagtcctagt accgaacaat ctgcaaaaaa agttagaaaa    1440
aaagcagaaa atgcacacaa tactccattg ctagttcttt atggttctaa tatgggaaca    1500
gcggaaggaa cggccaggga tctagctgac atagctatgt ccaagggatt tgccccgcaa    1560
gtagcaaccc tggattccca tgcaggtaac ttgccaagag aaggtgctgt tctaatagtt    1620
accgctagct acaatgggca ccctccagat aatgcgaagc agttcgtcga ttggttagat    1680
caagcatcag cagatgaagt taagggtgtt agatactctg ttttggatg tggagataag    1740
aattgggcca ccacatatca gaaggttccg gctttcatcg atgaaatgct tgctgcaaaa    1800
ggggctgaaa atatagcaga tcgtggtgag gccgacgcaa gcgacgattt tgagggtacc    1860
tatgaggagt ggagagagca catgtggtct gatgttgccg cgtatttaa tctagacata    1920
gaaaattctg aagacaataa aagtgcctta cttcttcaat tcgtcgatag tgctgcggac    1980
atgccccttag caaagatgca tggagccttt tcaacgaacg tagtagccag taaggaactt    2040
caacaaccag gtagtgccag aagtacacgt cacttggaaa ttgaattacc aaaagaggca    2100
tcctaccaag aaggtgacca tcttggtgta atcccaagaa actacgaagg tatagtcaat    2160
agggtaacgg caagatttgg gctggatgca agccaacaga taagactaga agcagaagaa    2220
gaaaaattgg cgcaccttcc actagcgaag acagtatccg ttgaagaatt attgcaatac    2280
```

```
gtggaattgc aggatcccgt cactagaacg caattgagag ctatggcagc aaagactgtt   2340
tgtccacctc acaaggttga acttgaagct ctacttgaaa acaagcata caaagagcaa    2400 gtgctagcaa agagactaac catgttagaa ttgctggaaa ataccggc atgcgaaatg    2460 gaattctccg aatttatcgc gttgttgcca agtattcgtc ccaggtatta ctcaatttca   2520
tcttcaccaa gggttgacga gaaacaggca tctattaccg tatctgtggt ctctggagaa   2580
gcttggagtg gttacggaga atacaagggt attgcttcca attatcttgc agaactgcag   2640 gaagggata caattacctg ctttatttct actcctcaat cagaatttac tcttccgaag    2700
gatccagaaa ctccgttaat tatggtaggt ccgggaacag gagtcgcccc tttcagaggc   2760
tttgtgcaag caaggaagca actaaaagaa cagggacaaa gtctgggtga ggcacatcta   2820
tatttcggtt gcagatctcc gcatgaggat tacttatacc aagaagaact tgaaaacgcc   2880
caatcagaag gtattatcac cttgcatact gcattcagta gaatgccaaa ccagccgaaa   2940
acttacgtac agcatgttat ggagcaagat ggtaagaagt taattgagct tttggataag   3000
ggcgcccact tctacatttg cggcgacgga tcccaaatgg cgcctgccgt tgaagccacc   3060
ttgatgaaat catatgcaga tgttcatcaa gtttcagaag cggacgcccg tctttggtta   3120
caacaactag aggagaaagg aaggtatgca aaagatgttg cttaa                  3165
```

<210> SEQ ID NO 112
<211> LENGTH: 1054
<212> TYPE: PRT
<213> ORGANISM: Artificial Sequence
<220> FEATURE:
<223> OTHER INFORMATION: KO-BMR fusion construct

<400> SEQUENCE: 112

```
Met Val Pro Gly Leu Pro Val Ile Gly Asn Leu Leu Gln Leu Lys Glu
1               5                   10                  15

Lys Lys Pro Tyr Gln Thr Phe Thr Arg Trp Ala Glu Glu Tyr Gly Pro
                20                  25                  30

Ile Tyr Ser Ile Arg Thr Gly Ala Ser Thr Met Val Val Leu Asn Thr
            35                  40                  45

Thr Gln Val Ala Lys Glu Ala Met Val Thr Arg Tyr Leu Ser Ile Ser
        50                  55                  60

Thr Arg Lys Leu Ser Asn Ala Leu Lys Ile Leu Thr Ala Asp Lys Cys
65                  70                  75                  80

Met Val Ala Ile Ser Asp Tyr Asn Asp Phe His Lys Met Ile Lys Arg
                85                  90                  95

Tyr Ile Leu Ser Asn Val Leu Gly Pro Ser Ala Gln Lys His Arg
            100                 105                 110

Ser Asn Arg Asp Thr Leu Arg Ala Asn Val Cys Ser Arg Leu His Ser
        115                 120                 125

Gln Val Lys Asn Ser Pro Arg Glu Ala Val Asn Phe Arg Arg Val Phe
    130                 135                 140

Glu Trp Glu Leu Phe Gly Ile Ala Leu Lys Gln Ala Phe Gly Lys Asp
145                 150                 155                 160

Ile Glu Lys Pro Ile Tyr Val Glu Glu Leu Gly Thr Thr Leu Ser Arg
                165                 170                 175

Asp Glu Ile Phe Lys Val Leu Val Leu Asp Ile Met Glu Gly Ala Ile
            180                 185                 190

Glu Val Asp Trp Arg Asp Phe Phe Pro Tyr Leu Arg Trp Ile Pro Asn
        195                 200                 205
```

```
Thr Arg Met Glu Thr Lys Ile Gln Arg Leu Tyr Phe Arg Arg Lys Ala
    210             215                 220
Val Met Thr Ala Leu Ile Asn Glu Gln Lys Lys Arg Ile Ala Ser Gly
225             230                 235                 240
Glu Glu Ile Asn Cys Tyr Ile Asp Phe Leu Leu Lys Glu Gly Lys Thr
                245                 250                 255
Leu Thr Met Asp Gln Ile Ser Met Leu Leu Trp Glu Thr Val Ile Glu
            260                 265                 270
Thr Ala Asp Thr Thr Met Val Thr Glu Trp Ala Met Tyr Glu Val
            275                 280                 285
Ala Lys Asp Ser Lys Arg Gln Asp Arg Leu Tyr Gln Glu Ile Gln Lys
    290                 295                 300
Val Cys Gly Ser Glu Met Val Thr Glu Glu Tyr Leu Ser Gln Leu Pro
305             310                 315                 320
Tyr Leu Asn Ala Val Phe His Glu Thr Leu Arg Lys His Ser Pro Ala
                325                 330                 335
Ala Leu Val Pro Leu Arg Tyr Ala His Glu Asp Thr Gln Leu Gly Gly
            340                 345                 350
Tyr Tyr Ile Pro Ala Gly Thr Glu Ile Ala Ile Asn Ile Tyr Gly Cys
                355                 360                 365
Asn Met Asp Lys His Gln Trp Glu Ser Pro Glu Glu Trp Lys Pro Glu
370                 375                 380
Arg Phe Leu Asp Pro Lys Phe Asp Pro Met Asp Leu Tyr Lys Thr Met
385                 390                 395                 400
Ala Phe Gly Ala Gly Lys Arg Val Cys Ala Gly Ser Leu Gln Ala Met
                405                 410                 415
Leu Ile Ala Cys Pro Thr Ile Gly Arg Leu Val Gln Glu Phe Glu Trp
            420                 425                 430
Lys Leu Arg Asp Gly Glu Glu Asn Val Asp Thr Val Gly Leu Thr
            435                 440                 445
Thr His Lys Arg Tyr Pro Met His Ala Ile Leu Lys Pro Arg Ser Pro
    450                 455                 460
Ser Arg Pro Ser Pro Ser Thr Glu Gln Ser Ala Lys Lys Val Arg Lys
465             470                 475                 480
Lys Ala Glu Asn Ala His Asn Thr Pro Leu Leu Val Leu Tyr Gly Ser
                485                 490                 495
Asn Met Gly Thr Ala Glu Gly Thr Ala Arg Asp Leu Ala Asp Ile Ala
            500                 505                 510
Met Ser Lys Gly Phe Ala Pro Gln Val Ala Thr Leu Asp Ser His Ala
    515                 520                 525
Gly Asn Leu Pro Arg Glu Gly Ala Val Leu Ile Val Thr Ala Ser Tyr
530                 535                 540
Asn Gly His Pro Pro Asp Asn Ala Lys Gln Phe Val Asp Trp Leu Asp
545                 550                 555                 560
Gln Ala Ser Ala Asp Glu Val Lys Gly Val Arg Tyr Ser Val Phe Gly
                565                 570                 575
Cys Gly Asp Lys Asn Trp Ala Thr Thr Tyr Gln Lys Val Pro Ala Phe
            580                 585                 590
Ile Asp Glu Met Leu Ala Ala Lys Gly Ala Glu Asn Ile Ala Asp Arg
            595                 600                 605
Gly Glu Ala Asp Ala Ser Asp Asp Phe Glu Gly Thr Tyr Glu Glu Trp
610                 615                 620
Arg Glu His Met Trp Ser Asp Val Ala Ala Tyr Phe Asn Leu Asp Ile
```

-continued

|     |     |     |     |     |     |     |     |     |     |     |     |     |     |     |
| --- | --- | --- | --- | --- | --- | --- | --- | --- | --- | --- | --- | --- | --- | --- |
|     625 |     |     |     |     630 |     |     |     |     635 |     |     |     |     640 |     |     |
| Glu | Asn | Ser | Glu | Asp | Asn | Lys | Ser | Ala | Leu | Leu | Gln | Phe | Val | Asp |
|     |     |     |     645 |     |     |     |     650 |     |     |     |     655 |     |     |     |
| Ser | Ala | Ala | Asp | Met | Pro | Leu | Ala | Lys | Met | His | Gly | Ala | Phe | Ser | Thr |
|     |     |     660 |     |     |     |     665 |     |     |     |     670 |     |     |     |
| Asn | Val | Val | Ala | Ser | Lys | Glu | Leu | Gln | Gln | Pro | Gly | Ser | Ala | Arg | Ser |
|     |     |     675 |     |     |     |     680 |     |     |     |     685 |     |     |     |
| Thr | Arg | His | Leu | Glu | Ile | Glu | Leu | Pro | Lys | Glu | Ala | Ser | Tyr | Gln | Glu |
|     690 |     |     |     |     695 |     |     |     |     700 |     |     |     |
| Gly | Asp | His | Leu | Gly | Val | Ile | Pro | Arg | Asn | Tyr | Glu | Gly | Ile | Val | Asn |
| 705 |     |     |     |     710 |     |     |     |     715 |     |     |     |     720 |
| Arg | Val | Thr | Ala | Arg | Phe | Gly | Leu | Asp | Ala | Ser | Gln | Gln | Ile | Arg | Leu |
|     |     |     |     725 |     |     |     |     730 |     |     |     |     735 |     |
| Glu | Ala | Glu | Glu | Glu | Lys | Leu | Ala | His | Leu | Pro | Leu | Ala | Lys | Thr | Val |
|     |     |     740 |     |     |     |     745 |     |     |     |     750 |     |     |
| Ser | Val | Glu | Glu | Leu | Leu | Gln | Tyr | Val | Glu | Leu | Gln | Asp | Pro | Val | Thr |
|     |     |     755 |     |     |     |     760 |     |     |     |     765 |     |     |
| Arg | Thr | Gln | Leu | Arg | Ala | Met | Ala | Ala | Lys | Thr | Val | Cys | Pro | Pro | His |
|     770 |     |     |     |     775 |     |     |     |     780 |     |     |     |
| Lys | Val | Glu | Leu | Glu | Ala | Leu | Leu | Glu | Lys | Gln | Ala | Tyr | Lys | Glu | Gln |
| 785 |     |     |     |     790 |     |     |     |     795 |     |     |     |     800 |
| Val | Leu | Ala | Lys | Arg | Leu | Thr | Met | Leu | Glu | Leu | Leu | Glu | Lys | Tyr | Pro |
|     |     |     |     805 |     |     |     |     810 |     |     |     |     815 |     |
| Ala | Cys | Glu | Met | Glu | Phe | Ser | Glu | Phe | Ile | Ala | Leu | Leu | Pro | Ser | Ile |
|     |     |     820 |     |     |     |     825 |     |     |     |     830 |     |     |
| Arg | Pro | Arg | Tyr | Tyr | Ser | Ile | Ser | Ser | Ser | Pro | Arg | Val | Asp | Glu | Lys |
|     |     |     835 |     |     |     |     840 |     |     |     |     845 |     |     |
| Gln | Ala | Ser | Ile | Thr | Val | Ser | Val | Val | Ser | Gly | Glu | Ala | Trp | Ser | Gly |
|     |     |     850 |     |     |     |     855 |     |     |     |     860 |     |     |
| Tyr | Gly | Glu | Tyr | Lys | Gly | Ile | Ala | Ser | Asn | Tyr | Leu | Ala | Glu | Leu | Gln |
| 865 |     |     |     |     870 |     |     |     |     875 |     |     |     |     880 |
| Glu | Gly | Asp | Thr | Ile | Thr | Cys | Phe | Ile | Ser | Thr | Pro | Gln | Ser | Glu | Phe |
|     |     |     |     885 |     |     |     |     890 |     |     |     |     895 |     |
| Thr | Leu | Pro | Lys | Asp | Pro | Glu | Thr | Pro | Leu | Ile | Met | Val | Gly | Pro | Gly |
|     |     |     900 |     |     |     |     905 |     |     |     |     910 |     |     |
| Thr | Gly | Val | Ala | Pro | Phe | Arg | Gly | Phe | Val | Gln | Ala | Arg | Lys | Gln | Leu |
|     |     |     915 |     |     |     |     920 |     |     |     |     925 |     |     |
| Lys | Glu | Gln | Gly | Gln | Ser | Leu | Gly | Glu | Ala | His | Leu | Tyr | Phe | Gly | Cys |
|     930 |     |     |     |     935 |     |     |     |     940 |     |     |     |
| Arg | Ser | Pro | His | Glu | Asp | Tyr | Leu | Tyr | Gln | Glu | Glu | Leu | Glu | Asn | Ala |
| 945 |     |     |     |     950 |     |     |     |     955 |     |     |     |     960 |
| Gln | Ser | Glu | Gly | Ile | Ile | Thr | Leu | His | Thr | Ala | Phe | Ser | Arg | Met | Pro |
|     |     |     |     965 |     |     |     |     970 |     |     |     |     975 |     |
| Asn | Gln | Pro | Lys | Thr | Tyr | Val | Gln | His | Val | Met | Glu | Gln | Asp | Gly | Lys |
|     |     |     980 |     |     |     |     985 |     |     |     |     990 |     |     |
| Lys | Leu | Ile | Glu | Leu | Leu | Asp | Lys | Gly | Ala | His | Phe | Tyr | Ile | Cys | Gly |
|     |     |     995 |     |     |     |     1000 |     |     |     |     1005 |     |     |
| Asp | Gly | Ser | Gln | Met | Ala | Pro | Ala | Val | Glu | Ala | Thr | Leu | Met | Lys |     |
|     1010 |     |     |     |     1015 |     |     |     |     1020 |     |     |     |
| Ser | Tyr | Ala | Asp | Val | His | Gln | Val | Ser | Glu | Ala | Asp | Ala | Arg | Leu |     |
|     1025 |     |     |     |     1030 |     |     |     |     1035 |     |     |     |
| Trp | Leu | Gln | Gln | Leu | Glu | Glu | Lys | Gly | Arg | Tyr | Ala | Lys | Asp | Val |     |
|     1040 |     |     |     |     1045 |     |     |     |     1050 |     |     |     |

Ala

<210> SEQ ID NO 113
<211> LENGTH: 1476
<212> TYPE: DNA
<213> ORGANISM: Saccharomyces cerevisiae

<400> SEQUENCE: 113

| | | | | | |
|---|---|---|---|---|---|
| atgaccagtt | tgtccaaaag | cttcatgcag | agtggacgaa | tctgcgcagc | atgtttctat | 60 |
| ctgttattca | cactactttc | aattccaatc | tcgtttaaag | ttggtggttt | ggaatgcggg | 120 |
| ctttccttca | cggtgacact | gttcacttta | tatttcataa | ctacgactct | taacgtgttg | 180 |
| gcaagacgac | atggaggaag | actatacatt | ttttttacca | actgtctgta | ttactcacaa | 240 |
| cattttatca | ttgcatcttt | gctatacctg | ttttgtctg | gattttctaa | tgatgagttg | 300 |
| ggaaacgttc | tgaaaaataa | atataatgag | tcggagtcgt | tcctggaagc | tttgaaaaat | 360 |
| agcttgaatt | ccaatcaaat | taactacgtc | ttatattatt | actactatcg | atttgttgta | 420 |
| caaccgtggc | aattcgtgct | taccaagtcc | acaccttttt | ttactctatc | ggaaggtttt | 480 |
| ttcactattt | tagccattca | ggccgtcggg | gaaactaata | tgggttatc | aaatgacttg | 540 |
| aattcaaaca | cgtggattat | ttcctcattg | ttaacctccg | gaggtgtgat | accgcatcg | 600 |
| ctgtactatt | tgtatcggat | ttatgtcacc | cccatatggc | cgttatccat | ccaaacggcg | 660 |
| tccttattag | gacttgtttt | gtctatggta | tgtggactgg | ggttgtatgg | tattgtgagt | 720 |
| caaaaaggat | ccgtcataga | gagctcttta | ttttttgcgt | atattgttcg | ttgtatttat | 780 |
| gaaatttccc | ccaaattagc | tactaccgcg | actgatgaaa | ttttaaattt | gttcaaagac | 840 |
| gtctggcaga | aacatcaaag | aaatctgccc | acagctgaca | atcttttgtg | ctactttcat | 900 |
| aatgtcatat | tgaaaaatgc | agaggtgtta | tgggggtcct | ttattcctag | aggaagaaag | 960 |
| aaaaccggtg | attttcatga | taaactcatt | agcattctat | cattcgaaaa | agtatccttg | 1020 |
| atatctaaac | cattttggaa | attttttcaag | aatttcacct | ttagtgttcc | gctatccatt | 1080 |
| aatgaatttt | gtcaagttac | aattaagatg | caagcgaat | cagtttcccc | agctatagta | 1140 |
| atcaattat | gctttagagt | tctgatgttt | tactcggcaa | cgaggattat | tccagcatta | 1200 |
| caaagaaaaa | atgacaaaca | gttgcgcaag | agtcgcagga | tcatgaaggg | attgtattgg | 1260 |
| tacagtcctt | gcatattaat | tgctatgtat | actcacctga | ttttacaata | ttcaggtgag | 1320 |
| ctaaagaaag | acctgtgcat | atggggttgc | agtgaaaagt | ggtttggcgt | agatcaacca | 1380 |
| gaaattatag | tagattcatg | gggattttgg | aactggtgca | acatttttctg | tactattttg | 1440 |
| gtatacgcta | cagaattaat | aggttctggt | agttga | | | 1476 |

<210> SEQ ID NO 114
<211> LENGTH: 491
<212> TYPE: PRT
<213> ORGANISM: Saccharomyces cerevisiae

<400> SEQUENCE: 114

Met Thr Ser Leu Ser Lys Ser Phe Met Gln Ser Gly Arg Ile Cys Ala
1               5                   10                  15

Ala Cys Phe Tyr Leu Leu Phe Thr Leu Leu Ser Ile Pro Ile Ser Phe
            20                  25                  30

Lys Val Gly Gly Leu Glu Cys Gly Leu Ser Phe Thr Val Thr Leu Phe
        35                  40                  45

Thr Leu Tyr Phe Ile Thr Thr Thr Leu Asn Val Leu Ala Arg Arg His

-continued

```
             50                  55                  60
Gly Gly Arg Leu Tyr Ile Phe Phe Thr Ser Cys Leu Tyr Tyr Ser Gln
 65                  70                  75                  80

His Phe Ile Ile Ala Ser Leu Leu Tyr Leu Phe Leu Ser Gly Phe Ser
                 85                  90                  95

Asn Asp Glu Leu Gly Asn Val Leu Lys Asn Lys Tyr Asn Glu Ser Glu
            100                 105                 110

Ser Phe Leu Glu Ala Leu Lys Asn Ser Leu Asn Ser Asn Gln Ile Asn
            115                 120                 125

Tyr Val Leu Tyr Tyr Tyr Tyr Arg Phe Val Val Gln Pro Trp Gln
130                 135                 140

Phe Val Leu Thr Lys Ser Thr Pro Phe Phe Thr Leu Ser Glu Gly Phe
145                 150                 155                 160

Phe Thr Ile Leu Ala Ile Gln Ala Val Gly Glu Thr Asn Arg Trp Leu
                165                 170                 175

Ser Asn Asp Leu Asn Ser Asn Thr Trp Ile Ile Ser Ser Leu Leu Thr
                180                 185                 190

Ser Gly Gly Val Ile Thr Ala Ser Leu Tyr Tyr Leu Tyr Arg Ile Tyr
            195                 200                 205

Val Thr Pro Ile Trp Pro Leu Ser Ile Gln Thr Ala Ser Leu Leu Gly
210                 215                 220

Phe Val Leu Ser Met Val Cys Gly Leu Gly Leu Tyr Gly Ile Val Ser
225                 230                 235                 240

Gln Lys Gly Ser Val Ile Glu Ser Ser Leu Phe Phe Ala Tyr Ile Val
                245                 250                 255

Arg Cys Ile Tyr Glu Ile Ser Pro Lys Leu Ala Thr Ala Thr Asp
                260                 265                 270

Glu Ile Leu Asn Leu Phe Lys Asp Val Trp Gln Lys His Gln Arg Asn
            275                 280                 285

Leu Pro Thr Ala Asp Asn Leu Leu Cys Tyr Phe His Asn Val Ile Leu
            290                 295                 300

Lys Asn Ala Glu Val Leu Trp Gly Ser Phe Ile Pro Arg Gly Arg Lys
305                 310                 315                 320

Lys Thr Gly Asp Phe His Asp Lys Leu Ile Ser Ile Leu Ser Phe Glu
                325                 330                 335

Lys Val Ser Leu Ile Ser Lys Pro Phe Trp Lys Phe Lys Asn Phe
            340                 345                 350

Thr Phe Ser Val Pro Leu Ser Ile Asn Glu Phe Cys Gln Val Thr Ile
            355                 360                 365

Lys Met Ala Ser Glu Ser Val Ser Pro Ala Ile Val Ile Asn Leu Cys
    370                 375                 380

Phe Arg Val Leu Met Phe Tyr Ser Ala Thr Arg Ile Ile Pro Ala Leu
385                 390                 395                 400

Gln Arg Lys Asn Asp Lys Gln Leu Arg Lys Ser Arg Arg Ile Met Lys
                405                 410                 415

Gly Leu Tyr Trp Tyr Ser Pro Cys Ile Leu Ile Ala Met Tyr Thr His
                420                 425                 430

Leu Ile Leu Gln Tyr Ser Gly Glu Leu Lys Lys Asp Leu Cys Ile Trp
            435                 440                 445

Gly Cys Ser Glu Lys Trp Phe Gly Val Asp Gln Pro Glu Ile Ile Val
            450                 455                 460

Asp Ser Trp Gly Phe Trp Asn Trp Cys Asn Ile Phe Cys Thr Ile Leu
465                 470                 475                 480
```

Val Tyr Ala Thr Glu Leu Ile Gly Ser Gly Ser
             485                 490

<210> SEQ ID NO 115
<211> LENGTH: 4957
<212> TYPE: DNA
<213> ORGANISM: Bacillus megaterium

<400> SEQUENCE: 115

| | | | | | |
|---|---|---|---|---|---:|
| agatctttat | gaagacatag | ctgcagaaga | aaaagcaaga | gctacatatc | aatggttaat | 60 |
| tgatatatca | gatgatcccg | atttaaacga | cagcttacga | tttttacgag | aaagagagat | 120 |
| tgttcactca | cagcggttcc | gcgaggccgt | ggagatttta | aaagatgaca | gagacaggaa | 180 |
| gaaaatcttt | taactagtaa | aaaaacatcc | cccttggcga | atgcaaacga | aggagggat | 240 |
| gttttttgtt | gtgactgcgt | tgattatgcg | ctagaactgc | agtgacaaga | aacaaccttt | 300 |
| aatttccctt | caacatcttt | ccaaactcgc | gtataactgt | attcacctcc | aatagattca | 360 |
| ccggttgcca | gtgccccatt | taacgctact | tttgtaacgg | taacggcaag | ttcttgaaac | 420 |
| agtttaactt | cttgttccaa | cacttccatg | cccgctatat | caagactttt | tgaacgatga | 480 |
| acatttatat | cttcttcttt | tgacaaccat | tgcccaaggt | gattcacaaa | aataagctca | 540 |
| tctgaaagta | attcttctaa | tagctctatg | ttattagaaa | gcatggctga | gcgaagcatt | 600 |
| tcttcgtatt | ctataactct | tgcttgattc | atttttaatc | ctcctttacg | ccttgtgtaa | 660 |
| ctcttttcta | tttccacgtt | gcttttcctt | taaacttctt | tcattaataa | ttcgtgctaa | 720 |
| attatgttaa | tagaggggat | aagtggacta | attttctgta | agcactaaat | attctgaaat | 780 |
| actctgttaa | ttacctttaa | atggtataaa | attagaatga | agaacctttt | tctttccact | 840 |
| tttctagtta | tctttttact | attaagatgc | agttttttat | acttgtaatt | gtagcggaat | 900 |
| gaacgttcat | tccgtttttg | aaaagaggtg | ataaagtgga | atctactcca | acaaaacaaa | 960 |
| aagcgatttt | ttctgcttcg | cttctgctgt | ttgcagaaag | agggtttgat | gcaaccacga | 1020 |
| tgccaatgat | tgcagagaat | gccaaagtag | gagcaggaac | aatttatcgc | tactttaaaa | 1080 |
| ataaagaaag | ccttgtaaat | gaattattcc | aacagcacgt | aaacgagttt | ttacagtgca | 1140 |
| ttgaaagcgg | tctggcaaac | gagagagatg | gataccgaga | tgggtttcat | catatctttg | 1200 |
| aaggtatggt | gacatttact | aaaaaccatc | ctcgtgctct | tggatttatt | aaaactcata | 1260 |
| gccaaggaac | ttttttaaca | aagagagcc | gcttagcata | tcaaaagctg | gtggaatttg | 1320 |
| tttgtacgtt | cttcagagaa | ggacaaaagc | aaggtgtgat | tagaaatctt | cctgaaaatg | 1380 |
| cgctaattgc | tattttattt | ggaagtttca | tggaagtata | tgaaatgatt | gaaaatgact | 1440 |
| acttatcttt | aactgatgaa | cttcttaccg | gtgtagaaga | gagtctgtgg | gcagcactta | 1500 |
| gcagacaatc | atgaaactta | acaagtgaaa | gagggataac | atgacaatta | agaaatgcc | 1560 |
| tcagccaaaa | acgtttggag | agcttaaaaa | tttaccgtta | ttaaacacag | ataaccggt | 1620 |
| tcaagctttg | atgaaaattg | cggatgaatt | aggagaaatc | tttaaattcg | aggcgcctgg | 1680 |
| tcgtgtaacg | cgctacttat | caagtcagcg | tctaattaaa | gaagcatgcg | atgaatcacg | 1740 |
| ctttgataaa | aacttaagtc | aagcgcttaa | atttgtacgt | gattttgcag | agacgggtt | 1800 |
| atttacaagc | tggacgcatg | aaaaaaattg | gaaaaagcg | cataatatct | tacttccaag | 1860 |
| cttcagtcag | caggcaatga | aaggctatca | tgcgatgatg | gtcgatatcg | ccgtgcagct | 1920 |
| tgttcaaaag | tgggagcgtc | taaatgcaga | tgagcatatt | gaagtaccgg | aagacatgac | 1980 |
| acgtttaacg | cttgatacaa | ttggtctttg | cggctttaac | tatcgcttta | acagcttta | 2040 |

```
ccgagatcag cctcatccat ttattacaag tatggtccgt gcactggatg aagcaatgaa    2100
caagctgcag cgagcaaatc cagacgaccc agcttatgat gaaaacaagc gccagtttca    2160
agaagatatc aaggtgatga acgacctagt agataaaatt attgcagatc gcaaagcaag    2220
cggtgaacaa agcgatgatt tattaacgca tatgctaaac ggaaaagatc cagaaacggg    2280
tgagccgctt gatgacgaga acattcgcta tcaaattatt acattcttaa ttgcgggaca    2340
cgaaacaaca agtggtcttt tatcatttgc gctgtatttc ttagtgaaaa atccacatgt    2400
attacaaaaa gcagcagaag aagcagcacg agttctagta gatcctgttc caagctacaa    2460
acaagtcaaa cagcttaaat atgtcggcat ggtcttaaac gaagcgctgc gcttatggcc    2520
aactgctcct gcgttttccc tatatgcaaa agaagatacg gtgcttggag gagaatatcc    2580
tttagaaaaa ggcgacgaac taatggttct gattcctcag cttcaccgtg ataaaacaat    2640
ttggggagac gatgtggaag agttccgtcc agagcgtttt gaaaatccaa gtgcgattcc    2700
gcagcatgcg tttaaaccgt ttggaaacgg tcagcgtgcg tgtatcggtc agcagttcgc    2760
tcttcatgaa gcaacgctgg tacttggtat gatgctaaaa cactttgact ttgaagatca    2820
tacaaactac gagctggata ttaagaaaac tttaacgtta aaacctgaag ctttgtggt    2880 aaaagcaaaa tcgaaaaaaa ttccgcttgg cggtattcct tcacctagca ctgaacagtc    2940
tgctaaaaaa gtacgcaaaa aggcagaaaa cgctctataa tacgccgctg cttgtgctata    3000 cggttcaaat atgggaacag ctgaaggaac ggcgcgtgat ttagcagata ttgcaatgag    3060
caaaggattt gcaccgcagg tcgcaacgct tgattcacac gccggaaatc ttccgcgcga    3120
aggagctgta ttaattgtaa cggcgtctta taacggtcat ccgcctgata acgcaaagca    3180
atttgtcgac tggttagacc aagcgtctgc tgatgaagta aaaggcgttc gctactccgt    3240
atttggatgc ggcgataaaa actgggctac tacgtatcaa aaagtgcctg cttttatcga    3300
tgaaacgctt gccgctaaag gggcagaaaa catccgctga ccgcggtgaag cagatgcaag    3360 cgacgacttt gaaggcacat atgaagaatg gcgtgaacat atgtggagtg acgtagcagc    3420
ctactttaac ctcgacattg aaaacagtga agataataaa tctactcttt cacttcaatt    3480
tgtcgacagc gccgcggata tgccgcttgc gaaaatgcac ggtgcgtttt caacgaacgt    3540
cgtagcaagc aaagaacttc aacagccagg cagtgcacga agcacgcgac atcttgaaat    3600
tgaacttcca aaagaagctt cttatcaaga aggagatcat ttaggtgtta ttcctcgcaa    3660
ctatgaagga atagtaaacc gtgtaacagc aaggttcggc ctagatgcat cacagcaaat    3720
ccgtctggaa gcagaagaag aaaaattagc tcatttgcca ctcgctaaaa cagtatccgt    3780
agaagagctt ctgcaatacg tggagcttca agatcctgtt acgcgcacgc agcttcgcgc    3840
aatggctgct aaaacggtct gcccgccgca taaagtagag cttgaagcct tgcttgaaaa    3900
gcaagcctac aaagaacaag tgctggcaaa acgtttaaca atgcttgaac tgcttgaaaa    3960
atacccggcg tgtgaaatga aattcagcga atttatcgcc cttctgccaa gcatacgccc    4020
gcgctattac tcgatttctt catcaccctg tgtcgatgaa aaacaagcaa gcatcacggt    4080
cagcgttgtc tcaggagaag cgtggagcgg atatggagaa tataaggaa ttgcgtcgaa    4140 ctatcttgcc gagctgcaag aaggagatac gattacgtgc tttatttcca caccgcagtc    4200
agaatttacg ctgccaaaag accctgaaac gccgcttatc atggtcggac cgggaacagg    4260
cgtcgcgccg tttagaggct ttgtgcaggc gcgcaaacag ctaaagaac aaggacagtc    4320 acttggagaa gcacatttat acttcggctg ccgttcacct catgaagact atctgtatca    4380
```

```
agaagagctt gaaaacgccc aaagcgaagg catcattacg cttcataccg cttttctcg      4440 catgccaaat cagccgaaaa catacgttca gcacgtaatg gaacaagacg gcaagaaatt      4500
gattgaactt cttgatcaag gagcgcactt ctatatttgc ggagacggaa gccaaatggc      4560
acctgccgtt gaagcaacgc ttatgaaaag ctatgctgac gttcaccaag tgagtgaagc      4620
agacgctcgc ttatggctgc agcagctaga agaaaaaggc cgatacgcaa aagacgtgtg      4680
ggctgggtaa attaaaaaga ggctaggata aaagtagttt agttggttga aggaagatcc      4740
gaacgatgaa tcgttcggat cttttttattg gtagagtaaa cgtagatttc atctatttag     4800
tgacttgtag cggttgattg gagggcaagg tgaagactcc aatcaaccgc ggtgtcacat      4860
gcaagccata cgaaattcat ttctcccatt tattcgtctt ttgtccccac ttaattttta     4920
tagcgcctta acgtttcttc tgcgtgacag cagatct                              4957
```

<210> SEQ ID NO 116
<211> LENGTH: 1049
<212> TYPE: PRT
<213> ORGANISM: Bacillus megaterium

<400> SEQUENCE: 116

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270
```

-continued

```
Leu Leu Ser Phe Ala Leu Tyr Phe Leu Val Lys Asn Pro His Val Leu
            275                 280                 285
Gln Lys Ala Ala Glu Ala Ala Arg Val Leu Val Asp Pro Val Pro
        290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Leu Met Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
        435                 440                 445
Ala Lys Ser Lys Lys Ile Pro Leu Gly Gly Ile Pro Ser Pro Ser Thr
    450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
        515                 520                 525
Ala Val Leu Ile Val Thr Ala Ser Tyr Asn Gly His Pro Pro Asp Asn
    530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
        595                 600                 605
Asp Phe Glu Gly Thr Tyr Glu Glu Trp Arg Glu His Met Trp Ser Asp
    610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
        675                 680                 685
Leu Pro Lys Glu Ala Ser Tyr Gln Glu Gly Asp His Leu Gly Val Ile
```

```
                690               695               700
Pro Arg Asn Tyr Glu Gly Ile Val Asn Arg Val Thr Ala Arg Phe Gly
705                 710               715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
    1010            1015                1020

Val Ser Glu Ala Asp Ala Arg Leu Trp Leu Gln Gln Leu Glu Glu
    1025            1030                1035

Lys Gly Arg Tyr Ala Lys Asp Val Trp Ala Gly
    1040            1045

<210> SEQ ID NO 117
<211> LENGTH: 1767
<212> TYPE: DNA
<213> ORGANISM: Artificial Sequence
<220> FEATURE:
<223> OTHER INFORMATION: Codon-optimized BMR

<400> SEQUENCE: 117
ccaagtccta gtaccgaaca atctgcaaaa aaagttagaa aaaaagcaga aaatgcacac      60
```

```
aatactccat tgctagttct ttatggttct aatatgggaa cagcggaagg aacggccagg    120
gatctagctg acatagctat gtccaaggga tttgccccgc aagtagcaac cctggattcc    180
catgcaggta acttgccaag agaaggtgct gttctaatag ttaccgctag ctacaatggg    240
caccctccag ataatgcgaa gcagttcgtc gattggttag atcaagcatc agcagatgaa    300
gttaagggtg ttagatactc tgttttggga tgtggagata agaattgggc caccacatat    360
cagaaggttc cggctttcat cgatgaaatg cttgctgcaa aaggggctga aaatatagca    420
gatcgtggtg aggccgacgc aagcgacgat tttgagggta cctatgagga gtggagagag    480
cacatgtggt ctgatgttgc cgcgtatttt aatctagaca tagaaaattc tgaagacaat    540
aaaagtgcct tacttcttca attcgtcgat agtgctgcgg acatgcccct tagcaaagatg   600 catggagcct tttcaacgaa cgtagtagcc agtaaggaac ttcaacaacc aggtagtgcc    660
agaagtacac gtcacttgga aattgaatta ccaaaagagg catcctacca agaaggtgac    720
catcttggtg taatcccaag aaactacgaa ggtatagtca atagggtaac ggcaagattt    780
gggctggatg caagccaaca gataagacta gaagcagaag aagaaaaatt ggcgcacctt    840
ccactagcga agacagtatc cgttgaagaa ttattgcaat acgtggaatt gcaggatccc    900
gtcactagaa cgcaattgag agctatggca gcaaagactg tttgtccacc tcacaaggtt    960
gaacttgaag ctctacttga aaacaagca tacaaagagc aagtgctagc aaagagacta   1020
accatgttag aattgctgga aaaatacccg gcatgcgaaa tggaattctc cgaatttatc   1080
gcgttgttgc caagtattcg tcccaggtat tactcaattt catcttcacc aagggttgac   1140
gagaaacagg catctattac cgtatctgtg gtctctggag aagcttggag tggttacgga   1200
gaatacaagg gtattgcttc caattatctt gcagaactgc aggaagggga tacaattacc   1260
tgctttattt ctactcctca atcagaattt actcttccga aggatccaga aactccgtta   1320
attatggtag gtccgggaac aggagtcgcc cctttcagag ctttgtgca agcaaggaag   1380 caactaaaag aacagggaca aagtctgggt gaggcacatc tatatttcgg ttgcagatct   1440
ccgcatgagg attacttata ccaagaagaa cttgaaaacg cccaatcaga aggtattatc   1500
accttgcata ctgcattcag tagaatgcca aaccagccga aaacttacgt acagcatgtt   1560
atggagcaag atggtaagaa gttaattgag cttttggata agggcgccca cttctacatt   1620
tgcggcgacg gatcccaaat ggcgcctgcc gttaagccaa ccttgatgaa atcatatgca   1680
gatgttcatc aagtttcaga agcggacgcc cgtctttggt tacaacaact agaggagaaa   1740
ggaaggtatg caaaagatgt ttggtaa                                      1767
```

<210> SEQ ID NO 118
<211> LENGTH: 588
<212> TYPE: PRT
<213> ORGANISM: Bacillus megaterium

<400> SEQUENCE: 118

```
Pro Ser Pro Ser Thr Glu Gln Ser Ala Lys Lys Val Arg Lys Lys Ala
1               5                   10                  15

Glu Asn Ala His Asn Thr Pro Leu Leu Val Leu Tyr Gly Ser Asn Met
            20                  25                  30

Gly Thr Ala Glu Gly Thr Ala Arg Asp Leu Ala Asp Ile Ala Met Ser
        35                  40                  45

Lys Gly Phe Ala Pro Gln Val Ala Thr Leu Asp Ser His Ala Gly Asn
    50                  55                  60
```

```
Leu Pro Arg Glu Gly Ala Val Leu Ile Val Thr Ala Ser Tyr Asn Gly
 65                  70                  75                  80

His Pro Pro Asp Asn Ala Lys Gln Phe Val Asp Trp Leu Asp Gln Ala
                 85                  90                  95

Ser Ala Asp Glu Val Lys Gly Val Arg Tyr Ser Val Phe Gly Cys Gly
            100                 105                 110

Asp Lys Asn Trp Ala Thr Thr Tyr Gln Lys Val Pro Ala Phe Ile Asp
        115                 120                 125

Glu Met Leu Ala Ala Lys Gly Ala Glu Asn Ile Ala Asp Arg Gly Glu
    130                 135                 140

Ala Asp Ala Ser Asp Asp Phe Glu Gly Thr Tyr Glu Glu Trp Arg Glu
145                 150                 155                 160

His Met Trp Ser Asp Val Ala Ala Tyr Phe Asn Leu Asp Ile Glu Asn
                165                 170                 175

Ser Glu Asp Asn Lys Ser Ala Leu Leu Leu Gln Phe Val Asp Ser Ala
                180                 185                 190

Ala Asp Met Pro Leu Ala Lys Met His Gly Ala Phe Ser Thr Asn Val
            195                 200                 205

Val Ala Ser Lys Glu Leu Gln Gln Pro Gly Ser Ala Arg Ser Thr Arg
            210                 215                 220

His Leu Glu Ile Glu Leu Pro Lys Glu Ala Ser Tyr Gln Glu Gly Asp
225                 230                 235                 240

His Leu Gly Val Ile Pro Arg Asn Tyr Glu Gly Ile Val Asn Arg Val
                245                 250                 255

Thr Ala Arg Phe Gly Leu Asp Ala Ser Gln Gln Ile Arg Leu Glu Ala
                260                 265                 270

Glu Glu Glu Lys Leu Ala His Leu Pro Leu Ala Lys Thr Val Ser Val
            275                 280                 285

Glu Glu Leu Leu Gln Tyr Val Glu Leu Gln Asp Pro Val Thr Arg Thr
        290                 295                 300

Gln Leu Arg Ala Met Ala Ala Lys Thr Val Cys Pro Pro His Lys Val
305                 310                 315                 320

Glu Leu Glu Ala Leu Leu Glu Lys Gln Ala Tyr Lys Glu Gln Val Leu
                325                 330                 335

Ala Lys Arg Leu Thr Met Leu Glu Leu Leu Glu Lys Tyr Pro Ala Cys
            340                 345                 350

Glu Met Glu Phe Ser Glu Phe Ile Ala Leu Leu Pro Ser Ile Arg Pro
        355                 360                 365

Arg Tyr Tyr Ser Ile Ser Ser Pro Arg Val Asp Glu Lys Gln Ala
    370                 375                 380

Ser Ile Thr Val Ser Val Val Ser Gly Glu Ala Trp Ser Gly Tyr Gly
385                 390                 395                 400

Glu Tyr Lys Gly Ile Ala Ser Asn Tyr Leu Ala Glu Leu Gln Glu Gly
                405                 410                 415

Asp Thr Ile Thr Cys Phe Ile Ser Thr Pro Gln Ser Glu Phe Thr Leu
            420                 425                 430

Pro Lys Asp Pro Glu Thr Pro Leu Ile Met Val Gly Pro Gly Thr Gly
        435                 440                 445

Val Ala Pro Phe Arg Gly Phe Val Gln Ala Arg Lys Gln Leu Lys Glu
    450                 455                 460

Gln Gly Gln Ser Leu Gly Glu Ala His Leu Tyr Phe Gly Cys Arg Ser
465                 470                 475                 480

Pro His Glu Asp Tyr Leu Tyr Gln Glu Glu Leu Glu Asn Ala Gln Ser
```

```
                485                 490                 495
Glu Gly Ile Ile Thr Leu His Thr Ala Phe Ser Arg Met Pro Asn Gln
            500                 505                 510

Pro Lys Thr Tyr Val Gln His Val Met Glu Gln Asp Gly Lys Lys Leu
            515                 520                 525

Ile Glu Leu Leu Asp Lys Gly Ala His Phe Tyr Ile Cys Gly Asp Gly
            530                 535                 540

Ser Gln Met Ala Pro Ala Val Glu Ala Thr Leu Met Lys Ser Tyr Ala
545                 550                 555                 560

Asp Val His Gln Val Ser Glu Ala Asp Ala Arg Leu Trp Leu Gln Gln
                565                 570                 575

Leu Glu Glu Lys Gly Arg Tyr Ala Lys Asp Val Trp
            580                 585

<210> SEQ ID NO 119
<211> LENGTH: 1767
<212> TYPE: DNA
<213> ORGANISM: Artificial Sequence
<220> FEATURE:
<223> OTHER INFORMATION: Codon-optimized BMR W1046A

<400> SEQUENCE: 119
ccaagtccta gtaccgaaca atctgcaaaa aaagttagaa aaaaagcaga aaatgcacac     60
aatactccat tgctagttct ttatggttct aatatgggaa cagcggaagg aacggccagg    120
gatctagctg acatagctat gtccaaggga tttgccccgc aagtagcaac cctggattcc    180
catgcaggta acttgccaag agaaggtgct gttctaatag ttaccgctag ctacaatggg    240
caccctccag ataatgcgaa gcagttcgtc gattggttag atcaagcatc agcagatgaa    300
gttaagggtg ttagatactc tgttttttgga tgtggagata agaattgggc caccacatat    360
cagaaggttc cggctttcat cgatgaaatg cttgctgcaa aggggctgaa aatatagca    420 gatcgtggtg aggccgacgc aagcgacgat tttgagggta cctatgagga gtggagagag    480
cacatgtggt ctgatgttgc cgcgtatttt aatctagaca tagaaaattc tgaagacaat    540
aaaagtgcct tacttcttca attcgtcgat agtgctgcgg acatgccctt agcaaagatg    600
catggagcct tttcaacgaa cgtagtagcc agtaaggaac ttcaacaacc aggtagtgcc    660
agaagtacac gtcacttgga aattgaatta ccaaaagagg catcctacca agaaggtgac    720
catcttggtg taatcccaag aaactacgaa ggtatagtca atagggtaac ggcaagattt    780
gggctggatg caagccaaca gataagacta gaagcagaag aagaaaaatt ggcgcacctt    840
ccactagcga agacagtatc cgttgaagaa ttattgcaat acgtggaatt gcaggatccc    900
gtcactagaa cgcaattgag agctatggca gcaaagactg tttgtccacc tcacaaggtt    960
gaacttgaag ctctacttga aaaacaagca tacaaagagc aagtgctagc aaagagacta   1020
accatgttag aattgctgga aaatacccg gcatgcgaaa tggaattctc cgaatttatc   1080
gcgttgttgc caagtattcg tcccaggtat tactcaattt catcttcacc aagggttgac   1140
gagaaacagg catctattac cgtatctgtg gtctctggag aagcttggag tggttacgga   1200
gaatacaagg gtattgcttc caattatctt gcagaactgc aggaagggga tacaattacc   1260
tgctttattt ctactcctca atcagaattt actcttccga aggatccaga aactccgtta   1320
attatggtag gtccgggaac aggagtcgcc ccttcagag gctttgtgca agcaaggaag   1380
caactaaaag aacagggaca aagtctgggt gaggcacatc tatatttcgg ttgcagatct   1440
ccgcatgagg attacttata ccaagaagaa cttgaaaacg cccaatcaga aggtattatc   1500
```

```
accttgcata ctgcattcag tagaatgcca aaccagccga aaacttacgt acagcatgtt   1560
atggagcaag atggtaagaa gttaattgag cttttggata agggcgccca cttctacatt   1620
tgcggcgacg gatcccaaat ggcgcctgcc gttgaagcca ccttgatgaa atcatatgca   1680
gatgttcatc aagtttcaga agcggacgcc cgtctttggt tacaacaact agaggagaaa   1740
ggaaggtatg caaaagatgt tgcttaa                                       1767
```

<210> SEQ ID NO 120
<211> LENGTH: 588
<212> TYPE: PRT
<213> ORGANISM: Artificial Sequence
<220> FEATURE:
<223> OTHER INFORMATION: BMR W1046A

<400> SEQUENCE: 120

```
Pro Ser Pro Ser Thr Glu Gln Ser Ala Lys Lys Val Arg Lys Lys Ala
1               5                   10                  15

Glu Asn Ala His Asn Thr Pro Leu Leu Val Leu Tyr Gly Ser Asn Met
            20                  25                  30

Gly Thr Ala Glu Gly Thr Ala Arg Asp Leu Ala Asp Ile Ala Met Ser
        35                  40                  45

Lys Gly Phe Ala Pro Gln Val Ala Thr Leu Asp Ser His Ala Gly Asn
    50                  55                  60

Leu Pro Arg Glu Gly Ala Val Leu Ile Val Thr Ala Ser Tyr Asn Gly
65                  70                  75                  80

His Pro Pro Asp Asn Ala Lys Gln Phe Val Asp Trp Leu Asp Gln Ala
                85                  90                  95

Ser Ala Asp Glu Val Lys Gly Val Arg Tyr Ser Val Phe Gly Cys Gly
            100                 105                 110

Asp Lys Asn Trp Ala Thr Thr Tyr Gln Lys Val Pro Ala Phe Ile Asp
        115                 120                 125

Glu Met Leu Ala Ala Lys Gly Ala Glu Asn Ile Ala Asp Arg Gly Glu
    130                 135                 140

Ala Asp Ala Ser Asp Asp Phe Glu Gly Thr Tyr Glu Glu Trp Arg Glu
145                 150                 155                 160

His Met Trp Ser Asp Val Ala Ala Tyr Phe Asn Leu Asp Ile Glu Asn
                165                 170                 175

Ser Glu Asp Asn Lys Ser Ala Leu Leu Leu Gln Phe Val Asp Ser Ala
            180                 185                 190

Ala Asp Met Pro Leu Ala Lys Met His Gly Ala Phe Ser Thr Asn Val
        195                 200                 205

Val Ala Ser Lys Glu Leu Gln Gln Pro Gly Ser Ala Arg Ser Thr Arg
    210                 215                 220

His Leu Glu Ile Glu Leu Pro Lys Glu Ala Ser Tyr Gln Glu Gly Asp
225                 230                 235                 240

His Leu Gly Val Ile Pro Arg Asn Tyr Glu Gly Ile Val Asn Arg Val
                245                 250                 255

Thr Ala Arg Phe Gly Leu Asp Ala Ser Gln Gln Ile Arg Leu Glu Ala
            260                 265                 270

Glu Glu Glu Lys Leu Ala His Leu Pro Leu Ala Lys Thr Val Ser Val
        275                 280                 285

Glu Glu Leu Leu Gln Tyr Val Glu Leu Gln Asp Pro Val Thr Arg Thr
    290                 295                 300

Gln Leu Arg Ala Met Ala Ala Lys Thr Val Cys Pro Pro His Lys Val
305                 310                 315                 320
```

```
Glu Leu Glu Ala Leu Leu Glu Lys Gln Ala Tyr Lys Glu Gln Val Leu
            325                 330                 335
Ala Lys Arg Leu Thr Met Leu Glu Leu Leu Glu Lys Tyr Pro Ala Cys
            340                 345                 350
Glu Met Glu Phe Ser Glu Phe Ile Ala Leu Leu Pro Ser Ile Arg Pro
            355                 360                 365
Arg Tyr Tyr Ser Ile Ser Ser Pro Arg Val Asp Glu Lys Gln Ala
            370                 375                 380
Ser Ile Thr Val Ser Val Ser Gly Glu Ala Trp Ser Gly Tyr Gly
385                 390                 395                 400
Glu Tyr Lys Gly Ile Ala Ser Asn Tyr Leu Ala Glu Leu Gln Glu Gly
            405                 410                 415
Asp Thr Ile Thr Cys Phe Ile Ser Thr Pro Gln Ser Glu Phe Thr Leu
            420                 425                 430
Pro Lys Asp Pro Glu Thr Pro Leu Ile Met Val Gly Pro Gly Thr Gly
            435                 440                 445
Val Ala Pro Phe Arg Gly Phe Val Gln Ala Arg Lys Gln Leu Lys Glu
            450                 455                 460
Gln Gly Gln Ser Leu Gly Glu Ala His Leu Tyr Phe Gly Cys Arg Ser
465                 470                 475                 480
Pro His Glu Asp Tyr Leu Tyr Gln Glu Glu Leu Glu Asn Ala Gln Ser
            485                 490                 495
Glu Gly Ile Ile Thr Leu His Thr Ala Phe Ser Arg Met Pro Asn Gln
            500                 505                 510
Pro Lys Thr Tyr Val Gln His Val Met Glu Gln Asp Gly Lys Lys Leu
            515                 520                 525
Ile Glu Leu Leu Asp Lys Gly Ala His Phe Tyr Ile Cys Gly Asp Gly
            530                 535                 540
Ser Gln Met Ala Pro Ala Val Glu Ala Thr Leu Met Lys Ser Tyr Ala
545                 550                 555                 560
Asp Val His Gln Val Ser Glu Ala Asp Ala Arg Leu Trp Leu Gln Gln
            565                 570                 575
Leu Glu Glu Lys Gly Arg Tyr Ala Lys Asp Val Ala
            580                 585

<210> SEQ ID NO 121
<211> LENGTH: 9
<212> TYPE: DNA
<213> ORGANISM: Artificial Sequence
<220> FEATURE:
<223> OTHER INFORMATION: Linker

<400> SEQUENCE: 121 ccatcaaga                                                                9

<210> SEQ ID NO 122
<211> LENGTH: 3
<212> TYPE: PRT
<213> ORGANISM: Artificial Sequence
<220> FEATURE:
<223> OTHER INFORMATION: Linker

<400> SEQUENCE: 122

Pro Ser Arg
1
```